United States Patent
Dayrell

(10) Patent No.: US 10,584,310 B2
(45) Date of Patent: Mar. 10, 2020

(54) INTEGRATED SYSTEM TO PRODUCE MICROALGAE

(71) Applicant: Ivan Araujo Dayrell, Belo Horizonte MG (BR)

(72) Inventor: Ivan Araujo Dayrell, Belo Horizonte MG (BR)

(*) Notice: Subject to any disclaimer, the term of this patent is extended or adjusted under 35 U.S.C. 154(b) by 98 days.

(21) Appl. No.: 15/453,765

(22) Filed: Mar. 8, 2017

(65) Prior Publication Data

US 2018/0258384 A1 Sep. 13, 2018

(51) Int. Cl.
| | | |
|---|---|---|
| *C12N 1/12* | (2006.01) | |
| *C12M 1/00* | (2006.01) | |
| *C12M 3/00* | (2006.01) | |
| *C12M 1/34* | (2006.01) | |
| *C12M 1/36* | (2006.01) | |

(52) U.S. Cl.
CPC .............. *C12N 1/12* (2013.01); *C12M 21/02* (2013.01); *C12M 23/42* (2013.01); *C12M 27/18* (2013.01); *C12M 29/00* (2013.01); *C12M 29/20* (2013.01); *C12M 29/22* (2013.01); *C12M 41/00* (2013.01); *C12M 41/34* (2013.01); *C12M 41/40* (2013.01); *C12M 41/48* (2013.01); *C12M 47/02* (2013.01)

(58) Field of Classification Search
CPC ......... C12N 1/12; C12M 21/02; C12M 23/42; C12M 27/18; C12M 29/20; C12M 29/22; C12M 29/00; C12M 41/00; C12M 41/34; C12M 41/48; C12M 41/40; C12M 47/02
USPC ........................................ 435/292.1; 47/1.4
See application file for complete search history.

(56) References Cited

U.S. PATENT DOCUMENTS

| | | | | |
|---|---|---|---|---|
| 2009/0081743 | A1* | 3/2009 | Hazelbeck | C12M 21/02 435/157 |
| 2009/0130706 | A1* | 5/2009 | Berzin | C12M 21/02 435/41 |
| 2014/0110252 | A1* | 4/2014 | Cooper | C25B 9/00 204/275.1 |

FOREIGN PATENT DOCUMENTS

WO 2010115412 10/2010

OTHER PUBLICATIONS

Written Opinion in corresponding International PCT Application PCT/BR2018/050060 dated Jun. 22, 2018.

* cited by examiner

*Primary Examiner* — Michael L Hobbs
(74) *Attorney, Agent, or Firm* — Z IP Law PLLC

(57) ABSTRACT

An integrated system to produce microalgae with autonomous fault identification and circumvention that can be deployed on land or at sea. The system comprises a fully scalable reactor, CO2 extraction, oxygen replenishment to surrounding water, and all necessary equipment to run it safely ensuring high energy efficiency and optimal control of environment variables to maximize biomass yield.

44 Claims, 92 Drawing Sheets

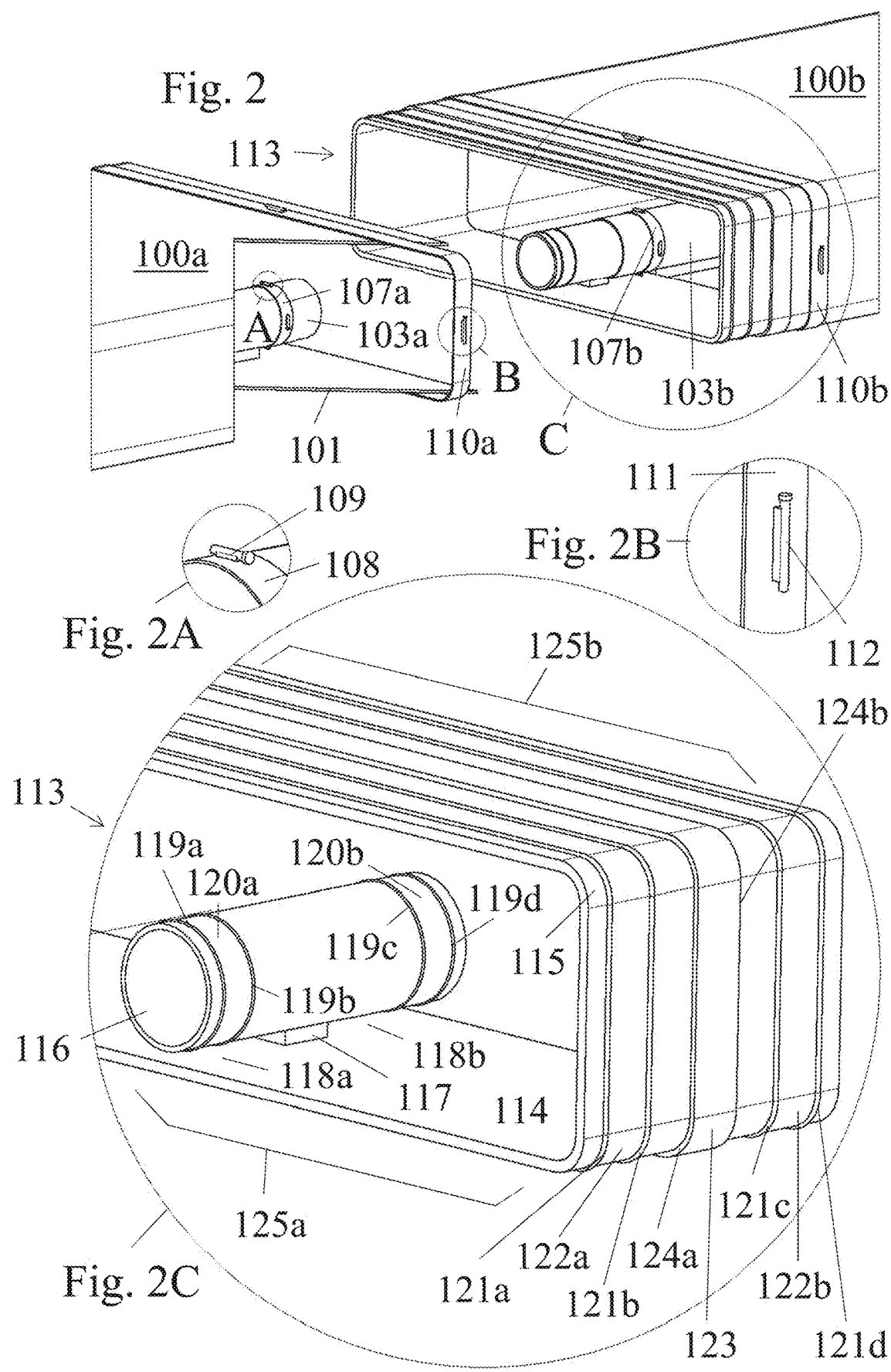

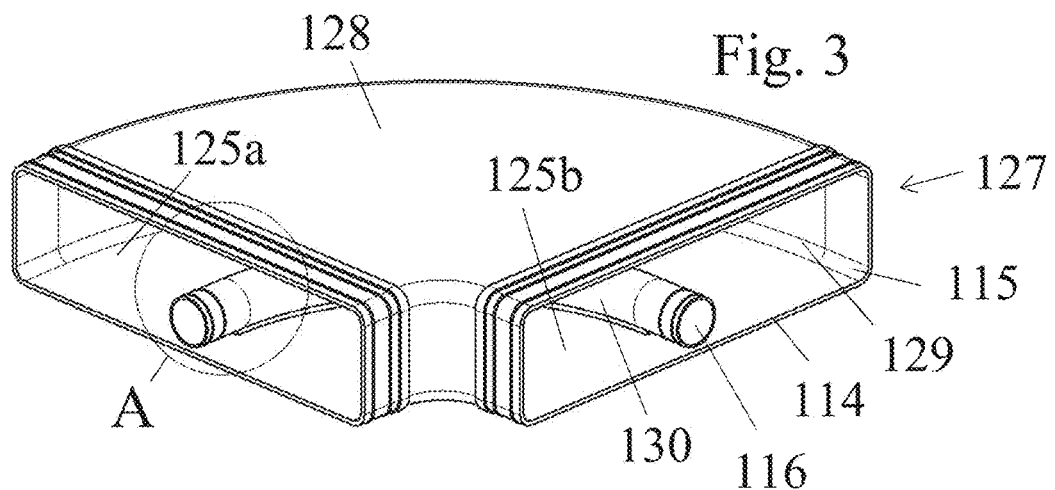
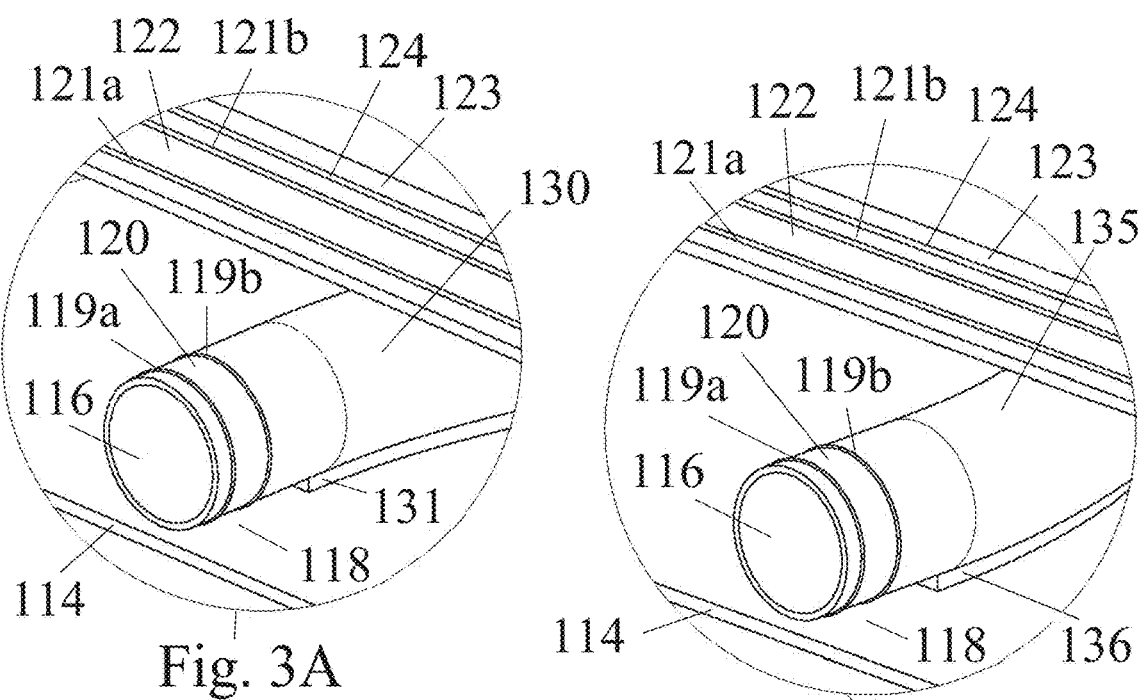
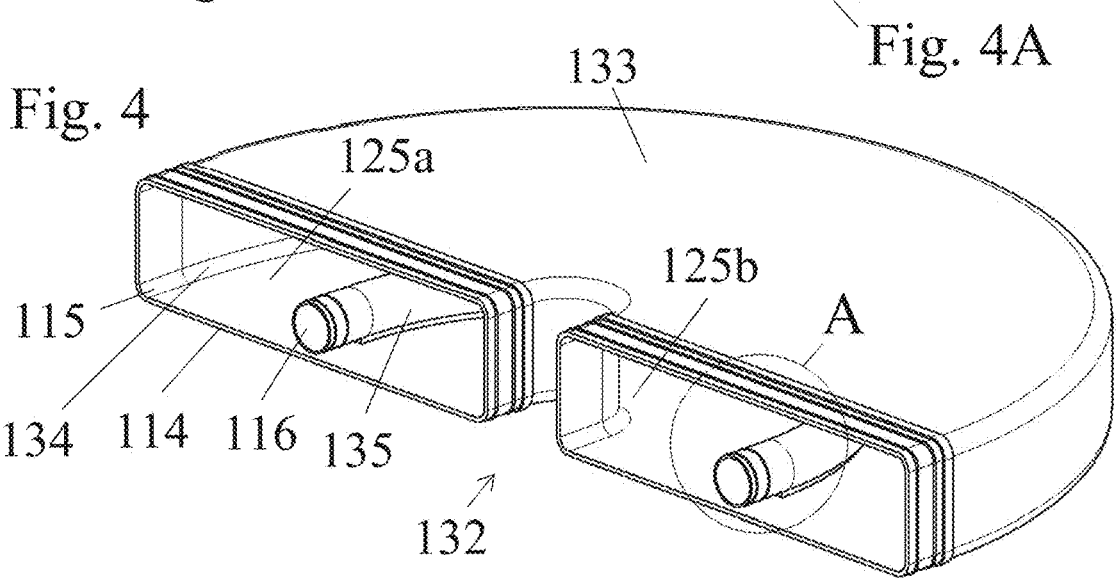

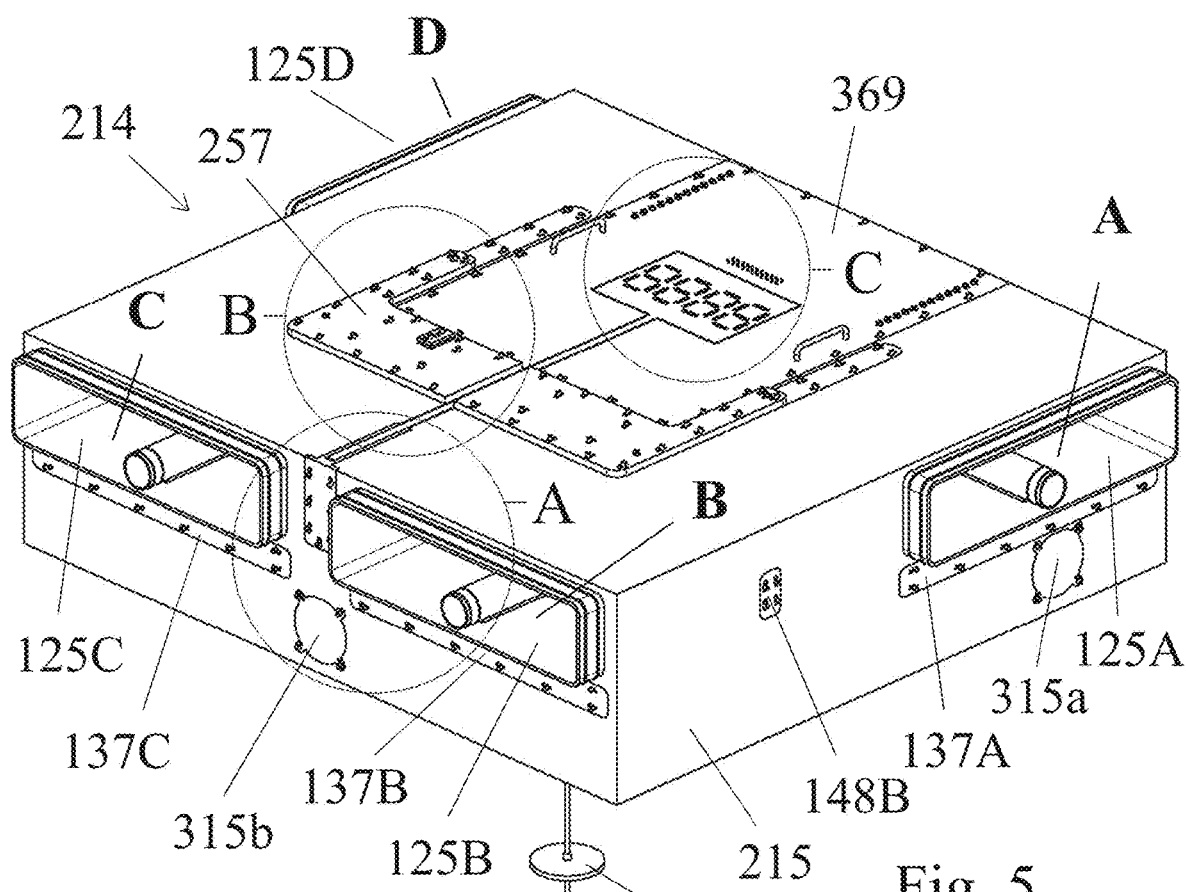
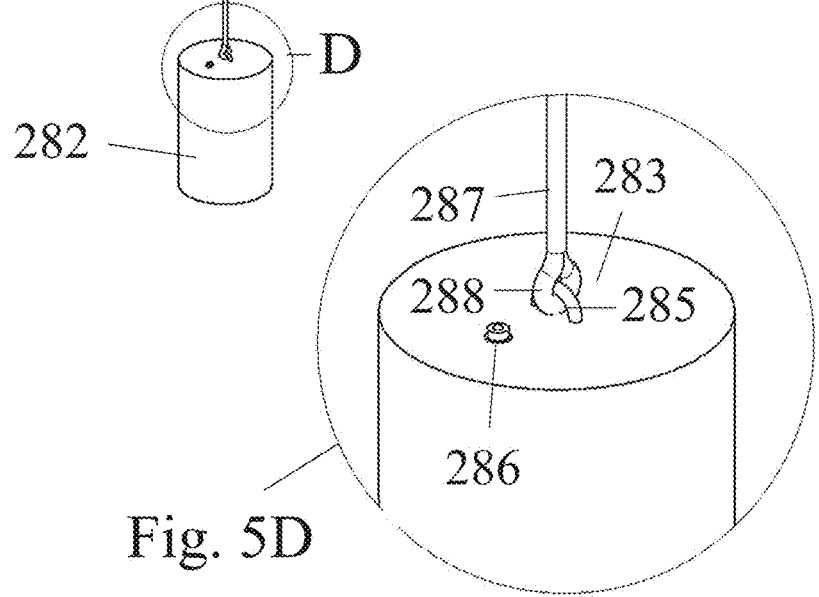
Fig. 5
Fig. 5D

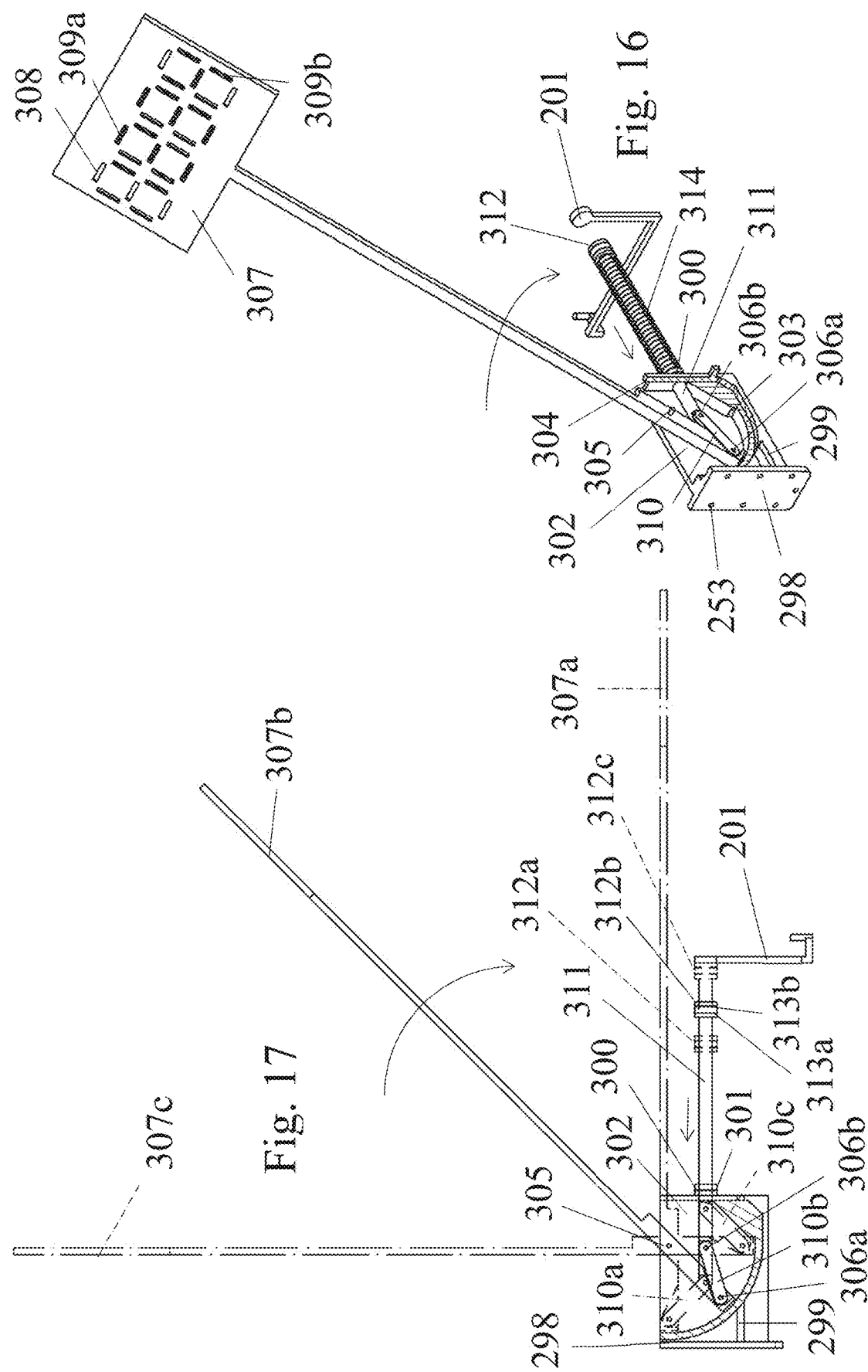

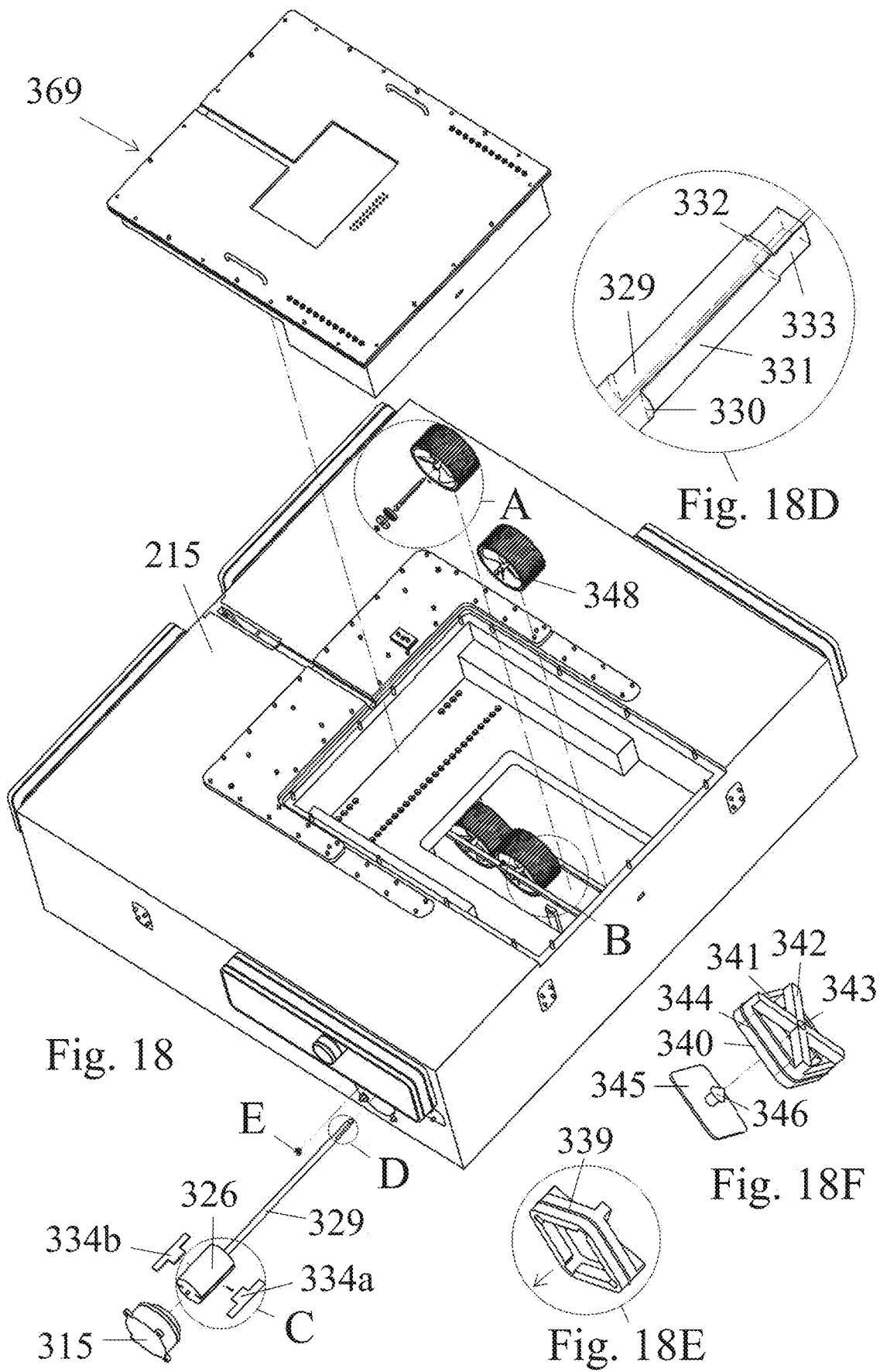

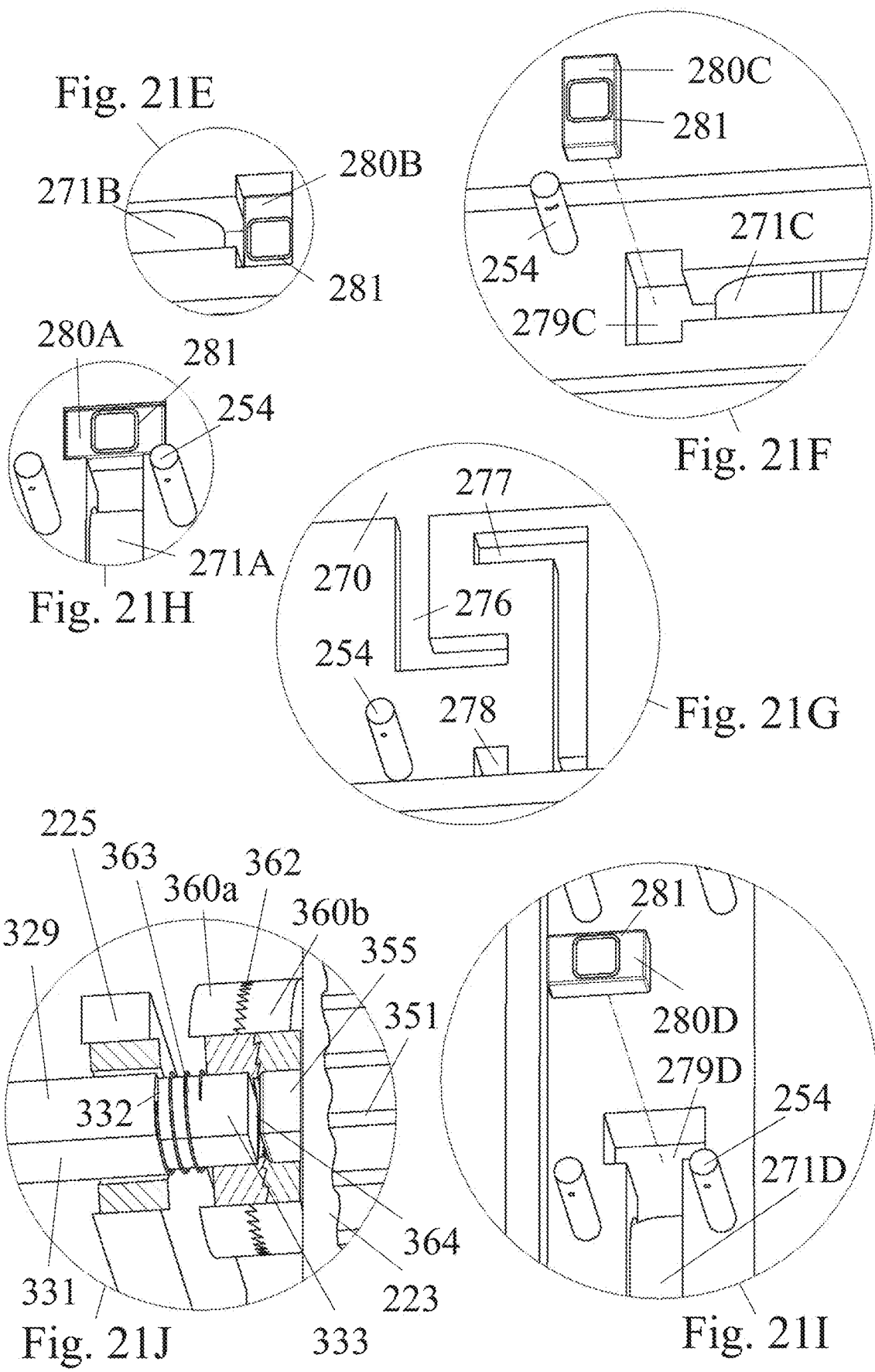

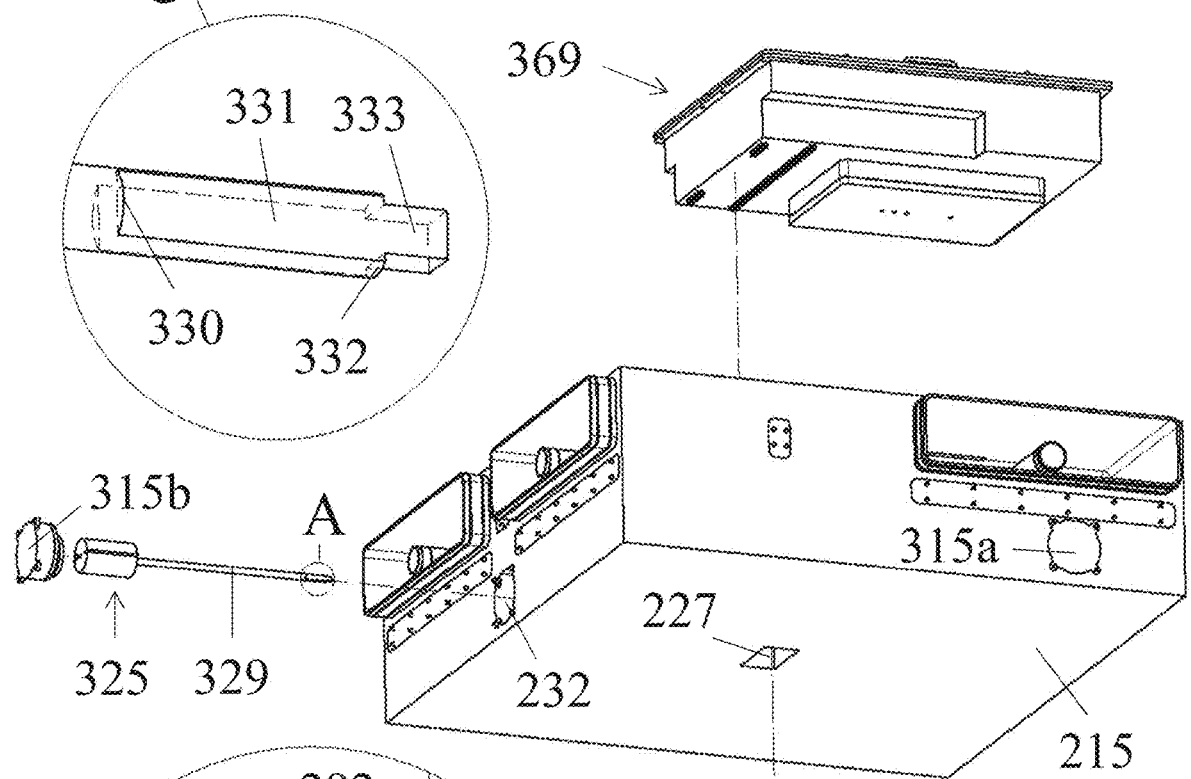
Fig. 23A
Fig. 23
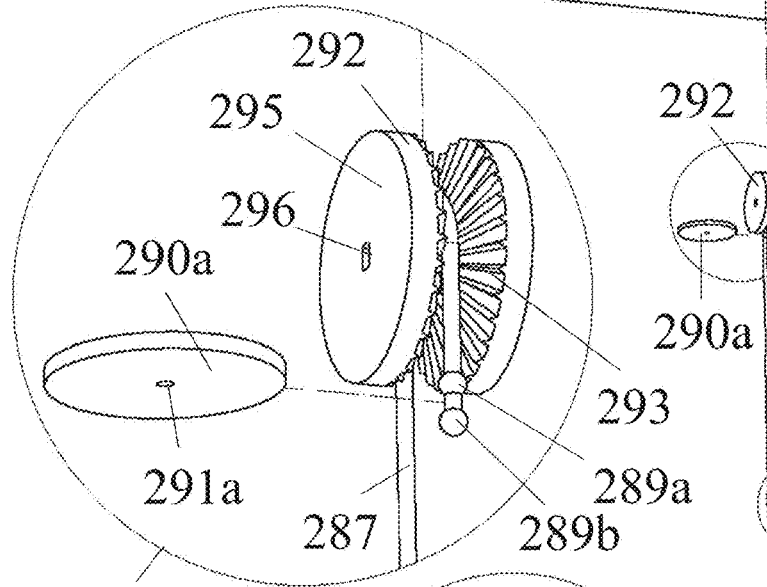
Fig. 23B
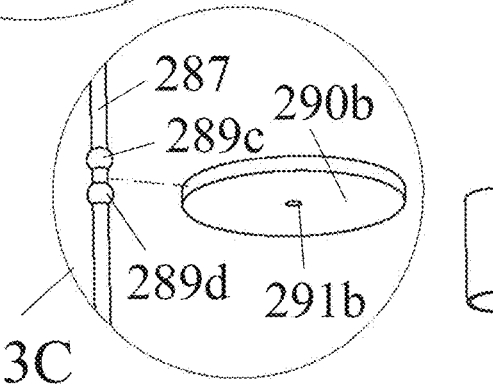
Fig. 23C

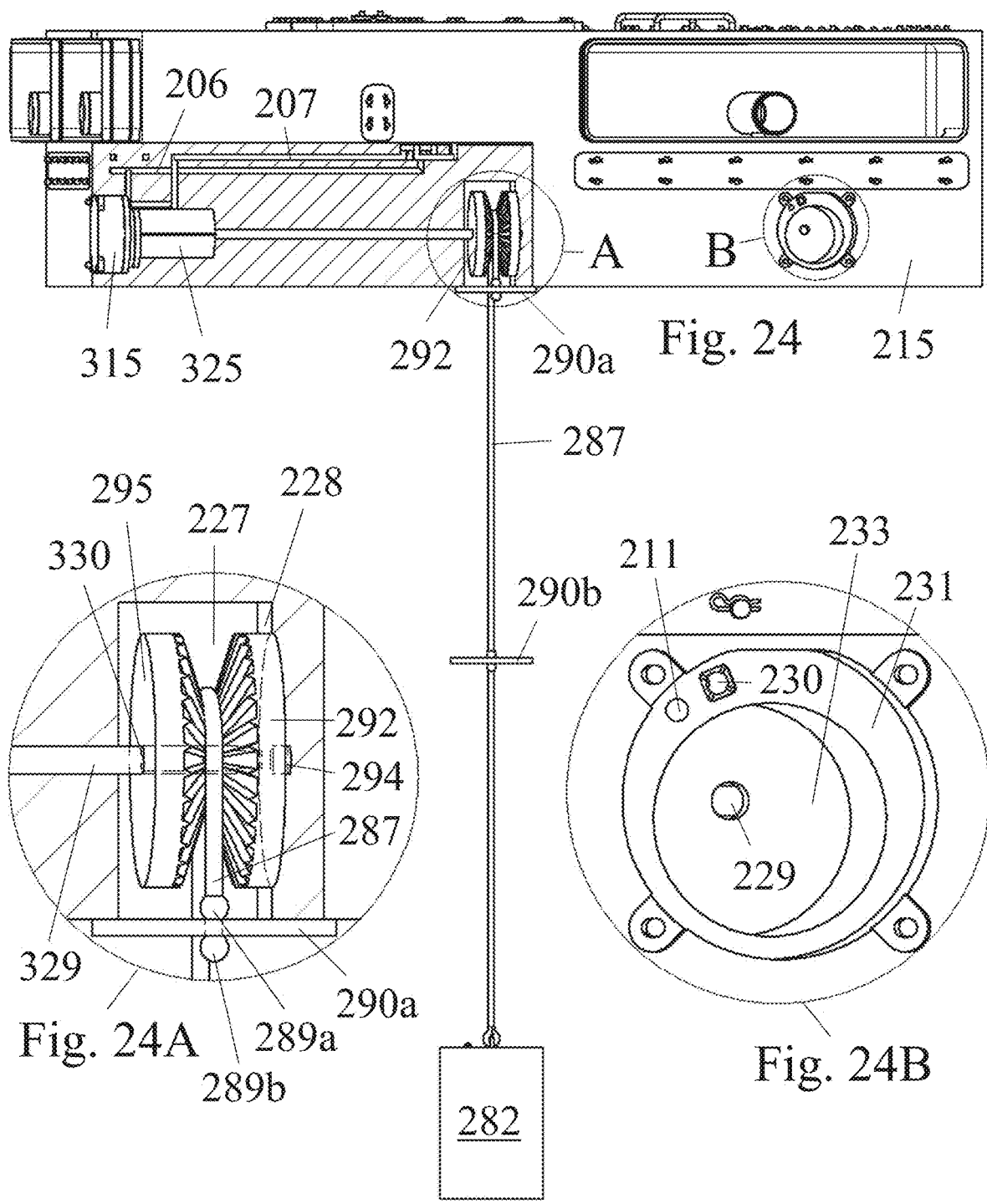

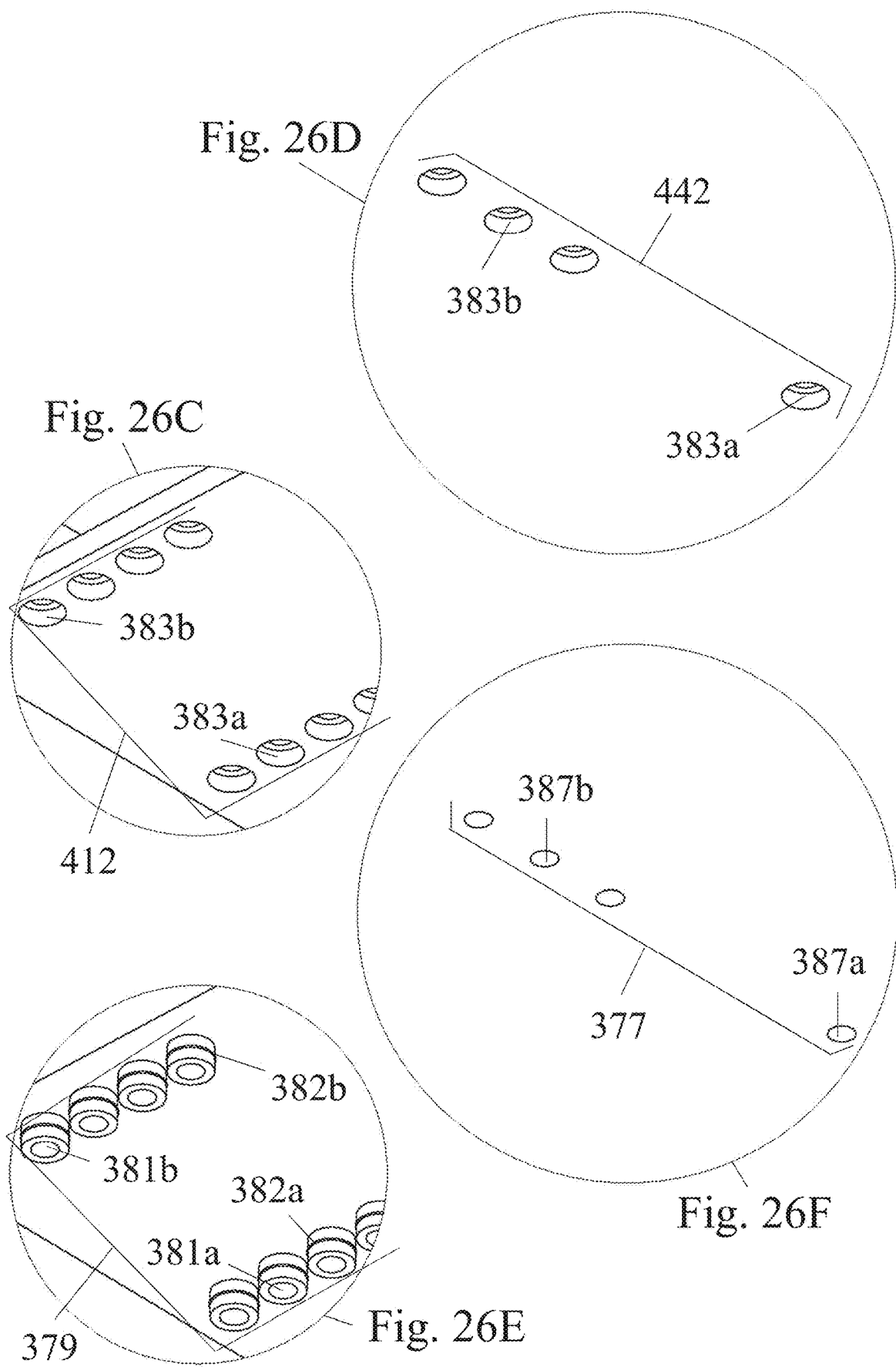

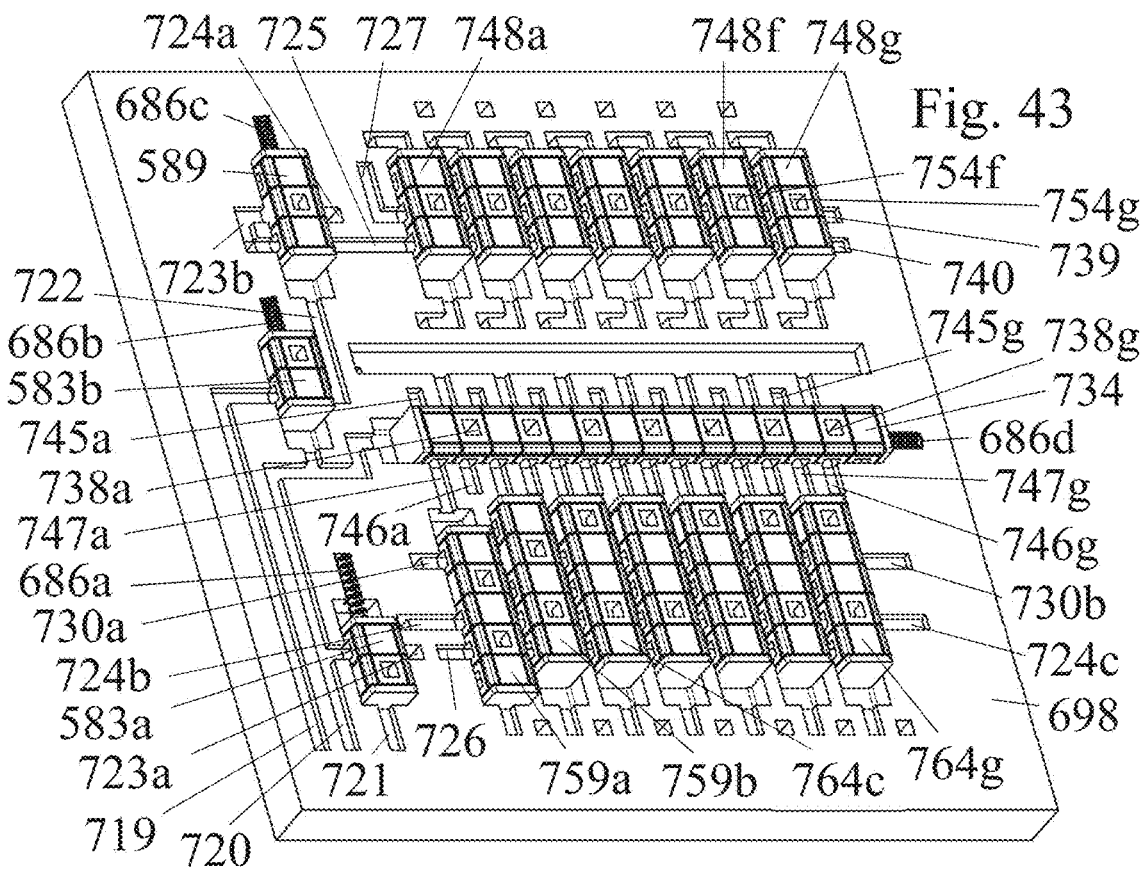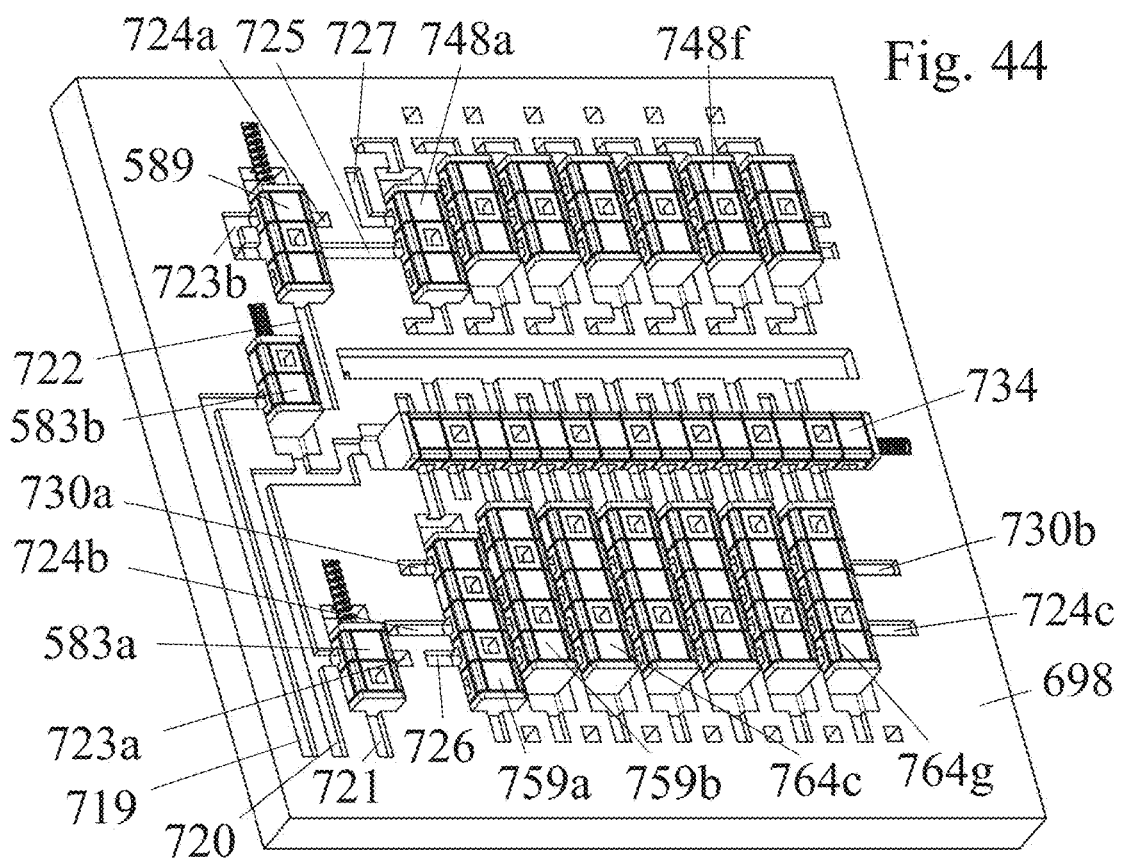

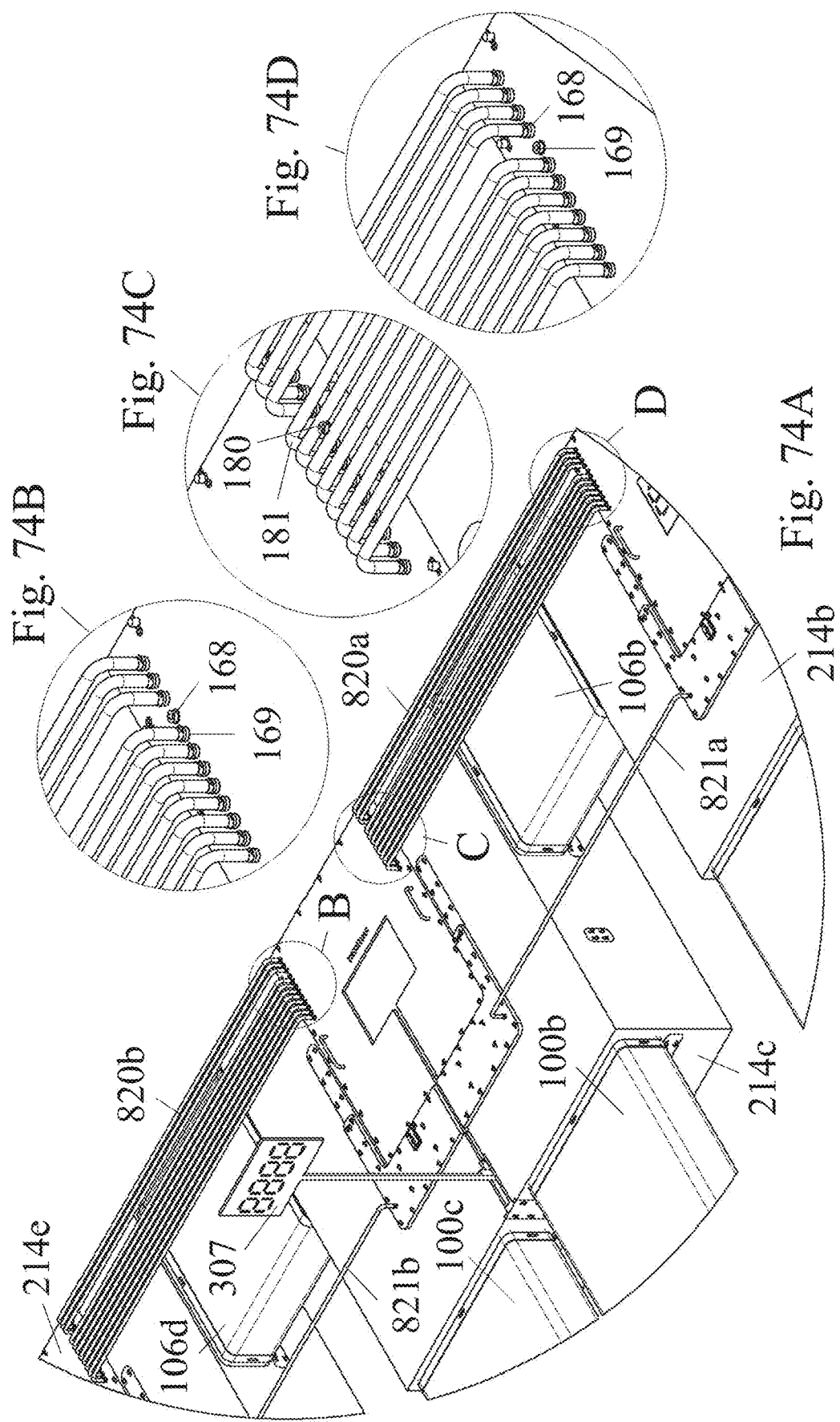

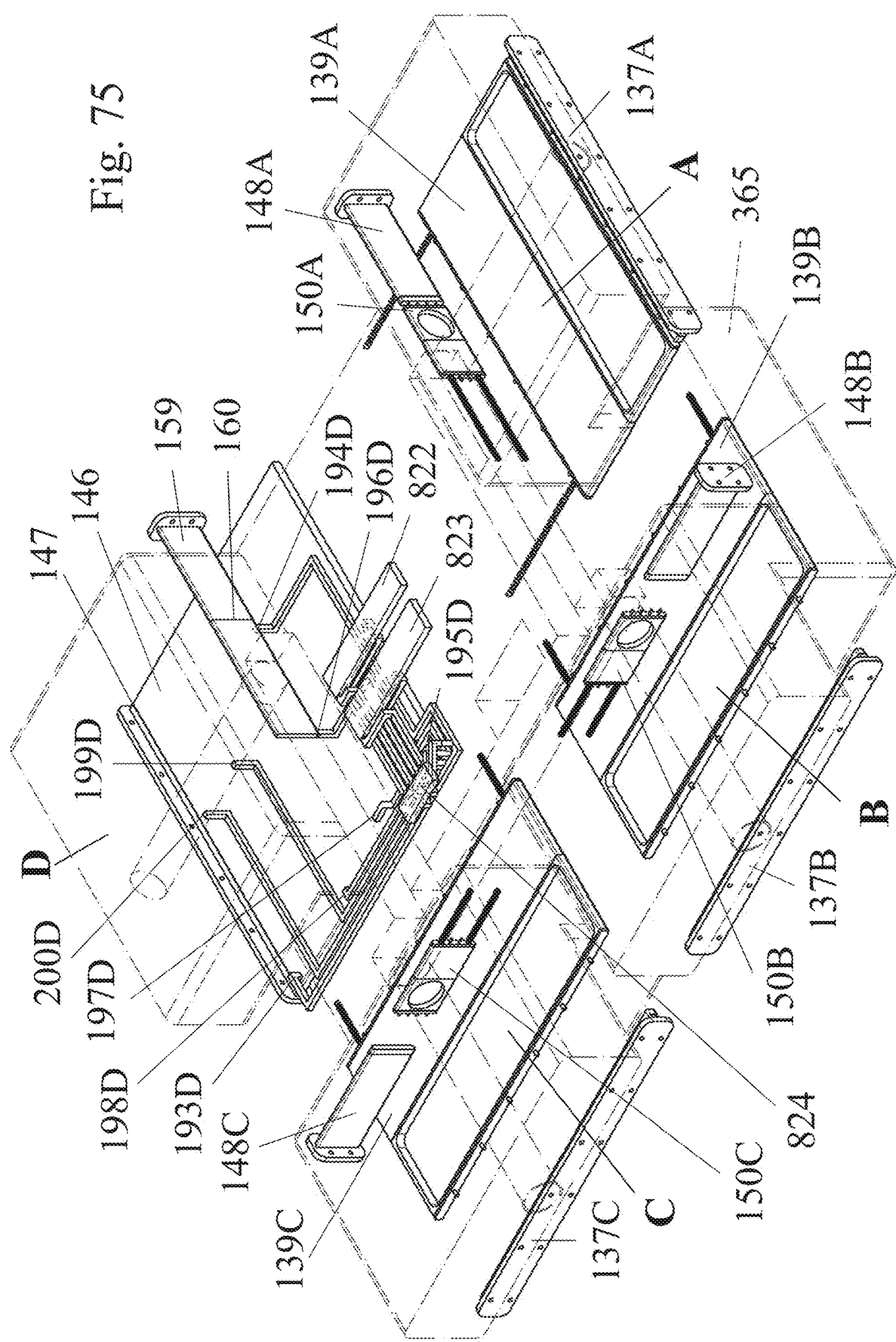

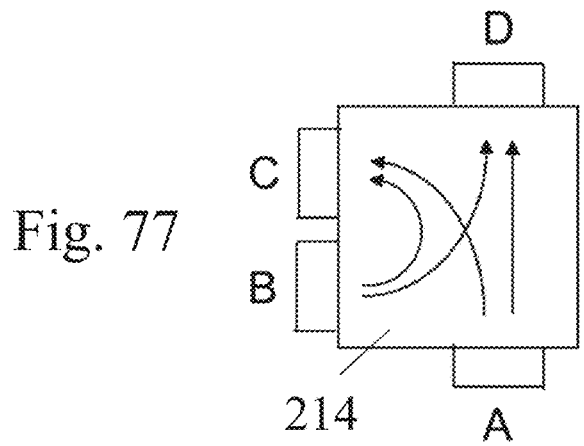
Fig. 77
Fig. 78
| Configuration | | Sequence | Port Rerouting |
|---|---|---|---|
| Direct | 1 | BC BD AC AD | A>A B>B C>C D>D |
| | 2 | AC AD BC BD | A>B B>A C>C D>D |
| | 3 | BD BC AD AC | A>A B>B C>D D>C |
| | 4 | AD AC BD BC | A>B B>A C>D D>C |
| Reverse | 5 | CB CA DB DA | A>D B>C C>B D>A |
| | 6 | DB DA CB CA | A>D D>B B>C C>A |
| | 7 | CA CB DA DB | A>C C>B B>D D>A |
| | 8 | DA DB CA CB | A>C B>D C>A D>B |
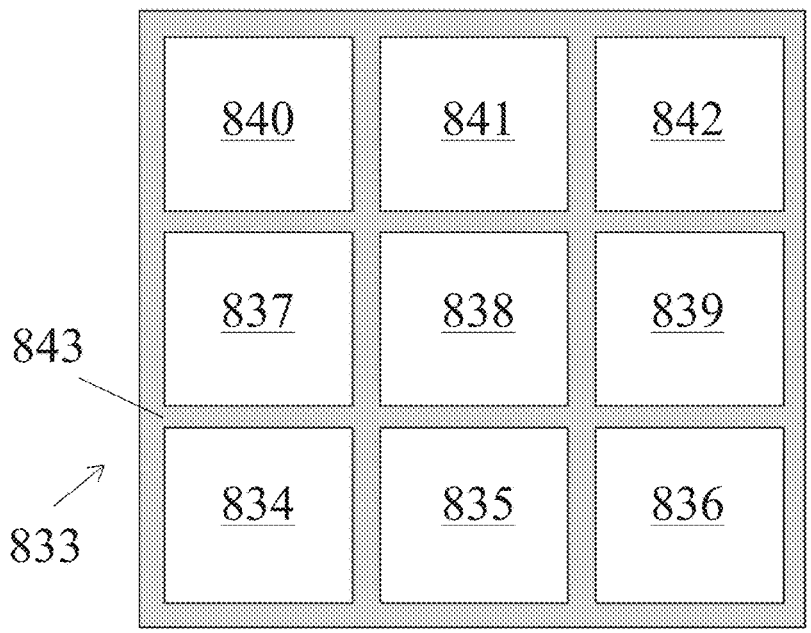
Fig. 79

Fig. 92

| # | Code | # | Code | # | Code | # | Code |
|---|------|---|------|---|------|---|------|
| 1 | 1111111 | 33 | 0100111 | 67 | 0111000 | 97 | 0110001 |
| 2 | 0111111 | 34 | 0010011 | 66 | 0011100 | 98 | 1011000 |
| 3 | 0011111 | 35 | 0001001 | 67 | 0001110 | 99 | 0101100 |
| 4 | 0001111 | 36 | 1000100 | 68 | 1000111 | 100 | 0010110 |
| 5 | 0000111 | 37 | 0100010 | 69 | 0100011 | 101 | 1001011 |
| 6 | 0000011 | 38 | 1010001 | 70 | 0010001 | 102 | 0100101 |
| 7 | 0000001 | 39 | 1101000 | 71 | 1001000 | 103 | 1010010 |
| 8 | 1000000 | 40 | 0110100 | 72 | 0100100 | 104 | 1101001 |
| 9 | 0100000 | 41 | 0011010 | 73 | 0010010 | 105 | 1110100 |
| 10 | 0010000 | 42 | 1001101 | 74 | 1001001 | 106 | 0111010 |
| 11 | 0001000 | 43 | 1100110 | 75 | 1100100 | 107 | 1011101 |
| 12 | 0000100 | 44 | 1110011 | 76 | 0110010 | 109 | 1101110 |
| 13 | 0000010 | 45 | 0111001 | 77 | 1011001 | 109 | 1110111 |
| 14 | 1000001 | 46 | 1011100 | 78 | 1101100 | 110 | 0111011 |
| 15 | 1100000 | 47 | 0101110 | 79 | 0110110 | 111 | 0011101 |
| 16 | 0110000 | 48 | 1010111 | 80 | 1011011 | 112 | 1001110 |
| 17 | 0011000 | 49 | 0101011 | 81 | 0101101 | 113 | 1100111 |
| 18 | 0001100 | 50 | 0010101 | 82 | 1010110 | 114 | 0110011 |
| 19 | 0000110 | 51 | 1001010 | 83 | 1101011 | 115 | 0011001 |
| 20 | 1000011 | 52 | 1100101 | 84 | 0110101 | 116 | 1001100 |
| 21 | 0100001 | 53 | 1110010 | 85 | 1011010 | 117 | 0100110 |
| 22 | 1010000 | 54 | 1111001 | 86 | 1101101 | 118 | 1010011 |
| 23 | 0101000 | 55 | 1111100 | 87 | 1110110 | 119 | 0101001 |
| 24 | 0010100 | 56 | 0111110 | 88 | 1111011 | 120 | 1010100 |
| 25 | 0001010 | 57 | 1011111 | 89 | 0111101 | 121 | 0101010 |
| 26 | 1000101 | 58 | 0101111 | 90 | 1011110 | 122 | 1010101 |
| 27 | 1100010 | 59 | 0010111 | 91 | 1101111 | 123 | 1101010 |
| 28 | 1110001 | 60 | 0001011 | 92 | 0110111 | 124 | 1110101 |
| 29 | 1111000 | 61 | 0000101 | 93 | 0011011 | 125 | 1111010 |
| 30 | 0111100 | 62 | 1000010 | 94 | 0001101 | 126 | 1111101 |
| 31 | 0011110 | 63 | 1100001 | 95 | 1000110 | 127 | 1111110 |
| 32 | 1001111 | 64 | 1110000 | 96 | 1100011 | 1 | 1111111 |

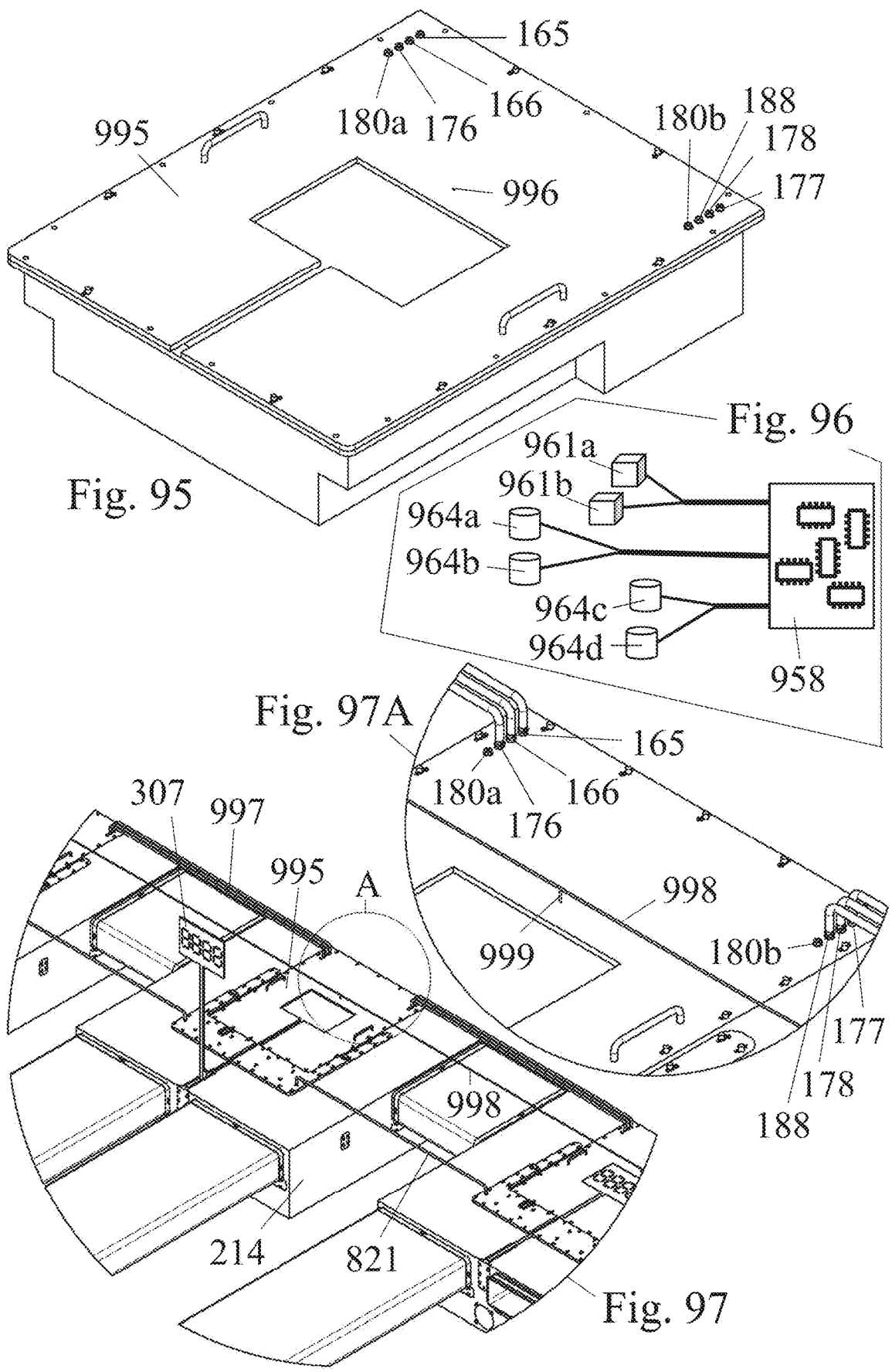

INTEGRATED SYSTEM TO PRODUCE MICROALGAE

FIELD OF THE INVENTION

The present invention is related to an integrated system to produce microalgae with autonomous fault identification and circumvention that can be deployed on land or at sea. The system comprises a fully scalable reactor, CO2 extraction, oxygen replenishment to surrounding water, and all necessary equipment to run it safely ensuring high energy efficiency and optimal control of environment variables to maximize biomass yield.

BACKGROUND

A lot of attention has been given recently to biodiesel production from all sorts of oil sources. One of the most promising ones is the use of microalgae, whether from marine or fresh water strains. These algae are known to be able to achieve very high productivity and good oil yields if the right conditions are met. A lot of research has been dedicated to try to find the most productive and/or resilient algae streams at universities and research institutes. This part of the field is advancing at a relatively good pace.

The same is not true though to cultivation methods. Mostly the research has been conducted at laboratory scales or small scale pilot projects and the main focus so far has been to verify the yield potential of the most promising streams into crude bioreactors or race ponds.

The main concept behind growing the selected stream is relatively straightforward, all that is needed is a suitable infrastructure capable of holding the necessary amount of water, keep critical culture parameters such as water temperature, PH, nutrient and carbon dioxide (CO2) concentration within acceptable boundaries and prevent contamination of the water culture from other undesirable organisms.

Despite the relatively straight forward requirements, many technical challenges arise when trying to scale up designs that work on table tops or producing new ones that are from the beginning designed as large scale. Particularly challenging is to find ways to keep costs as low as possible without losing the ability to effectively perform all necessary tasks. Those challenges have so far prevented the successful design and deployment of cost effective bioreactors that perform to the required level.

The high capital and operating costs of existing cultivation alternatives have so far prevented the promise of microalgae to be fully fulfilled. The main cost incurring items are the procurement of large cultivation areas close to a source of CO2, the preparation of the terrain and the installation of costly equipment such as the bioreactor structures, pumps, filters, sensors etc. All this equipment needs a lot of energy to operate generating high operating costs that in conjunction with the initial high capital costs create a very demanding productivity threshold to have an economical project.

The operating cost is a big challenge to overcome. So far existing reactor designs require a considerable amount of energy to run, mostly in pumping and controlling water temperature throughout the day and over the year. Most microalgae streams are very sensitive to temperature and PH levels outside their ideal growth range and if the ideal conditions are not met the productivity drops significantly and in some cases the algae die or are harmed and the productivity is irrecoverably reduced.

A lot of research has been dedicated to find better suited streams, more resilient to variations of the water culture and at the same time able to produce high oil yield. Some lines of research have tried to genetically modify high productivity streams to become resilient or high resilient ones to become more productive for oil yield but this created a concern of what could happen if these streams escape into the environment during the large scale phase of the project.

What is needed is an integrated approach that tackles the multiple aspects of the cultivation of microalgae which requires: 1) a system that significantly reduces capital and operational costs and ensures good control of the environment parameters; 2) a system that maintains the ideal conditions for the growth of the selected microalgae stream during all the different phases of the cultivation so productivity can be as high as possible. For any system to be successful, the system needs to be constructed with cheap materials to minimize capital costs, be very simple and robust to reduce maintenance costs, run as much as possible autonomously not requiring constant human intervention and have integrated safety mechanisms to prevent contamination of the culture and the environment in case of failure of the equipment.

PRIOR ART

There have been many approaches to the cultivation of microalgae. The traditional approach is to use race ponds that consist basically of closed circuit pools normally of oval shape. In these ponds the water is kept circulating by means of pumps or rotating paddles. Nutrients and carbon dioxide (CO2) are added at fixed points and the algae are inoculated at the beginning of the process.

Race ponds are expensive to construct: A big extension of suitable land close to a CO2 source must be procured and then a lot of civil works is required: leveling the terrain, digging the pits, pouring concrete and creating water tight structures so that water will not sip into the terrain potentially damaging the structure and/or causing soil or underground water contamination.

Most race ponds are left open to the environment and that creates many problems:

a) The contamination of the algae culture by undesirable organisms can cause a significant drop in productivity by consuming a part of the nutrients or even harming the algae culture with residues or toxins they produce;

b) The difficulty in controlling the water temperature that may vary significantly during day time and night time and over the year. Variations in temperature are particularly more severe if areas such as deserts are selected to install the race ponds. Because of the lower value of the land that is not suitable for agriculture or pastures, these areas tend to be an attractive alternative to locate microalgae farms with respect to the initial capital cost. Desert areas however have the disadvantage that the ambient temperature changes significantly from day to night and over the year. Unless appropriate measures are taken to prevent that these temperature variations reflect on the cultivation media of the algae, productivity will be impaired and the algae may even die. The alternatives are to insulate the race ponds with some material and place transparent covers over them that will reduce the heat transfer between the water and the atmosphere or use a system to actively control the temperature, involving heat exchangers. Both alternatives increase capital and/or operating costs;

c) Water evaporation and/or rain can potentially move nutrient concentration, PH or salinity outside the desired culture ranges and sophisticated monitoring systems consisting of multiple sensors and actuators are needed to ensure the culture will be out of trouble. If the ponds are located close to urban areas or facilities such as industries or power plants discharging pollutants into the atmosphere there is also a risk that the rain will capture some of these pollutants and carry them to the pond potentially poisoning the algae;

d) Injected $CO_2$ can potentially escape the pond to the atmosphere and be lost. Costly injection systems, able to inject only the necessary amount of $CO_2$ the algae culture is consuming through very small bubbles at the bottom of the pond by means of pumping high pressure gas through a very fine diffuser, have been proposed to mitigate this risk. These systems are sophisticated and have high capital and operating costs but still have limitations that make it very difficult to achieve the desirable target of having the race pond culture run so that no $CO_2$ escapes and $CO_2$ concentration remains in the desired concentration levels;

e) The race ponds require constant cleaning and maintenance and typically need to be drained, disinfected and reset at the end of each batch. The energy cost of pumping all the water to drain the pond is a major part of the operating costs reducing the overall efficiency of the process. Also, the cost of disinfecting and the after treatment needed to process the effluents to avoid damaging the environment needs to be considered.

Other solutions have been proposed to circumvent the limitations of race ponds and different bioreactor designs have been proposed. Many designs are based on the race pond concept, only creating a means to isolate the algae culture from the environment by means of a physical barrier around the culture. This can be achieved with a transparent material such as glass, plastic or acrylic resins.

The simplest approach is to use covers made of plastic or any other transparent material to cover the ponds. That creates some insulation for thermal loss and reduces or eliminates the evaporation and contamination problems. The covers need to span a relatively large distance and normally require some sort of supporting structure. They need to be sturdy but at the same time as thin as possible to avoid reducing light penetration. This is not a simple thing to achieve, particularly considering they remain exposed to the elements and susceptible to damage by strong winds, rain or hail. Covers can indeed improve overall productivity of race ponds but also imply higher capital costs.

Another approach is to replace the ponds and/or covers by plastic material. Instead of constructing concrete pits, the terrain is simply prepared so plastic bags or a plastic lining can be put on the ground to contain the water. To that effect normally a trench with not very steep edges is excavated and sand or another pliable material is used to produce a support layer for the plastic material that is used to create an impermeable layer. Using just a plastic lining is a cheaper alternative and produces a reactor similar to a traditional race pond that remains open to the elements. Using closed plastic bags produces a reactor similar to a traditional race pond fitted with covers. In both cases the construction costs are a fraction of the construction costs of traditional race ponds.

The drawback is that the so called plastic bag race ponds are not as durable as the traditional race ponds. The plastic lining and/or plastic bag will require maintenance and replacement at regular intervals. All other infrastructure equipment remains basically the same: pumps, filters, sensors and actuators need to be employed and special interface structures need to be created to allow these to be fitted into the plastic bag reactor. These interfaces need to be carefully designed and regularly inspected because they create discontinuities on the plastic surface and as such create weak spots for leaks.

Plastic bag race ponds have lower capital cost than traditional ones, but the operating costs remain basically unchanged or can be slightly higher.

Other more elaborate bioreactors have been suggested. In one extreme there are approaches that try to create cheap structures to minimize capital costs such as vertically mounted plastic bags with supporting frames, self-supporting plastic bag reactors that rely on particular shapes to create reinforcement and structure stability in some directions and be able to contain a certain volume of water requiring no or little external support or plastic bags that are dropped into a water body such as a lake or at sea working only as a physical barrier.

These reactors tend to be fragile and susceptible to breakdowns, leaks and other problems. The operation is complicated and requires constant human intervention. Many times the reactors are too simple to allow effective control of water flow, $CO_2$ or nutrient concentrations and the algae growth can be non-uniform throughout the reactor with some areas producing higher growth rates than others. If harvesting is delayed to allow all the different portions of the reactor to fully develop, the algae in the sections that have experienced higher growth can be left with no nutrients or no $CO_2$ and may end up tapping into their oil reserves consuming part of the produced oil. In more severe cases critical spots may offer unacceptable living conditions killing the algae there.

A compromise needs to be found and that typically means productivity and yield will suffer. The harvesting process also tends to be more complicated in these reactors and may involve pumping water over heights of several meters or having to physically haul and move the plastic bags containing all the water and algae to a processing point impacting operating costs and reducing the benefit of having low capital costs.

On the other extreme we have very sophisticated bioreactors consisting of a series of acrylic or plastic pipes fully supported by metal structures and fittings that can be mounted at favorable inclinations to maximize land usage and catch most of the sun light. These reactors offer the advantage to allow better control on the $CO_2$ injection, nutrient concentration and can be operated on a continuous flow regime, reducing down time, simplifying harvesting and increasing efficiency. The idea is to achieve higher productivities and lower operating costs at the expense of a significantly higher initial capital cost. To be viable the equipment needs to be sturdy enough to last many years of operation and the design needs to be sufficiently good to allow a substantial reduction on operating costs to compensate for the initial high capital costs.

Unfortunately, however this so far has not been possible mostly due to high pumping costs created by a very long extension of small diameter pipes. To reduce these pumping costs, it would be necessary to use pipes of a larger diameter but that in turn would require thicker walls that would increase the weight and cost of the pipes and support structures as well as impair light transparency of the pipes.

Advantages

The proposed system has been designed considering multiple aspects of the algae production cycle and offers solutions to reduce both capital and operating costs without sacrificing productivity or safety.

Cheap, readily available materials are used in the construction of the reactors that are designed so that manufacture, assembly, deployment and maintenance are facilitated and operational costs reduced.

The system is designed so it can be deployed on land or water. Land operation is convenient in case a big producer of CO2 such as a power plant, cement factory, steel mill etc. wants to remediate its CO2 production and land is available nearby.

Water operation is convenient because this solves the problems of land availability, land capital cost, land preparation costs and competing pressure with food production, animal farming or natural reserves. Any water body can be used provided that the operation of the bioreactors does not conflict with other uses of the particular water body or conservation of fauna and flora.

A key advantage of the proposed system is the capability to extract the necessary CO2 from sea water. The extraction process is integrated with other processes and uses waste energy coming from these processes such as, but not limited to, waste heat and pressure differences. The oceans are known to be the repository of tremendous amounts of CO2 many times over the quantities in the atmosphere or produced annually by human activity. Extracting CO2 from the sea is estimated to be cheaper than having the CO2 delivered to the farm and also provides the benefit of combating ocean acidity.

The oceans have a very large surface area and its surface is in constant motion due to currents, waves and weather patterns creating an even larger interface with the atmosphere. Any CO2 extracted at a particular point will be quickly replenished by water mixing with nearby waters and ultimately from CO2 absorbed from the atmosphere. In that way, extracting the CO2 from sea water provides a means of harnessing natural processes to transport the CO2 from emitters scattered all over the world and make it available where it is needed, wherever the farm may be. The expected long term overall effect will be the reduction of CO2 levels both in the atmosphere and dissolved on sea waters, a very desirable goal currently being advocated by ecologists and scientists all over the world.

An algae farm operating at sea has the benefit of unrestricted CO2 availability at marginal cost, availability of very large contiguous areas, the elimination of land capital costs and land conflicting usage. Additionally, since ocean water temperature varies very little due to the enormous amount of heat stored in the ocean, monitoring and control systems for water temperature can be eliminated from algae farms, saving the equipment and energy costs that such systems would impose.

This creates a decisive advantage for sea based operations and it is therefore estimated that the most attractive areas for cultivation of microalgae using the proposed technology will be located at sea, preferably at locations having water depths of 15 m or more. There is no limit to the maximum depth of the selected area and that means a vast extension of the oceans can be used to deploy algae production farms.

The reactors are capable of fully autonomous operation, being able to operate and survive at sea under any weather condition. In case severe weather threatens the area, the exposed units are capable of diving to a safe depth and stay at the designated depth as long as necessary and then return to surface unimpaired when the conditions are clear.

The system is capable of autonomous detection and circumvention of faults, bypassing faulty units to allow operation to continue on the unaffected sections and reporting the detected faults back to the management system that is then able to identify each individual unit affected and generate trouble notes for maintenance. Custom software pin points faulty units in a map and assigns repair priority to support maintenance crew efforts.

As a result, the system can operate on continuous flow for extended periods of time without need of intervention from operators. At regular intervals, all that is needed is that a collection team visits the farms to collect the produced algae slurry, emptying or replacing the product tanks and resupplying consumables such as nutrients or fuel. At such times, preventive or corrective maintenance following received low priority trouble notes can be made ensuring that everything is in proper working condition until the next scheduled visit. In case urgent trouble notes are received, a specialized crew is mobilized and after a quick inspection at the location, performs the required repairs.

The system integrates algae harvesting, distributed pumping of the water culture and distributed nutrient dispersal. Pressurized water coming from the algae harvester is used as power source in the wet part of the reactors. By doing so some energy used in the harvesting processes is recycled for water culture pumping and nutrient dispersal, improving overall energy efficiency.

Distributed water pumping provides the additional benefit of reducing pressure spikes throughout the system and the possibility of using thinner walls on the reactor elements, further improving pumping efficiency and reducing energy consumption and operating costs.

Components that remain in permanent contact with sea water (wet equipment) are made of materials that are not susceptible to corrosion, performance degradation or failure when exposed to sea water for extended periods. The used materials are also highly resistant to UV light and chemical degradation by all chemicals used in the production process. To prevent or reduce biological fouling additives may be added to the wet elements. Each individual component is constructed to be cheap and easily replaceable so that with time, if some fouling eventually occurs and cleaning proves to be too difficult, they can be replaced without big cost impact.

No electric components such as wires, motors, pumps, sensors, etc. are used in the wet equipment that also does not require any electricity as a power source. Any equipment in permanent contact with sea water is powered only with compressed water and/or compressed air. All logic, control devices and monitoring functions are performed using only hydraulic and pneumatic devices.

Eliminating electricity altogether from the reactor design (wet part) means costly insulation able to withstand the marine environment for extended periods of time is not needed, equipment cost is reduced and system reliability is dramatically improved.

SUMMARY OF THE INVENTION

One object of the proposed invention is the integration of multiple aspects of the algae production cycle in a single system in such a way that capital and operating costs can be reduced without sacrificing productivity or safety.

Another object of the proposed invention is a design of a reactor that allows the system to be deployed both on land or water. In case of water based operation, the reactor is able to be submerged to a predefined depth to avoid dangerous weather conditions.

Another object of the proposed invention is a design that allows the use of cheap, readily available materials in the construction of the reactor parts that are designed so that manufacture, assembly, deployment and maintenance are facilitated and operational costs reduced. Components that remain in permanent contact with water (wet equipment) are made of materials that are not susceptible to corrosion, performance degradation or failure when exposed for extended periods of time to fresh water or sea water, UV light and the chemicals used in the production process. To prevent or reduce biological fouling, additives may be added to the wet elements but as the components are constructed to be cheap and easily replaceable if some fouling eventually occurs they can be replaced without big cost impact.

A key object of the proposed invention is the capability to extract the necessary $CO_2$ from sea water. The extraction process is integrated with other processes and uses waste energy coming from these processes such as, but not limited to, waste heat and pressure differences.

Another object of the proposed invention is the ability to autonomously detect and circumvent faults, bypass faulty units to allow operation to continue on the unaffected sections and report the detected faults back to the management system. The management system is able to identify each individual unit affected and generates trouble notes listing the affected units and the nature of the problem. The trouble notes are transmitted to a control center and addressed according to severity and urgency. Custom software pin points faulty units in a map and assigns repair priority to support maintenance crew efforts.

Another object of the proposed invention is the integration of algae harvesting and distributed nutrient dispersal and distributed pumping of the water culture. Pressurized water coming from the algae harvester is used as power source in the wet part of the reactor allowing energy used in the harvesting processes to be recycled for water culture pumping and nutrient dispersal, improving overall energy efficiency.

Another object of the invention is to use only hydraulic and pneumatic power to operate all equipment in permanent contact with water. All functions, including pumping, controlling equipment, logic implementation, monitoring, etc. are performed using only hydraulic and pneumatic powered devices.

The present invention is related to an integrated system for the production and harvesting of microalgae, comprising a reactor having a plurality of reactor nodes and a plurality of pipe elements, the plurality of reactor nodes and the plurality of pipe elements configured to create an isolated water culture suitable for algae growth; and an algae separation unit. The integrated system for the production and harvesting of microalgae may comprise a $CO_2$ extraction unit comprising a water degasifier; a plurality of pumps configured to supply water to the water degasifier; an engine configured to power the plurality of pumps and heat water in the water degasifier; a heat exchanger configured to heat water from the water degasifier and recirculate the heated water to the water degasifier; a vaporizer supplied with exhaust gases from the engine and with boil-off gases from the water degasifier, the vaporizer configured to use the boil-off gases to sublimate solid $CO_2$; a $CO_2$ extractor supplied by pre-cooled boil-off gases coming from the vaporizer; a $CO_2$ separator configured to supply solid $CO_2$ to the vaporizer; and a heat exchanger configured to heat waste gases from the $CO_2$ separator and vent the heated waste gases to the atmosphere.

The integrated system for the production and harvesting of microalgae may comprise a condensed water cleaner; a heat exchanger configured to exchange heat from the engine exhaust gases and the boil off gases from the water degasifier to condensate water vapor contained in the engine exhaust gases and the boil off gases into condensed water. The integrated system for the production and harvesting of microalgae may comprise an oxygen extractor configured to extract oxygen from water culture supplied by the reactor; a discharge water aerator supplied with water from the condensed water cleaner and with oxygen from the oxygen extractor; a heat exchanger configured to heat water culture from the reactor entering the oxygen extractor; a heat exchanger configured to recover heat from the water leaving the oxygen extractor.

The integrated system for the production and harvesting of microalgae, wherein the algae separation unit may comprise an algae separator comprising a concentrator; and a helical pusher; an algae storage unit. The integrated system for the production and harvesting of microalgae, wherein the concentrator is conical in shape and the helical pusher is configured to rotate to scrape algae from the concentrator, force water culture from the reactor through the concentrator, and thereby produce an algae slurry. The integrated system for the production and harvesting of microalgae, may comprise a culture diluter configured to replenish the reactor with water culture; a flow divider configured to divide water culture from the reactor between the algae separator and the culture diluter; and a pump configured to extract water from the algae separator through the oxygen extractor and supply water to the reactor.

The integrated system for the production and harvesting of microalgae wherein each pipe element may comprise an inner pipe configured to permeate $CO_2$ to feed the algae culture; each reactor node may comprise pipe ports configured to open and close the pipe elements attached to the reactor node; a propeller pump configured to pump water through the pipe elements; and a vane pump powered by pressurized water from the algae separator, the pressurized water having nutrients, the vane pump configured to power the propeller pump.

The integrated system for the production and harvesting of microalgae, wherein the reactor node may comprise a module assembly having hydraulic and pneumatic components, the module assembly may comprise an i/o unit assembly configured to generate hydraulic and pneumatic output signals to control the reactor node and transmit hydraulic and pneumatic output signals to other reactor nodes; a logic unit assembly configured to process hydraulic and pneumatic output signals received from the i/o unit assembly, generate logic functions, and output hydraulic and pneumatic logic signals to be received by the i/o unit assembly.

The integrated system for the production and harvesting of microalgae, wherein the logic unit assembly having at least one of a plurality of replaceable router plates, each router plate configured to re-route signals to and from the reactor node in a specific way. The integrated system for the production and harvesting of microalgae, wherein the logic unit assembly comprising a plurality of logic gates selected from a group consisting of AND gates, NAND gates, OR gates, SEL gates, XOR gates, SW gates, zero gates, memory gates, register gates, and diagnose gates. The integrated system for the production and harvesting of microalgae may comprise a linear feed shift register; and wherein the state of the linear feed shift register is used to select one logic unit assembly at a time to be active among the plurality of logic unit assemblies in the reactor. The integrated system for the production and harvesting of microalgae wherein the logic gates of the logic unit assembly are hydraulically actuated. The integrated system for the production and harvesting of microalgae wherein the logic gates of the logic unit assembly are pneumatically actuated.

The integrated system for the production and harvesting of microalgae may comprise an input bus having a plurality of input lines; a plurality of analog to digital converters, each analog to digital converter connected to each of the plurality of input lines; an output bus having a plurality of output lines; a plurality of solenoid valves, each solenoid valve connected to each of the plurality of output lines; a plurality of output pressure lines, each output pressure line fed by a corresponding solenoid valve and connected to an input pressure line on the reactor node; a plurality of input pressure lines, each input pressure line fed by an output pressure line coming from the reactor node and connected to the corresponding analog to digital converter; and wherein each solenoid valve in a first position allows fluid flow to move a logic gate to a high position; and wherein each solenoid valve in a second position allows fluid flow to move a logic gate to a low position; and wherein the position of each of the plurality of solenoid valves is configured to transmit commands to control the reactor node; and wherein the position of each logic gate is configured to transmit the status of the reactor node to each analog to digital converter.

The integrated system for the production and harvesting of microalgae wherein each reactor node may comprise a master designation or slave designation with each slave reactor node being associated to a designated master reactor node; and wherein the plurality of logic gates, may comprise a zero logic gate fed with a digital zero pressure signal; a clock logic gate fed with a digital clock pressure signal; a master logic gate fed with a digital master pressure signal; a help logic gate fed with a digital help pressure signal; a query logic gate fed with a digital query pressure signal; a status logic gate fed with a digital status pressure signal; and wherein the zero logic gate, the clock logic gate and the master logic gate generate a sequence of commands to the remaining plurality of logic gates in the logic unit assembly allowing only one logic unit assembly within the reactor to be selected at any time; wherein the help gate in a selected logic unit assembly is configured to transmit an alarm signal to the next reactor node if any abnormal condition is present in the reactor node where the selected logic unit assembly is installed or if an alarm is received from the previous reactor node from the help pressure line; wherein the query logic gate and the status logic gate in a logic unit assembly that is not selected are configured to retransmit to the next reactor node the signals received from the previous reactor node from the query pressure line and the status pressure line respectively and the query logic gate and the status logic gate in the selected logic unit assembly are configured to ignore the signals received from the previous reactor node and transmit to the next reactor node the alarm signals active in the reactor node where the selected logic unit assembly is installed; and wherein the query logic gate in a selected logic unit assembly is configured to generate an alarm signal in the query pressure line if any abnormal condition generates an alarm in the reactor node where the selected logic unit assembly is installed and the status logic gate in a selected logic unit assembly is configured to generate an alarm signal through the status pressure line if an alarm signal is received from the previous reactor node through the help pressure line.

The integrated system for the production and harvesting of microalgae, wherein the reactor node may comprise a plurality of pipe ports, each pipe port having a door configured to seal each pipe element attached to each of the plurality pipe ports; a plurality of actuators configured to open or close the plurality of doors that open or close each pipe port; and wherein the detection of an alarm within a reactor node activates the actuators to close a first pipe port to circumvent a fault and open a second pipe port to bypass a faulty pipe element.

The integrated system for the production and harvesting of microalgae may comprise at least one controller comprising a pressure controller cavity; a pressure controller device aligned within the pressure controller cavity; a controller spring configured to move as pressure within the controller cavity changes thereby moving the pressure controller device to align inputs within the pressure controller cavity with openings within the pressure controller device; and wherein a pressure signal is generated from the alignment of the pressure controller device within the pressure controller cavity. The integrated system for the production and harvesting of microalgae wherein the number of inputs to the controller determines the number of bits of the pressure signal. The integrated system for the production and harvesting of microalgae wherein the controller is hydraulically powered. The integrated system for the production and harvesting of microalgae wherein the controller is pneumatically powered.

The integrated system for the production and harvesting of microalgae wherein the pressure controller device is in the shape of a parallelogram with cutouts of material removed from each corner of the pressure controller device creating two central extensions at the extremities of the pressure controller device so inputs on the end of the pressure controller cavity are not closed by the surface of the pressure controller device. The integrated system for the production and harvesting of microalgae wherein a pressure controller device has an orifice that runs through the middle of the pressure controller device to accommodate the controller spring; wherein the orifice stops short of perforating the full length of the pressure controller device so that the remaining material in the central extension has sufficient structural integrity to withstand the force provided by the controller spring and the orifice has the longest possible length.

The integrated system for the production and harvesting of microalgae may comprise a plurality of controllers, the plurality of controllers may comprise at least one pneumatic CO2 pressure controller; at least one hydraulic water pressure controller; at least one hydraulic ground pressure controller; at least one pneumatic signal input pressure controller; and at least one hydraulic signal input pressure controller.

The integrated system for the production and harvesting of microalgae may comprise a hydraulic depth sensor having a plastic bag and a movable depth detector wherein each reactor node in the reactor is configured to be submerged to a predefined depth to avoid dangerous weather conditions.

The integrated system for the production and harvesting of microalgae wherein the controller comprising a reset pressure input in the pressure controller cavity; a reset opening in the pressure controller device; and a pressure supply output in the pressure controller cavity. The integrated system for the production and harvesting of microalgae wherein the controller may comprise a pressure regulate input in the pressure controller cavity; a pressure control opening with a tapered V-shape on one end in the pressure controller device; and a pressure supply output in the pressure controller cavity. The integrated system for the production and harvesting of microalgae wherein the controller may comprise a pressure lsb low input in the pressure controller cavity; a pressure lsb high input in the pressure controller cavity; a pressure lsb low opening in the pressure controller device; a pressure lsb high opening in the pressure controller device; and a pressure lsb output in the pressure controller cavity. The integrated system for the production and harvesting of microalgae wherein the controller may comprise a pressure msb low input in the pressure controller cavity; a pressure msb high input in the pressure controller cavity; a pressure msb low opening in the pressure controller device; a pressure msb high opening in the pressure controller device; and a pressure msb output in the pressure controller cavity.

The integrated system for the production and harvesting of microalgae may comprise a $CO_2$ pressure controller, the $CO_2$ pressure controller may comprise a $CO_2$ pressure controller cavity comprising at least one $CO_2$ pressure input; a $CO_2$ pressure reset input; a $CO_2$ pressure regulate input; a $CO_2$ pressure supply output configured to supply $CO_2$ to the inner pipe of the pipe element; at least one digitized signal bit may comprise a $CO_2$ pressure lsb low input; a $CO_2$ pressure lsb high input; a $CO_2$ pressure lsb output; a $CO_2$ pressure controller device may comprise a $CO_2$ pressure reset opening configured to align with the $CO_2$ pressure reset input and the $CO_2$ pressure supply output; a $CO_2$ pressure control opening configured to align with the $CO_2$ pressure regulate input and the $CO_2$ pressure supply output; a $CO_2$ pressure lsb low opening configured to align with the $CO_2$ pressure lsb low input and the $CO_2$ pressure lsb output; a $CO_2$ pressure lsb high opening configured to align with the $CO_2$ pressure lsb high input and the $CO_2$ pressure lsb output; a $CO_2$ pressure controller rubber grid configured to envelop the $CO_2$ pressure controller device and create physical barriers to avoid leaks to the $CO_2$ pressure controller cavity; a controller spring configured to compress as pressure within the $CO_2$ pressure controller cavity increases moving the $CO_2$ pressure controller device in a first direction and to a position within the $CO_2$ pressure controller cavity determined by the amount of increase in pressure; and the controller spring configured to stretch as pressure within the $CO_2$ pressure controller cavity decreases moving the $CO_2$ pressure controller device in a second direction and to a position within the $CO_2$ pressure controller cavity determined by the amount of decrease in pressure. The integrated system for the production and harvesting of microalgae wherein the position of the $CO_2$ pressure controller device generates a one bit digitized output based on the alignment of the $CO_2$ pressure lsb low opening with the $CO_2$ pressure lsb low input, and the $CO_2$ pressure lsb high opening with the $CO_2$ pressure lsb high input; determines the state of the $CO_2$ pressure according to the state of the one bit digitized output, if the output bit is low indicating a leak or a reset state, or if the output bit is high indicating $CO_2$ pressure within operating range; and controls the $CO_2$ pressure in the $CO_2$ pressure supply output based on the state of alignment of the $CO_2$ pressure reset opening with the $CO_2$ pressure reset input and the $CO_2$ pressure control opening with the $CO_2$ pressure regulate input.

The integrated system for the production and harvesting of microalgae may comprise a water pressure controller, the water pressure controller may comprise a water pressure controller cavity comprising: at least one water pressure input; a water pressure reset input; a water pressure regulate input; a water pressure supply output configured to supply water to the outer pipe of the pipe element; at least two digitized signal bits may comprise a water pressure lsb low input; a water pressure lsb high input; a water pressure lsb output; a water pressure msb low input; a water pressure msb high input; a water pressure msb output; a water pressure controller device may comprise a water pressure reset opening configured to align with the water pressure reset input and the water pressure supply output; a water pressure control opening configured to align with the water pressure regulate input and the water pressure supply output; a water pressure lsb low opening 1 and a water pressure lsb low opening 2 configured to align with the water pressure lsb low input and the water pressure lsb output; a water pressure lsb high opening configured to align with the water pressure lsb high input and the water pressure lsb output; a water pressure msb low opening configured to align with the water pressure msb low input and the water pressure msb output; a water pressure msb high opening configured to align with the water pressure msb high input and the water pressure msb output; a water pressure controller rubber grid configured to envelop the water pressure controller device and create physical barriers to avoid leaks to the water pressure controller cavity; a controller spring configured to compress as pressure within the water pressure controller cavity increases moving the water pressure controller device in a first direction and to a position within the water pressure controller cavity determined by the amount of increase in pressure; and the controller spring configured to stretch as pressure within the water pressure controller cavity decreases moving the water pressure controller device in a second direction and to a position within the water pressure controller cavity determined by the amount of decrease in pressure. The integrated system for the production and harvesting of microalgae wherein the position of the water pressure controller device generates a two bit digitized output based on the alignment of the water pressure lsb low opening 1 and the water pressure lsb low opening 2 with the water pressure lsb low input, the water pressure lsb high opening with the water pressure lsb high input, of the water pressure msb low opening with the water pressure msb low input, the water pressure msb high opening with the water pressure msb high input; determines the state of the water pressure according to the state of the two bit digitized output, if the two bit digitized output is 00 indicating a leak state or a reset state, if the two bit digitized output is 01 indicating a stand by state, if the two bit digitized output is 11 indicating a normal operation state, and if the two bit digitized output is 10 indicating a closed state; and controls the water pressure in the water pressure supply output based on the state of alignment of the water pressure reset opening with the water pressure reset input, the water pressure control opening with the water pressure regulate input.

The integrated system for the production and harvesting of microalgae may comprise a ground pressure controller, the ground pressure controller comprising a ground pressure controller cavity may comprise at least one ground pressure input; a ground pressure regulate input; a ground pressure supply output configured to supply water to the water culture cavity inside the reactor node; at least one digitized signal bit may comprise a ground pressure lsb low input; a ground pressure lsb high input; a ground pressure lsb output; a ground pressure controller device may comprise a ground pressure control opening configured to align with the ground pressure regulate input and the ground pressure supply output; a ground pressure lsb low opening configured to align with the ground pressure lsb low input and the ground pressure lsb output; a ground pressure lsb high opening configured to align with the ground pressure lsb high input and the ground pressure lsb output; a ground pressure controller rubber grid configured to envelop the ground pressure controller device and create physical barriers to avoid leaks to the ground pressure controller cavity; a controller spring configured to compress as pressure within the ground pressure controller cavity increases moving the ground pressure controller device in a first direction and to a position within the ground pressure controller cavity determined by the amount of increase in pressure; and the controller spring configured to stretch as pressure within the ground pressure controller cavity decreases moving the ground pressure controller device in a second direction and to a position within the ground pressure controller cavity determined by the amount of decrease in pressure. The integrated system for the production and harvesting of microalgae wherein the position of the ground pressure controller device generates a one bit digitized output based on the alignment of the ground pressure lsb low opening with the ground pressure lsb low input, and the ground pressure lsb high opening with the ground pressure lsb high input; determines the state of the ground pressure according to the state of the one bit digitized output, if the output bit is low indicating ground pressure too high, outside operational range, or if the output bit is high indicating ground pressure within operating range; and controls the water pressure in the ground pressure supply output based on the state of alignment of the ground pressure control opening with the ground pressure regulate input.

The integrated system for the production and harvesting of microalgae may comprise a signal pressure controller, the signal pressure controller may comprise a signal pressure controller cavity comprising at least one signal pressure input; at least two digitized signal bits comprising a signal pressure lsb low input; a signal pressure lsb high input; a signal pressure lsb output; a signal pressure msb low input; a signal pressure msb high input; a signal pressure msb output; a signal pressure controller device may comprise a signal pressure lsb low opening configured to align with the signal pressure lsb low input and the signal pressure lsb output; a signal pressure lsb high opening configured to align with the signal pressure lsb high input and the signal pressure lsb output; a signal pressure msb low opening configured to align with the signal pressure msb low input and the signal pressure msb output; a signal pressure msb high opening configured to align with the signal pressure msb high input and the signal pressure msb output; a signal pressure controller rubber grid configured to envelop the signal pressure controller device and create physical barriers to avoid leaks to the signal pressure controller cavity; a controller spring configured to compress as pressure within the signal pressure controller cavity increases moving the signal pressure controller device in a first direction and to a position within the signal pressure controller cavity determined by the amount of increase in pressure; and the controller spring configured to stretch as pressure within the signal pressure controller cavity decreases moving the signal pressure controller device in a second direction and to a position within the signal pressure controller cavity determined by the amount of decrease in pressure. The integrated system for the production and harvesting of microalgae wherein the position of the signal pressure controller device generates a two bit digitized output based on the alignment of the signal pressure lsb low opening with the signal pressure lsb low input, the signal pressure lsb high opening with the signal pressure lsb high input, the signal pressure msb low opening with the signal pressure msb low input, the signal pressure msb high opening with the signal pressure msb high input; and determines the state of the signal pressure according to the state of the two bit digitized output, if the two bit digitized output is 00 indicating a leak state, if the two bit digitized output is 01 indicating low state, if the two bit digitized output is 11 indicating a high state.

The integrated system for the production and harvesting of microalgae wherein the reactor node may comprise a flag configured to be raised to identify an alarm in the reactor node. The integrated system for the production and harvesting of microalgae may comprise an anchor assembly configured to anchor each reactor node and allow it to be sunk to a predefined depth.

The present invention is further related to a method for the production and harvesting of microalgae comprising pumping water through a reactor having a plurality of reactor nodes, each reactor node having a plurality of pipe elements; supplying the reactor with $CO_2$; growing algae in the water culture within the pipe elements; pumping the water culture from the pipe elements to a flow divider; splitting the water culture between an algae separator and a culture diluter; replenishing the pipe elements with water culture from the culture diluter; collecting algae from the algae separator.

The method for the production and harvesting of microalgae may further comprise extracting $CO_2$ comprising powering at least one pump using an engine; pumping water to a water degasifier; heating water within the water degasifier; supplying a vaporizer with exhaust gases from the engine and with boil-off gases from the water degasifier; sublimating solid $CO_2$ in the vaporizer; precipitating solid $CO_2$ in the $CO_2$ separator further cooling pre-cooled boil-off gases coming from the vaporizer; and supplying solid $CO_2$ to replenish the solid $CO_2$ supply in the vaporizer.

The method for the production and harvesting of microalgae may further comprise condensing water from the engine exhaust gases and from the boil-off gases from the water degasifier before they are fed into the vaporizer; extracting oxygen from the water culture supplied by the reactor; aerating condensed water and water to be discharged with the extracted oxygen; and discharging aerated water.

The method for the production and harvesting of microalgae may further comprise extracting heat from the engine to heat water supplied to the water degasifier; extracting heat from the engine exhaust to heat water from the water degasifier; and recirculating the heated water to the water degasifier. The method for the production and harvesting of microalgae may further comprise extracting heat from the engine exhaust gases and the boil off gases from the water degasifier to condensate the engine exhaust gases in a heat exchanger and remove contaminants in a condensed water cleaner; using the extracted heat to pre heat incoming water to feed the water degasifier.

The method for the production and harvesting of microalgae may further comprise extracting heat from water submitted to the extraction of oxygen to heat water supplied to the water degasifier. The method for the production and harvesting of microalgae may further comprise extracting heat from water to be discharged to heat water culture from the reactor to extract oxygen. The method for the production and harvesting of microalgae may further comprise forcing water through a concentrator within the algae separator using a helical pusher.

The method for the production and harvesting of microalgae may further comprise determining the status of the plurality of reactor nodes; detecting an alarm within at least one of the plurality of reactor nodes; stopping the pumping of water to at least one pipe element within the reactor node associated with the alarm; and starting the flow of water to another pipe element thereby circumventing a fault without stopping the operation of the reactor.

The present invention is further related to an integrated system for the production and harvesting of microalgae, comprising a reactor having a plurality of reactor nodes and a plurality of pipe elements, the plurality of reactor nodes and the plurality of pipe elements configured to create an isolated water culture suitable for algae growth; each of the plurality of reactor nodes having a module assembly having electronic components, analog to digital converters and solenoid valves, the module assembly configured to receive electronic input signals from other module assemblies in other reactor nodes; convert pressure signals coming from the reactor node where the module assembly is installed into electronic status signals using the analog to digital converters; process the electronic input signals and electronic status signals and generate electronic control signals to control the reactor node where the module assembly is installed and electronic output signals to be transmitted to other module assemblies in other reactor nodes; feed the electronic control signals into the solenoid valves and generate output pressure signals to control the reactor node; and an algae separation unit.

BRIEF DESCRIPTION OF THE DRAWINGS

Capital letters A through D in bold are used in some figures to identify sections of a component or assembly and when applicable are attached to component numbers in normal font to differentiate components pertaining to the correspondingly identified sections. Multiple copies of a component used in an assembly not associated with a section are differentiated by lowercase letters.

Detail Figures locations in a parent figure are indicated by capital letters in normal font associated with a circle.

Drawing 1 contains FIG. 1 and Detail FIG. 1A.

Figure 1:
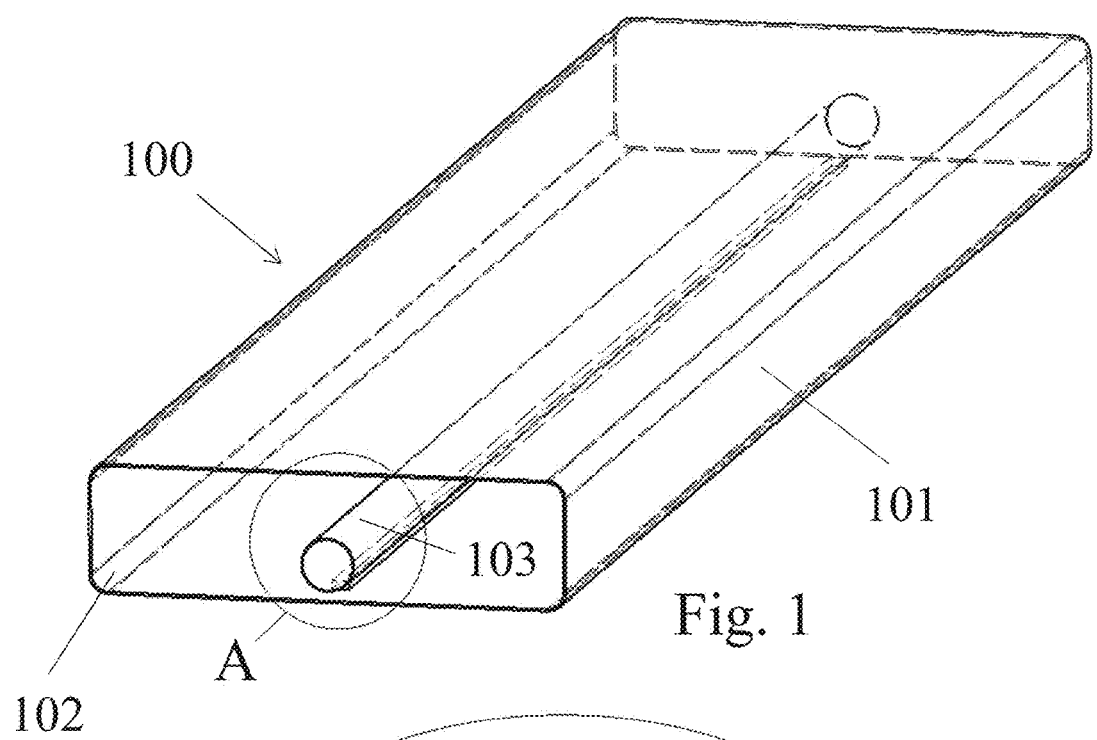
FIG. 1 shows an isometric view of the pipe element 100. Detail

Drawing 2 contains FIG. 2, Detail FIG. 2A, Detail FIG. 2B, and Detail FIG. 2C.

FIG. 2 shows a partially exploded isometric view of two pipe elements 100 attached to the straight joint 113. Detail FIG. 2A shows the inner band 108 securing the inner pipe 103. Detail FIG. 2B shows the pipe band 111 securing the outer pipe 101. Detail FIG. 2C shows features of the straight joint in greater magnification.

Drawing 3 contains FIG. 3, Detail FIG. 3A, FIG. 4, and Detail FIG. 4A. FIG. 3 shows an isometric view of the 90 degrees joint 127. Detail FIG. 3A shows features of the 90 degrees joint in greater magnification. FIG. 4 shows an isometric view of the 180 degrees joint 132. Detail FIG. 4A shows features of the 180 degrees joint in greater magnification.

Drawing 4 contains FIG. 5 and Detail FIG. 5D. FIG. 5 shows an isometric view of the reactor node 214 from a top front angle. Detail FIG. 5D shows features of the anchor assembly.

Figure 5A:
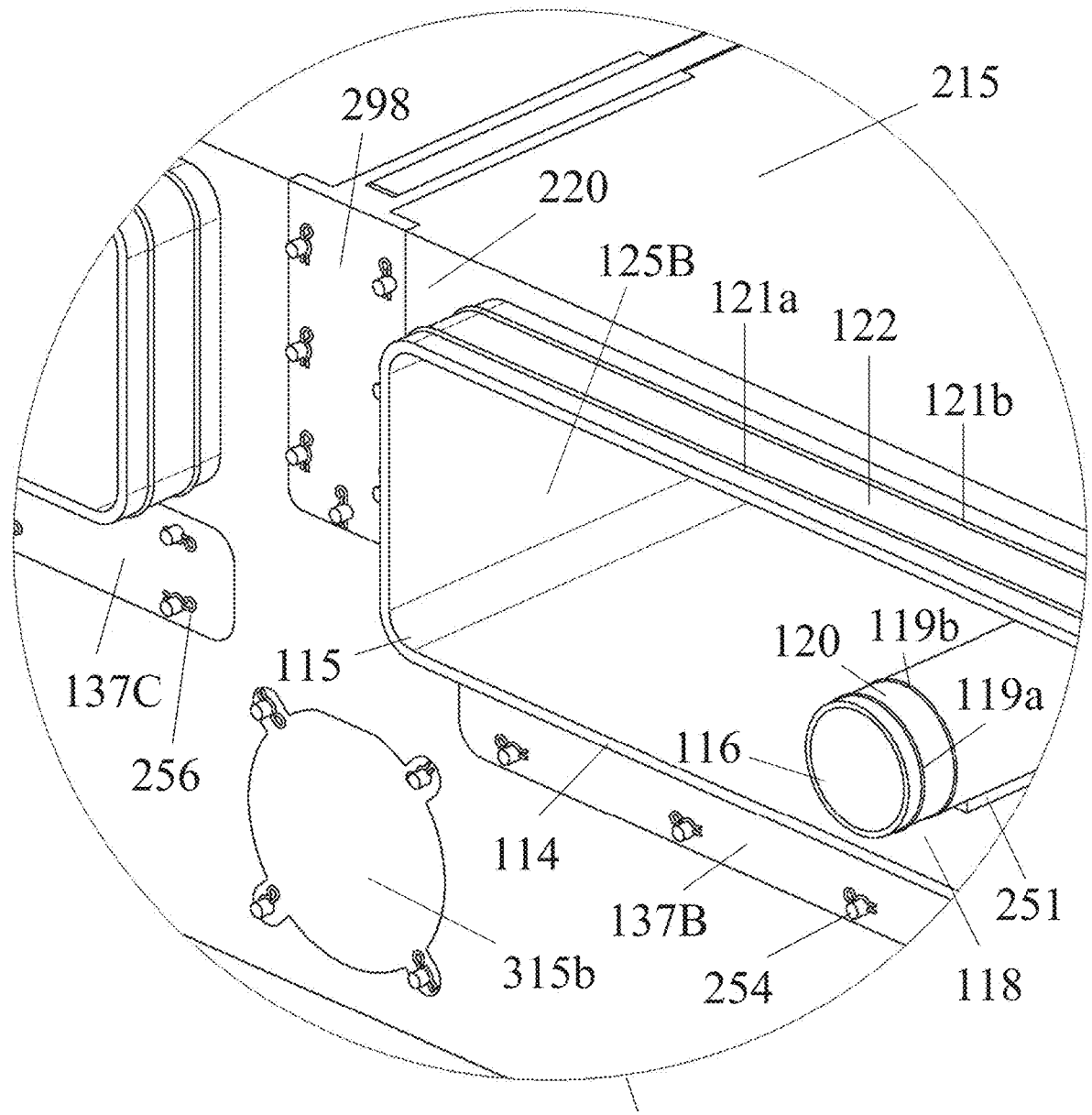

Drawing 5 contains Detail FIG. 5A. Detail FIG. 5A shows features of the front side of the reactor node in greater magnification.

Figure 5B:
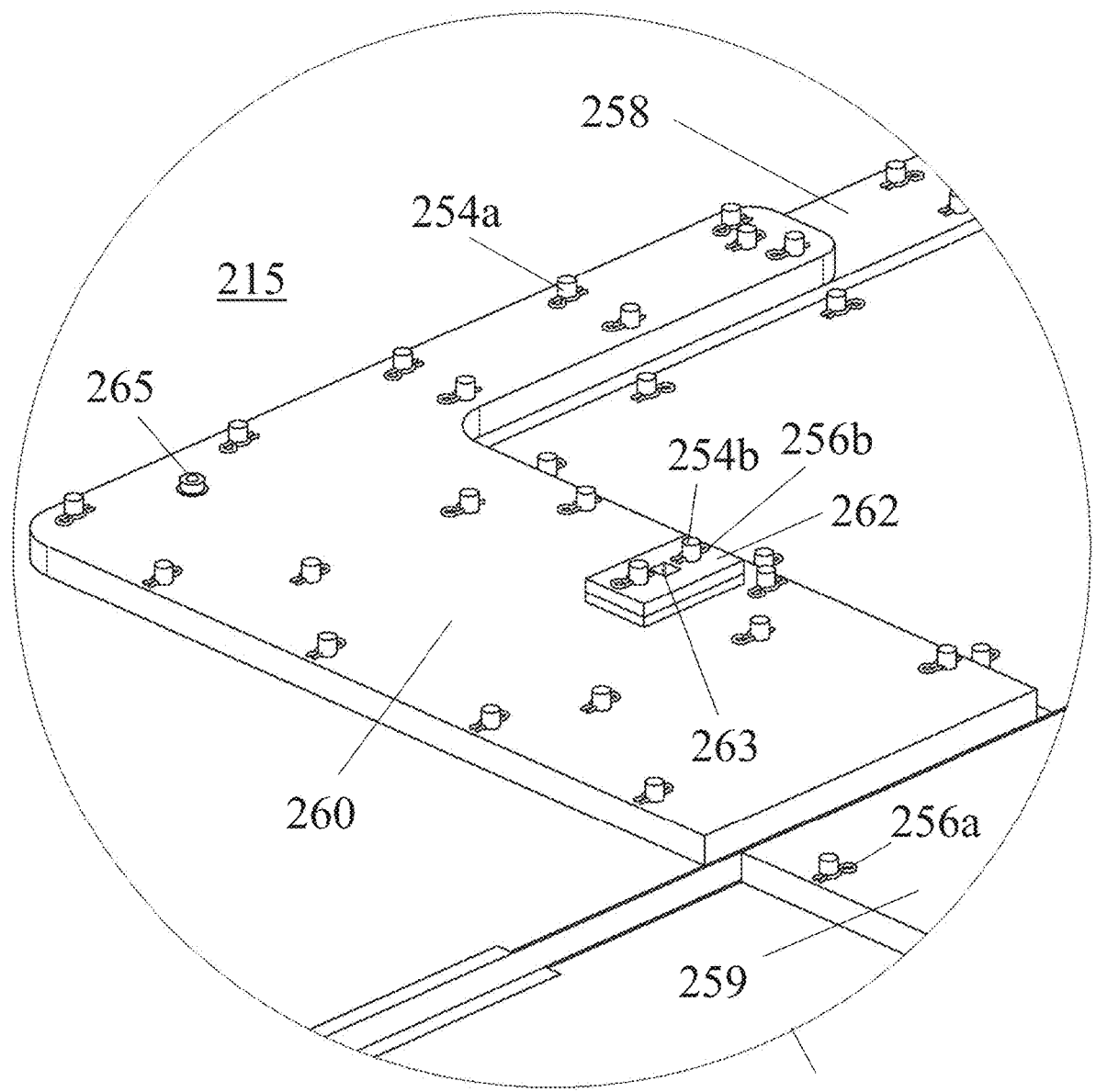

Drawing 6 contains Detail FIG. 5B. Detail FIG. 5B shows features of the air release assembly in the reactor node top side.

Figure 5C:
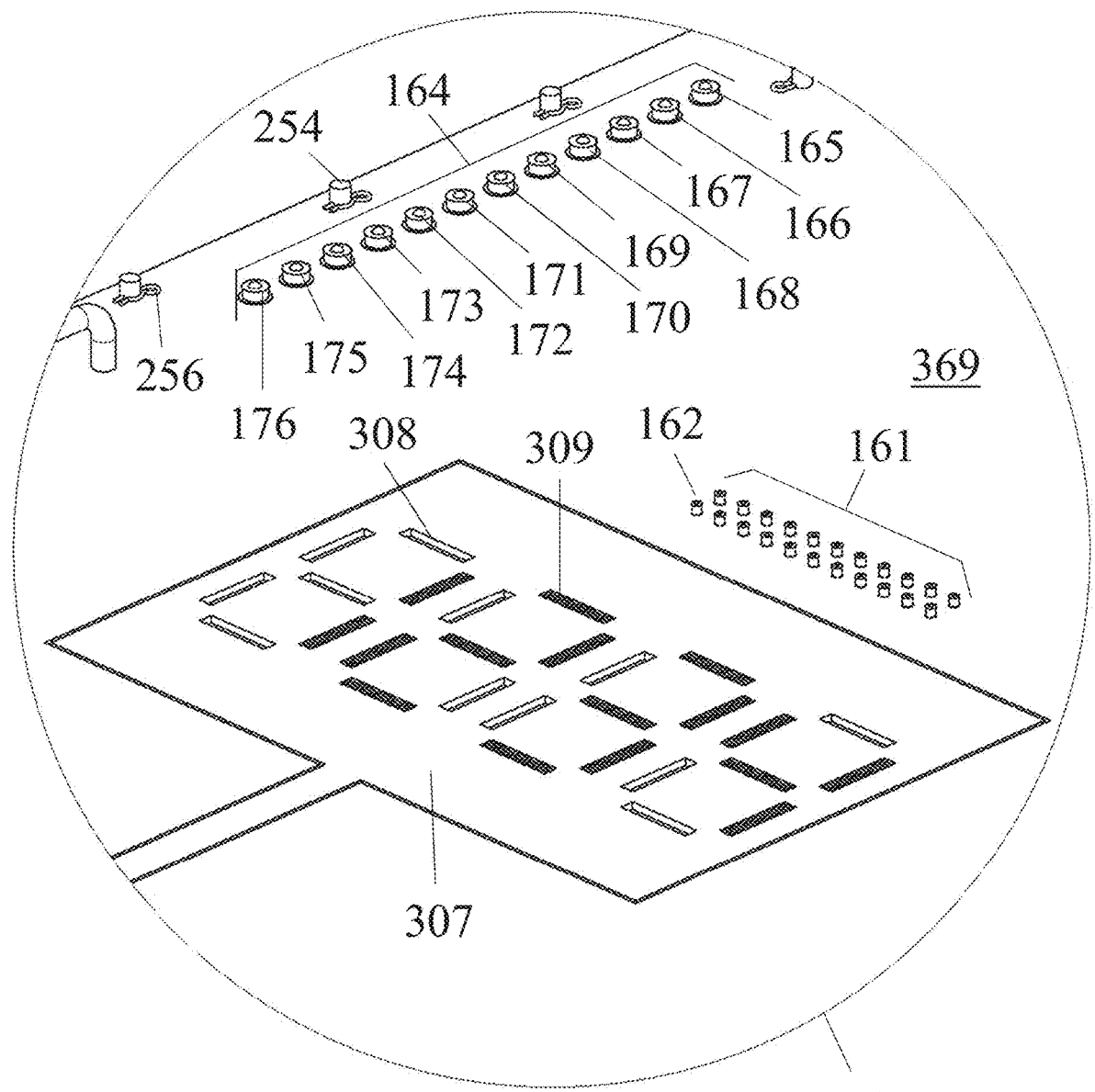

Drawing 7 contains Detail FIG. 5C. Detail FIG. 5C shows the flag 307, the signal port right 164, and the diagnose port 161 in the reactor node top side.

Figure 6:
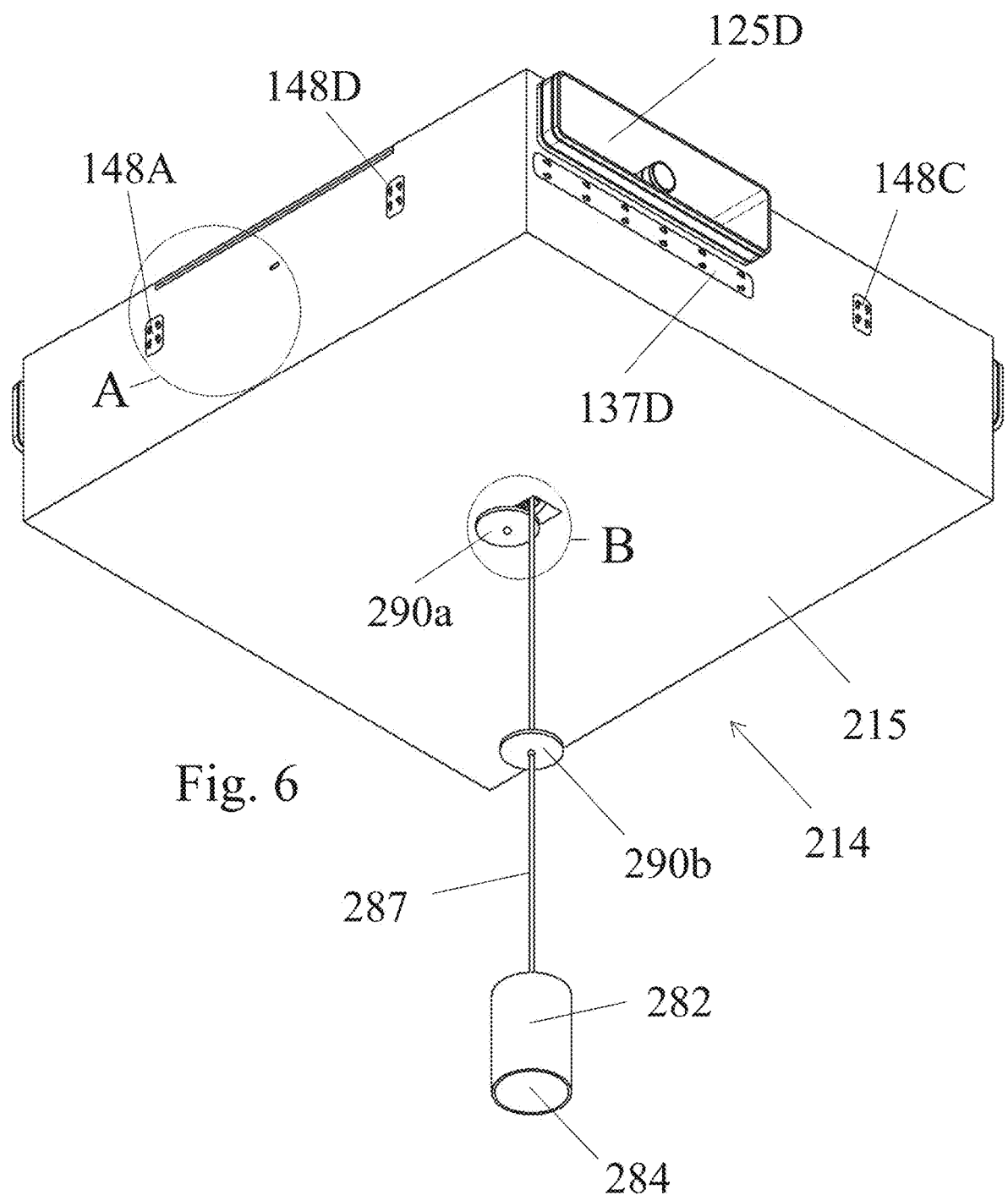

Drawing 8 contains FIG. 6. FIG. 6 shows an isometric view of the reactor node from the bottom back angle.

Figure 6A:
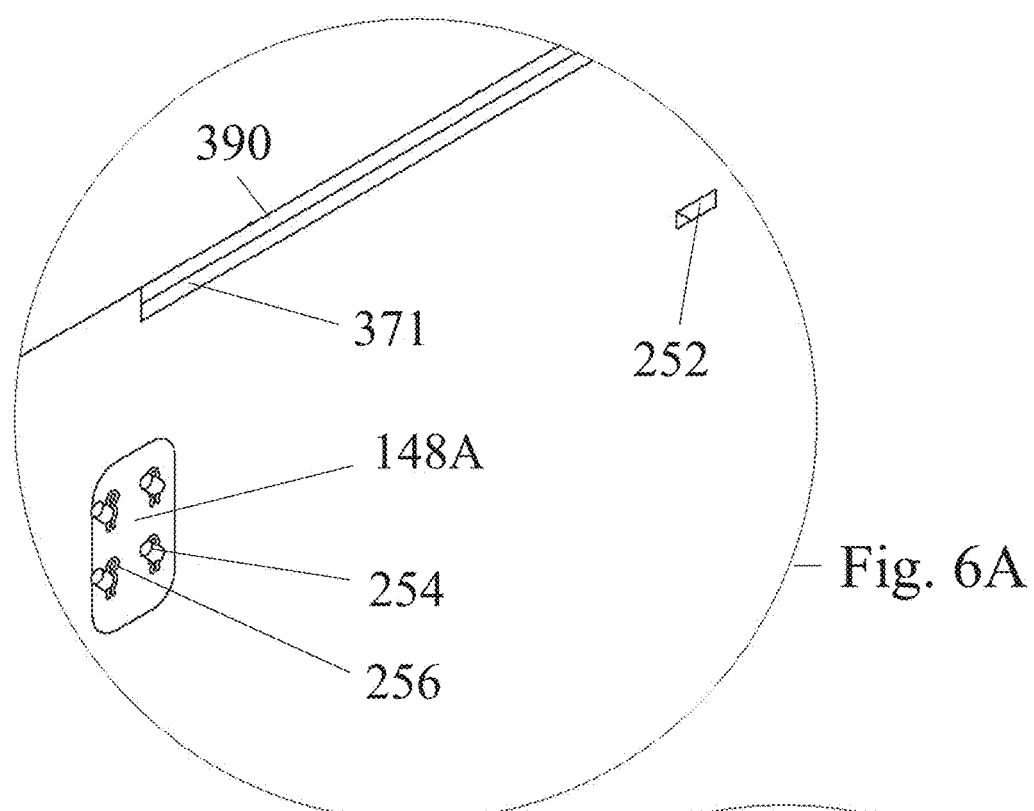
Figure 6B:
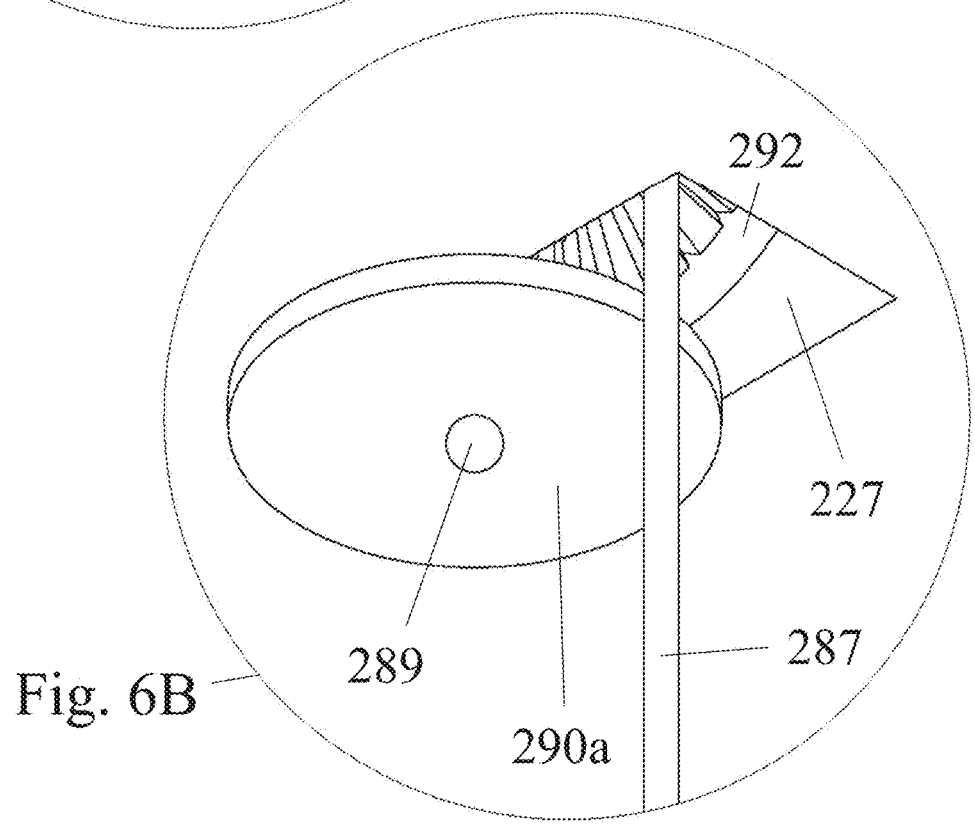

Drawing 9 contains Detail FIG. 6A and Detail FIG. 6B. Detail FIG. 6A shows features on the reactor node back side. Detail FIG. 6B shows features of the anchoring system on the reactor node bottom side.

Figure 7:
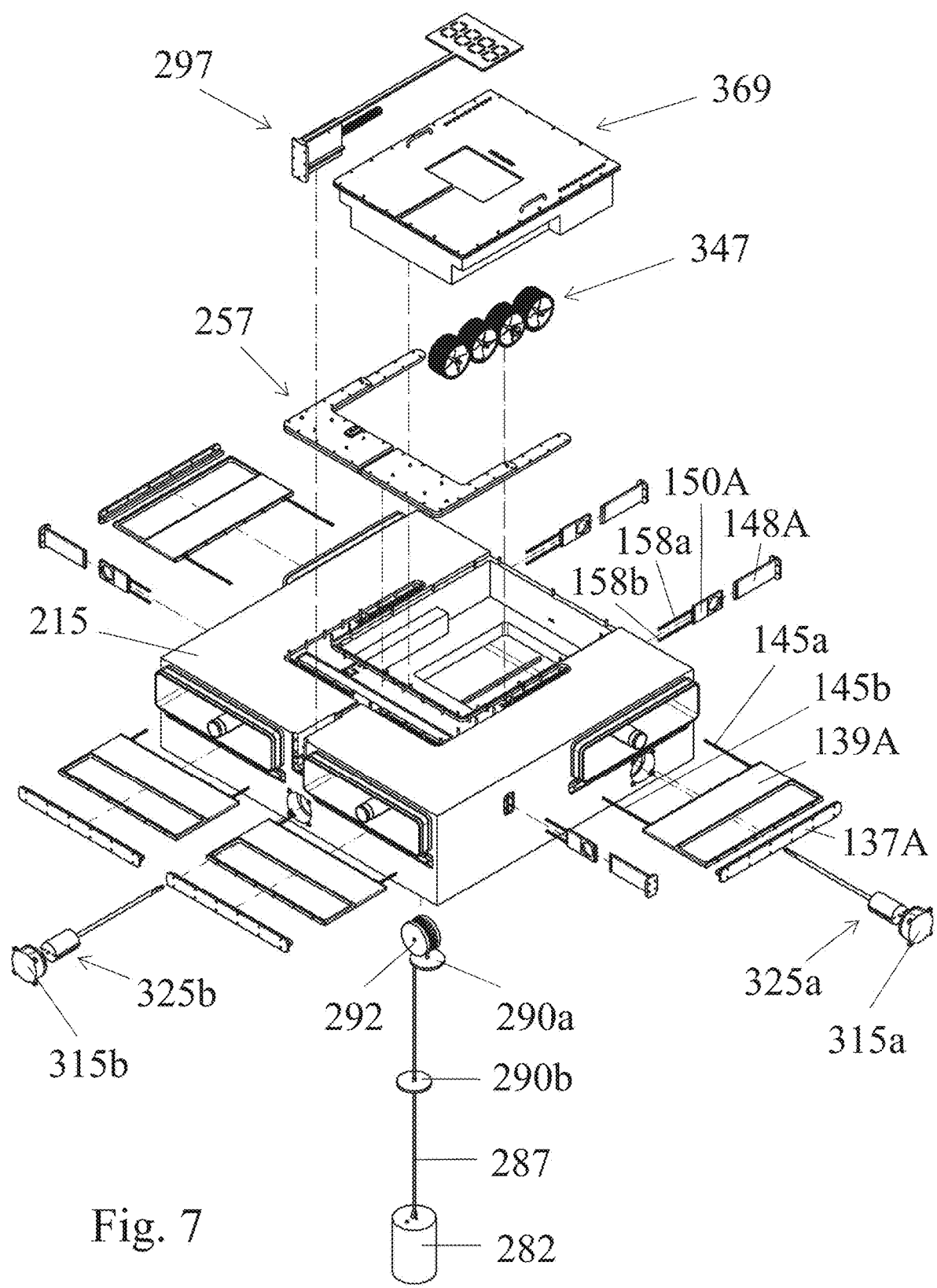

Drawing 10 contains FIG. 7. FIG. 7 is an exploded view of the node core from the top front angle featuring major components and sub assemblies.

Figure 8:
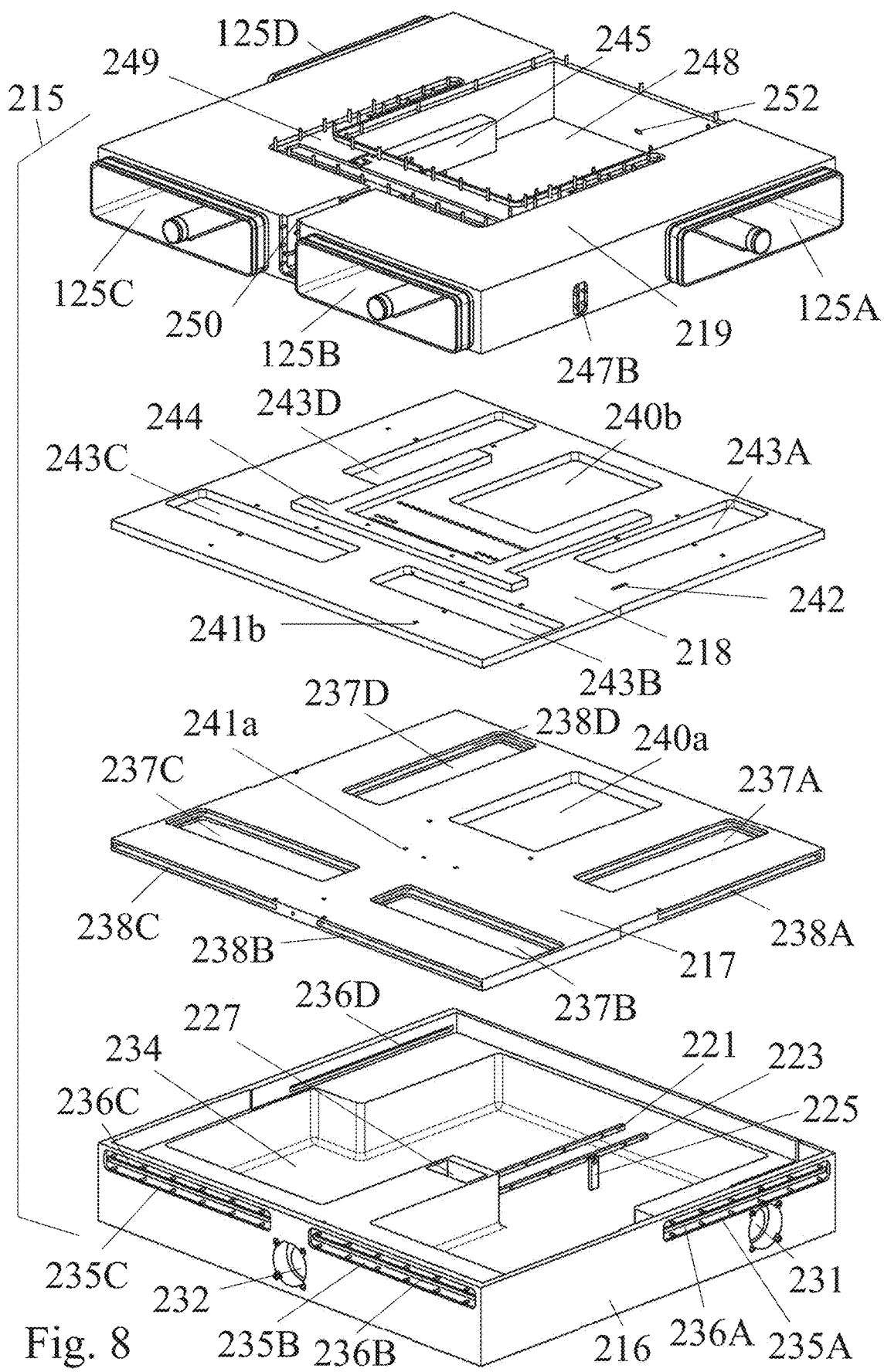

Drawing 11 contains FIG. 8. FIG. 8 is an exploded view of the node core from the top front angle.

Figure 9:
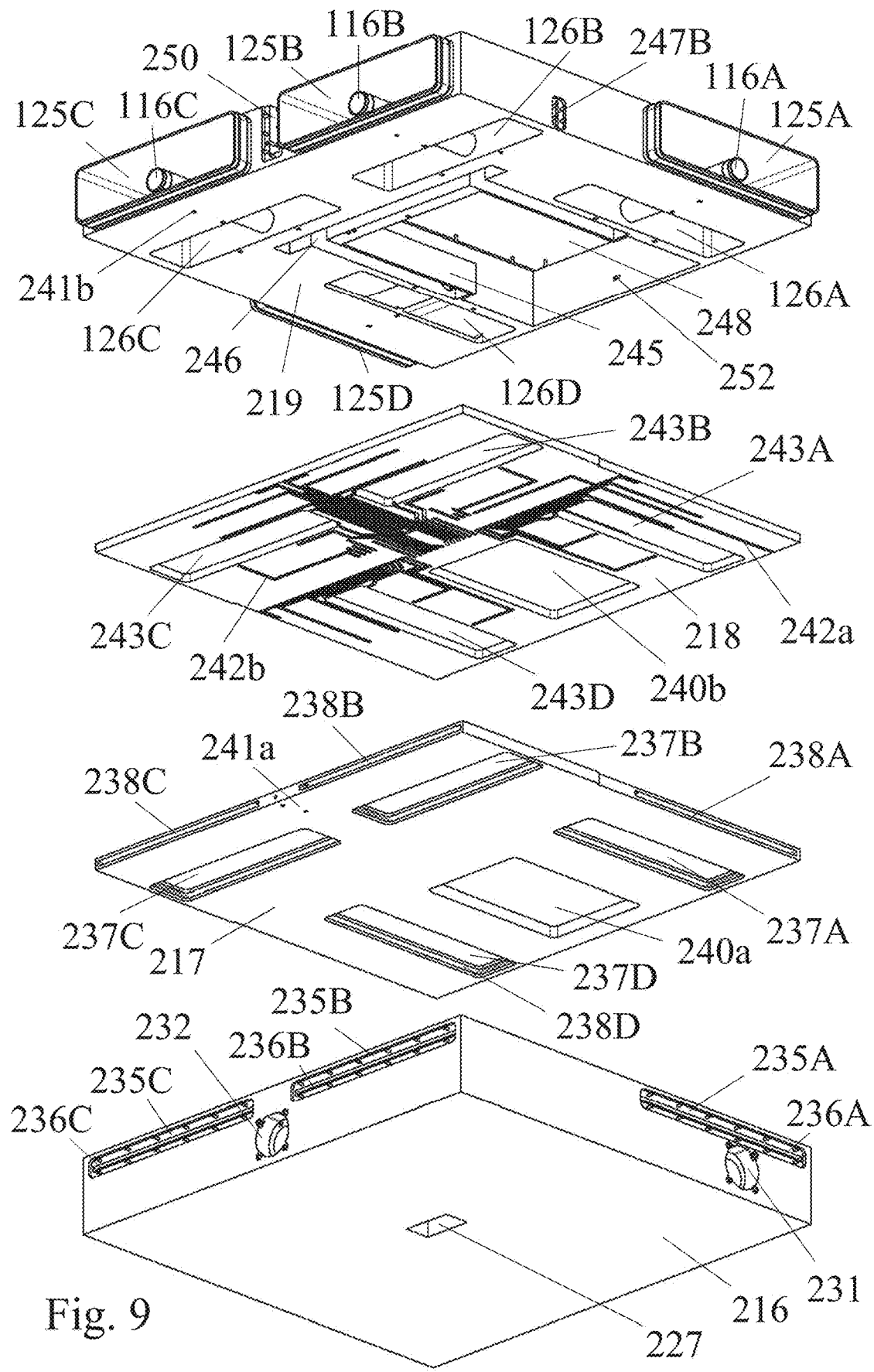

Drawing 12 contains FIG. 9. FIG. 9 is an exploded view of the node core from the bottom back angle.

Figure 10:
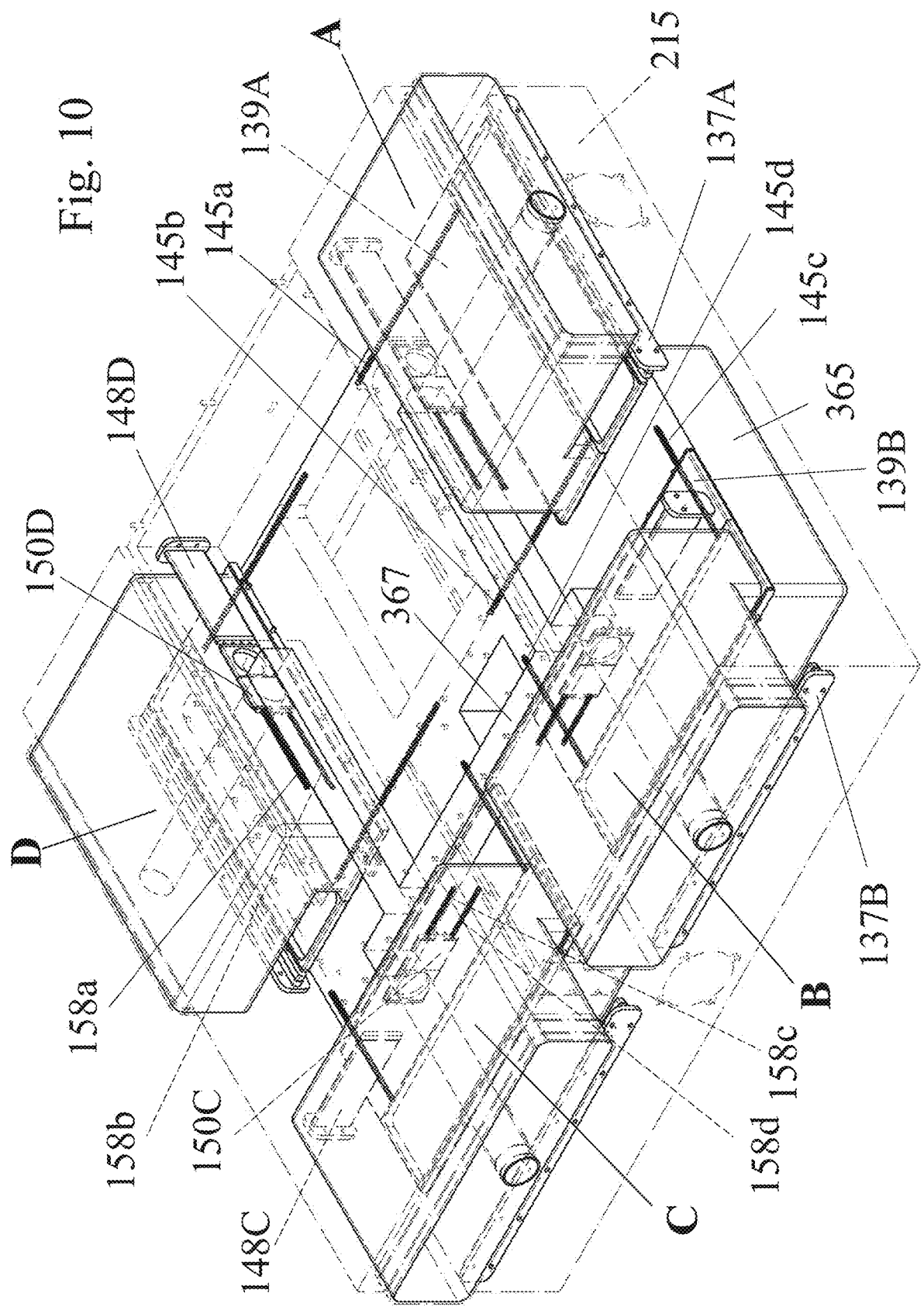

Drawing 13 contains FIG. 10. FIG. 10 is an isometric view of the reactor node showing the water body 365, the CO2 body 367, doors 139 and CO2 valves 150.

Figure 11:
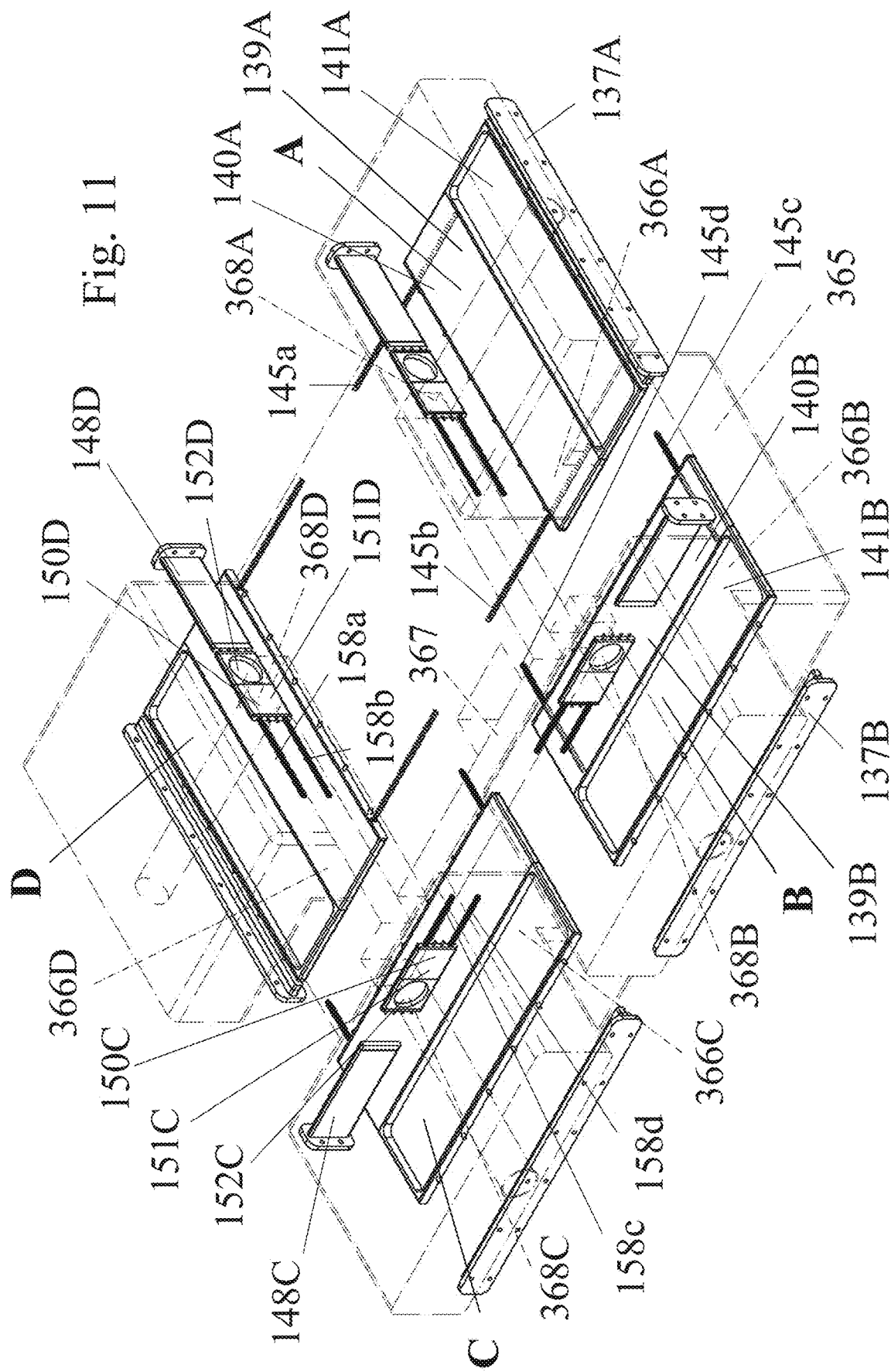

Drawing 14 contains FIG. 11. FIG. 11 is an isometric view of the water body 365 and the CO2 body 367 showing the doors 139 and CO2 valves 150.

Figure 12:
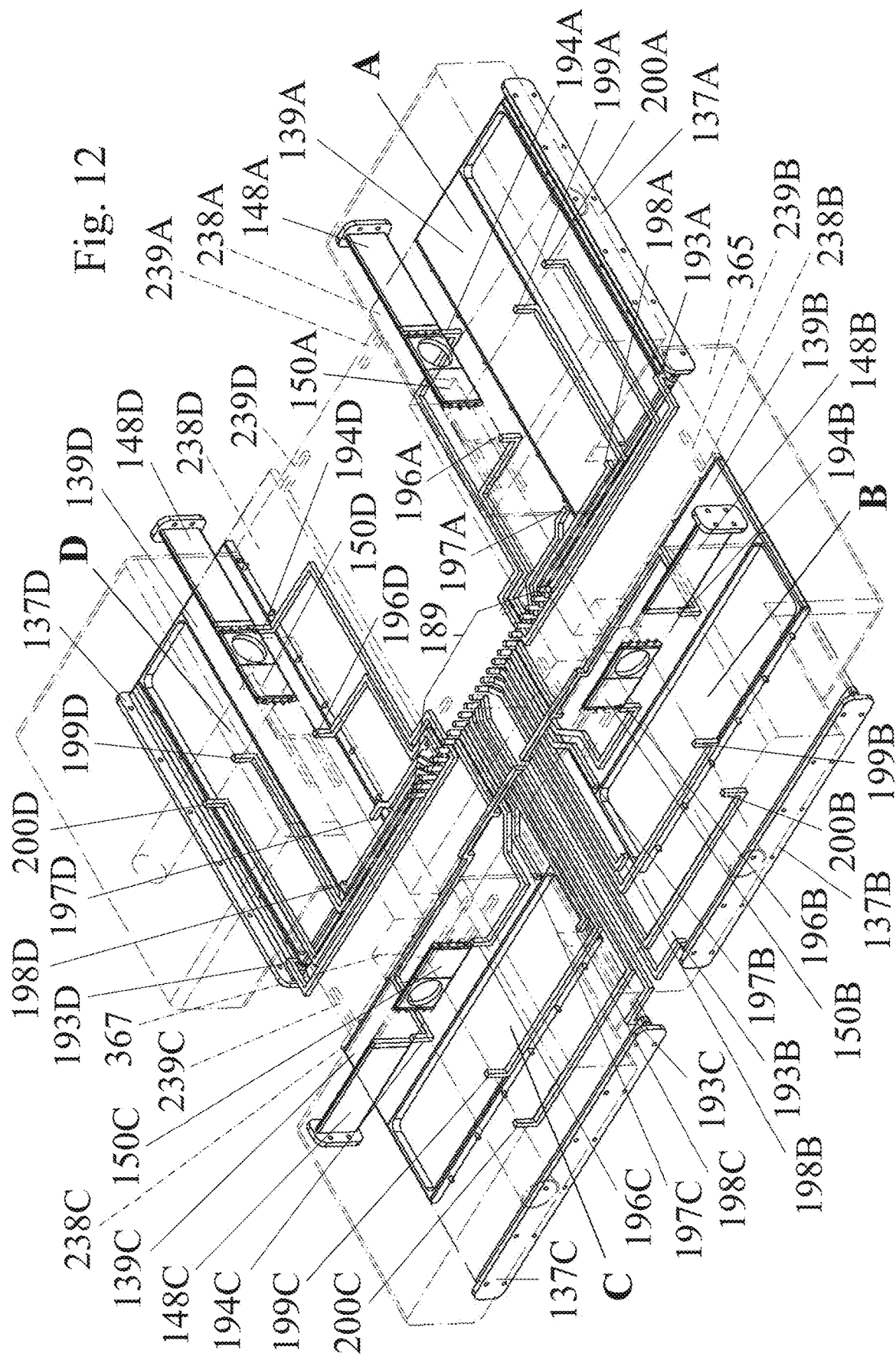

Drawing 15 contains FIG. 12. FIG. 12 is an isometric view of the water body 365 and the CO2 body 367 showing the control pipes.

Figure 13:
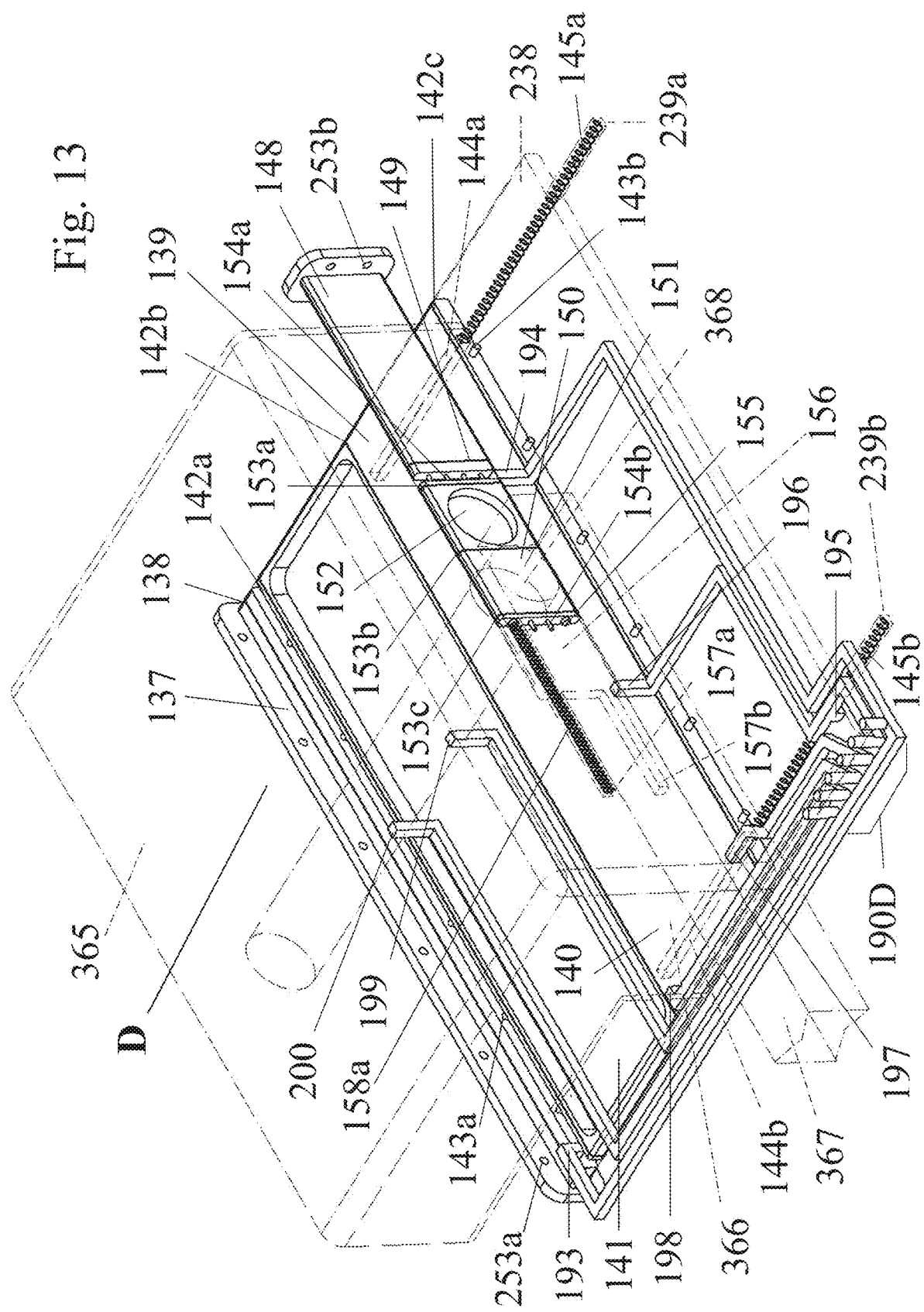

Drawing 16 contains FIG. 13. FIG. 13 is an isometric view of the D port showing the door 139, CO2 valve 150, and control pipes.

Figure 14:
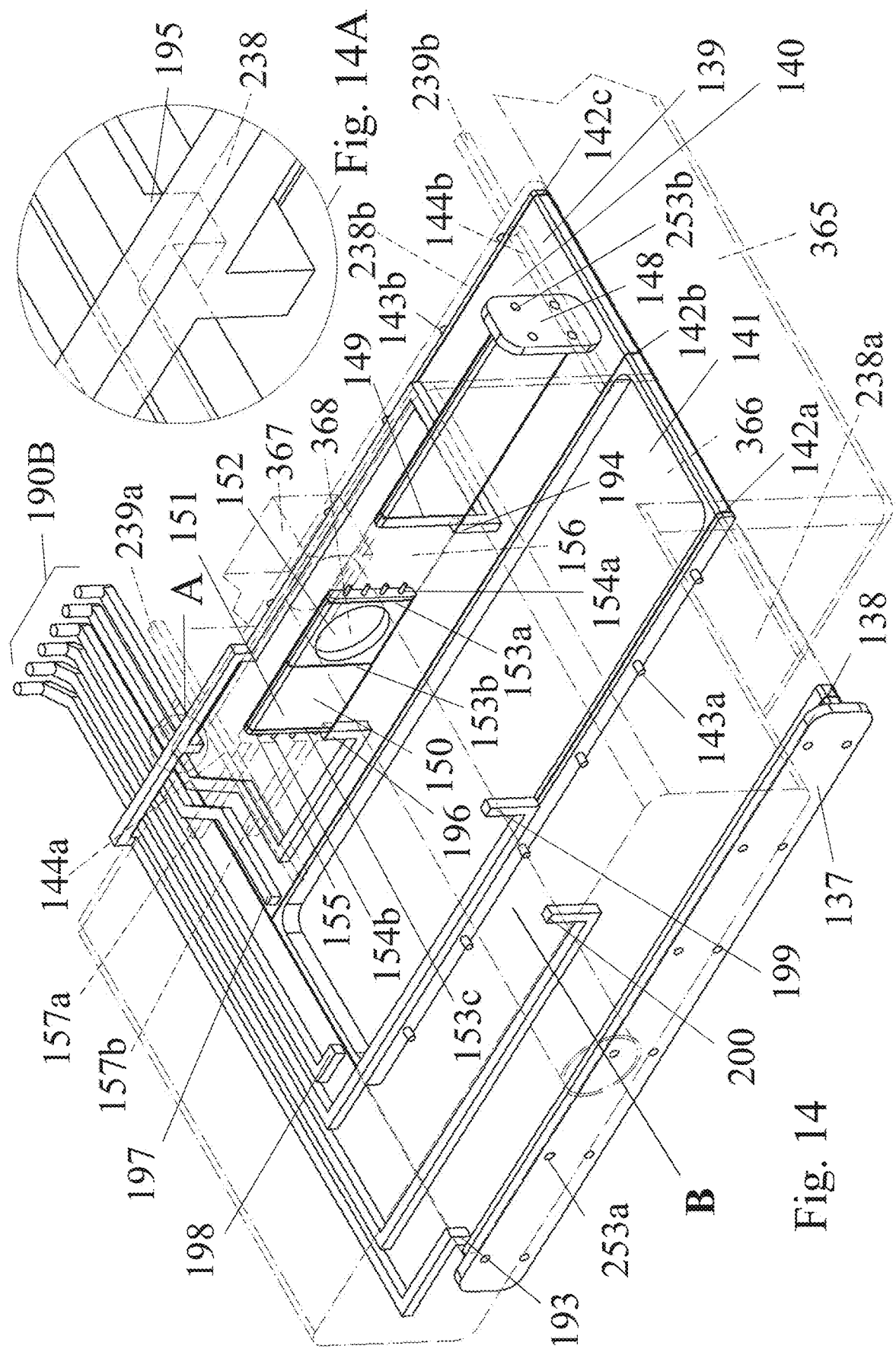

Drawing 17 contains FIG. 14 and Detail FIG. 14A. FIG. 14 is an isometric view of the B port showing the door 139, CO2 valve 150, and control pipes. Detail FIG. 14A shows a detail of the B port control pipes.

Figure 15:
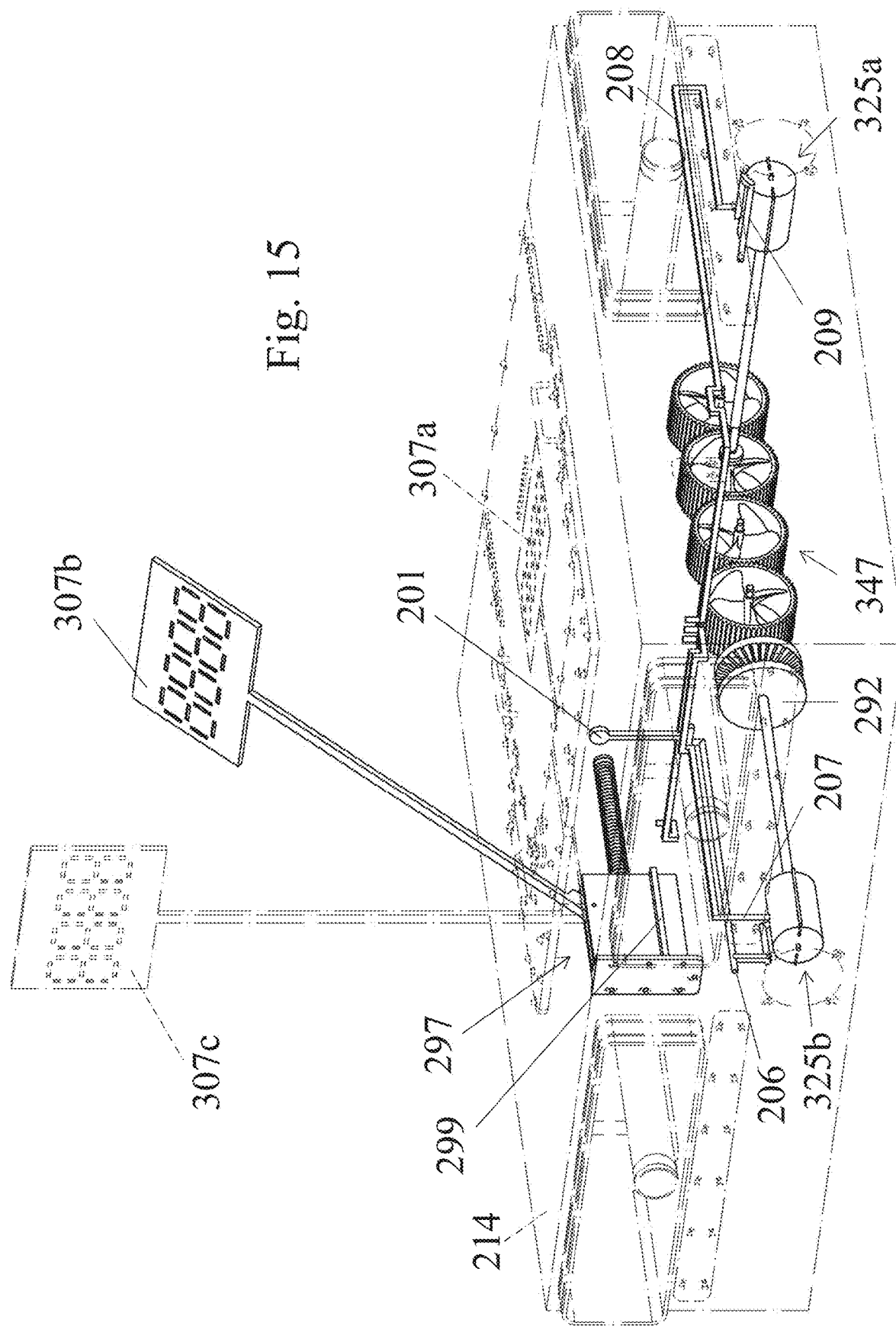

Drawing 18 contains FIG. 15. FIG. 15 is an isometric view of the reactor node showing the flag assembly 297, the cable winch 292 and the water pump.

Drawing 19 contains FIG. 16 and FIG. 17. FIG. 16 is an isometric cutout view of the flag assembly. FIG. 17 is an overlay cutout view of the flag assembly.

Drawing 20 contains FIG. 18, Detail FIG. 18D, Detail FIG. 18E, and Detail FIG. 18F. FIG. 18 is an exploded view of the reactor node showing the water pump components. Detail FIG. 18D shows features of the pump rotor shaft end. Detail FIG. 18E is an isometric view of the check valve 339. Detail FIG. 18F is an exploded view of the check valve.

Figure 18A:
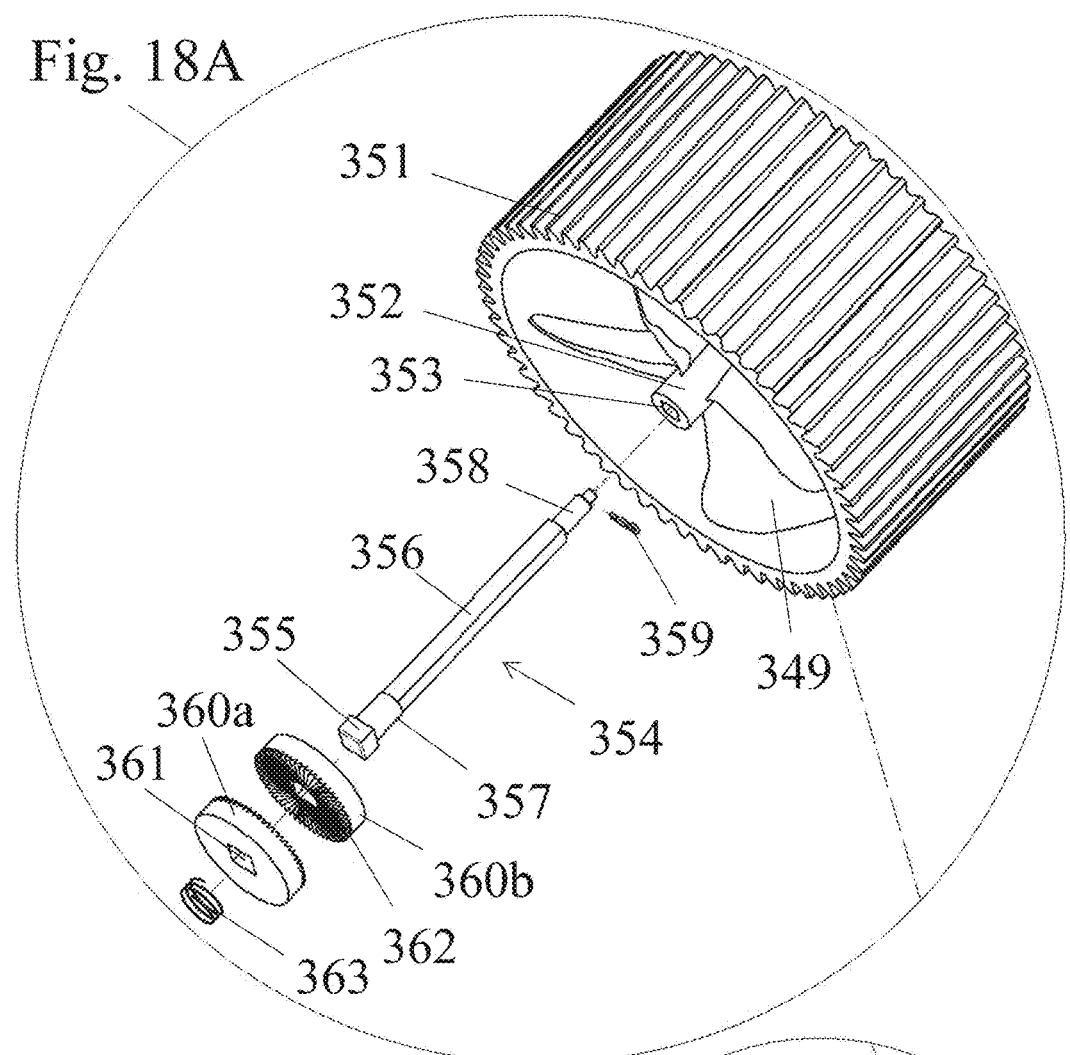
Figure 18C:
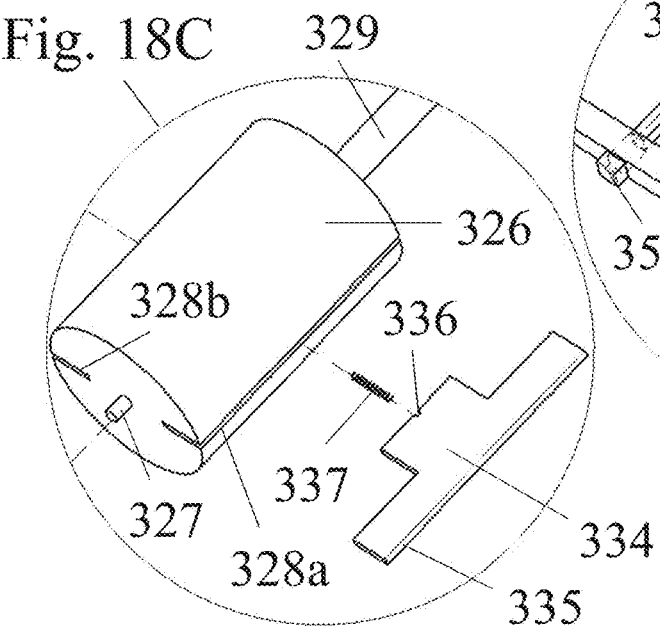
Figure 18B:
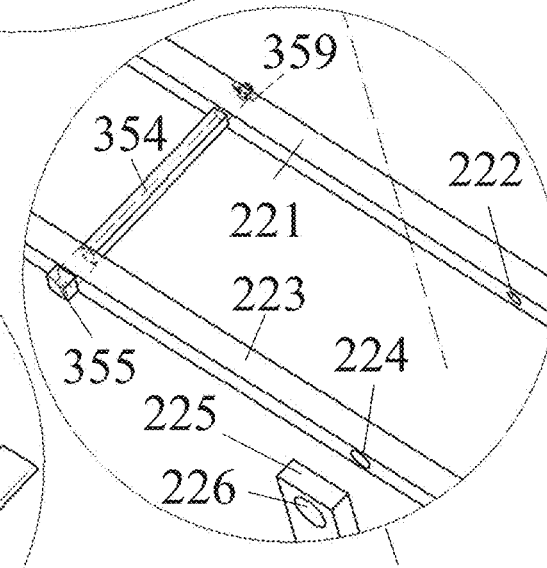

Drawing 21 contains Detail FIG. 18A, Detail FIG. 18B, and Detail FIG. 18C. Detail FIG. 18A is an exploded view of the propeller set. Detail FIG. 18B shows features of the propeller mounting supports. Detail FIG. 18C shows components of the pump rotor assembly.

Figure 19:
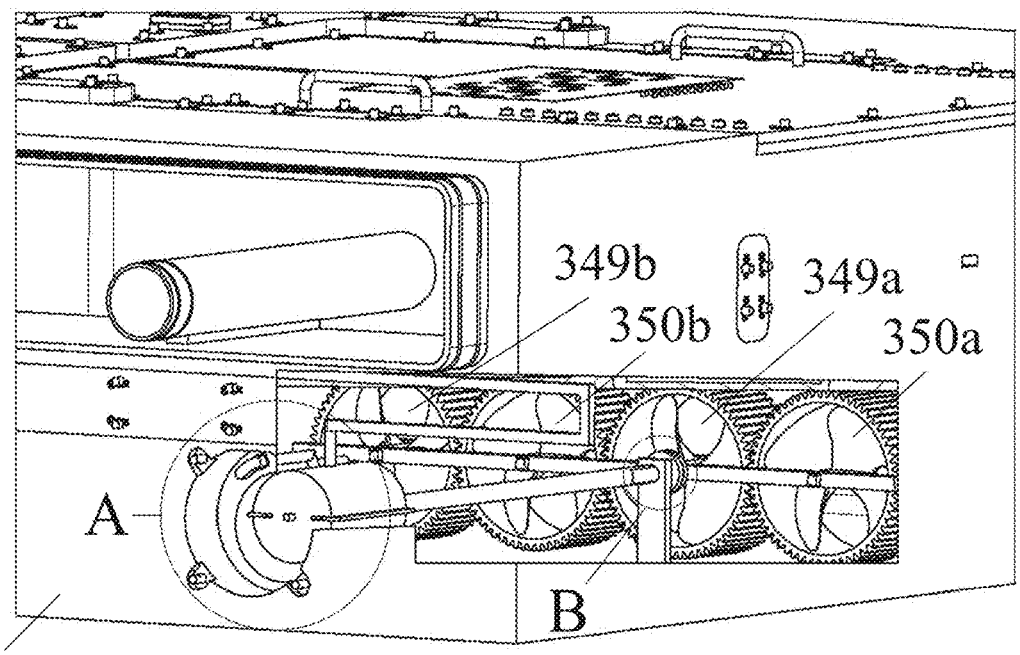
Figures 19A, 19B:
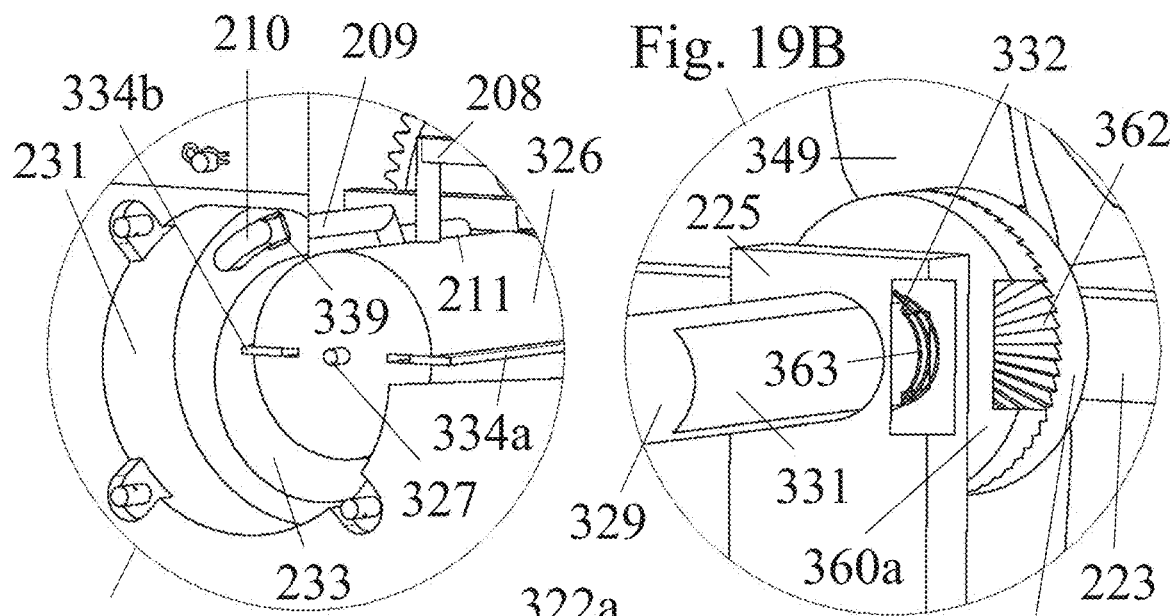
Figure 20:
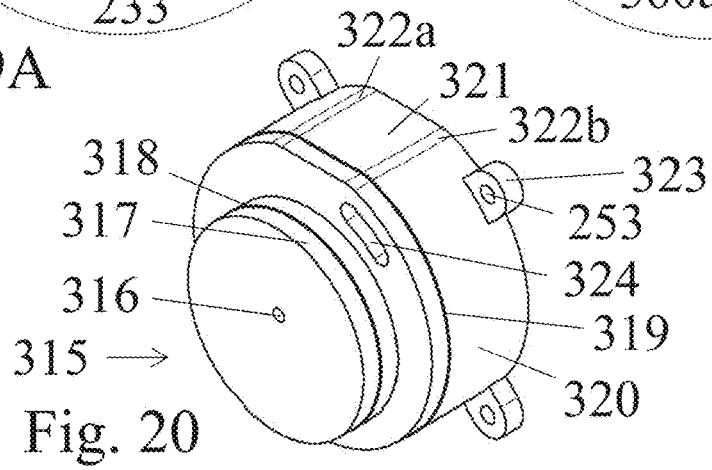

Drawing 22 contains FIG. 19, Detail FIG. 19A, Detail FIG. 19B, and FIG. 20. FIG. 19 is a partial cutout view of the reactor node showing the water pump components in place. Detail FIG. 19A shows the pump rotor 326. Detail FIG. 19B shows features of ratchet drive 360. FIG. 20 is an isometric view of the pump cover.

Figure 21:
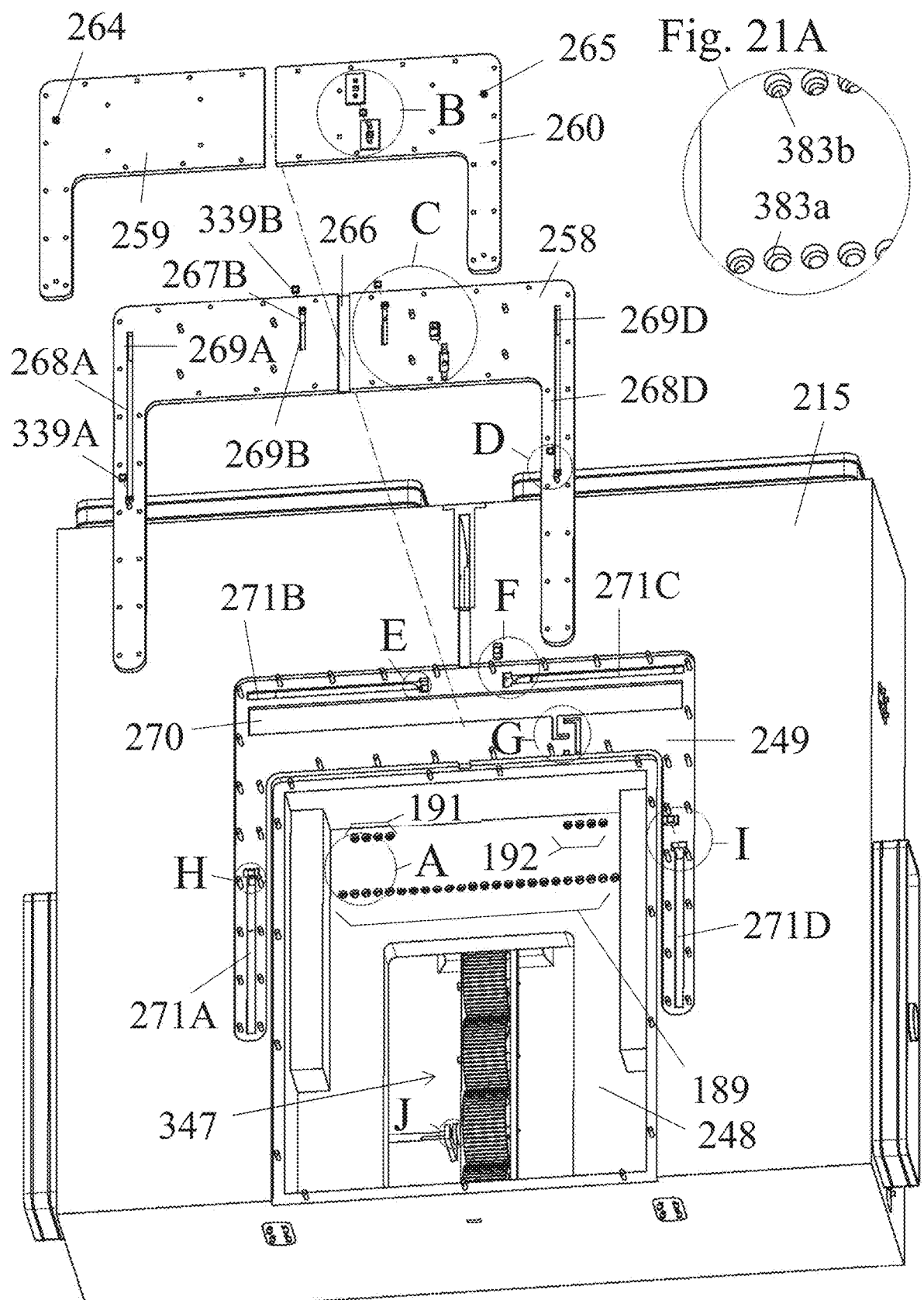

Drawing 23 contains FIG. 21 and Detail FIG. 21A. FIG. 21 is an exploded view of the air release assembly from the reactor node. Detail FIG. 21A shows features of the module bay connections.

Figure 21B:
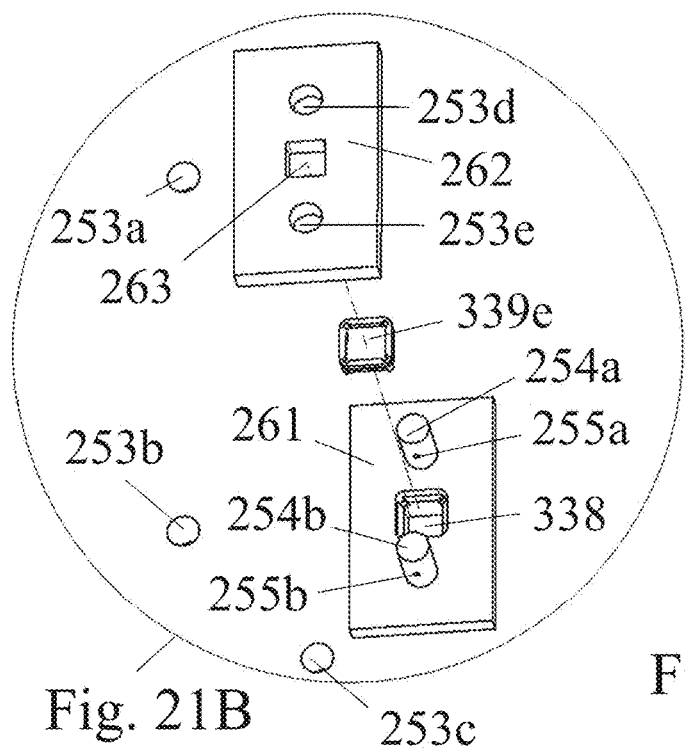
Figure 21D:
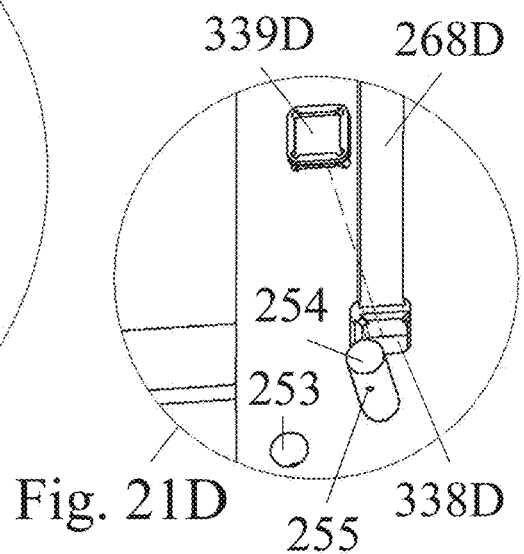
Figure 21C:
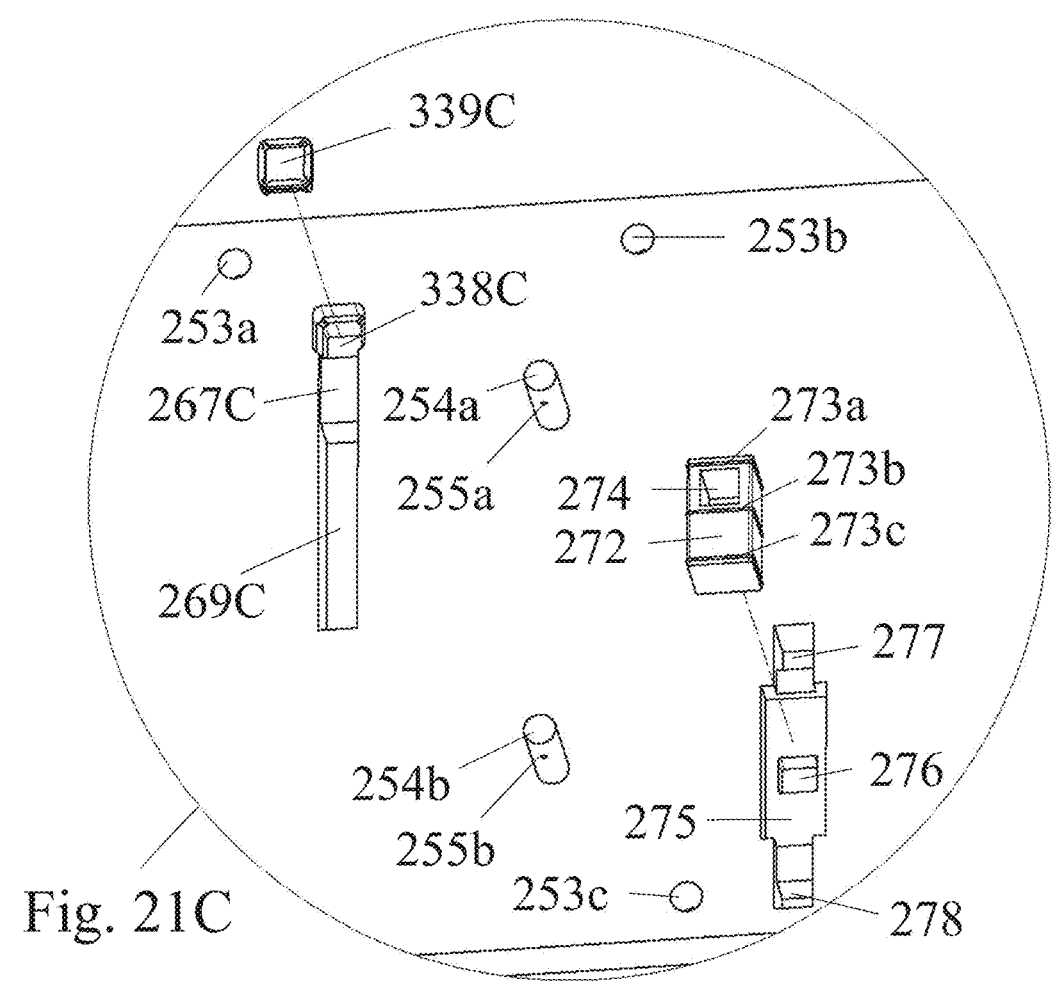

Drawing 24 contains Detail FIG. 21B, Detail FIG. 21C and Detail FIG. 21D. Detail FIG. 21B shows features of the air release right upper cover. Detail FIG. 21C shows features of the air release lower cover and the air vent valve 272. Detail FIG. 21D shows features of the air release lower cover and the air release long channel D 268D.

Drawing 25 contains Detail FIG. 21E, Detail FIG. 21F, Detail FIG. 21G, Detail FIG. 21H, Detail FIG. 21I, and Detail FIG. 21J. Detail FIG. 21E shows the air release cut B 271B with float B in sunk position. Detail FIG. 21F shows the air release cut C with float C exploded. Detail FIG. 21G shows the air release bay and the air release control pipes. Detail FIG. 21H shows the air release cut A 271A with float A in raised position. Detail FIG. 21I shows the air release cut D with float D exploded. Detail FIG. 21J is a cutout view showing features of the pump rotor shaft 329 and the ratchet drive 360.

Figure 22:
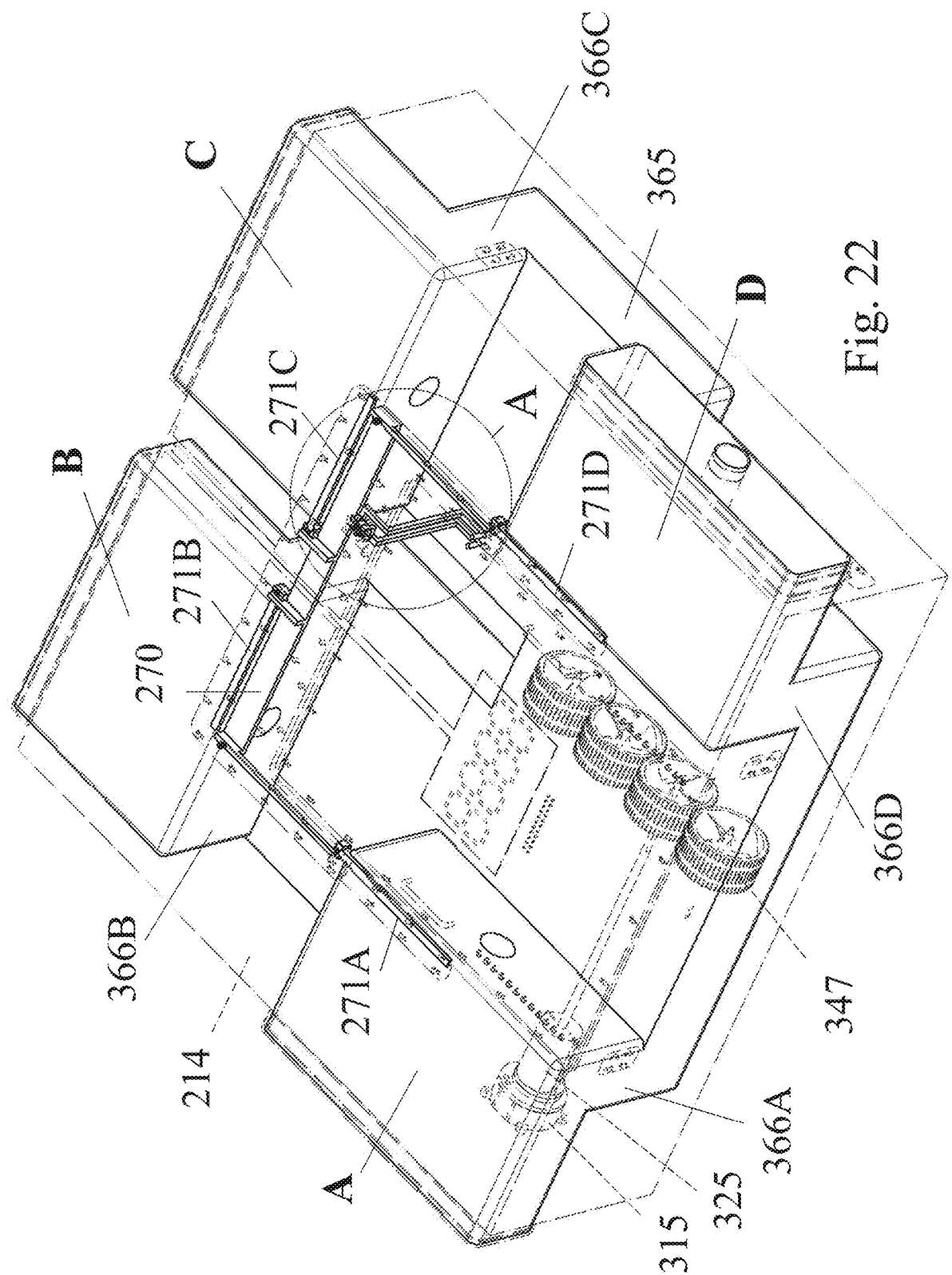

Drawing 26 contains FIG. 22. FIG. 22 is an isometric view of the reactor node showing the air release pipework.

Figure 22A:
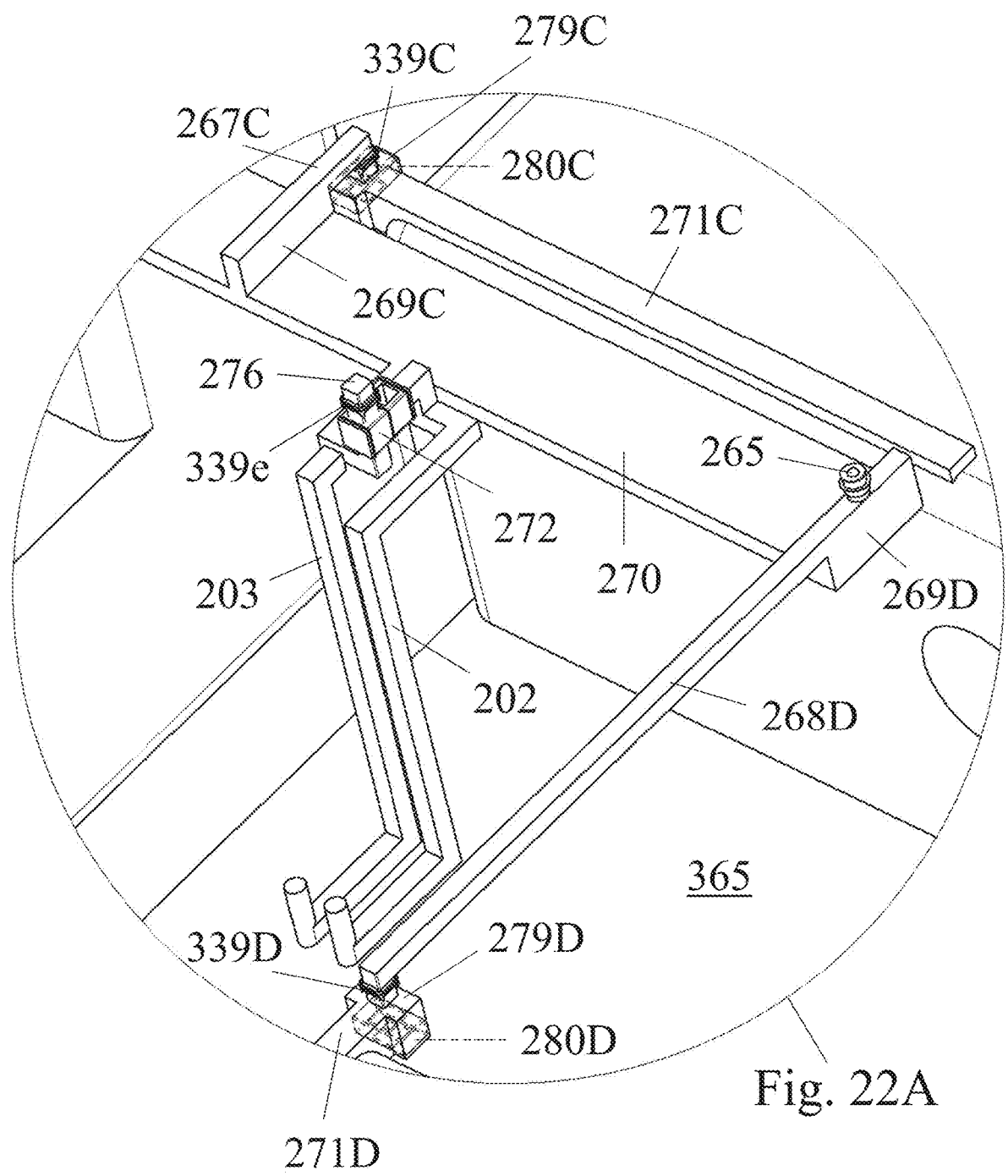

Drawing 27 contains Detail FIG. 22A. Detail FIG. 22A shows the control pipes of the air release assembly.

Drawing 28 contains FIG. 23, Detail FIG. 23A, Detail FIG. 23B, and Detail FIG. 23C. FIG. 23 is an exploded view of the reactor node showing the anchoring system and module assembly 369. Detail FIG. 23A shows features of the pump rotor drive end. Detail FIG. 23B is an exploded view showing the cable winch 292, the anchor cable 287, and the surface stopper 290*a*. Detail FIG. 23C is an exploded view showing the anchor cable 287 and bottom stopper 290*b*, Drawing 29 contains FIG. 24, Detail FIG. 24A, and Detail FIG. 24B. FIG. 24 is a cutout view of the reactor node showing the anchoring components in place. Detail FIG. 24A shows the cable winch 292 griping the anchor cable 287. Detail FIG. 24B shows features of the water pump cavity 231.

Figure 25:
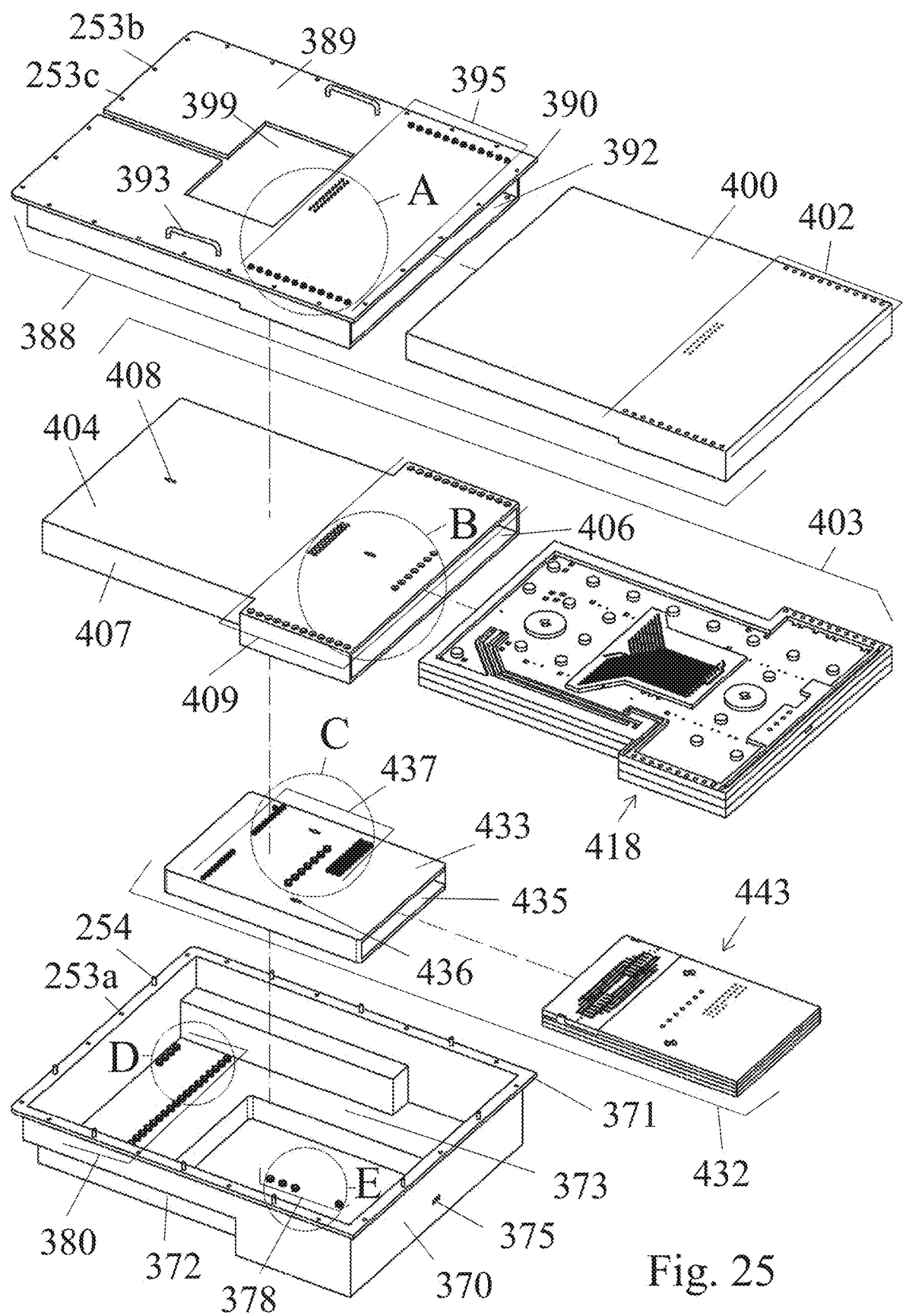

Drawing 30 contains FIG. 25. FIG. 25 is an exploded top view of the module assembly.

Figure 25A:
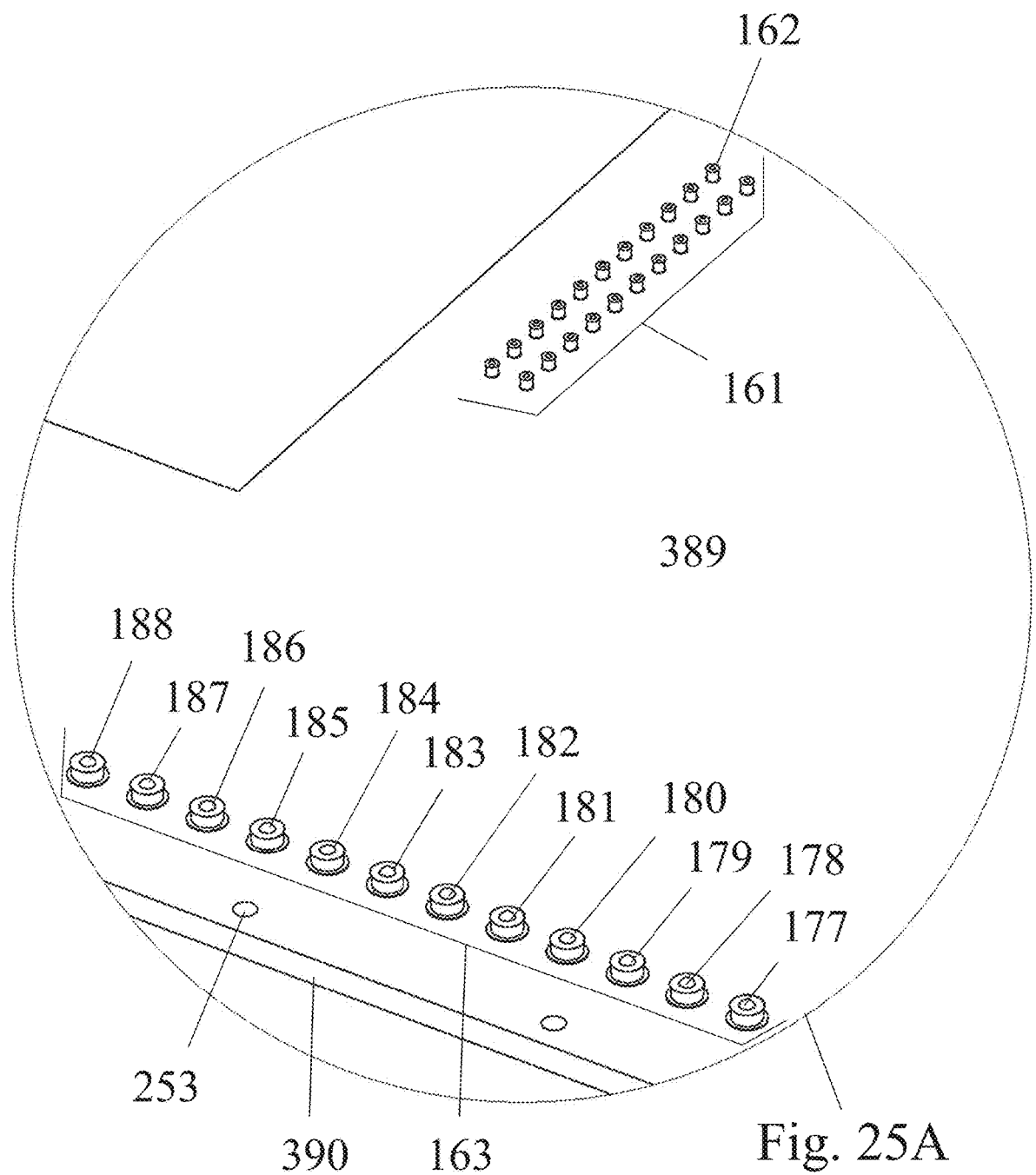

Drawing 31 contains Detail FIG. 25A. Detail FIG. 25A shows the signal port left 163 and diagnose port 161.

Figure 25B:
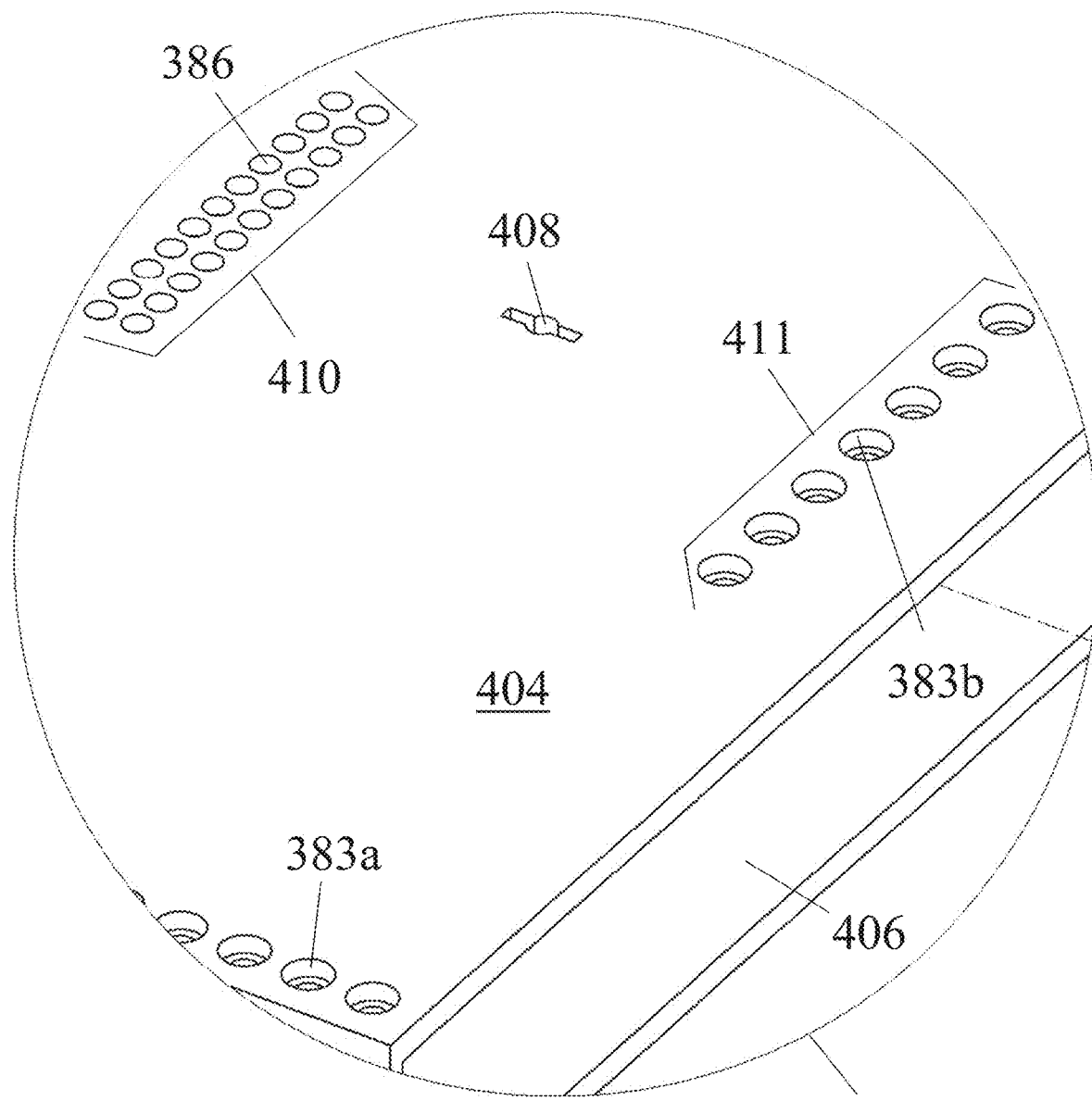

Drawing 32 contains Detail FIG. 25B. Detail FIG. 25B shows the i/o case top connections.

Figure 25C:
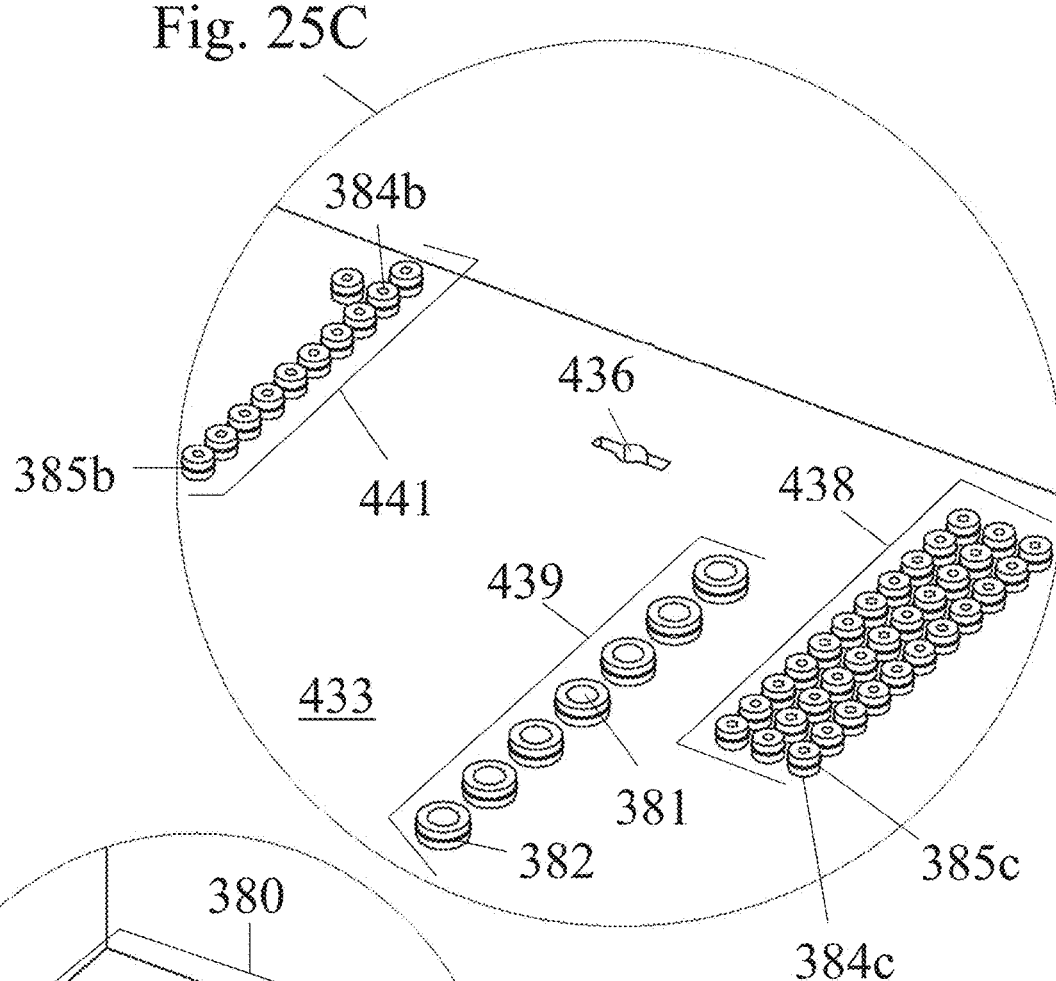
Figure 25D:
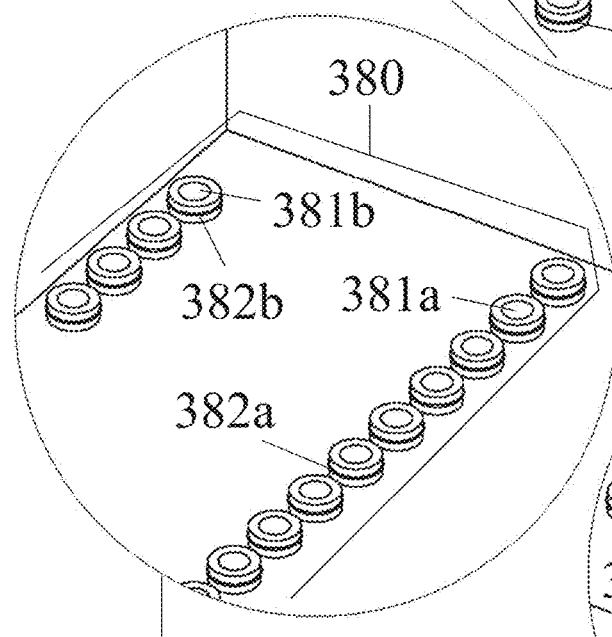
Figure 25E:
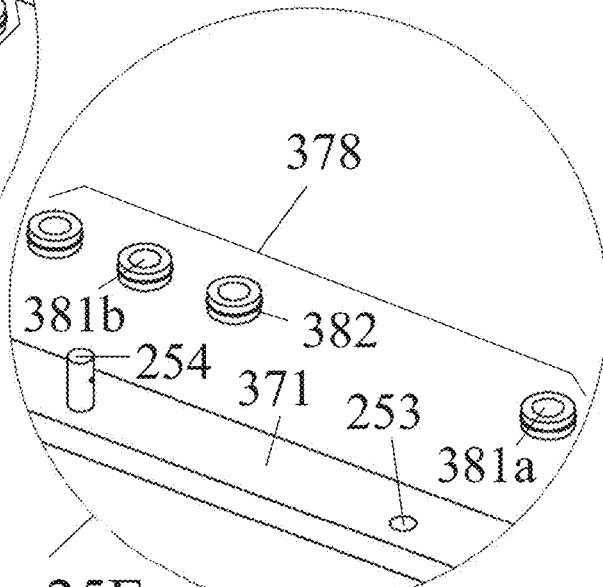

Drawing 33 contains Detail FIG. 25C, Detail FIG. 25D, and Detail FIG. 25E. Detail FIG. 25C shows features of the logic case top connections. Detail FIG. 25D shows fratures of the module control top connector 380. Detail FIG. 25E shows features of the module case and the module ground pipe connector 378.

Figure 26:
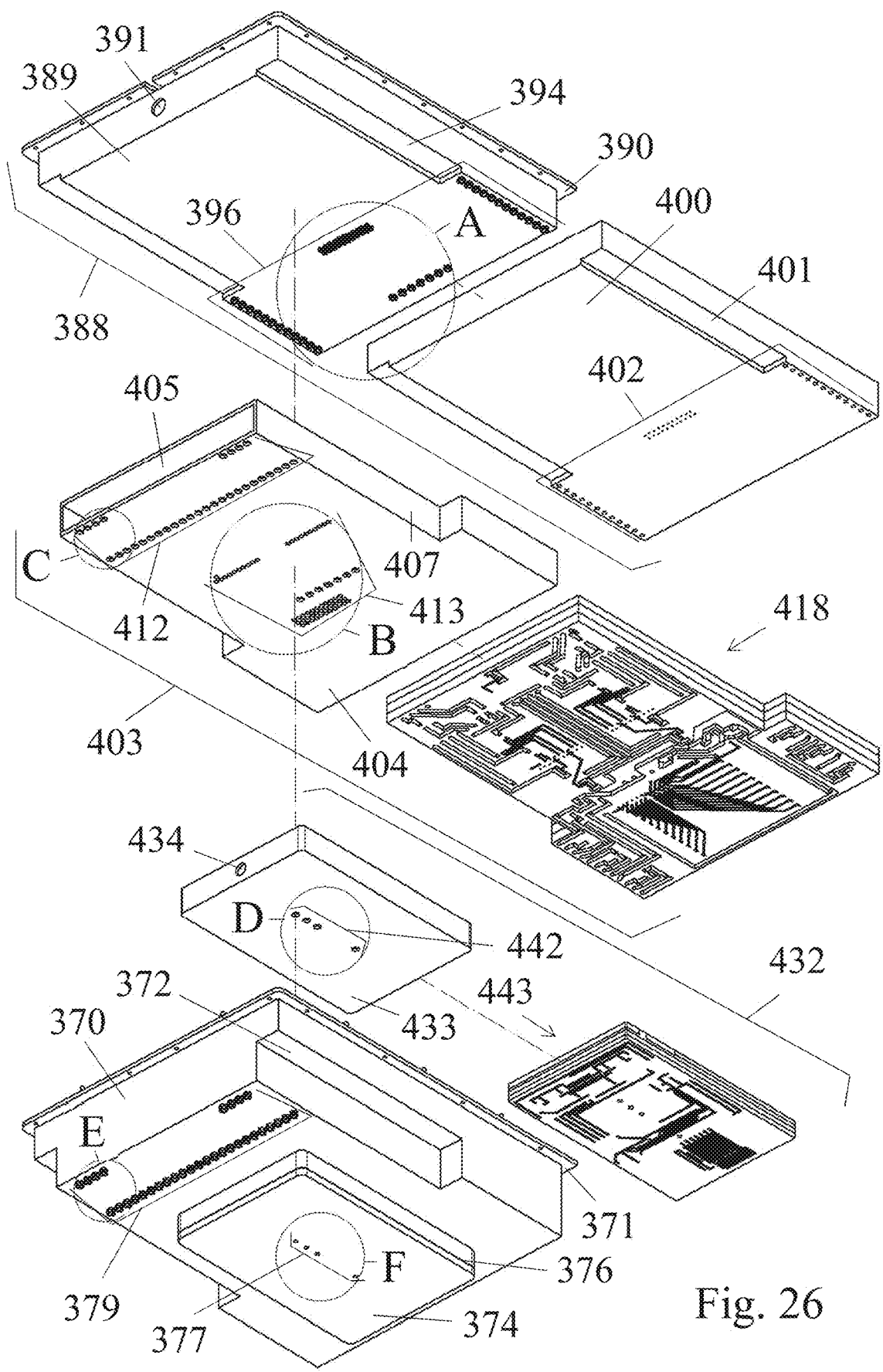

Drawing 34 contains FIG. 26. FIG. 26 is an exploded bottom view of the module assembly.

Figure 26A:
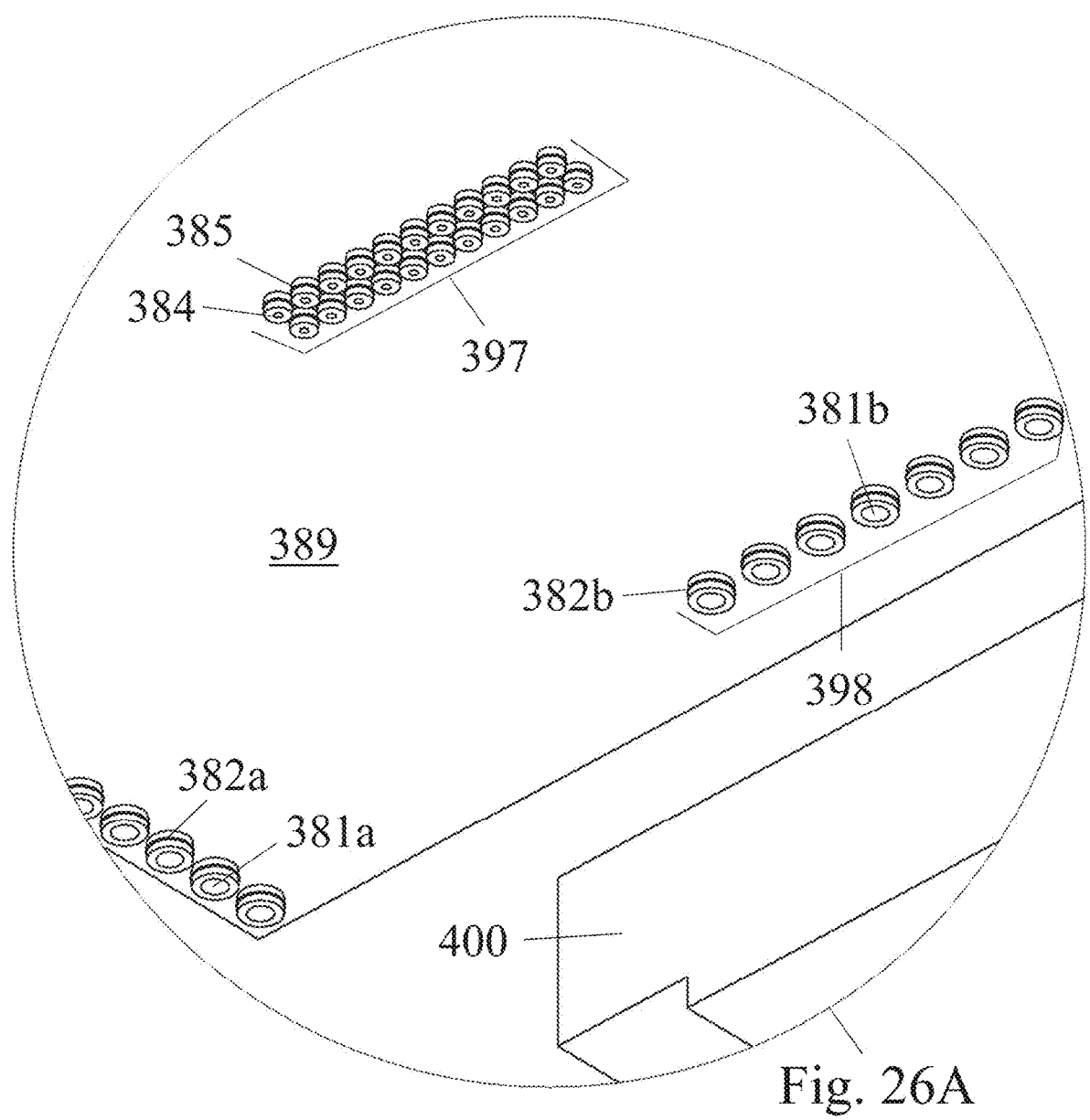

Drawing 35 contains Detail FIG. 26A. Detail FIG. 26A shows features of the expansion case bottom connections.

Figure 26B:
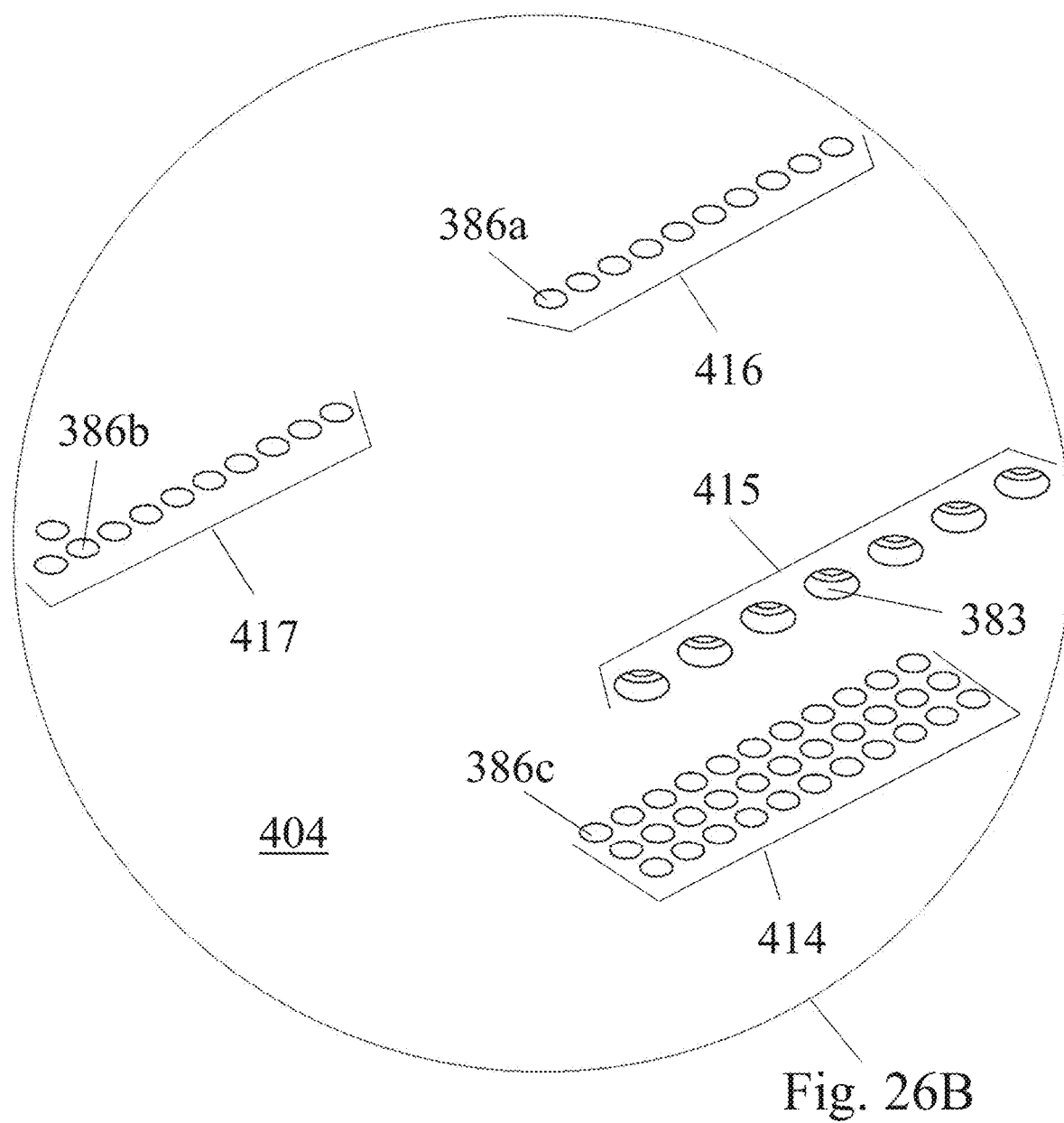

Drawing 36 contains Detail FIG. 26B. Detail FIG. 26B shows features of the i/o case logic connector.

Drawing 37 contains Detail FIG. 26C, Detail FIG. 26D, Detail FIG. 26E, and Detail FIG. 26F. Detail FIG. 26C shows features of the i/o case bottom control connector 412. Detail FIG. 26D shows features of the logic case bottom connector 442. Detail FIG. 26E shows features of the module control bottom connector 379. Detail FIG. 26F shows features of the module ground pipe port 377.

Figure 27:
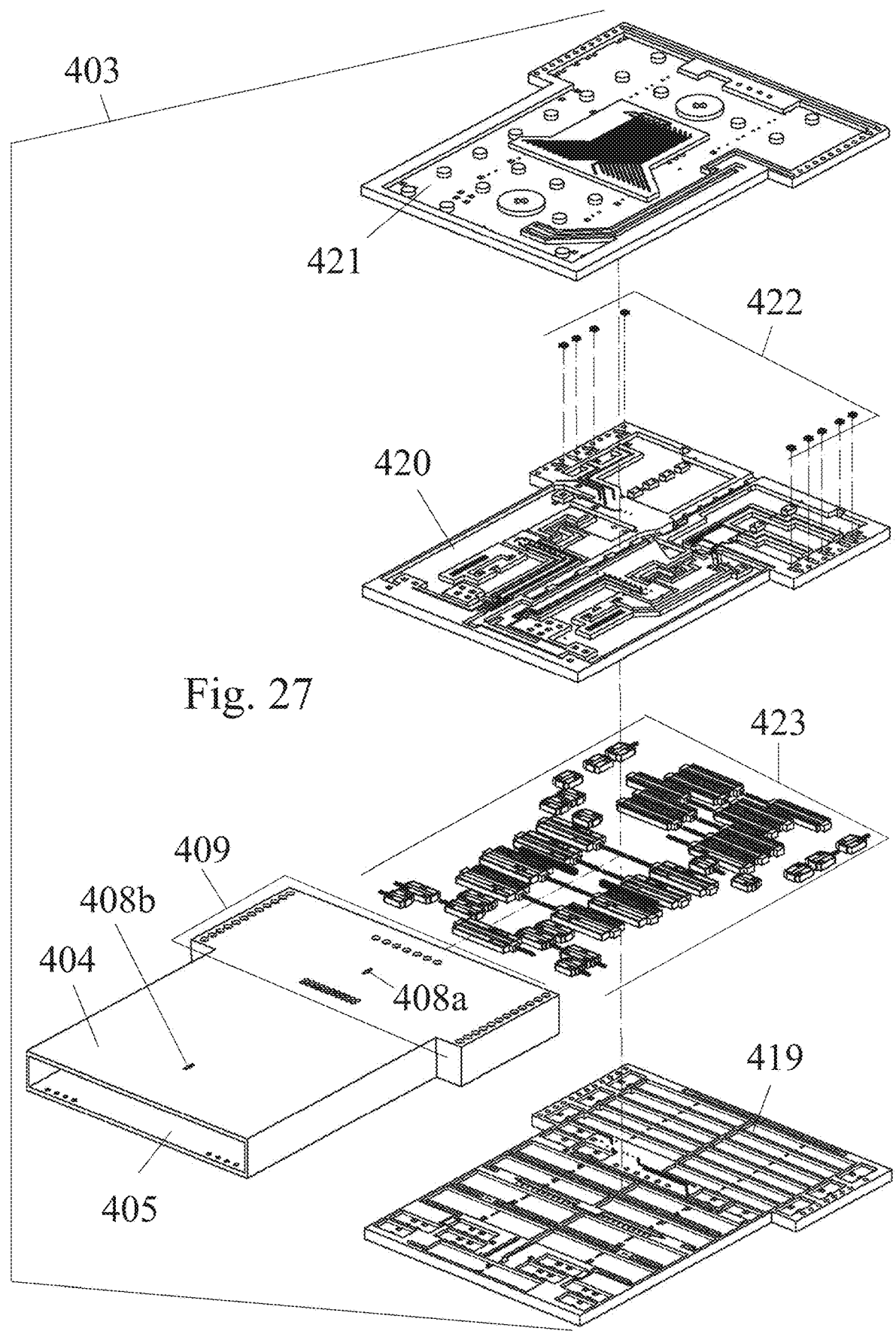

Drawing 38 contains FIG. 27. FIG. 27 is an exploded view of the i/o unit assembly 403.

Figure 28:
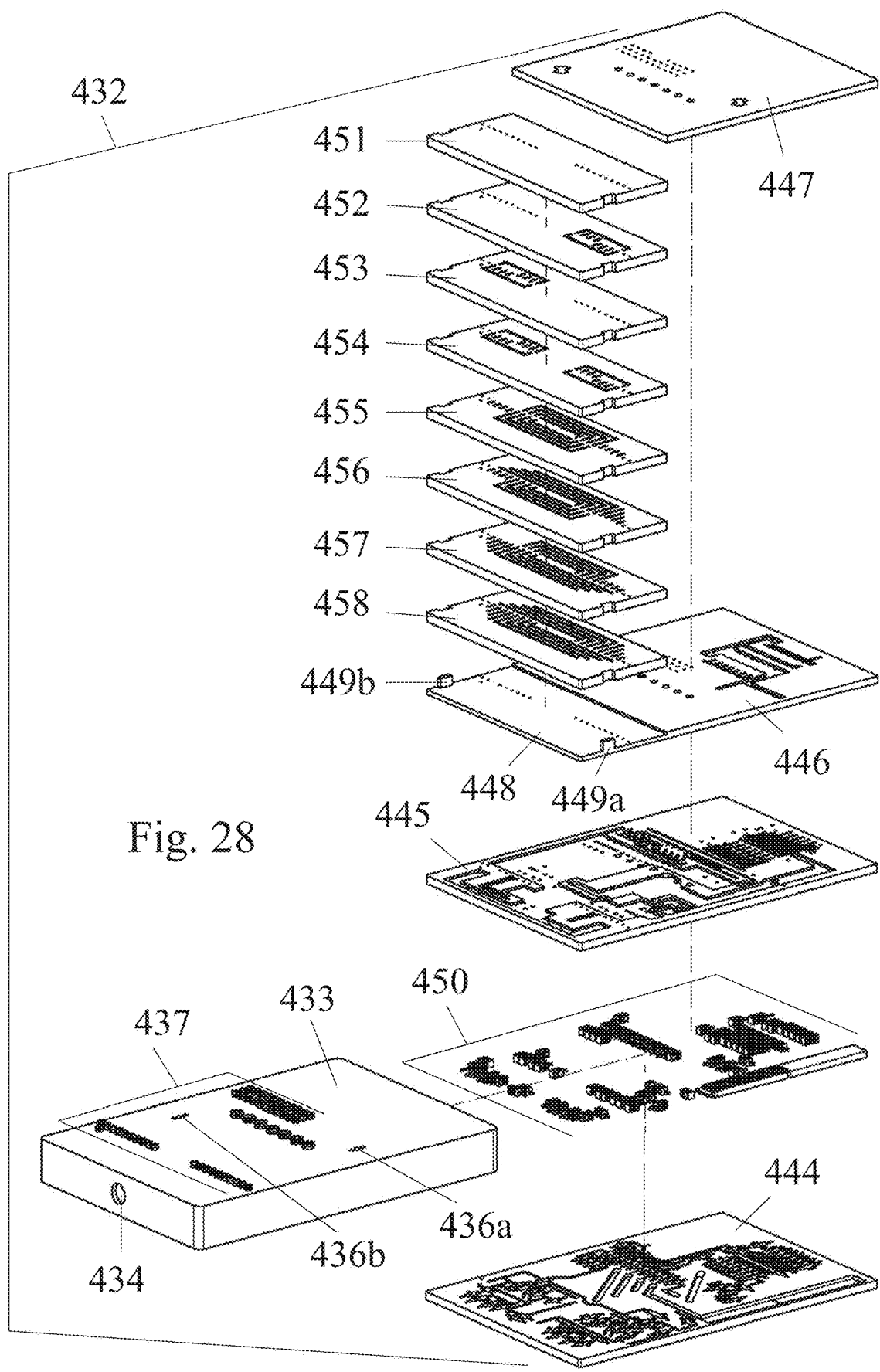

Drawing 39 contains FIG. 28. FIG. 28 is an exploded view of the logic unit assembly 432.

Figure 29:
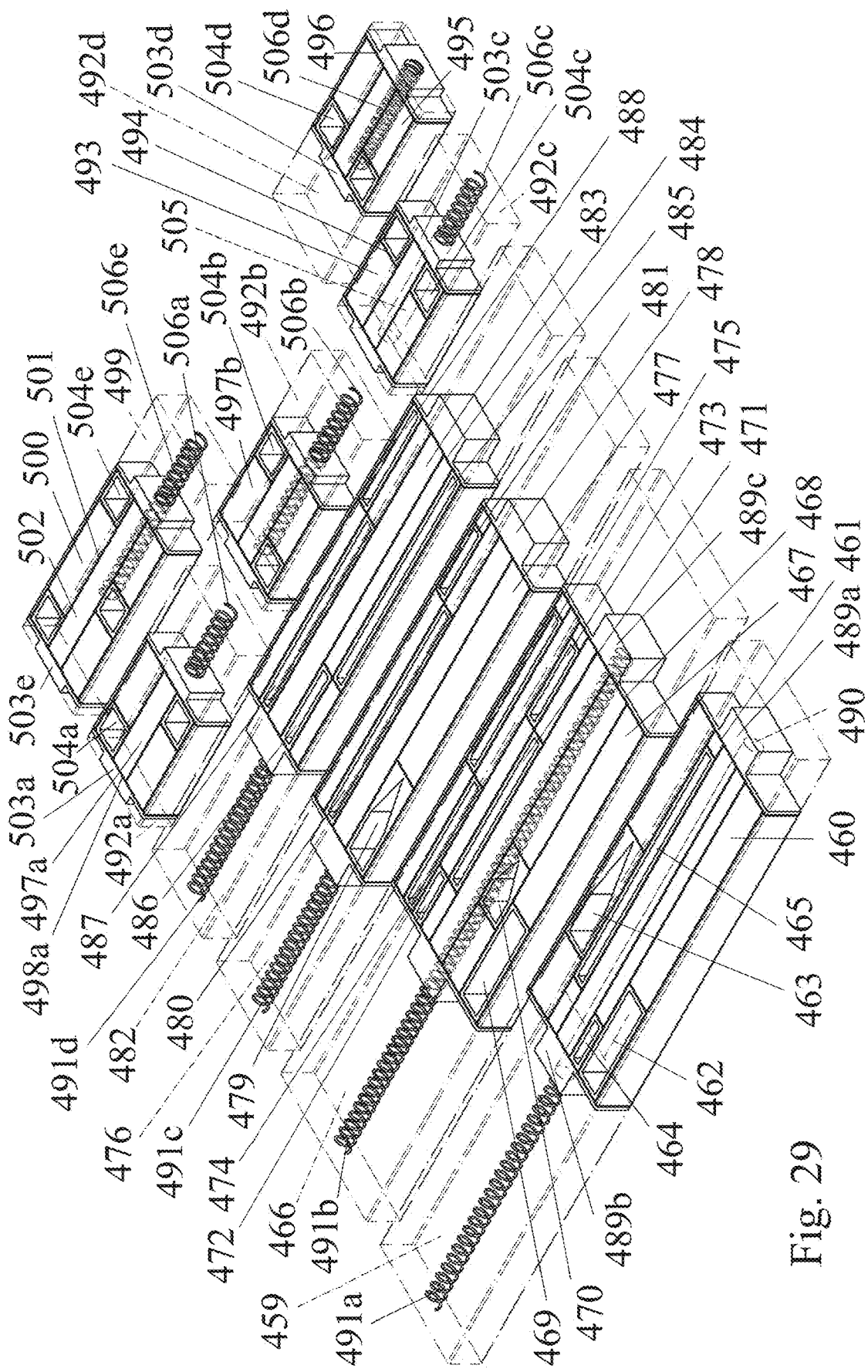

Drawing 40 contains FIG. 29. FIG. 29 is an isometric view of the i/o components.

Figure 30:
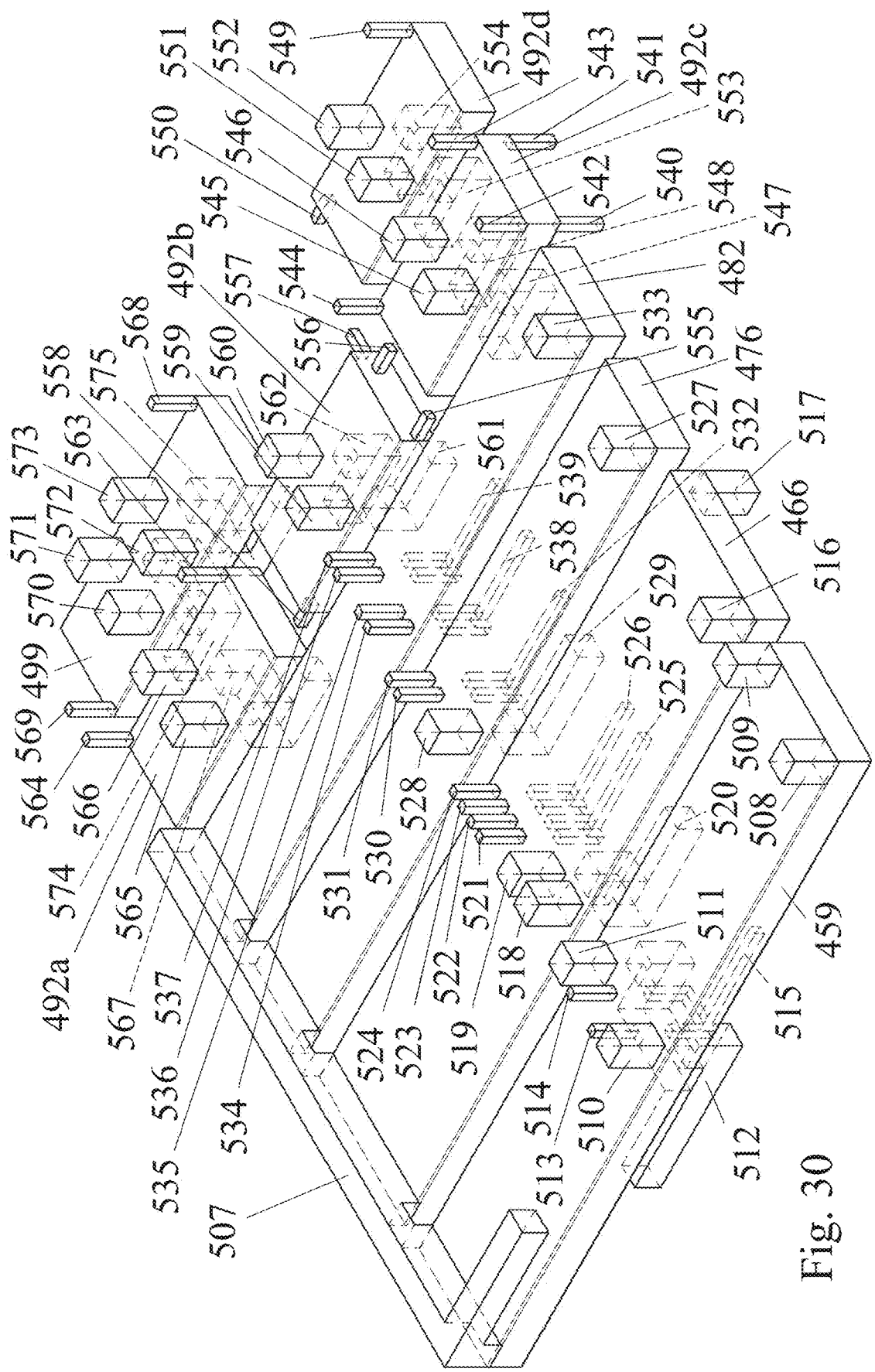

Drawing 41 contains FIG. 30. FIG. 30 is an isometric view of i/o connections.

Figure 31:
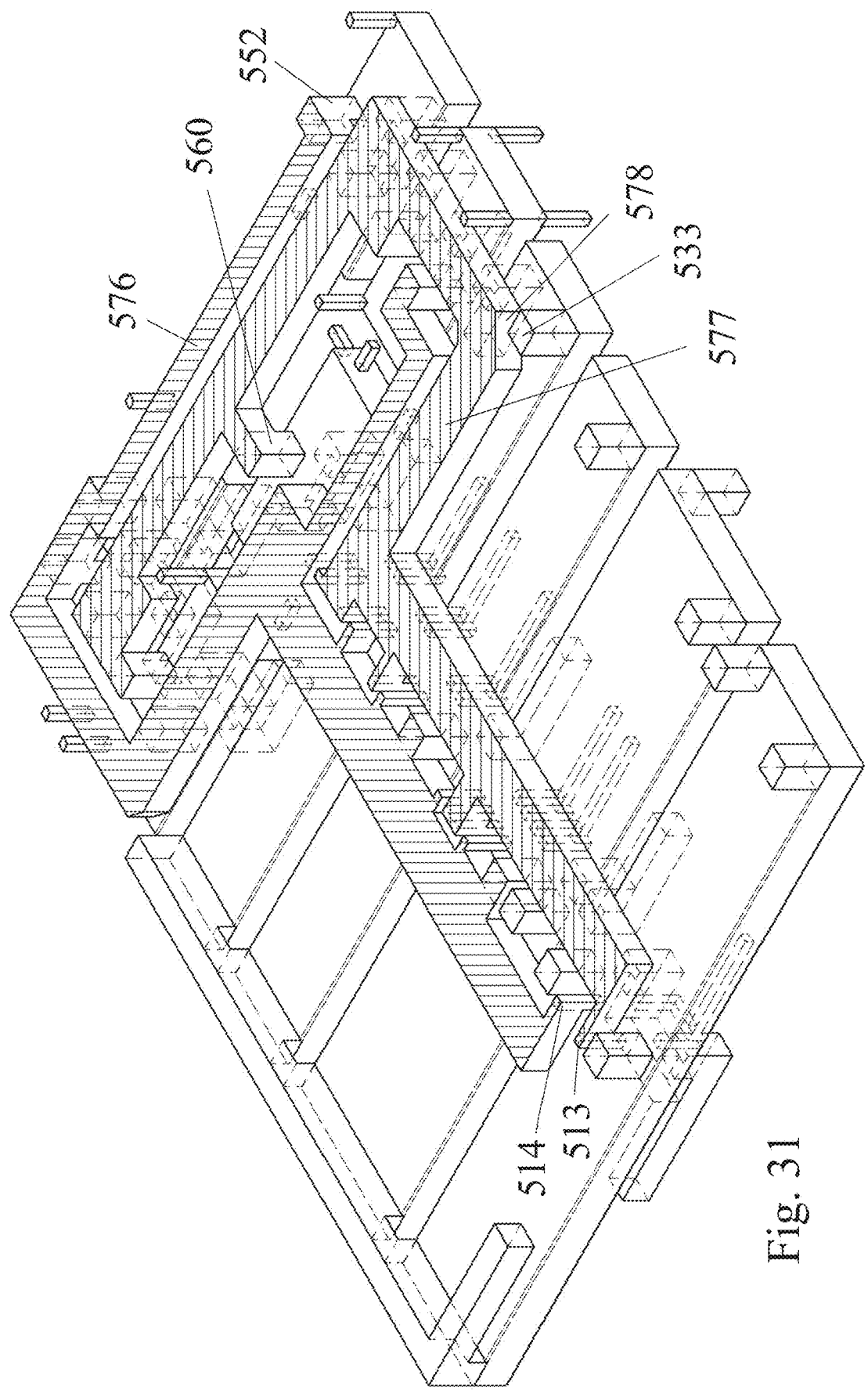

Drawing 42 contains FIG. 31. FIG. 31 is an isometric view of i/o connections showing the high pressure supply plane 576 and the ground plane 577.

Figure 32:
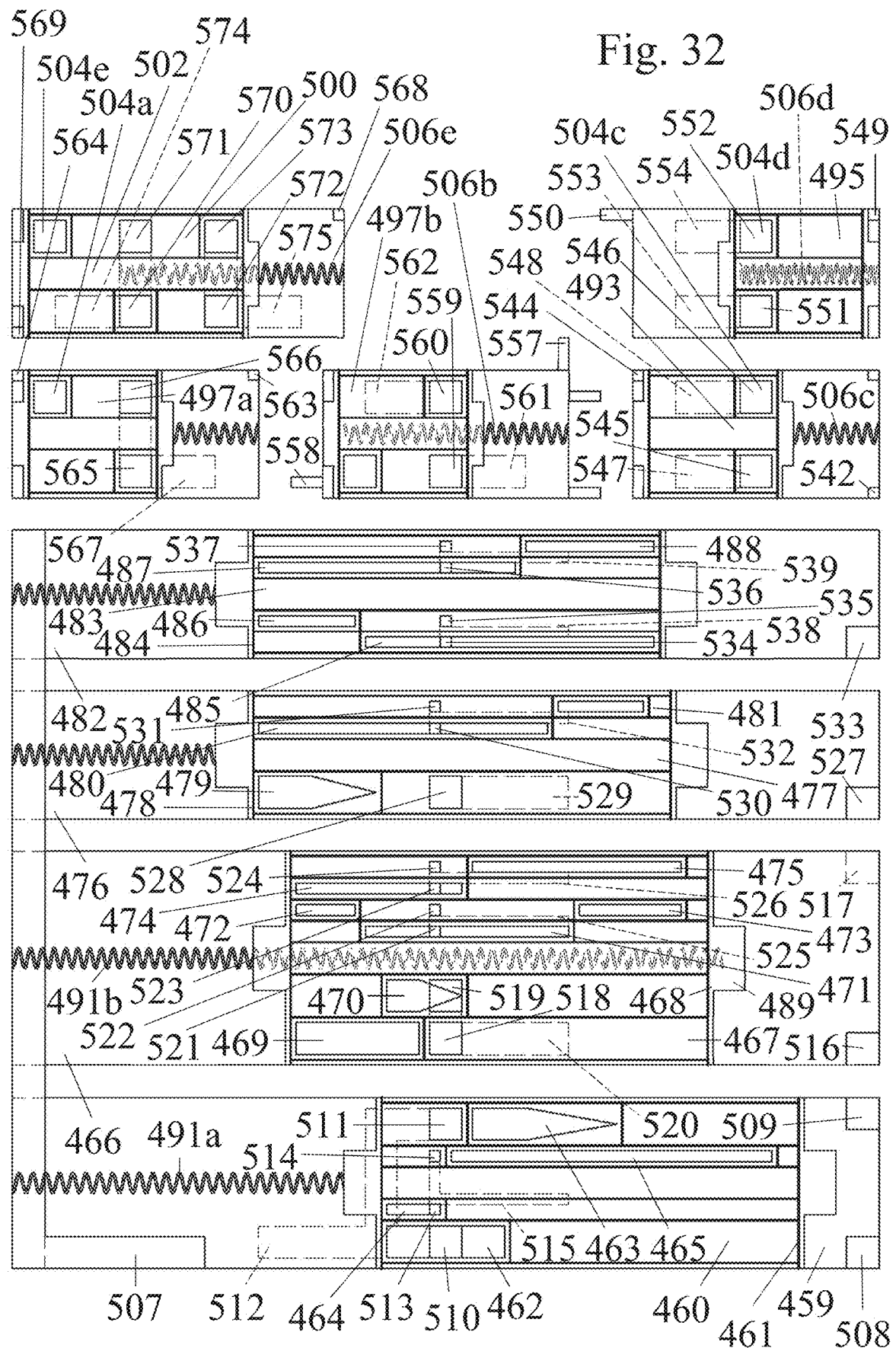

Drawing 43 contains FIG. 32. FIG. 32 is a top view of i/o components and i/o connections.

Figure 33:
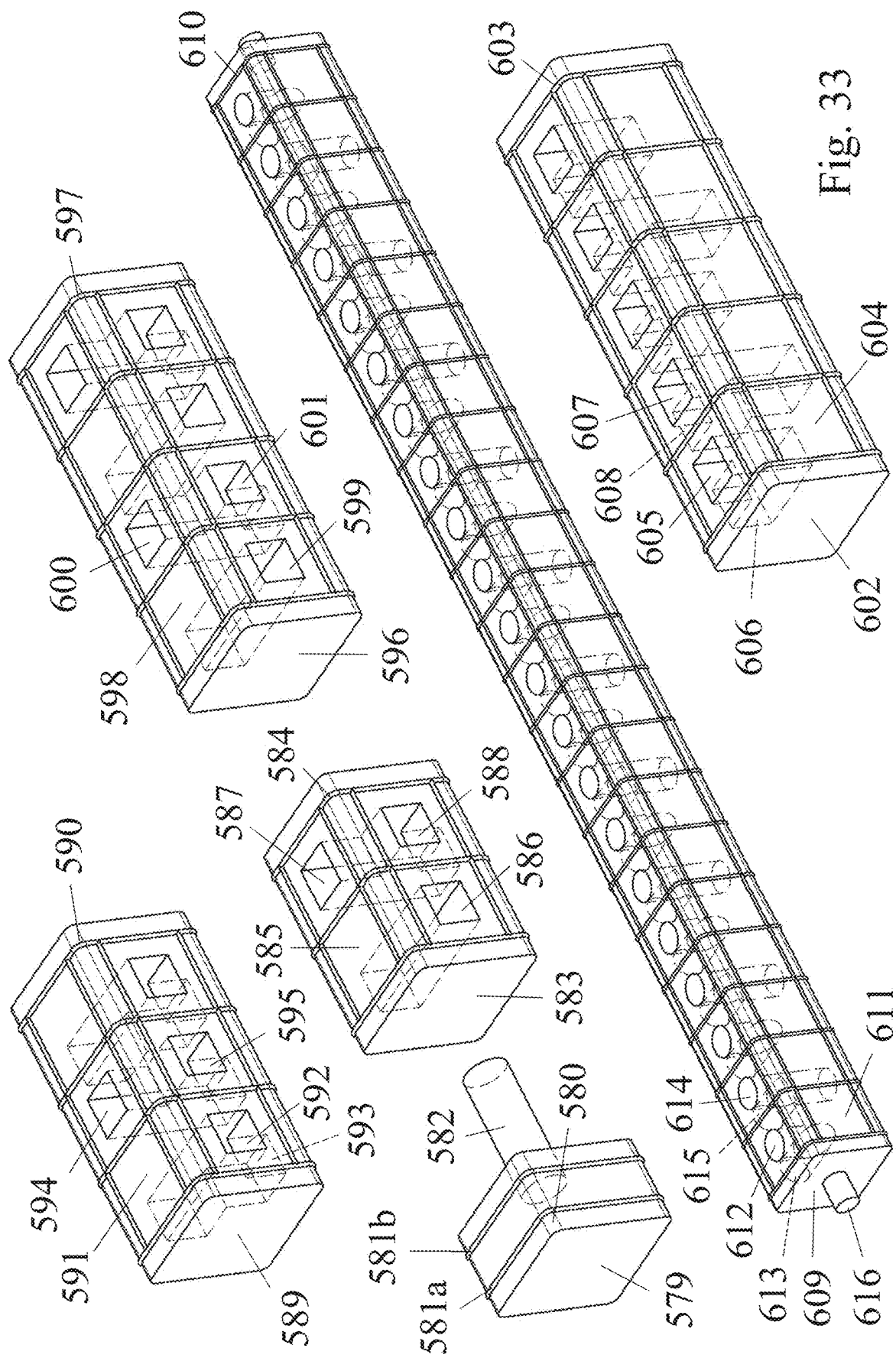

Drawing 44 contains FIG. 33. FIG. 33 is an isometric view of the logic components.

Figure 34:
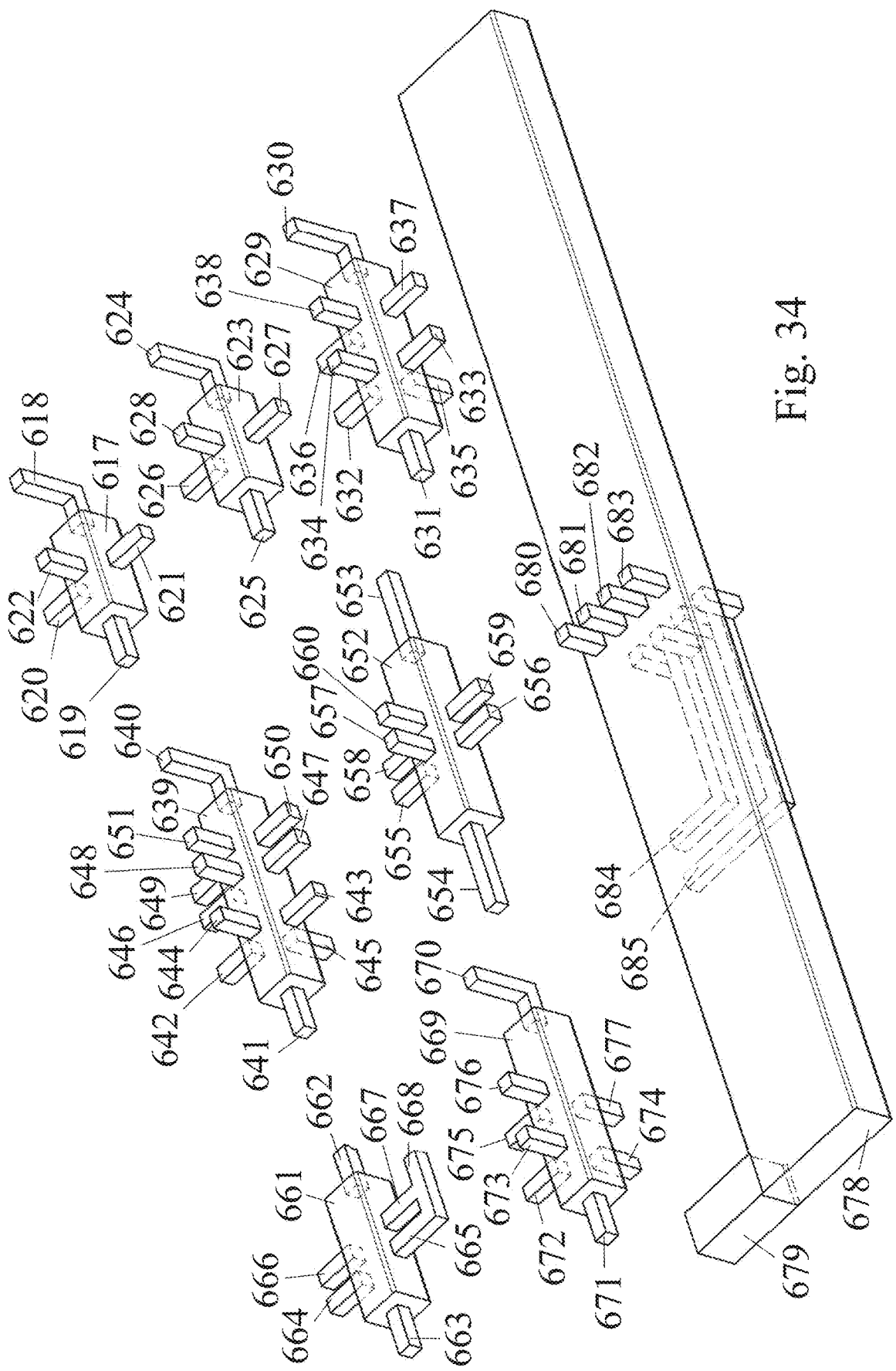

Drawing 45 contains FIG. 34. FIG. 34 is an isometric view of logic connections.

Figure 35:
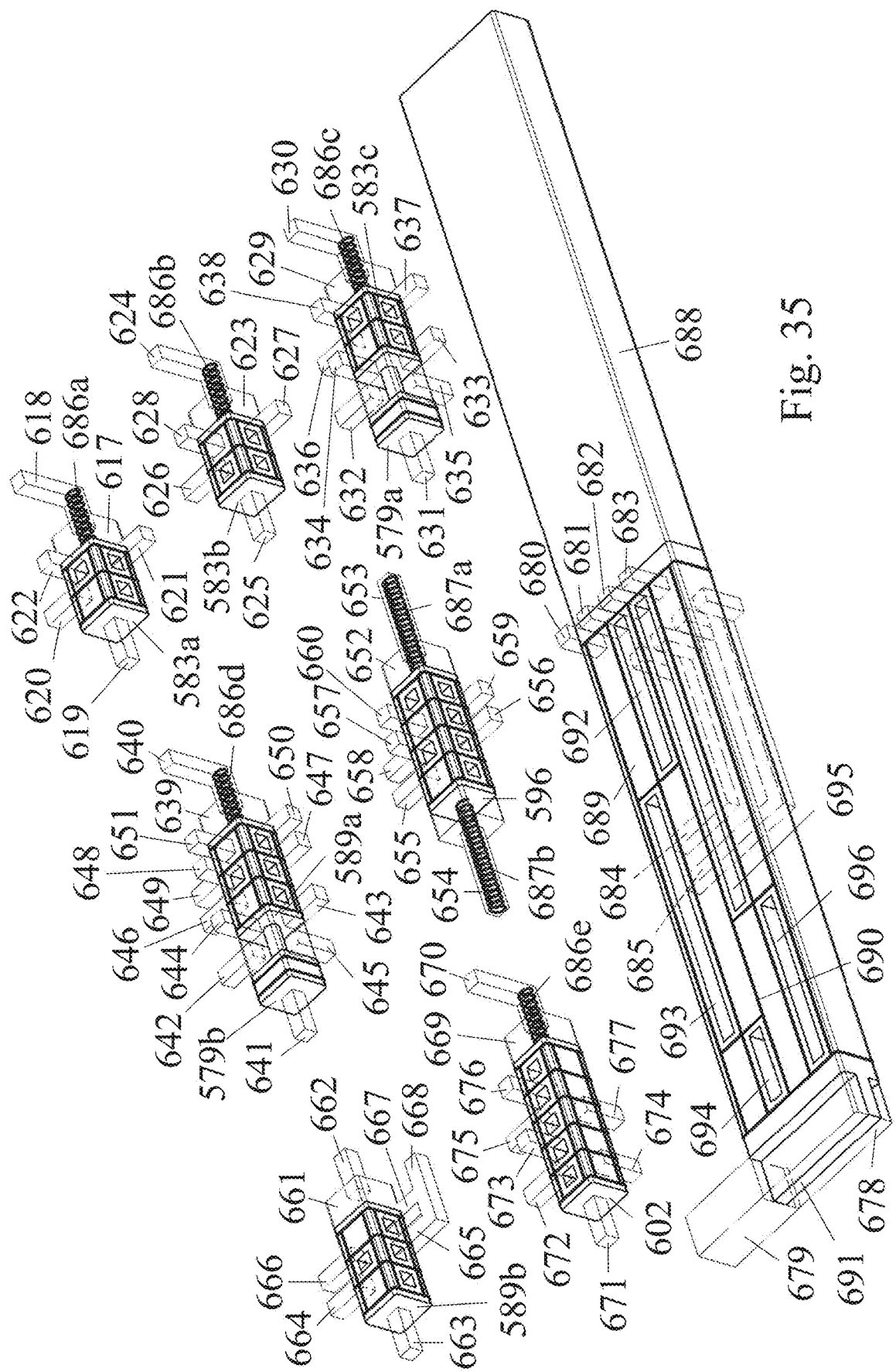

Drawing 46 contains FIG. 35. FIG. 35 is an isometric view of logic components and logic connections in position 1.

Figure 36:
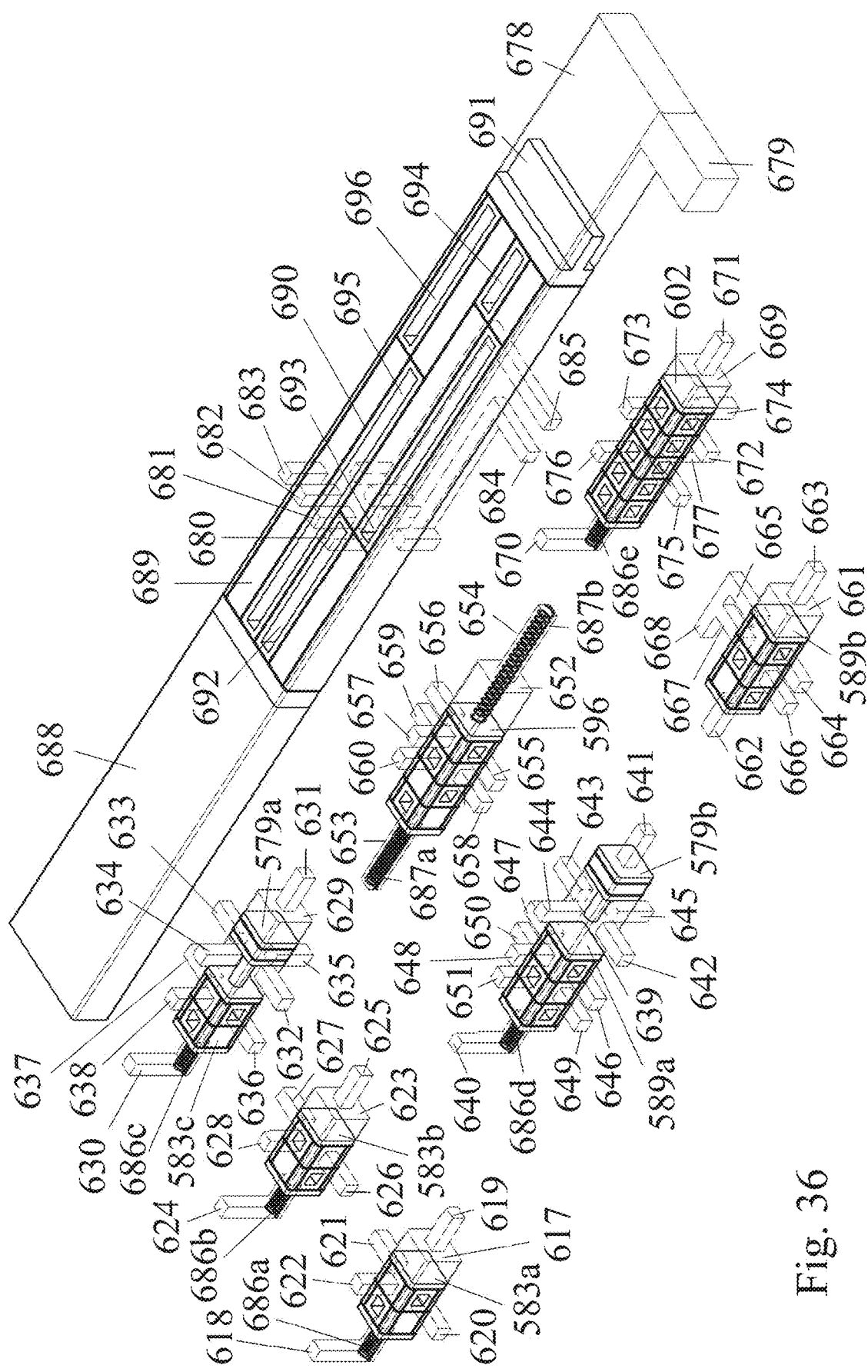

Drawing 47 contains FIG. 36. FIG. 36 is an isometric view of logic components and logic connections in position 2.

Figure 37:
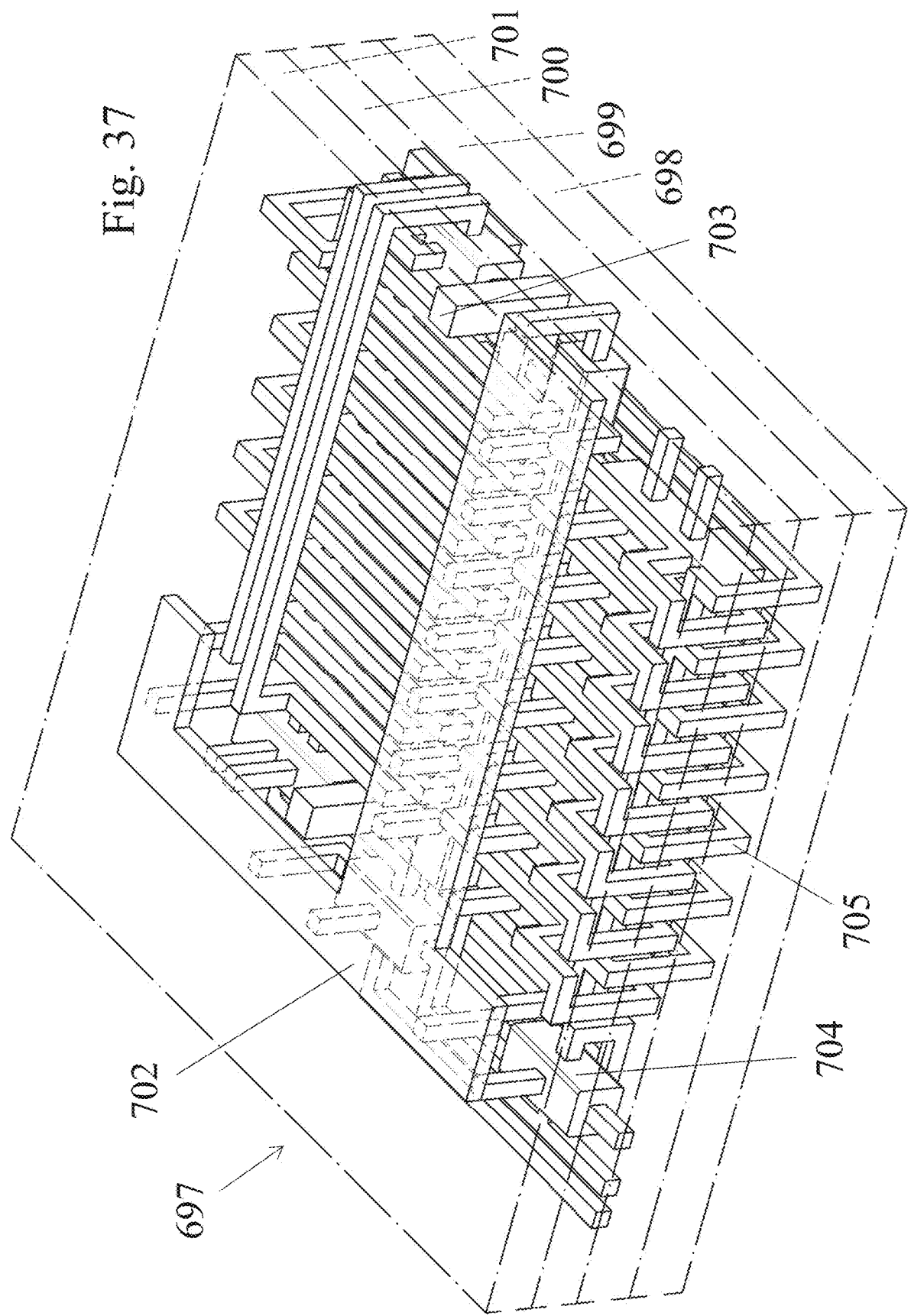

Drawing 48 contains FIG. 37. FIG. 37 is an isometric view of the LFSR assembly 697.

Figure 38:
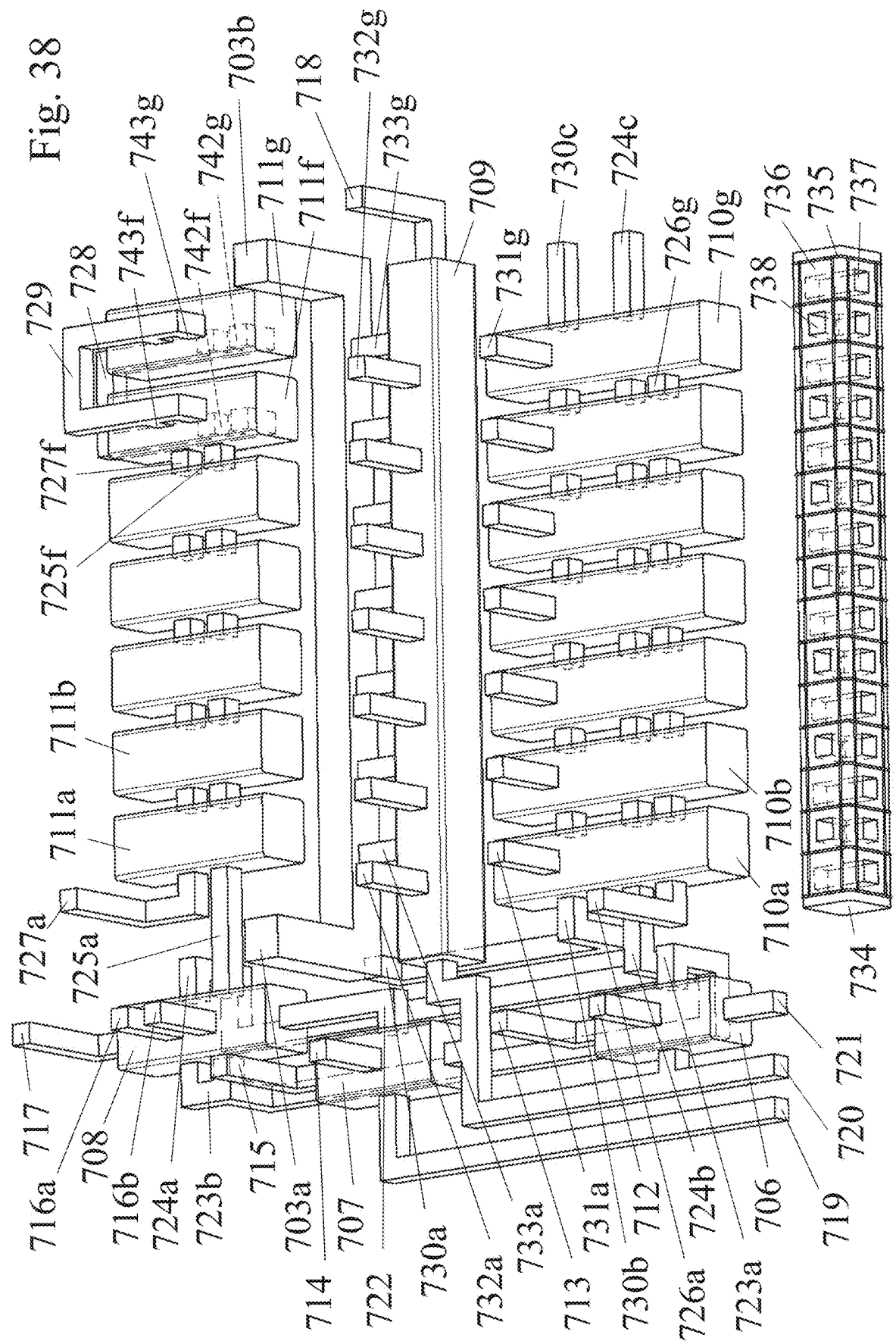

Drawing 49 contains FIG. 38. FIG. 38 is an isometric view of the LFSR assembly showing feed connections and the zero gate 734.

Figure 39:
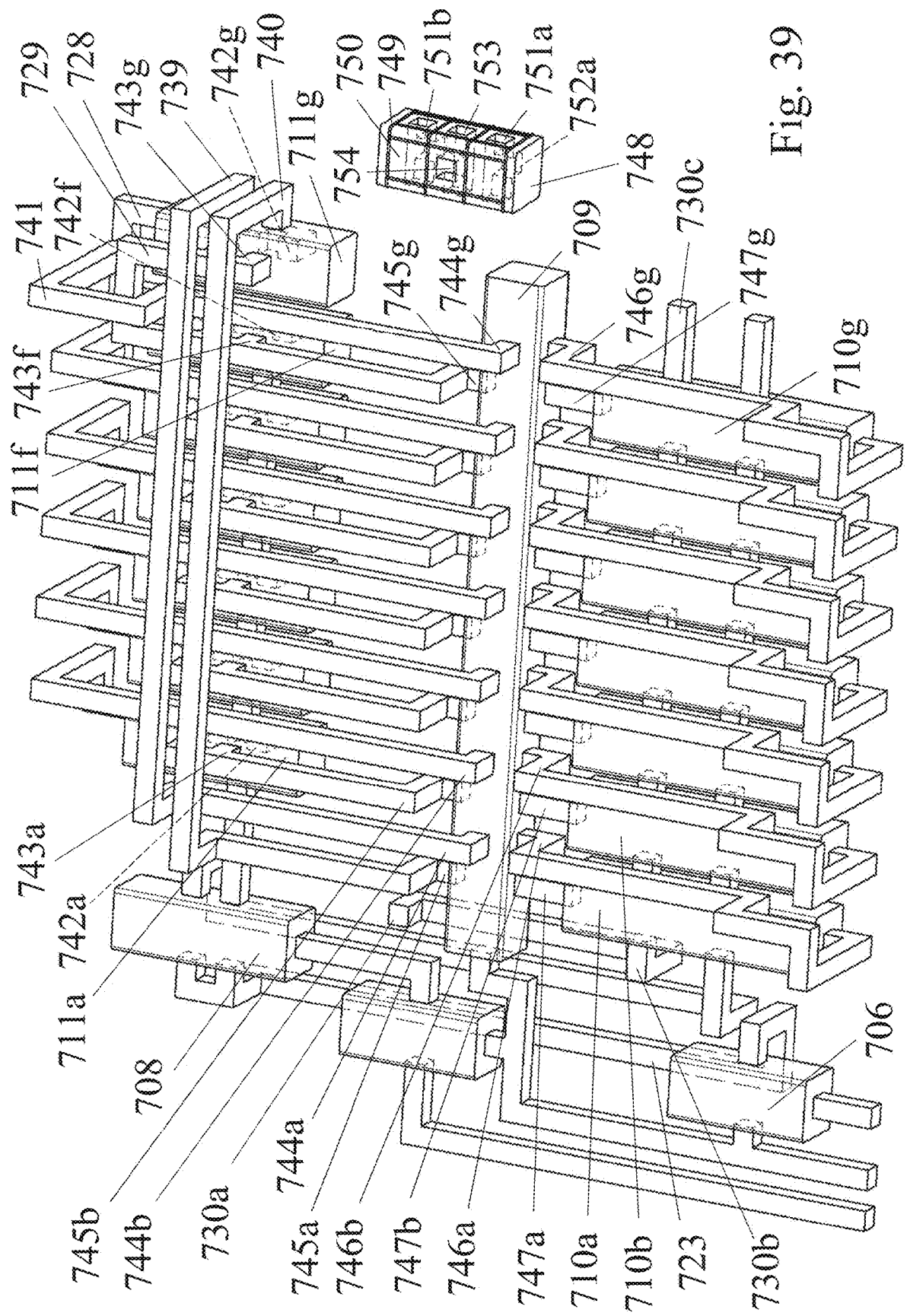

Drawing 50 contains FIG. 39. FIG. 39 is an isometric view of the LFSR assembly showing register connections and the memory gate 748.

Figure 40:
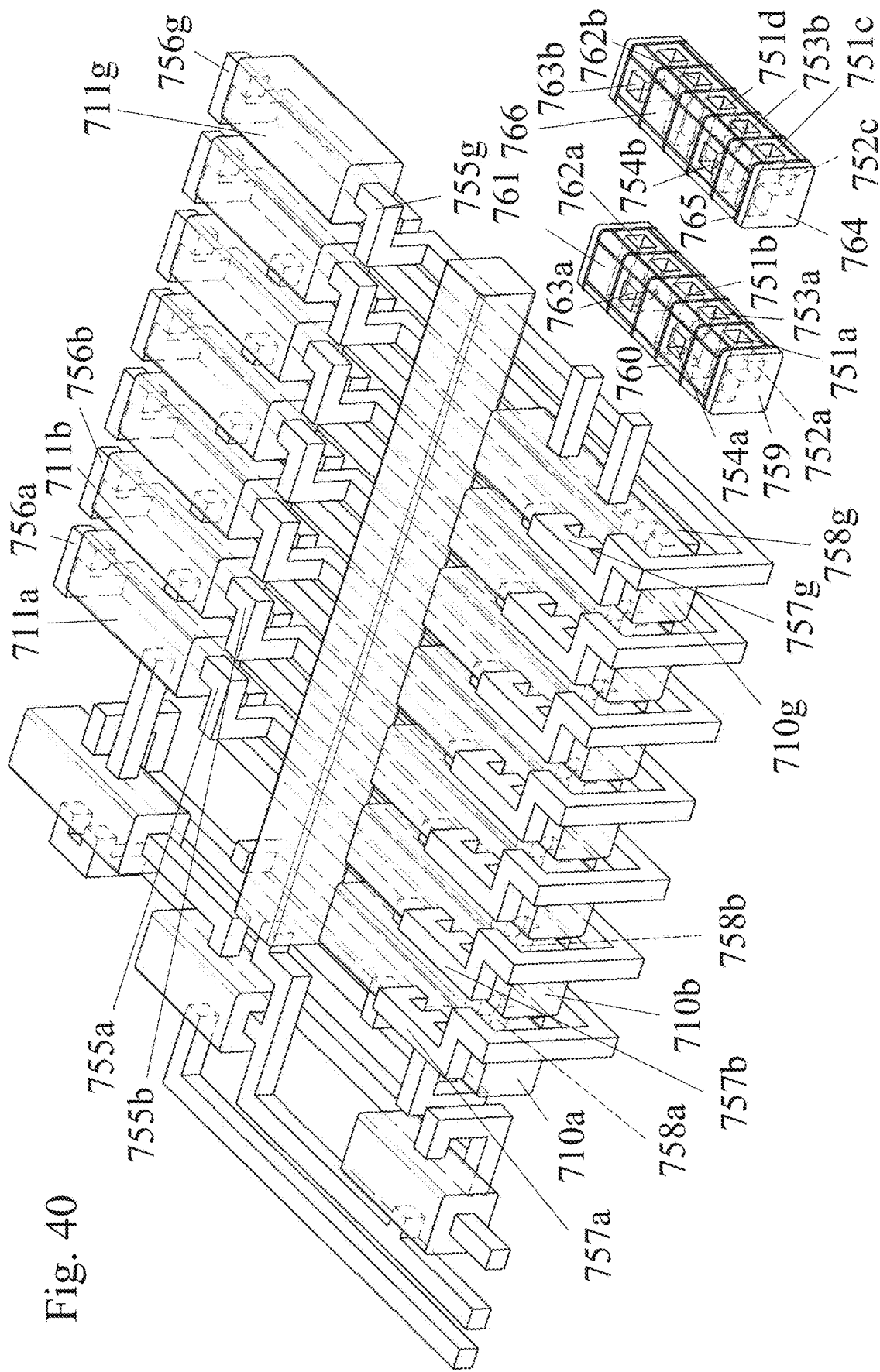

Drawing 51 contains FIG. 40. FIG. 40 is an isometric view of the LFSR assembly showing memory connections, the register gate low 759, and the register gate high 764.

Figure 41:
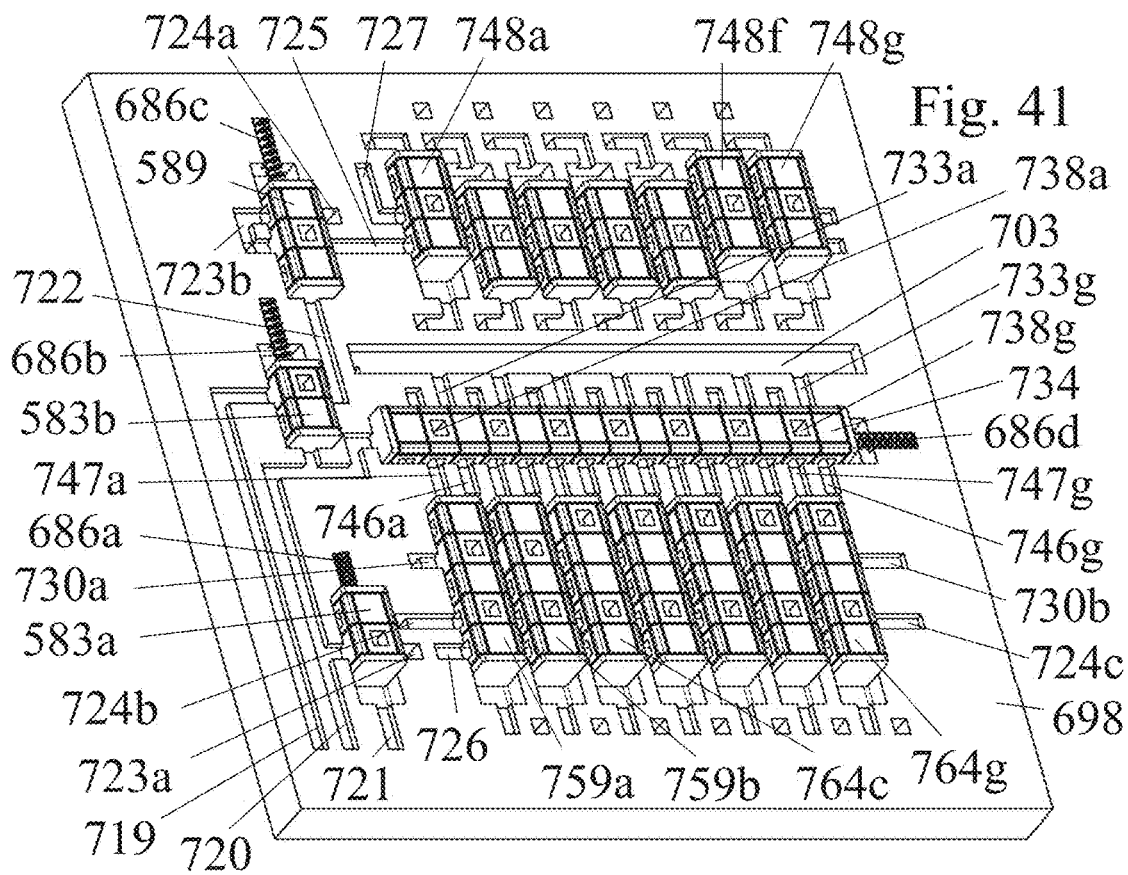
Figure 42:
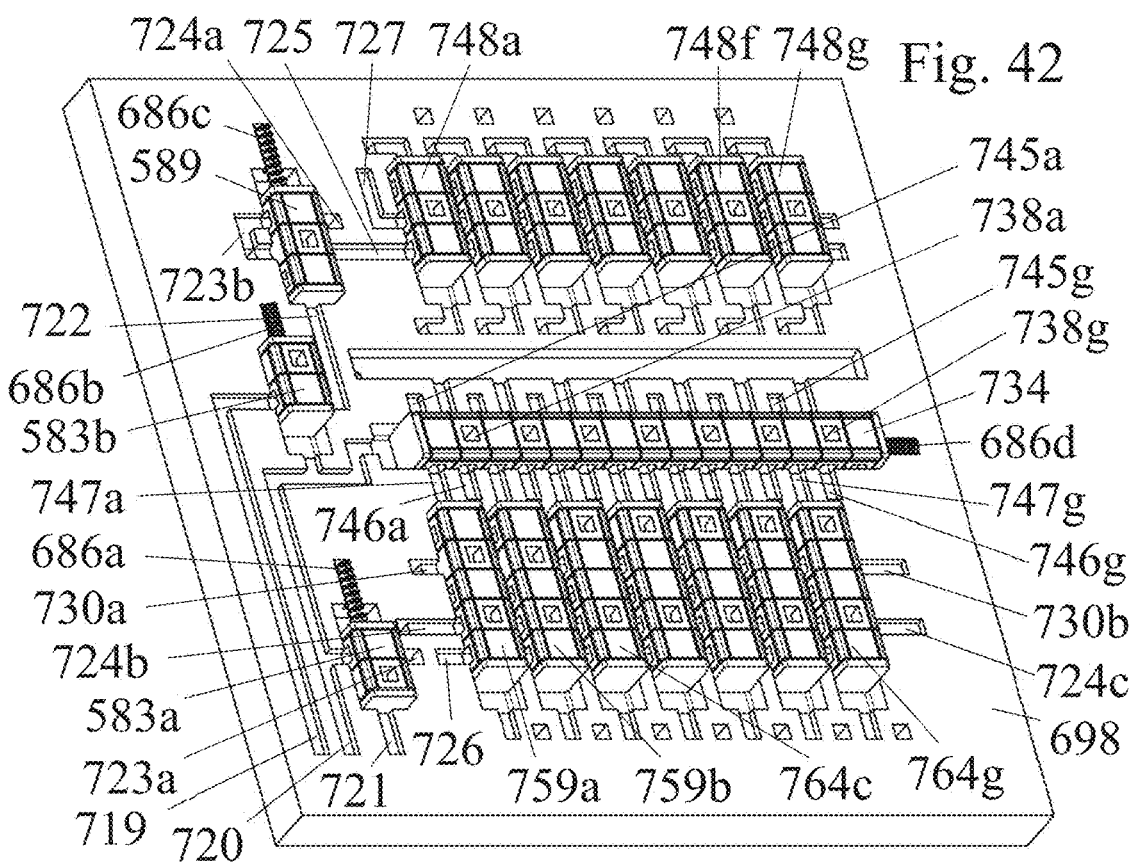

Drawing 52 contains FIG. 41 and FIG. 42. FIG. 41 is an isometric view of the LFSR assembly in disabled state. FIG. 42 is an isometric view of the LFSR assembly in zero state.

Drawing 53 contains FIG. 43 and FIG. 44. FIG. 43 is an isometric view of the LFSR assembly in state 1 clock hi. FIG. 44 is an isometric view of the LFSR assembly in state 1 clock low.

Figure 45:
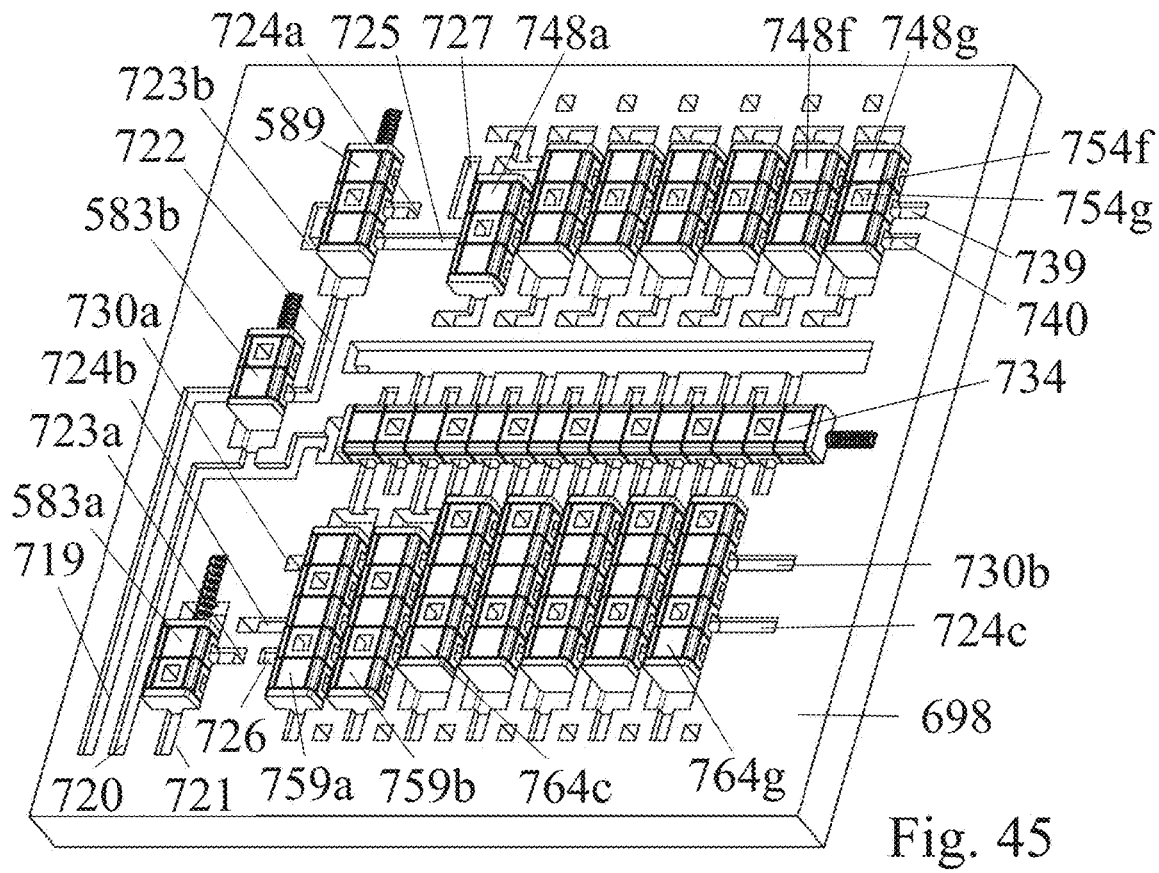
Figure 46:
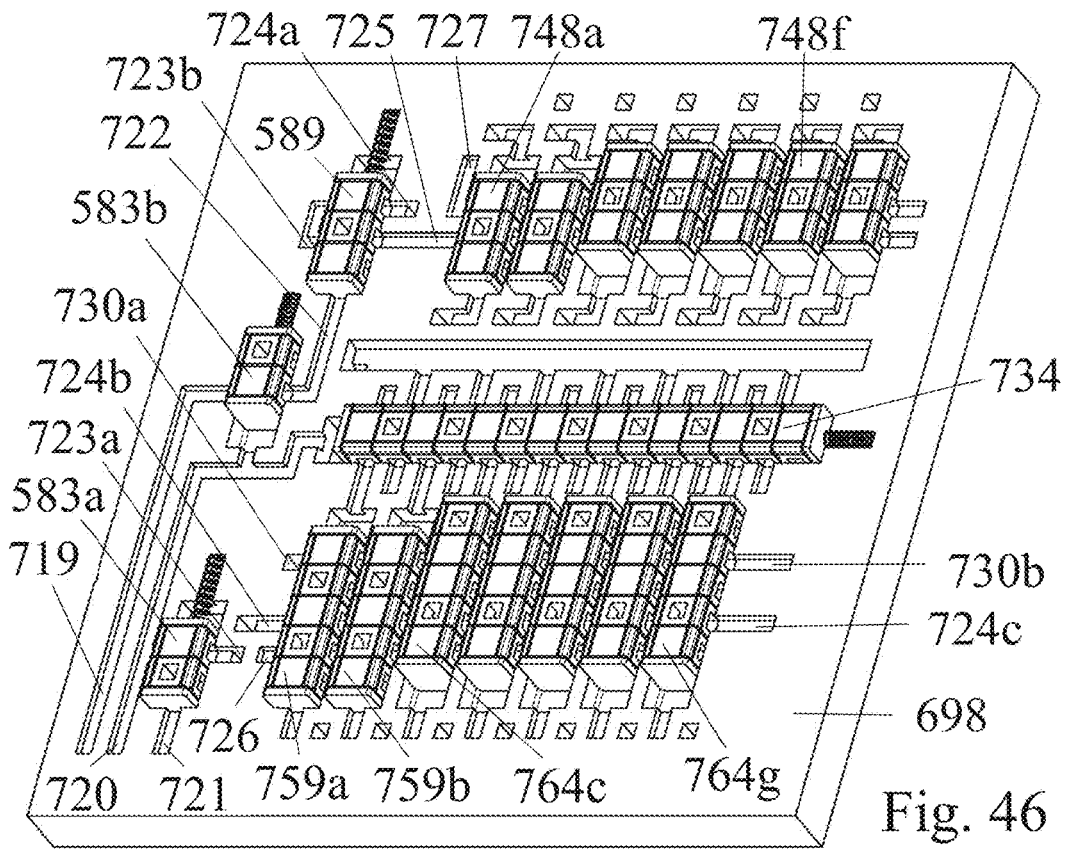

Drawing 54 contains FIG. 45 and FIG. 46. FIG. 45 is an isometric view of the LFSR assembly in state 2 clock hi. FIG. 46 is an isometric view of the LFSR assembly in state 2 clock low.

Figure 47:
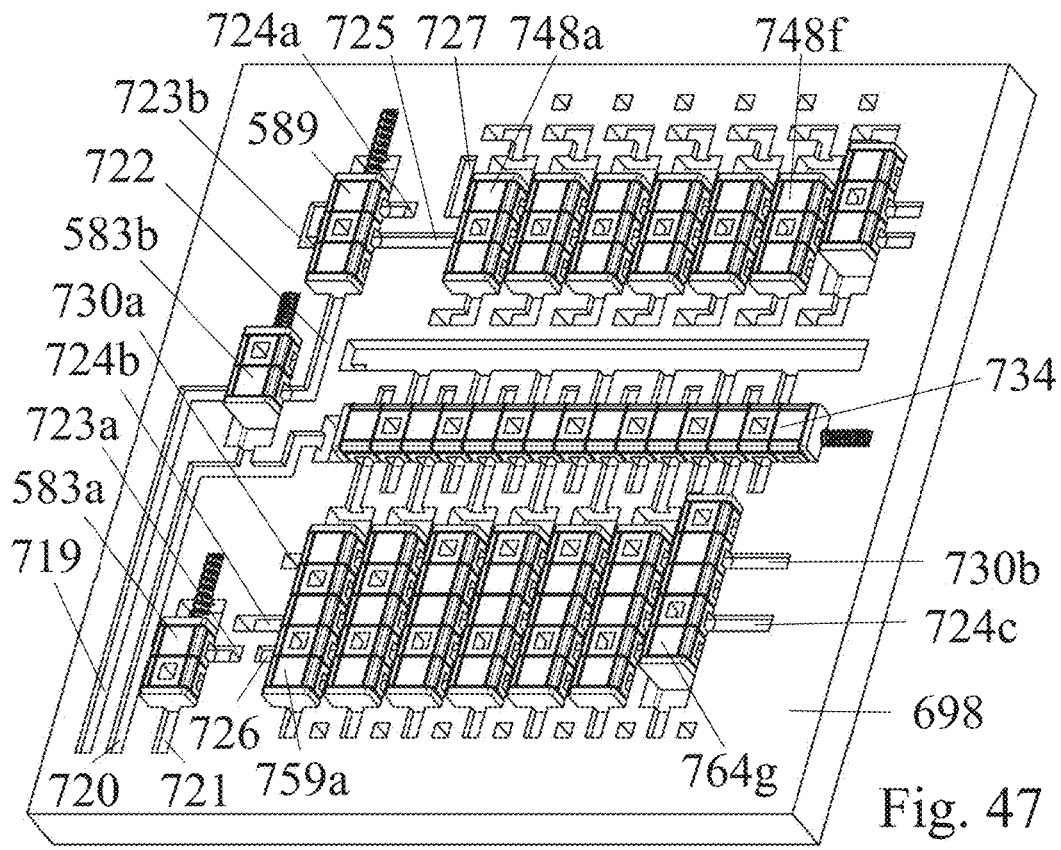
Figure 48:
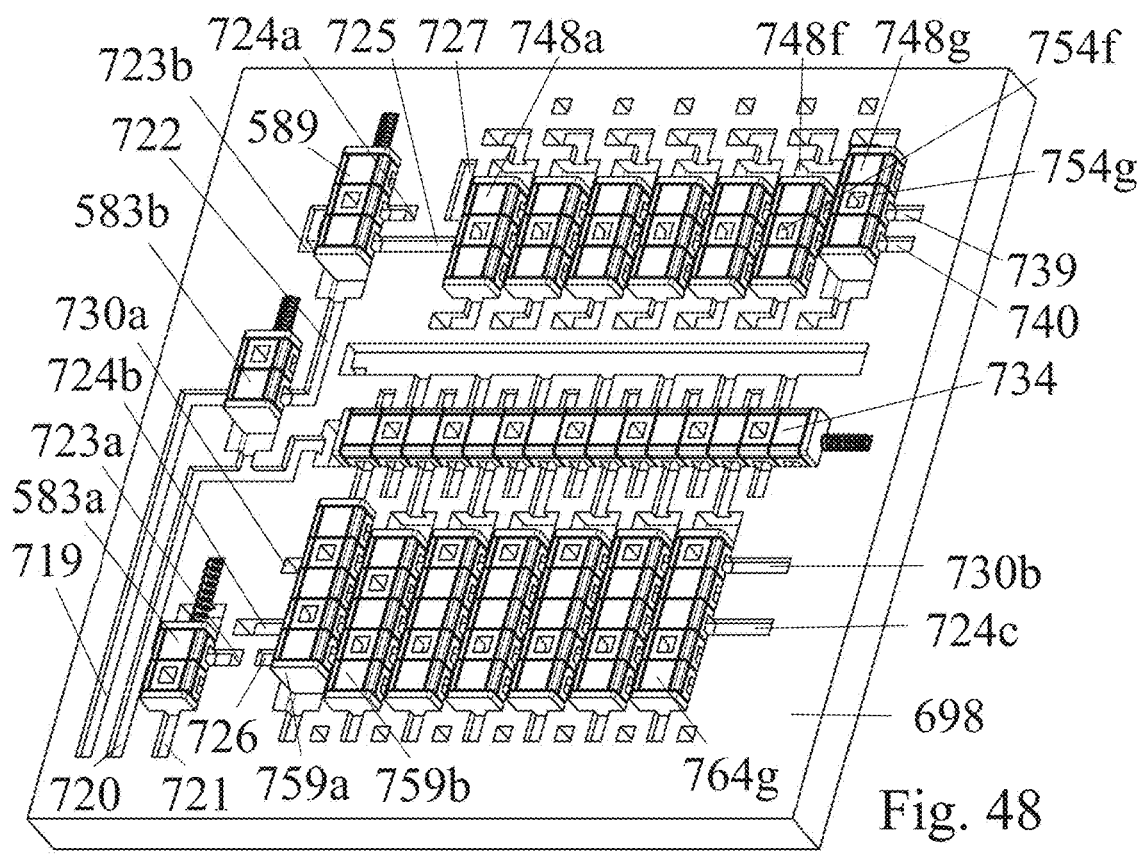

Drawing 55 contains FIG. 47 and FIG. 48. FIG. 47 is an isometric view of the LFSR assembly in state 6 clock low. FIG. 48 is an isometric view of the LFSR assembly in state 6 clock hi.

Figure 49:
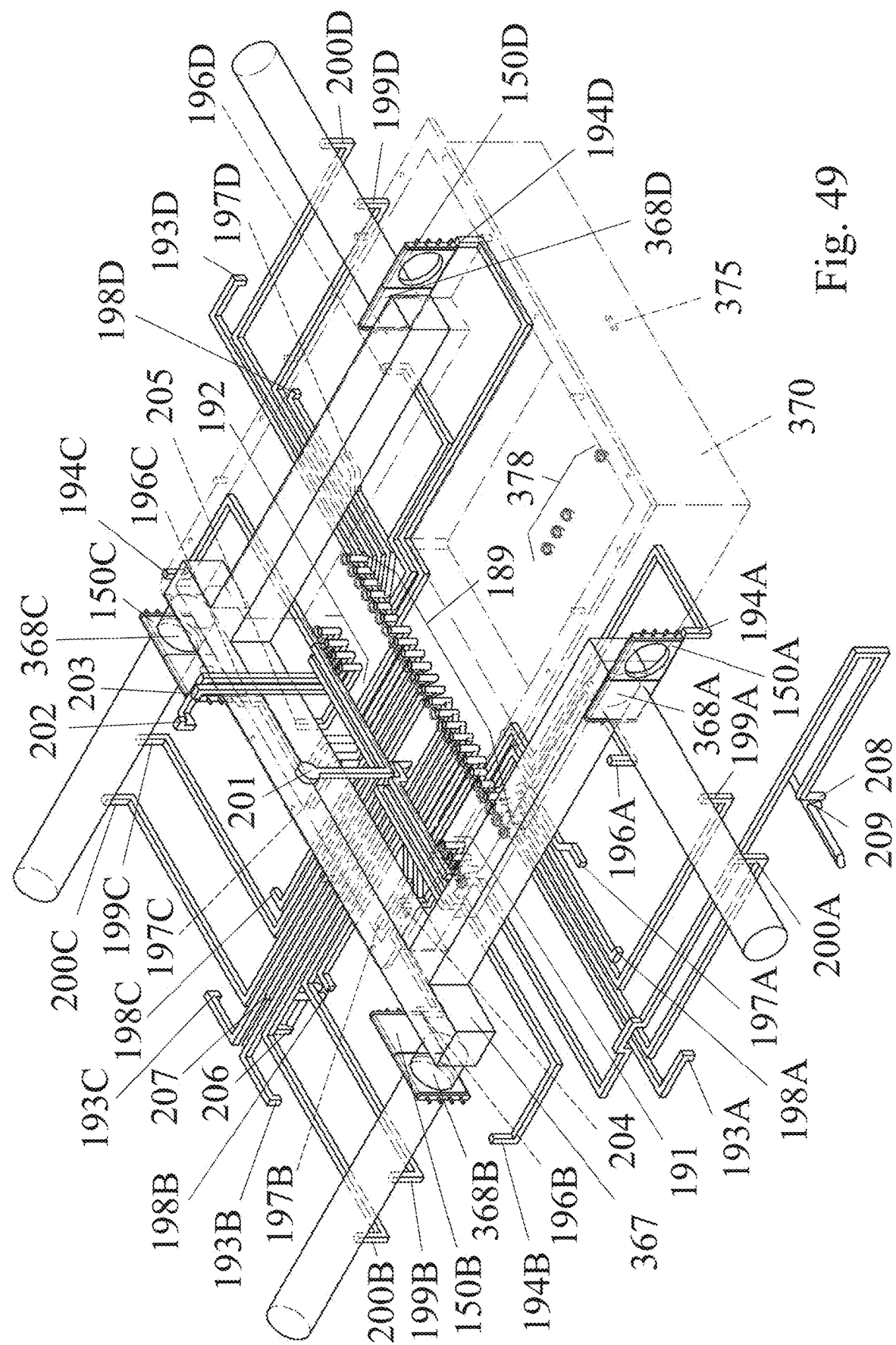

Drawing 56 contains FIG. 49. FIG. 49 is an isometric view of node core pipes routing into the module assembly.

Figure 50:
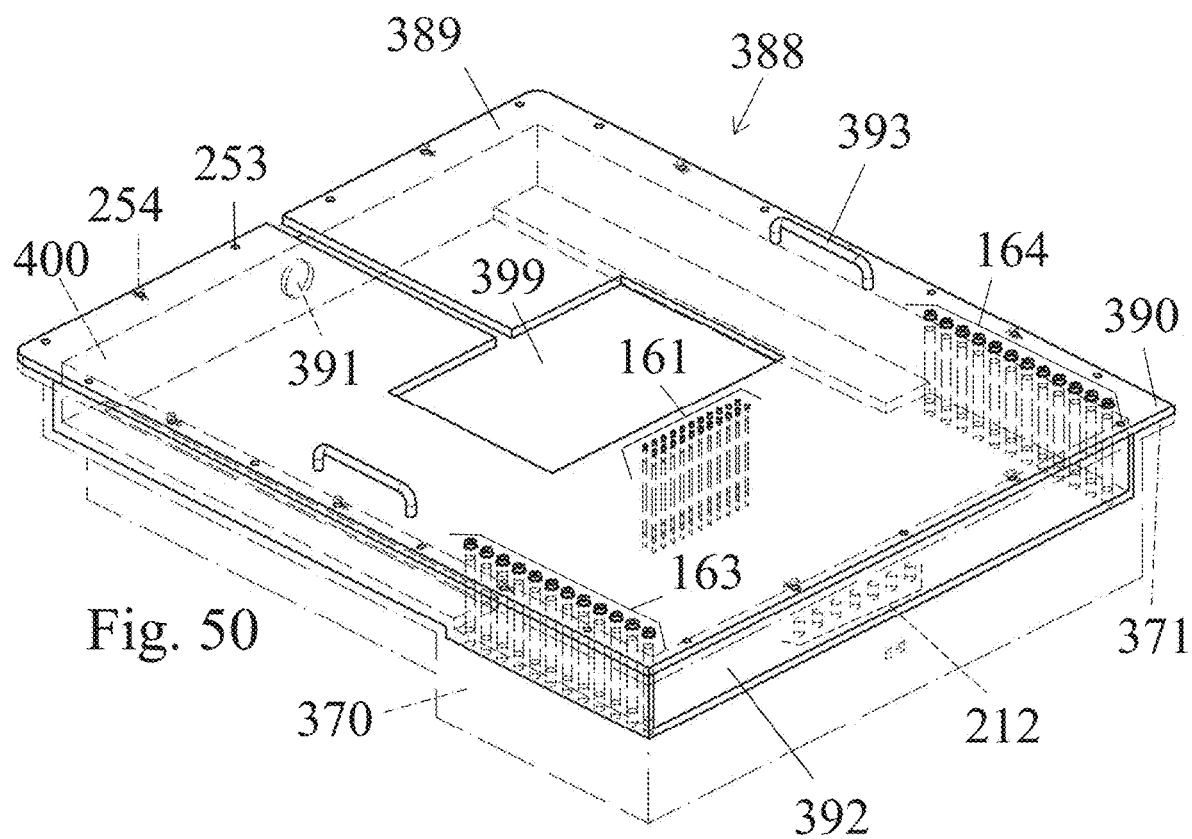
Figure 51:
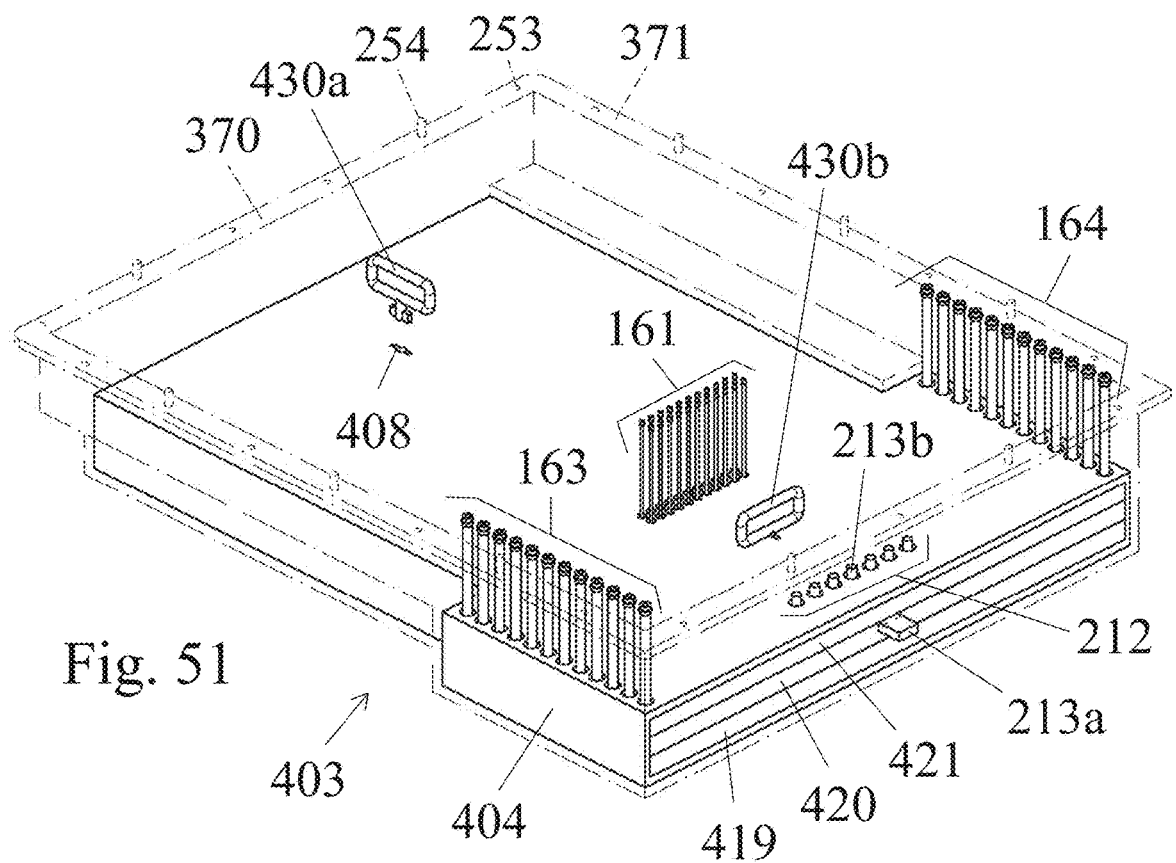

Drawing 57 contains FIG. 50 and FIG. 51. FIG. 50 is an isometric view of expansion unit assembly 388. FIG. 51 is an isometric view of i/o unit assembly showing the extractor 430.

Figure 52:
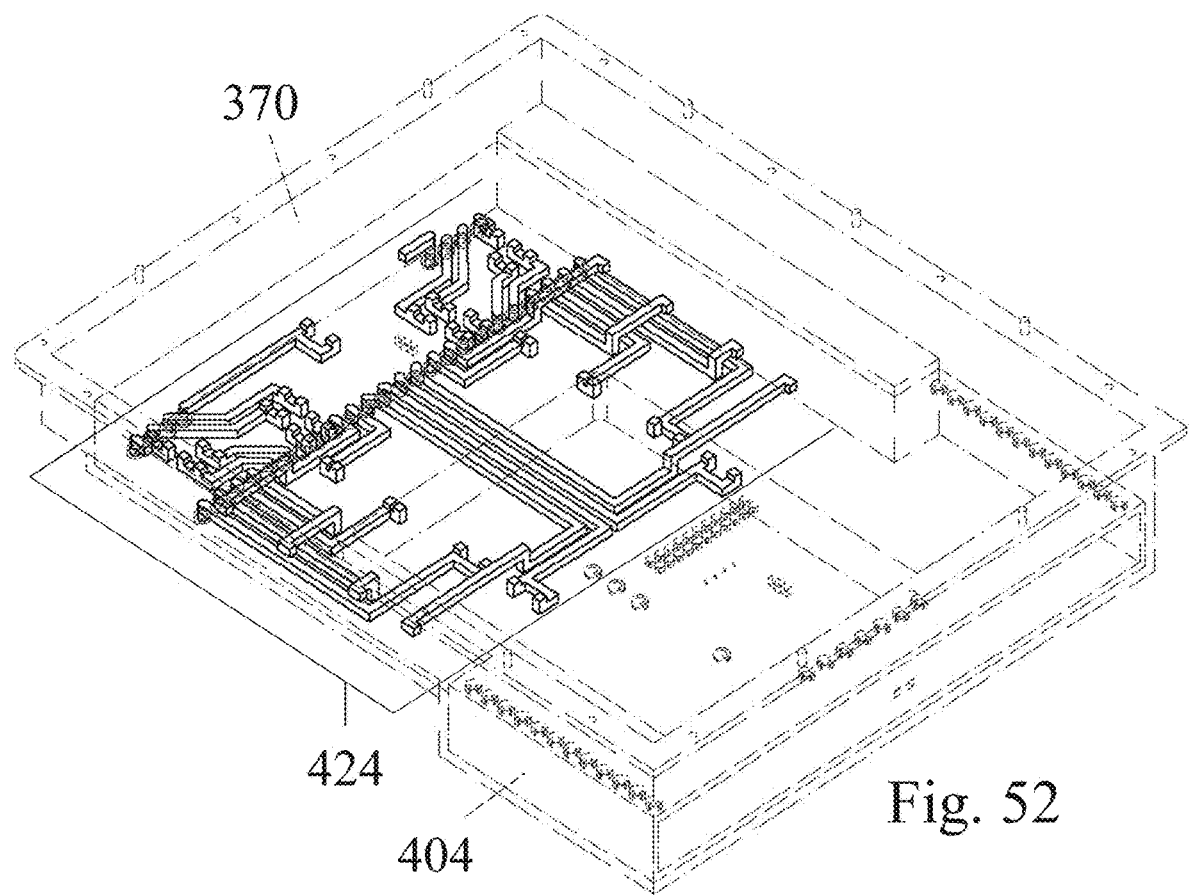
Figure 53:
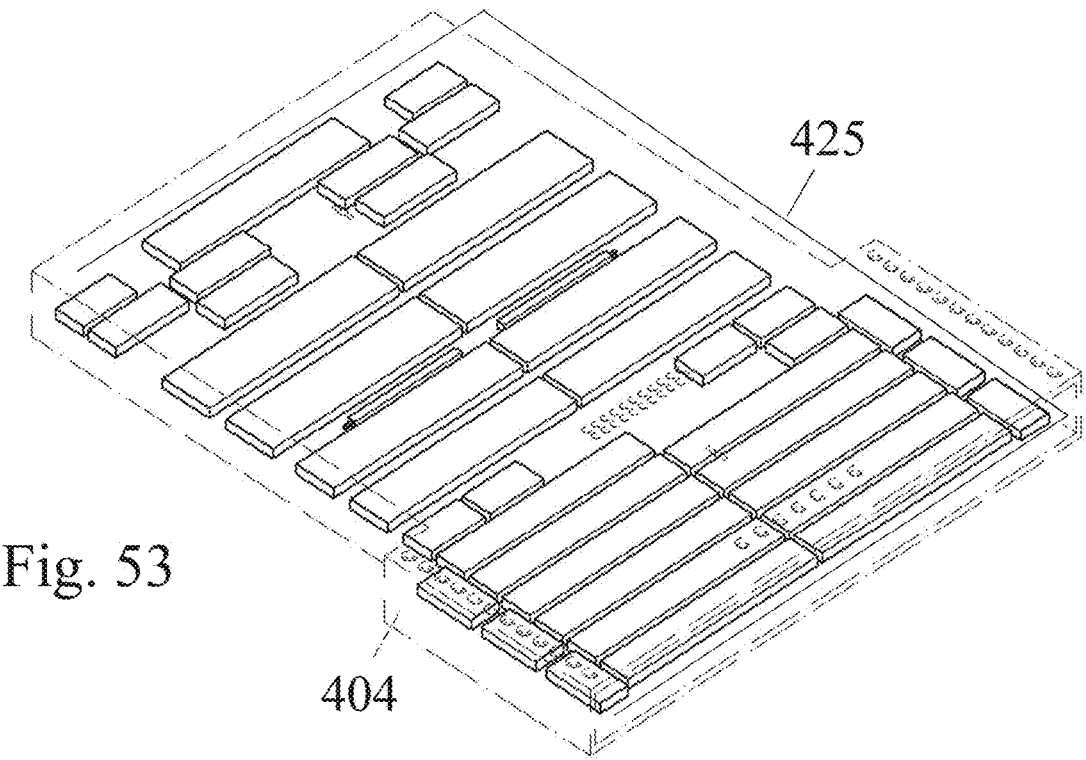

Drawing 58 contains FIG. 52 and FIG. 53. FIG. 52 is an isometric view of control pipes routing into i/o unit assembly. FIG. 53 is an isometric view of i/o unit assembly showing the i/o components cavities 425.

Figure 54:
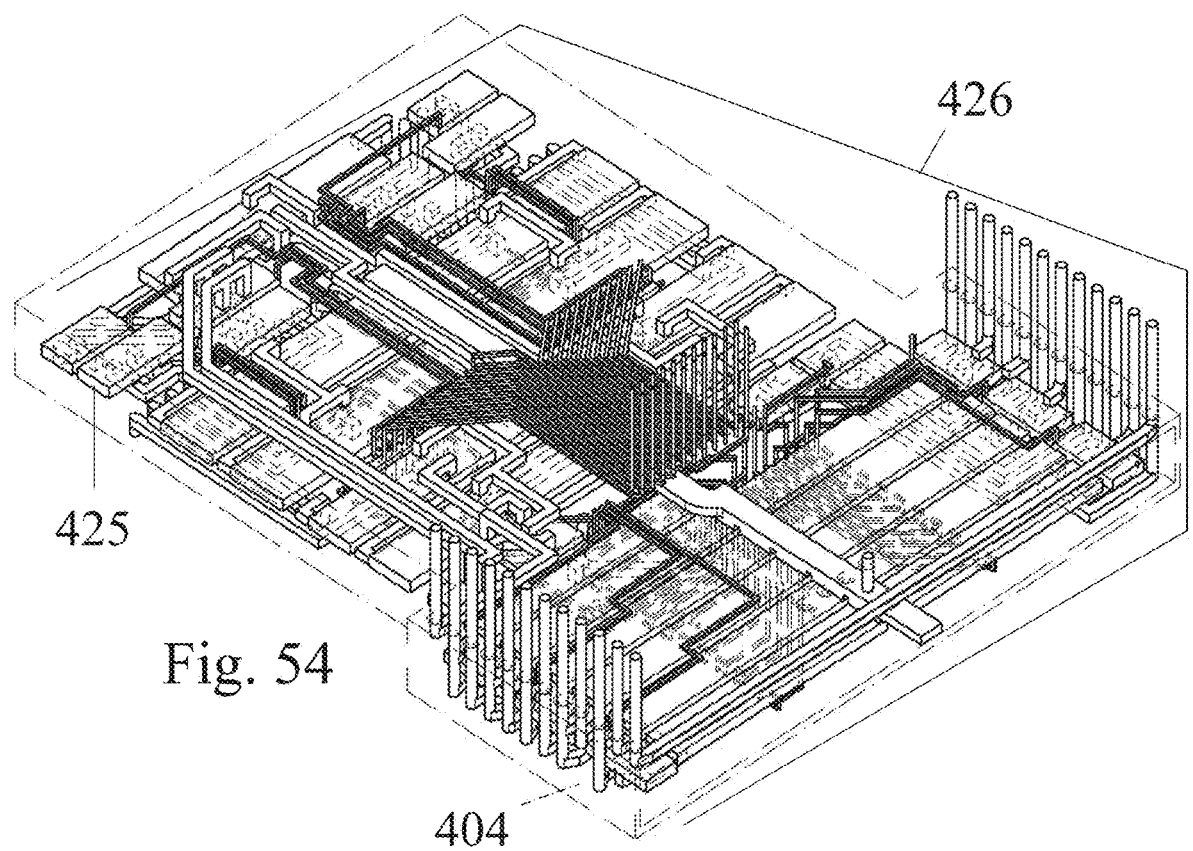
Figure 55:
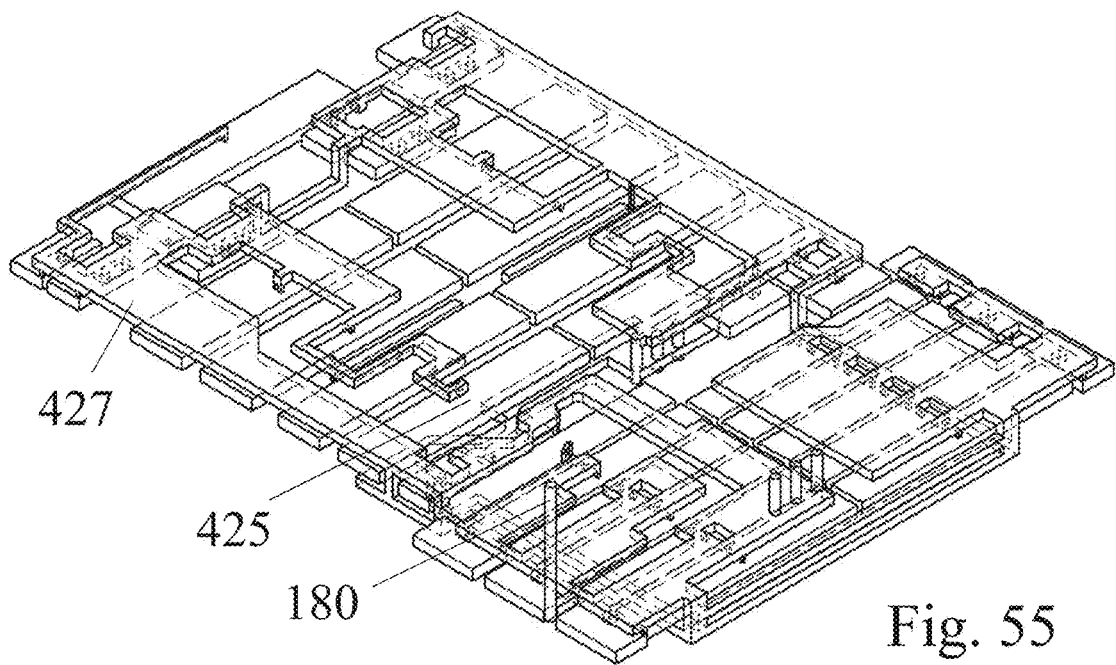

Drawing 59 contains FIG. 54 and FIG. 55. FIG. 54 is an isometric view of i/o unit assembly showing the i/o components cavities 425 and the i/o pipework 426. FIG. 55 is an isometric view of i/o unit assembly showing the i/o components cavities 425 and the i/o ground plane 427.

Figure 56:
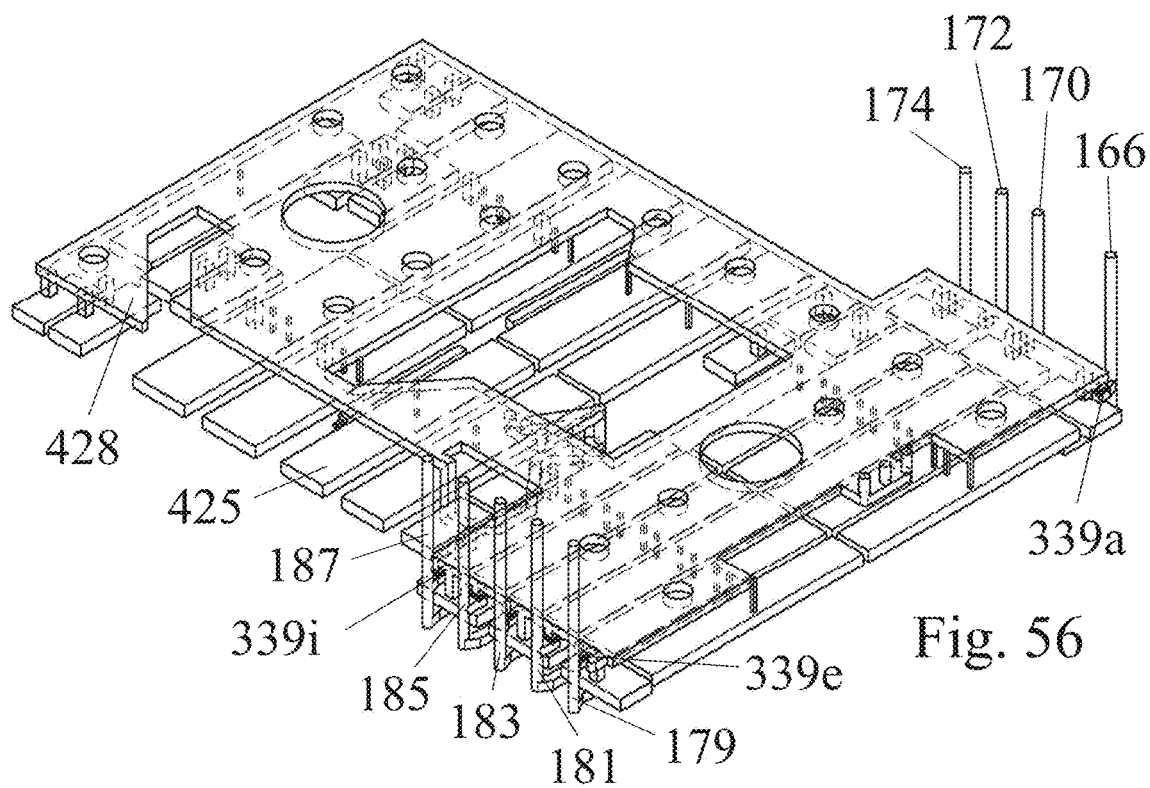
Figure 57:
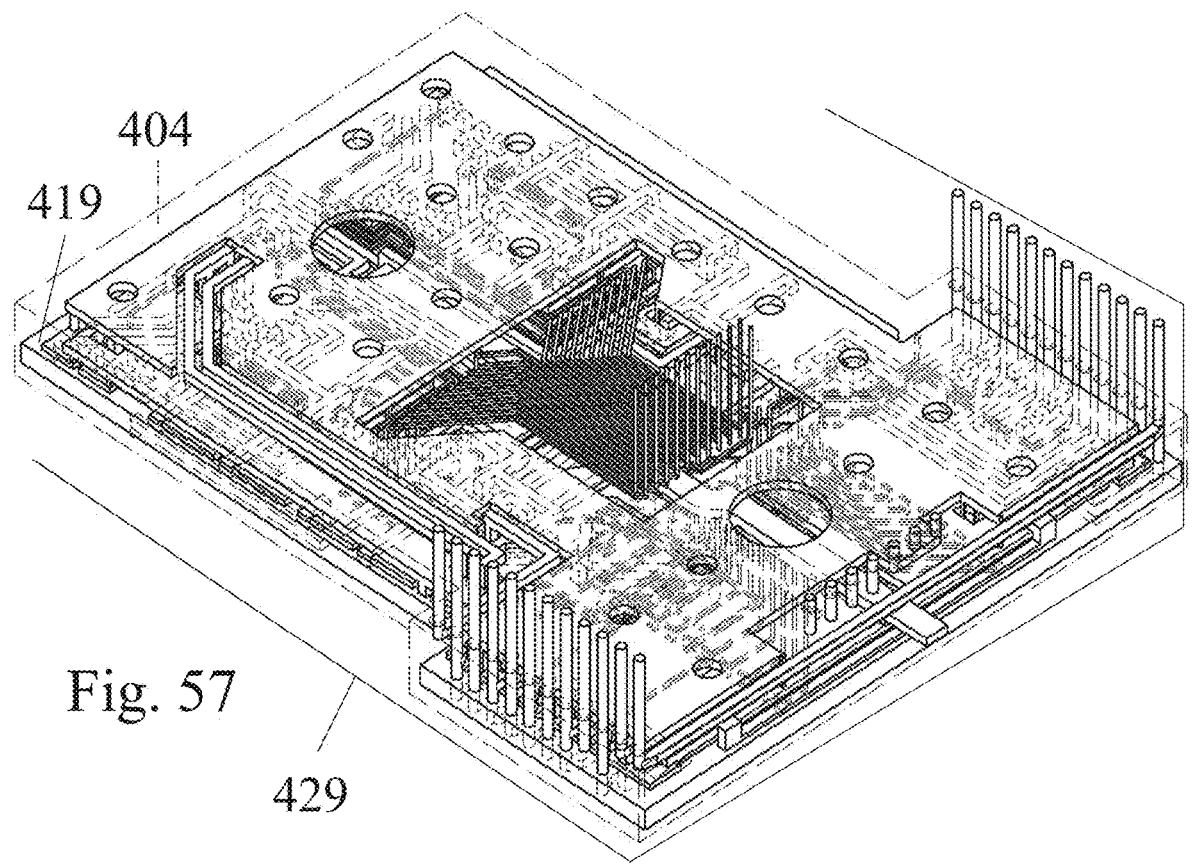

Drawing 60 contains FIG. 56 and FIG. 57. FIG. 56 is an isometric view of i/o unit assembly showing the i/o components cavities 425 and the i/o high pressure plane 428. FIG. 57 is an isometric view of the i/o layer a 419 showing all i/o layer cutouts 429.

Figure 58:
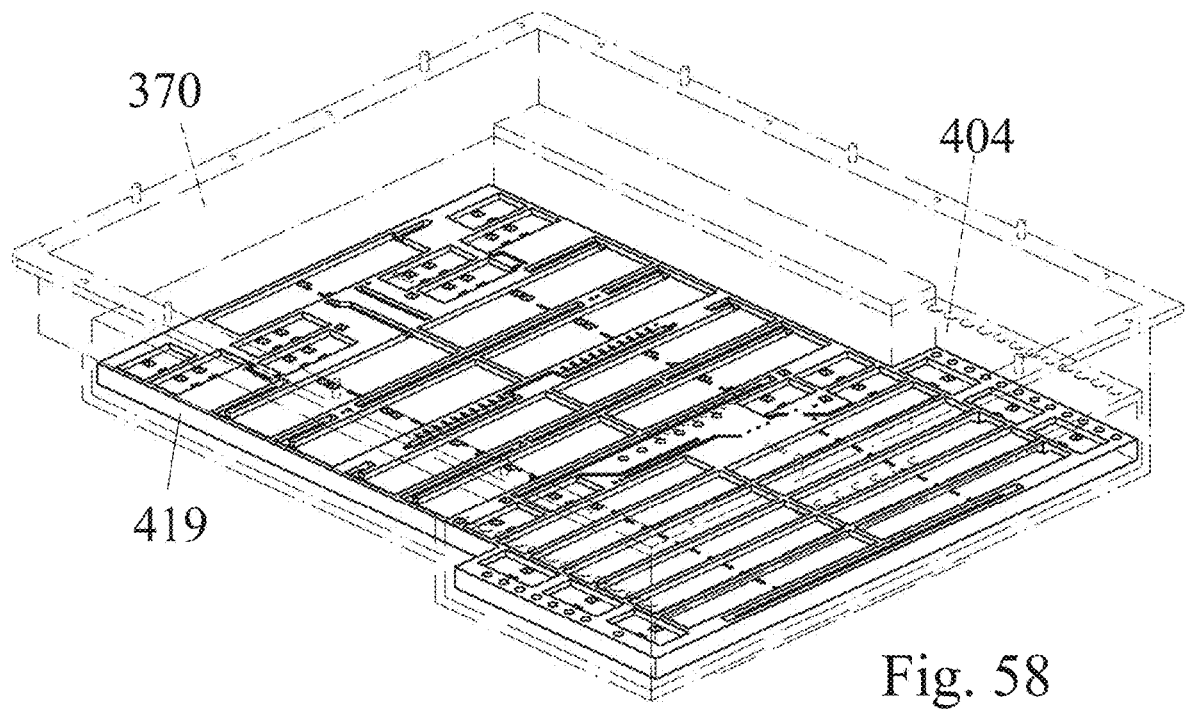
Figure 59:
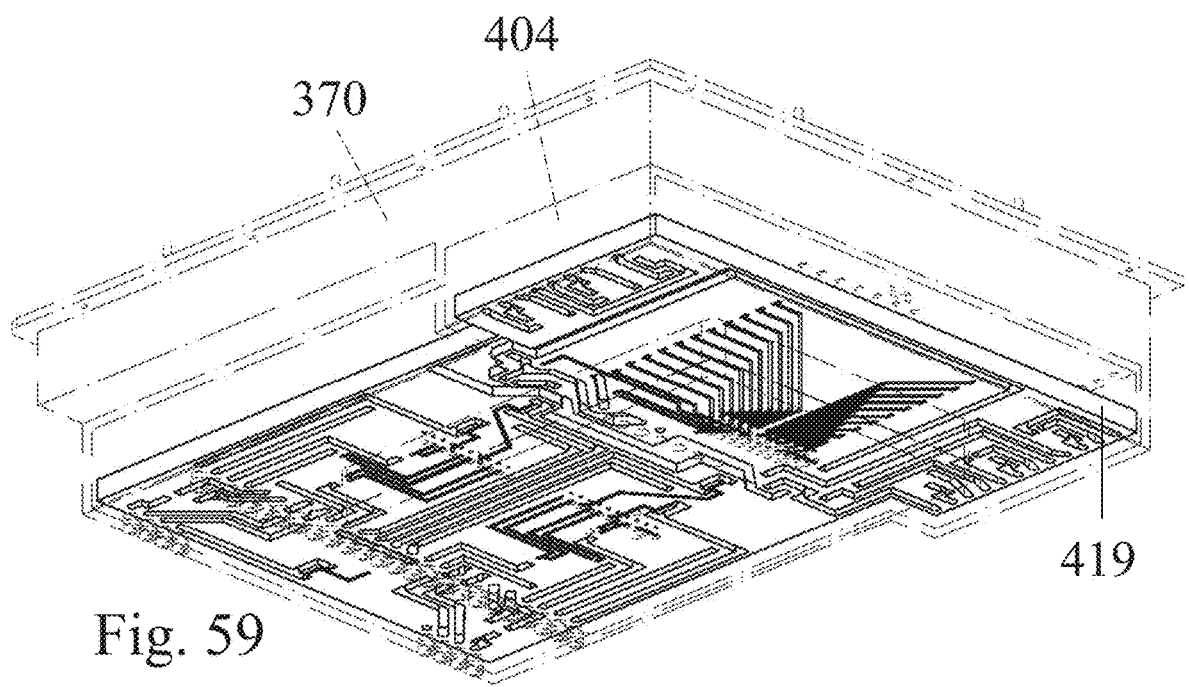

Drawing 61 contains FIG. 58 and FIG. 59. FIG. 58 is an isometric top view of i/o layer a 419. FIG. 59 is an isometric bottom view of i/o layer a 419.

Figure 60:
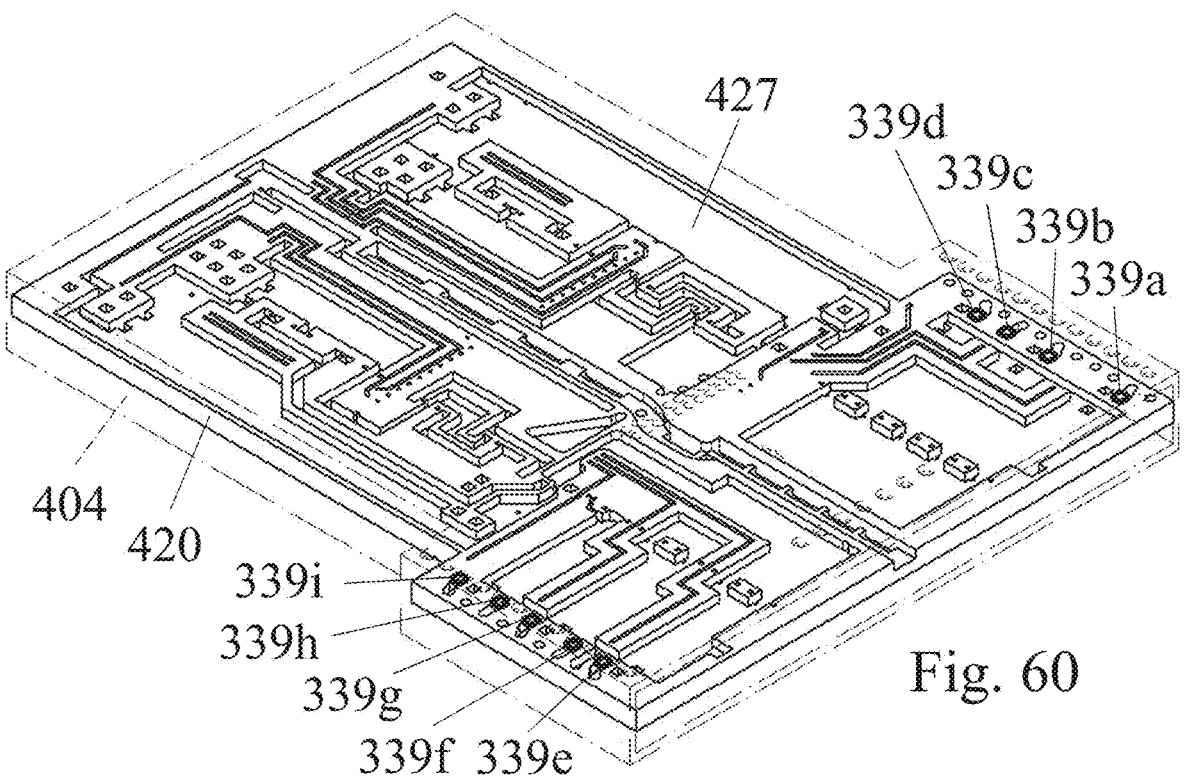
Figure 61:
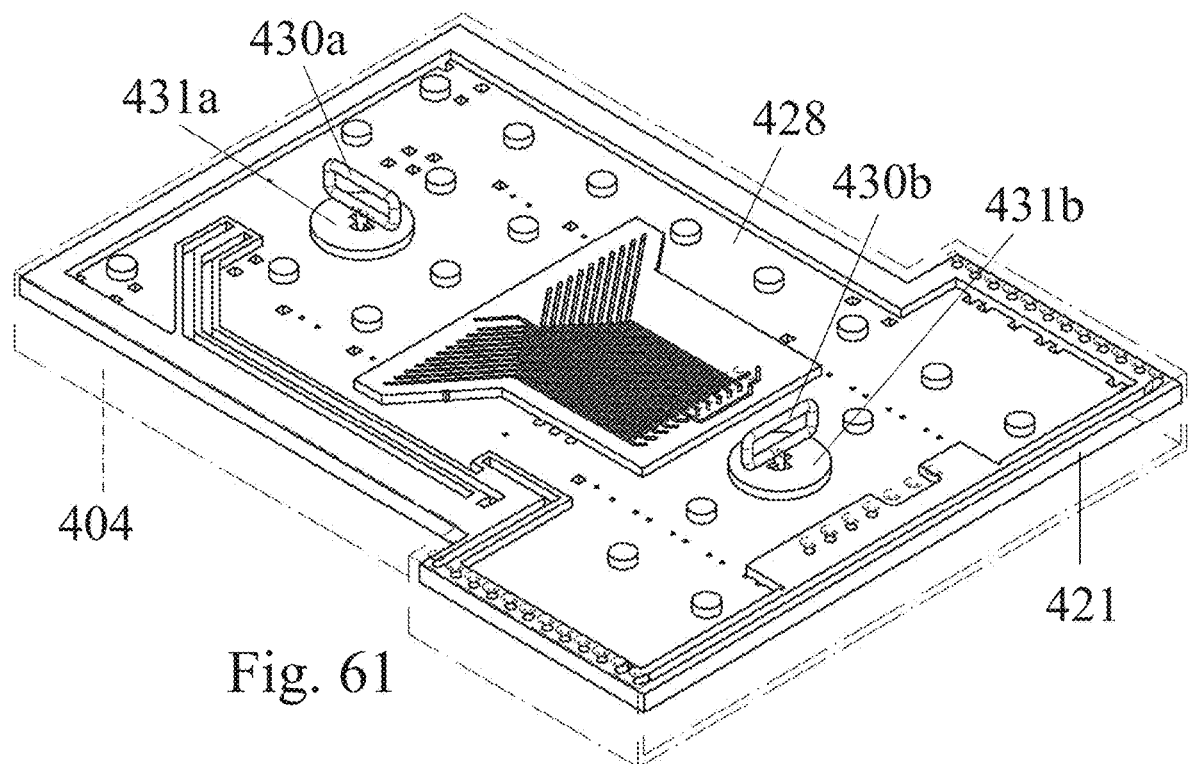

Drawing 62 contains FIG. 60 and FIG. 61. FIG. 60 is an isometric top view of i/o layer b 420 showing the installed check valves 339. FIG. 61 is an isometric top view of i/o layer c 421 showing the extractor 430.

Figure 62:
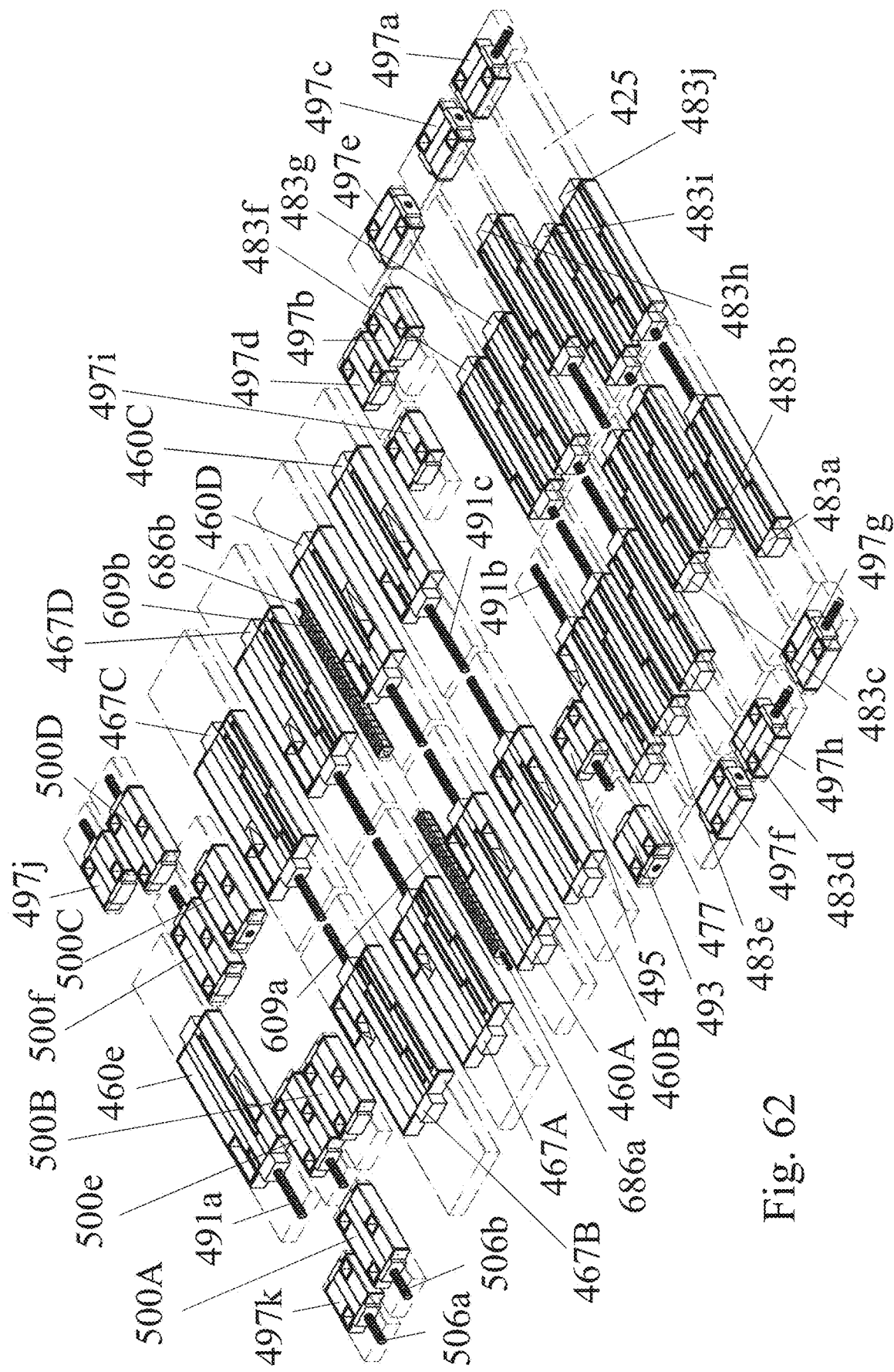

Drawing 63 contains FIG. 62. FIG. 62 is an isometric view of the i/o components in the i/o components cavities 425.

Figure 63:
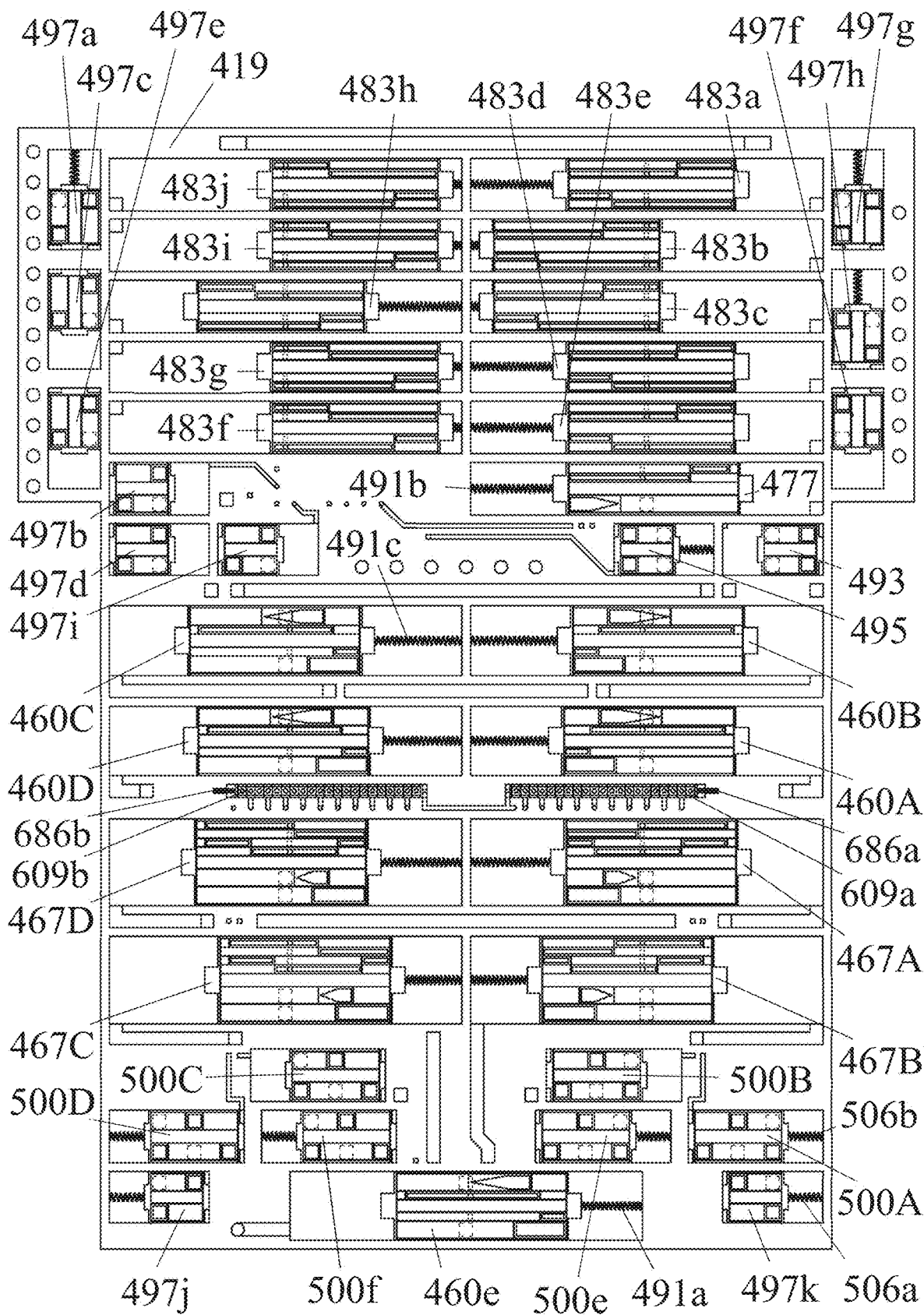

Drawing 64 contains FIG. 63. FIG. 63 is a top view of i/o layer a 419 with the i/o components.

Figure 64:
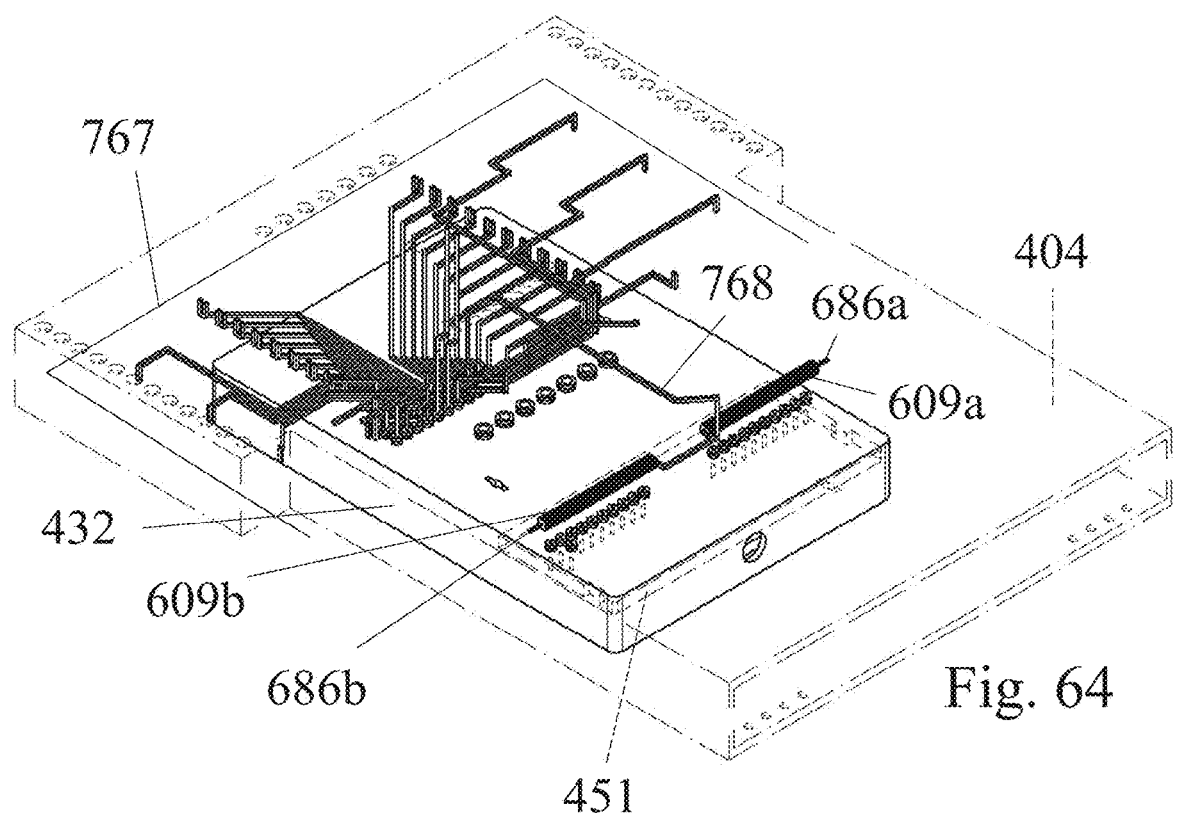
Figure 65:
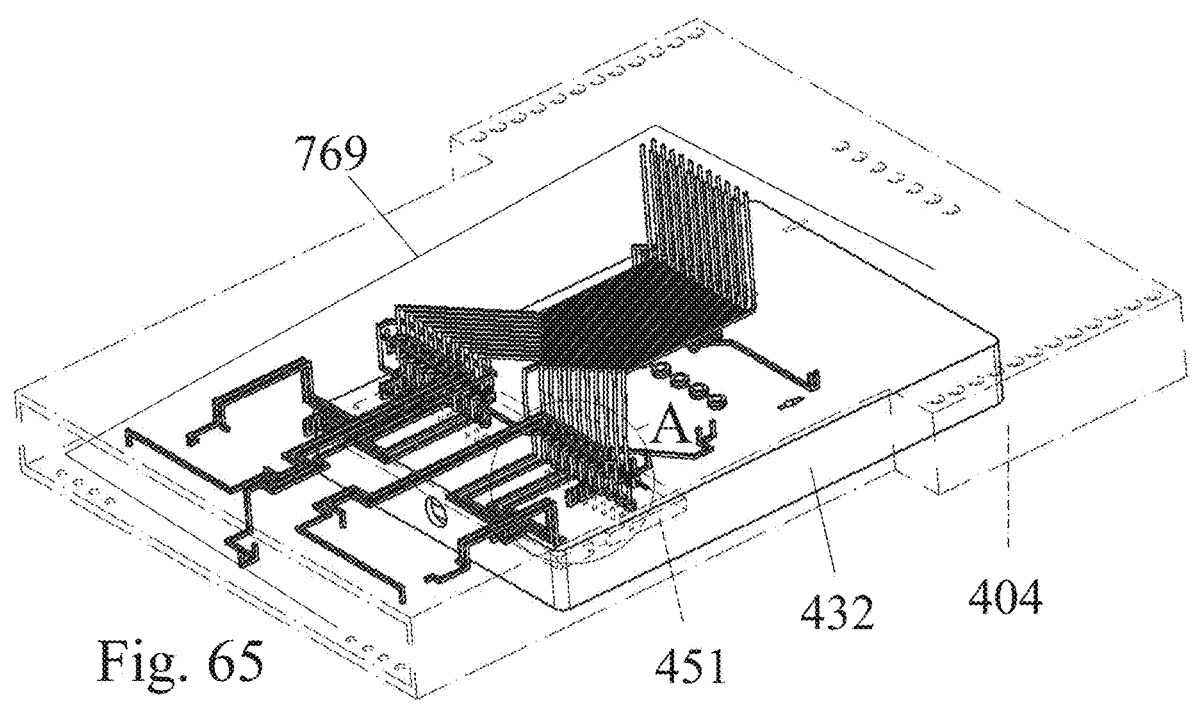

Drawing 65 contains FIG. 64 and FIG. 65. FIG. 64 is an isometric view of the logic signal connections 767 between the logic unit assembly and the i/o unit assembly. FIG. 65 is an isometric view of the logic unit assembly showing the diagnose connections 769.

Figure 65A:
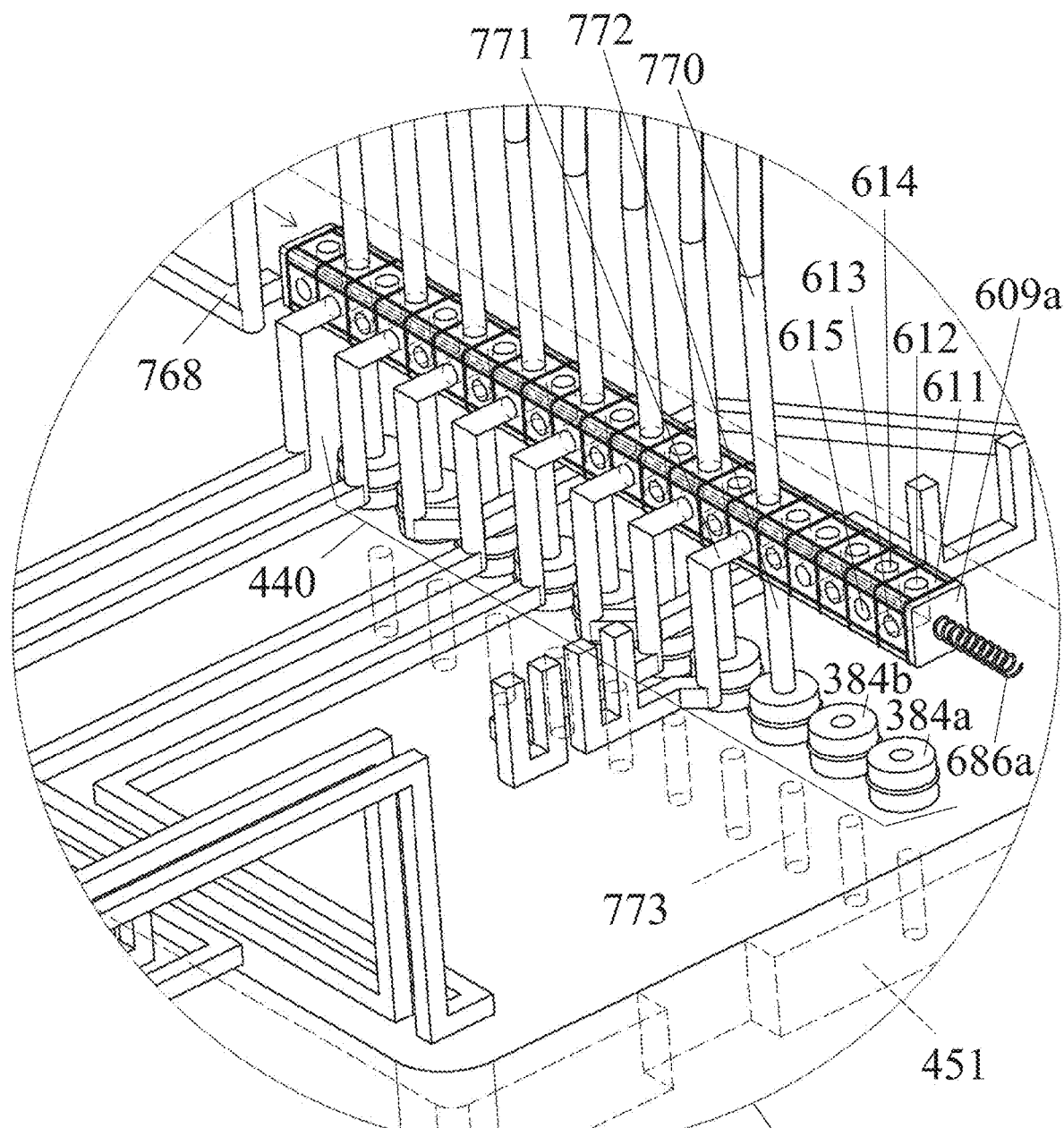

Drawing 66 contains Detail FIG. 65A. Detail FIG. 65A shows the diagnose gate 609 and the diagnose connections.

Figure 66:
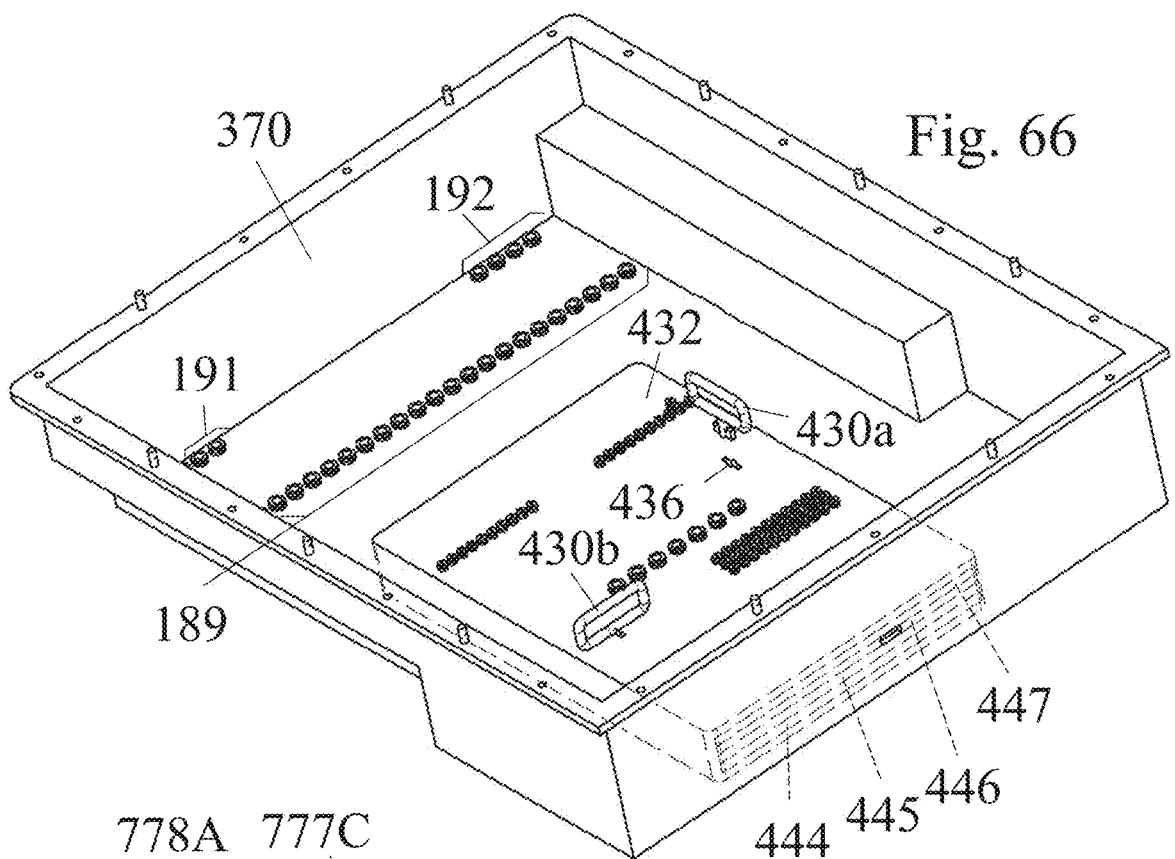
Figure 67:
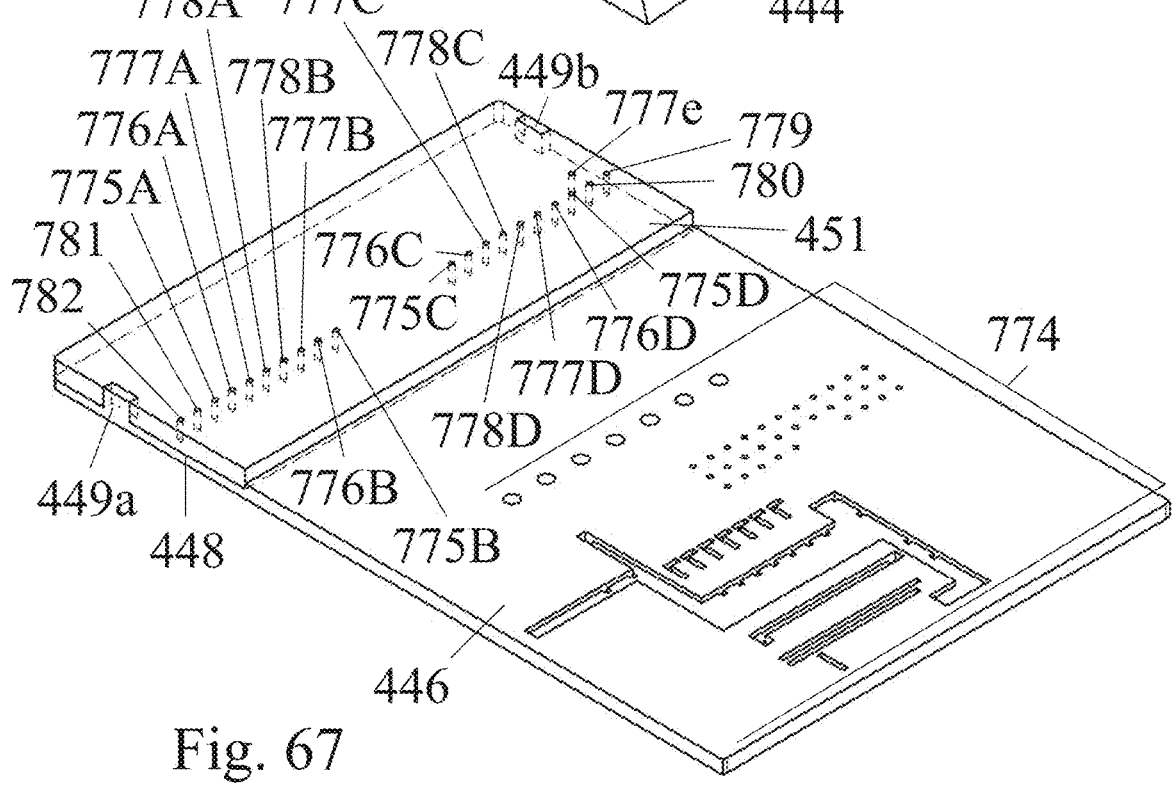

Drawing 67 contains FIG. 66 and FIG. 67. FIG. 66 is an isometric view of the logic unit assembly 432 showing the extractor 430. FIG. 67 is an isometric view of the logic layer c 446 with installed router plate direct 451.

Figure 68:
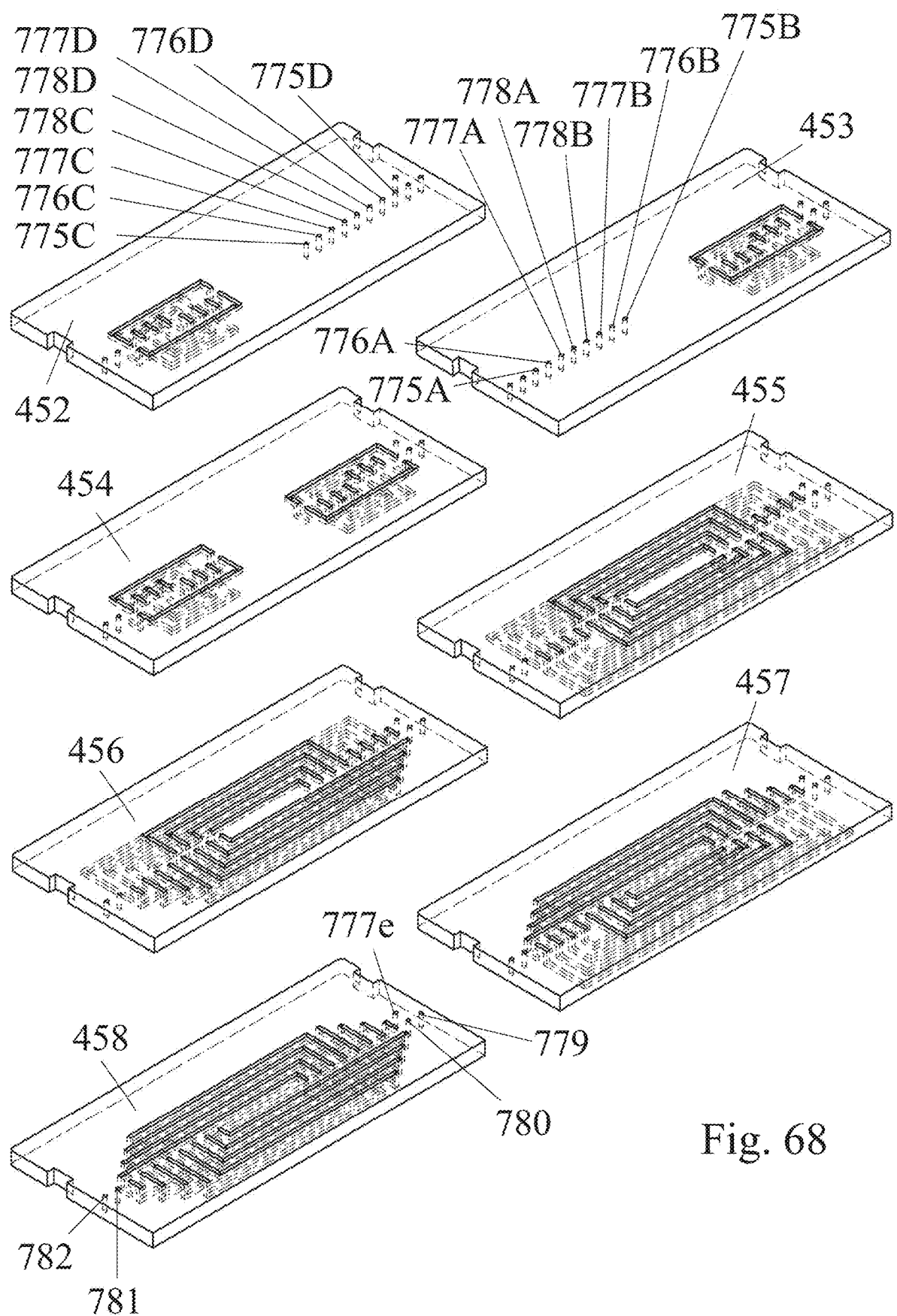

Drawing 68 contains FIG. 68. FIG. 68 is an isometric view of the router plates.

Figure 69:
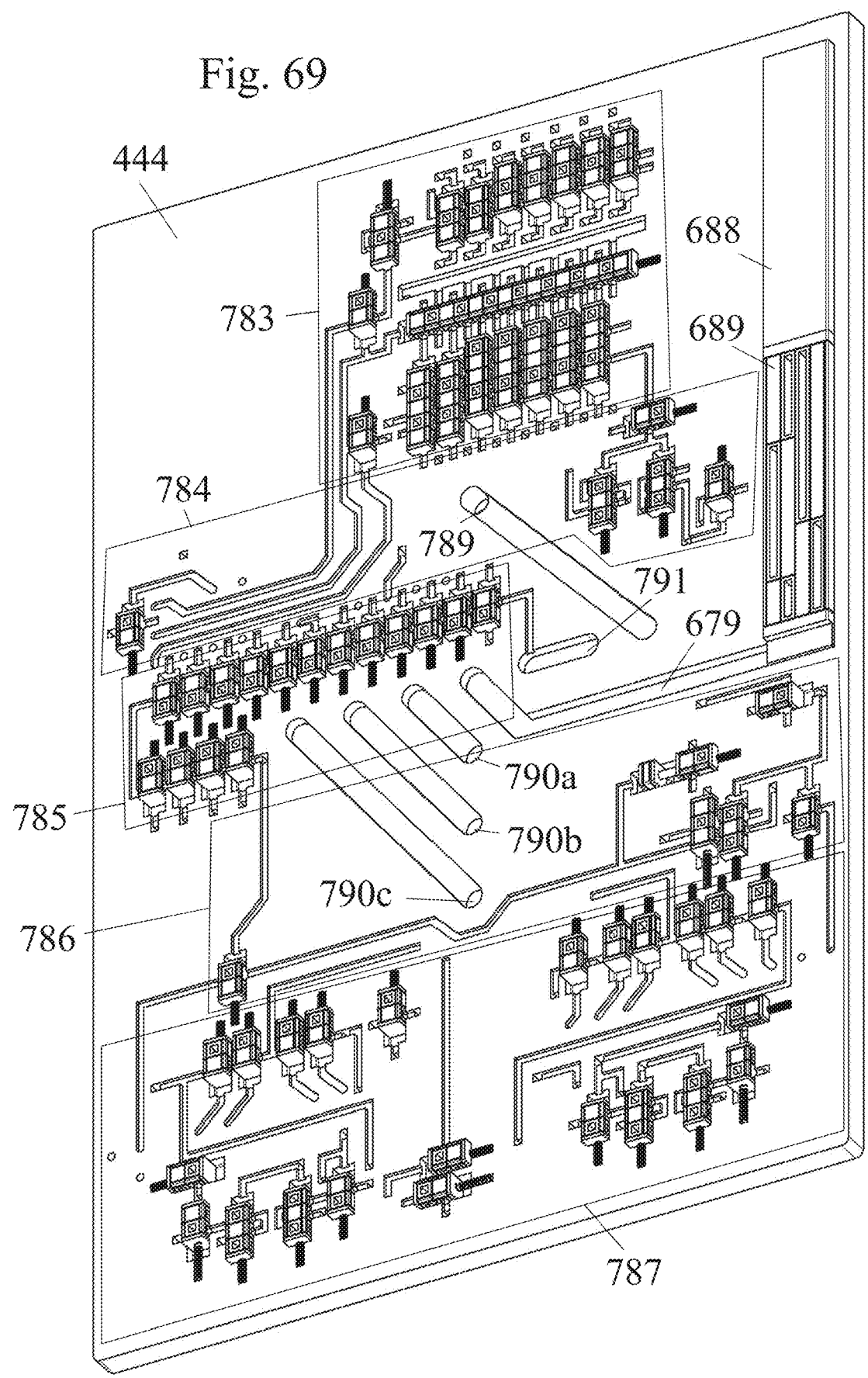

Drawing 69 contains FIG. 69. FIG. 69 is an isometric view of the logic layer a 444 showing the logic blocks.

Figure 70:
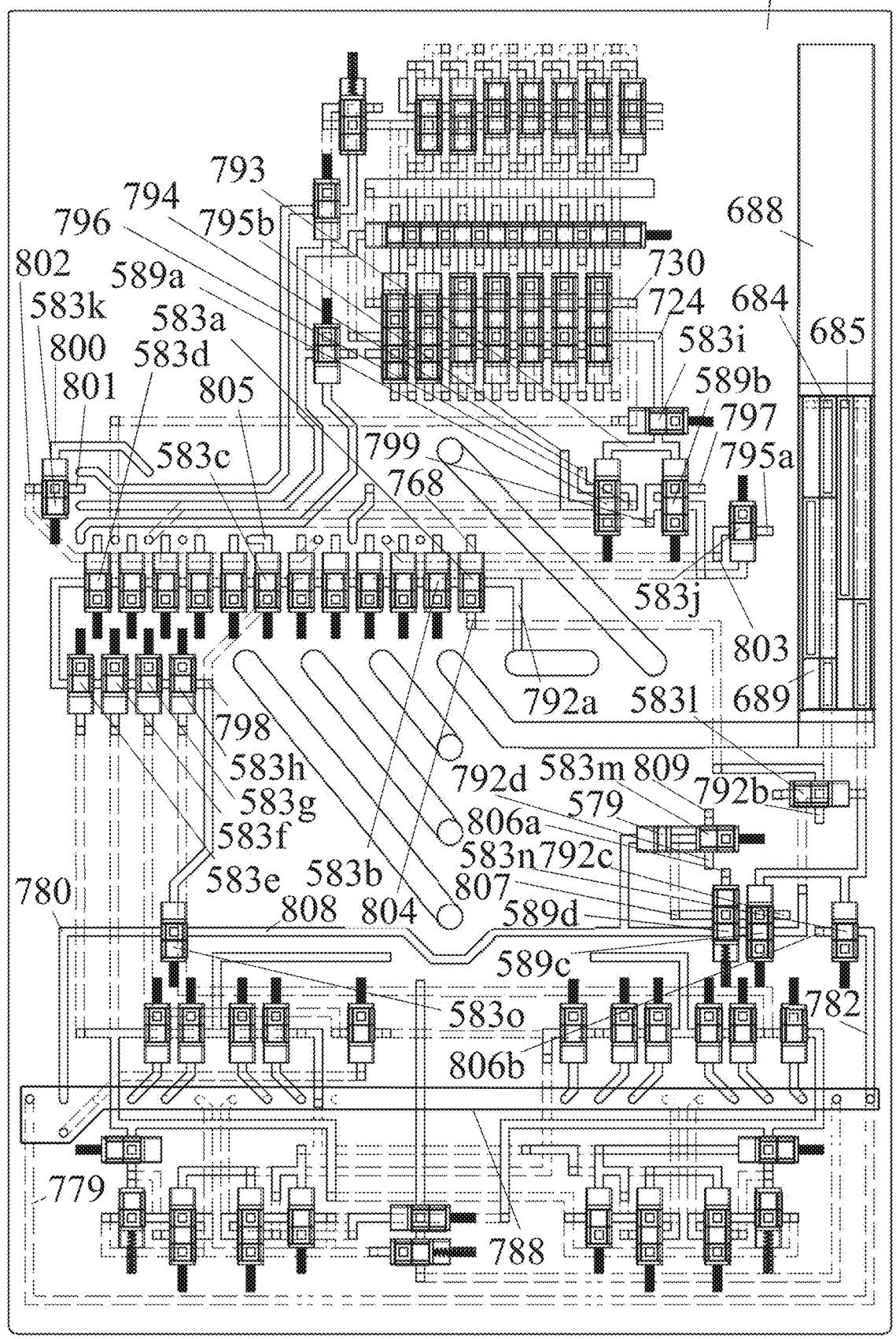

Drawing 70 contains FIG. 70. FIG. 70 is a top view of the logic layer a 444 showing the installed logic components.

Figure 71:
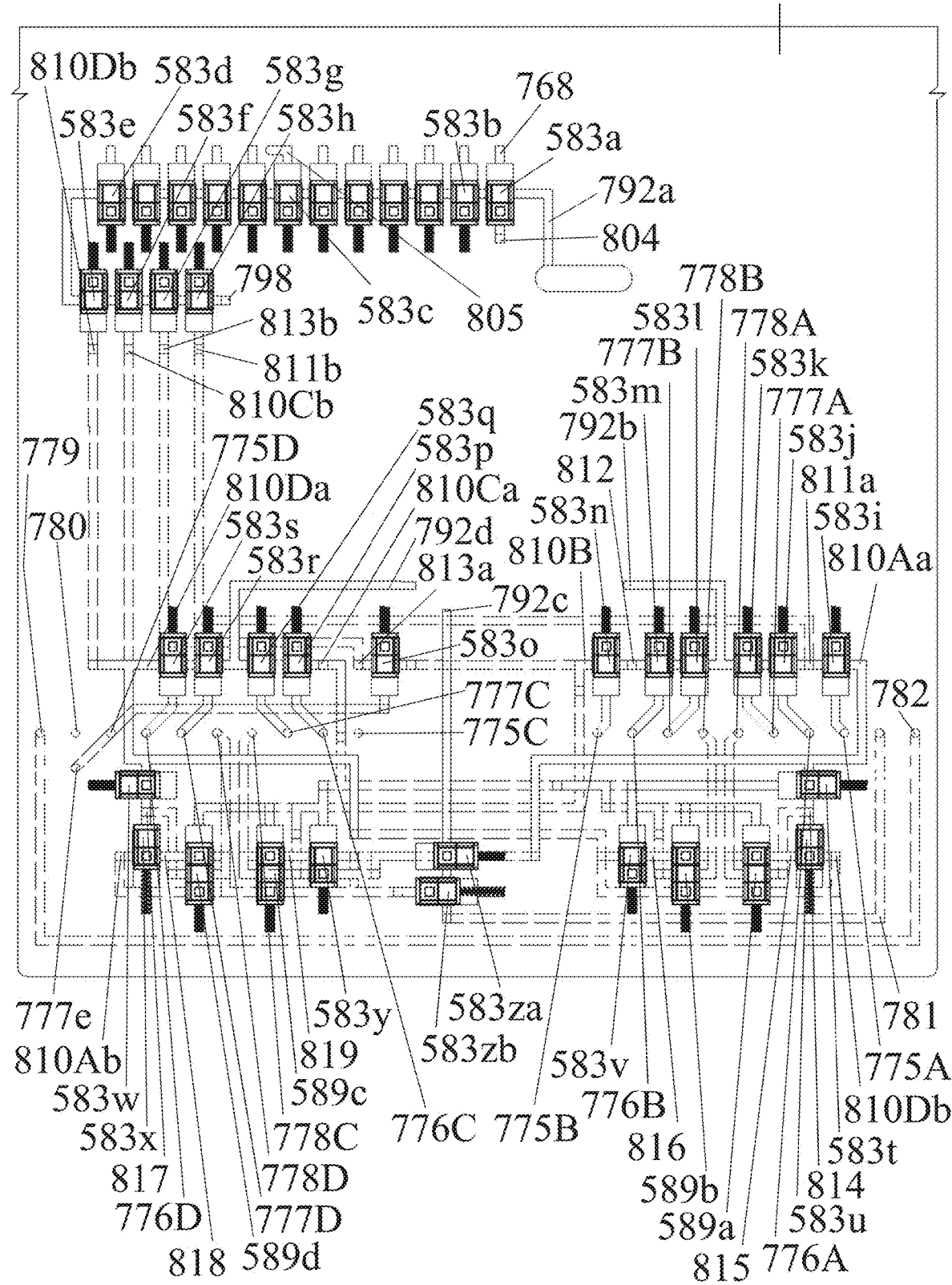

Drawing 71 contains FIG. 71. FIG. 71 is a top view of a portion of the logic layer a 444 and the logic components.

Figure 72:
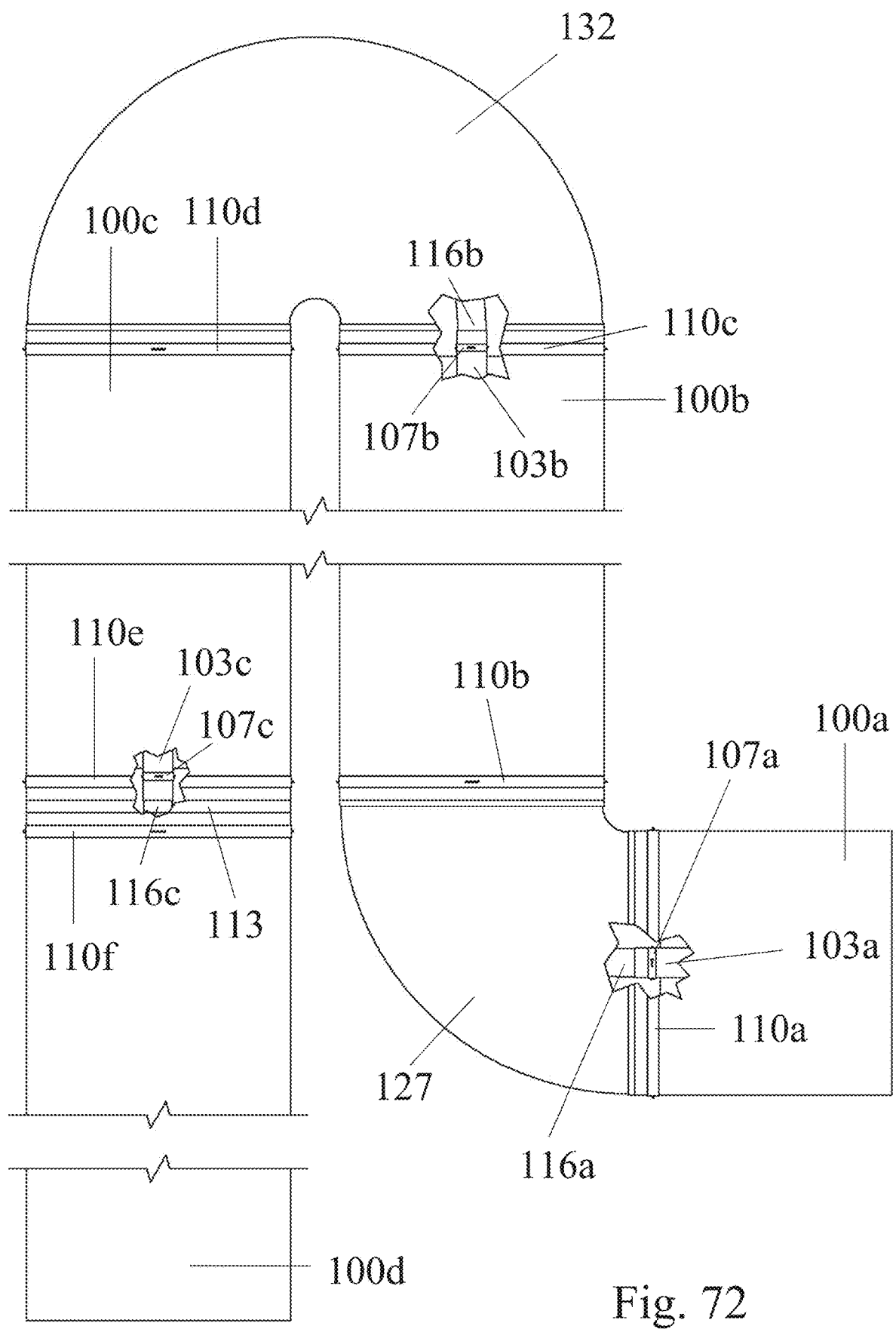

Drawing 72 contains FIG. 72. FIG. 72 is a top cutout view of a reactor section showing the use of joints.

Figure 73:
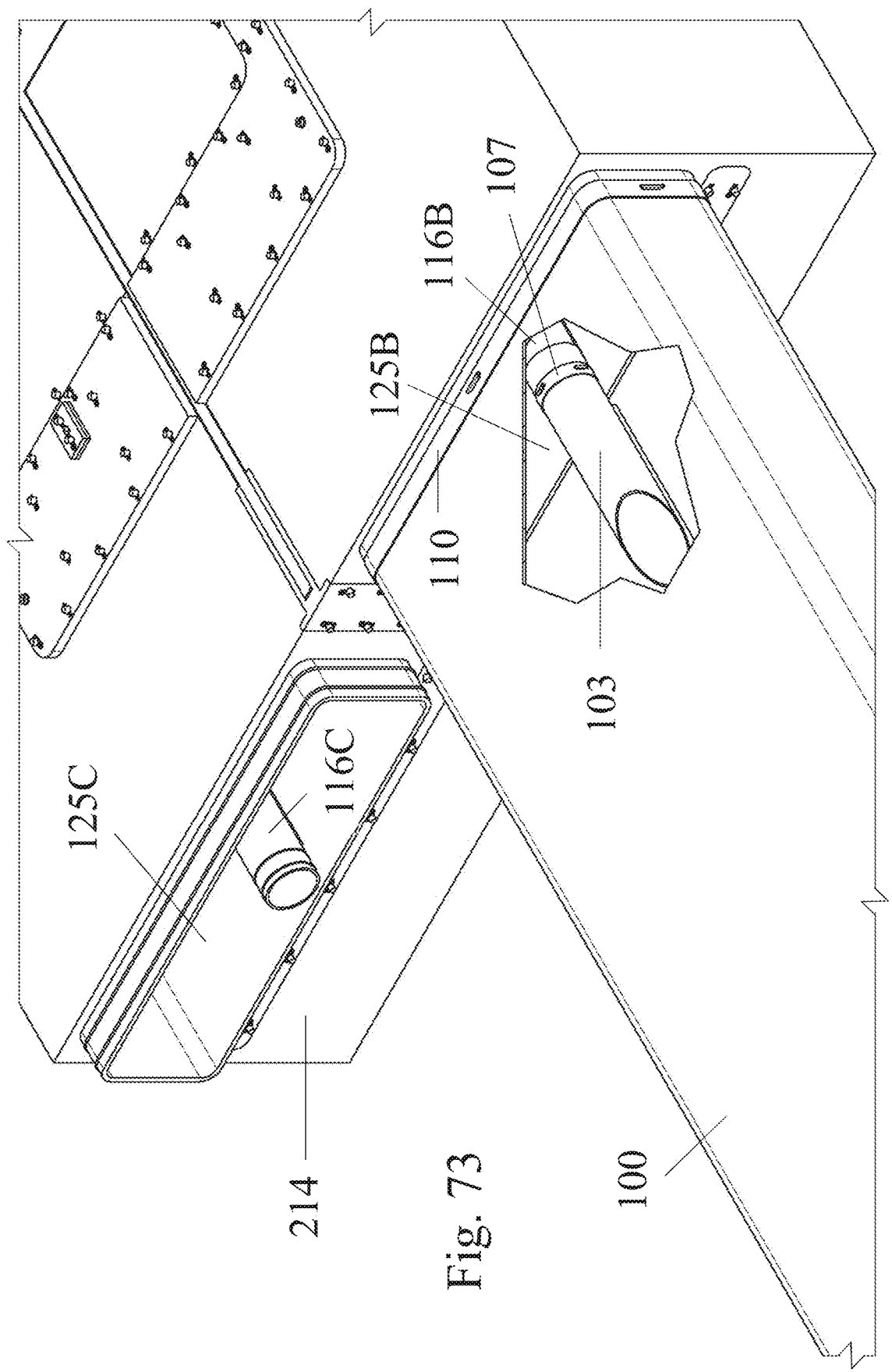

Drawing 73 contains FIG. 73. FIG. 73 is an isometric cutout view of the reactor node 214 showing the fixation of the pipe element 100.

Figure 74:
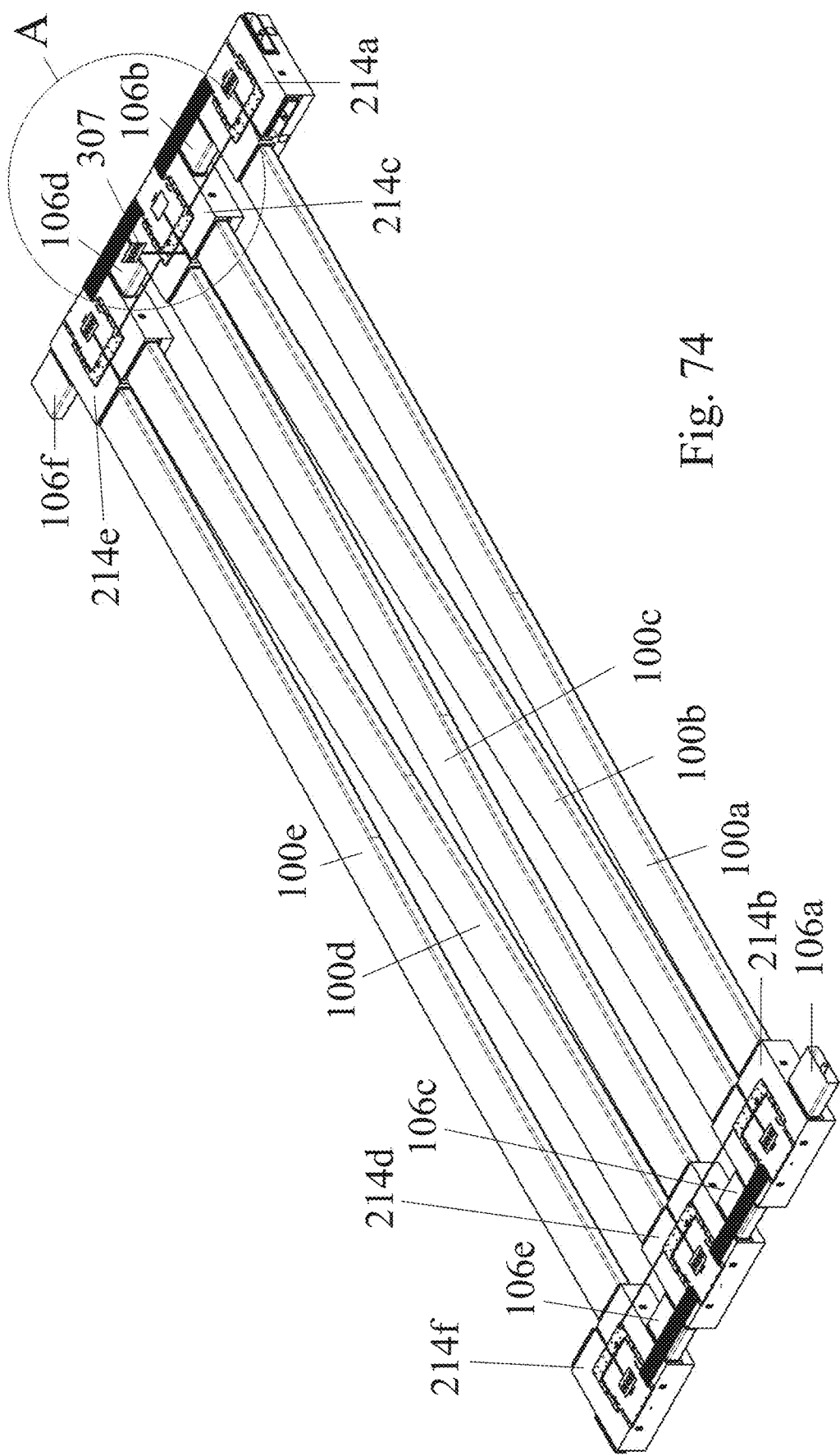

Drawing 74 contains FIG. 74. FIG. 74 is an isometric view of a reactor section.

Drawing 75 contains Detail FIG. 74A, Detail FIG. 74B, Detail FIG. 74C, and Detail FIG. 74D. Detail FIG. 74A shows the hose connections in the reactor section. Detail FIG. 74B shows the hose connections to a slave reactor node. Detail FIG. 74C shows the hose connections from the previous reactor node. Detail FIG. 74D shows the hose connections to the next reactor node.

Drawing 76 contains FIG. 75. FIG. 75 is an isometric view of a reactor node with stubs to disable port D.

Figure 76:
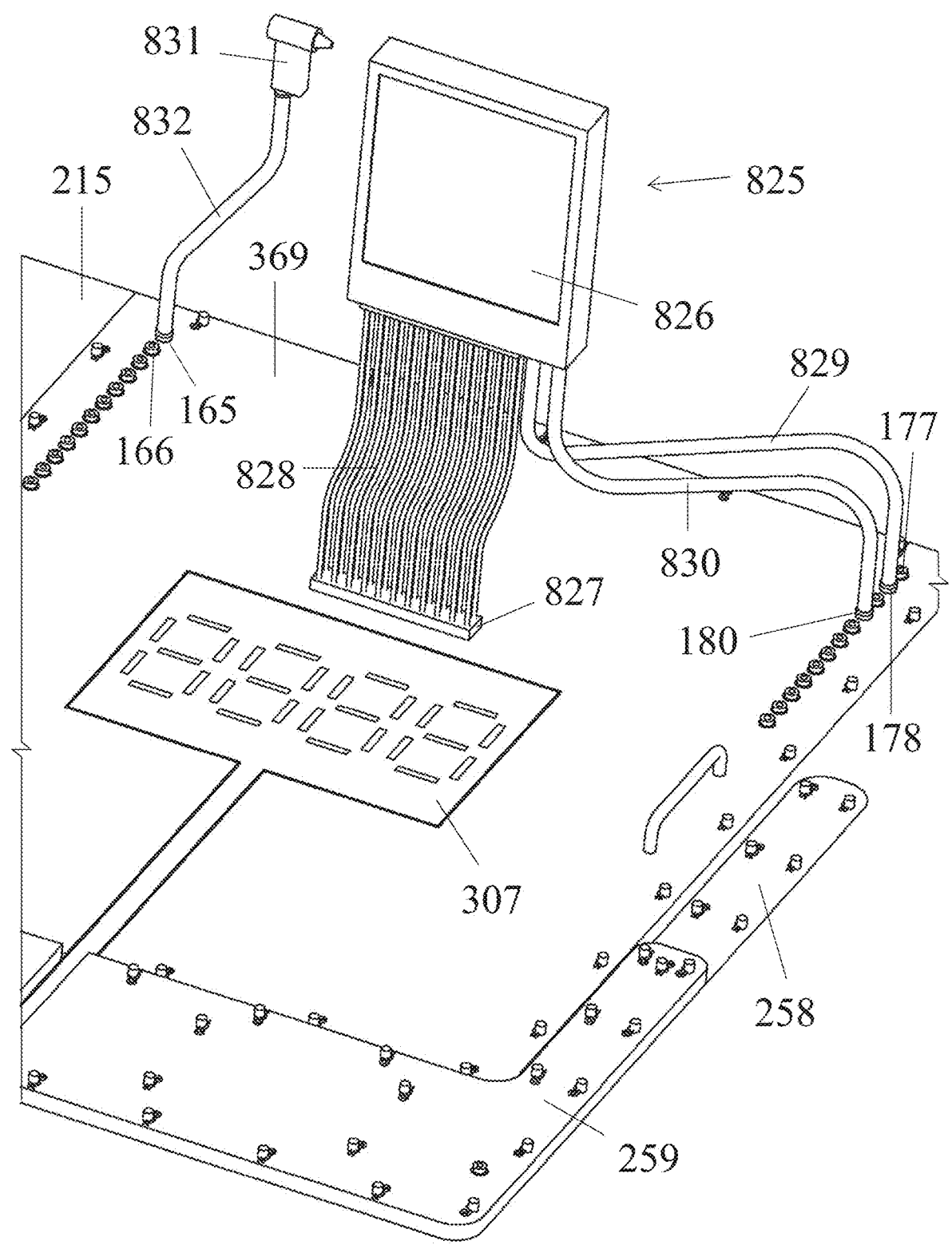

Drawing 77 contains FIG. 76. FIG. 76 is an isometric view of the diagnose device 825 attached to a reactor node.

Drawing 78 contains FIG. 77, FIG. 78, and FIG. 79. FIG. 77 is a top view of a reactor node 214 showing port routing. FIG. 78 is a table of the reactor node configurations and port rerouting. FIG. 79 is a lay out view of the barge assembly 833.

Figure 80:
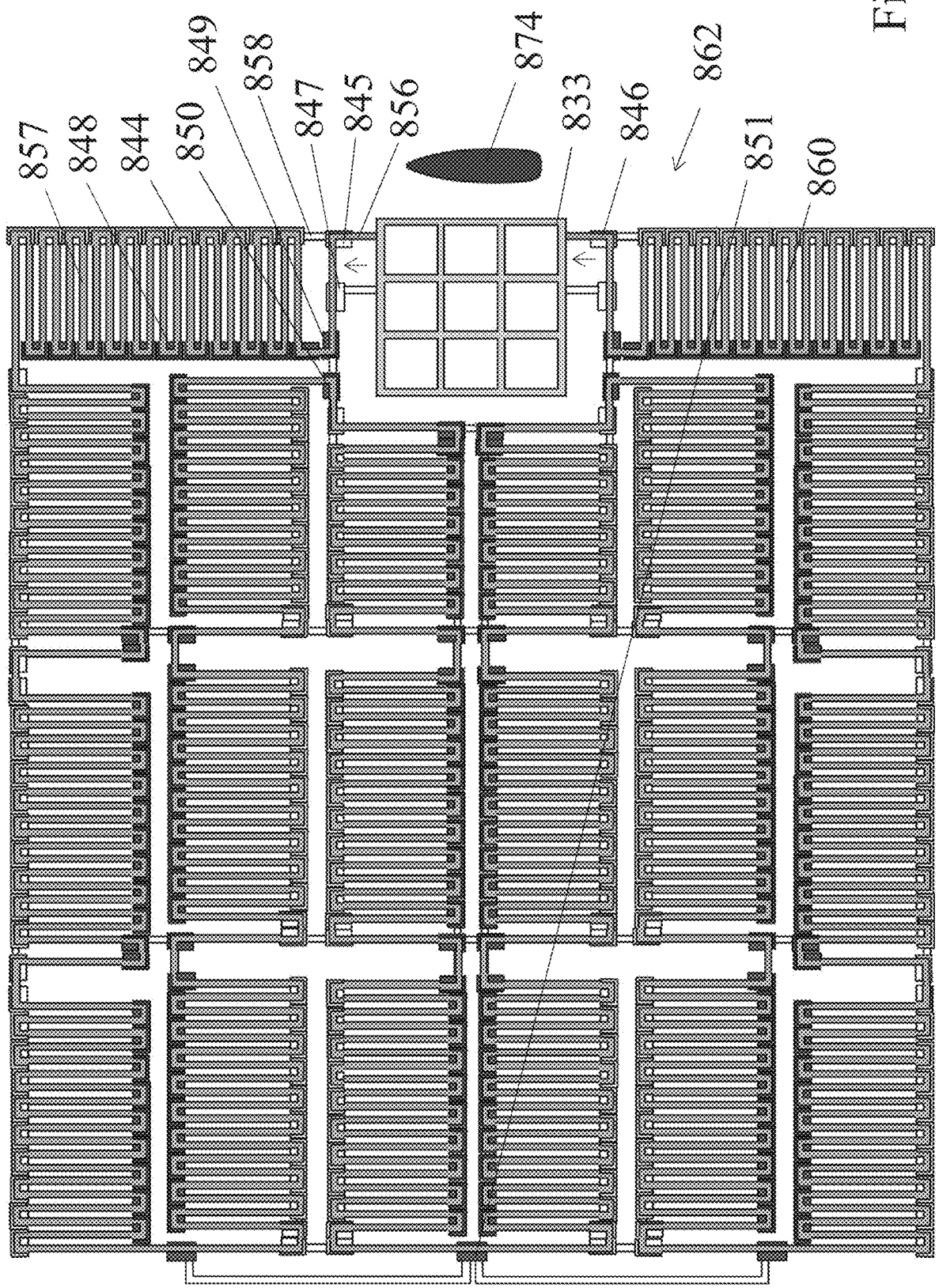

Drawing 79 contains FIG. 80. FIG. 80 is a top view of a unit farm 862.

Figure 81:
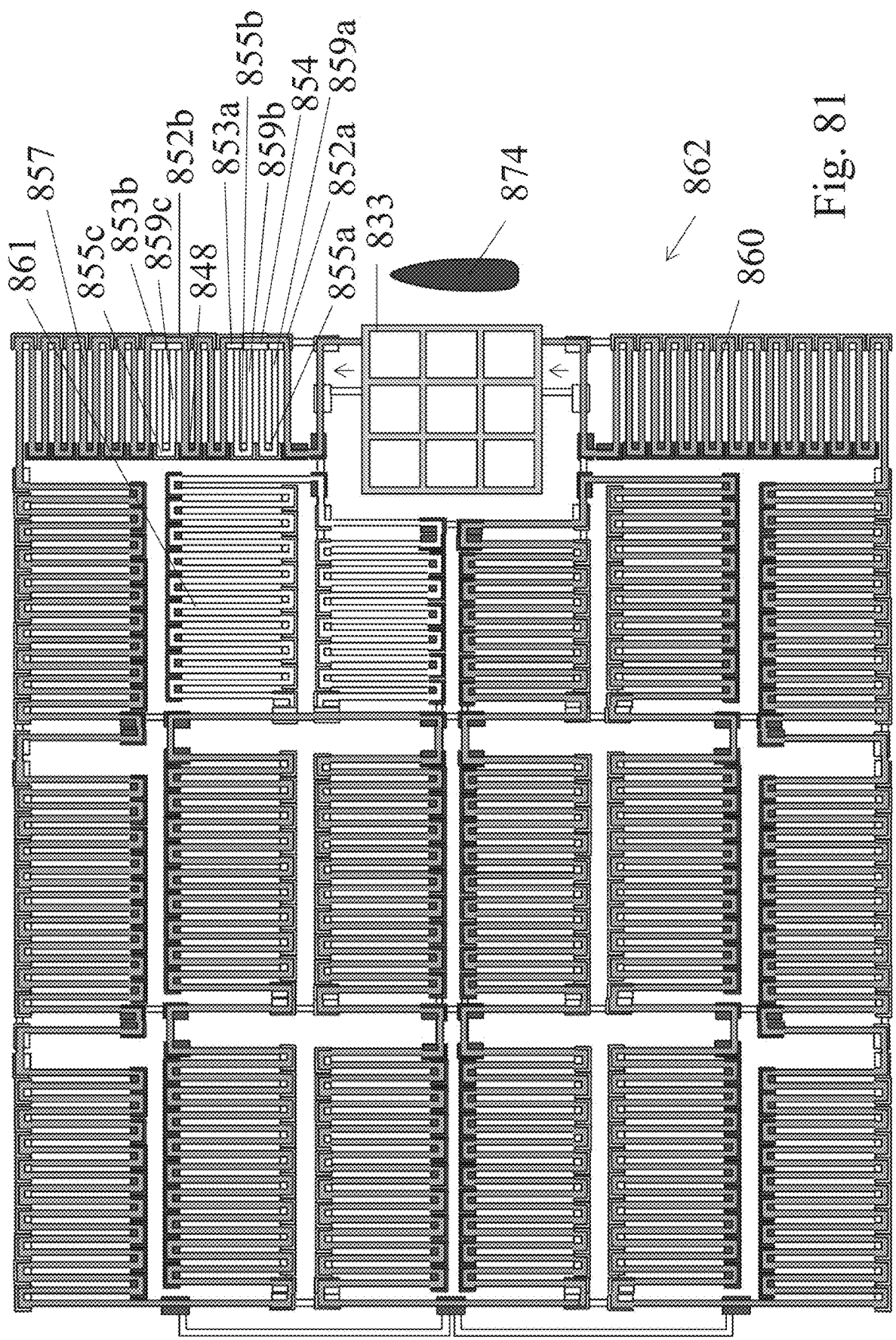

Drawing 80 contains FIG. 81. FIG. 81 is a top view of a unit farm 862 showing faulty reactor sections.

Figure 82:
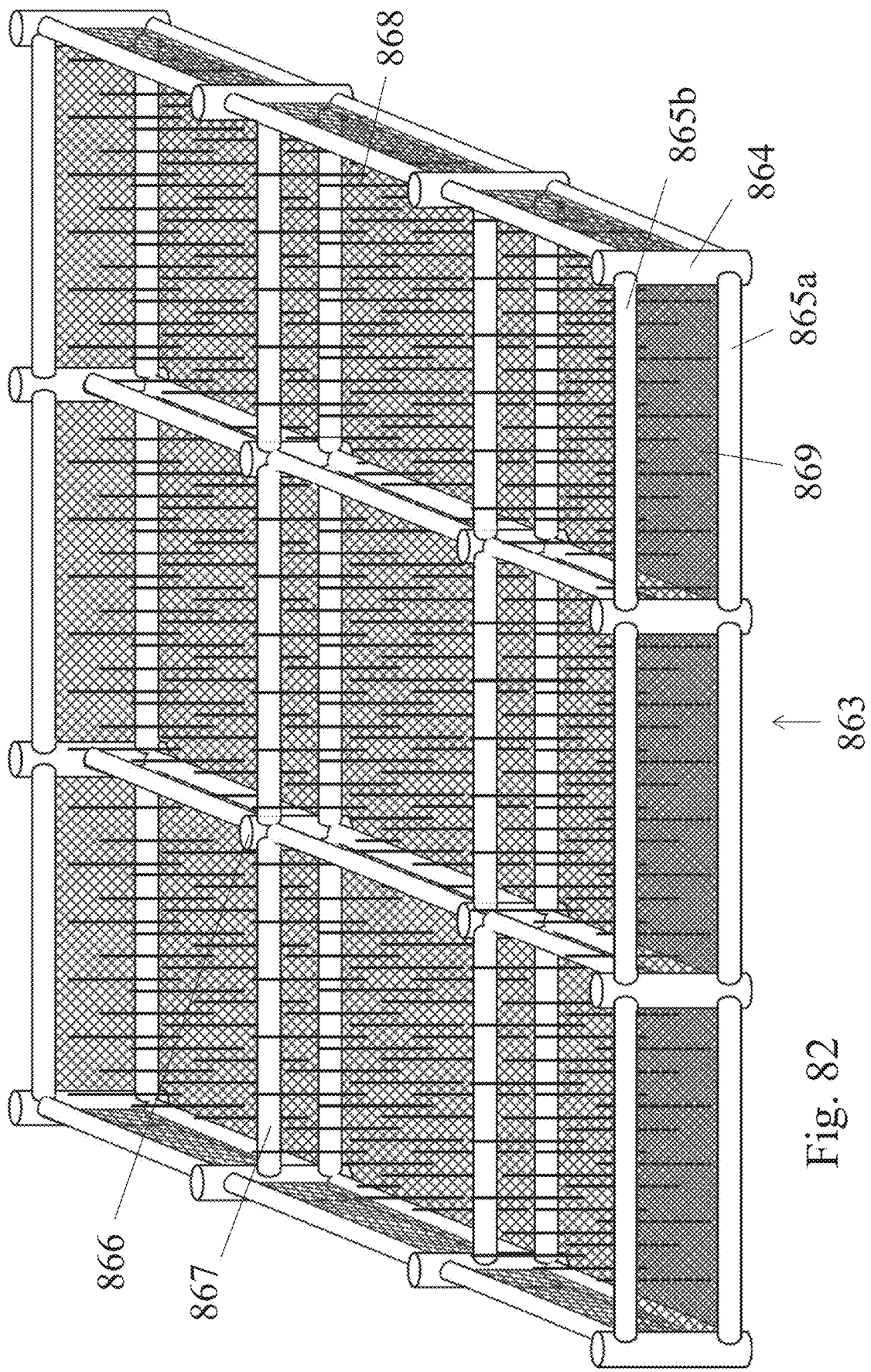

Drawing 81 contains FIG. 82. FIG. 82 is an isometric view of the protection cage 863.

Figure 83:
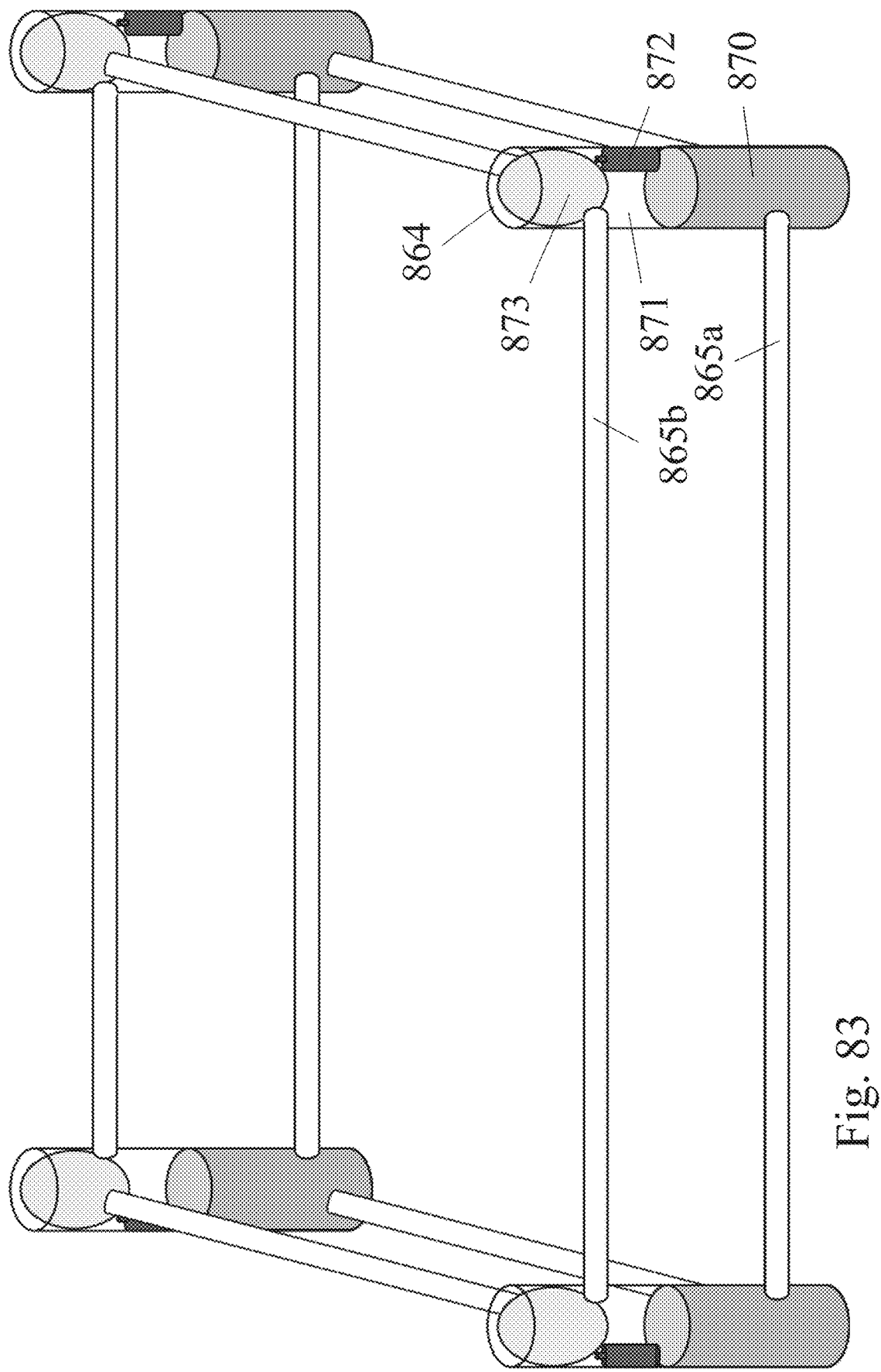

Drawing 82 contains FIG. 83. FIG. 83 is an isometric view of the protection cage buoyance control.

Figure 84:
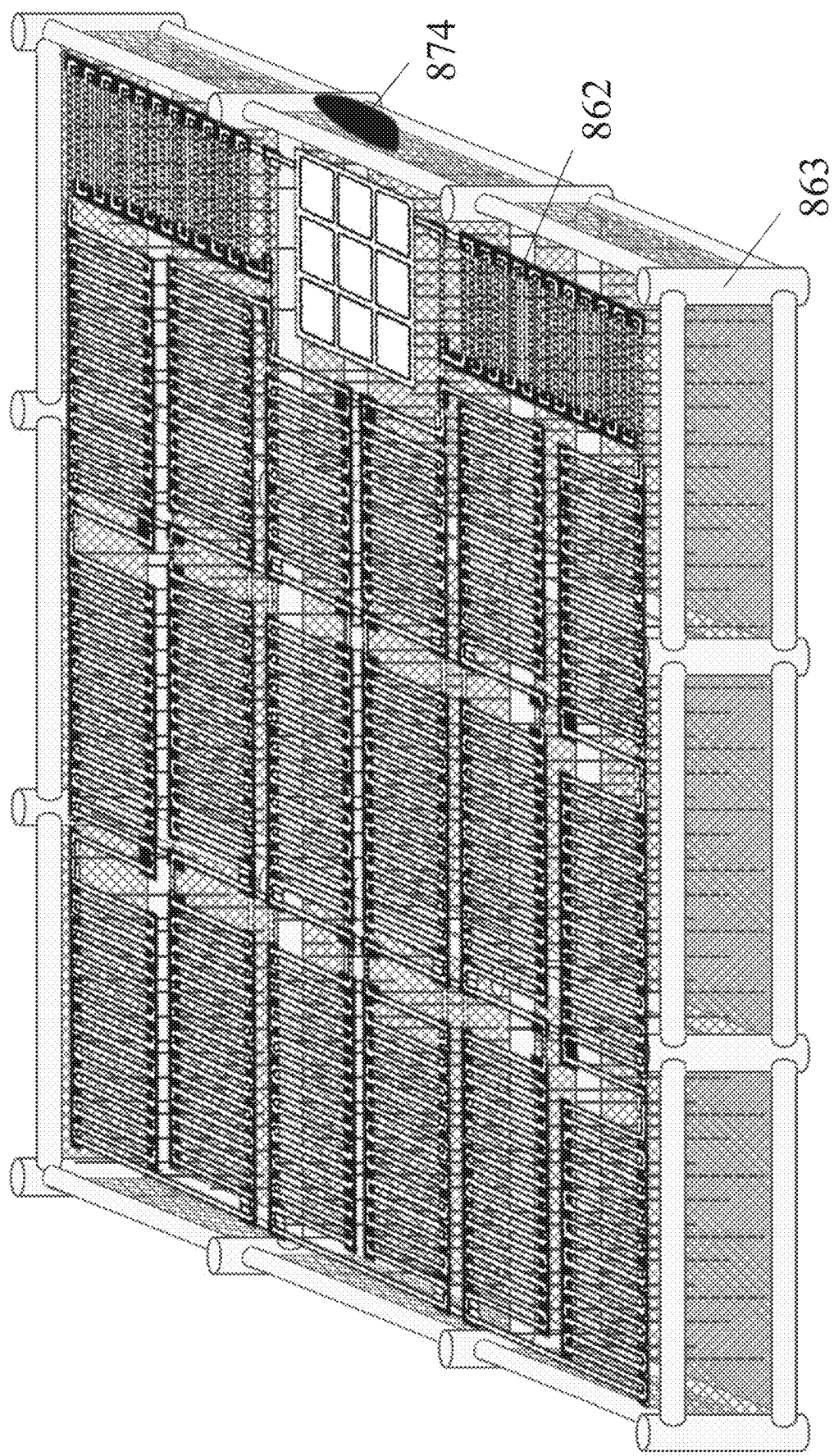

Drawing 83 contains FIG. 84. FIG. 84 is an isometric view of an unit farm 862 with protection cage 863.

Figure 85:
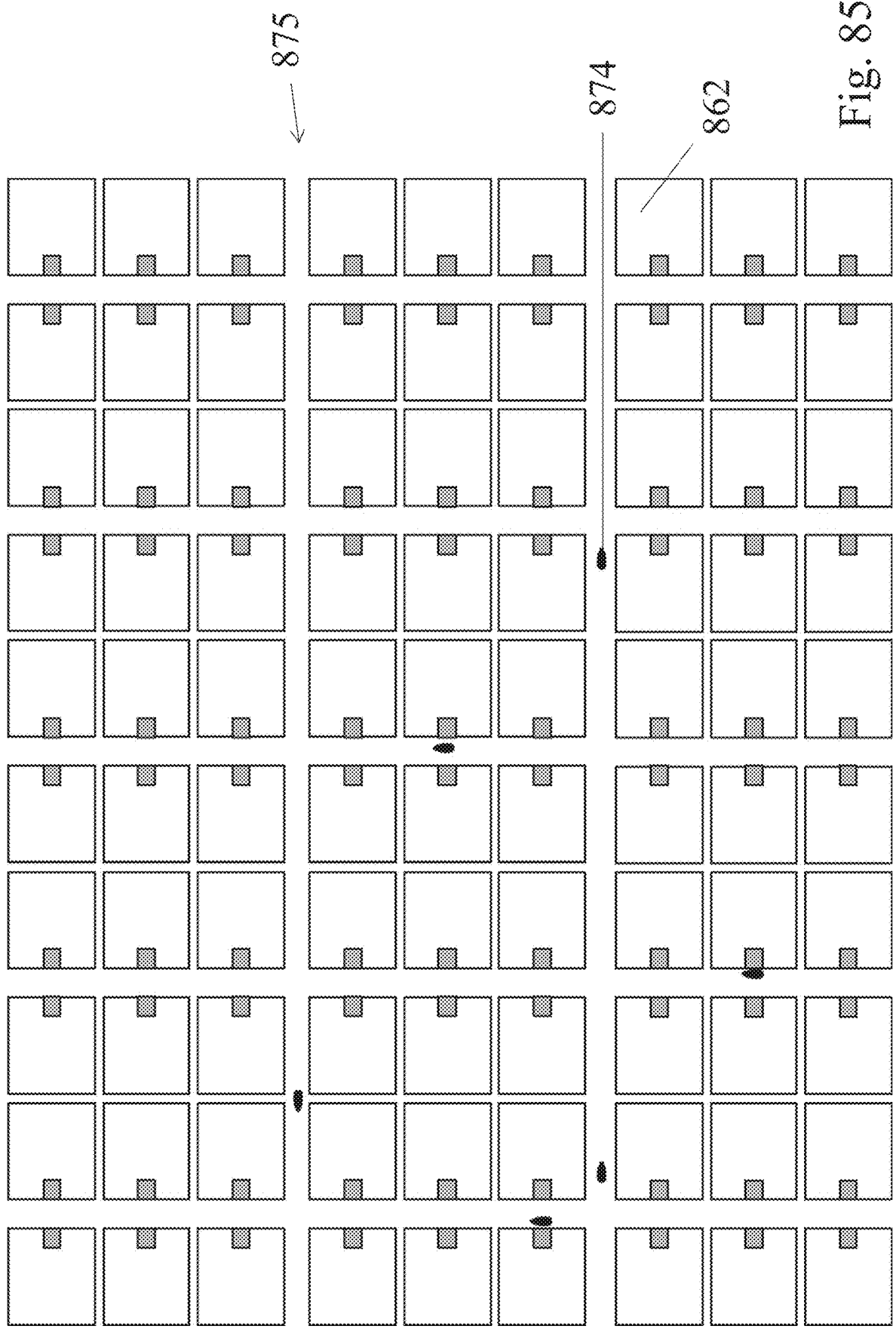

Drawing 84 contains FIG. 85. FIG. 85 is a top view of a farm array 875.

Figure 86:
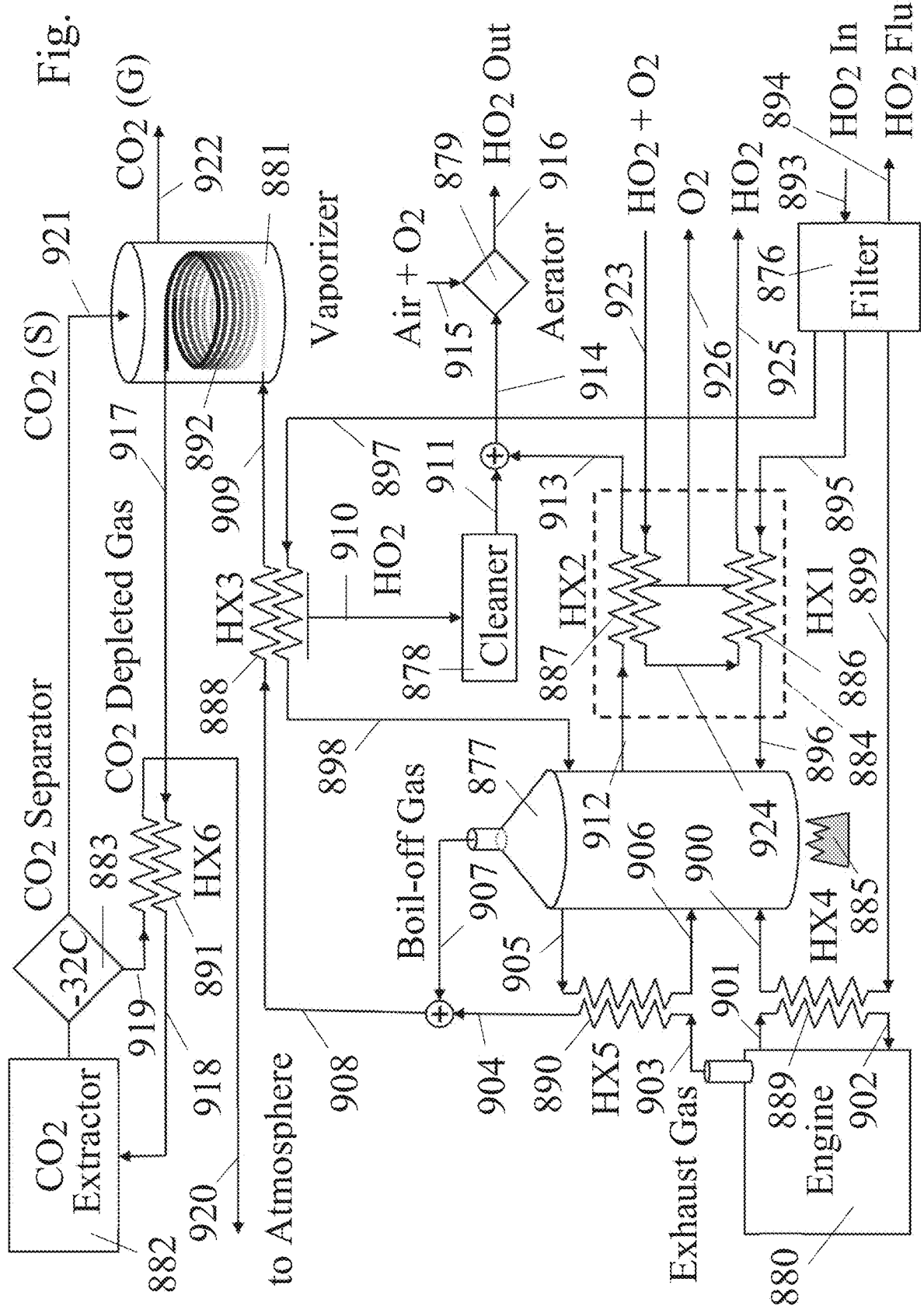

Drawing 85 contains FIG. 86. FIG. 86 is a diagrammatic view of the CO2 extraction unit.

Figure 87:
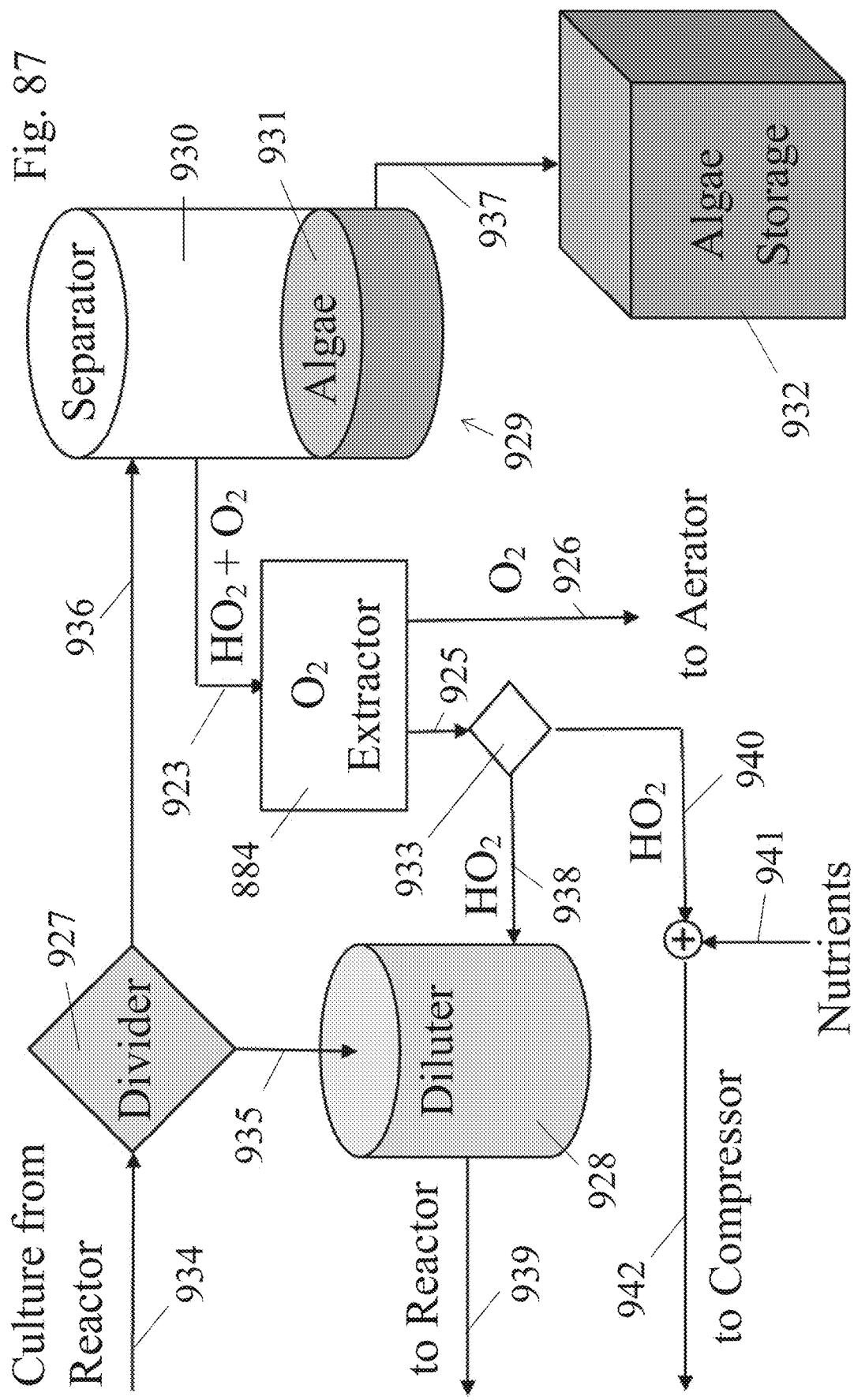
Figure 88:
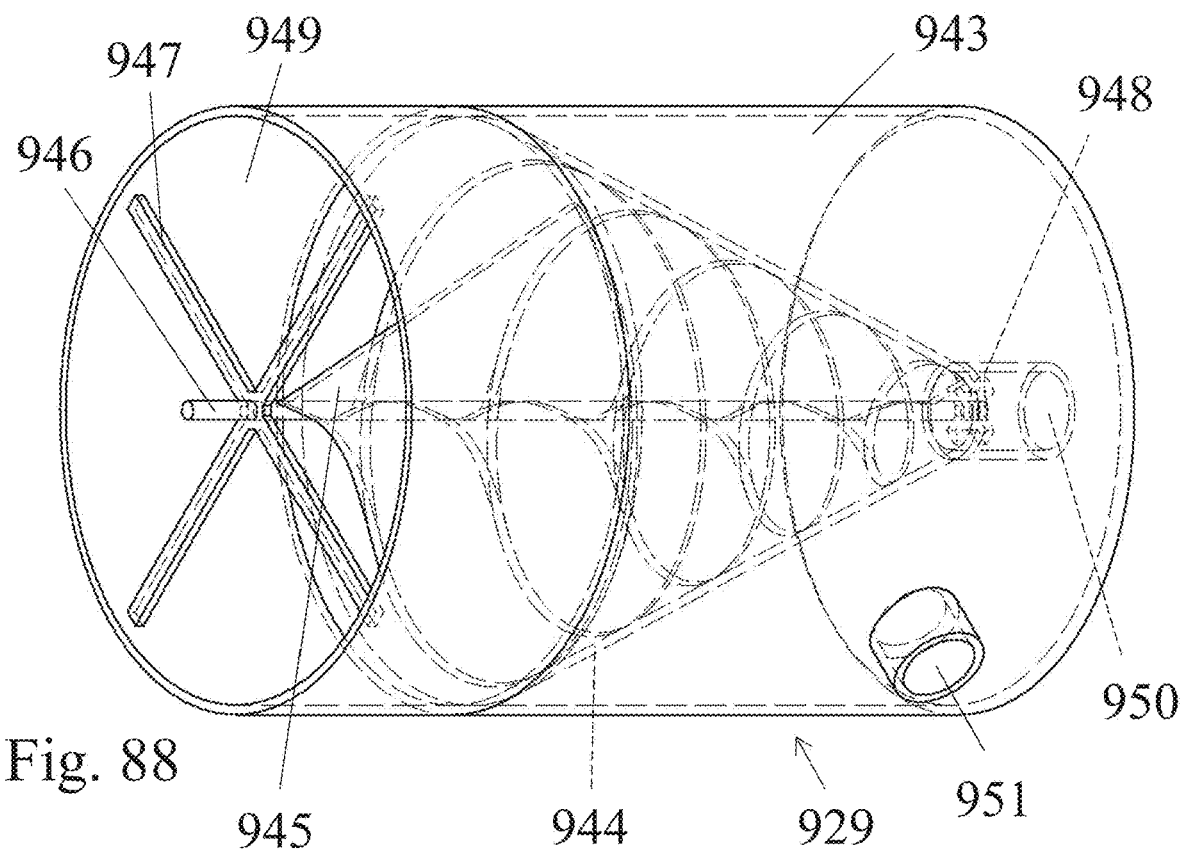
Figure 89:
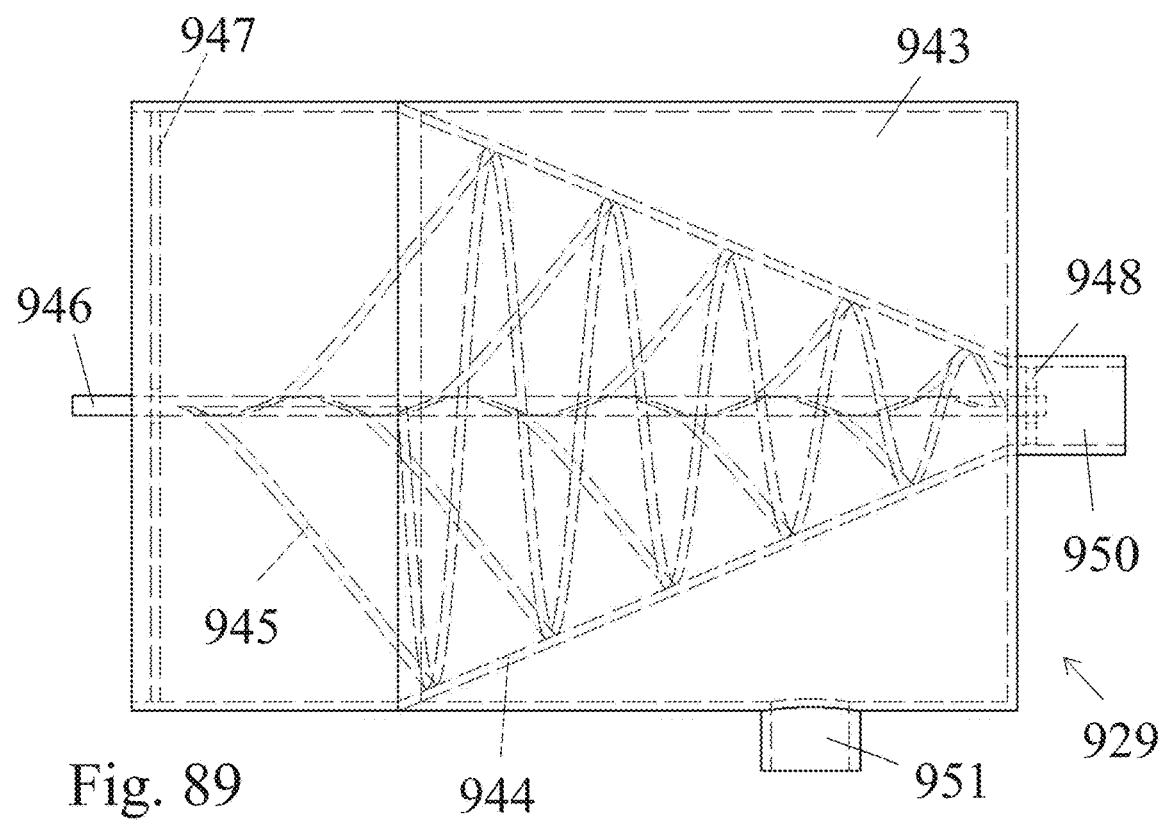

Drawing 86 contains FIG. 87. FIG. 87 is a diagrammatic view of the algae separation unit, Drawing 87 contains FIG. 88 and FIG. 89. FIG. 88 is an isometric view of the algae separator 929. FIG. 89 is a side view of algae separator 929.

Figure 90:
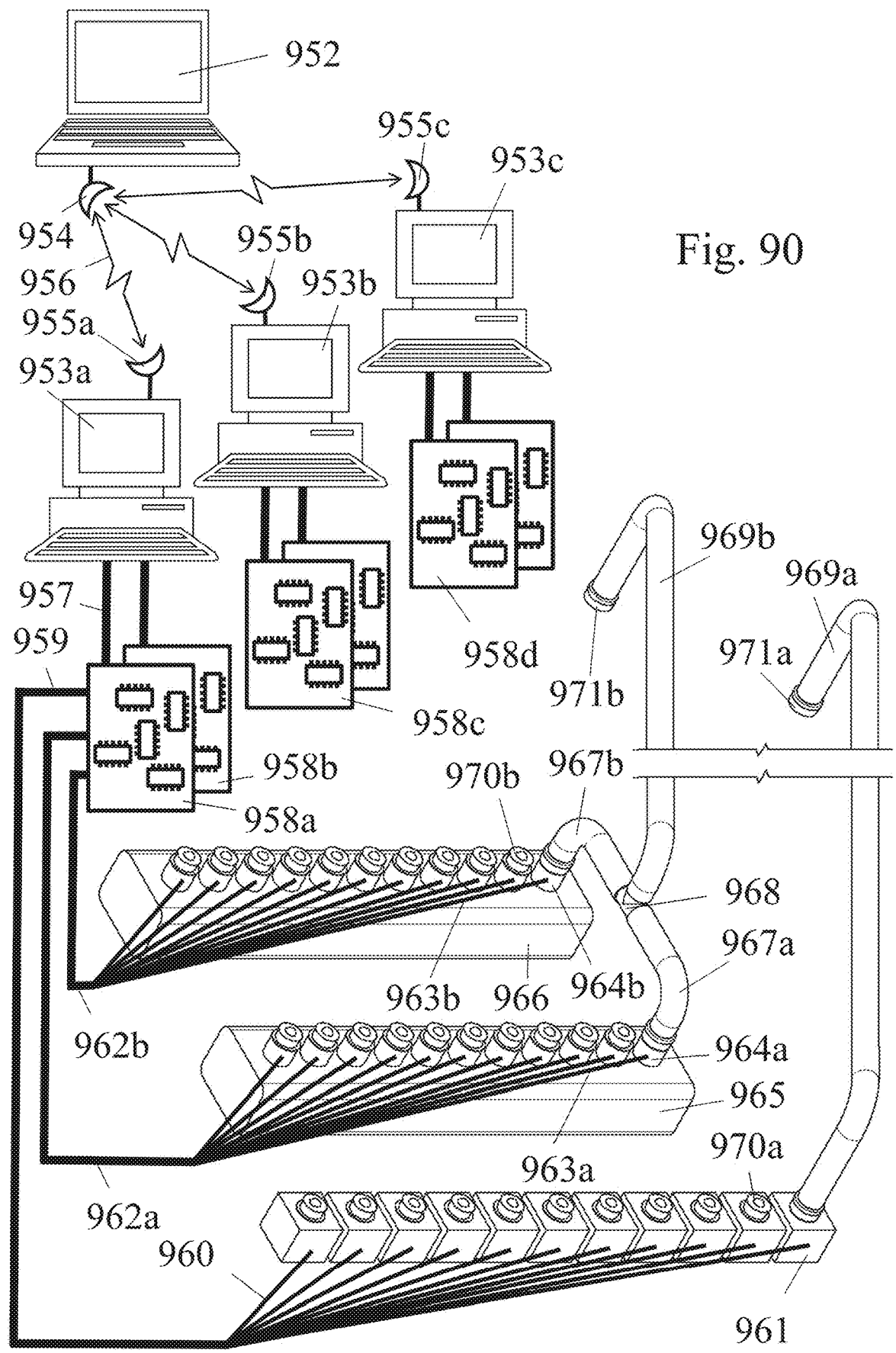

Drawing 88 contains FIG. 90. FIG. 90 is a diagrammatic view of the control unit and farm monitoring.

Figure 91:
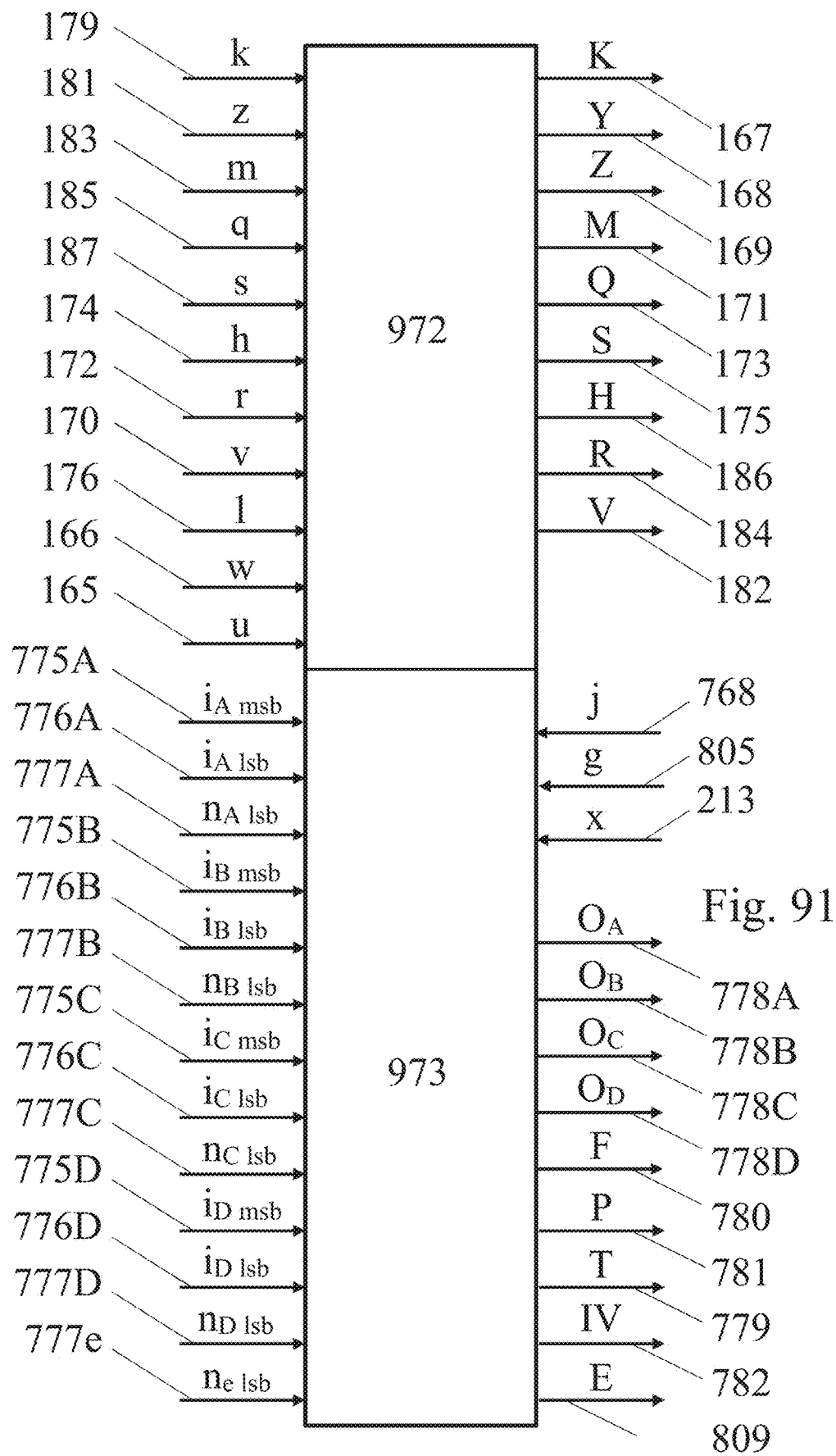

Drawing 89 contains FIG. 91. FIG. 91 is a diagrammatic view of the reactor node input and output signals.

Drawing 90 contains FIG. 92. FIG. 92 is a table with the sequence of 7-bit linear feed shift register states.

Figure 93:
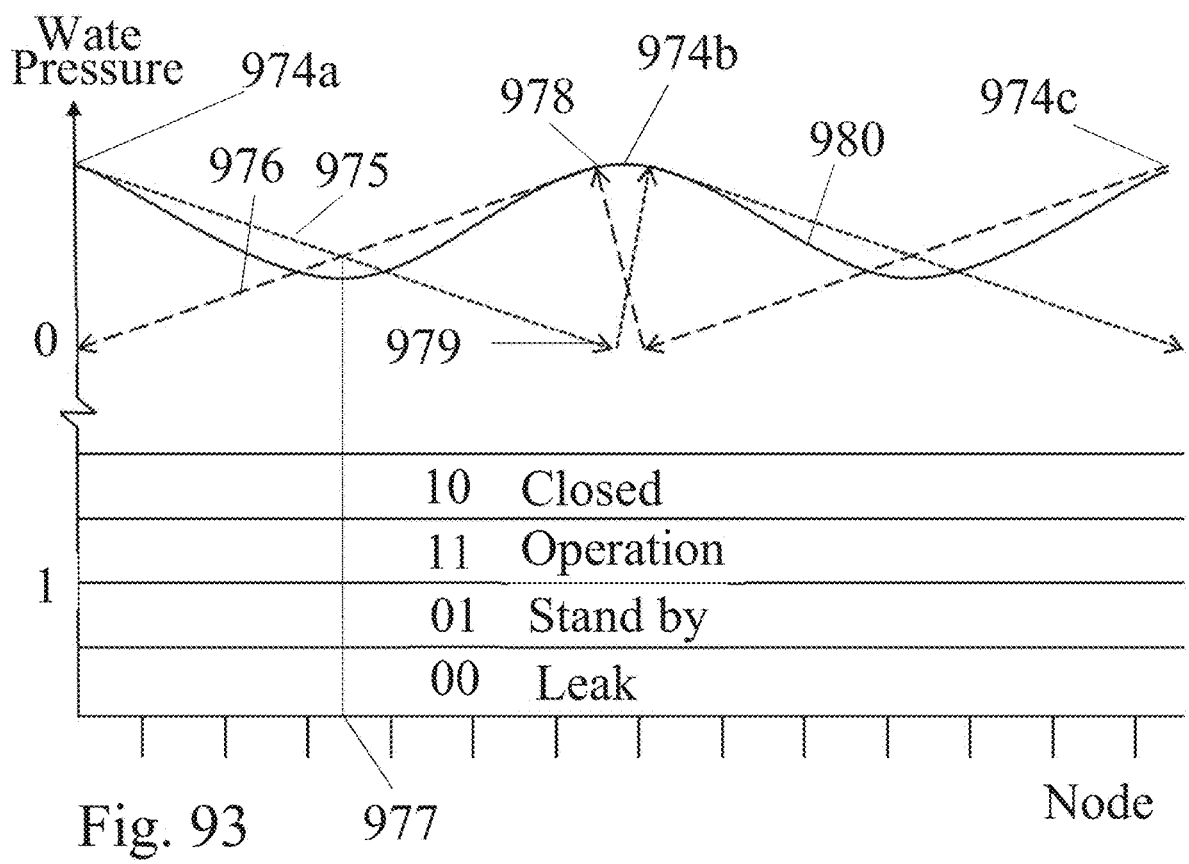
Figure 94:
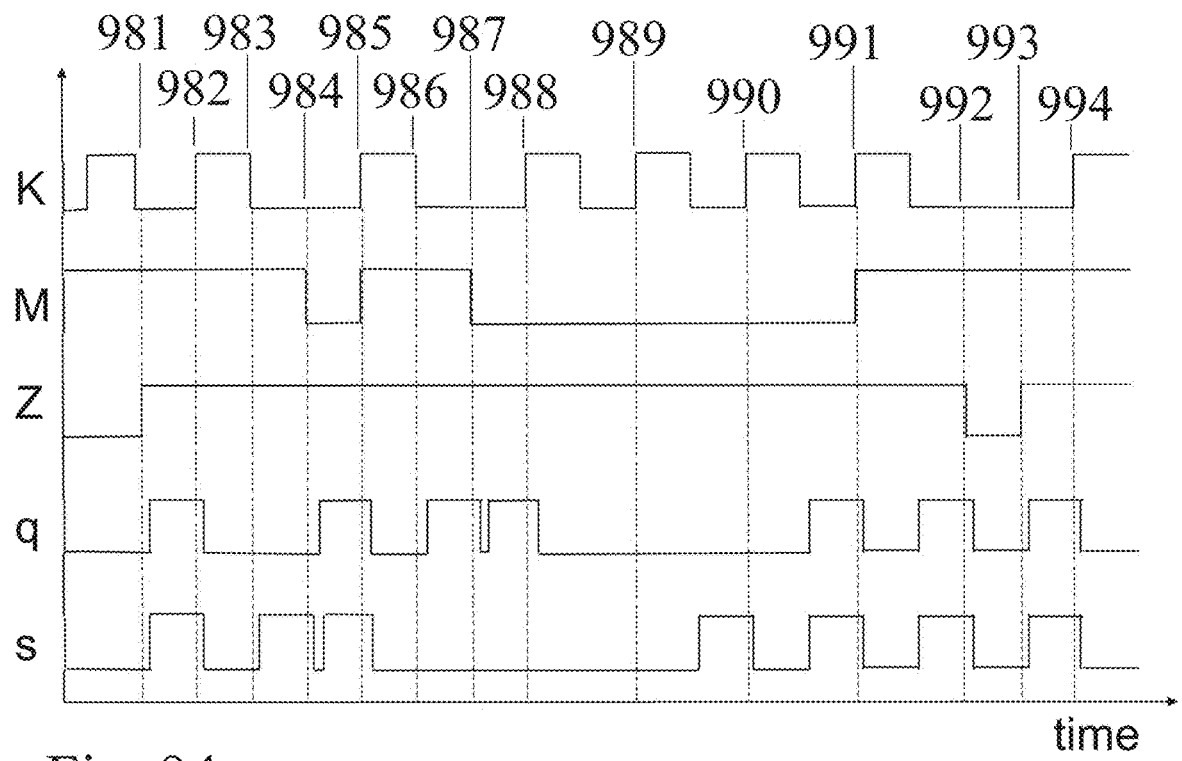

Drawing 91 contains FIG. 93 and FIG. 94. FIG. 93 is a graphic of water pressure variations on a farm. FIG. 94 is a graphic of the timing of the query signals.

Drawing 92 contains FIG. 95, FIG. 96, FIG. 97, and Detail FIG. 97A. FIG. 95 is an isometric view of the alternate module assembly. FIG. 96 is a diagrammatic view of the alternate module assembly electronics and parts. FIG. 97 is an isometric view of a reactor section using the alternate module assembly. Detail FIG. 97A shows the alternate module assembly connections.

DRAWINGS—REFERENCE NUMERALS

TABLE 1

List of reference numbers and Figures where they are indicated

| N | Item Name | Shown in FIGS. |
|---|---|---|
| 100 | pipe element | 1 2 72 73 74 74A |
| 101 | outer pipe | 1 1A 2 |
| 102 | pipe rounded edges | 1 |
| 103 | inner pipe | 1 1A 2 72 73 |
| 104 | rim | 1A |
| 105 | gap | 1A |
| 106 | short pipe element | 74 74A |
| 107 | inner tie | 2 72 73 |
| 108 | inner band | 2A |
| 109 | inner band fastener | 2A |
| 110 | pipe tie | 2 72 73 |
| 111 | pipe band | 2B |
| 112 | pipe band fastener | 2B |
| 113 | straight joint | 2 2C 72 |
| 114 | outer wall | 2C 3 3A 4 4A 5A |
| 115 | wall rounded edges | 2C 3 4 5A |
| 116 | inner guide | 2C 3 3A 4 4A 5A 9 72 73 |
| 117 | support | 2C |
| 118 | guide support gap | 2C 3A 4A 5A |
| 119 | inner rim | 2C 3A 4A 5A |
| 120 | inner tie slot | 2C 3A 4A 5A |
| 121 | outer rim | 2C 3A 4A 5A |
| 122 | outer tie slot | 2C 3A 4A 5A |
| 123 | wall band | 2C 3A 4A |
| 124 | vertical edge | 2C 3A 4A |
| 125 | pipe port | 2C 3 4 5 5A 6 8 9 73 |
| 126 | pipe port bottom | 9 |
| 127 | 90 degrees joint | 3 72 |
| 128 | 90 degrees middle body | 3 |
| 129 | 90 degrees rounded rims | 3 |
| 130 | 90 degrees inner guide | 3 3A |
| 131 | 90 degrees support | 3A |
| 132 | 180 degrees joint | 4 72 |
| 133 | 180 degrees middle body | 4 |
| 134 | 180 degrees rounded rims | 4 |
| 135 | 180 degrees inner guide | 4 4A |
| 136 | 180 degrees support | 4A |
| 137 | door plug | 5 5A 6 7 10 11 12 13 14 75 |
| 138 | door plug O-ring | 13 14 |
| 139 | door | 7 10 11 12 13 14 75 |
| 140 | door body | 11 13 14 |
| 141 | door opening | 11 13 14 |
| 142 | door O-ring | 13 14 |
| 143 | door spacer | 13 14 |
| 144 | door spring cut | 13 14 |
| 145 | door spring | 7 10 11 13 |
| 146 | door stub | 75 |
| 147 | door stub O-ring | 75 |
| 148 | CO2 valve plug | 5 6 6A 7 10 11 12 13 14 75 |
| 149 | CO2 valve plug O-ring | 13 14 |
| 150 | CO2 valve | 7 10 11 12 13 14 49 75 |
| 151 | CO2 valve body | 11 13 14 |
| 152 | CO2 valve opening | 11 13 14 |
| 153 | CO2 valve O-ring | 13 14 |
| 154 | CO2 valve spacer | 13 14 |
| 155 | CO2 valve spring guide | 13 14 |
| 156 | CO2 valve cavity | 13 14 |
| 157 | CO2 valve cavity spring cut | 13 14 |
| 158 | CO2 valve spring | 7 10 11 13 |

TABLE 1-continued

List of reference numbers and Figures where they are indicated

| N | Item Name | Shown in FIGS. |
|---|---|---|
| 159 | CO2 valve stub | 75 |
| 160 | CO2 valve stub O-ring | 75 |
| 161 | diagnose port | 5C 25A 50 51 |
| 162 | diagnose attachment | 5C 25A |
| 163 | signal port left | 25A 50 51 |
| 164 | signal port right | 5C 50 51 |
| 165 | (u) air resupply right | 5C 76 91 95 97A |
| 166 | (w) water resupply right | 5C 56 76 91 95 97A |
| 167 | (K) clock out | 5C 91 |
| 168 | (Y) unit ready out | 5C 74B 74D 91 |
| 169 | (Z) zero out | 5C 74B 74D 91 |
| 170 | (v) dive in | 5C 56 91 |
| 171 | (M) master/slave out | 5C 91 |
| 172 | (r) reset in | 5C 56 91 |
| 173 | (Q) query out | 5C 91 |
| 174 | (h) help in | 5C 56 91 |
| 175 | (S) status out | 5C 91 |
| 176 | (l) CO2 resupply right | 5C 91 95 97A |
| 177 | (U) air resupply left | 25A 76 95 97A |
| 178 | (W) water resupply left | 25A 76 95 97A |
| 179 | (k) clock in | 25A 56 91 |
| 180 | (gnd) ground | 25A 55 74C 76 95 97A |
| 181 | (z) zero in | 25A 56 74C 91 |
| 182 | (V) dive out | 25A 91 |
| 183 | (m) master/slave in | 25A 56 91 |
| 184 | (R) reset out | 25A 91 |
| 185 | (q) query in | 25A 56 91 |
| 186 | (H) help out | 25A 91 |
| 187 | (s) status in | 25A 56 91 |
| 188 | (L) CO2 resupply left | 25A 95 97A |
| 189 | node core main control port | 12 21 49 66 |
| 190 | node core main control port section | 13 14 |
| 191 | node core aux control port left | 21 49 66 |
| 192 | node core aux control port right | 21 49 66 |
| 193 | open door pipe | 12 13 14 49 75 |
| 194 | open CO2 valve pipe | 12 13 14 49 75 |
| 195 | close door pipe | 13 14A 75 |
| 196 | close CO2 valve pipe | 12 13 14 49 75 |
| 197 | water sensor pipe | 12 13 14 49 75 |
| 198 | water feed pipe | 12 13 14 49 75 |
| 199 | CO2 sensor pipe | 12 13 14 49 75 |
| 200 | CO2 feed pipe | 12 13 14 49 75 |
| 201 | flag pipe | 15 16 17 49 |
| 202 | air release open pipe | 22A 49 |
| 203 | air release close pipe | 22A 49 |
| 204 | CO2 sensor main pipe | 49 |
| 205 | CO2 feed main pipe | 49 |
| 206 | dive control close pipe | 15 24 49 |
| 207 | dive control open pipe | 15 24 49 |
| 208 | pump feed pipe | 15 19A 49 |
| 209 | pump exhaust pipe | 15 19A 49 |
| 210 | pump exhaust front pipe | 19A |
| 211 | pump exhaust discharge pipe | 19A 24B |
| 212 | expansion feed pipes | 50 51 |
| 213 | (x) external pressure | 51 91 |
| 214 | reactor node | 5 6 15 22 73 74 74A 77 97 |
| 215 | node core | 5 5A 5B 6 7 8 10 18 19 21 23 24 76 |
| 216 | node core a | 8 9 |
| 217 | node core b | 8 9 |
| 218 | node core c | 8 9 |
| 219 | node core d | 8 9 |
| 220 | node core wall | 5A |
| 221 | back propeller shaft support | 8 18B |
| 222 | back propeller shaft hole | 18B |
| 223 | front propeller shaft support | 8 18B 19B 21J |
| 224 | front propeller shaft hole | 18B |
| 225 | rotor shaft support | 8 18B 19B 21J |
| 226 | rotor shaft hole | 18B |
| 227 | cable winch cavity | 6B 8 9 23 24A |
| 228 | cable winch cavity wall | 24A |
| 229 | rotor shaft insert hole | 24B |
| 230 | water pump check valve cavity | 24B |
| 231 | water pump cavity | 8 9 19A 24B |
| 232 | winch rotor cavity | 8 9 23 |
| 233 | rotor cavity | 19A 24B |
| 234 | water culture cavity | 8 |
| 235 | door plug cavity | 8 9 |
| 236 | door insertion opening | 8 9 |
| 237 | door channel | 8 9 |
| 238 | door cavity | 8 9 12 13 14 14A |
| 239 | door cavity spring cut | 12 13 14 |
| 240 | propeller access opening | 8 9 |
| 241 | pipe hole | 8 9 |
| 242 | pipe trail | 8 9 |
| 243 | water culture channel | 8 9 |
| 244 | CO2 cavity lid | 8 |
| 245 | CO2 cavity body | 8 9 |
| 246 | CO2 cavity | 9 |
| 247 | CO2 valve insertion opening | 8 9 |
| 248 | module bay | 8 9 21 |
| 249 | air release bay | 8 21 |
| 250 | flag bay | 8 9 |
| 251 | node support | 5A |
| 252 | node core external opening | 6A 8 9 |
| 253 | fastener hole | 13 14 16 20 21B 21C 21D 25 25A 25E 50 51 |
| 254 | fastener | 5A 5B 5C 6A 21B 21C 21D 21F 21G 21H 21I 25 25E 50 51 |
| 255 | R-clip insertion hole | 21B 21C 21D |
| 256 | R-clip | 5A 5B 5C 6A |
| 257 | air release assembly | 5 7 |
| 258 | air release lower cover | 5B 21 76 |
| 259 | air release left upper cover | 5B 21 76 |
| 260 | air release right upper cover | 5B 21 |
| 261 | air release top cover base | 21B |
| 262 | air release top cover | 5B 21B |
| 263 | air purge | 5B 21B |
| 264 | air release attachment left | 21 |
| 265 | air release attachment right | 5B 21 22A |
| 266 | flag recess cut | 21 |
| 267 | air release short channel | 21 21C 22A |
| 268 | air release long channel | 21 21D 22A |
| 269 | air release pass | 21 21C 22A |
| 270 | air release chamber | 21 21G 22 22A |
| 271 | air release cut | 21 21E 21F 21H 21I 22 22A |
| 272 | air vent valve | 21C 22A |
| 273 | air vent valve O-ring | 21C |
| 274 | air vent valve opening | 21C |
| 275 | air vent valve cavity | 21C |
| 276 | air vent purge cutout | 21C 21G 22A |
| 277 | air vent open cutout | 21C 21G |
| 278 | air vent close cutout | 21C 21G |
| 279 | float cavity | 21F 21I 22A |
| 280 | float | 21E 21F 21H 21I 22A |
| 281 | float O-ring | 21E 21F 21H 21I |
| 282 | anchor assembly | 5 6 7 23 24 |
| 283 | anchor body | 5D |
| 284 | anchor opening | 6 |
| 285 | anchor handle | 5D |
| 286 | anchor valve | 5D |
| 287 | anchor cable | 5 5D 6 6B 7 23 23B 23C 24 24A |
| 288 | anchor cable loop | 5D |
| 289 | knot | 6B 23B 23C 24A |
| 290 | stopper | 5 6 6B 7 23 23B 23C 24 24A |
| 291 | stopper hole | 23B 23C |
| 292 | cable winch | 6B 7 15 23 23B 24 24A |
| 293 | cable winch teeth | 23B 24A |
| 294 | cable winch axle | 24A |
| 295 | cable winch face | 23B 24A |
| 296 | cable winch drive hole | 23B |
| 297 | flag assembly | 7 15 |
| 298 | flag port | 5A 16 17 |
| 299 | flag port rim | 15 16 17 |
| 300 | flag port plug | 16 17 |
| 301 | flag port O-ring | 17 |
| 302 | flag port cavity | 16 17 |
| 303 | flag raised stopper | 16 |
| 304 | flag lowered stopper | 16 |
| 305 | flag pin | 16 17 |

TABLE 1-continued

List of reference numbers and Figures where they are indicated

| N | Item Name | Shown in FIGS. |
|---|---|---|
| 306 | lever pin | 16 17 |
| 307 | flag | 5C 15 16 17 74 74A 76 97 |
| 308 | digit notch | 5C 16 |
| 309 | digit pad | 5C 16 |
| 310 | flag lever | 16 17 |
| 311 | flag piston | 16 17 |
| 312 | flag piston head | 16 17 |
| 313 | flag piston O-ring | 17 |
| 314 | flag spring | 16 |
| 315 | pump cover | 5 5A 7 18 20 22 23 24 |
| 316 | pump cover axle hole | 20 |
| 317 | pump cover cavity plug | 20 |
| 318 | pump cover inner O-ring | 20 |
| 319 | pump cover outer O-ring | 20 |
| 320 | pump cover outer plug | 20 |
| 321 | pump cover key | 20 |
| 322 | pump cover key rounded edge | 20 |
| 323 | pump cover fastener | 20 |
| 324 | pump cover exhaust pipe cut | 20 |
| 325 | pump rotor assembly | 7 15 22 23 24 |
| 326 | pump rotor | 18 18C 19A |
| 327 | pump rotor axle | 18C 19A |
| 328 | pump vane insert | 18C |
| 329 | pump rotor shaft | 18 18C 18D 19B 21J 23 24A |
| 330 | pump rotor shaft rim | 18D 23A 24A |
| 331 | pump rotor shaft drive | 18D 19B 21J 23A |
| 332 | pump rotor drive rim | 18D 19B 21J 23A |
| 333 | pump rotor drive end | 18D 21J 23A |
| 334 | pump vane | 18 18C 19A |
| 335 | pump vane edge | 18C |
| 336 | pump vane spring notch | 18C |
| 337 | vane spring | 18C |
| 338 | check valve cavity | 21B 21C 21D |
| 339 | check valve | 18E 19A 21 21B 21C 21D 22A 56 60 |
| 340 | check valve body | 18F |
| 341 | check valve body rim | 18F |
| 342 | check valve support | 18F |
| 343 | check valve support insert hole | 18F |
| 344 | check valve O-ring | 18F |
| 345 | check valve rubber | 18F |
| 346 | check valve rubber spear | 18F |
| 347 | propeller set assembly | 7 15 21 22 |
| 348 | propeller set | 18 |
| 349 | propeller left hand | 18A 19 19B |
| 350 | propeller right hand | 19 |
| 351 | outer gear | 18A 21J |
| 352 | propeller hub | 18A |
| 353 | shaft insert square hole | 18A |
| 354 | propeller shaft | 18A 18B |
| 355 | propeller shaft nut | 18A 18B 21J |
| 356 | propeller shaft drive | 18A |
| 357 | propeller shaft bigger axle | 18A |
| 358 | propeller shaft smaller axle | 18A |
| 359 | propeller shaft lock key | 18A 18B |
| 360 | ratchet drive | 18A 19B 21J |
| 361 | ratchet drive shaft insert hole | 18A |
| 362 | ratchet drive teeth | 18A 19B 21J |
| 363 | ratchet spring | 18A 19B 21J |
| 364 | drive gap | 21J |
| 365 | water body | 10 11 12 13 14 22 22A |
| 366 | water body channel | 11 13 14 22 |
| 367 | CO2 body | 10 11 12 13 14 49 |
| 368 | CO2 body channel | 11 13 14 49 |
| 369 | module assembly | 5 5C 7 18 23 76 |
| 370 | module case | 25 26 49 50 51 52 58 59 66 |
| 371 | module rim | 6A 25 25E 26 50 51 |
| 372 | module case shape fit | 25 26 |
| 373 | module net volume | 25 |
| 374 | propeller access door plug | 26 |
| 375 | module external opening | 25 49 |
| 376 | propeller access door O-ring | 26 |
| 377 | module ground pipe port | 26 26F |
| 378 | module ground pipe connector | 25 25E 49 |
| 379 | module control bottom connector | 26 26E |
| 380 | module control top connector | 25 25D |
| 381 | connector large insert | 25C 25D 25E 26A 26E |
| 382 | connector large O-ring | 25C 25D 25E 26A 26E |
| 383 | connector large input | 21A 25B 26B 26C 26D |
| 384 | connector small insert | 25C 26A 65A |
| 385 | connector small O-ring | 25C 26A |
| 386 | connector small input | 25B 26B |
| 387 | pipe opening | 26F |
| 388 | expansion unit assembly | 25 26 50 |
| 389 | expansion case | 25 25A 26 26A 50 |
| 390 | expansion case rim | 6A 25 25A 26 50 |
| 391 | expansion case front opening | 26 50 |
| 392 | expansion case back opening | 25 50 |
| 393 | expansion case handle | 25 50 |
| 394 | expansion case shape fit | 26 |
| 395 | expansion case top connections | 25 |
| 396 | expansion case bottom connections | 26 |
| 397 | expansion case diagnose connector | 26A |
| 398 | expansion case expand connector | 26A |
| 399 | expansion case flag cutout | 25 50 |
| 400 | expansion layer | 25 26 26A 50 |
| 401 | expansion layer shape fit | 26 |
| 402 | expansion layer through cut | 25 26 |
| 403 | i/o unit assembly | 25 26 27 51 |
| 404 | i/o case | 25 25B 26 26B 27 51 52 53 54 57 58 59 60 61 64 65 |
| 405 | i/o case front opening | 26 27 |
| 406 | i/o case back opening | 25 25B |
| 407 | i/o case shape fit | 25 26 |
| 408 | i/o case extractor hole | 25 25B 27 51 |
| 409 | i/o case top connections | 25 27 |
| 410 | i/o case diagnose connector | 25B |
| 411 | i/o case expand connector | 25B |
| 412 | i/o case bottom control connector | 26 26C |
| 413 | i/o case logic connector | 26 |
| 414 | i/o case signal connector | 26B |
| 415 | i/o case power connector | 26B |
| 416 | i/o case logic left control connector | 26B |
| 417 | i/o case logic right control connector | 26B |
| 418 | i/o layer assembly | 25 26 |
| 419 | i/o layer a | 27 51 57 58 59 63 |
| 420 | i/o layer b | 27 51 60 |
| 421 | i/o layer c | 27 51 61 |
| 422 | i/o check valve set | 27 |
| 423 | i/o components | 27 |
| 424 | i/o control pipes | 52 |
| 425 | i/o components cavities | 53 54 55 56 62 |
| 426 | i/o pipework | 54 |
| 427 | i/o ground plane | 55 60 |
| 428 | i/o high pressure plane | 56 61 |
| 429 | i/o layer cutout | 57 |
| 430 | extractor | 51 61 66 |
| 431 | extractor nut base | 61 |
| 432 | logic unit assembly | 25 26 28 64 65 66 |
| 433 | logic case | 25 25C 26 28 |
| 434 | logic case front opening | 26 28 |
| 435 | logic case back opening | 25 |
| 436 | logic case extractor hole | 25 25C 28 66 |
| 437 | logic case top connections | 25 28 |
| 438 | logic case signal connector | 25C |
| 439 | logic case power connector | 25C |
| 440 | logic case left control connector | 65A |
| 441 | logic case right control connector | 25C |
| 442 | logic case bottom connector | 26 26D |
| 443 | logic layer assembly | 25 26 |
| 444 | logic layer a | 28 66 69 70 71 |
| 445 | logic layer b | 28 66 |
| 446 | logic layer c | 28 66 67 |
| 447 | logic layer d | 28 66 |
| 448 | router plate insertion bay | 28 67 |
| 449 | router plate insertion key | 28 67 |
| 450 | logic components | 28 |
| 451 | router plate direct | 28 64 65 65A 67 |
| 452 | router plate AB | 28 68 |
| 453 | router plate CD | 28 68 |

TABLE 1-continued

List of reference numbers and Figures where they are indicated

| N | Item Name | Shown in FIGS. |
|---|---|---|
| 454 | router plate ABCD | 28 68 |
| 455 | router plate ADBC | 28 68 |
| 456 | router plate DBCA | 28 68 |
| 457 | router plate CBDA | 28 68 |
| 458 | router plate ACBD | 28 68 |
| 459 | CO2 pressure controller cavity | 29 30 32 |
| 460 | CO2 pressure controller device | 29 32 62 63 |
| 461 | CO2 pressure controller rubber grid | 29 32 |
| 462 | CO2 pressure reset opening | 29 32 |
| 463 | CO2 pressure control opening | 29 32 |
| 464 | CO2 pressure lsb low opening | 29 32 |
| 465 | CO2 pressure lsb high opening | 29 32 |
| 466 | water pressure controller cavity | 29 30 32 |
| 467 | water pressure controller device | 29 32 62 63 |
| 468 | water pressure controller rubber grid | 29 32 |
| 469 | water pressure reset opening | 29 32 |
| 470 | water pressure control opening | 29 32 |
| 471 | water pressure lsb high opening | 29 32 |
| 472 | water pressure lsb low opening 1 | 29 32 |
| 473 | water pressure lsb low opening 2 | 29 32 |
| 474 | water pressure msb low opening | 29 32 |
| 475 | water pressure msb high opening | 29 32 |
| 476 | ground pressure controller cavity | 29 30 32 |
| 477 | ground pressure controller device | 29 32 62 63 |
| 478 | ground pressure controller rubber grid | 29 32 |
| 479 | ground pressure control opening | 29 32 |
| 480 | ground pressure lsb high opening | 29 32 |
| 481 | ground pressure lsb low opening | 29 32 |
| 482 | signal pressure controller cavity | 29 30 32 |
| 483 | signal pressure controller device | 29 32 62 63 |
| 484 | signal pressure controller rubber grid | 29 32 |
| 485 | signal pressure lsb high opening | 29 32 |
| 486 | signal pressure lsb low opening | 29 32 |
| 487 | signal pressure msb low opening | 29 32 |
| 488 | signal pressure msb high opening | 29 32 |
| 489 | controller central extension | 29 32 |
| 490 | controller spring hole | 29 |
| 491 | controller spring | 29 32 62 |
| 492 | actuator mono cavity | 29 30 |
| 493 | actuator mono normally open | 29 32 62 63 |
| 494 | actuator mono n. open rubber grid | 29 |
| 495 | actuator mono normally closed | 29 32 62 63 |
| 496 | actuator mono n. closed rubber grid | 29 |
| 497 | actuator mono | 29 32 62 63 |
| 498 | actuator mono rubber grid | 29 |
| 499 | actuator dual cavity | 29 30 |
| 500 | actuator dual | 29 32 62 63 |
| 501 | actuator dual rubber grid | 29 |
| 502 | actuator dual spring guard | 29 32 |
| 503 | actuator central extension | 29 |
| 504 | actuator opening | 29 32 |
| 505 | actuator spring hole | 29 |
| 506 | actuator spring | 29 32 62 |
| 507 | reference pressure pipe | 30 32 |
| 508 | CO2 pressure input 1 | 30 32 |
| 509 | CO2 pressure input 2 | 30 32 |
| 510 | CO2 pressure reset input | 30 32 |
| 511 | CO2 pressure regulate input | 30 32 |
| 512 | CO2 pressure supply output | 30 32 |
| 513 | CO2 pressure lsb low input | 30 31 32 |
| 514 | CO2 pressure lsb high input | 30 31 32 |
| 515 | CO2 pressure lsb output | 30 32 |
| 516 | water pressure input 1 | 30 32 |
| 517 | water pressure input 2 | 30 32 |
| 518 | water pressure reset input | 30 32 |
| 519 | water pressure regulate input | 30 32 |
| 520 | water pressure supply output | 30 32 |
| 521 | water pressure lsb high input | 30 32 |
| 522 | water pressure lsb low input | 30 32 |
| 523 | water pressure msb low input | 30 32 |
| 524 | water pressure msb high input | 30 32 |
| 525 | water pressure lsb output | 30 32 |
| 526 | water pressure msb output | 30 32 |
| 527 | ground pressure input | 30 32 |
| 528 | ground pressure regulate input | 30 32 |
| 529 | ground pressure supply output | 30 32 |
| 530 | ground pressure lsb high input | 30 32 |
| 531 | ground pressure lsb low input | 30 32 |
| 532 | ground pressure lsb output | 30 32 |
| 533 | signal pressure input | 30 31 32 |
| 534 | signal pressure lsb high input | 30 32 |
| 535 | signal pressure lsb low input | 30 32 |
| 536 | signal pressure msb low input | 30 32 |
| 537 | signal pressure msb high input | 30 32 |
| 538 | signal pressure lsb output | 30 32 |
| 539 | signal pressure msb output | 30 32 |
| 540 | actuator mono 1 input bottom 1 | 30 |
| 541 | actuator mono 1 input bottom 2 | 30 |
| 542 | actuator mono 1 input top 1 | 30 32 |
| 543 | actuator mono 1 input top 2 | 30 |
| 544 | actuator mono 1 input top 3 | 30 32 |
| 545 | actuator mono 1 supply 1 | 30 32 |
| 546 | actuator mono 1 supply 2 | 30 32 |
| 547 | actuator mono 1 output 1 | 30 32 |
| 548 | actuator mono 1 output 2 | 30 32 |
| 549 | actuator mono 2 input top 1 | 30 32 |
| 550 | actuator mono 2 input side 1 | 30 32 |
| 551 | actuator mono 2 supply 1 | 30 32 |
| 552 | actuator mono 2 supply 2 | 30 31 32 |
| 553 | actuator mono 2 output 1 | 30 32 |
| 554 | actuator mono 2 output 2 | 30 32 |
| 555 | actuator mono 3 input side 1 | 30 |
| 556 | actuator mono 3 input side 2 | 30 |
| 557 | actuator mono 3 input side 3 | 30 32 |
| 558 | actuator mono 3 input side 4 | 30 32 |
| 559 | actuator mono 3 supply 1 | 30 32 |
| 560 | actuator mono 3 supply 2 | 30 31 32 |
| 561 | actuator mono 3 output 1 | 30 32 |
| 562 | actuator mono 3 output 2 | 30 32 |
| 563 | actuator mono 4 input top 1 | 30 32 |
| 564 | actuator mono 4 input top 2 | 30 32 |
| 565 | actuator mono 4 supply 1 | 30 32 |
| 566 | actuator mono 4 supply 2 | 30 32 |
| 567 | actuator mono 4 output 1 | 30 32 |
| 568 | actuator dual input top 1 | 30 32 |
| 569 | actuator dual input top 2 | 30 32 |
| 570 | actuator dual supply top 1 | 30 32 |
| 571 | actuator dual supply top 2 | 30 32 |
| 572 | actuator dual supply top 3 | 30 32 |
| 573 | actuator dual supply top 4 | 30 32 |
| 574 | actuator dual output 1 | 30 32 |
| 575 | actuator dual output 2 | 30 32 |
| 576 | high pressure supply plane | 31 |
| 577 | ground plane | 31 |
| 578 | clearance cut | 31 |
| 579 | OR gate | 33 35 36 70 |
| 580 | gate rounded edges | 33 |
| 581 | OR gate O-ring | 33 |
| 582 | OR gate rod | 33 |
| 583 | AJD gate | 33 35 36 41 42 43 44 45 46 47 48 70 71 |
| 584 | AJD gate rubber grid | 33 |
| 585 | AJD gate section | 33 |
| 586 | AJD gate through hole 1 | 33 |
| 587 | AJD gate through hole 2 | 33 |
| 588 | AJD gate side hole | 33 |
| 589 | SAL gate | 33 35 36 41 42 43 44 45 46 47 48 70 71 |
| 590 | SAL gate rubber grid | 33 |
| 591 | SAL gate section | 33 |
| 592 | SAL gate through hole 1 | 33 |
| 593 | SAL gate side hole 1 | 33 |
| 594 | SAL gate through hole 2 | 33 |
| 595 | SAL gate side hole 2 | 33 |
| 596 | XOR gate | 33 35 36 |
| 597 | XOR gate rubber grid | 33 |
| 598 | XOR gate section | 33 |
| 599 | XOR gate through hole 1 | 33 |
| 600 | XOR gate through hole 2 | 33 |
| 601 | XOR gate side hole 2 | 33 |

TABLE 1-continued

List of reference numbers and Figures where they are indicated

| N | Item Name | Shown in FIGS. |
|---|---|---|
| 602 | SW gate | 33 35 36 |
| 603 | SW gate rubber grid | 33 |
| 604 | SW gate section | 33 |
| 605 | SW gate face hole 1 | 33 |
| 606 | SW gate side hole 1 | 33 |
| 607 | SW gate through hole 2 | 33 |
| 608 | SW gate side hole 2 | 33 |
| 609 | diagnose gate | 33 62 63 64 65A |
| 610 | diagnose gate rubber grid | 33 |
| 611 | diagnose gate section | 33 65A |
| 612 | diagnose gate face hole 1 | 33 65A |
| 613 | diagnose gate side hole 1 | 33 65A |
| 614 | diagnose gate through hole 2 | 33 65A |
| 615 | diagnose gate side hole 2 | 33 65A |
| 616 | diagnose gate spring guide | 33 |
| 617 | AJD 1 cavity | 34 35 36 |
| 618 | AJD 1 aux | 34 35 36 |
| 619 | AJD 1 main | 34 35 36 |
| 620 | AJD 1 input | 34 35 36 |
| 621 | AJD 1 output | 34 35 36 |
| 622 | AJD 1 clear | 34 35 36 |
| 623 | AJD 2 cavity | 34 35 36 |
| 624 | AJD 2 aux | 34 35 36 |
| 625 | AJD 2 main | 34 35 36 |
| 626 | AJD 2 input | 34 35 36 |
| 627 | AJD 2 output | 34 35 36 |
| 628 | AJD 2 clear | 34 35 36 |
| 629 | AJD 3 cavity | 34 35 36 |
| 630 | AJD 3 aux | 34 35 36 |
| 631 | AJD 3 main | 34 35 36 |
| 632 | AJD 3 OR input 1 | 34 35 36 |
| 633 | AJD 3 OR input 2 | 34 35 36 |
| 634 | AJD 3 OR input 3 | 34 35 36 |
| 635 | AJD 3 OR input 4 | 34 35 36 |
| 636 | AJD 3 input | 34 35 36 |
| 637 | AJD 3 output | 34 35 36 |
| 638 | AJD 3 clear | 34 35 36 |
| 639 | SAL 1 cavity | 34 35 36 |
| 640 | SAL 1 aux | 34 35 36 |
| 641 | SAL 1 main | 34 35 36 |
| 642 | SAL 1 OR input 1 | 34 35 36 |
| 643 | SAL 1 OR input 2 | 34 35 36 |
| 644 | SAL 1 OR input 3 | 34 35 36 |
| 645 | SAL 1 OR input 4 | 34 35 36 |
| 646 | SAL 1 input 1 | 34 35 36 |
| 647 | SAL 1 output 1 | 34 35 36 |
| 648 | SAL 1 clear 1 | 34 35 36 |
| 649 | SAL 1 input 2 | 34 35 36 |
| 650 | SAL 1 output 2 | 34 35 36 |
| 651 | SAL 1 clear 2 | 34 35 36 |
| 652 | XOR cavity | 34 35 36 |
| 653 | XOR signal 1 | 34 35 36 |
| 654 | XOR signal 2 | 34 35 36 |
| 655 | XOR input 1 | 34 35 36 |
| 656 | XOR output 1 | 34 35 36 |
| 657 | XOR clear 1 | 34 35 36 |
| 658 | XOR input 2 | 34 35 36 |
| 659 | XOR output 2 | 34 35 36 |
| 660 | XOR clear 2 | 34 35 36 |
| 661 | SAL 2 cavity | 34 35 36 |
| 662 | SAL 2 aux | 34 35 36 |
| 663 | SAL 2 main | 34 35 36 |
| 664 | SAL 2 input 1 | 34 35 36 |
| 665 | SAL 2 output 1 | 34 35 36 |
| 666 | SAL 2 input 2 | 34 35 36 |
| 667 | SAL 2 output 2 | 34 35 36 |
| 668 | SAL 2 output connection | 34 35 36 |
| 669 | SW cavity | 34 35 36 |
| 670 | SW aux | 34 35 36 |
| 671 | SW main | 34 35 36 |
| 672 | SW input 1 | 34 35 36 |
| 673 | SW monitor 1 | 34 35 36 |
| 674 | SW output 1 | 34 35 36 |
| 675 | SW input 2 | 34 35 36 |
| 676 | SW monitor 2 | 34 35 36 |
| 677 | SW output 2 | 34 35 36 |
| 678 | depth sensor cavity | 34 35 36 |
| 679 | depth external water pressure pipe | 34 35 36 69 |
| 680 | depth lsb gnd | 34 35 36 |
| 681 | depth lsb high pressure | 34 35 36 |
| 682 | depth msb high pressure | 34 35 36 |
| 683 | depth msb gnd | 34 35 36 |
| 684 | (x) external pressure lsb | 34 35 36 70 |
| 685 | (x) external pressure msb | 34 35 36 70 |
| 686 | logic spring | 35 36 41 42 43 62 63 64 65A |
| 687 | logic long spring | 35 36 |
| 688 | depth sensor | 35 36 69 70 |
| 689 | depth detector | 35 36 69 70 |
| 690 | depth detector rubber grid | 35 36 |
| 691 | depth detector input guard | 35 36 |
| 692 | depth lsb high pressure slot 1 | 35 36 |
| 693 | depth lsb gnd slot | 35 36 |
| 694 | depth lsb high pressure slot 2 | 35 36 |
| 695 | depth msb high pressure slot | 35 36 |
| 696 | depth msb gnd slot | 35 36 |
| 697 | LBSR assembly | 37 |
| 698 | LBSR layer a | 37 41 42 43 44 45 46 47 48 |
| 699 | LBSR layer b | 37 |
| 700 | LBSR layer c | 37 |
| 701 | LBSR layer d | 37 |
| 702 | LBSR gnd layer | 37 |
| 703 | LBSR high pressure feed | 37 38 41 |
| 704 | LBSR cavities | 37 |
| 705 | LBSR connections | 37 |
| 706 | mz cavity | 38 39 |
| 707 | zk cavity | 38 |
| 708 | zkm cavity | 38 39 |
| 709 | zero cavity | 38 39 |
| 710 | register cavity | 38 39 40 |
| 711 | memory cavity | 38 39 40 |
| 712 | mz cavity clear | 38 |
| 713 | mz cavity aux | 38 |
| 714 | zk cavity clear | 38 |
| 715 | zk cavity aux | 38 |
| 716 | zkm cavity clear | 38 |
| 717 | zkm cavity aux | 38 |
| 718 | zero cavity aux | 38 |
| 719 | (k) clock in msb | 38 41 42 43 44 45 46 47 48 |
| 720 | (z) zero in msb | 38 41 42 43 44 45 46 47 48 |
| 721 | (m) master/slave in msb | 38 41 42 43 44 45 46 47 48 |
| 722 | register signal zk | 38 41 42 43 44 45 46 47 48 |
| 723 | register signal mz | 38 39 41 42 43 44 45 46 47 48 |
| 724 | register signal ¬kzm | 38 41 42 43 44 45 46 47 48 70 |
| 725 | register signal kzm | 38 41 42 43 44 45 46 47 48 |
| 726 | register gnd rail | 38 41 42 43 44 45 46 47 48 |
| 727 | memory gnd rail | 38 41 42 43 44 45 46 47 48 |
| 728 | lower XOR input | 38 39 |
| 729 | upper XOR input | 38 39 |
| 730 | (y) unit ready | 38 39 41 42 43 44 45 46 47 48 70 |
| 731 | register y clear | 38 |
| 732 | register zero clear | 38 |
| 733 | register zero set | 38 41 |
| 734 | zero gate | 38 41 42 43 44 45 46 47 48 |
| 735 | zero gate rubber grid | 38 |
| 736 | zero gate section | 38 |
| 737 | zero gate through hole | 38 |
| 738 | zero gate top hole | 38 41 42 43 |
| 739 | XOR output high | 39 43 45 48 |
| 740 | XOR output low | 39 43 45 48 |
| 741 | lower XOR input loop | 39 |
| 742 | twin under connection | 38 39 |
| 743 | twin upper connection | 38 39 |
| 744 | carry output high | 39 |
| 745 | carry output low | 39 42 43 |
| 746 | register input high | 39 41 42 43 |
| 747 | register input low | 39 41 42 43 |
| 748 | memory gate | 39 41 42 43 44 45 46 47 48 |
| 749 | memory gate rubber grid | 39 |
| 750 | memory gate section | 39 |
| 751 | memory gate through hole down | 39 40 |
| 752 | memory gate down hole | 39 40 |

TABLE 1-continued

List of reference numbers and Figures where they are indicated

| N | Item Name | Shown in FIGS. |
|---|---|---|
| 753 | memory gate through hole up | 39 40 |
| 754 | memory gate up hole | 39 40 43 45 48 |
| 755 | memory input high | 40 |
| 756 | memory input low | 40 |
| 757 | memory feed high | 40 |
| 758 | memory feed low | 40 |
| 759 | register gate low | 40 41 42 43 44 45 46 47 48 |
| 760 | register gate low rubber grid | 40 |
| 761 | register gate low section | 40 |
| 762 | register gate through hole | 40 |
| 763 | register gate top hole | 40 |
| 764 | register gate high | 40 41 42 43 44 45 46 47 48 |
| 765 | register gate high rubber grid | 40 |
| 766 | register gate high section | 40 |
| 767 | logic signal connections | 64 |
| 768 | (j) maintenance job | 64 70 71 91 |
| 769 | diagnose connections | 65 |
| 770 | diagnose interface pipe | 65A |
| 771 | diagnose control pipe | 65A |
| 772 | diagnose logic pipe | 65A |
| 773 | router pipe | 65A |
| 774 | i/o layer c cuts | 67 |
| 775 | (i) internal water pressure msb | 67 68 71 91 |
| 776 | (i) internal water pressure lsb | 67 68 71 91 |
| 777 | (n) internal CO2 pressure lsb | 67 68 71 91 |
| 778 | (O) open door control | 67 68 71 91 |
| 779 | (T) vent air control | 67 68 70 71 91 |
| 780 | (B) raise flag control | 67 68 70 71 91 |
| 781 | (P) stop water pump control | 67 68 71 91 |
| 782 | (IV) dive control | 67 68 70 71 91 |
| 783 | LFSR logic block | 69 |
| 784 | signal answer logic block | 69 |
| 785 | signal leak alarm logic block | 69 |
| 786 | depth management logic block | 69 |
| 787 | pipe port management logic block | 69 |
| 788 | routed pipe block | 70 |
| 789 | ground feed | 69 |
| 790 | ground pipe | 69 |
| 791 | high pressure water source | 69 |
| 792 | high pressure supply | 70 71 |
| 793 | (TX) transmit signal | 70 |
| 794 | (s) status in msb | 70 |
| 795 | (h) help in msb | 70 |
| 796 | (S) status control | 70 |
| 797 | (q) query in msb | 70 |
| 798 | (AL) alarm | 70 71 |
| 799 | (Q) query control | 70 |
| 800 | (r) reset in msb | 70 |
| 801 | (r) reset in lsb | 70 |
| 802 | (R) reset control | 70 |
| 803 | (H) help control | 70 |
| 804 | (OV) depth overshoot | 70 71 |
| 805 | (g) ground lsb | 70 71 91 |
| 806 | (v) dive in msb | 70 |
| 807 | (pl) dive complete | 70 |
| 808 | (FE) flag enable control | 70 |
| 809 | (E) dive disable control | 70 91 |
| 810 | (pp) pipe port status | 71 |
| 811 | ppA alarm | 71 |
| 812 | ppB alarm | 71 |
| 813 | ppB alarm ^ ne | 71 |
| 814 | ¬BA | 71 |
| 815 | ¬BAD | 71 |
| 816 | BD | 71 |
| 817 | ¬CD | 71 |
| 818 | ¬CDA | 71 |
| 819 | CA | 71 |
| 820 | signal hose | 74A |
| 821 | oxygen hose | 74A |
| 822 | CO2 pressure stub | 75 |
| 823 | water pressure stub | 75 |
| 824 | actuator dual stub | 75 |
| 825 | diagnose device | 76 |
| 826 | diagnose device body | 76 |
| 827 | diagnose connector | 76 |
| 828 | diagnose band | 76 |
| 829 | diagnose high pressure supply hose | 76 |
| 830 | diagnose ground supply hose | 76 |
| 831 | air powered tool | 76 |
| 832 | air supply hose | 76 |
| 833 | barge assembly | 79 80 81 |
| 834 | CO2 storage unit | 79 |
| 835 | CO2 extraction unit | 79 |
| 836 | control and materials storage room | 79 |
| 837 | O2 storage unit | 79 |
| 838 | engine room | 79 |
| 839 | fuel storage unit | 79 |
| 840 | pump room | 79 |
| 841 | algae separation unit | 79 |
| 842 | algae storage unit | 79 |
| 843 | floating structure | 79 |
| 844 | reactor node in configuration 1 | 80 |
| 845 | reactor node in configuration 2 | 80 |
| 846 | reactor node in configuration 3 | 80 |
| 847 | reactor node in configuration 4 | 80 |
| 848 | reactor node in configuration 5 | 80 81 |
| 849 | reactor node configuration 6 | 80 |
| 850 | reactor node in configuration 7 | 80 |
| 851 | reactor node in configuration 8 | 80 |
| 852 | reactor node switching BC to BD | 81 |
| 853 | reactor node switching BC to AC | 81 |
| 854 | reactor node switching BC to AD | 81 |
| 855 | reactor node disabled | 81 |
| 856 | pipe element connected to the barge | 80 |
| 857 | pipe element in normal operation | 80 |
| 858 | pipe element in stand by | 80 |
| 859 | pipe element leaking | 81 |
| 860 | section in normal operation | 80 81 |
| 861 | section with multiple failures | 81 |
| 862 | unit farm | 80 81 84 85 |
| 863 | protection cage | 82 84 |
| 864 | protection cage pole | 82 83 |
| 865 | protection cage frame bar | 82 83 |
| 866 | protection cage structural pole | 82 |
| 867 | protection cage structural bar | 82 |
| 868 | protection cage fixation line | 82 |
| 869 | protection cage net | 82 |
| 870 | water ballast | 83 |
| 871 | air bubble | 83 |
| 872 | emergency air supply | 83 |
| 873 | emergency floating device | 83 |
| 874 | service boat | 80 81 84 85 |
| 875 | farm array | 85 |
| 876 | sea water intake filter | 86 |
| 877 | water degasifier | 86 |
| 878 | condensed water cleaner | 86 |
| 879 | discharge water aerator | 86 |
| 880 | engine | 86 |
| 881 | vaporizator | 86 |
| 882 | CO2 extractor | 86 |
| 883 | CO2 separator | 86 |
| 884 | oxygen extractor | 86 87 |
| 885 | extra heat source | 86 |
| 886 | heat exchanger 1 | 86 |
| 887 | heat exchanger 2 | 86 |
| 888 | heat exchanger 3 | 86 |
| 889 | heat exchanger 4 | 86 |
| 890 | heat exchanger 5 | 86 |
| 891 | heat exchanger 6 | 86 |
| 892 | vaporizator heat exchanger | 86 |
| 893 | sea water intake | 86 |
| 894 | sea water flush | 86 |
| 895 | cold water intake heat exchanger 1 | 86 |
| 896 | hot water exit heat exchanger 1 | 86 |
| 897 | cold water intake heat exchanger 3 | 86 |
| 898 | hot water exit heat exchanger 3 | 86 |
| 899 | cold water intake heat exchanger 4 | 86 |
| 900 | hot water exit heat exchanger 4 | 86 |
| 901 | hot water intake heat exchanger 4 | 86 |
| 902 | cold water exit heat exchanger 4 | 86 |
| 903 | hot gas intake heat exchanger 5 | 86 |
| 904 | cold gas exit heat exchanger 5 | 86 |

TABLE 1-continued

List of reference numbers and Figures where they are indicated

| N | Item Name | Shown in FIGS. |
|---|---|---|
| 905 | cold water intake heat exchanger 5 | 86 |
| 906 | hot water exit heat exchanger 5 | 86 |
| 907 | boil off gas pipe | 86 |
| 908 | hot gas intake heat exchanger 3 | 86 |
| 909 | cold gas exit heat exchanger 3 | 86 |
| 910 | condensate drain heat exchanger 3 | 86 |
| 911 | cleaner exit | 86 |
| 912 | hot water intake heat exchanger 2 | 86 |
| 913 | cold water exit heat exchanger 2 | 86 |
| 914 | water intake aerator | 86 |
| 915 | oxygen enriched air | 86 |
| 916 | aerated water discharge | 86 |
| 917 | hot gas intake heat exchanger 6 | 86 |
| 918 | cold gas exit heat exchanger 6 | 86 |
| 919 | cold gas intake heat exchanger 6 | 86 |
| 920 | hot gas exit heat exchanger 6 | 86 |
| 921 | solid CO2 supply to vaporizator | 86 |
| 922 | gaseous CO2 supply to reactor | 86 |
| 923 | cold intake heat exchanger 2 | 86 87 |
| 924 | hot link of heat exchanger 2 and 1 | 86 |
| 925 | cold exit heat exchanger 1 | 86 87 |
| 926 | boil off oxygen pipe | 86 87 |
| 927 | flow divider | 87 |
| 928 | culture diluter | 87 |
| 929 | algae separator | 87 |
| 930 | water culture phase | 87 |
| 931 | algae slurry phase | 87 |
| 932 | algae storage unit | 87 |
| 933 | flow splitter | 87 |
| 934 | culture from reactor | 87 |
| 935 | culture to diluter | 87 |
| 936 | culture to separator | 87 |
| 937 | algae slurry conduct | 87 |
| 938 | water to diluter | 87 |
| 939 | diluted water to reactor | 87 |
| 940 | water to add nutrients | 87 |
| 941 | nutrients | 87 |
| 942 | enriched water | 87 |
| 943 | separator case | 88 89 |
| 944 | concentrator | 88 89 |
| 945 | helical pusher | 88 89 |
| 946 | helical axis | 88 89 |
| 947 | entry support | 88 89 |
| 948 | exit support | 88 89 |
| 949 | slurry entry | 88 89 |
| 950 | slurry exit | 88 89 |
| 951 | water exit | 88 89 |
| 952 | central computer | 90 |
| 953 | local computer | 90 |
| 954 | central antenna | 90 |
| 955 | local antenna | 90 |
| 956 | satellite link | 90 |
| 957 | data link | 90 |
| 958 | interface | 90 96 |
| 959 | input bus | 90 |
| 960 | input line | 90 |
| 961 | analog to digital converter | 90 96 |
| 962 | output bus | 90 |
| 963 | output line | 90 |
| 964 | solenoid valve | 90 96 |
| 965 | hi pressure vessel | 90 |
| 966 | low pressure sink | 90 |
| 967 | short hose | 90 |
| 968 | T joint | 90 |
| 969 | long hose | 90 |
| 970 | auto lock fitting | 90 |
| 971 | quick release fitting | 90 |
| 972 | remote interface | 91 |
| 973 | local interface | 91 |
| 974 | water resupply node | 93 |
| 975 | forward water pressure | 93 |
| 976 | backward water pressure | 93 |
| 977 | equal water pressure node | 93 |
| 978 | higher water pressure | 93 |
| 979 | lower water pressure | 93 |
| 980 | mean pressure | 93 |

TABLE 1-continued

List of reference numbers and Figures where they are indicated

| N | Item Name | Shown in FIGS. |
|---|---|---|
| 981 | timing point 1 | 94 |
| 982 | timing point 2 | 94 |
| 983 | timing point 3 | 94 |
| 984 | timing point 4 | 94 |
| 985 | timing point 5 | 94 |
| 986 | timing point 6 | 94 |
| 987 | timing point 7 | 94 |
| 988 | timing point 8 | 94 |
| 989 | timing point 9 | 94 |
| 990 | timing point 10 | 94 |
| 991 | timing point 11 | 94 |
| 992 | timing point 12 | 94 |
| 993 | timing point 13 | 94 |
| 994 | timing point 14 | 94 |
| 995 | alternative module assembly | 95 97 |
| 996 | orifice | 95 |
| 997 | supply hose | 97 |
| 998 | power supply and signal cable | 97 97A |
| 999 | cable tap | 97A |

Detailed Description—First Embodiment

The present invention consists of several parts that are conceived to work together in an integrated system to allow the cultivation of marine algae in land based or sea based farms. The system is basically the same the only difference being that in case of land operation some parts are not needed and are therefore removed to save costs.

The system is composed of three main parts: a) the individual components and assemblies used to create a volume to contain the algae water culture henceforward also called the wet components, reactor, wet reactor or wet part of the system; b) the parts that are necessary to control and operate the system at the required degree of precision henceforward also called the dry components or the dry part of the system; c) the monitoring system.

The named dry components does not mean these components are not in contact with water at all but rather that they are not part of the wet reactor. Wet components are in direct contact with water algae culture and in case of a farm operating at sea also with external sea water and may also be submerged for safety during severe weather conditions. Most dry components are not in contact with external sea water at any time and do not need to be submerged during storms.

There are many tasks that need to be performed simultaneously in perfect coordination to enable the system to cope with all requirements. Therefore, an important part of the design is a monitoring system able to transmit information over relatively long distances so that the status of all individual units is available at a central control room and appropriate actions can be taken depending on the messages received.

FIG. 1 shows one embodiment of a pipe element 100. A number of these pipe elements, together with other components are assembled in such a way to create a continuous isolated volume that constitutes the water culture of the wet reactor. The pipe element 100 consists of an outer pipe 101 with a cross section in the shape of a rectangle with pipe rounded edges 102. The outer pipe 101 contains the water, nutrients, algae and byproducts such as oxygen. The outer pipe 101 is made of a low cost suitable material such as a plastic resin or other suitable material using extrusion or another production method that is both cheap and reliable.

The selected material needs to be highly transparent; resistant to chemical degradation and impermeable to: sea water, $CO_2$, Oxygen and other chemicals used in the cultivation of the microalgae; resistant to UV light; flexible, with high resistance to flexure fatigue and small impacts such as those that could be caused by a small boat or jet ski used by the maintenance crews and resistant to biological fouling by sea organisms.

The outer pipe 101 may also have a coating or an intermediate layer of a reflective material running along its lower part so that the light that has passed through the algae culture instead of escaping to the sea is reflected back to the culture, increasing the availability of light at the deeper part of the unit boosting algae productivity. The selected material also needs to be slightly positive buoyant so that the pipe element 100 will not sink in case of a failure causes one or more pipe elements to become loose.

Inside the outer pipe 101 there is an inner pipe 103 made of silicone rubber or another material that is low cost; malleable and resistant to flexure fatigue; impermeable to water; resistant to chemical attack from sea water and other chemical used in the cultivation of the microalgae and highly permeable to $CO_2$. The inner pipe is used to contain the $CO_2$ under pressure so that $CO_2$ permeates into the algae culture contained between the inner pipe and the outer pipe of the pipe element. The amount of $CO_2$ that permeates into the culture at a given section of the wet reactor can be controlled by means of adjusting the pressure inside the inner pipe of the referred section. Increasing the pressure causes more $CO_2$ to permeate into the culture and likewise, reducing the pressure causes less $CO_2$ to permeate into the culture. By carefully adjusting the $CO_2$ pressure throughout the reactor, the necessary quantities of $CO_2$ can be made available to the microalgae as they grow and multiply avoiding the problems of shortage of $CO_2$ that limits the growth or $CO_2$ excess that impacts the PH of the water and may harm the microalgae.

Figure 1A:
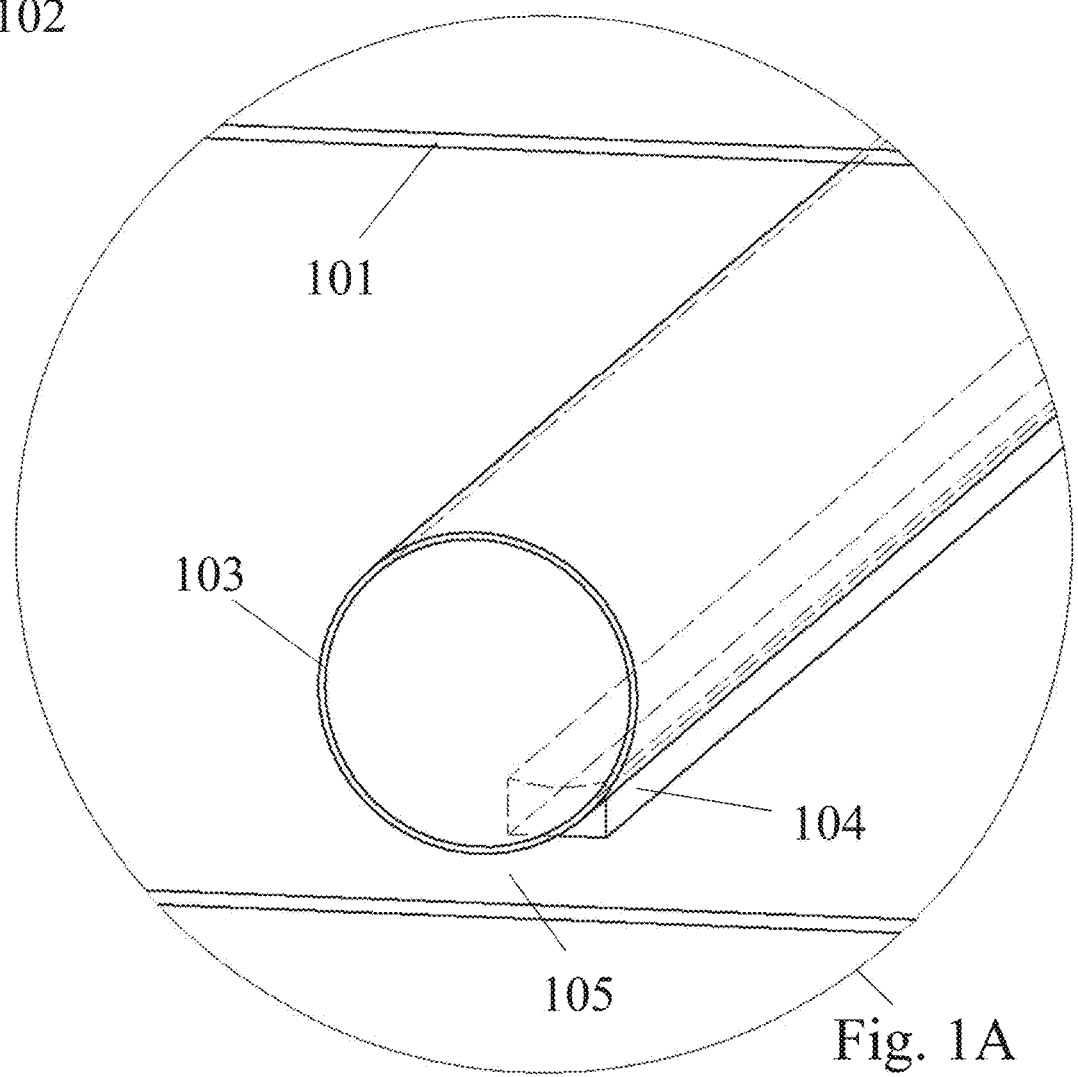
FIG. 1A shows the center of the pipe element in greater magnification to better display its features and the inner pipe 103.

FIG. 1A shows in detail how the inner pipe 103 is attached to the inside of the outer pipe 101 by means of a rim 104 made of the same material as the outer pipe or a suitable material to achieve a better bondage. The rim 104 that bonds the inner pipe 103 and the outer pipe 101 is made in such a way to leave a gap 105 at both ends of the pipe element to allow both the inner pipe 103 and the outer pipe 101 of the pipe element 100 to be tightened to other parts. The thickness of both the inner pipe 103 and the outer pipe 101 are adjusted to be as thin as possible to save material and reduce costs while ensuring the necessary strength, resistance and durability. The inner pipe 103 may be extruded together or just prior to the outer pipe 101 in such a way that the materials will fuse together creating a highly resistant bondage. Alternatively, another process such as welding or gluing may be used depending on cost and reliability to produce the pipe element 100. The pipe element 100 may be precut at the factory to standard sizes or collapsed and rolled in heels for transport convenience and later be cut according to requirements during installation.

FIG. 2 shows a partially exploded assembly of one embodiment of a straight joint 113 and two pipe element 100a and 100b. To secure each inner pipe 103a and 103b an inner tie 107a and 107b respectively is used and to secure the outer pipe 101, a pipe tie 110a and 110b respectively is used. The straight joint 113 is constructed to fit perfectly to the pipe element 100 and provide tight connections to link up the outer pipe 101 and inner pipe 103 of the pipe element in two independent, isolated circuits so that the water culture and the $CO_2$ remain separated throughout the reactor. The pipe element 100a represented at the left side has been offset from the straight joint 113 and has been cut out to show the inner tie 107a as well as the pipe tie 110a. The pipe element 100b at the right side is represented in the proper place with no cut out to show the correct placement of inner tie 107b and the pipe tie 110b.

The straight joint is made with a material that is low cost, impermeable to water and other chemicals used in the cultivation of the microalgae, resistant to UV light and suitable to be used at sea. The material also needs to be rigid and slightly positive buoyant so that it will provide a stable frame to attach the pipe elements and will not sink in case a failure causes a straight joint or a section of one or several pipe elements and straight joints becomes loose.

Detail FIG. 2A shows that the inner tie is composed of an inner band 108 and an inner band fastener 109. The inner band 108 is made with a flexible material that is durable, resistant to UV light and sea water and has a low stretch coefficient when subjected to tension. The inner band fastener 109 creates a means to reduce the length of the inner band 108 creating friction between the inner wall of the inner pipe of a pipe element and the component to that it is being fixated.

Detail FIG. 2B shows that the pipe tie is composed of a pipe band 111 and a pipe band fastener 112. The pipe band 111 is made with a flexible material that is durable, resistant to UV light and sea water and has a low stretch coefficient when subjected to tension. The pipe band fastener 112 creates a means to reduce the length of the pipe band 111 creating friction between the inner wall of the outer pipe of a pipe element and the component to which it is being fixated.

Detail FIG. 2C shows a zoomed view of the first embodiment of the straight joint 113 with the pipe element 100b that was visible in FIG. 2 not shown for better clarity. The straight joint 113 has an outer wall 114 with wall rounded edges 115 made with dimensions so that it will fit tightly into the outer pipe of a pipe element. The outer wall 114 of the straight joint 113 is thicker in the center creating a wall band 123 that divides the straight joint 113 in two symmetrical pipe ports 125a and 125b. The wall band 123 has two vertical edges 124a and 124b that work as stoppers for the pipe elements attached to each pipe port of the straight joint, allowing the pipe elements to be properly placed with respect to the straight joint and to each other. In that way the wall band prevents one pipe element from moving beyond its proper position to a point in that it would displace the other pipe element compromising the fixation. The wall band also reinforces the straight joint so that it can better withstand the pressure applied by the pipe ties when they are tightened in place to secure the pipe elements on each pipe port 125. To improve the retention of the pipe element, the outer wall 114 of each pipe port has two parallel outer rims 121a and 121b on pipe port 125a and two parallel outer rims 121c and 121d on pipe port 125b creating an outer tie slot 122a on pipe port 125a and an outer tie slot 122b on pipe port 125b. A pipe tie is to be installed around the middle of each outer tie slot so that when the pipe tie is tightened the outer rims are compressed against the inner wall of the outer pipe of the pipe element creating more friction and improving fixation.

The straight joint 113 also has an inner guide 116 with dimensions that enable it to fit tightly into the inner pipe of a pipe element. The inner guide 116 is attached to the outer wall 114 of the straight joint 113 by means of a support 117 with dimensions that allow the inner guide 116 to be in perfect alignment with the inner pipe of a pipe element when the outer pipe of the mentioned pipe element is attached to the outer wall 114 of the straight joint 113. Two guide support gaps 118*a* and 118*b* one on each pipe port 125*a* and 125*b* respectively allow the inner pipes of the pipe elements and the inner ties used to secure the inner pipes to reach their assembly position on each side of the straight joint.

The inner guide 116 of the straight joint 113 has two parallel inner rims 119*a* and 119*b* on pipe port 125*a* and two parallel inner rims 119*c* and 119*d* on pipe port 125*b* creating an inner tie slot 120*a* on pipe port 125*a* and an inner tie slot 120*b* on pipe port 125*b*. An inner tie is to be installed around the middle of each inner tie slot so that when the inner tie is tightened the inner rims are compressed against the inner wall of the inner pipe of the pipe element creating additional friction that improves fixation.

FIG. 3 shows one embodiment of a 90 degrees joint 127 that may be used when needed to create a pipework able to make turns and cover a higher percentage of the available surface either on land or at sea. The 90 degrees joint 127 is constructed so that it has two pipe ports 125*a* and 125*b* that have the same shape as the pipe ports in the straight joint in order to allow it to fit perfectly to pipe elements in the same way the straight joint does. Differently from the straight joint where the pipe ports are aligned at either end, the 90 degrees joint 127 has a 90 degrees middle body 128 connecting the outer wall 114 of both pipe ports that creates the 90 degrees turn to the joint. To avoid creating undesired turbulence in the flow, the 90 degrees middle body 128 has 90 degrees rounded rims 129 with the same curvature as the wall rounded edges 115 of the pipe port. The inner guides 116 on each end of the 90 degrees joint 127 are connected by a 90 degrees inner guide 130 that creates the required 90 degrees turn. The 90 degrees joint is made with a material that is low cost, impermeable to water and other chemicals used in the cultivation of the microalgae, resistant to UV light and suitable to be used at sea. The material also needs to be rigid and slightly positive buoyant so that it will provide a stable frame to attach the pipe elements and will not sink in case a failure causes a 90 degrees joint or a section of one or several pipe elements and one or more 90 degrees joints and straight joints to become loose.

Detail FIG. 3A shows that the 90 degrees joint is constructed so that each of its pipe ports has an outer wall 114 and an inner guide 116 made with the same dimensions as pipe ports of the straight joint. To improve the retention of the pipe element, each pipe port of the 90 degrees joint has two parallel outer rims 121*a* and 121*b* on the outer wall 114 of each pipe port creating an outer tie slot 122. The pipe tie is to be installed around the middle of that outer tie slot 122 so that, when the pipe tie is tightened, the outer rims 121 are compressed against the inner wall of the outer pipe of the pipe element creating more friction and improving fixation. Similarly, each pipe port of the 90 degrees joint has two inner rims 119*a* and 119*b* on the inner guide 116, creating an inner tie slot 120 on each pipe port around which the inner tie is to be installed. When the inner tie is tightened, the inner rims are compressed against the inner wall of the inner pipe of the pipe element creating additional friction that improves fixation. Each pipe port has a wall band 123 located at the point the pipe port and the 90 degrees middle body 128 are connected. A vertical edge 124 on each wall band 123 works as a stopper for the pipe element attached to each pipe port, allowing the pipe elements to be properly placed with respect to the 90 degrees joint. The wall bands also reinforce the pipe ports of the 90 degrees joint so they can better withstand the pressure applied by the pipe ties when they are tightened in place to secure the pipe elements. The inner guide 116 on each pipe port is attached to the 90 degrees inner guide 130 that is in turn attached to the 90 degrees middle body by means of a 90 degrees support 131. The dimensions of the 90 degrees support 131 allow the inner guide 116 to be in perfect alignment with the inner pipe of a pipe element when the outer pipe of the mentioned pipe element is attached to the outer wall of the pipe port of the mentioned 90 degrees joint. A guide support gap 118 on each pipe port allows the inner pipes of the pipe elements and the inner ties used to secure the inner pipes to reach their assembly position on each pipe port of the 90 degrees joint.

FIG. 4 shows one embodiment of an 180 degrees joint 132 that may be used when needed to create a pipework able to make turns and cover a higher percentage of the available surface either on land or at sea. The 180 degrees joint 132 is constructed so that it has two pipe ports 125*a* and 125*b* that have the same standard shape as the ones in the straight joint in order to allow it to fit perfectly to pipe elements in the same way as the straight joint. Differently from the straight joint where the pipe ports are aligned at either end, the 180 degrees joint 132 has a 180 degrees middle body 133 connecting the outer wall 114 of both pipe ports 125 that creates the 180 degrees turn to the joint. To avoid creating undesired turbulence in the flow, the 180 degrees middle body 133 has 180 degrees rounded rims 134 with the same curvature as the wall rounded edges 115 of the pipe port. The inner guides 116 on each side of the 180 degrees joint 132 are connected by a 180 degrees inner guide 135 that creates the required 180 degrees turn. The 180 degrees joint is made with a material that is low cost, impermeable to water and other chemicals used in the cultivation of the microalgae, resistant to UV light and suitable to be used at sea. The material also needs to be rigid and slightly positive buoyant so that it will provide a stable frame to attach the pipe elements and will not sink in case a failure causes a 180 degrees joint or a section of one or several pipe elements and one or more joints to become loose.

Detail FIG. 4A shows that the 180 degrees joint is constructed so that each of its pipe ports has an outer wall 114 and an inner guide 116 made with the same dimensions as pipe ports of the straight joint. To improve the retention of the pipe element, each pipe port of the 180 degrees joint has two parallel outer rims 121*a* and 121*b* on the outer wall 114 of each pipe port creating an outer tie slot 122. The pipe tie is to be installed around the middle of that outer tie slot 122 so that, when the pipe tie is tightened, the outer rims are compressed against the inner wall of the outer pipe of the pipe element creating more friction and improving fixation. Similarly, each pipe port of the 180 degrees joint has two inner rims 119*a* and 119*b* on the inner guide 116, creating an inner tie slot 120 on each pipe port around that the inner tie is to be installed. When the inner tie is tightened, the inner rims are compressed against the inner wall of the inner pipe of the pipe element creating additional friction that improves fixation. Each pipe port has a wall band 123 located at the point where the pipe port and the 180 degrees middle body 133 are connected. A vertical edge 124 on each wall band 123 works as a stopper for the pipe elements attached to each pipe port, allowing the pipe elements to be properly placed with respect to the 180 degrees joint. The wall bands also reinforce the pipe ports of the 180 degrees joint so the pipe ports can better withstand the pressure applied by the pipe ties when the pipe ties are tightened in place to secure the pipe elements. The inner guide 116 on each pipe port is attached to the 180 degrees inner guide 135 that is in turn attached to the 180 degrees middle body by means of a 180 degrees support 136. The dimensions of the 180 degrees support 136 allow the inner guide 116 to be in perfect alignment with the inner pipe of a pipe element when the outer pipe of the mentioned pipe element is attached to the outer wall of the pipe port of the mentioned 180 degrees joint. A guide support gap 118 on each pipe port allows the inner pipes of the pipe elements and the inner ties used to secure the inner pipes to reach their assembly position on each pipe port of the 180 degrees joint.

FIG. 5 shows one embodiment of a reactor node 214. The reactor node 214 main component is a node core 215 that works as structural framework and support for other parts. The parts fit into cavities and recesses specifically designed so that the corresponding parts can be easily inserted and removed even if other components are in place. The node core 215 is constructed to create 4 sections that contain components to manage the connection of up to four pipe elements and other parts necessary to perform the associated functions. To facilitate the identification and understanding of the design, each of the four sections is identified with an uppercase bold letter A, B, C and D and the parts used in each section are marked with an uppercase letter identical to the section letter. Other parts that appear multiple times are differentiated with a lowercase letter unrelated to the sections.

FIG. 5 shows the parts that are accessible from the outside. These parts when removed grant access to other parts that need to operate inside the node core 215, isolated from the outside environment. Each section of the node core 215 contains a pipe port 125, a door plug 137 and a CO2 valve plug 148. Also visible at the top of the node core is an air release assembly 257 and a module assembly 369 and at the sides, two pump covers 315*a* and 315*b*. FIG. 5 also shows that in case of sea operation, the reactor node 214 may be attached to an anchor assembly 282 by means of an anchor cable 287 that allows it to stay in place at the surface of the sea or be submerged to a specific depth to protect the reactor node and attached pipe elements from strong waves during a storm or due to other reason that may require the reactor node to be submerged. The anchor cable 287 has a stopper 290 placed at a convenient point between the anchor assembly 282 and the reactor node 214 that determines the maximum depth the reactor node 214 can be submerged.

The four pipe ports allow the reactor node 214 to connect to up to four pipe elements simultaneously. The reactor node is constructed with materials such as plastic resins e.g. polycarbonate, PET, or another suitable option that are low cost, resistant to sea water, UV light and biological fouling (additives may be used to improve these properties). The material also needs to be rigid so that it will provide a stable frame to attach the pipe elements and to install a number of components that are required so that the reactor node can perform all its functions. The selected materials should also allow the reactor node 214 to be slightly positive buoyant so it will not sink in case a failure causes a reactor node or a section of one or several pipe elements and one or more reactor nodes, 180 degrees joints, 90 degrees joint and straight joints to become loose. The reactor node is the key element in the wet reactor and contains a number of sub-assemblies and parts that implement a number of different functionalities that are critical to the operation of the wet reactor.

Detail FIG. 5D shows one possible type of anchor assembly that may be used to secure a reactor node to the sea floor that consists of an anchor body 283 made of a hollow compartment, cylindrical in shape, closed at the top and open at the bottom. The anchor cable 287 is secured to the top of the anchor body 283 at an anchor handle 285 by means of an anchor cable loop 288 at the end of the anchor cable 287. An anchor valve 286 placed on the top of the anchor body 283 allows air and water to flow in and out of the anchor body 283.

Detail FIG. 5A shows that components such as the door plugs 137B and 137C, the pump cover 315*b* and the flag port 298 are attached to the node core 215 by means of fasteners 254 and secured by inserting R-clips 256 into the fasteners to secure the components in place. The shape of the fasteners 254 and the R-clips 256 are standardized so that the same R-clips 256 can be used to secure all components, facilitating the work of maintenance crews.

Detail FIG. 5A also shows that each of the reactor node pipe ports 125 has an outer wall 114 with wall rounded edges 115 and an inner guide 116 made with the same dimensions as pipe ports of the straight joint, 90 degrees joint and 180 degrees joint. To improve the retention of the pipe element, each pipe port has two parallel outer rims 121*a* and 121*b* on the outer wall 114 of the pipe port creating an outer tie slot 122. The pipe tie is to be installed around the middle of that outer tie slot 122 so that, when the pipe tie is tightened, the outer rims are compressed against the inner wall of the outer pipe of the pipe element creating more friction and improving fixation. Similarly, each pipe port has two inner rims 119*a* and 119*b* on the inner guide 116, creating an inner tie slot 120 around that the inner tie is to be installed. When the inner tie is tightened, the inner rims are compressed against the inner wall of the inner pipe of the pipe element creating additional friction that improves fixation. The pipe ports on the reactor node terminate at a node core wall 220 that works as a stopper for the pipe elements attached to each pipe port. For proper positioning, each pipe element is inserted into the pipe port until its extremity touches the node core wall 220. The inner guide 116 on each pipe port is attached to the node core 215 by means of a node support 251. The dimensions of the node support 251 allow the inner guide 116 to be in perfect alignment with the inner pipe of a pipe element when the outer pipe of the mentioned pipe element is attached to the outer wall of the pipe port. A guide support gap 118 on each pipe port allows the inner pipes of the pipe elements and the inner ties used to secure the inner pipes to reach their assembly position on each pipe port.

Detail FIG. 5B shows that various components such as the air release lower cover 258, the air release left upper cover 259, the air release right upper cover 260 and the air release top cover 262 that are part of the air release assembly (see FIG. 7 and FIG. 21) are fixated using standard fasteners 254*a*, 254*b*, etc. and R-clips 256*a*, 256*b*, etc. as in other parts of the reactor node. FIG. 5B also shows that the air release right upper cover 260 contains an air release attachment right 265 from where air can be extracted from the reactor node and that the air release top cover 262 contains an air purge 263 opening from where air can be released into the environment.

Detail FIG. 5C shows that the module assembly 369 is fixated using standard fasteners 254 and R-clips 256 as in other parts of the reactor node. A flag 307 used to indicate that the reactor node has a fault and needs service is shown in its rest or lowered position. The flag 307 is made of a suitable material mixed with a high visibility color pigment to make the flag easily visible against the background in the ocean or land when it is raised. The flag has a series of digit notches 308 disposed to make four figures "8" in the front and four figures "8" in the back so that digit pads 309 made of a high contrast color material can be fitted into appropriate places to create a unique combination of color patterns and numbers for each reactor node in the wet reactor.

Also visible in FIG. 5C is a diagnose port 161, composed of twenty-two (22) diagnose attachments arranged in a 11×2 array, each one identical to diagnose attachment 162 and a signal port right 164 composed of 12 identical hose attachments where hoses with matching fittings are connected to carry pressurized water, pressurized air, pressurized CO2 and signals carried by pressurized water in and out of the module assembly. The signal port right 164 is composed of: (u) air resupply right 165, (w) water resupply right 166, (K) clock out 167, (Y) unit ready out 168, (Z) zero out 169, (v) dive in 170, (M) master/slave out 171, (r) reset in 172, (Q) query out 173, (h) help in 174, (S) status out 175, and (l) CO2 resupply right 176. Whenever possible, a single lowercase or uppercase letter from the signal name is used to identify each signal. These letters are later used to facilitate the description of the logic functions implemented. A lowercase letter indicates an input signal and an uppercase letter indicates an output signal with the exception of (w), (u) and (l) that are bidirectional. The letter case for these three signals is used to differentiate signals on the signal port right (lowercase) from signals on signal port left (uppercase).

FIG. 6 shows the reactor node from a bottom back angle allowing pipe port 125D door plug 137D, CO2 valve plug 148A, 148C and 148D and an anchor opening 284 at the bottom of the anchor assembly 282 to be seen. FIG. 6 also shows that two stoppers 290a and 290b are used to set the depth the reactor node 214 is maintained. The stopper 290a is adjusted so that it touches the node core 215 when the reactor node 214 reaches the surface and prevents the reactor node 214 to become loose from the anchor cable 287 and the stopper 290b prevents the reactor node 214 to dive deeper than a maximum set depth.

Detail FIG. 6A shows the fixation of CO2 valve plug 148A using standard fasteners 254 and standard R-clips 256. Also visible in FIG. 6A is the node core external opening 252 that allows the module assembly to sense the outside water pressure and the fitting of the module rim 371 and the expansion case rim 390 on top of each other and flush with the node core (see FIG. 8 and FIG. 25).

Detail FIG. 6B shows the placement of a cable winch cavity 227 that contains a cable winch 292. The cable winch 292 grips the anchor cable 287 and moves it up and down to enable the reactor node to be placed at the surface or at a preset depth depending on need. The anchor cable is terminated by a knot 289 that holds the stopper 290a in place.

FIG. 7 shows the different components and sub-assemblies that compose the reactor node in an exploded view. The base component of the reactor node is the node core 215 that serves as support for all other components and sub-assemblies. The node core is designed to allow up to four (4) pipe elements to be connected to four (4) pipe ports. To control the flow of water and CO2 in and out of each pipe port, four (4) identical sets of components are used. To reduce the number of lines and numbers in the drawing and improve clarity, only the set used in pipe port A is indicated, the other sets are identical. To control the water flow, each set is composed of a door 139A, two door springs 145a and 145b and a door plug 137A. The door springs 145a and 145b and the door 139A are kept in place by the fixation of the door plug 137A into the node core 215. To control the CO2 flow, each set further contains a CO2 valve 150A, two CO2 valve springs 158a and 158b and a CO2 valve plug 148A. The CO2 valve springs 158a and 158b and the CO2 valve 150A are kept in place by the fixation of the CO2 valve plug 148A into the node core 215.

The reactor node contains one anchor assembly 282, one anchor cable 287 with two stoppers 290a and 290b and one cable winch 292 in case of operation on water to prevent it from drifting away and to be able to be submerged if necessary. The cable winch 292 is installed before a pump rotor assembly 325b is inserted into the node core 215 and a pump cover 315b is fixated to the node core 215. The cable winch is engaged and held in place by the pump rotor assembly 325b that in turn is held in place by the pump cover 315b.

Similarly, a propeller set assembly 347 needs to be installed before a pump rotor assembly 325a is inserted into the node core 215 and a pump cover 315a is fixated to the node core 215. The propeller set assembly 347 is engaged by the pump rotor assembly 325a that in turn is kept in place by the fixation of the pump cover 315a into the node core 215.

Finally, an air release assembly 257, a flag assembly 297 and a module assembly 369 complete the reactor node. The node core 215 can be constructed using various construction methods such as plastic injection, composite materials molding, milling, etc.

FIG. 8 shows that to facilitate the construction and reduce costs it is envisaged that the first embodiment of the node core 215 is divided into four parts: node core a 216, node core b 217, node core c 218 and node core d 219. The parts are designed to be easily manufactured by simple standard methods regardless of the technique used in their fabrication by allowing direct access to all internal cavities. The parts fit perfectly together and can later be glued, welded or fixated to build the node core 215.

The node core a 216 has an internal water culture cavity 234 that allows the water culture to flow inside the node core. A water pump cavity 231 and a rotor shaft support 225 provide space and support to insert one pump rotor assembly that drives the propeller set assembly. One pump cover is used to seal the water pump cavity 231 from the outside and keep the pump rotor assembly in place inside the water pump cavity. A back propeller shaft support 221 and a front propeller shaft support 223 are used to install the propeller set assembly and are located in the middle of the water culture cavity 234 to allow the propellers to push water from one side to the other. In that way water can be pumped from pipe port A or pipe port B towards pipe port C or pipe port D and vice versa.

A cable winch cavity 227 allows the installation of the cable winch. A winch rotor cavity 232 provides space and support to insert a second pump rotor assembly that drives the cable winch and keeps the cable winch in place. A second pump cover is used to seal the winch rotor cavity 232 from the outside and keep the pump rotor assembly in place inside the winch rotor cavity.

Four door insertion openings 236A, 236B, 236C and 236D allow access to insert or remove four doors into the node core. A door plug cavity 235A, 235B, 235C (and 235D not visible from the view angle) surrounds each door insertion opening, allowing the installation of a door plug to seal each door insertion opening.

The node core b 217 is made of a simple sheet perforated by four door channels 237A, 237B, 237C, and 237D. Each door channel 237A, 237B, 237C, and 237D passes through a respective door cavity 238A, 238B, 238C, and 238D that accommodate one door and two door springs each. When joined to the node core a 216, each door cavity 238A, 238B, 238C and 238D aligns perfectly with the respective door insertion opening 236A, 236B, 236C and 236D located on node core a 216. Each door channel 237A, 237B, 237C, and 237D allows water to flow through the node core b 217 in and out of the water culture cavity 234 when the corresponding door is in the open position.

The node core b 217 is also perforated by a propeller access opening 240*a* that enables access to install and service the propeller set assembly on node core a 216 and a series of pipe holes 241*a* that enable water or CO2 to pass through the node core b 217 and reach their intended termination points.

The node core c 218 is made of a simple sheet of material that is perforated by four water culture channels 243A, 243B, 243C, and 243D that are aligned with door channels 237A, 237B, 237C, and 237D respectively on the node core b 217 below and by a propeller access opening 240*b* that has the same shape and is aligned with the propeller access opening 240*a* on the node core b 217 below. The node core c 218 also has a series of pipe holes 241*b* and pipe trails 242 that create a pipework that enables water or CO2 to flow in isolated independent circuits and reach their intended termination points. Finally node core c 218 has a CO2 cavity lid 244 that is raised from the surface of the basic sheet.

The node core d 219 has four pipe ports 125A, 125B, 125C, and 125D where up to four pipe elements can be secured. The node core d 219 also has four CO2 valve insertion openings 247B (247A, 247C, and 247D not visible from the view angle), on each of those a CO2 valve with two CO2 valve springs are inserted and a CO2 valve plug installed to secure the CO2 valve and the CO2 valve springs in place. Additionally, node core d 219 has a flag bay 250 where the flag assembly is installed, a module bay 248 to install the module assembly and an air release bay 249 to install the air release assembly. Surrounding the module bay 248 there is a CO2 cavity body 245 that creates the internal space to contain the CO2 used in the reactor. A node core external opening 252 creates an opening to the exterior through which the module assembly can sense the external water pressure.

FIG. 9 shows the first embodiment of the node core from a different perspective (bottom left) to show node core a 216, node core b 217, node core c 218, and node core d 219 in more detail.

The water pump cavity 231 provides space and support to insert one pump rotor assembly that drives the propeller set assembly. One pump cover is used to seal the water pump cavity 231 from the outside and keep the pump rotor assembly in place inside the water pump cavity. The cable winch cavity 227 allows the installation of the cable winch. The winch rotor cavity 232 provides space and support to insert a second pump rotor assembly that drives the cable winch and keeps the cable winch in place. A second pump cover is used to seal the winch rotor cavity 232 from the outside and keep the pump rotor assembly in place inside the winch rotor cavity.

Four door insertion openings 236A, 236B, 236C (and 236D not visible from the view angle) allow access to insert or remove four doors into the node core. A door plug cavity 235A, 235B, 235C (and 235D not visible from the view angle) surrounds each door insertion opening, allowing the installation of a door plug to seal each door insertion opening.

The node core b 217 is made of a simple sheet perforated by four door channels 237A, 237B, 237C, and 237D. Each door channel 237A, 237B, 237C, and 237D passes through the respective door cavity 238A, 238B, 238C and 238D that accommodate one door and two door springs each. When joined to the node core a 216, each door cavity 238A, 238B, 238C and 238D aligns perfectly with the respective door insertion opening 236A, 236B, 236C, and 236D located on node core a 216.

The node core b 217 is also perforated by the propeller access opening 240*a* that enables access to install and service the propeller set assembly on node core a 216. The node core b 217 also has a series of pipe holes 241*a* that creates a pipework that enables water or CO2 to flow in isolated independent circuits and reach their intended termination points.

The node core c 218 is made of a simple sheet of material that is perforated by four water culture channels 243A, 243B, 243C, and 243D that are aligned with door channels 237A, 237B, 237C, and 237D respectively on the node core b 217 below and by the propeller access opening 240*b* that has the same shape and is aligned with the propeller access opening 240*a* on the node core b 217 below. The node core c 218 also has a series of pipe trails 242*a*, 242*b* etc. that create a pipework that enables water or CO2 to flow in isolated independent circuits and reach their intended termination points.

The node core d 219 has four pipe ports 125A, 125B, 125C, and 125D where up to four pipe elements can be secured. Each pipe port continues to a respective pipe port bottom 126A 126B, 126C, and 126D that allow the water culture to continue down through the respective water culture channels 243A, 243B, 243C, and 243D and door channels 237A, 237B, 237C, and 237D to reach the water culture cavity on node core a 216. The node core d 219 also has four CO2 valve insertion openings 247B (247A, 247C, and 247D not visible from the view angle), on each of those a CO2 valve with two CO2 valve springs are inserted and a CO2 valve plug installed to secure the CO2 valve and the CO2 valve springs in place.

The CO2 cavity body 245 is hollow, containing a CO2 cavity 246. When the node core d 219 and node core c 218 are joined together, the CO2 cavity lid seals the CO2 cavity 246 creating an isolated volume to contain the CO2 that is used in the wet reactor so that the CO2 and water culture remain separated at all times. The CO2 that is contained inside the inner pipes of the pipe elements reaches each inner guide 116A, 116B, 116C, and 116D (116D not visible from the view angle) passes through the respective CO2 valve cavity (see FIG. 10 and FIG. 11) and continues directly into the CO2 cavity 246. Also visible in FIG. 9 are the flag bay 250 where the flag assembly is installed and the module bay 248 where the module assembly is installed. The node core external opening 252 creates an opening to the exterior through which the module assembly can sense the external water pressure. The node core d 219 also has a series of pipe holes 241*b* that creates a pipework that enables water or CO2 to flow in isolated independent circuits and reach their intended termination points.

FIG. 10 shows a perspective view of some components of the reactor node with the node core 215 drawn in phantom lines enabling the view of a water body 365 that is composed of all water culture contained inside the reactor node and a CO2 body 367 that is composed of the CO2 supply contained inside the CO2 cavity in the reactor node. FIG. 10 shows the internal positioning of the doors, door springs and door plugs with respect to the water body 365 and CO2 valves, CO2 valve springs and CO2 valve plugs with respect to the CO2 body 367. The drawing is symmetrical; components located at sections A and D as well as B and C are mirror images of each other. To reduce the number of lines and improve clarity components that interact with the water body 365 are indicated on sections A and B only and components that interact with the CO2 body 367 are indicated on sections C and D only.

The door 139A (and mirror image 139D drawn but not indicated) is in the closed position and as a result, door springs 145a and 145b are extended and the door 139A is in contact with the door plug 137A. The door 139B (and mirror image 139C drawn but not indicated) is in the open position and as a result, door springs 145c and 145d are compressed and the door 139B is at the furthest from door plug 137B.

The CO2 valves move together with the corresponding doors so that in case of a leak both the water culture flow and the CO2 supply of the affected section is shut off. As such CO2 valve 150D (and mirror image 150A drawn but not indicated) is in the closed position and as a result, CO2 valve springs 158a and 158b are extended and the CO2 valve 150D is in contact with the CO2 valve plug 148D. CO2 valve 150C (and mirror image 150B drawn but not indicated) is in the open position and as a result, CO2 valve springs 158c and 158d are compressed and the CO2 valve 150C is at the furthest from the CO2 valve plug 148C.

The door springs and CO2 valve springs are included in the design of the reactor node to provide a constant push to the doors and CO2 valves towards the respective door plugs and CO2 valve plugs so that in case of power failure, all doors and CO2 valves automatically close.

FIG. 11 shows a perspective view of the water body 365 and the CO2 body 367 drawn in phantom lines to better show the relative positioning of doors, door springs, door plugs, CO2 valves, CO2 valve springs and CO2 valve plugs. The drawing is symmetrical; components located at sections A and D as well as B and C are mirror images of each other. To reduce the number of lines and improve clarity components that interact with the water body 365 are indicated on sections A and B only and components that interact with the CO2 body 367 are indicated on sections C and D only.

The water body 365 has four water body channels 366A, 366B, 366C, and 366D that pass through the respective doors 139A, 139B (and mirror images 139C, 139D drawn but not indicated). The CO2 body 367 has four CO2 body channels 368A, 368B, 368C, and 368D that pass through the respective CO2 valves 150C, 150D (and mirror images 150A, 150B drawn but not indicated).

The door 139A, 139B is composed of a door body 140A, 140B that is solid and a door opening 141A, 141B that is hollow and allows fluid to pass through. The door 139A (and mirror image 139D drawn but not indicated) is in the closed position and as a result, door springs 145a and 145b are extended and the door 139A is in contact with the door plug 137A. The door body 140A is aligned with the water body channel 366A, closing the channel and preventing water flow. The door 139B (and mirror image 139C drawn but not indicated) is in the open position and as a result, door springs 145c and 145d are compressed and the door 139B is at the furthest from door plug 137B. The door opening 141B is aligned with the water body channel 366B, allowing water flow.

To accommodate material and design limitations, each door spring is installed in a cavity that begins in the node core and continues into the door body allowing the door spring to be as long as possible and so have a better ratio of maximum compression to initial length. The cavity reaches as far into the door body as the door material strength allows, leaving sufficient material before the door opening to ensure strength and durability (see FIG. 13 and FIG. 14). The two door springs inside the doors 139A and 139B are shown in dashed lines for reference. The other doors 139C and 139D are identical, but only the visible parts of the door springs are shown for comparison and clarity.

The CO2 valve 150C, 150D is composed of a CO2 valve body 151C, 151D that is solid and a CO2 valve opening 152C, 152D that is hollow and allows fluid to pass through. The CO2 valves move together with the corresponding doors so that in case of a leak both the water culture and the CO2 supply of the affected section are shut off. As such CO2 valve 150D (and mirror image 150A drawn but not indicated) is in the closed position and as a result, CO2 valve springs 158a and 158b are extended and the CO2 valve 150D is in contact with the CO2 valve plug 148D. The CO2 valve body 151D is aligned with the CO2 body channel 368D, closing the channel and preventing CO2 flow. The CO2 valve 150C (and mirror image 150B drawn but not indicated) is in the open position and as a result, CO2 valve springs 158c and 158d are compressed and the CO2 valve 150C is at the furthest from the CO2 valve plug 148C. The CO2 valve opening 152C is aligned with the CO2 body channel 368C, allowing CO2 flow.

CO2 valves are considerably shorter in length than doors and as a result there is sufficient space available for CO2 valve springs in the node core without the need to create cavities in the CO2 valve body. To reduce costs, CO2 valves are therefore designed without spring cavities.

Considering the construction of the pipe ports and the cavities that contain components that control water culture and CO2 flow such as doors, CO2 valves and their respective springs, the node core sections A and D as well as sections B and C are constructed symmetric, being mirror images of each other. The doors and CO2 valves are moving components and in one section move independent from doors and CO2 valves in other sections according to the operational state of the reactor node. Despite being separate parts, in normal operation the doors and CO2 valves on each section move the same way so they are either both open or both closed.

The drawings of FIG. 10, FIG. 11 and FIG. 12 are made with components drawn on the same position to facilitate the understanding. Furthermore, to facilitate the description, doors and CO2 valves are drawn on mirrored positions for sections A and D and for sections B and C. This does not mean that the movement of doors and CO2 valves in one section is constrained by the position of the doors and CO2 valves in other sections. During normal operation, doors and CO2 valves in all sections can assume any position, the only constraint being that on a particular section both the door and the CO2 valve move the same way so that, after movement has ceased, they are either both open or both closed.

FIG. 12 shows a perspective view of the water body 365 and the CO2 body 367 drawn in phantom lines to serve as reference to the position of all control pipes and sensor pipes that are available to monitor and operate the pipe ports on the four sections of the reactor node. The doors, door plugs, CO2 valves and CO2 valve plugs are drawn in normal lines. For clarity door springs and CO2 valve springs are not drawn so that control pipes and sensor pipes can be better viewed.

Each control or sensor pipe is composed of pipe trails and pipe holes in node core a, node core b, node core c, and node core d. When the node core is assembled joining these four component parts, one part seals the exposed pipe trails in the other, creating pipe sections. One or more of these pipe sections, joined together with pipe holes across different parts, connect the intended termination points for each control and sensor pipes in individual isolated pipes producing an intricate pipework using only four parts that are easy to manufacture.

All pipes in the pipework originate at a node core main control port 189 so that the pipes can be routed to the module assembly that processes sensor signals and generates control signals. Each section has the same set of control and sensor pipes, the only difference being the route each pipe takes to reach the intended termination point on the different sections. The node core main control port 189 has 24 pipes, 6 for each section.

FIG. 12 shows all four sections of the node core with each pipe in each section marked with the corresponding upper case letter A, B, C, and D according to the section it pertains. Other parts such as doors, door plugs, CO2 valves, CO2 valve plugs are also indicated with corresponding upper case letters. The water body 365 the CO2 body 367, each door cavity 238A, 238B, 238C, and 238D with respective door cavity spring cuts 239A, 239B, 239C, and 239D, as well as each CO2 valve cavity with respective CO2 valve cavity spring cuts are drawn in phantom lines to serve as reference. Some indications of components are not made in FIG. 12 to avoid cluttering. Instead all indications are made on FIG. 13 and FIG. 14 that each show only one section in greater detail. Since the components that appear on FIG. 12 in a section are also shown in FIG. 13 and FIG. 14 and the description is the same for each of the four pipe ports, for concision the description is made only for FIG. 13 for a closed configuration and for FIG. 14 for an open configuration. FIG. 12 serves as an overall view of all four sections.

FIG. 13 is a partial view of the reactor node showing section D with door and CO2 valve closed and is a mirror image of section A. All parts shown are for section D and as a result the uppercase letter D is not needed to differentiate these parts from others in other sections so they are indicated with their plain numbers or with a lowercase letter if more than one of the same part is indicated in the drawing. A node core main control port section 190D that is a portion of the node core main control port that contains only pipes that serve section D is the only component marked with D.

FIG. 13 shows the water body 365, the CO2 body 367, and the door cavity 238 with its two door cavity spring cuts 239a and 239b drawn in phantom lines. A CO2 valve cavity 156 with its two CO2 valve cavity spring cuts 157a and 157b is also drawn in phantom lines. The door plug 137 contains a series of fastener holes 253a to fixate it to the node core and a door plug O-ring 138 to help seal the door cavity 238 preventing pressurized water injected into the door cavity 238 from escaping into the environment. The CO2 valve plug 148 contains a series of fastener holes 253b to fixate it to the node core and a CO2 valve plug O-ring 149 to help seal the CO2 valve cavity 156 preventing pressurized water injected into the CO2 valve cavity 156 from escaping into the environment.

The door 139 is composed of the door body 140 that closes the water body channel 366 when the door 139 is in the closed position (in contact with the door plug 137, as drawn) and a door opening 141 that allows water to flow in the water body channel 366 if the door 139 is in the open position. A set of three door O-rings 142a, 142b, and 142c isolates the door body 140 and the door opening 141 to avoid leaks and a series of door spacers 143a and 143b on both sides of the door 139 prevents the door from fully closing the door cavity 238 when open or closed and creates two gaps where water is injected to push the door 139 in both directions. An open door pipe 193 terminates at the gap created by the door spacers 143a between the door and the door plug 137 so that if high pressure water is injected at this point when the door is closed, the door will be pushed away from the door plug 137 and open. A close door pipe 195 terminates at the gap created by the door spacers 143b between the door and the edge of the door cavity 238 so that if high pressure water is injected at this point when the door is open, the door will be pushed towards the door plug 137 and close. Two door spring cuts 144a and 144b one on each side of the door and aligned with the corresponding door cavity spring cut 239a and 239b respectively create spaces to accommodate two door springs 145a, 145b that are used to ensure that in case of power failure the door automatically closes. To facilitate the visualization, the door spring cuts are drawn in dashed lines and the portion of the door springs inside the door spring cuts is omitted.

The CO2 valve 150 is composed of a CO2 valve body 151 that closes the CO2 body channel 368 when the CO2 valve 150 is in the closed position (in contact with the CO2 valve plug 148, as drawn) and a CO2 valve opening 152 that allows CO2 to flow in the CO2 body channel 368 if the CO2 valve 150 is in the open position. A set of three CO2 valve O-rings 153a, 153b, and 153c isolates the CO2 valve body 151 and the CO2 valve opening 152 to avoid leaks and a series of CO2 valve spacers 154a and 154b on both sides of the CO2 valve 150 prevents the CO2 valve from fully closing the CO2 valve cavity 156 when open or closed and creates two gaps where water is injected to push the CO2 valve 150 in both directions. Two CO2 valve spring guides 155 aligned with the two CO2 valve cavity spring cuts 157a and 157b accommodate two CO2 valve springs 158a (the CO2 valve spring inside the CO2 valve cavity spring cut 157b is not drawn to improve visualization) that are used to ensure that in case of power failure the CO2 valve will automatically close. An open CO2 valve pipe 194 terminates at the gap created by the CO2 valve spacers 154a between the CO2 valve and the CO2 valve plug 148 so that if high pressure water is injected at this point when the CO2 valve 150 is closed the CO2 valve will be pushed away from the CO2 valve plug 148 and open. A close CO2 valve pipe 196 terminates at the gap created by the CO2 valve spacers 154b between the CO2 valve and the edge of the CO2 valve cavity 156 so that if high pressure water is injected at this point when the CO2 valve is open, the CO2 valve 150 will be pushed towards the CO2 valve plug 148 and close.

The open door pipe 193 and the open CO2 valve pipe 194 are connected to the same termination point at the node core main control port section 190D and the close door pipe 195 and the close CO2 valve pipe 196 are connected to another same termination point at the node core main control port section 190D so that both the door and CO2 valve open and close together. Control devices located inside the module assembly ensure that when the water pressure at the open door pipe 193 and open CO2 valve pipe 194 is high, the water pressure at the close door pipe 195 and close CO2 valve pipe 196 is low and vice versa so that a consistent pressure difference is generated to push the door and CO2 valve in the desired direction.

A water sensor pipe 197 terminates at the near edge of the water body channel 366 to allow the control devices inside the module assembly to monitor the water pressure in the water body channel and detect water leaks in the pipe element connected to the pipe port D. A water feed pipe 198 terminates at the far edge of the water body channel 366 to allow the control devices inside the module assembly to supply water into the water body channel and control the water pressure in the pipe element attached to pipe port D.

A CO2 sensor pipe 199 terminates at the near edge of the CO2 body channel 368 to allow the control devices inside the module assembly to monitor the CO2 pressure in the CO2 body channel and detect CO2 leaks in the pipe element connected to the pipe port D. A CO2 feed pipe 200 terminates at the far edge of the CO2 body channel 368 to allow the control devices inside the module assembly to supply CO2 into the CO2 body channel and control the CO2 pressure in the pipe element attached to pipe port D.

FIG. 14 is a partial view of the reactor node showing section B with door and CO2 valve open and is a mirror image of section C. All parts shown are for section B and as a result the uppercase letter B is not needed to differentiate these parts from others in other sections so they are indicated with their plain numbers or with a lowercase letter if more than one of the same part is indicated in the drawing. The node core main control port section 190B that is a portion of the node core main control port that contains only pipes that serve section B is the only component marked with B.

FIG. 14 shows the water body 365, the CO2 body 367, the door cavity 238 with its two door cavity spring cuts 239a and 239b, the CO2 valve cavity 156 with its two CO2 valve cavity spring cuts 157a and 157b drawn in phantom lines. The door plug 137 contains a series of fastener holes 253a to fixate it to the node core and the door plug O-ring 138 to help seal the door cavity 238a preventing pressurized water injected into the door cavity 238a from escaping into the environment. The CO2 valve plug 148 contains a series of fastener holes 253b to fixate it to the node core and the CO2 valve plug O-ring 149 to help seal the CO2 valve cavity 156 preventing pressurized water injected into the CO2 valve cavity 156 from escaping into the environment.

The door 139 is composed of the door body 140 that closes the water body channel 366 if the door 139 is in the closed position (in contact with the door plug 137) and a door opening 141 that allows water to flow in the water body channel 366 when the door 139 is in the open position (away from the door plug 137, as drawn). A set of three door O-rings 142a, 142b, and 142c isolates the door body 140A and the door opening 141 to avoid leaks and a series of door spacers 143a and 143b on both sides of the door 139 prevents the door from fully closing the door cavity 238a, 238b when open or closed and creates two gaps where water is injected to push the door 139 to both directions. An open door pipe 193 terminates at the gap created by the door spacers 143a between the door and the door plug 137 so that if high pressure water is injected at this point when the door is closed, the door will be pushed away from the door plug 137 and open. A close door pipe 195 terminates at the gap created by the door spacers 143b between the door and the edge of the door cavity 238 so that if high pressure water is injected at this point when the door is open, the door will be pushed towards the door plug 137 and close. Two door spring cuts 144a, 144b each one aligned with a corresponding door cavity spring cut 239a and 239b one on each side of the door cavity create space to accommodate two door springs (not drawn) that are used to ensure that in case of power failure the door automatically closes.

The CO2 valve 150 is composed of a CO2 valve body 151 that closes the CO2 body channel 368 if the CO2 valve 150 is in the closed position (in contact with the CO2 valve plug 148) and a CO2 valve opening 152 that allows CO2 to flow in the CO2 body channel 368 when the CO2 valve 150 is in the open position (away from the CO2 valve plug 148, as drawn). A set of three CO2 valve O-rings 153a, 153b, and 153c isolates the CO2 valve body 151 and the CO2 valve opening 152 to avoid leaks and a series of CO2 valve spacers 154a and 154b on both sides of the CO2 valve 150 prevents the CO2 valve from fully closing the CO2 valve cavity 156 when open or closed and creates two gaps where water is injected to push the CO2 valve 150 in both directions. Two CO2 valve spring guides 155 aligned with the two CO2 valve cavity spring cuts 157a and 157b accommodate the two CO2 valve springs (not drawn) that are used to ensure that in case of power failure the CO2 valve automatically closes. The open CO2 valve pipe 194 terminates at the gap created by the CO2 valve spacers 154a between the CO2 valve and the CO2 valve plug 148 so that if high pressure water is injected at this point when the CO2 valve 150 is closed the CO2 valve will be pushed away from the CO2 valve plug 148 and open. The close CO2 valve pipe 196 terminates at the gap created by the CO2 valve spacers 154b between the CO2 valve and the edge of the CO2 valve cavity 156 so that if high pressure water is injected at this point when the CO2 valve is open, the CO2 valve 150 will be pushed towards the CO2 valve plug 148 and close.

The open door pipe 193 and the open CO2 valve pipe 194 are connected to the same termination point at the node core main control port section 190B and the close door pipe 195 and the close CO2 valve pipe 196 are connected to another same termination point at the node core main control port section 190B so that both the door and CO2 valve open and close together. Control devices located inside the module assembly ensure that when the water pressure at the open door pipe 193 and open CO2 valve pipe 194 is high, the water pressure at the close door pipe 195 and close CO2 valve pipe 196 is low and vice versa so that a consistent pressure difference is generated to push the door and CO2 valve in the desired direction.

The water sensor pipe 197 terminates at the near edge of the water body channel 366 to allow the control devices inside the module assembly to monitor the water pressure in the water body channel and detect water leaks in the pipe element connected to the pipe port B. The water feed pipe 198 terminates at the far edge of the water body channel 366 to allow the control devices inside the module assembly to supply water into the water body channel and control the water pressure in the pipe element attached to pipe port B.

The CO2 sensor pipe 199 terminates at the near edge of the CO2 body channel 368 to allow the control devices inside the module assembly to monitor the CO2 pressure in the CO2 body channel and detect CO2 leaks in the pipe element connected to the pipe port B. The CO2 feed pipe 200 terminates at the far edge of the CO2 body channel 368 to allow the control devices inside the module assembly to supply CO2 into the CO2 body channel and control the CO2 pressure in the pipe element attached to pipe port B.

Detail FIG. 14A shows the termination point of the close door pipe 195 at the edge of the door cavity 238 so that if high pressure water is injected at this point when the door is open, the door will be pushed towards the door plug and close.

FIG. 15 shows the reactor node 214 drawn in phantom lines to show the assembled position of the flag assembly 297, the pump rotor assembly 325a, the propeller set assembly 347, the pump rotor assembly 325b and the cable winch 292.

The flag assembly 297 is depicted with the flag 307b in an intermediary position moving between two overlaid positions 307a lowered and 307c raised. A flag pipe 201 provides the pressurized water to control the flag 307b. A pair of flag port rims 299 help better secure the flag assembly in place when it is fixated to the node core. The pump rotor assembly 325a is powered by a pump feed pipe 208 that supplies pressurized water and a pump exhaust pipe 209 that allows low pressure water to be discharged into the water body inside the reactor node. That way the pump rotor assembly 325a either turns in the clockwise direction or stops. The pump rotor assembly 325b is powered by a dive control close pipe 206 and a dive control open pipe 207. When the dive control close pipe 206 supplies a way out to low pressure water and the dive control open pipe 207 supplies pressurized water the pump rotor assembly 325b turns in the clockwise direction and alternatively when the dive control close pipe 206 and the dive control open pipe 207 swap roles the pump rotor assembly 325b turns in the counter clockwise direction. That way the cable winch 292 is driven in the desired direction to submerge or surface the reactor node.

FIG. 16 on the right of drawing sheet 19, shows an isometric cutout view of the flag assembly with components seen in place. A flag port 298 provides support and space to fit the other components. The flag port 298 has a series of fastener holes 253 to allow it to be fixated to the node core and the flag port rim 299 (partially cut by the cutout) that strengthens the flag port 298 and allows it to be better secured to the node core. The flag port has an internal flag port cavity 302 that creates space to accommodate a flag lever 310 and allow the flag 307 and a flag piston 311 to move. The flag piston 311 has a flag piston head 312 so that high pressure water injected by the flag pipe 201 can push the flag piston 311 in the direction of the straight arrow shown. The flag piston 311 can partially slide in and out of the flag port cavity 302 through a flag port plug 300 that has a hole in the middle. The flag lever 310 is linked to the flag 307 and the flag piston 311 by means of lever pins 306a and 306b. The flag 307 is fixed to the flag port by means of a flag pin 305 that allows the flag to rotate around it. That way when the flag piston is pushed in the direction of the straight arrow, the flag lever moves and rotates causing the flag to move in the direction of the curved arrow shown and be lowered. A flag spring 314 compressed between the flag port plug 300 and the flag piston head 312 provides a force in the opposite direction so that if the water pressure pushing the flag piston 311 is reduced or a power failure occurs the flag spring 314 pushes back the flag piston head 312 in the opposite direction of the straight arrow, causing the flag to move in the opposite direction of the curved arrow and be raised. A flag raised stopper 303 limits the range of movement of the flag, stopping it when it is perfectly straight. Similarly, a flag lowered stopper 304 limits the range of the movement of the flag stopping it when it reaches the lowered position. The flag 307 is made of a suitable material mixed with a high visibility color pigment so that it will be easily seen against the background of the ocean or land when it is raised. The flag 307 has digit notches 308 disposed to make four figures in the shape of an "8" in the front and four figures in the shape of an "8" in the back so that digit pads 309a, 309b, etc. made of a high contrast color material can be fitted into appropriate places to create a unique combination of color pattern and number for each flag to facilitate the identification of a particular reactor node in the wet reactor.

FIG. 17 on the left of drawing sheet 19 shows a cutout overlaid view of the flag assembly to show the position of the internal components when the flag 307b is in the raised, intermediate and lowered positions. The flag assembly base component is the flag port 298 that provides support and space to fit the other components. The flag port rim 299 (partially cut by the cutout) strengthens the flag port 298 and allows it to be better secured to the reactor node. The flag port has an internal flag port cavity 302 that creates space to accommodate a flag lever 310b and allow the flag 307b and the flag piston 311 to move. The flag piston 311 has a flag piston head 312b with two flag piston O-rings 313a and 313b that improve water tightness so that high pressure water injected by the flag pipe 201 can push the flag piston 311 in the direction of the straight arrow without leaks. The flag piston 311 can partially slide in and out of the flag port cavity 302 through the flag port plug 300 that has a flag port O-ring 301 to seal the cavity where the flag piston head 312b is located. The flag lever 310b is linked to the flag 307b and the flag piston 311 by means of lever pins 306a and 306b. The flag 307b is fixed to the flag port by means of the flag pin 305 that allows the flag to rotate around it. That way when the flag piston is pushed in the direction of the straight arrow, the flag lever moves and rotates causing the flag to move in the direction of the curved arrow. The overlaid components show the positions at the extremes of the movement so that when the flag 307a is in the horizontal or rest position, the flag lever 310a and the flag piston head 312a are in the positions indicated (a). When on the other hand the flag 307c is in the vertical or alarm position, the flag lever 310c and the flag piston head 312c are in the positions indicated (c). The flag spring is not drawn to better display the overlaid flag piston head 312a, 312b and 312c.

FIG. 18 shows a partially exploded view of a reactor node showing the module assembly 369 offset from its installed position in the node core 215. Also offset are the parts that constitute the water pump, the propeller set assembly, the pump rotor assembly and the pump cover 315. The propeller set assembly is composed of four propeller sets 348 and other components shown in detailed FIG. 18A. The pump rotor assembly is composed of a pump rotor 326 that has a pump rotor shaft 329, two pump vanes 334a and 334b and a vane spring, shown in detailed FIG. 18C.

Detail FIG. 18D shows that the extremity of the pump rotor shaft 329 is formed with two sets of chamfers of different lengths. One set of two parallel chamfers extends to a pump rotor drive rim 332 and the other set of two parallel chamfers goes deeper extending to a pump rotor shaft rim 330. The two sets of chamfers produce together a pump rotor drive end 333 with a squared shape cross section that fits into the ratchet drive shaft insert hole in order to drive the ratchet drive (see FIG. 18A and FIG. 21J). The deeper set of parallel chamfers produces a pump rotor shaft drive 331 that is used to drive the cable winch in conjunction with the pump rotor drive end 333 (see FIG. 24A).

Detailed FIG. 18E shows one embodiment of a check valve 339 that allows water to flow only in the direction of the arrow indicated.

Detailed FIG. 18F shows an exploded view of the check valve from a different angle to show its components. The check valve is composed of a check valve body 340 that is made of a rigid material and a check valve rubber 345 made of a flexible material. The check valve rubber 345 has a flat surface and a check valve rubber spear 346 that terminates in a cone that allows the check valve rubber 345 to be fixated to the check valve body 340. The check valve body 340 is hollow to allow water to flow in its center and has a check valve O-ring 344 on the outside perimeter to seal it against the walls of the cavity where it is installed. A check valve support 342 makes an "X" at the bottom of the check valve body 340, flushed to a check valve body rim 341. A check valve support insert hole 343 into which the check valve rubber spear 346 is inserted is located at the center of the check valve support 342. Once inserted, the check valve rubber spear 346 gets hooked holding the check valve rubber 345 in place.

Detail FIG. 18A shows an exploded view of a propeller set and the components used to drive the propellers. A propeller left hand 349 (or a propeller right hand) serves as spokes of an outer gear 351. A propeller hub 352 with a shaft insert square hole 353 in the middle allows the propeller to be fitted into a propeller shaft 354. The propeller shaft 354 has a propeller shaft smaller axle 358 with a diameter smaller than the shaft insert square hole 353, a propeller shaft drive 356 with the cross section of a square the same size of the shaft insert square hole 353 to drive the propeller, a propeller shaft bigger axle 357 with a diameter bigger than the shaft insert square hole 353 so that when the propeller shaft 354 is inserted into the shaft insert square hole 353 the propeller hub 352 stops at the edge of the propeller shaft bigger axle 357. The propeller shaft terminates in a propeller shaft nut 355 in the shape of a square of bigger size than the propeller shaft bigger axle 357. A propeller shaft lock key 359 in the shape of an R-clip is used to lock the propeller shaft 354 on its installation place.

Two identical ratchet drives 360a and 360b with a ratchet drive shaft insert hole 361 in the center and ratchet drive teeth 362 in the front, placed facing each other are used to drive the propeller shaft 354. A ratchet spring 363 presses the two ratchet drives 360a and 360b against each other ensuring the asymmetrical ratchet drive teeth 362 remain engaged when ratchet drive 360a turns in the clockwise direction, transmitting the movement from ratchet drive 360a to the ratchet drive 360b and to the propeller shaft nut 355 that is fitted into ratchet drive 360b.

Detail FIG. 18B shows the back propeller shaft support 221 that has four back propeller shaft holes 222 and the front propeller shaft support 223 that has four front propeller shaft holes 224 used to install the propeller set assembly. One propeller shaft 354 (with propeller not drawn to facilitate visualization) is shown in its installation position locked in place by the propeller shaft nut 355 and the propeller shaft lock key 359. The rotor shaft support 225 with a rotor shaft hole 226 that provides support to the pump rotor is placed in line with a front propeller shaft hole 224. The two ratchet drives and the ratchet spring fit in the space between the front propeller shaft support 223 and the rotor shaft support 225.

Detail FIG. 18C shows that the pump rotor assembly is composed of the pump rotor 326 that has a pump rotor axle 327 and the pump rotor shaft 329 located in the symmetry axis so the pump rotor can rotate around them. The pump rotor has two pump vane inserts 328a and 328b. On each one of those pump vane inserts a pump vane 334 is inserted. Each pump vane has a rounded pump vane edge 335 and a pump vane spring notch 336 that holds a vane spring 337 in place so it can press both pump vanes apart against the walls of the cavity where the pump rotor assembly is inserted.

FIG. 19 shows a partial view of the reactor node with the pump cover removed and a cutout in the node core 215 to display the water pump parts in place: the pump rotor assembly and the propeller set assembly. The propeller set assembly is composed of four propeller sets, two fitted with propeller left hand 349a and 349b and two fitted with propeller right hand 350a and 350b. The propellers engage through the outer gears so that all propellers either turn or remain stationary. Two configurations are possible: configuration 1 or direct flow with the propellers installed in the indicated position and configuration 2 or reverse flow with the position of the propeller left hands and propeller right hands swapped. Because the pump rotor assembly in the water pump always turns in the clockwise direction, in configuration 1 the propellers will push the water away from the pump rotor assembly whereas in configuration 2 the propellers will push the water in the opposite direction towards the pump rotor assembly.

Detail FIG. 19A shows the pump rotor assembly in place. The pump rotor fits inside a portion of the water pump cavity 231 in a rotor cavity 233 that has a circular shape with axis offset from the pump rotor axis in such a way that the pump rotor 326 touches one side of the rotor cavity 233 between the pump feed pipe 208 and the pump exhaust pipe 209. The two pump vanes 334a and 334b forced out by the vane spring extend towards the walls of the rotor cavity 233 creating separate compartments in a standard liquid vane pump configuration. The pump feed pipe 208 injects high pressure water into the rotor cavity producing a force into pump vane 334a forcing the pump rotor 326 to turn around the pump rotor axle 327 in the clockwise direction. As the pump rotor turns, water between the pump vane 334b and the pump exhaust pipe 209 opening is forced out through the pump exhaust pipe 209 until pump vane 334b passes the pump feed pipe 208 opening and the cycle repeats producing a continuous clockwise rotation of the pump rotor as long as high pressure water is fed through the pump feed pipe 208. The water flowing in the pump exhaust pipe 209 then passes through a check valve 339 that prevents water from the water body that contains algae cells that may stick together in clumps to move into the rotor cavity when the water pump is off line avoiding a potential cause of jamming. The exhaust water then continues through a pump exhaust front pipe 210 and a pump exhaust discharge pipe 211 to reach the water body inside the reactor node where it is discharged.

Detail FIG. 19B shows the positioning of the two ratchet drives 360a and 360b located in the space between the front propeller shaft support 223 and the rotor shaft support 225. A cutout is made on the rotor shaft support 225 to show the ratchet spring 363 in position located around the pump rotor shaft 329 and compressed between the pump rotor drive rim 332 and the ratchet drive 360a. A second cutout is made on a section of ratchet drive 360a to show the ratchet drive teeth 362 on ratchet drive 360b that is attached to a propeller shaft driving, in the case of configuration 1 illustrated, a propeller left hand 349. The pump rotor shaft drive 331 causes the pump rotor shaft 329 to have a circular shape in half of its perimeter still allowing for stable rotation of the pump rotor shaft in the rotor shaft hole located at the rotor shaft support 225.

FIG. 20 shows the pump cover 315 that is used to seal the water pump cavity and the rotor cavity and provide support for the pump rotor. The pump cover 315 has a pump cover cavity plug 317 that has a pump cover inner O-ring 318 to seal the rotor cavity. A pump cover axle hole 316 with the proper size to insert the pump rotor axle is located at the correct point to support the pump rotor and allow it to rotate around its symmetry axis when the pump cover 315 is secured in place in the node core. The pump cover 315 also has a pump cover outer plug 320 that has a pump cover key 321 with pump cover key rounded edges 322a and 322b to accommodate a pump cover outer O-ring 319 that seals the water pump cavity or the cable winch cavity depending on where the pump cover is installed. The pump cover key 321 ensures that the pump cover 315 can be inserted only in the proper installation orientation. The pump cover has four pump cover fasteners 323 each with a fastener hole 253 in the middle to allow the pump cover to be fixated at the node core. A pump cover exhaust pipe cut 324 creates the opening of the pump exhaust front pipe that allows the exhaust water to flow through the check valve and into the pump exhaust discharge pipe.

FIG. 21 shows a partially exploded view of the reactor node to illustrate the various components of the air release assembly. The flag assembly and the module assembly are not shown for clarity and to allow a view of the inside of the module bay 248 and the propeller set assembly 347 in the installed position.

Inside the module bay 248, the node core main control port 189, a node core aux control port left 191 and a node core aux control port right 192 that together route all signal and control pipes of the node core into the module assembly can be seen. The air release bay 249 cut on top of the node core 215 contains a set of four air release cuts 271A, 271B, 271C and 271D, one for each respective pipe port that are openings half of the width of the pipe port in length that reach all the way to the water body so that air, oxygen or any gas that is released from the water culture solution can be captured and channeled into an air release chamber 270 to be extracted. The air release bay 249 is covered by an air release lower cover 258 that has two air release long channels 268A and 268D for pipe ports A and D respectively and two air release short channels 267B for pipe port B and 267C (indicated only in detail FIG. 21C) for pipe port C. Each long and each short channel terminates with an air release pass 269A, 269B, 269C (indicated only in detail FIG. 21C) and 269D that connects the respective channel with the air release chamber 270. Four check valves 339A, 339B, 339C, and 339D are installed into the air release lower cover 258 (see FIG. 21C and FIG. 21D) to prevent air to flow back into the air release cut and then into the corresponding pipe port. Without the check valves, wave movement in the ocean producing temporary low pressure in the water culture inside a pipe port could cause air to be sucked from the air release chamber 270. The air release lower cover 258 has a flag recess cut 266 to allow the flag to reach its lowered position.

The air release lower cover 258 is covered by an air release left upper cover 259 and an air release right upper cover 260 that seal the air release long channels and the air release short channels on the air release lower cover 258. The air release left upper cover 259 has an air release attachment left 264 that allows the connection of a hose to extract the air and/or oxygen from the air release chamber 270. The air release right upper cover 260 has an air release attachment right 265 that allows the connection of a hose to extract the air and/or oxygen from the air release chamber 270.

Detail FIG. 21A shows that the node core main control port, the node core aux control port left, and the node core aux control port right are made of identical connector large inputs 383a, 383b, etc. The node core main control port is made of 24 connector large inputs identical to connector large input 383a placed in one line. The node core aux control port left and the node core aux control port right are each made of 4 connector large inputs identical to connector large input 383b placed in a second parallel line with same spacing between connector large inputs. The node core aux control port left and the node core aux control port right are symmetrically placed with respect to the symmetry axis of the module bay skipping the positions at both extremities of the node core main control port (connector large input 383b is placed in front of connector large input 383a).

Detail FIG. 21B shows that the air release right upper cover has a series of fastener holes such as 253a, 253b, 253c, etc. so it can be fixated to the air release lower cover and an air release top cover base 261 that has a check valve cavity 338 where a check valve 339e is installed. The air release top cover base 261 has two fasteners 254a and 254b, each with a R-clip insertion hole 255a and 255b respectively where R-clips are inserted to fixate an air release top cover 262 that has two matching fastener holes 253d and 253e so that when it is in place fixated to the air release top cover base 261 the air release top cover 262 holds the check valve 339 in place. The air release top cover 262 has an air purge 263 opening that allows air to escape into the outside environment. The check valve 339e prevents air or water from the outside environment to enter the reactor node.

Detail FIG. 21C shows a portion of the air release lower cover. The air release short channel 267C begins in the check valve cavity 338C where the check valve 339C is installed and terminates in the air release pass 269C for pipe port C. An air vent valve 272 with three air vent valve O-rings 273a, 273b and 273c and an air vent valve opening 274 is installed in an air vent valve cavity 275. The air vent valve cavity 275 is connected to an air vent open cutout 277 and an air vent close cutout 278 at its extremities and has an air vent purge cutout 276 in its center. When pressurized water injected at the air vent open cutout 277 while the air vent close cutout 278 has low pressure water the air vent valve 272 is pushed towards the extremity of the air vent valve cavity 275 connected to the air vent close cutout 278 and the air vent valve opening 274 aligns with the air vent purge cutout 276 allowing air to escape into the environment.

The air release lower cover has fastener holes such as 253a, 253b, 253c, that allow it to be fixated to the air release bay and fasteners such 254a, 254b, etc. each with a R-clip insertion hole 255a, 255b, etc. respectively where R-clips are inserted to fixate the air release right upper cover.

Detail FIG. 21D shows a portion of the air release lower cover where the air release long channel 268D for pipe port D is located. The air release long channel 268D begins in the check valve cavity 338D where the check valve 339D is installed. A fastener hole 253 that allows the air release lower cover to be fixated to the air release bay and a fastener 254 with a R-clip insertion hole 255 where an R-clip is inserted to fixate the air release right upper cover can also be seen.

Detail FIG. 21E shows the air release cut 271B where a float 280B with a float O-ring 281 is in place in the sunken position. Air inside the air release cut 271B causes the float 280B to sink and the float O-ring 281 to loose contact with the bottom of the air release lower cover installed above opening the access to the check valve cavity and the air release short channel.

Detail FIG. 21F shows one of a set of fasteners 254 that allow the fixation of the air release lower cover to seal the air release bay. The air release cut 271C terminates in a float cavity 279C where a float 280C with a float O-ring 281 at the top is installed.

Detail FIG. 21G shows a fastener 254 that allows the fixation of the air release lower cover to seal the air release bay. The air vent purge cutout 276 connected to the air release chamber 270 is made so that air reaches the middle of the air vent valve cavity situated in the air release lower cover above. The air vent open cutout 277 and the air vent close cutout 278 are made to allow water to reach both extremities of the air vent valve cavity situated in the air release lower cover above so that the air vent valve can be moved as required.

Detail FIG. 21H shows a set of fasteners 254 that allow the fixation of the air release lower cover to seal the air release bay and the air release cut 271A with the float 280A in place in the raised position. Water inside the air release cut 271A causes the float 280A to rise until the float O-ring 281 is pressed against the bottom of the air release lower cover installed above closing the access to the check valve cavity and the air release long channel.

Detail FIG. 21I shows a set of fasteners 254 that allow the fixation of the air release lower cover to seal the air release bay and the air release cut 271D that terminates in a float cavity 279D where a float 280D with a float O-ring 281 at the top is installed.

Detail FIG. 21J shows a cutout in the rotor shaft support 225 and in the two ratchet drives 360a and 360b so that the pump rotor shaft 329 and the propeller shaft nut 355 can be seen. The ratchet spring 363 inserted into the pump rotor drive end 333 compressed between the pump rotor drive rim 332 and ratchet drive 360a pushes ratchet drive 360a towards ratchet drive 360b that is hold back by the front propeller shaft support 223 causing the ratchet drive teeth 362 to be pressed against each other. A drive gap 364 separates the pump rotor drive end 333 and the propeller shaft nut 355 allowing them to rotate at different speeds in the event that the pump rotor shaft 329 stops and/or the propeller inserted into the propeller shaft is driven by the outer gear 351 at a different speed. The pump rotor shaft drive 331 causes the pump rotor shaft 329 to have a circular shape in half of its perimeter still allowing for stable rotation of the pump rotor shaft in the rotor shaft hole located at the rotor shaft support 225.

FIG. 22 shows the reactor node 214 drawn in phantom lines to show the water body 365, the four pipe ports A, B, C, and D and the four water body channels 366A, 366B, 366C, and 366D so the path of water culture and air extraction can be clearly seen. Water culture enters the reactor node at a pipe port and goes down through the corresponding water body channel to the lower level where the propeller set assembly 347 is located. The air (oxygen) passing through a pipe port escapes through the corresponding air release cut 271A, 271B, 271C, and 271D reaching the air release chamber 270. The pump cover 315 and pump rotor assembly 325 are shown for reference.

Detail FIG. 22A shows the components of the air release system in greater detail. Air bubbles present in the water body 365 eventually pass through the air release cut 271D reaching the float cavity 279D where float 280D is installed. As long as air is present in the float cavity 279D, the float 280D sinks opening the access to check valve 339D. The air passes through the check valve 339D and continues into the air release long channel 268D until the air release pass 269D reaching the air release chamber 270. The air release attachment right 265 connected to the air release chamber 270 by the air release pass 269D allows the air to be extracted by a hose. Similarly, air bubbles collected at the air release cut 271C reach float cavity 279C where float 280C is installed. As long as air is present in the float cavity 279C, the float 280C sinks opening the access to the check valve 339C. The air escapes through the check valve 339C and continues into the air release short channel 267C until the air release pass 269C reaching the air release chamber 270. As the air escapes, water level rises inside the air release cut 271C and the float cavity 279C causing the float 280C to rise until it seals the access to the check valve 339C and the air release short channel 267C, preventing water to flow into the air release chamber 270.

Air accumulated in the air release chamber 270 can be vented by means of shifting the air vent valve 272 so that the air vent purge cutout 276 is unobstructed opening the access to the check valve 339e that allows air to escape into the environment but prevents water and air from the environment to enter and reach the air release chamber 270. The air vent valve 272 is controlled by an air release open pipe 202 and an air release close pipe 203. If pressurized water is injected into the air release open pipe 202 at the same time the air release close pipe 203 has low pressure water the air vent valve 272 moves towards the air release close pipe 203 opening the access to check valve 339e. If on the other hand pressurized water is injected into the air release close pipe 203 at the same time the air release open pipe 202 has low pressure water the air vent valve 272 moves towards the air release open pipe 202 (as drawn) closing the access to check valve 339e.

The construction of the wet reactor air release pipework is such that pipe ports B and C as well as pipe ports A and D are mirror images of each other. A single detailed view of one side is therefore sufficient to illustrate the construction. For greater magnification and better viewing, FIG. 22A shows structures in pipe ports C and D only as this has the added benefit of allowing the display of air vent components in the same drawing.

FIG. 23 shows a partially exploded view of the reactor node with components of the anchoring system offset from the node core 215. The module assembly 369 is also offset to show it in assembled configuration from a different angle than in FIG. 18.

The anchor assembly 282 is attached to the anchor cable 287 that has two stoppers 290a and 290b. The anchor cable goes around the cable winch 292 that is installed into the cable winch cavity 227 and keeps the anchor cable taut between the anchor assembly and the reactor node. The pump cover 315b seals the winch rotor cavity 232, provides support and holds the pump rotor assembly 325 in place inside the winch rotor cavity 232. To reduce the number of unique parts needed, save costs and increase maintenance efficiency, the pump cover 315b used in the anchoring system and the pump cover 315a used in the water pump system (drawn in the installed position) are identical. When the pump rotor assembly is in place the extremity of the pump rotor shaft 329 is slotted into the cable winch drive hole 296 (see FIG. 23B).

Detail FIG. 23A shows the extremity of the pump rotor shaft 329 that has two sets of chamfers of different lengths made into it. One set of two parallel chamfers extends to the pump rotor drive rim 332 and the other set of two parallel chamfers extends deeper to the pump rotor shaft rim 330. The two sets of chamfers produce together the pump rotor drive end 333 with a squared shape cross section that fits into the ratchet drive shaft insert hole in order to drive the ratchet drive in the water pump. The deeper set of parallel chamfers produces the pump rotor shaft drive 331 that is used to drive the cable winch in conjunction with the pump rotor drive end 333 that penetrates deeper into the cable winch until it reaches its slotted position. The pump rotor shaft rim 330 locks against the cable winch face 295 (see FIG. 23B) and the pump rotor drive rim 332 locks against a matching surface inside the cable winch. By this arrangement, the pump rotor at the same time drives and secures the cable winch in place, allowing only rotational movement of the cable winch that rotates merged with the pump rotor assembly.

Detail FIG. 23B shows the cable winch 292, the anchor cable 287 and the stopper 290a. The cable winch 292 has the shape of a conical pulley with two flat circular cable winch faces 295 with a cable winch drive hole 296 at the center. The cable winch 292 has a series of cable winch teeth 293 made in the conical surfaces of the pulley so that the cable winch teeth 293 bite into the anchor cable with increased pressure and grip as the anchor cable 287 gets closer to the axis of the cable winch 292. The stopper 290a with a stopper hole 291a at the center is fixated to the free end of the anchor cable 287 by means of two knots 289a and 289b.

Detail FIG. 23C shows how the stopper 290b with a stopper hole 291b at the center is fixated to a point of the anchor cable 287 by means of passing the anchor cable 287 through the stopper hole 291b and making two knots 289c and 289d, one at each side of the stopper 290b.

FIG. 24 shows the reactor node with a cutout in the node core 215 to show the components of the anchoring system in place. The dive control open pipe 207 and a dive control close pipe 206 control the movement of the pump rotor assembly 325 that holds the cable winch 292 in place. The pump cover 315 holds the pump rotor assembly 325 in place and provides support for the pump rotor assembly 325 to turn. The stoppers 290a and 290b keep the anchor cable 287 captive holding the node core 215 attached to anchor assembly 282.

Detail FIG. 24A shows the cable winch 292 in place, inside the cable winch cavity 227. The pump rotor shaft 329 lodges into the cable winch 292 and the pump rotor shaft rim 330 engages the cable winch face 295 holding the cable winch 292 in place against a cable winch cavity wall 228. The cable winch 292 is supported and rotates around the axis provided by a cable winch axle 294 that fits into an appropriate notch in the node core and the pump rotor shaft 329. The anchor cable 287 goes around the cable winch 292 and terminates in a stopper 290a that is held in place by two knots 289a and 289b. As the stoppers 290a (and 290b) are bigger than the cable winch cavity 227, the anchor cable 287 is held captive. As the cable winch 292 turns, the cable winch teeth 293 grip the anchor cable 287 moving it up or down according to the direction of rotation.

Detail FIG. 24B shows the reactor node with pump cover removed to show in detail the water pump cavity 231 and the rotor cavity 233. Inside the rotor cavity 233, a rotor shaft insert hole 229 is cut that allows the insertion of the pump rotor shaft. Inside the water pump cavity 231, a water pump check valve cavity 230 allows the insertion of one check valve. When the pump cover is installed, it holds the check valve in place inside the water pump check valve cavity 230 and the pump cover exhaust pipe cut 324 (see FIG. 20) connects the water pump check valve cavity 230 and pump exhaust discharge pipe 211.

FIG. 25 shows an exploded view of one embodiment of a module assembly. The module assembly contains all components necessary to process the hydraulic and pneumatic inputs coming from other reactor nodes or collected from within or from the exterior of the reactor node where the module assembly is installed. The module assembly generates the control signals necessary to implement the appropriate actions in the reactor node where the module assembly is installed and the signals that are transmitted to the other reactor nodes. No electric components are used in the module assembly and no electric power is needed for normal operation of the module assembly. Avoiding electricity and using only mechanical, hydraulic and/or pneumatic components and circuits made of low cost materials such as plastic resins, rubbers, stainless steel springs, etc. that are suitable for the oceanic environment reduces capital and operational costs and increases system reliability.

The module assembly is composed of a module case 370 that has an internal module net volume 373. The module case 370 works as a base providing support and connectivity to fit a logic unit assembly 432, an i/o unit assembly 403 and an expansion unit assembly 388 that works also as a cover that closes the module case 370.

The module case 370 has a module rim 371 with a series of fasteners 254 and fastener holes 253a. The expansion unit assembly 388 has an expansion case rim 390 that has a series of fastener holes 253b, 253c, etc. that align with either a fastener 254 or a fastener hole 253a located in the module rim 371 of the module case 370. When the expansion unit assembly 388 is placed on the top of the module case 370, some fastener holes in the expansion unit assembly align with a fastener in the module case such as the case of 253b and 254 respectively. R-clips are inserted into R-clip insertion holes at the top of these fasteners to secure the expansion unit assembly 388 and the module case 370 together. Other fastener holes in the expansion unit assembly align with a fastener hole in the module case such as the case of 253c and 253a respectively. These two fastener holes in the module assembly are placed in such a way that they align with a fastener in the node core that is correspondingly longer so that it will extend through both fastener holes. R-clips are inserted into R-clip insertion holes at the top of these longer fasteners to secure the module assembly into the node core and at the same time provide additional grip to secure the expansion unit assembly and the module case together.

To maximize the module net volume 373, the module case 370 has a module case shape fit 372 that allows the module case to use all the space available in the module bay in the node core without interfering with the CO2 cavity body. A module external opening 375 in line with the node core external opening allows water access to the external environment to detect external water pressure. A module ground pipe connector 378 allows access to the water body initially to the logic unit assembly 432 and then through other connections to the i/o unit assembly 403 and the expansion unit assembly 388 (see FIG. 26). A module control top connector 380 allows the i/o unit assembly 403 to connect to all sensor pipes and control pipes that go in and out of the node core through the module case 370 (see FIG. 26).

The logic unit assembly 432 is composed of a logic layer assembly 443 that contains all components and the interconnections that allow the components in the logic unit assembly 432 to perform their intended functions and a logic case 433 that provides interconnection to other units and support for the logic layer assembly 443. The logic layer assembly 443 is inserted into a logic case back opening 435 in the logic case 433. Once inside, the logic case 433 holds all components of the logic layer assembly 443 together allowing them to work as intended and be easily manipulated. Two logic case extractor holes 436 are used to assist in the process of installation and removal of the logic unit assembly 432 into the module case 370. A group of logic case top connections 437 provides connections with the i/o unit assembly 403 (see FIG. 26).

The i/o unit assembly 403 is composed of an i/o layer assembly 418 that contains all components and the interconnections that allow the components in the i/o unit assembly 403 to perform their intended functions and an i/o case 404 that provides interconnection to other units and support for the i/o layer assembly 418. The i/o unit assembly 403 is inserted into an i/o case back opening 406 in the i/o case 404. Once inside, the i/o case 404 holds all components of the i/o layer assembly 418 together allowing them to work as intended and be easily manipulated. Two i/o case extractor holes 408 are used to assist in the process of installation and removal of the i/o unit assembly 403 into the module case 370. An i/o case shape fit 407 allows the i/o case 404 to fit into the module case 370. A group of i/o case top connections 409 provide connections with the expansion unit assembly 388 (see FIG. 26).

The expansion unit assembly 388 is composed of an expansion layer 400 and an expansion case 389 that provides interconnection to other units and support for the expansion layer 400. The expansion case 389 has an expansion case flag cutout 399 to accommodate the flag when it is in its lowered position and two expansion case handles 393 that provide a good grip for maintenance personnel to handle it. A group of expansion case top connections 395 provide external connections to other reactor nodes, maintenance tools and an interface to a diagnostic device. An expansion case back opening 392 allows the insertion of the expansion layer 400 into the expansion case 389. As it has been possible to implement all necessary functions for the operation of the reactor node using only the i/o unit assembly 403 and the logic unit assembly 432, the expansion layer 400 is made of just one thick sheet of material in the appropriate shape to fit perfectly into the expansion case 389 and with an expansion layer through cut 402 that allows the signals from the expansion case top connections 395 to pass through the expansion unit assembly 388, reach the expansion case bottom connections and be available to the i/o unit assembly 403 (see FIG. 26). In case future expansions replace the expansion layer 400 by an expansion layer assembly with a set of components that performs additional functions, the connections of the expansion layer through cut 402 need to be preserved to avoid changes or loss of functionality in the i/o unit assembly 403.

The module case 370, expansion case 389, i/o case 404 and logic case 433 are designed to provide support and interconnection to the various signals travelling to all different parts and in principle do not need to be changed unless a major change requires new connections to be established. All components and the interconnections that allow the components to perform their intended functions are encased in the active inserts (the logic layer assembly 443, the i/o layer assembly 418 and eventually a new insert replacing the expansion layer 400 if new features are implemented there in the future). In case an upgrade or a correction of a design error is needed, this will probably only require changes in the active inserts, affecting a reduced set of components. As these parts are much smaller than the rest of the reactor node and many changes such as a correction of a mistake are likely to require alterations only in a small area of the affected active insert, the cost and the time needed to implement changes or upgrades is reduced increasing system flexibility.

Detail FIG. 25A shows that the expansion case 389 has an expansion case rim 390 with a series of fastener holes 253. Also, visible in detail FIG. 25A is a portion of the expansion case top connections. A diagnose port 161, composed of 22 diagnose attachments arranged in an 11×2 array, each one identical to diagnose attachment 162 and a signal port left 163 composed of 12 identical hose attachments where hoses with matching fittings are connected to carry pressurized water, pressurized air, pressurized CO2 and signals carried by pressurized water in and out of the module assembly. The signal port left 163 is composed of: (U) air resupply left 177, (W) water resupply left 178, (k) clock in 179, (gnd) ground 180, (z) zero in 181, (V) dive out 182, (m) master/slave in 183, (R) reset out 184, (q) query in 185, (H) help out 186, (s) status in 187, and (L) CO2 resupply left 188. Whenever possible, a single lowercase or uppercase letter from the signal name is used to identify each signal. These letters are later used to facilitate the description of the logic functions implemented. A lowercase letter indicates an input signal and an uppercase letter indicates an output signal with the exception of (W), (U) and (L) that are bidirectional. The letter case for these three above mentioned signals is used to differentiate signals on the signal port right (lowercase) from signals on signal port left (uppercase).

The signal port right 164 is shown and all its signals indicated on detail FIG. 5C. The description of signal port left and signal port right was split in two drawings to allow the drawings to be made in greater magnification with clearer details and to show the module assembly in an installed position in the node core with R-clips in place in detail FIG. 5C and in an exploded position so that the case rim and fastener holes can be seen in detail FIG. 25A.

Detail FIG. 25B shows one i/o case extractor hole 408 and the i/o case back opening 406 where the i/o layers assembly is inserted into the i/o case 404. Also visible in detail FIG. 25B is a portion of the i/o case top connections that shows an i/o case diagnose connector 410 made of a set of 22 connector small inputs, each identical to connector small input 386 arranged in an 11×2 array directly below and in the same pattern as the diagnose attachments in the diagnose port (see detail FIG. 25A). Another portion of the i/o case top connections shows that a set of 12 connector large inputs, each identical to connector large input 383a (only some of them visible in detail FIG. 25B) is placed directly below and in the same pattern as the hose attachments in the signal port left (see FIG. 25 and detail FIG. 25A). The same is the case for the other side of the i/o case where another set of 12 identical connector large inputs is placed directly below and in the same pattern as the hose attachments in the signal port right (see FIG. 25 and detail FIG. 5C). An i/o case expand connector 411 is made of a set of seven connector large inputs, each identical to connector large input 383b placed at the same interval as the connector large inputs for signal port left and signal port right in a straight line perpendicular to the symmetry axis of the i/o case 404 that crosses the center of connector large input 383a and with the center of connector large input 383b that occupies the central position of the i/o case expand connector 411 placed at the symmetry axis of the i/o case 404.

The i/o case expand connector 411 is intended to make high pressure water, water at ground pressure and an external pressure signal with sufficient water volume (power) available at a convenient point to supply the expansion unit assembly. These power signals will likely be needed in case of a future expansion at the expansion unit assembly and are provided at this point to avoid having to modify the i/o case later. They are however for the moment not needed so all connections of the i/o case expand connector are closed in the expansion unit by the expansion layer.

Detail FIG. 25C shows the logic case 433, one logic case extractor hole 436 and a portion of the logic case top connections. A logic case signal connector 438 is composed of a set of 33 connector small inserts, each identical to connector small insert 384c and each with a connector small O-ring identical to connector small O-ring 385c arranged in an 11×3 array. A logic case right control connector 441 is composed of a set of 11 connector small inserts, each identical to connector small insert 384b and each with a connector small O-ring identical to connector small O-ring 385b. 10 connector small inserts are placed in a straight line and the last one is placed in front of the connector small insert 384b at the 9th position with same spacing as between other connector small inserts. The connector small inserts (384b, 384c, etc.) are used to exchange information signals between the logic unit assembly and the i/o unit assembly. Because information signals do not need to drive big components the diameter of the pipes and connectors can be reduced to save space, material costs and power. A logic case power connector 439 is composed of a set of 7 connector large inserts, each identical to connector large insert 381 and each with a connector large O-ring identical to connector large O-ring 382 placed in a straight line with the center of the connector large insert 381 that occupies the central position placed at the symmetry axis of the logic case 433.

Detail FIG. 25D shows a portion of the module control top connector 380 that is made of 32 identical connector large inserts 381a, 381b, etc. each with an identical connector large O-ring 382a, 382b, etc. 24 connector large inserts 381a are placed in one line and the remaining 8 connector large inserts 381b are placed in a second parallel line in two separated groups of 4 connector large inserts with same spacing between connector large inserts. The two groups of 4 connector large inserts are symmetrically placed with respect to the symmetry axis of the module case skipping the positions at both extremities of the line with 24 connector large inserts (connector large insert 381b is placed in front of connector large insert 381a).

Detail FIG. 25E shows a section of the module rim 371 of the module case showing a fastener 254 that is used to secure the expansion case to the module case and a fastener hole 253 that is used in conjunction with a fastener hole in the same position in the expansion case to secure the module assembly to the node core. Detail FIG. 25E also shows the module ground pipe connector 378 that is made of 4 identical connector large inserts 381a, 381b, etc. each with a connector large O-ring identical to the connector large O-ring 382 placed in one line at the symmetry axis of the module case with 3 connector large inserts grouped together with the connector large insert 381b in the middle and 1 connector large insert 381a isolated to the right.

FIG. 26 shows an exploded view of one embodiment of the module assembly seen from the bottom to show additional details. The module assembly is composed of a module case 370 that works as a base providing support, connectivity and space to fit the logic unit assembly 432, the i/o unit assembly 403 and the expansion unit assembly 388 that works also as a cover that closes the module case 370. Once properly assembled the expansion case rim 390 rests on top of the module rim 371 allowing the expansion unit assembly 388 to be secured to the module case 370 using R-clips.

The module case shape fit 372 allows the module case 370 to fit inside the module bay in the node core without interfering with the CO2 cavity body. The module case 370 has a propeller access door plug 374 with a propeller access door O-ring 376 that seals the propeller access opening when the module assembly is installed in the module bay of the node core. A module ground pipe port 377 connected to the module ground pipe connector at the other side of the module case allows access to the water body through the module case initially to the logic unit assembly 432 and then through other connections to the i/o unit assembly 403 and the expansion unit assembly 388 (see FIG. 25). A module control bottom connector 379 connected to the module control top connector at the other side of the module case allows the i/o unit assembly 403 to connect to all sensor pipes and control pipes that go in and out of the node core through the module case 370 (see FIG. 25).

The logic unit assembly 432 is composed of the logic layer assembly 443 that contains all components and the interconnections that allow the components in the logic unit assembly 432 to perform their intended functions and the logic case 433 that provides interconnection to other units and support for the logic layer assembly 443. A logic case front opening 434 allows the logic layer assembly 443 to be easily removed from the logic case 433 by inserting a long rod or another suitable tool into the logic case front opening 434 to push the previously inserted logic layer assembly 443 out of the logic case 433. A logic case bottom connector 442 in the proper shape and location to fit into the module ground pipe connector at the top of the module case 370 allows access to the water body from the logic unit assembly 432 (see FIG. 25).

The i/o unit assembly 403 is composed of the i/o layer assembly 418 that contains all components and the interconnections that allow the components in the i/o unit assembly 403 to perform their intended functions and the i/o case 404 that provides interconnection to other units and support for the i/o layer assembly 418. An i/o case front opening 405 allows the i/o layer assembly 418 to be easily removed from the i/o case 404 by inserting a long rod or another suitable tool into the i/o case front opening 405 to push the previously inserted i/o layer assembly 418 out of the i/o case 404. The i/o case shape fit 407 allows the i/o case 404 to fit into the module case 370. An i/o case bottom control connector 412 in the proper shape and location to fit into the module control top connector at the other side of the module case 370 allows the i/o unit assembly 403 to connect to all sensor pipes and control pipes that go in and out of the node core through the module case 370 (see FIG. 25). An i/o case logic connector 413 in the proper shape and location to fit into the logic case top connections at the other side of the logic case provides connections with the logic unit assembly 432 (see FIG. 25).

The expansion unit assembly 388 is composed of the expansion layer 400 and the expansion case 389 that provides interconnection to other units and support for the expansion layer 400. An expansion case shape fit 394 allows the expansion case 389 to fit into the module case 370. An expansion case front opening 391 allows the expansion layer 400 to be easily removed from the expansion case 389 by inserting a long rod or another suitable tool into the expansion case front opening 391 to push the previously inserted expansion layer 400 out of the expansion case 389. A set of expansion case bottom connections 396 in the proper shape and location to fit into the i/o case top connections at the top of the i/o case 404 provides connections with the i/o unit assembly 403 (see FIG. 25).

As it has been possible to implement all necessary functions for the operation of the reactor node using only the i/o unit assembly 403 and the logic unit assembly 432, the expansion layer 400 is made of just one thick sheet of material. An expansion layer shape fit 401 cut is made into the expansion layer 400 to allow it to fit perfectly into the expansion case 389. The expansion layer through cut 402 allows the signals from the expansion case top connections at the top of the expansion case 389 (see FIG. 25) to pass through the expansion layer 400 and be available to the i/o unit assembly 403 at the expansion case bottom connections 396. In case future expansions replace the expansion layer 400 by an expansion layer assembly with a set of components that perform additional functions, the connections of the expansion layer through cut 402 need to be preserved to avoid changes or loss of functionality in the i/o unit assembly 403.

Detail FIG. 26A shows a portion of the expansion layer 400 and a portion of the expansion case bottom connections. An expansion case diagnose connector 397, composed of 22 connector small inserts arranged in an 11×2 array, each identical to connector small insert 384 and each with a connector small O-ring identical to connector small O-ring 385 is placed directly below and in the same pattern as the diagnose attachments in the diagnose port (see detail FIG. 25A) and directly above and in the same pattern as the i/o case diagnose connector (see detail FIG. 25B). Once the i/o case and the expansion case are installed inside the module case, each connector small insert in the expansion case diagnose connector fits into the corresponding connector small input in the i/o case diagnose connector and the connector small O-ring on each connector small insert seals the connection preventing leaks and signal crosstalk.

Another portion of the expansion case bottom connections visible in detail FIG. 26A shows that a set of 12 connector large inserts, each identical to connector large insert 381*a* and each with a connector large O-ring identical to the connector large O-ring 382*a* is placed directly below and in the same pattern as the hose attachments in the signal port right and directly above and in the same pattern as the connector large inputs in the top of the i/o case (see FIG. 25 and detail FIG. 5C). The same is the case for the other side of the expansion case where another set of 12 identical connector large inserts each with a connector large O-ring is placed directly below and in the same pattern as the hose attachments in the signal port left and directly above and in the same pattern as the connector large inputs in the top of the i/o case (see FIG. 25 and detail FIG. 25A).

An expansion case expand connector 398 made of a set of seven connector large inserts each identical to connector large insert 381*b* and each with a connector large O-ring identical to the connector large O-ring 382*b* placed at the same interval as the connector large inserts for signal port left and signal port right. The expansion case expand connector 398 is placed in a straight line perpendicular to the symmetry axis of the expansion case 389 that crosses the center of the connector large insert 381*a* and with the center of connector large insert 381*b* that occupies the central position of the expansion case expand connector 398 placed at the symmetry axis of the expansion case 389. Once the i/o case and the expansion case are installed inside the module case, each connector large insert on the bottom of the expansion case fits into the corresponding connector large input on the top of the i/o case and the connector large O-ring on each connector large insert seals the connection preventing leaks and signal crosstalk.

Detail FIG. 26B shows the i/o case logic connector at the bottom of the i/o case 404 that is composed of an i/o case signal connector 414, an i/o case power connector 415, an i/o case logic left control connector 416 and an i/o case logic right control connector 417.

The i/o case signal connector 414 is a set of 33 connector small inputs, each identical to connector small input 386*c*, arranged in an 11×3 array directly above and in the same pattern as the logic case signal connector (see detail FIG. 25C).

The i/o case logic left control connector 416 is a set of 10 connector small inputs, each identical to connector small input 386*a*, placed in a single line directly above and in the same pattern as the logic case left control connector. The i/o case logic right control connector 417 is a set of 11 connector small inputs, each identical to connector small input 386*b*. A set of 10 connector small inputs are placed in a straight line and the last one is placed in front of connector small input 386*b* at the 9th position with same spacing as between other connector small inputs. The i/o case logic right control connector 417 is placed directly above and in the same pattern as the logic case right control connector (see detail FIG. 25C).

Once the logic case and i/o case are installed inside the module case, each connector small insert on the top of the logic case fits into the corresponding connector small input in the bottom of the i/o case and the connector small O-ring on each connector small insert seals the connection preventing leaks and signal crosstalk.

The i/o case power connector 415 is made of seven identical connector large inputs 383 arranged in a straight line perpendicular to the symmetry axis of the i/o case 404 with the center of connector large input 383 that occupies the central position placed at the symmetry axis of the i/o case 404. The i/o case power connector 415 is placed directly above and in the same pattern as the logic case power connector. Once the logic case and the i/o case are installed inside the module case, each connector large insert on the top of the logic case fits into the corresponding connector large input on the bottom of the i/o case and the connector large O-ring on each connector large insert seals the connection preventing leaks and signal crosstalk.

Detail FIG. 26C shows a portion of the i/o case bottom control connector 412 that is made of 32 identical connector large inputs 383*a*, 383*b*, etc. 24 connector large inputs 383*a* are placed in one line and the remaining 8 connector large inputs 383*b* are placed in a second parallel line in two separated groups of 4 connector large inputs with same spacing between connector large inputs. The two groups of 4 connector large inputs are symmetrically placed with respect to the symmetry axis of the i/o case skipping the positions at both extremities of the line with 24 connector large inputs (connector large input 383*b* is placed in front of connector large input 383*a*). The i/o case bottom control connector 412 is placed directly above and in the same pattern as the module control top connector on the top of the module case. Once the logic case and the i/o case are installed inside the module case, each connector large insert of the module control top connector fits into the corresponding connector large input on the bottom of the i/o case and the connector large O-ring on each connector large insert seals the connection preventing leaks and signal crosstalk.

Detail FIG. 26D shows the logic case bottom connector 442 that is made of 4 identical connector large inputs 383*a*, 383*b* etc. placed in one line at the symmetry axis of the logic case with 3 connector large inputs grouped together with connector large input 383*b* in the middle and 1 connector large input 383*a* isolated to the right. The logic case bottom connector 442 is placed directly above and in the same pattern as the module ground pipe connector on the top of the module case. Once the logic case is installed inside the module case, each connector large insert on the module ground pipe connector on the top of the module case fits into the corresponding connector large input on the bottom of the logic case and the connector large O-ring on each connector large insert seals the connection preventing leaks and signal crosstalk.

Detail FIG. 26E shows a portion of the module control bottom connector 379 that is made of 32 identical connector large inserts 381*a*, 381*b*, etc. each with a connector large O-ring 382*a*, 382*b*, etc. 24 connector large inserts 381*a* are placed in one line and the remaining 8 connector large inserts 381*b* are placed in a second parallel line in two separated groups of 4 connector large inserts with same spacing between connector large inserts. The two groups of 4 connector large inserts are symmetrically placed with respect to the symmetry axis of the module case skipping the positions at both extremities of the line with 24 connector large inserts (connector large insert 381*b* is placed in front of connector large insert 381*a*). The module control bottom connector 379 is placed directly above and in the same pattern as the cluster of connector large inserts of the node core main control port, node core aux control port left and node core aux control port right on the bottom of the module bay of the node core. Once the module case is installed inside the module bay, each connector large insert on the bottom of the module case fits into the corresponding connector large input on the bottom of the module bay and the connector large O-ring on each connector large insert seals the connection preventing leaks and signal crosstalk (see FIG. 21).

Detail FIG. 26F shows the module ground pipe port 377 that is made of 4 identical pipe openings 387a, 387b, etc. placed in one line at the symmetry axis of the module case with 3 pipe openings grouped together with pipe opening 387b in the middle and 1 pipe opening 387a isolated to the right. The module ground pipe port 377 is placed directly below and in the same pattern as the module ground pipe connector on the top of the module case so each pipe opening provides one access channel to the water body that goes through the module ground pipe connector into the logic unit assembly.

FIG. 27 shows an exploded view of the first embodiment of the i/o unit assembly 403 that implements hydraulic and pneumatic circuits that condition and process the input and output signals originating and terminating in the module assembly. An i/o layer a 419, an i/o layer b 420, and an i/o layer c 421 provide support and connectivity to a set of i/o components 423 and an i/o check valve set 422 in a similar way that a multilayer electric circuit board provides support and connectivity to electric components in an electric circuit. The i/o components 423 are located and held in place between i/o layer a 419 and i/o layer b 420 and the i/o check valve set 422 is located and held in place between i/o layer b 420 and i/o layer c 421.

The i/o layer a 419, i/o layer b 420, and i/o layer c 421, i/o components 423, and i/o check valve set 422 constitute the i/o layer assembly that once properly assembled is inserted into the i/o case 404. The result is a compact standard i/o unit assembly 403 that is used in all module assemblies installed in reactor nodes that have all four pipe ports enabled (connected to pipe elements). Pre-assembled and pre-tested units can be kept in inventory as a major part for installation in a new module assembly in a simplified production line and kept in reserve as spares for replacement of faulty units detected in the field.

Also visible in FIG. 27 is the i/o case front opening 405 that facilitates the removal of the i/o layer assembly from the i/o case 404, two i/o case extractor holes 408a and 408b that facilitate the installation and removal of the i/o unit assembly into the module case and the i/o case top connections 409 that connect the i/o unit assembly to the expansion unit assembly.

FIG. 28 shows an exploded view of the first embodiment of the logic unit assembly 432 that implements hydraulic circuits to process conditioned logic signals received from the i/o unit assembly, generates intermediary logic functions necessary to produce more complicated logic signals and produces output logic signals to send back to the i/o unit assembly. The i/o unit assembly then uses these output logic signals to generate appropriate output signals to control the reactor node containing the module assembly where the logic unit assembly and the i/o unit assembly are installed and transmit information to other reactor nodes.

A logic layer a 444, a logic layer b 445, a logic layer c 446, and a logic layer d 447 provide support and connectivity to a set of logic components 450 in a similar way that a multilayer electric circuit board provides support and connectivity to electric components in an electric circuit. The logic components 450 are located and held in place between the logic layer a 444 and the logic layer b 445. A router plate insertion bay 448 on top of the logic layer c 446 allows the insertion of a router plate that works as a configuration device. Eight different types of router plates are available but only one can be inserted at a time in a given logic layer assembly. To prevent the chosen router plate to be incorrectly placed, two asymmetrically placed router plate insertion keys 449a and 449b are located at the sides of the router plate insertion bay 448 allowing the selected router plate to fit only in the proper orientation. The router plates reroute signals related to the pipe ports that enter the logic unit assembly through the logic case left control connector (pipe port A and pipe port B) and logic case right control connector (pipe port C and pipe port D) before they are processed by other components in the logic layer assembly. That way individual signals belonging to a pipe port may be rerouted into corresponding positions of signals belonging to another pipe port according to the rerouting plan of the installed router plate (see FIG. 77 and FIG. 78).

The available router plates are: 1) router plate direct 451 that does not reroute signals and simply forwards signals from each pipe port in the same position they came in; 2) router plate AB 452 that exchanges pipe port A signals with pipe port B signals and forwards pipe port C and pipe port D signals; 3) router plate CD 453 that forwards pipe port A and pipe port B signals and exchanges pipe port C signals with pipe port D signals; 4) router plate ABCD 454 that exchanges pipe port A signals with pipe port B signals and pipe port C signals with pipe port D signals; 5) router plate ADBC 455 that exchanges pipe port A signals with pipe port D signals and pipe port B signals with pipe port C signals; 6) router plate DBCA 456 that reroutes pipe port A signals into pipe port D, pipe port D signals into pipe port B, pipe port B signals into pipe port C and pipe port C signals into pipe port A; 7) router plate CBDA 457 that reroutes pipe port A signals into pipe port C, pipe port C signals into pipe port B, pipe port B signals into pipe port D and pipe port D signals into pipe port A; 8) router plate ACBD 458 that exchanges pipe port A signals with pipe port C signals and exchanges pipe port B signals with pipe port D signals.

The logic layer a 444, logic layer b 445, logic layer c 446, logic layer d 447, logic components 450, and one router plate constitute the logic layer assembly that once properly assembled is inserted into the logic case 433 that provides support and connectivity to the logic layer assembly. The result is a compact logic unit assembly 432 that is used in all module assemblies installed in reactor nodes. Also visible in FIG. 28 is the logic case front opening 434 that facilitates the removal of the logic layer assembly from the logic case 433, two logic case extractor holes 436a and 436b that facilitate the installation and removal of the logic unit assembly into the module case and the logic case top connections 437 that connect the logic unit assembly to the i/o unit assembly.

To describe the implementation and operation of components and other parts of the invention in a convenient and simple way, the following notation is used:

A digital signal is encoded by one or more bits. A single bit signal, when the fluid (water, air, CO2, etc.) pressure is above the proper threshold is represented by the number 1. A single bit signal when the fluid pressure is below the proper threshold is represented by the number 0. For signals having more than one bit, an appropriate combination of bits (1s and 0s) is used.

The following Boolean logic functions are used:

AND; denoted $x \wedge y$, satisfies $x \wedge y = 1$ if $x = y = 1$ and $x \wedge y = 0$ otherwise.

OR; denoted $x \vee y$, satisfies $x \vee y = 0$ if $x = y = 0$ and $x \vee y = 1$ otherwise.

NOT; denoted ¬x, satisfies ¬x=0 if x=1 and ¬x=1 if x=0.

XOR (exclusive or); denoted x⊗y satisfies x⊗y=0 if x=y and x⊗y=1 if x≠y.

EQV (equivalence); denoted x≡y satisfies x≡y=1 if x=y and x≡y=0 if x≠y.

FIG. 29 shows one embodiment of components that are used in the i/o unit assembly to process input and output signals and perform other functions. Each component is installed in a cavity with appropriate length to allow the component to slide and of the same width and thickness as the component to provide a tight fit. To allow better visualization of components details these cavities are drawn in phantom lines. There are two types of components illustrated in FIG. 29: controllers and actuators.

Controllers and actuators have similar shapes: a parallelogram with material removed from the corners producing a symmetric shape with central extensions at both extremities (lengthwise) that prevent the body of the component to shut off the input signals when it is located at either side of its cavity. A cylindrical spring hole is made around the free sliding symmetry axis of each component starting at the center of one central extension to a sufficient depth to accommodate a spring with appropriate length for the specific component and leaving sufficient material at the other side of the component to ensure structural integrity of the other central extension and of the component. Away from the component symmetry axis, at a safe distance to skip the spring hole and maintain component structural integrity, two symmetric bands are available to be perforated at specific places by openings of various shapes that allow fluids (liquid and/or gas) to pass through. A rubber grid envelops all openings and the main body of the component isolating each opening so that fluid passing through each opening does not leak into other openings. The number, shape and location of the openings and as a result the length and width of each component vary depending on its task and the number and type of functions implemented.

Actuators are components used to convert a low power digital input signal (reduced water flow signal running in a small pipe diameter) into one or more high power digital output signals (higher water flows allowed by larger pipe diameters) that transmit information to other reactor nodes and control the reactor node where the actuators are installed. Actuators can also be used as an additional component implementing logic functions necessary for the operation of the reactor node. As actuators generate output signals based on digital input signals, all actuator openings 504a, 504b, 504c, 504d, 504e on a specific component have the same shape and size.

Controllers are used to digitize an input signal into one or more bits encoded in gray code (only one bit is allowed to change at a time). A controller can also have additional functionalities in conjunction with digitalization of the input signal such as a mechanism to regulate the input signal pressure provided that it remains within a specified range and to implement additional logic functions necessary for the operation of the reactor node. Controller openings have different shapes and sizes.

To improve the precision of the digitalization of the input signal the controller length is increased and made as long as the space in the i/o unit assembly allows. The actuator length on the other hand is made as short as possible to accommodate the necessary number of actuator openings it needs to perform its function. As a result, a controller spring hole 490 is longer than an actuator spring hole 505 and a controller spring 491a, 491b, 491c, 491d is longer than an actuator spring 506a, 506b, 506c, 506d, 506e.

The elastic coefficient of the controller springs is adjusted so that the controller will slide in the cavity reaching designed positions according to the pressure of its analog input signal. The elastic coefficient of the actuator springs is adjusted so that the actuators move all the way to one or the other side of the cavity according to the status of the digital input signals.

The low power digital input signals that drive actuators can be delivered in pipes with reduced cross section compared to the signals that drive controllers. As a result, actuator central extensions (503a, 503c, 503d, 503e) can be made shorter than controller central extensions (489a, 489b, 489c).

When an input signal pushes the component towards the side of the cavity where the spring is located, the spring is compressed until the applied force produced by the input signal is balanced by the force provided by the compressed spring or the central extension touches the cavity wall and the spring is completely located inside the spring hole reaching its maximum compression. This position is called the active position and represented by the number 1.

When the force applied by the input signal pushing the component subsides, the spring extends out of the spring hole pushing the component back to the other side until the applied force is balanced by the force provided by the compressed spring or the central extension at the other side touches the cavity wall and the spring reaches its maximum extension. This position is called the rest position and represented by the number 0.

An opening located at the opposite side of the input signal allows the displaced fluid to flow in and out of the cavity when the installed component moves from one side to the other eliminating positive and negative pressure build ups that would otherwise prevent the component from moving.

For situations where no spring is used, a set of two complementary input signals feeding the cavity where the component is installed is necessary: a main input signal at one side of the cavity and an auxiliary input signal that has the inverse polarity of the main input signal at the opposite side of the cavity. The active position (1) is defined as the position the component moves when the main input signal is high (1) and the rest position (0) is defined as the position the component moves when the main input signal is low (0). The active side is therefore the side of the cavity opposite to the main input signal and the rest side is the side of the cavity where the main input signal is located. For notation consistency, the input signal in applications with spring and the main input signal in applications without spring are equivalent. The main and auxiliary input signals may in some cases not be complementary and assume both the same value at times. The active side is nevertheless still defined as the side of the cavity opposite to the main input signal and the rest side is the side of the cavity where the main input signal is located.

The notation xxx↔0 or xxx↔1, where xxx is the component reference numeral and 0 or 1 is the position of the component as described in the previous 4 paragraphs, is used to facilitate the description of the position of the various components in a drawing.

Some components are designed so that they may be installed in more than one orientation. A suitable symbol is used to differentiate the alternate orientation from the normal orientation. The notation ~xxx↔0 or ~xxx↔1 is used to indicate that the component xxx has been installed in a different orientation (flipped, reversed, turned or a combination of those) that produces the effect of introducing a NOT function into the input signal, so that the outputs that it produces are the same compared to a component installed on the normal orientation with the input signal inverted.

This notation is used primarily to describe the positions of components subjected to digital signals, but can be extrapolated for analog signals, using a number between 0 and 1 to indicate the relative position of the component. The notation xxx↔0.4 indicates that the component xxx is located at a position 40% of the length of its cavity.

FIG. 29 shows the first embodiments of four types of controllers: a CO2 pressure controller device 460; a water pressure controller device 467; a ground pressure controller device 477; a signal pressure controller device 483.

The CO2 pressure controller device 460 is used to control the CO2 pressure inside a section of the wet reactor and to produce a one digit digital signal of the current CO2 pressure reading at the point being controlled. The CO2 pressure controller device 460 is made in the shape of a parallelogram with material removed from the corners producing a symmetric shape with controller central extensions 489a and 489b at both extremities (lengthwise). A cylindrical controller spring hole 490 is made around the symmetry axis starting at the center of one controller central extension 489b to a sufficient depth to accommodate a controller spring 491a, leaving sufficient material in the controller central extension 489a at the other side to ensure structural integrity of the controller central extension 489a and of the CO2 pressure controller device 460. The CO2 pressure controller device 460 is installed inside a CO2 pressure controller cavity 459 that has suitable dimensions to allow a tight fit and conveys the input and output signals to the appropriate places. A CO2 pressure controller rubber grid 461 envelops all openings and the main body of the CO2 pressure controller device 460 isolating each opening so that fluid passing through an opening does not leak into other openings.

When the CO2 pressure controller device 460 is pushed towards the side of the CO2 pressure controller cavity 459 where the controller spring 491a is located, the spring is compressed until the applied force is balanced by the force provided by the compressed spring or the controller central extension 489b touches the CO2 pressure controller cavity 459 wall and the controller spring 491a reaches its maximum compression being completely located inside the controller spring hole 490 (to avoid cluttering and better display details in the CO2 pressure controller device 460, the portion of the controller spring 491a located inside the controller spring hole 490 is not drawn). When the force pushing the CO2 pressure controller device 460 subsides, the controller spring 491a extends out of the controller spring hole 490 pushing the CO2 pressure controller device 460 back to the other side until the applied force is balanced by the force provided by the compressed spring or the controller central extension 489a at the other side touches the CO2 pressure controller cavity 459 wall and the spring reaches its maximum extension. Away from the symmetry axis, at a safe distance to skip the controller spring hole 490 and maintain structural integrity of the CO2 pressure controller device 460, two symmetric bands are perforated at specific places by openings of various shapes allowing fluids (liquid or gas depending on the opening) to pass through. The CO2 pressure controller device 460 has four openings: 1) a CO2 pressure reset opening 462; 2) a CO2 pressure control opening 463; 3) a CO2 pressure lsb low opening 464; 4) a CO2 pressure lsb high opening 465.

The water pressure controller device 467 is used to control the water pressure inside a section of the wet reactor and to produce a two digit gray coded digital signal of the current water pressure reading at the point being controlled. The water pressure controller device 467 is made in the shape of a parallelogram with material removed from the corners producing a symmetric shape with controller central extensions at both extremities (lengthwise). A cylindrical controller spring hole is made around the symmetry axis to accommodate a controller spring 491b (for additional clarity, the portion of the controller spring 491b located inside the controller spring hole is drawn in dashed lines), leaving sufficient material in the controller central extension 489c at the other side to ensure structural integrity of the controller central extension 489c and of the water pressure controller device 467. The water pressure controller device 467 is installed inside a water pressure controller cavity 466 that has suitable dimensions to allow a tight fit and conveys the input and output signals to the appropriate places. A water pressure controller rubber grid 468 envelops all openings and the main body of the water pressure controller device 467 isolating each opening so that fluid passing through an opening does not leak into other openings.

When the water pressure controller device 467 is pushed towards the side of the water pressure controller cavity 466 where the controller spring 491b is located, the spring is compressed until the applied force is balanced by the force provided by the compressed spring or the controller central extension touches the water pressure controller cavity 466 wall and the controller spring 491b reaches its maximum compression being completely located inside the controller spring hole. When the force pushing the water pressure controller device 467 subsides, the controller spring 491b extends out of the controller spring hole pushing the water pressure controller device 467 back to the other side until the applied force is balanced by the force provided by the compressed spring or the controller central extension 489c at the other side touches the water pressure controller cavity 466 wall and the spring reaches its maximum extension. Away from the symmetry axis, at a safe distance to skip the controller spring hole and maintain structural integrity of the water pressure controller device 467, two symmetric bands are perforated at specific places by openings of various shapes allowing fluids to pass through. The water pressure controller device 467 has seven openings: 1) a water pressure reset opening 469; 2) a water pressure control opening 470; 3) a water pressure lsb high opening 471; 4) a water pressure lsb low opening 1 472; 5) a water pressure lsb low opening 2 473; 6) a water pressure msb low opening 474; 7) a water pressure msb high opening 475.

The ground pressure controller device 477 is used to control the ground water pressure inside each reactor node and to produce a one digit digital signal of the current ground water pressure reading at the point being controlled. The ground pressure controller device 477 is made in the shape of a parallelogram with material removed from the corners producing a symmetric shape with controller central extensions at both extremities (lengthwise). A cylindrical controller spring hole is made around the symmetry axis to accommodate a controller spring 491c, leaving sufficient material in the controller central extension at the other side to ensure structural integrity of the controller central extension and of the ground pressure controller device 477. The ground pressure controller device 477 is installed inside a ground pressure controller cavity 476 that has suitable dimensions to allow a tight fit and conveys the input and output signals to the appropriate places. A ground pressure controller rubber grid 478 envelops all openings and the main body of the ground pressure controller device 477 isolating each opening so that fluid passing through an opening does not leak into other openings.

When the ground pressure controller device 477 is pushed towards the side of the ground pressure controller cavity 476 where the controller spring 491c is located, the spring is compressed until the applied force is balanced by the force provided by the compressed spring or the controller central extension touches the ground pressure controller cavity 476 wall and the spring reaches its maximum compression being completely located inside the controller spring hole. When the force pushing the ground pressure controller device 477 subsides, the controller spring 491c extends out of the controller spring hole pushing the ground pressure controller device 477 back to the other side until the applied force is balanced by the force provided by the compressed spring or the controller central extension at the other side touches the ground pressure controller cavity 476 wall and the spring reaches its maximum extension. Away from the symmetry axis, at a safe distance to skip the controller spring hole and maintain structural integrity of the ground pressure controller device 477, two symmetric bands are perforated at specific places by openings of various shapes allowing fluids to pass through. The ground pressure controller device 477 has three openings: 1) a ground pressure control opening 479; 2) a ground pressure lsb high opening 480; 3) a ground pressure lsb low opening 481.

The signal pressure controller device 483 is used to produce a two-digit gray coded digital signal of each individual input signal. The signal pressure controller device 483 is made in the shape of a parallelogram with material removed from the corners producing a symmetric shape with controller central extensions at both extremities (lengthwise). A cylindrical controller spring hole is made around the symmetry axis to accommodate a controller spring 491d, leaving sufficient material in the controller central extension at the other side to ensure structural integrity of the controller central extension and of the signal pressure controller device 483. The signal pressure controller device 483 is installed inside a signal pressure controller cavity 482 that has suitable dimensions to allow a tight fit and conveys the input and output signals to the appropriate places. A signal pressure controller rubber grid 484 envelops all openings and the main body of the signal pressure controller device 483 isolating each opening so that fluid passing through an opening does not leak into other openings.

When the signal pressure controller device 483 is pushed towards the side of the signal pressure controller cavity 482 where the controller spring 491d is located, the spring is compressed until the applied force is balanced by the force provided by the compressed spring or the controller central extension touches the signal pressure controller cavity 482 wall and the spring reaches its maximum compression being completely located inside the controller spring hole. When the force pushing the signal pressure controller device 483 subsides, the controller spring 491d extends out of the controller spring hole pushing the signal pressure controller device 483 back to the other side until the applied force is balanced by the force provided by the compressed spring or the controller central extension at the other side touches the signal pressure controller cavity 482 wall and the spring reaches its maximum extension. Away from the symmetry axis, at a safe distance to skip the controller spring hole and maintain structural integrity of the signal pressure controller device 483, two symmetric bands are perforated at specific places by openings of various shapes allowing fluids to pass through. The signal pressure controller device 483 has four openings: 1) a signal pressure lsb high opening 485; 2) a signal pressure lsb low opening 486; 3) a signal pressure msb low opening 487; 4) a signal pressure msb high opening 488.

FIG. 29 shows the first embodiments of two types of actuators: single and dual. An actuator single has actuator openings 504a, 504b, 504c and 504d organized in two lines perpendicular to the symmetry axis of the actuator spring hole whereas an actuator dual 500 has actuator openings 504e organized in three lines perpendicular to the symmetry axis of the actuator spring hole. The actuator openings are organized in such a way that the central positions of the cavity where the actuator is installed (one line for actuators single and two lines for actuators dual) will align with an actuator opening or be fully covered by a section of the actuator containing no actuator opening when the actuator moves to position 0 or position 1 causing the actuator spring (if installed) to be fully extended or fully compressed respectively. Rubber grids of appropriate shapes envelop all openings and the main body of the actuators single and actuators dual isolating each opening so that fluid passing through an opening does not leak into other openings.

The actuators single are divided into three types depending on where the actuator openings are located: 1) actuator mono normally open 493 that has the actuator opening 504c located in the same line, at the side of the actuator spring hole 505; 2) actuator mono normally closed 495 that has the actuator opening 504d located in the same line, at the opposite side of the actuator spring hole; 3) actuator mono 497a (and actuator mono 497b) that has the actuator opening 504a (and the actuator opening 504b) located in alternate positions in two lines, one actuator opening at the side of the actuator spring hole and one actuator opening at the alternate opposite side of the actuator spring hole. The actuator mono 497a and actuator mono 497b are in effect identical components, the difference being that one has been placed in its cavity in one orientation and the other has been placed flipped with respect to the symmetry axis around the actuator spring hole.

The actuator mono normally open 493 is made in the shape of a parallelogram with material removed from the corners producing a symmetric shape with actuator central extensions 503c at both extremities (lengthwise). A cylindrical actuator spring hole 505 is made around the symmetry axis starting at the center of one actuator central extension 503c with sufficient depth to accommodate the actuator spring 506c, leaving sufficient material in the actuator central extension at the other side to ensure structural integrity of the actuator central extension and of the actuator mono normally open 493. The actuator mono normally open 493 is installed inside an actuator mono cavity 492c that has suitable dimensions to allow a tight fit and conveys the input and output signals to the appropriate places. An actuator mono n. open rubber grid 494 envelops all actuator openings and the main body of the actuator mono normally open 493 isolating each actuator opening so that fluid passing through an actuator opening does not leak into the other actuator openings.

When the actuator mono normally open 493 is pushed towards the side of the actuator mono cavity 492c where the actuator spring 506c is located, the actuator spring is compressed until the actuator central extension 503c touches the actuator mono cavity 492c wall and the spring reaches its maximum compression being completely located inside the actuator spring hole. When the force pushing the actuator mono normally open 493 subsides, the actuator spring 506c extends out of the actuator spring hole pushing the actuator mono normally open 493 back to the other side until the actuator central extension at the other side touches the actuator mono cavity 492c wall and the actuator spring reaches its maximum extension. Away from the symmetry axis, at a safe distance to skip the actuator spring hole and maintain structural integrity of the actuator mono normally open 493, two actuator openings 504c are located in the same line, at the side of the actuator spring hole 505 so that when the actuator mono normally open 493 is located at the position indicated in FIG. 29 with the actuator spring 506c in maximum extension (rest position) both actuator openings 504c align with the center of the actuator mono cavity 492c.

The actuator mono normally closed 495 is made in the shape of a parallelogram with material removed from the corners producing a symmetric shape with actuator central extensions 503d at both extremities (lengthwise). A cylindrical actuator spring hole is made around the symmetry axis starting at the center of one actuator central extension with sufficient depth to accommodate the actuator spring 506d, leaving sufficient material in the actuator central extension 503d at the other side to ensure structural integrity of the actuator central extension 503d and of the actuator mono normally closed 495. The actuator mono normally closed 495 is installed inside an actuator mono cavity 492d that has suitable dimensions to allow a tight fit and conveys the input and output signals to the appropriate places. An actuator mono n. closed rubber grid 496 envelops all actuator openings and the main body of the actuator mono normally closed 495 isolating each actuator opening so that fluid passing through an actuator opening does not leak into the other actuator openings.

When the actuator mono normally closed 495 is pushed towards the side of the actuator mono cavity 492d where the actuator spring 506d is located, the actuator spring is compressed until the actuator central extension touches the actuator mono cavity 492d wall and the spring reaches its maximum compression being completely located inside the actuator spring hole. When the force pushing the actuator mono normally closed 495 subsides, the actuator spring 506d extends out of the actuator spring hole pushing the actuator mono normally closed 495 back to the other side until the actuator central extension 503d at the other side touches the actuator mono cavity 492d wall and the spring reaches its maximum extension. Away from the symmetry axis, at a safe distance to skip the actuator spring hole and maintain structural integrity of the actuator mono normally closed 495, two actuator openings 504d are located in the same line, at the opposite side of the actuator spring hole so that when the actuator mono normally closed 495 is located at the position indicated in FIG. 29 with the actuator spring 506d in maximum compression (active position) both actuator openings 504d align with the center of the actuator mono cavity 492d. For added information, the portion of the actuator spring 506d inside the actuator spring hole is drawn in dashed lines.

The actuator mono 497a is made in the shape of a parallelogram with material removed from the corners producing a symmetric shape with actuator central extensions 503a at both extremities (lengthwise). A cylindrical actuator spring hole is made around the symmetry axis starting at the center of one actuator central extension with sufficient depth to accommodate the actuator spring 506a, leaving sufficient material in the actuator central extension 503a at the other side to ensure structural integrity of the actuator central extension 503a and of the actuator mono 497a. The actuator mono 497a is installed inside an actuator mono cavity 492a that has suitable dimensions to allow a tight fit and conveys the input and output signals to the appropriate places. An actuator mono rubber grid 498a envelops all actuator openings and the main body of the actuator mono 497a isolating each actuator opening so that fluid passing through an actuator opening does not leak into the other actuator openings.

When the actuator mono 497a is pushed towards the side of the actuator mono cavity 492a where the actuator spring 506a is located, the actuator spring is compressed until the actuator central extension touches the actuator mono cavity 492a wall and the spring reaches its maximum compression being completely located inside the actuator spring hole. When the force pushing the actuator mono 497a subsides, the actuator spring 506a extends out of the actuator spring hole pushing the actuator mono 497a back to the other side until the actuator central extension 503a at the other side touches the actuator mono cavity 492a wall and the spring reaches its maximum extension. Away from the symmetry axis, at a safe distance to skip the actuator spring hole and maintain structural integrity of the actuator mono 497a, two actuator openings 504a are located in alternate positions in two lines, one actuator opening at the side of the actuator spring hole and one actuator opening at the alternate opposite side of the actuator spring hole so that when the actuator mono 497a is located at the position indicated in FIG. 29 with the actuator spring 506a in maximum extension (rest position) one actuator opening aligns with the center of the actuator mono cavity 492a. When the actuator mono 497a is located at the other side of the actuator mono cavity 492a with the actuator spring 506a in maximum compression (active position) the other actuator opening 504a aligns with the center of the actuator mono cavity 492a.

The actuator mono 497b is the same component as actuator mono 497a the only difference being that actuator mono 497b has been installed flipped with respect to the symmetry axis around the actuator spring hole so that when the actuator spring 506b is in maximum extension (rest position), the actuator opening 504b aligns with the center of the actuator mono cavity 492b whereas actuator opening 504a aligns with the center of the actuator mono cavity 492a when the actuator spring 506a is in maximum compression (active position). For added information, the portion of the actuator spring 506b inside the actuator spring hole is drawn in dashed lines.

This asymmetry provides an additional flexibility to the actuator mono that can be installed in one orientation to produce an output power signal that is a function of the input signal or be installed in the flipped orientation to produce an output power signal that is a function of the negated input signal (an additional NOT function can be implemented by flipping the actuator mono with respect to the symmetry axis around the actuator spring hole).

The actuator dual 500 is made in the shape of a parallelogram with material removed from the corners producing a symmetric shape with actuator central extensions 503e at both extremities (lengthwise). A cylindrical actuator spring hole is made around the symmetry axis starting at the center of one actuator central extension with sufficient depth to accommodate an actuator spring 506e. To reduce the number of unique components and obtain a consistent response to input signals in the actuators, the same actuator spring is used for both actuators single and actuators dual. As the actuator springs are designed to fit inside actuators single that are shorter, the actuator spring hole leaves an additional actuator dual spring guard 502 at the other side of the actuator dual 500 that provides additional structural integrity to the actuator central extension 503e and to the actuator dual 500. The actuator dual 500 is installed inside an actuator dual cavity 499 that has suitable dimensions to allow a tight fit and conveys the input and output signals to the appropriate places. An actuator dual rubber grid 501 envelops all actuator openings and the main body of the actuator dual 500 isolating each actuator opening so that fluid passing through an actuator opening does not leak into other actuator openings.

When the actuator dual 500 is pushed towards the side of the actuator dual cavity 499 where the actuator spring 506$e$ is located, the actuator spring is compressed until the actuator central extension touches the actuator dual cavity 499 wall and the spring reaches its maximum compression being completely located inside the actuator spring hole. When the force pushing the actuator dual 500 subsides, the actuator spring 506$e$ extends out of the actuator spring hole pushing the actuator dual 500 back to the other side until the actuator central extension 503$e$ at the other side touches the actuator dual cavity 499 wall and the spring reaches its maximum extension. Away from the symmetry axis, at a safe distance to skip the actuator spring hole and maintain structural integrity of the actuator dual 500, three alternate actuator openings 504$e$ are located in three lines perpendicular to the symmetry axis, one at the side of the actuator spring hole, one at the opposite side of the actuator spring hole and one at the middle of the actuator dual 500 at the alternate side so that when the actuator dual 500 is located at the position indicated in FIG. 29 with the actuator spring 506$e$ in maximum extension (rest position) the two actuator openings at the center of the actuator dual cavity 499 are in a certain pattern and when the actuator dual 500 is located at the other side of the actuator dual cavity 499 with the actuator spring 506$e$ in maximum compression (active position) the pattern of actuator openings is reversed.

Similarly to actuator monos, actuator duals can be installed in one orientation to produce an output power signal that is a function of the input signal or be installed in the flipped orientation to produce an output power signal that is a function of the negated input signal.

The position and orientation of the actuators in FIG. 29 can be easily indicated using the notation:

493↔0; 495↔1; 497$a$↔0; ~497$b$↔0; 500↔0.

FIG. 30 shows the various input and output connections that are needed in the component cavities for the proper operation of the controllers and actuators. Many alternative arrangements are possible depending on available space and other design considerations. The connections in FIG. 30 are provided as reference of possible configurations that implement a viable working component cavity where a suitable controller or actuator can be installed. To facilitate the view of the several connections, the components are not drawn in FIG. 30.

A reference pressure pipe 507 connects the extremities of the cavities that contain controllers to a common reference pressure signal. A CO2 pressure input 1 508 and a CO2 pressure input 2 509 are two possible locations for a CO2 pressure input signal to be injected at the opposite side of the CO2 pressure controller cavity 459 with respect to the reference pressure pipe 507. Up or down orientations for the CO2 pressure input pipe are more convenient to save space in the layout but any alternative orientation and location of the input pipe that delivers the input signal flushed to the edge of the cavity, preferably arriving at one of the corners of the cavity is acceptable. More than one pipe can be used, provided that both are interconnected at some point and therefore have the same signal (same pressure).

A CO2 pressure regulate input 511 provides pressurized CO2 in a circuit that is always on (unless a fault causes the CO2 supply to be shut off). A CO2 pressure reset input 510 provides pressurized CO2 in a separate circuit that can be switched on or off independently of the CO2 pressure regulate input 511 if the reset signal is active or inactive respectively. Openings in the CO2 pressure controller device (not shown in FIG. 30, see FIG. 32) allow or prevent the CO2 to pass through the CO2 pressure controller device and reach the other side of the CO2 pressure controller cavity 459 where the CO2 is collected at a CO2 pressure supply output 512 and forwarded to the delivery point in the reactor node.

A CO2 pressure lsb low input 513 provides a low-pressure water signal (0) to generate the CO2 pressure lsb (least significant bit). A CO2 pressure lsb high input 514 provides a high-pressure water signal (1) to generate the CO2 pressure lsb. Openings in the CO2 pressure controller device (not shown in FIG. 30, see FIG. 32) allow either the CO2 pressure lsb low input 513 or the CO2 pressure lsb high input 514 signal to pass through the CO2 pressure controller device and reach the other side of the CO2 pressure controller cavity 459 where the CO2 is collected at a CO2 pressure lsb output 515 generating a one bit digital signal for the CO2 pressure at the particular point where the CO2 pressure input signal was taken.

A water pressure input 1 516 and a water pressure input 2 517 are two possible locations for a water pressure input signal to be injected at the opposite side of the water pressure controller cavity 466 with respect to the reference pressure pipe 507. Up or down orientations for the water pressure input pipe are more convenient to save space in the layout but any alternative orientation and location of the input pipe that delivers the input signal flushed to the edge of the cavity, preferably arriving at one of the corners of the cavity is acceptable. More than one pipe can be used, provided that both are interconnected at some point and therefore have the same signal (same pressure).

A water pressure regulate input 519 provides pressurized water in a circuit that is always on (unless a fault causes the water supply to be shut off). A water pressure reset input 518 provides pressurized water in a separate circuit that can be switched on or off independently of the water pressure regulate input 519 if the reset signal is active or inactive respectively. Openings in the water pressure controller device (not shown in FIG. 30, see FIG. 32) allow or prevent the water to pass through the water pressure controller device and reach the other side of the water pressure controller cavity 466 where the water is collected at a water pressure supply output 520 and forwarded to the delivery point in the reactor node.

A water pressure lsb low input 522 and a water pressure msb low input 523 provide a low pressure water signal (0) to generate the water pressure lsb and the water pressure msb (most significant bit) respectively. A water pressure lsb high input 521 and a water pressure msb high input 524 provide a high pressure water signal (1) to generate the water pressure lsb and the water pressure msb respectively. Openings in the water pressure controller device (not shown in FIG. 30, see FIG. 32) allow either the water pressure lsb low input 522 or the water pressure lsb high input 521 water signal to pass through the water pressure controller device and reach the other side of the water pressure controller cavity 466 where the water is collected at a water pressure lsb output 525. Other openings in the water pressure controller device (not shown in FIG. 30, see FIG. 32) allow either the water pressure msb low input 523 or the water pressure msb high input 524 water signal to pass through the water pressure controller device and reach the other side of the water pressure controller cavity 466 where the water is collected at a water pressure msb output 526. The water pressure lsb output 525 and the water pressure msb output 526 together encode the water pressure at the particular point where the water pressure input signal was taken into a 2 bit gray coded digital signal.

A ground pressure input 527 is injected at the opposite side of the ground pressure controller cavity 476 with respect to the reference pressure pipe 507. Up or down orientations for the ground pressure input pipe are more convenient to save space in the layout but any alternative orientation and location of the input pipe that delivers the input signal flushed to the edge of the cavity, preferably arriving at one of the corners of the cavity is acceptable. More than one pipe can be used, provided that both are interconnected at some point and therefore have the same signal (same pressure).

A ground pressure regulate input 528 provides pressurized water in a circuit that is always on (unless a fault causes the water supply to be shut off). An opening in the ground pressure controller device (not shown in FIG. 30, see FIG. 32) allow or prevent the water to pass through the ground pressure controller device and reach the other side of the ground pressure controller cavity 476 where the water is collected at a ground pressure supply output 529 and forwarded to the delivery point in the reactor node.

A ground pressure lsb low input 531 provides a low-pressure water signal (0) to generate the ground pressure lsb. A ground pressure lsb high input 530 provides a high-pressure water signal (1) to generate the ground pressure lsb. Openings in the ground pressure controller device (not shown in FIG. 30, see FIG. 32) allow either the ground pressure lsb low input 531 or the ground pressure lsb high input 530 water signal to pass through the ground pressure controller device and reach the other side of the ground pressure controller cavity 476 where the water is collected at a ground pressure lsb output 532 generating a one bit digital signal for the ground pressure at the particular point where the ground pressure input signal was taken.

A signal pressure input 533 is injected at the opposite side of the signal pressure controller cavity 482 with respect to the reference pressure pipe 507. Up or down orientations for the signal pressure input pipe are more convenient to save space in the layout but any alternative orientation and location of the input pipe that delivers the input signal flushed to the edge of the cavity, preferably arriving at one of the corners of the cavity is acceptable. More than one pipe can be used, provided that both are interconnected at some point and therefore have the same signal (same pressure).

A signal pressure lsb low input 535 and a signal pressure msb low input 536 provide a low pressure water signal (0) to generate the signal lsb and the signal msb respectively. A signal pressure lsb high input 534 and a signal pressure msb high input 537 provide a high pressure water signal (1) to generate the signal lsb and the signal msb respectively. Openings in the signal pressure controller device (not shown in FIG. 30, see FIG. 32) allow either the signal pressure lsb low input 535 or the signal pressure lsb high input 534 water signal to pass through the signal pressure controller device and reach the other side of the signal pressure controller cavity 482 where the water is collected at a signal pressure lsb output 538. Other openings in the signal pressure controller device (not shown in FIG. 30, see FIG. 32) allow either the signal pressure msb low input 536 or the signal pressure msb high input 537 water signal to pass through the signal pressure controller device and reach the other side of the signal pressure controller cavity 482 where the water is collected at a signal pressure msb output 539. The signal pressure lsb output 538 and the signal pressure msb output 539 together encode the particular input signal into a 2 bit gray coded digital signal.

An actuator mono 1 input bottom 1 540, an actuator mono 1 input bottom 2 541, an actuator mono 1 input top 1 542, an actuator mono 1 input top 2 543 and an actuator mono 1 input top 3 544 are some of possible locations for inputs connected to the bottom and to the top of the actuator mono cavity 492c. Any orientation and location of the input pipes that deliver the input signals flushed to the edge of the cavity, preferably arriving at the corners of the cavity is acceptable. At least one input must be connected at each side of the cavity for proper functioning of the actuator. In the example represented in FIG. 30, for simplicity only one input is shown at the left side of actuator mono cavity 492c: actuator mono 1 input top 3 544 that carries the signal that commands the installed actuator mono normally open (not shown in FIG. 30, see FIG. 32). At least one of the four inputs (540, 541, 542, 543) shown on the other side must be implemented. Assuming for simplicity it is input actuator mono 1 input top 1 542, it must be either connected to ground (542=0) if an actuator spring is installed (as the case in the example in FIG. 32) or the opposite polarity of the signal supplied at actuator mono 1 input top 3 544 (542=¬544) if no actuator spring is installed (in a possible other use of the actuator).

An actuator mono 1 supply 1 545 and an actuator mono 1 supply 2 546 located at the top center of the actuator mono cavity 492c provide two input power signals to the actuator. Two independent lines on the bottom center of the cavity, an actuator mono 1 output 1 547 and an actuator mono 1 output 2 548 can be simultaneously either connected to the respective input power signal on the top or closed depending on the position of the actuator mono normally open (not shown in FIG. 30, see FIG. 32). At any time, both outputs 547 and 548 will be connected to a water or CO2 supply and have a meaningful logic value (high or low) or disconnected and have an undetermined logic value (3rd state) depending on the position of the actuator mono normally open in the cavity (see FIG. 32).

An actuator mono 2 input top 1 549 and an actuator mono 2 input side 1 550 are one possible combination of two inputs for the actuator mono cavity 492d, one input connected to the side and one input connected to the top of the cavity. Any orientation and location of the input pipes that deliver the input signals flushed to the edge of the cavity, preferably arriving at the corners of the cavity is acceptable. At least one input must be connected at each side of the actuator mono cavity 492d for proper functioning of the actuator. In the example represented in FIG. 30, actuator mono 2 input side 1 550 carries the signal that commands the installed actuator mono normally closed (not shown in FIG. 30, see FIG. 32) and actuator mono 2 input top 1 549 is connected to either ground (549=0) if an actuator spring is installed (as the case in the example in FIG. 32) or the opposite polarity of the signal supplied at actuator mono 2 input side 1 550 (549=¬550) if no actuator spring is installed (in a possible other use of the actuator).

An actuator mono 2 supply 1 551 and an actuator mono 2 supply 2 552 located at the top center of the actuator mono cavity 492d provide two input power signals to the actuator. Two independent lines on the bottom center of the cavity, an actuator mono 2 output 1 553 and an actuator mono 2 output 2 554 can be simultaneously either connected to the respective input power signal on the top or closed depending on the position of the actuator mono normally closed (not shown in FIG. 30, see FIG. 32). At any time, both outputs 553 and 554 will be connected to a water or CO2 supply and have a meaningful logic value (high or low) or disconnected and have an undetermined logic value (3rd state) depending on the position of the actuator mono normally closed in the cavity (see FIG. 32).

An actuator mono 3 input side 1 555, an actuator mono 3 input side 2 556, an actuator mono 3 input side 3 557 and an actuator mono 3 input side 4 558 are some of possible locations for inputs for the actuator mono cavity 492b connected to the sides of the cavity. Any orientation and location of the input pipes that deliver the input signals flushed to the edge of the cavity, preferably arriving at the corners of the cavity is acceptable. Layout or design constraints may require that one or more inputs be placed offset from the cavity edges as the case of actuator mono 3 input side 2 556 that is located slightly offset from the edge of the cavity. At least one input must be connected at each side of the cavity for proper functioning of the actuator. In the example in FIG. 30, actuator mono 3 input side 4 558 carries the signal that commands the installed actuator mono (not shown in FIG. 30, see FIG. 32) and at least one of the three inputs on the other side (555, 556, 557) must be implemented. Assuming for simplicity it is the actuator mono 3 input side 3 557, it must be either connected to ground (557=0) if an actuator spring is installed (as the case in the example in FIG. 32) or the opposite polarity of the signal supplied at actuator mono 3 input side 4 558 (557=¬558) if no actuator spring is installed (in a possible other use of the actuator).

An actuator mono 3 supply 1 559 and an actuator mono 3 supply 2 560 located at the top center of the actuator mono cavity 492b provide two input power signals to the actuator. Two independent lines on the bottom center of the cavity, an actuator mono 3 output 1 561 and an actuator mono 3 output 2 562 can be alternately either connected to the respective input power signal on the top or closed depending on the position of the actuator mono (not shown in FIG. 30, see FIG. 32).

An actuator mono 4 input top 1 563 and an actuator mono 4 input top 2 564 are one possible viable combination of inputs connected to the top of actuator mono cavity 492a. Any orientation and location of the input pipes that deliver the input signals flushed to the edge of the cavity, preferably arriving at the corners of the cavity is acceptable. At least one input must be connected at each side of the actuator mono cavity 492a for proper functioning of the actuator. In the example in FIG. 30, actuator mono 4 input top 2 564 carries the signal that commands the installed actuator mono (not shown in FIG. 30, see FIG. 32) and actuator mono 4 input top 1 563 is connected to either ground (563=0) if an actuator spring is installed (as the case in the example in FIG. 32) or the opposite polarity of the signal supplied at actuator mono 4 input top 2 564 (563=¬564) if no actuator spring is installed (in a possible other use of the actuator).

An actuator mono 4 supply 1 565 and an actuator mono 4 supply 2 566 located at the top center of the actuator mono cavity 492a provide two input power signals to the actuator. A single actuator mono 4 output 1 567 located at the bottom center of the cavity combines the two inputs actuator mono 4 supply 1 565 and actuator mono 4 supply 2 566 producing a single power output that is a logic function of actuator mono 4 input top 2 564, actuator mono 4 supply 1 565 and an actuator mono 4 supply 2 566.

An actuator dual input top 1 568 and an actuator dual input top 2 569 are one possible viable combination of inputs connected to the top of the actuator dual cavity 499. Any orientation and location of the input pipes that deliver the input signals flushed to the edge of the cavity, preferably arriving at the corners of the cavity is acceptable. At least one input must be connected at each side of the actuator dual cavity 499 for proper functioning of the actuator dual. In the example in FIG. 30, actuator dual input top 2 569 carries the signal that commands the installed actuator dual (not shown in FIG. 30, see FIG. 32) and actuator dual input top 1 568 is connected to either ground (568=0) if an actuator spring is installed (as the case in the example in FIG. 32) or the opposite polarity of the signal supplied at actuator dual input top 2 569 (568=¬569) if no actuator spring is installed (in a possible other use of the actuator).

An actuator dual supply top 1 570, an actuator dual supply top 2 571, an actuator dual supply top 3 572 and an actuator dual supply top 4 573 located at the top of the actuator dual cavity 499 provide four input power signals to the actuator. An actuator dual output 1 574 located at the bottom of the cavity combines two inputs above: actuator dual supply top 1 570 and actuator dual supply top 2 571 and an actuator dual output 2 575 located at the bottom of the cavity combines the other two inputs above: actuator dual supply top 3 572 and actuator dual supply top 4 573.

FIG. 31 shows an implementation of a high pressure supply plane 576 that is used to connect all inputs that need to be connected to a high pressure water source (1) such as CO2 pressure lsb high input 514, actuator mono 2 supply 2 552, etc. and an implementation of a ground plane 577 that is used to connect all inputs that need to be connected to a low pressure common ground sink (0) such as CO2 pressure lsb low input 513, actuator mono 3 supply 2 560, etc. These planes create larger conduits that equalize the water pressure and avoid bottlenecks that could cause pressure variations and undesirable logic jitter. As the components switching on and off the inputs to the outputs will have variable positions during normal operation, not all inputs will be connected at a certain point in time creating a statistic average load to the high-pressure supply plane and to the ground plane. A clearance cut 578 may be used on selected spots to keep minimum clearances and ensure structural integrity of the parts. In this example, the clearance cut 578 ensures that the material separating the ground plane 577 and the signal pressure input 533 will be able to withstand the water pressure difference including a safety margin and not break or crack when subjected to a worst case condition during normal operation or a fault.

FIG. 32 shows a top view of the controllers and actuators with the input and output connections to clarify the interaction between the components and the connections and the operation of these components. FIG. 32 is further referred to in the operation section.

FIG. 33 shows first embodiments of components used to implement logic functions.

An OR gate 579 is composed of a body in the shape of a parallelogram with gate rounded edges 580. The OR gate 579 has a set of two OR gate O-rings 581a and 581b and an OR gate rod 582 attached to the center of one of the faces. The OR gate 579 is a device that enables two input signals to command another gate installed in the cavity where the OR gate is installed (see FIG. 35 and FIG. 36).

An AND gate 583 is composed of a body in the shape of a parallelogram with gate rounded edges with same cross section as the OR gate 579 but longer in the axial direction to accommodate two AND gate sections 585. Each section has four faces that may or may not have a hole creating a pattern of connections. In the first section an AND gate through hole 1 586 connects the front and back faces. In the second section an AND gate through hole 2 587 connects the top and bottom faces and an AND gate side hole 588 connects the front face to the AND gate through hole 2 587. The top and bottom faces remain closed in the first section and the back face remains closed in the second section. An AND gate rubber grid 584 envelops all holes and the main body of the AND gate 583 isolating each hole and each face so that fluid passing through a hole does not leak into other holes.

A SEL gate 589 is composed of a body in the shape of a parallelogram with gate rounded edges with same cross section as the OR gate 579 and the AND gate 583 but longer in the axial direction to accommodate three SEL gate sections 591. Each section has four faces that may or may not have a hole creating a pattern of connections. In the first section a SEL gate through hole 1 592 connects the front and back faces and a SEL gate side hole 1 593 connects the bottom face to the SEL gate through hole 1 592. In the second section a SEL gate through hole 2 594 connects the top and bottom faces and a SEL gate side hole 2 595 connects the front face to the SEL gate through hole 2 594. The third section repeats the same arrangement of connections of the first section. The top face remains closed in the first and third sections and the back face remains closed in the second section. A SEL gate rubber grid 590 envelops all holes and the main body of the SEL gate 589 isolating each hole and each face so that fluid passing through a hole does not leak into other holes.

A XOR gate 596 is composed of a body in the shape of a parallelogram with gate rounded edges with same cross section as the OR gate 579, the AND gate 583 and the SEL gate 589 but longer in the axial direction to accommodate four XOR gate sections 598. Each section has four faces that may or may not have a hole creating a pattern of connections. In the first section a XOR gate through hole 1 599 connects the front and back faces. In the second section a XOR gate through hole 2 600 connects the top and bottom faces and a XOR gate side hole 2 601 connects the front face to the XOR gate through hole 2 600. The third section repeats the same arrangement of connections of the first section. The fourth section repeats the same arrangement of connections of the second section. The top and bottom faces remain closed in the first and third sections and the back face remains closed in the second and fourth sections. A XOR gate rubber grid 597 envelops all holes and the main body of the XOR gate 596 isolating each hole and each face so that fluid passing through a hole does not leak into other holes.

A SW gate 602 is composed of a body in the shape of a parallelogram with gate rounded edges with same cross section as the OR gate 579, the AND gate 583. the SEL gate 589, and the XOR gate 596 but longer in the axial direction to accommodate five SW gate sections 604. Each section has four faces that may or may not have a hole creating a pattern of connections. In the first section a SW gate face hole 1 605 and a SW gate side hole 1 606 connect the top and back faces. In the second section a SW gate through hole 2 607 connects the top and bottom faces and a SW gate side hole 2 608 connects the back face to the SW gate through hole 2 607. The third and fifth sections (odd sections) repeat the same arrangement of connections of the first section. The fourth section (even) repeats the same arrangement of connections of the second section. The front and bottom faces remain closed in the odd sections and the front face remains closed in the even sections. A SW gate rubber grid 603 envelops all holes and the main body of the SW gate 602 isolating each hole and each face so that fluid passing through a hole does not leak into other holes.

A diagnose gate 609 is composed of a body in the shape of a parallelogram with gate rounded edges with same cross section as the OR gate 579, the AND gate 583, the SEL gate 589, the XOR gate 596 and the SW gate 602 but longer in the axial direction to accommodate twenty one diagnose gate sections 611. Each section has four faces that may or may not have a hole creating a pattern of connections. In the first section a diagnose gate face hole 1 612 and a diagnose gate side hole 1 613 connect the top and back faces. In the second section a diagnose gate through hole 2 614 connects the top and bottom faces and a diagnose gate side hole 2 615 connects the back face to the diagnose gate through hole 2 614. The odd sections repeat the same arrangement of connections of the first section. The even sections repeat the same arrangement of connections of the second section. The front and bottom faces remain closed in the odd sections and the front face remains closed in the even sections. A diagnose gate rubber grid 610 envelops all holes and the main body of the diagnose gate 609 isolating each hole and each face so that fluid passing through a hole does not leak into other holes.

A diagnose gate spring guide 616 attached to each extremity provides support for a spring and works as a stopper to maintain a clearance at the edge of the cavity where the diagnose gate 609 is installed.

The SW gate 602 and the diagnose gate 609 are topologically similar: both have an odd number of sections and the even sections and the odd sections of both components have the same connections. The differences of hole shapes: circular in the diagnose gate 609 and squared in the SW gate 602 and the availability or not of spring guides do not affect the primary function of the component. The SW gate 602 is not used on the first embodiment of the reactor node but as it is shorter it can be drawn in more detail and therefore is used as a better way to illustrate the shape and explain the workings of the diagnose gate 609.

FIG. 34 shows various cavities that accommodate logic components and the corresponding input and output connections that implement examples of logic functions. Many alternative arrangements are possible to implement more complex logic functions. Depending on specific needs such as available space, simplicity, quick response, availability of intermediary functions and other design considerations a certain arrangement may be selected. The illustrations in FIG. 34, FIG. 35 and FIG. 36 are provided as reference of simple configurations that implement basic logic functions that can be used as building blocks to produce more complex logic functions. To better illustrate the connections the components are not shown in FIG. 34.

An AND 1 cavity 617 fitted with the necessary connections has the size to fit a first AND gate. An AND 1 aux 618 connects the cavity to a ground signal. An AND 1 main 619 supplies the main input to the AND gate. An AND 1 input 620 supplies the other logic input to the AND gate. An AND 1 clear 622 is an additional input that is connected to ground and an AND 1 output 621 collects the result.

An AND 2 cavity 623 fitted with the necessary connections has the size to fit a second AND gate that is installed flipped (see FIG. 35 and FIG. 36) as a means to introduce an additional NOT function to the main input. An AND 2 aux 624 connects the cavity to a ground signal. An AND 2 main 625 supplies the main input to the AND gate. An AND 2 input 626 supplies the other logic input to the AND gate. An AND 2 clear 628 is an auxiliary input that is connected to ground and an AND 2 output 627 collects the result.

An AND 3 cavity 629 fitted with the necessary connections has the size to fit a third AND gate with an OR gate. An AND 3 aux 630 connects the cavity to a ground signal. An AND 3 main 631 supplies the main input to the OR gate. One among four options: an AND 3 OR input 1 632, an AND 3 OR input 2 633, an AND 3 OR input 3 634 or an AND 3 OR input 4 635 is needed to provide the other logic input to the OR gate. The four options are drawn to indicate all possible locations for the input line that may be chosen depending on the design. The AND 3 main 631 and the selected other logic input for the OR gate (for simplicity assumed to be AND 3 OR input 1 632) produce the output of the OR gate (631\/632) that is in turn the main input to the AND gate. An AND 3 input 636 supplies the other logic input to the AND gate. An AND 3 clear 638 is an auxiliary input that is connected to ground and an AND 3 output 637 collects the result.

A SEL 1 cavity 639 fitted with the necessary connections has the size to fit a SEL gate with an OR gate. A SEL 1 aux 640 connects the cavity to a ground signal. A SEL 1 main 641 supplies the main input to the OR gate. One among four options: a SEL 1 OR input 1 642, a SEL 1 OR input 2 643, a SEL 1 OR input 3 644 or a SEL 1 OR input 4 645 is needed to provide the other logic input to the OR gate. The four options are drawn to indicate all possible locations for the input line that may be chosen depending on the design. The SEL 1 main 641 and the selected other logic input for the OR gate (for simplicity assumed to be SEL 1 OR input 1 642) produce the output of the OR gate (641\/642) that is in turn the main input to the SEL gate. A SEL 1 input 1 646 supplies a first input to the SEL gate. A SEL 1 clear 1 648 is a first auxiliary input that is connected to ground and a SEL 1 output 1 647 collects the first output. A SEL 1 input 2 649 supplies a second input to the SEL gate. A SEL 1 clear 2 651 is a second auxiliary input that is connected to ground and a SEL 1 output 2 650 collects the second output.

A XOR cavity 652 fitted with the necessary connections has the size to fit a first XOR gate. A XOR signal 1 653 supplies the first input signal to the XOR gate. A XOR signal 2 654 supplies the second input signal to the XOR gate. A XOR input 1 655 is a first auxiliary input that is connected to high pressure (1), a XOR clear 1 657 is a first auxiliary input that is connected to ground (0) and a XOR output 1 656 collects the first output. A XOR input 2 658 is a second auxiliary input that is connected to high pressure (1), a XOR clear 2 660 is a second auxiliary input that is connected to ground and a XOR output 2 659 collects the second output.

A SEL 2 cavity 661 fitted with the necessary connections has the size to fit a second SEL gate without a logic spring. Applications without spring require complementary signals as inputs but offer some useful possibilities such as a means to implement memory. A SEL 2 main 663 supplies the main input to the SEL gate. A SEL 2 aux 662 supplies the negated main input (662=¬663) to the SEL gate. A SEL 2 input 1 664 supplies a first input to the SEL gate. A SEL 2 output 1 665 collects the first output. A SEL 2 input 2 666 supplies a second input to the SEL gate. A SEL 2 output 2 667 collects the second output. A SEL 2 output connection 668 is constructed connecting outputs 665 and 667 to produce a combined output 668=665\/667.

A SW cavity 669 fitted with the necessary connections has the size to fit a SW gate. A SW aux 670 connects the cavity to a ground signal. A SW main 671 supplies the switching signal to the SW gate. A SW input 1 672 supplies the first input to the SW gate. A SW monitor 1 673 and a SW output 1 674 are signals that will be connected or not to the SW input 1 672 depending on the SW main 671. A SW input 2 675 supplies the second input to the SW gate. A SW monitor 2 676 and a SW output 2 677 are signals that will be connected or not to the SW input 2 675 signal depending on the SW main 671.

A depth sensor cavity 678 fitted with the necessary connections has the size to fit a depth detector and a depth sensor (see FIG. 35 and FIG. 36). A depth external water pressure pipe 679 conveys the (x) external pressure signal to the edge of the depth sensor cavity 678. A depth lsb gnd 680 and a depth msb gnd 683 are connected to water at ground pressure and a depth lsb high pressure 681 and a depth msb high pressure 682 are connected to water at high pressure. Slots on the depth sensor (not seen on FIG. 34, see FIG. 35 and FIG. 36) connect either a low pressure supply or a high pressure supply to a (x) external pressure lsb 684 and a (x) external pressure msb 685 depending on the position of the depth sensor.

FIG. 35 shows various cavities with the respective logic components in place and the corresponding input and output connections described in FIG. 34 that implement examples of logic functions. Whenever applicable a logic spring 686a, 686b, 686c, 686d, and 686e or a logic long spring 687a and 687b are used in association with input signals as a means to move the components into the desired position.

A depth detector 689 is made of a plastic slab with the cross section of a rectangle with gate rounded edges so that it fits perfectly inside the depth sensor cavity 678. A depth detector input guard 691 is a tapering that allows water coming from a depth external water pressure pipe 679 to enter the depth sensor cavity 678 even when the depth detector 689 is at the end of its excursion.

The depth detector 689 has five slots that allow fluids to pass through: 1) a depth lsb high pressure slot 1 692; 2) a depth lsb gnd slot 693; 3) a depth lsb high pressure slot 2 694; 4) a depth msb high pressure slot 695; 5) a depth msb gnd slot 696. A depth detector rubber grid 690 envelops all slots and the main body of the depth detector 689 isolating each slot so that fluid passing through a slot does not leak into other slots.

A depth sensor 688 is made of a flexible plastic bag containing air that has been sealed at one atmospheric pressure. The depth sensor 688 has the same rectangular cross section with gate rounded edges as the depth detector 689 so that both fit perfectly inside the depth sensor cavity 678.

FIG. 36 shows various cavities and the corresponding input and output connections with the respective logic components in place in a different position than as seen on FIG. 35 and from a different point of view to provide additional detail on the implemented logic functions.

FIG. 35 and FIG. 36 are further referred to in the operation section to explain the operation of the logic components, the depth sensor and the depth detector.

FIG. 37 shows the first embodiment of LFSR assembly (linear feedback shift register) 697 that enables each individual reactor node in the system to have its own unique address and be able to exchange information with a central monitoring system. The LFSR assembly 697 is encased by four slabs or layers: a LFSR layer a 698, a LFSR layer b 699, a LFSR layer c 700, and a LFSR layer d 701. These layers have cuts of various shapes and sizes on their faces, made in such a way that when the layers are stacked the cuts on a face of a layer match the cuts on the adjacent face of the next layer creating recesses that provide support and connectivity to a series of components that implement the necessary functions. Each layer has an appropriate thickness that facilitates the construction and allows the components to be easily placed and removed. A LFSR gnd layer 702 is connected to the common ground and interconnects all points that require a connection to a logic low level signal (702=0). A LFSR high pressure feed 703 is connected to the common high pressure supply and interconnects all points that require a connection to a logic high level signal (703=1). The four layers create a series of LFSR cavities 704 where a set of components is installed and corresponding LFSR connections 705 that allow the components to operate as intended.

The LFSR assembly 697 implements the function of a linear feedback shift register of seven bits. The LFSR connections 705 provide the necessary paths to conduct signals to the appropriate points in such a way that the inputs of the $2^{nd}$ up to the $7^{th}$ bits are the values of the previous ones (n=n−1) and the input of the $1^{st}$ bit is a feedback of the XOR (exclusive or) function of the 6th and the $7^{th}$ bit of the shift register (1=6⊗7). Once initialized to a state of all bits high (1) and driven by a periodic digital clock signal, this device goes through a defined cyclical sequence of 127 states FIG. 92 shows the list of all states of a seven-bit linear feedback shift register (LFSR). The initial state 1 (1111111) is produced when the LFSR is enabled and each subsequent state is produced by one additional cycle of the clock signal. As seen on the table, after 127 clock cycles, the LFSR returns to state 1.

FIG. 38 shows that the LFSR cavities are composed of: a mz cavity 706, a zk cavity 707, a zkm cavity 708, a zero cavity 709, seven register cavity 710a, 710b, . . . , 710g, and seven memory cavity 711a, 711b, . . . , 711f, 711g. The mz cavity 706 is connected to the LFSR gnd layer that provides low pressure water supply through a mz cavity clear 712 and a mz cavity aux 713 (712=0; 713=0). The zk cavity 707 is connected to the LFSR gnd layer through a zk cavity clear 714 and a zk cavity aux 715 (714=0; 715=0). The zkm cavity 708 is connected to the LFSR gnd layer through two zkm cavity clear 716a and 716b and a zkm cavity aux 717 (716=0; 717=0). The zero cavity 709 is connected to the LFSR gnd layer through seven register zero clear 732a, . . . , 732g and a zero cavity aux 718 (732a=0, . . . , 732g=0; 718=0).

A register gnd rail 726a connected to the LFSR gnd layer provides low pressure water supply to each register cavity 710a, 710b, . . . , 710g passing through each cavity and continuing into the next one until stopping (726g) at register cavity 710g (726a=726g=0). Seven register y clear 731a, . . . , 731g connected to the LFSR gnd layer provide an additional low pressure water supply (731a=0, . . . , 731g=0) to each register cavity 710a, 710b, . . . , 710g. A memory gnd rail 727a connected to the LFSR gnd layer provides low pressure water supply to each of the first 6 memory cavity 711a, 711b, . . . , 711f passing through each cavity and continuing into the next one until 727f stops at memory cavity 711f (727a=727f=0). A lower XOR input 728 connects the bottom of the sixth memory cavity 711f at a twin under connection 742f to the bottom of the seventh memory cavity 711g at a twin under connection 742g (742f=742g). An upper XOR input 729 connects the top of the sixth memory cavity 711f at a twin upper connection 743f to the top of the seventh memory cavity 711g at a twin upper connection 743g (743f=743g).

A (k) clock in msb 719 signal is fed into the zk cavity 707. A (z) zero in msb 720 signal is fed into the mz cavity 706, the zk cavity 707, and zero cavity 709. A (m) master/slave in msb 721 signal is fed into the mz cavity 706. A register signal zk 722, conducts the signal zk=z/\k from the zk cavity 707 to the zkm cavity 708. A register signal mz 723a conducts the signal mz=m/\z from the mz cavity 706 to the zkm cavity 708 where it terminates (723b).

A register signal kzm 725a conducts the signal kzm=k/\z/\m from the zkm cavity 708 to the memory cavity 711a, continues through each memory cavity, terminating (725f) at memory cavity 711f. A register signal ¬kzm 724a that during active states of normal operation of the LFSR assembly is the inverse of the register signal kzm (724=¬725) conducts the signal ¬kzm=¬k/\z/\m from the zkm cavity 708 to the register cavity 710a (724b), continues through each register cavity until past the register cavity 710g and is available to further use by additional logic (724c).

A (y) unit ready 730a starts at the LFSR high pressure feed 703a, is routed (730b) until register cavity 710a, continues through each register cavity until past the register cavity 710g and is available to further use by additional logic (730c). The LFSR high pressure feed 703a, 703b also provides high pressure water supply to seven register zero set 733a, . . . , 733g connected to the zero cavity 709.

A zero gate 734 is composed of a body in the shape of a parallelogram with gate rounded edges with same cross section as the OR gate, the AND gate the SEL gate, the XOR gate, and the SW gate but longer in the axial direction to accommodate fifteen zero gate sections 736. Each section has four faces that may or may not have a hole creating a pattern of connections. In the first section a zero gate through hole 737 connects the front and back faces. In the second section a zero gate top hole 738 connects the top and front faces. The odd sections repeat the same arrangement of connections of the first section and the even sections repeat the same arrangement of connections of the second section. The top and bottom faces remain closed in the odd sections and the back and bottom faces remain closed in the even sections. A zero gate rubber grid 735 envelops all holes and the main body of the zero gate 734 isolating each hole and each face so that fluid passing through a hole does not leak into other holes. The zero gate 734 is installed into the zero cavity 709 (see FIGS. 41 to 48).

FIG. 39 shows the LFSR cavities and some of the LFSR connections from a different angle that facilitates the visualization of these particular LFSR connections and also provides additional detail of the register signal mz 723 that connects the mz cavity 706 and the zkm cavity 708 and the (y) unit ready 730a that starts at the LFSR high pressure feed, is routed (730b) until register cavity 710a, continues through each register cavity until past the register cavity 710g and is available (730c) to further use by additional logic as already described in FIG. 38.

A XOR output high 739 is routed into a carry output high 744a (739=744a) and a XOR output low 740 is routed into a carry output low 745a (740=745a). The carry output high 744a and the carry output low 745a feed the first position of the zero cavity 709 and align with a register input high 746a and with a register input low 747a respectively that terminate at the extremities of the first register cavity 710a. A twin under connection 742a at the bottom of the first memory cavity 711a is connected to a carry output high 744b (742a=744b) and a twin upper connection 743a at the top of the first memory cavity 711a is connected to a carry output low 745b (743a=745b). The carry output high 744b and the carry output low 745b feed the second position of the zero cavity 709 and align with a register input high 746b and with a register input low 747b respectively that terminate at the extremities of the second register cavity 710b. The same pattern follows until a twin under connection 742f at the bottom of the sixth memory cavity 711f is connected to a carry output high 744*g* passing through a lower XOR input loop 741 (742*f*=741=744*g*) and a twin upper connection 743*f* at the top of the sixth memory cavity 711*f* is connected to a carry output low 745*g* (743*f*=745*g*). The carry output high 744*g* and the carry output low 745*g* feed the seventh and last position of the zero cavity 709 and align with a register input high 746*g* and with a register input low 747*g* respectively that terminate at the extremities of the seventh register cavity 710*g*. The upper XOR input 729 connects the upper part of the memory cavity 711*g* to the upper part of the memory cavity 711*f* starting at the twin upper connection 743*g* passing by the twin upper connection 743*f* and terminating at the carry output low 745*g* (743*f*=743*g*=745*g*). Similarly, the lower XOR input 728 connects the lower part of the memory cavity 711*g* to the lower part of the memory cavity 711*f* starting at the twin under connection 742*g*, reaching the twin upper connection 743*f* and continuing through the lower XOR input loop 741 until the carry output high 744*g* (742*f*=742*g*=741=744*g*).

The connections described in the previous paragraph produce an arrangement in that, when the zero gate placed inside the zero cavity 709 is in the active position (734↔1), (see FIG. 42) the signals coming from memory cavity n are routed into the extremities of register cavity n+1 for n=1 to 6 counted from left to right and at the same time the signals coming from memory cavity 7 are routed into the extremities of register cavity 1. This arrangement enables the components inside register cavity n+1 to be made to move according to the position of the components inside memory cavity n for n=1 to 6 and at the same time, the components inside register cavity 1 to be made to move according to the position of the components inside memory cavity 6 and memory cavity 7.

If 734↔1; then 742*a*=744*b*=746*b*; 743*a*=745*b*=747*b* for memory cavity 1 and register cavity 2 and so on until 742*f*=744*g*=746*g*; 743*f*=745*g*=747*g* for memory cavity 6 and register cavity 7. And 739=744*a*=746*a*; 740=745*a*=747*a* for memory cavity 7 and register cavity 1.

FIG. 39 also shows a memory gate 748 that is placed inside each memory cavity (see FIG. 41 to FIG. 48). The memory gate 748 is composed of a body in the shape of a parallelogram with gate rounded edges and three memory gate sections 750 with same cross section as the OR gate, the AND gate, the SEL gate, the XOR gate, and the SW gate. Each section has four faces that may or may not have a hole creating a pattern of connections. In the first section a memory gate through hole down 751*a* and a memory gate down hole 752*a* connect the front, the back and the down faces. In the second section a memory gate through hole up 753 and a memory gate up hole 754 connect the front, the back and the top faces. The third section repeats the same arrangement of connections of the first section (to avoid cluttering only memory gate through hole down 751*b* is indicated in the third section). A memory gate rubber grid 749 envelops all holes and the main body of the memory gate 748 isolating each hole and each face so that fluid passing through a hole does not leak into other holes.

The memory gate 748 is so constructed that signals going into the front face pass directly to the back face and vice versa. Additionally, a signal that goes into the first or third memory gate sections will be branched down and a signal that goes into the second memory gate section will be branched up.

FIG. 40 shows the LFSR cavities and remaining LFSR connections from a different angle that facilitates the visualization of these particular LFSR connections. Other connections have been omitted to avoid cluttering. A memory feed high 757*a* at the top of the first register cavity 710*a* is connected to a memory input high 755*a* at one extremity of the first memory cavity 711*a* (755*a*=757*a*) and a memory feed low 758*a* at the bottom of the first register cavity 710*a* is connected to a memory input low 756*a* at the other extremity of the first memory cavity 711*a* (756*a*=758*a*). A memory feed high 757*b* at the top of the second register cavity 710*b* is connected to a memory input high 755*b* at one extremity of the second memory cavity 711*b* (755*b*=757*b*) and a memory feed low 758*b* at the bottom of the second register cavity 710*b* is connected to a memory input low 756*b* at the other extremity of the second memory cavity 711*b* (756*b*=758*b*). The same pattern follows until a memory feed high 757*g* at the top of the seventh register cavity 710*g* is connected to a memory input high 755*g* at one extremity of the seventh memory cavity 711*g* (755*g*=757*g*) and a memory feed low 758*g* at the bottom of the seventh register cavity 710*g* is connected to a memory input low 756*g* at the other extremity of the seventh memory cavity 711*a* (756*g*=758*g*).

The connections described in the previous paragraph produce an arrangement in that the signals coming from register cavity n are routed into the extremities of memory cavity n for n=1 to 7 counted from left to right. This arrangement enables the components inside memory cavity n to be made to move according to the position of the components inside register cavity n.

755*a*=757*a*; 756*a*=758*a* for register cavity 1 and memory cavity 1 and so on until 755*g*=757*g*; 756*g*=758*g* for register cavity 7 and memory cavity 7.

FIG. 40 also shows a register gate low 759 that is composed of a body in the shape of a parallelogram with gate rounded edges and five register gate low sections 761 with same cross section as the memory gate. Each section has four faces that may or may not have a hole creating a pattern of connections. The first three sections of the register gate low 759 are identical to the first three sections of the memory gate. In the first section a memory gate through hole down 751*a* and a memory gate down hole 752*a* connect the front, the back and the down faces. In the second section a memory gate through hole up 753*a* and a memory gate up hole 754*a* connect the front, the back and the top faces. The third section repeats the same arrangement of connections of the first section (to avoid cluttering only memory gate through hole down 751*b* is indicated in the third section). In the fourth section a register gate top hole 763*a* connects the top face to the front face and in the fifth section a register gate through hole 762*a* connects the front face to the back face. A register gate low rubber grid 760 envelops all holes and the main body of the register gate low 759 isolating each hole and each face so that fluid passing through a hole does not leak into other holes.

The register gate low 759 is so constructed that signals going into the front face pass directly to the back face and vice versa with the exception of the fourth register gate low section where a signal going into the back face will be isolated and a signal going into the top face will be routed into the front face. Additionally, a signal that goes into the first or third register gate low sections will be branched down and a signal that goes into the second register gate low section will be branched up.

A register gate high 764 is composed of a body in the shape of a parallelogram with gate rounded edges and five register gate high sections 766 with same cross section as the memory gate. Each section has four faces that may or may not have a hole creating a pattern of connections. The first three sections of the register gate high 764 are identical to the first three sections of the memory gate. In the first section a memory gate through hole down 751*c* and a memory gate down hole 752*c* connect the front, the back and the down faces. In the second section a memory gate through hole up 753*b* and a memory gate up hole 754*b* connect the front, the back and the top faces. The third section repeats the same arrangement of connections of the first section (to avoid cluttering only memory gate through hole down 751*d* is indicated in the third section). In the fourth section a register gate through hole 762*b* connects the front face to the back face and in the fifth section a register gate top hole 763*b* connects the top face to the front face. A register gate high rubber grid 765 envelops all holes and the main body of the register gate high 764 isolating each hole and each face so that fluid passing through a hole does not leak into other holes.

The register gate high 764 is so constructed that signals going into the front face pass directly to the back face and vice versa with the exception of the fifth register gate high section where a signal going into the back face will be isolated and a signal going into the top face will be routed into the front face. Additionally, a signal that goes into the first or third register gate high sections will be branched down and a signal that goes into the second register gate high section will be branched up.

A unique combination of zero to six register gate low 759 and one to seven register gate high 764 adding up to seven components in total is installed in the seven register cavity (see FIG. 41 to FIG. 48).

Components have not been drawn inside their respective cavities in FIG. 38, FIG. 39 and FIG. 40 to avoid clutter and by doing so facilitate the comprehension of the LFSR connections interconnecting the LFSR cavities.

In FIG. 41 to FIG. 48 the LFSR connections are omitted and only the components are drawn with the LFSR layer a 698 as reference to ascertain the position of each component inside its cavity (the portion of its cavity that is cut into the LFSR layer a 698), with respect to each other and to the LFSR connections so that the construction and operation of the LFSR assembly can be explained.

The 7 bit combination produced by considering a 0 for each register gate low and a 1 for each register gate high installed in each register cavity according to the position from left to right each one that is installed is called an address. A combination of two register gate low 759*a* and 759*b* and five register gate high 764*c*, . . . , 764*g*, producing the address 0011111 is illustrated in FIG. 41 to FIG. 48. Any address apart from 0000000 is valid. Address 0011111 has been chosen to explain the operation of the LFSR assembly for convenience. Seven identical memory gates 748*a*, 748*b*, . . . , 748*g* are installed, one component in each memory cavity. The memory gates and register gates are in an active or high position (1) when they are at the top of their respective cavities (as seen on FIG. 42) and in a rest or low position (0) when they are at the bottom of their respective cavities. The seven register gates taken from left to right produce a 7-digit register position and the seven memory gates taken from left to right produce a 7-digit memory position. A register gate low is said to be properly aligned when it is in the low position (0) and a register gate high is said to be properly aligned when it is in the high position (1) so that when all seven register gates of the installed 7-bit address are properly aligned, the (7-digit) register position matches the (7-digit) address.

In FIG. 41 to FIG. 48 the AND gate 583*a* has been installed in the normally open position, so that the output register signal mz 723*a* will be high ($723a=1$) when the (m) master/slave in msb 721 is low ($721=0$) or the flipped AND gate 583*a* is in its rest position ($\sim 583a \leftrightarrow 0$) producing $723a = \neg m / \wedge z$ as intended to a slave reactor node. For a master reactor node, the AND gate 583*a* must be installed in the normally closed position, so that the output register signal mz 723*a* will be high ($723a=1$) when the (m) master/slave in msb 721 is high ($721=1$) or the AND gate 583*a* is in its active position ($583a \leftrightarrow 1$) producing $723a = m / \wedge z$. Using the compact notation m/s=1 if the signal (m) master/slave in msb matches the configuration of the reactor node (m=1 if the reactor node is configured as master or m=0 if the reactor node is configured as slave) and m/s=0 otherwise, for any reactor node $723a = m/s / \wedge z$.

FIG. 41 to FIG. 48 are further referred to in the operation section to explain the operation of the LFSR assembly.

FIG. 49 shows the module case 370 in phantom lines seen from a back above left angle to illustrate the node core pipes routing into the module assembly through the module case. The CO2 body 367, the four CO2 body channels 368A, 368B, 368C, and 368D and the corresponding four CO2 valves 150A, 150B, 150C, and 150D are shown as reference to better visualize the pipes corning from pipe ports A, B, C, and D.

To keep the consistency with FIG. 10, FIG. 11, FIG. 12, FIG. 13, and FIG. 14 the CO2 valves 150A and 150D are drawn in the closed position interrupting the corresponding CO2 body channels 368A and 368D and the CO2 valves 150B and 150C are drawn in the open position allowing CO2 flow in the corresponding CO2 body channels 368B and 368C.

The pipe ports A, B, C, and D control pipes: open door pipe 193, open CO2 valve pipe 194, close door pipe (drawn but not indicated to avoid cluttering, see FIG. 13, and FIG. 14), close CO2 valve pipe 196, water sensor pipe 197, water feed pipe 198, CO2 sensor pipe 199, and CO2 feed pipe 200 terminate at the node core main control port 189. An uppercase letter (A, B, C, or D) is added to each pipe numeral to indicate the pipe port it pertains.

The control pipes: CO2 sensor main pipe 204, dive control close pipe 206, dive control open pipe 207, pump feed pipe 208 terminate at the node core aux control port left 191 and the control pipes: flag pipe 201, air release open pipe 202, air release close pipe 203, CO2 feed main pipe 205 terminate at the node core aux control port right 192. The pump exhaust pipe 209 discharges the water supplied to the water pump through the pump feed pipe 208 into the water body and does not route into the module assembly. It is drawn for reference.

The CO2 sensor main pipe 204, senses the CO2 pressure inside the CO2 body 367 and the CO2 feed main pipe 205 controls the CO2 pressure inside the CO2 body 367 by means of injecting additional quantities of CO2 if the CO2 pressure falls below the control target. The CO2 sensor main pipe 204 and the CO2 feed main pipe 205 work for the CO2 body 367 in the same way as the CO2 sensor pipe 199, and CO2 feed pipe 200 work for the CO2 body channels in the pipe ports. During normal operation the CO2 sensor main pipe 204 and the CO2 feed main pipe 205 work together with the CO2 sensor pipe 199, and CO2 feed pipe 200 to regulate the CO2 pressure of the open pipe ports. In the event that all CO2 valves 150A, 150B, 150C, and 150D close the CO2 pressure inside the CO2 body 367 remains under control by the CO2 sensor main pipe 204 and the CO2 feed main pipe 205.

The remaining signals arrive through the module external opening 375 that conveys the (x) external pressure and the module ground pipe connector 378 that connects the module assembly to the water body conveys ground signals and allows the module assembly to monitor and control ground pressure in the water body.

FIG. 50 shows the expansion unit assembly 388 and the module case 370 fitted together seen from the same angle as in FIG. 49. The module case 370 is shown in phantom lines to improve the visualization of details. The expansion case 389 is secured to the module case 370 by attaching R-clips to each of the fasteners 254 in the module case 370 securing the expansion case rim 390 to the module rim 371. The remaining fastener holes 253 that do not align with fasteners 254 in the module rim 371 align with another set of fasteners in the node core allowing the module assembly to be secured to the node core.

The expansion layer 400, seen in its installed position, is inserted through the expansion case back opening 392 and when necessary removed by inserting a long rod or another suitable tool into the expansion case front opening 391 to push it out. The diagnose port 161, the signal port left 163, and the signal port right 164 that provide connections to external signals are located on the top of the in expansion case 389. As these signals are not yet used in the expansion unit assembly they go straight through the module case 370 and the expansion layer 400 to be available to other units in the module assembly. The expansion feed pipes 212 that come from the i/o unit assembly go through the module case 370 and terminate at expansion layer 400 where they are available for future use.

Also seen on FIG. 50 is the expansion case handle 393 that is used to grip and manipulate the module case 370 and the expansion case flag cutout 399 that accommodates the flag when it is in its lowered position.

FIG. 51 shows the i/o unit assembly 403 fitted inside the module case 370 seen from the same angle as in FIG. 49 and FIG. 50. The module case 370 is shown in phantom lines to improve the visualization of details. The fasteners 254 in the module rim 371 are used to secure the expansion unit assembly to the module case 370 and the fastener holes 253 in the module rim 371 are aligned with fasteners in the node core that are used to secure the module assembly to the node core.

The signals coming through the diagnose port 161, the signal port left 163, and the signal port right 164 are routed into the i/o unit assembly 403 as well as the (x) external pressure 213a that provides an external water pressure reference to the i/o unit assembly 403. The (x) external pressure 213b continues into the expansion unit assembly in the middle position of the expansion feed pipes 212 as provision for possible future use.

The module case 370 ensures that the i/o layer a 419, i/o layer b 420, and i/o layer c 421 remain in their installed position inside the i/o case 404. A pair of extractors 430a and 430b is used to help install and remove the i/o unit assembly 403 in the module case 370. The extractor 430a is first inserted into the i/o case extractor hole 408 and then turned 90 degrees 430b to lock it in.

FIG. 52 shows the i/o case 404 and the module case 370 drawn in phantom lines to illustrate the position of a set of i/o control pipes 424 that route the signals arriving trough the node core main control port, node core aux control port left 191, and node core aux control port right 192 to their termination points inside the i/o unit assembly (see FIG. 49).

FIG. 53 shows the i/o case 404 drawn in phantom lines to illustrate the position of a set of i/o components cavities 425 that contain the i/o components of the i/o unit assembly.

FIG. 54 shows the i/o case 404 drawn in phantom lines to illustrate the position of an i/o pipework 426 that route the signals necessary to operate the components inside the i/o components cavities 425 in the i/o unit assembly to their proper termination points.

FIG. 55 shows the i/o components cavities 425 as reference to illustrate the position of an i/o ground plane 427 that supplies ground connection to all i/o components inside the i/o components cavities 425 in the i/o unit assembly allowing them to operate. The i/o ground plane 427 is connected to the (gnd) ground 180 pipe to make available a ground reference to maintenance crews working on the reactor node (see FIG. 76).

FIG. 56 shows the i/o components cavities 425 as reference to illustrate the position of an i/o high pressure plane 428 that supplies high pressure water to all i/o components inside the i/o components cavities 425 in the i/o unit assembly allowing them to operate. The i/o high pressure plane 428 is supplied with high pressure water by the input pipes: (w) water resupply right 166, (v) dive in 170, (r) reset in 172, (h) help in 174, (k) clock in 179, (z) zero in 181, (m) master/slave in 183, (q) query in 185, and (s) status in 187 through a set of check valves 339a, . . . , 339e, . . . , 339i. Each input pipe is connected to the i/o high pressure plane 428 through a separate check valve (see FIG. 60). As the reactor node consumes power in form of high pressure water to operate, the pressure inside the i/o high pressure plane 428 drops until the pressure in one or more input pipes is higher than the pressure in the i/o high pressure plane 428. The affected check valves open supplying additional water to the i/o high pressure plane 428 increasing its pressure until an equilibrium is reached and the flow stops. The check valves prevent water to flow in the opposite direction from the i/o high pressure plane 428 into an input pipe that momentarily is carrying a low signal (low pressure water).

FIG. 57 shows the i/o case 404 drawn in phantom lines as reference to illustrate the position of an i/o layer cutout 429 that is the sum of all cuts that must be made into a plain slab of material to produce the i/o layer a 419.

FIG. 58 is a back above left view of the i/o case 404 inside the module case 370 drawn in phantom lines as reference to show the i/o layer a 419 in its installed position, allowing a view of the cuts made into its top face as the result of the process described in FIG. 57.

FIG. 59 is a back below left view of the i/o case 404 inside the module case 370 drawn in phantom lines as reference to show the i/o layer a 419 in its installed position, allowing a view of the cuts made into its bottom face as the result of the process described in FIG. 57.

FIG. 60 is a back above left view of the i/o case 404 drawn in phantom lines as reference to show the i/o layer b 420 in its installed position, allowing a view of the cuts made into its top face as the result of a similar process as described in FIG. 57 using i/o layer b 420 instead of i/o layer a. The indentation that creates the i/o ground plane 427 is the biggest feature of the i/o layer b 420. The check valves 339a, 339b, 339c, 339d, 339e, 339f, 339g, 339h, and 339i, that connect each input pipe to the i/o high pressure plane (see FIG. 56) are seen on their installed positions.

FIG. 61 is a back above left view of the i/o case 404 drawn in phantom lines as reference to show the i/o layer c 421 in its installed position, allowing a view of the cuts made into its top face as the result of a similar process as described in FIG. 57 using i/o layer c 421 instead of i/o layer a. The indentation that creates the i/o high pressure plane 428 is the biggest feature of the i/o layer c 421. Another feature of the i/o layer c 421 is a pair of extractor nut bases 431a and 431b where the extractors 430a and 430b fit and turn. The extractor 430*a* is drawn in the inserted position and extractor 430*b* is drawn in the inserted and turned position (locked).

FIG. 62 and FIG. 63 show the i/o components from different points of view for better visualization and understanding. FIG. 62 is an isometric view of the i/o components of the i/o unit assembly with the i/o components cavities 425 drawn in phantom lines for reference. FIG. 63 is a top view of the i/o components of the i/o unit assembly also showing the i/o layer a 419 that serves as reference. FIG. 62 and FIG. 63 are further referred to in the operation section to explain the digitization of the input signals and generation of the output signals used in the reactor node.

FIG. 64 shows the i/o case 404 in phantom lines to allow a better view of a set of logic signal connections 767 that run between the logic unit assembly 432 and the i/o unit assembly. Some of the signals in the logic signal connections 767 convey the digitized input signals produced inside the i/o unit assembly by the controllers to the logic unit assembly 432 where these signals are used to implement the control logic necessary to operate the reactor node. Another set of signals in the logic signal connections 767 conveys logic signals generated inside the logic unit assembly to the actuators in the i/o unit assembly to control the actuators and produce digital output signals. A (j) maintenance job 768 that is one of the signals of the logic signal connections 767 controls two diagnose gates 609*a* and 609*b* that are fitted with logic springs 686*a* and 686*b*. If the (j) maintenance job 768 is low (j=0) the logic springs 686*a* and 686*b* push the diagnose gates 609*a* and 609*b* towards each other and the reactor node operates in normal mode. If the (j) maintenance job 768 is high (j=1) it pushes the diagnose gates 609*a* and 609*b* apart from each other and the reactor node operates in controlled mode. A router plate direct 451 that as other router plates is installed right beneath the two diagnose gates 609*a* and 609*b* is visible drawn in dashed lines inside the i/o case 404.

FIG. 65 shows the i/o case 404 in phantom lines to allow a better view of a set of diagnose connections 769 that connect the logic unit assembly 432 passing through the i/o unit assembly and the expansion unit assembly to the top of the module assembly where they are available to connect the diagnose device. A router plate direct 451 drawn in dashed lines can be seen in its installed position inside the i/o case 404. Inside the i/o unit assembly two diagnose gates control if the reactor node operates in normal mode or in controlled mode (see FIG. 65A and FIG. 76).

Detail FIG. 65A shows the top of the logic unit assembly where a logic case left control connector 440 made of 10 connector small inserts identical to connector small inserts 384*a* and 384*b* is located. To improve the clarity of FIG. 65A and facilitate the explanation, the pipes that pass through the connector small inserts 384*a* and 384*b* of the logic case left control connector 440 that can be seen on FIG. 65 have not been drawn in detail FIG. 65A.

A diagnose interface pipe 770 is a pipe of the diagnose connections that begins on the top of the diagnose gate, passes through the i/o unit assembly and the expansion unit assembly and terminates at the top of the module assembly in the diagnose port. A diagnose control pipe 771 is a pipe of the diagnose connections that begins on the front of the diagnose gate and terminates inside the i/o unit assembly. A diagnose logic pipe 772 is a pipe of the diagnose connections that begins on the bottom of the diagnose gate passes through the i/o unit assembly and terminates inside the logic unit assembly. A router pipe 773 is a pipe that goes through the router plate direct 451 or any other router plate installed instead of the router plate direct 451. All diagnose logic pipes 772 are connected to the top of the corresponding router pipes 773. These connections are however not drawn in FIG. 65A to avoid cluttering and better show the router plate direct 451 and router pipes 773. Detail FIG. 65A is further referred to in the operation section of this document.

FIG. 66 shows the logic unit assembly 432 in its installed position inside the module case 370. Two extractors 430*a* and 430*b* are used to help install and remove the logic unit assembly 432. The extractor 430*a* is first inserted into the logic case extractor hole 436 and then turned 90 degrees 430*b* to lock it in. The module case 370 ensures that the logic layer a 444, the logic layer b 445, the logic layer c 446, and the logic layer d 447 remain in their installed position inside the logic case.

Part of the node core main control port 189, part of the node core aux control port left 191 and the node core aux control port right 192 that together route all signal and control pipes of the node core into the module assembly can be seen on the bottom of the module case 370.

FIG. 67 shows the router plate direct 451 installed in the router plate insertion bay 448 on top of the logic layer c 446. Eight different types of router plates are available but only one can be inserted at a time. To prevent the chosen router plate to be incorrectly placed, two asymmetrically placed router plate insertion keys 449*a* and 449*b* are located at the sides of the router plate insertion bay 448 allowing the selected router plate to fit only in the proper orientation.

The signals that arrive at the router plate are: (i) internal water pressure msb 775A, 775B, 775C; 775D; (i) internal water pressure lsb 776A, 776B, 776C, 776D; (n) internal $CO_2$ pressure lsb 777A, 777B, 777C, 777D, 777*e*; (O) open door control 778A, 778B, 778C, 778D; (T) vent air control 779; (F) raise flag control 780; (P) stop water pump control 781; (IV) dive control 782.

The signals closest to the edges of a router plate: (n) internal $CO_2$ pressure lsb 777*e*, (T) vent air control 779, (F) raise flag control 780, (P) stop water pump control 781, and (IV) dive control 782 are not rerouted and are always forward in the same position they came in. The 16 signals in the center of a router plate marked with a capital letter: A, B, C, or D depending on the pipe port they belong may or may not be rerouted according to the routing plan of each router plate.

The 16 pipe port signals are arranged in a symmetric way with respect to the center line of the router plate: to the left of the center line the first 4 signals belong to pipe port B and the next 4 signals belong to pipe port A making the total of 8 pipe port signals to the left of the center line. To the right of the center line the first 4 signals belong to pipe port C and the next 4 signals belong to pipe port D making the total of 8 pipe port signals to the right of the center line. A pipe port A signal (such as 775A) is placed in a symmetric position to its counterpart in pipe port D (775D) and a pipe port B signal (such as 775B) is placed in a symmetric position to its counterpart in pipe port C (775C). Additionally the pipe port signals at each side: pipe port A and B signals on the left side and pipe port C and D signals on the right side are arranged in a symmetric way with respect to an imaginary line that separates one pipe port from the other at each side. This double symmetry arrangement puts the pipe port signals in the following sequence as seen in FIG. 67: 775A 776A 777A 778A][778B 777B 776B 775B][775C 776C 777C 778C][778D 777D 776D 775D. The symbol][separates the pipe ports and also indicates a symmetry line: a signal located at a certain position to the left of a symbol][will have the same number as a signal located at the same distance to the right of the chosen symbol. This arrangement makes it easier to reroute pipe port A, B, C, and D signals simplifying the construction of the router plates (see FIG. 68).

The router plate direct 451 does not re-route pipe port signals and simply forwards all signals in the same position they came in. The router plate direct 451 is one of the 8 available router plates. Also seen in FIG. 67 is a set of i/o layer c cuts 774 that are created in the logic layer c 446 as the result of the process described in FIG. 57 applied to the logic unit assembly instead of the i/o unit assembly.

FIG. 68 shows the remaining 7 of the 8 types of router plates: 2) router plate AB 452 that exchanges pipe port A signals with pipe port B signals and forwards pipe port C and pipe port D signals; 3) router plate CD 453 that forwards pipe port A and pipe port B signals and exchanges pipe port C signals with pipe port D signals; 4) router plate ABCD 454 that exchanges pipe port A signals with pipe port B signals and pipe port C signals with pipe port D signals; 5) router plate ADBC 455 that exchanges pipe port A signals with pipe port D signals and pipe port B signals with pipe port C signals; 6) router plate DBCA 456 that reroutes pipe port A signals into pipe port D, pipe port D signals into pipe port B, pipe port B signals into pipe port C and pipe port C signals into pipe port A; 7) router plate CBDA 457 that reroutes pipe port A signals into pipe port C, pipe port C signals into pipe port B, pipe port B signals into pipe port D and pipe port D signals into pipe port A; 8) router plate ACBD 458 that exchanges pipe port A signals with pipe port C signals and exchanges pipe port B signals with pipe port D signals. The rerouting introduced by the router plates are listed in the table of FIG. 78. The configuration numbers in FIG. 78 are the same as used in the above description to facilitate the identification, with configuration 1 being the router plate direct that does not reroute the signals.

As seen on FIG. 67, the signals closest to the edges of all router plates (indicated in FIG. 68 only in router plate ACBD 458 to avoid cluttering): (n) internal CO2 pressure lsb 777e, (T) vent air control 779, (F) raise flag control 780, (P) stop water pump control 781, and (IV) dive control 782 are not rerouted and are always forward in the same position they came in.

The 16 signals in the center of a router plate belong to pipe ports and are rerouted or not according to the routing plan of each router plate. All router plates have pipe port signals that originate in the same place at the top and terminate at different places at the bottom according to their routing plan. For convenience, pipe port A and B signals are indicated in router plate CD 453 and pipe port C and D signals are indicated in router plate AB 452. The same positions in other router plates have the same signals. The (i) internal water pressure msb 775A, 775B, 775C; 775D; (i) internal water pressure lsb 776A, 776B, 776C, 776D; (n) internal CO2 pressure lsb 777A, 777B, 777C, 777D; (O) open door control 778A, 778B, 778C, 778D are indicated for reference to illustrate their double symmetry arrangement.

FIG. 69 is an isometric view of the logic layer a 444 and the installed logic components. The logic layer a serves as reference to ascertain the relative positions of the logic components in their respective cavities. To facilitate the understanding, the logic components are divided into blocks that perform a certain function.

A LFSR logic block 783 described in FIG. 37 to FIG. 48 and its operation explained in FIG. 41 to FIG. 48 allows each reactor node to have its own address and respond to a periodic poll when it is selected. A signal answer logic block 784 processes input signals and produces adequate output signals to communicate with adjacent reactor nodes and respond to the periodic poll using local signals when the reactor node address is selected and retransmitting received signals when it is not selected. A signal leak alarm logic block 785 produces an alarm if a leak or another problem is detected in any part of the reactor node. As described in FIG. 34, FIG. 35 and FIG. 36 the (x) external pressure signal is supplied through the depth external water pressure pipe 679 pushing the depth detector 689 against the depth sensor 688 producing the external pressure msb and the (x) external pressure lsb signals that encodes the current depth of the reactor node. A depth management logic block 786 uses the 2 bit depth code (x msb, x lsb) to produce adequate output signals to control the subsystems affected by the current depth of the reactor node.

A pipe port management logic block 787 processes the input signals from each pipe port and produces output signals to open or close each pipe port circumventing eventual faults and rerouting the water culture in the wet reactor according to the assigned priorities defined by the installed router plate (see FIG. 67 and FIG. 68). Additionally, the pipe port management logic block 787 produces the output signals to control the water pump enabling it if the reactor node is operational and two pipe ports are open despite eventual faults and disabling the water pump if a valid combination of two pipe ports cannot be open due to faults.

FIG. 69 also shows a ground feed 789 that is a continuation of the ground pressure supply output that injects regulated high pressure water produced at the ground pressure controller device into the water body to regulate the ground water pressure as explained in the ground pressure controller device portion of the description in FIG. 29, FIG. 30, and FIG. 31, and explanation of operation in FIG. 32. A series of ground pipes 790a, 790b, and 790c provides separate connections to the water body to supply water at ground pressure (reference pressure) to various components in the reactor node and produce the (g) ground lsb signal in the ground pressure controller device. A high pressure water source 791 fed by two high pressure water pipes that come from the i/o unit assembly provides high pressure water to supply power to the logic components.

FIG. 70 is a top view of the logic layer a 444 and the installed logic components. Connections outside the logic layer a 444 that do not introduce excessive clutter have been drawn in dashed lines to facilitate the visualization of the circuits. Connections that would make the identification or visualization of the components more difficult have not been drawn and are explained by other means in the text.

The depth detector 689 moving against the depth sensor 688 generates the (x) external pressure lsb 684 and the (x) external pressure msb 685 producing a 2 bit digital signal that encodes the current depth of the reactor node. The (x) external pressure lsb 684 is connected to the main input on the left and the (x) external pressure msb 685 is connected to the aux input on the right of the AND gate 583l that is not fitted with a logic spring. This arrangement causes the AND gate 583l to move to the left (as drawn) if the (x) external pressure lsb 684 is low and the (x) external pressure msb 685 is high and to the right if the (x) external pressure lsb 684 is high and the (x) external pressure msb 685 is low. If both the (x) external pressure lsb 684 and the (x) external pressure msb 685 are either low or high, the AND gate 583l remains stationary on its current position. A high pressure supply 792b provides high pressure water into the other logic input of the AND gate 583l and low pressure water is fed by the clear input at the top (not indicated in FIG. 70; see FIG. 34, FIG. 35 and FIG. 36). The output of the AND gate 583l is a (OV) depth overshoot 804 signal that assumes a high value if the reactor node goes to a depth greater than the maximum depth envisaged encoded into the depth detector 689.

In the case of the AND gate 583*l* the left side is defined as the rest position (0), resulting in the following notation: 583*l*↔0⇒804=0 and 583*l*↔1⇒804=1.

The high pressure supply 792*a* provides high pressure water into the side input of the AND gate 583*a*. The output of the AND gate 583*a* is then forwarded into the side input of the AND gate 583*b* and to subsequent AND gates, passing through the AND gate 583*c*, the AND gate 583*d*, the AND gate 583*e*, AND gate 583*f*, AND gate 583*g*, and the AND gate 583*h* forming an AND chain (alarm chain). The main input of the AND gate 583*a* is connected to the (j) maintenance job 768 and the aux input is connected to the (OV) depth overshoot 804 (output of the AND gate 583*l*).

If the reactor node goes too deep so that the (OV) depth overshoot 804 is high (1), the AND gate 583*a* moves to the rest position and, as no logic spring is installed, stays there even after the dive overshoot situation is cleared until the (j) maintenance job 768 signal is high (1). This requires the intervention of a maintenance crew that will then inspect the reactor node for problems since it is not supposed to get to a depth that will cause a dive overshoot situation under normal circumstances (see FIG. 76).

Using the symbol ↑ as "set to 1" and the symbol ↓ as "reset to 0" (as in a set reset register) by the condition provided to the right of the symbol, the (OV) depth overshoot can be defined as: OV↑¬msb∧x lsb; OV↓j.

With the exception of AND gate 583*c* that is fed with the (g) ground lsb 805 coming from the ground pressure controller device the remaining AND gates located at the beginning of the alarm chain, between AND gate 583*b* and AND gate 583*d* are fed with the digitized lsb input signals produced by their respective signal pressure controller devices coming from the i/o unit assembly into their respective main inputs. From left to right the signals supplied into the main inputs of AND gate 583*b* to AND gate 583*d* are: (s) status in lsb, (q) query in lsb, (m) master/slave in lsb, (z) zero in lsb, (k) clock in lsb, (g) ground lsb 805, (w) water resupply lsb, (u) air resupply lsb, (v) dive in lsb, (r) reset in lsb 801, (h) help in lsb.

The four AND gates located at the end of the alarm chain (from right to left): AND gate 583*h*, AND gate 583*g*, AND gate 583*f*, and AND gate 583*e* are used to detect problems in the pipe ports A, B, C, and D respectively (see description in FIG. 71).

The (AL) alarm 798 signal is fed into the main input and a (h) help in msb 795*a* is fed into the side input of the AND gate 583*j* producing a (H) help control 803 output with the logic function 803=798∧795*a* or replacing the numbers for the signal names: H=AL∧h msb. This is used to produce a daisy chain of the alarm status of the reactor nodes up to the current one.

A (s) status in msb 794 digitized from the (s) status in received from the previous reactor node is fed into the first input and the (h) help in msb 795*b* digitized from the (h) help in received from the previous reactor node is fed on the second input of the SEL gate 589*a*. The first and second clear inputs of the SEL gate 589*a* are not connected allowing the first and second outputs to be joined producing a single output (S) status control 796.

A (q) query in msb 797 digitized from the (q) query in received from the previous reactor node is fed into the first input and the (AL) alarm 798 is fed into the second input of the SEL gate 589*b*. The first and second clear inputs of the SEL gate 589*b* are not connected allowing the first and second outputs to be joined producing a single output (Q) query control 799.

The (y) unit ready 730 is fed into the main input and the register signal ¬kzm 724 is fed into the side input of the AND gate 583*i* producing as output a (TX) transmit signal 793. The (TX) transmit signal 793 is fed into the main inputs of the SEL gate 589*a* and the SEL gate 589*b*.

Using the compact notation m/s=1 if the signal (m) master/slave in msb matches the configuration of the reactor node (m=1 if the reactor node is configured as master or m=0 if the reactor node is configured as slave) and m/s=0 otherwise, the logic function produced is: 793=730∧724 or replacing the numbers for the signal names: TX=y∧¬k msb∧z msb∧m/s.

The (TX) transmit signal 793 is high (793=1) if the following conditions are simultaneously satisfied: a) m/s=1 (the unit type is correct); b) (z) zero in msb=1 (counting is enabled); c) (y) unit ready=1 (the reactor node address is selected); d) (k) clock in msb=0 (low clock cycle).

If 793=0, the SEL gate 589*a* and the SEL gate 589*b* produce as output the chain signals coming from the previous reactor node fed into their first inputs forwarding the messages received. If 793=1, the SEL gate 589*a* and the SEL gate 589*b* produce as output the local information fed into the second inputs. The implemented logic functions are: 796=(¬793∧794)∨(793∧795*b*); 799=(¬793∧797)∨(793∧798) or replacing the numbers for the signal names: S=(¬TX∧s msb)∨(TX∧h msb); Q=(¬TX∧q msb)∨(TX∧AL).

The reset signal is active low so it has to be tested for leaks to avoid false commands. A (r) reset in msb 800 is fed into the main input and a (r) reset in lsb 801 is fed into the side input of the AND gate 583*k* producing a (R) reset control 802 output. The AND gate 583*k* is installed flipped producing: 802=¬800∧801 or replacing the numbers for the signal names: R=¬r msb∧r lsb.

In case of a leak (r lsb=0) then R=0. If no leak is present (r lsb=1) and the reset signal is not active (r msb=1), then ¬r msb=0 and R=0. If no leak is present (r lsb=1) and the reset signal is active (r msb=0), then ¬r msb=0 and R=1. The (R) reset control is sent to the i/o unit assembly to control the actuator mono normally closed that enables the reset signals inside the reactor node. To regenerate the reset signal to the following reactor node an additional NOT function is required. This is achieved by flipping the actuator mono that produces the (R) reset out that is transmitted producing R out=¬R=¬(¬r msb∧r lsb) (see FIG. 62 and FIG. 63).

The high pressure supply 792*c* is fed into the first input and the (x) external pressure lsb 684 is channeled into the second input of the SEL gate 589*c* that is installed flipped to introduce a NOT function at the main input that is fed with the (x) external pressure msb 685. A (v) dive in msb 806*a* signal, that is high in case the reactor node is commanded to dive, is supplied into the main input of the SEL gate 589*d*. The first and second outputs of the SEL gate 589*c* are forwarded into the first and second inputs of the SEL gate 589*d* respectively producing a (pl) dive complete 807 in the first output and a (FE) flag enable control 808 in the second output of the SEL gate 589*d*. The logic functions produced are: 807=806*a*∧¬685; 808=¬806*a*∧684∧685 or replacing the numbers for the signal names: pl=v msb∧¬x msb; FE=¬v msb∧x lsb∧x msb.

The (FE) flag enable control 808 is fed into the side input of the AND gate 583*o* that is installed flipped introducing a NOT function at its main input that is fed with the (AL) alarm 798. The resulting (F) raise flag control 780 has the logic function 780=¬798∧808 or replacing the numbers for the signal names: F=¬AL∧FE. The (F) raise flag control 780 is low (the flag remains stowed) if the (AL) alarm 798 is high (¬798=0) when there is no current active alarm or the (FE) flag enable control 808 is low (808=0) when the flag cannot be safely raised.

The (FE) flag enable control 808 is fed into the main input of the OR gate 579, the (pl) dive complete 807 is fed into the underside input of the OR gate 579 and the high pressure supply 792d is supplied into the side input of the AND gate 583m producing an output (E) dive disable control 809 that disables the movement of the cable winch with the following logic function: 809=(808∨807)∧792d=(808∨807)∧(¬806a∧684∧685)∨(806a∧¬685). Replacing the numbers for the signal names: E=FE∨pl=(¬v msb∧x lsb∧x msb)∨(v msb∧¬x msb).

A different suffix letter is used to differentiate between different relevant points of the same (v) dive in msb 806a, 806b signal that originates in the signal pressure controller device that digitizes the (v) dive in signal in the i/o unit assembly and continues into the logic unit assembly.

The (x) external pressure msb 685 is fed in the main input and the (v) dive in msb 806b is fed into the side input of the AND gate 583n producing as outputs the (IV) dive control 782 and the (T) vent air control 779. The logic function is: 782=779=685∧806b or replacing the numbers for the signal names: IV=T=x msb∧v msb.

A routed pipe block 788 shows the arrival points of the signals coming from the router plate installed in the router plate insertion bay. For simplicity the descriptions in FIG. 70 and FIG. 71 are made assuming a router plate direct is installed that does not reroute the signals. The description in the case of a different router plate installed would be the same apart from changing the capital letters A, B, C, and D from any indication containing these capital letters according to the rerouting plan of the selected router plate (see FIG. 67 and FIG. 68).

FIG. 71 is a top view of the lower portion of the logic layer a 444 and the installed logic components with the connections outside the logic layer a 444 drawn in dashed lines to facilitate the visualization of the circuits of the signal leak alarm logic block and the pipe port management logic block (see FIG. 69). Other components, their connections and other features in the logic layer a 444 that are not necessary for the explanation have been omitted to avoid clutter and make space for the indication numerals. All components and connections drawn in FIG. 71 are also drawn in FIG. 70 that can be used as reference if necessary.

The (n) internal CO2 pressure lsb 777A is fed into the main input and the high pressure supply 792b provides high pressure water into the side input of the AND gate 583k. The (i) internal water pressure lsb 776A is fed into the main input and the output of the AND gate 583k is forwarded into the side input of the AND gate 583j. The output of the AND gate 583j is tapped out as a ppA alarm 811a and forwarded into the side input of the AND gate 583i that is also fed with the (i) internal water pressure msb 775A into the main input producing the output (pp) pipe port status 810Aa. The implemented functions are: 811a=777A∧776A; 810Aa=777A∧776A∧775A or using the signal names: ppA alarm=nA lsb∧iA lsb; ppA=nA lsb∧iA lsb∧iA msb.

The (n) internal CO2 pressure lsb 777B is fed into the main input and the high pressure supply 792b provides high pressure water into the side input of the AND gate 583l. The (i) internal water pressure lsb 776B is fed into the main input and the output of the AND gate 583l is forwarded into the side input of the AND gate 583m. The output of the AND gate 583m is tapped out as a ppB alarm 812 and forwarded into the side input of the AND gate 583n that is also fed with the (i) internal water pressure msb 775B into the main input producing the output (pp) pipe port status 810B. The ppB alarm 812 is forwarded into the side input of the AND gate 583o that is also fed with the (n) internal CO2 pressure lsb 777e into the main input producing a ppB alarm^ne 813a. The implemented functions are: 813a=777B∧776B∧777e; 810B=777B∧776B∧775B or using the signal names: ppB alarm^ne=nB lsb∧iB lsb∧ne lsb; ppB=nB lsb∧iB lsb∧iB msb.

The (n) internal CO2 pressure lsb 777C is fed into the main input and the high pressure supply 792d provides high pressure water into the side input of the AND gate 583q. The (i) internal water pressure lsb 776C is fed into the main input and the output of the AND gate 583q is forwarded into the side input of the AND gate 583p producing the output (pp) pipe port status 810Ca. The implemented function is: 810Ca=777C∧776C or using the signal names: ppC=nC lsb∧iC lsb.

The (n) internal CO2 pressure lsb 777D is fed into the main input and the high pressure supply 792d provides high pressure water into the side input of the AND gate 583r. The (i) internal water pressure lsb 776D is fed into the main input and the output of the AND gate 583r is forwarded into the side input of the AND gate 583s producing the output (pp) pipe port status 810Da. The implemented function is: 810Da=777D∧776D or using the signal names: ppD=nD lsb∧iD lsb.

The (pp) pipe port status 810B is fed into the main input and the (pp) pipe port status 810Aa is fed into the side input of the AND gate 583t that is installed flipped producing an output ¬BA 814. The implemented function is: 814=¬810B∧810Aa or using the signal names: ¬BA=¬ppB∧ppA.

The ¬BA 814 is fed into the main input and the (pp) pipe port status 810Da is fed into the side input of the AND gate 583u producing an output ¬BAD 815. The implemented function is: 815=814∧810Da or using the signal names ¬BAD=¬ppB∧ppA∧ppD.

The (pp) pipe port status 810Ca is fed into the main input, the ¬BAD 815 is fed into the first input and the ¬BA 814 is fed into the second input of the SEL gate 589a that has the first and second output joined to produce a single output (O) open door control 778A. The implemented function is: 778A=(¬810Ca∧815)∨(810Ca∧814) or replacing the numbers for the signal names: OA=(¬ppC∧¬ppB∧ppA∧ppD)∨(ppC∧¬ppB∧ppA).

The (pp) pipe port status 810B is fed into the main input and the (pp) pipe port status 810Da is fed into the side input of the AND gate 583v producing an output BD 816. The implemented function is: 816=810B∧810Da or using the signal names: BD=ppB∧ppD.

The (pp) pipe port status 810Ca is fed into the main input, the BD 816 is fed into the first input and the (pp) pipe port status 810B is fed into the second input of the SEL gate 589b that has the first and second output joined to produce a single output (O) open door control 778B. The implemented function is: 778B=(¬810Ca∧816)∨(810Ca∧810B) or replacing the numbers for the signal names: OB=(¬ppC∧ppB∧ppD)∨(ppC∧ppB).

The (pp) pipe port status 810Ca is fed into the main input and the (pp) pipe port status 810Da is fed into the side input of the AND gate 583w that is installed flipped producing an output ¬CD 817. The implemented function is: 817=¬810Ca∧810Da or using the signal names: ¬CD=¬ppC∧ppD.

The ¬CD 817 is fed into the main input and the (pp) pipe port status 810Ab is fed into the side input of the AND gate 583x producing an output ¬CDA 818. The implemented function is: 818=817∧810Ab or using the signal names: ¬CDA=¬ppC∧ppD∧ppA.

The (pp) pipe port status 810B is fed into the main input, the ¬CDA 818 is fed into the first input and the ¬CD 817 is fed into the second input of the SEL gate 589d that has the first and second output joined to produce a single output (O) open door control 778D. The implemented function is: 778D=(¬810B∧818)∨(810B∧817) or replacing the numbers for the signal names: OD=(¬ppB∧¬ppC∧ppD∧ppA)∨(ppB∧¬ppC∧ppD).

The (pp) pipe port status 810Ca is fed into the main input and the (pp) pipe port status 810Aa is fed into the side input of the AND gate 583y producing an output CA 819. The implemented function is: 819=810Ca∧810Aa or using the signal names: CA=ppC∧ppA.

The (pp) pipe port status 810B is fed into the main input, the CA 819 is fed into the first input and the (pp) pipe port status 810Ca is fed into the second input of the SEL gate 589c that has the first and second output joined to produce a single output (O) open door control 778C. The implemented function is: 778C=(¬810B∧819)∨(810B∧810Ca) or replacing the numbers for the signal names: OC=(¬ppB∧ppC∧ppA)∨(ppB∧ppC).

The high pressure supply 792c provides high pressure water into the side input and the (O) open door control 778C is fed into the main input of the AND gate 583za that is installed flipped introducing a NOT function into the input. The output of the AND gate 583za is forwarded into the side input and the (O) open door control 778D is fed into the main input of the AND gate 583zb that is installed flipped introducing a NOT function into the input. The implemented logic function of the produced (P) stop water pump control 781 is: 781=¬778C∧¬778D or replacing the numbers for the signal names: P=¬OC∧¬OD.

The (i) internal water pressure msb 775C and the (i) internal water pressure msb 775D are not used and terminate at the router plate before reaching the logic circuits. The (T) vent air control 779, the (F) raise flag control 780 and the (IV) dive control 782 signals are indicated to complete the signals in the routed pipe block 788 (indicated in FIG. 70).

The high pressure supply 792a provides high pressure water into the side input of the AND gate 583a. The output of the AND gate 583a is then forwarded into the side input of the AND gate 583b and to subsequent AND gates, passing through the AND gate 583c, the AND gate 583d, the AND gate 583e, AND gate 583f, AND gate 583g, and the AND gate 583h forming an AND chain (alarm chain). The main input of the AND gate 583a is connected to the (j) maintenance job 768 and the aux input is connected to the (OV) depth overshoot 804.

The eleven AND gates located at the beginning of the alarm chain, between AND gate 583b and AND gate 583d (from left to right) are fed with the digitized lsb input signals produced by their respective signal pressure controller devices (or ground pressure controller device in the case of AND gate 583c) coming from the i/o unit assembly into their respective main inputs: (s) status in lsb, (q) query in lsb, (m) master/slave in lsb, (z) zero in lsb, (k) clock in lsb, (g) ground lsb 805, (w) water resupply lsb, (u) air resupply lsb, (v) dive in lsb, (r) reset in lsb 801, (h) help in lsb.

The AND gate 583h main input is fed with the ppA alarm 811b. The AND gate 583g main input is fed with the ppB alarm∧ne 813b. The AND gate 583f main input is fed with the (pp) pipe port status 810Cb. The AND gate 583e main input is fed with the (pp) pipe port status 810Db.

The resulting alarm function is: AL=OV∧s lsb∧q lsb∧m lsb∧z lsb∧k lsb∧g lsb∧w lsb∧u lsb∧v lsb∧r lsb∧h lsb∧(nA lsb∧iA lsb)∧(nB lsb∧iB lsb∧ne lsb)∧(nC lsb∧iC lsb)∧(nD lsb∧iD lsb).

The alarm function produces AL=1 in case no fault is present and AL=0 if a leak is present in any input signal (the corresponding lsb signal is low), the ground pressure is too high or if any pipe port has a problem.

FIG. 70 and FIG. 71 are further referred to in the operation section of this document.

FIG. 72 is a top view of a section of a reactor containing pipes and joints showing cutouts to allow the visualization of the fixation of elements in the interior of the pipes and joints.

Four pipe elements 100a, 100b, 100c, and 100d are drawn connected by joints. The pipe elements 100a and 100b are connected by the 90 degrees joint 127. The pipe element 100a is fixated to the 90 degrees joint 127 by the pipe tie 110a and the pipe element 100b is fixated to the 90 degrees joint 127 by the pipe tie 110b. The cutout shows the fixation of the inner pipe 103a of the pipe element 100a to the inner guide 116a of the 90 degrees joint 127 by the inner tie 107a.

The pipe element 100b is fixated to the 180 degrees joint 132 by the pipe tie 110c and the pipe element 100c is fixated to the 180 degrees joint 132 by the pipe tie 110d. The cutout shows the fixation of the inner pipe 103b of the pipe element 100b to the inner guide 116b of the 180 degrees joint 132 by the inner tie 107b. The pipe element 100c is fixated to the straight joint 113 by the pipe tie 110e and the pipe element 100d is fixated to the straight joint 113 by the pipe tie 110f. The cutout shows the fixation of the inner pipe 103c of the pipe element 100c to the inner guide 116c of the straight joint 113 by the inner tie 107c.

FIG. 73 is an isometric view of a portion of a reactor node with one pipe element attached showing a cutout to allow the visualization of the fixation of pipe elements to the pipe ports of reactor nodes.

The reactor node 214 is drawn with only pipe port 125B and pipe port 125C visible. The pipe port 125C has no pipe element attached to it so the position of the pipe port 125C and the inner guide 116C can be clearly visible. The pipe element 100 is fixated to the pipe port 125B by a pipe tie 110 and the inner pipe 103 is fixated to the inner guide 116B by an inner tie 107. All pipe elements are fixated to the pipe ports of the reactor nodes that way.

FIG. 74 is an isometric view of a portion of the wet reactor with multiple reactor nodes and pipe elements properly connected.

A short pipe element 106a that has the same cross section as a regular pipe element but a much shorter length so that adjacent reactor nodes stay near is shown connected to the reactor node 214b. The pipe elements and short pipe elements interconnect the reactor nodes creating multiple paths between two reactor nodes. The pipe element 100a connects reactor node 214a to reactor node 214b and the pipe element 100b connects reactor node 214b to reactor node 214c creating one path from reactor node 214a to reactor node 214c over reactor node 214b. A second path is provided by the short pipe element 106b that connects reactor node 214a to reactor node 214c directly.

Similarly, the pipe element 100c connects reactor node 214c to reactor node 214d and the pipe element 100d connects reactor node 214c to reactor node 214d creating one path from reactor node 214c to reactor node 214e over reactor node 214*d*. A second path is provided by the short pipe element 106*d* that connects reactor node 214*c* to reactor node 214*e* directly.

The pipe element 100*e* connects reactor node 214*e* to reactor node 214*f*, the short pipe element 106*c* connects reactor node 214*b* to reactor node 214*d*, the short pipe element 106*e* connects reactor node 214*d* to reactor node 214*f*, and the short pipe element 106*f* connects reactor node 214*e* to the next reactor node and so on. This creates a structure where water flows from one reactor node to the next over the long path provided by the pipe elements and in the event that a leak occurs in the long path an alternative path can be found using one or more short pipe elements to keep the reactor operating. In case a leak is detected the affected reactor node takes appropriate action closing the pipe port where the leak was detected and opening another pipe port to allow operation to continue and raising the flag 307 to facilitate the localization of the problem by the maintenance crews.

Detail FIG. 74A shows the reactor node 214*c* and its connections. A set of eleven signal hoses 820*a* connects the reactor node 214*c* to reactor node 214*b* and another set of eleven signal hoses 820*b* connects the reactor node 214*c* to reactor node 214*e*. The signal hoses provide a means to convey signals between consecutive reactor nodes enabling the exchange of information and commands among the reactor nodes and a central control unit. An oxygen hose 821*a* connects the reactor node 214*c* to reactor node 214*b* and another oxygen hose 821*b* connects the reactor node 214*c* to reactor node 214*e* providing a means to extract the oxygen that accumulates in the reactor over a period of time. If a leak occurs in one of the signal hoses or one of the pipe elements 100*b*, 100*c* or short pipe elements 106*b*, 106*d* the flag 307 is raised to facilitate the identification of troubled units by the maintenance crew.

Detail FIG. 74B shows how the signal hoses are connected at the transmission side to keep the next reactor node in the same hierarchy as the current one. The signal hoses are installed parallel, each one connected to its corresponding counterpart in the next reactor node. The (Y) unit ready out 168 (the fourth from right to left) is left unused and the (Z) zero out 169 (the fifth from right to left) is connected to the (z) zero in (the fifth from right to left) at the next reactor node (see FIG. 74C).

Detail FIG. 74C shows how the signal hoses are connected at the reception side for all reactor nodes. All signal hoses are connected to its corresponding counterpart in the previous reactor node except for the (gnd) ground 180 (the unused attachment is drawn in dashed lines to facilitate identification) that is not connected and the (z) zero in 181 that may be connected to either the (Y) unit ready out 168 (the fourth from right to left) or the (Z) zero out 169 (the fifth from right to left) (see FIG. 74B and FIG. 74D).

Detail FIG. 74D shows how the signal hoses are connected at the transmission side to make the next reactor node a slave of the current reactor node. The (Y) unit ready out 168 (the fourth from right to left) is connected to the (z) zero in at the next reactor node and the (Z) zero out 169 (the fifth from right to left) is left unused (see FIG. 74C).

FIG. 75 shows a perspective view of a possible configuration of a reactor node that has one of its pipe ports disabled (pipe port D in this case). The water body 365 is drawn in phantom lines as reference to identify the position of the other components.

The pipe ports that have not been disabled (A, B, and C) are equipped with the standard components: the door plugs 137A, 137B, and 137C, the doors 139A, 139B, and 139C, and the door springs, the CO2 valve plugs 148A, 148B, and 148C, the CO2 valves 150A, 150B, and 150C, and the CO2 valve springs.

The disabled pipe port D is equipped with a door stub 146 that replaces the door plug, the door, and the door springs and a CO2 valve stub 159 that replaces the CO2 valve plug, the CO2 valve, and the CO2 valve springs. The door stub 146 has a door stub O-ring 147 similar to the door plug O-ring in the door plug to help seal the door cavity. The CO2 valve stub 159 has a CO2 valve stub O-ring 160 similar to the CO2 valve plug O-ring in the CO2 valve plug that help seal the CO2 valve cavity. The CO2 valve stub 159 is also used to isolate sections of the wet reactor to allow the CO2 pressure to be controlled at different levels at each section to cope with algae growth resulting in different CO2 consumption levels along the reactor.

Additionally to disable the pipe port D, some components assigned to pipe port D need to be replaced in the in the i/o unit assembly. A CO2 pressure stub 822 replaces the D CO2 pressure controller device to prevent CO2 from escaping into the environment through the CO2 sensor pipe 199D or the CO2 feed pipe 200D. A water pressure stub 823 replaces the D water pressure controller device to prevent water from escaping into the environment through the water sensor pipe 197D or the water feed pipe 198D. An actuator dual stub 824 replaces the actuator dual that controls the door and the CO2 valve in pipe port D to prevent water from escaping through the open door pipe 193D, the open CO2 valve pipe 194D, the close door pipe 195D and the close CO2 valve pipe 196D.

Another pipe port (provided that the two pipe ports are not both inputs nor both outputs) can be disabled by replacing the corresponding components as explained in the two paragraphs above.

FIG. 76 shows an isometric partial view of a reactor node, showing the module assembly 369, the air release lower cover 258, the air release left upper cover 259 and the flag 307 installed into the node core 215. A diagnose device 825 and an air powered tool 831 are seen attached to the module assembly 369.

The diagnose device 825 is composed of a diagnose device body 826, a diagnose connector 827, a diagnose band 828, a diagnose high pressure supply hose 829, and a diagnose ground supply hose 830. The diagnose device body 826 is a portable battery operated device similar to a notepad that houses all components necessary to implement its functionalities and an LCD touch screen display to show information and receive inputs from the user. The diagnose connector 827 attaches to the diagnose port in the module assembly 369 and is connected to the diagnose device body 826 by the diagnose band 828 that is composed of 22 individual flexible hoses binded together. The diagnose high pressure supply hose 829 attaches to the high pressure water supply (using either the (w) water resupply right 166 or the (W) water resupply left 178) to provide hydraulic power and the diagnose ground supply hose 830 attaches to the (gnd) ground 180 to close the hydraulic circuit.

An air supply hose 832 attaches the air powered tool 831 to the compressed air (using either the (u) air resupply right 165 or the (U) air resupply left 177). Air powered tools are the ideal tools to be used at sea to facilitate the work of the maintenance crews: they are smaller, lighter and do not pose the threat of short circuits as their electric counterparts. The air supply hose 832 can also be used to supply air to a diver, supply air to fill a buoyance bag to prevent hardware from sinking and other uses.

FIG. 77 shows four arrows indicating possible flows of water culture in and out of the of the reactor node 214. The arrow orientation shows the input and the output pipe ports open in a particular configuration as listed in the table of FIG. 78. The four direct configurations have the arrows as indicated and the four reverse configurations have the arrows reversed.

FIG. 78 shows the eight configurations that are produced by the installation of the different router plates and the corresponding pipe port rerouting introduced. The letters in the column "Sequence" indicate the priorities assigned to the pairs of pipe ports, the first letter is the input pipe port and the second letter the output pipe port. The priorities are assigned from left to right from 1 to 4. For example if the router plate direct is installed, the configuration 1 is produced with the first priority BC meaning that pipe port B is the input and pipe port C is the output. In case faults occur that prevent the first priority BC to be open, the second priority BD, third priority AC or forth priority AD will be attempted in this order (see Table 3). If a router plate other than the router plate direct is installed a different configuration is produced. The logic in the logic unit assembly remains the same however as the installed router plate reroutes the pipe port signals according to its design into different places, the logic unit assembly behaves in a different way producing a new sequence of priorities. For example if the router plate ADBC is installed the configuration 5 is produced: the first priority is CB meaning that pipe port C is the input and pipe port B is the output. In case faults occur that prevent the first priority CB to be open, the second priority CA, third priority DB or forth priority DA will be attempted in this order (see FIG. 67 and FIG. 68).

FIG. 79 shows a top view of a barge assembly 833 that contains the equipment (dry components) needed to operate the reactor. The barge assembly 833 is composed of a floating structure 843, a CO2 storage unit 834, a CO2 extraction unit 835, a control and materials storage room 836, a O2 storage unit 837, an engine room 838, a fuel storage unit 839, a pump room 840, an algae separation unit 841, and an algae storage unit 842.

The floating structure 843 provides space, support and floatability to hold the other equipment. The CO2 extraction unit 835 contains the equipment that extracts CO2 and O2 from the sea water. The CO2 storage unit 834 and the O2 storage unit 837 provides space to store the CO2 and the O2 extracted as primary and secondary products of the CO2 extraction unit 835. The control and materials storage room 836 provides a space to store spare parts and consumables and working space to support the maintenance crew. The control and materials storage room 836 also houses the monitoring system, the computer and other hardware responsible for the control and monitoring of the reactor. The engine room 838 contains the engine and electric generator that provides power to drive the equipment in the barge assembly 833 and in the reactor. The fuel storage unit 839 provides storage to the fuel used by the engine. The pump room 840 contains the pumps that provide pressurized water and pressurized air. The algae separation unit 841 is used to separate the produced algae from the water culture into a concentrated slurry that is stored into the algae storage unit 842.

FIG. 80 shows a top view of a unit farm 862. The unit farm 862 is composed of one barge assembly 833 connected to a functional wet reactor composed of several pipe elements and short pipe elements interconnected to reactor nodes creating alternative paths so that if a path is interrupted an alternative path can be established. To achieve that a plan is prepared and the reactor nodes are configured according to the position they are going to be in the farm. To increase the resilience to leaks bypasses are created at regular intervals creating sections that can be isolated in case multiple leaks render it impossible to find an alternative path within a faulty section. The arrows provide the direction of the water flow leaving and entering the barge assembly 833 for reference.

A reactor node in configuration 1 844 is configured to connect pipe port B to pipe port C in the first priority (direct flow) creating a 180 degree turn that can be bypassed from the right or to the left. A reactor node in configuration 5 848 is configured to connect pipe port C to pipe port B in the first priority (reverse flow) creating a 180 degree turn that can be bypassed from the left or to the right. Most of the reactor nodes in the unit farm 862 are configured as reactor node in configuration 1 844 or reactor node in configuration 5 848 to construct zig zag shaped paths that go from one reactor node to the next and come back covering as much surface as possible. The remaining reactor nodes are configured in one of the remaining configurations to implement other connections with specific functions such as a spare connection to the barge assembly, a bypass to a section or group of sections, etc. Some reactor nodes may be installed with a pipe port disabled to implement the planned paths.

A reactor node in configuration 2 845 is configured to connect pipe port A to pipe port C in the first priority (direct flow) and is useful to create 90 degree curves to the left that can be bypassed ahead or from a 180 degrees turn. A reactor node configuration 6 849 is configured to connect pipe port D to pipe port B in the first priority (reverse flow) and is useful to create 90 degree curves to the right that can be bypassed ahead or from a 180 degrees turn. A reactor node in configuration 3 846 is configured to connect pipe port B to pipe port D in the first priority (direct flow) and is useful to create 90 degree curves to the left that can be bypassed from the right or to turn 180 degrees. A reactor node in configuration 7 850 is configured to connect pipe port C to pipe port A in the first priority (reverse flow) and is useful to create 90 degree curves to the right that can be bypassed from the left or to turn 180 degrees. A reactor node in configuration 4 847 is configured to connect pipe port A to pipe port D in the first priority (direct flow) and is useful to create straight lines that can be bypassed from or to the left. A reactor node in configuration 8 851 is configured to connect pipe port D to pipe port A in the first priority (reverse flow) and is useful to create straight lines that can be bypassed from or to the right.

FIG. 80 shows a pipe element connected to the barge 856, a pipe element in normal operation 857, a pipe element in stand by 858, and a section in normal operation 860. The pipe elements operating normally are shown shaded indicating the algae inside. The pipe elements operating in standby are shown in white to differentiate them from the pipe elements operating normally. A service boat 874 comes at regular intervals to replenish consumables such as fuel and nutrients and to collect the produced concentrated algae slurry.

FIG. 81 shows a top view of a unit farm 862 composed of the barge assembly 833 connected to a reactor where leaks have occurred causing the affected reactor nodes to switch from first priority connections to lower priority connections activating stand by pipe elements as a means to open alternative paths to keep the farm in operation. Troubled components such as a pipe element leaking 859a, 859b, 859c and a section with multiple failures 861 are shown in white to differentiate them from a pipe element in normal operation 857 and a section in normal operation 860 respectively.

The circumvention of faults is done when a reactor node detects a leak in one of its pipe ports and reacts opening an alternative path. The reactor node switching BC to BD 852a reacts to a pipe element leaking 859a detected in its output pipe port C and opens stand by pipe ports D. A reactor node switching BC to AD 854 detects the normal pressure in the input pipe port A but it cannot open pipe port C due to another pipe element leaking 859b detected so it opens the pipe port D. A reactor node switching BC to AC 853a detects the normal pressure in the input pipe port A and opens its pipe port C. A reactor node disabled 855a, 855b has detected a leak in its input pipe port and does not participate in the construction of the alternative path. Further explanation of leak detection and fault circumvention by means of alternative paths is done in the operation section of this document.

FIG. 82 shows an isometric view of a protection cage 863 designed to be used in areas visited by big animals that feed on algae such as manta rays or whale sharks to prevent them from striking a pipe element expecting a meal. The protection cage 863 is composed of a series of protection cage poles 864 connected by protection cage frame bars 865a, 865b creating an outer frame. A series of shorter protection cage structural poles 866 interconnected by protection cage structural bars 867 connects to the outer frame at the protection cage poles 864 providing structural integrity to create a structure able to resist the stresses created by the waves and possible impacts from animals. The protection cage 863 is closed by a protection cage net 869 that is big enough to allow most animals to pass without problems only preventing the big herbivores from reaching the reactor. A series of protection cage fixation lines 868 is used to attach the protection cage 863 to components of the reactor.

FIG. 83 is an isometric view of the basic structure of the protection cage showing the protection cage poles 864 connected by the protection cage frame bars 865a, 865b. The protection cage poles 864 are hollow and contain a water ballast 870 and an air bubble 871. The level of the water ballast 870 and the resulting buoyancy of the protection cage can be adjusted by means of injecting or venting pressurized air into protection cage poles 864. In the event that a leak in one or more protection cage poles and/or a failure in the air compressor causes a cage to go too deep or be unable to surface an independent emergency system composed of an emergency air supply 872 connected to a sealed emergency floating device 873 is capable of bringing the cage to the surface and prevent its loss.

FIG. 84 shows an isometric view of an the unit farm 862 equipped with the protection cage 863. The service boat 874 must stop outside the protection cage 863 to avoid hitting it.

FIG. 85 is a top view of a farm array 875 composed of a grid of unit farms 862 that may or may not be equipped with protection cages separated by corridors to allow access to service boats 874. The farm array 875 can cover vast areas of the ocean in selected regions specified by the authorities that do not affect shipping, fishing, leisure, etc. The authorities may also close a specific area for other uses for the deployment of a farm array 875 to help remediate ocean acidification or coastal dead zones.

FIG. 86 is a diagrammatic view of the CO2 extraction unit composed of a sea water intake filter 876, a water degasifier 877, a condensed water cleaner 878, a discharge water aerator 879, an engine 880, a vaporizer 881, a CO2 extractor 882, a CO2 separator 883, and an oxygen extractor 884. The CO2 extraction unit also has seven heat exchangers that are used to increase the energy efficiency of the processes: a heat exchanger 1 886, a heat exchanger 2 887, a heat exchanger 3 888, a heat exchanger 4 889, a heat exchanger 5 890, a heat exchanger 6 891, and a vaporizer heat exchanger 892.

The sea water intake filter 876 takes sea water from a sea water intake 893 filters a large portion of it and returns the rest out to a sea water flush 894 to carry living organisms and unwanted debris or suspended material. The incoming filtered sea water is supplied preheated to the water degasifier 877 by three different paths: 1) through heat exchanger 1 886 entering from a cold water intake heat exchanger 1 895 and exiting to the water degasifier 877 by a hot water exit heat exchanger 1 896; 2) through heat exchanger 3 888 entering from a cold water intake heat exchanger 3 897 and exiting to the water degasifier 877 by a hot water exit heat exchanger 3 898; 3) through heat exchanger 4 889 entering from a cold water intake heat exchanger 4 899 and exiting to the water degasifier 877 by a hot water exit heat exchanger 4 900. The volume flowing on each path is adjusted to recover the available heat at the corresponding heat exchangers monitoring the temperature at the hot water exit of each heat exchanger.

The sea water at the water degasifier 877 circulates through the heat exchanger 5 890 passing through a cold water intake heat exchanger 5 905 and returning from a hot water exit heat exchanger 5 906. In the heat exchanger 5 890 the sea water is further heated exchanging heat with the exhaust gases coming from the engine 880 through a hot gas intake heat exchanger 5 903 and leaving through a cold gas exit heat exchanger 5 904. If necessary, an extra heat source 885 provides additional energy to heat the sea water to a point that causes the dissolved gases to boil off and leave the water degasifier 877 through a boil off gas pipe 907 joining the engine exhaust gases that have been cooled in the heat exchanger 5 890 and continuing through a hot gas intake heat exchanger 3 908 to the heat exchanger 3 888.

The heat exchanger 1 886 and the heat exchanger 2 887 are part of the oxygen extractor 884 designed to remove excess oxygen from the reactor water culture to prevent oxygen induced growth impairment of the algae culture. The water culture containing oxygen comes from the reactor from a cold intake heat exchanger 2 923 passes through the heat exchanger 2 887 where it exchanges heat with the hot sea water that has had its dissolved gases removed and is being discharged from the water degasifier 877 by a hot water intake heat exchanger 2 912. The temperature of the water culture increases causing the dissolved gases rich in oxygen to boil off and be removed from the oxygen extractor 884 by a boil off oxygen pipe 926 to be stored or used elsewhere. At the same time the temperature of the discarded sea water decreases to as close to ambient as possible to avoid wasting energy and allow the discarded sea water to be safely returned to the ocean. The water culture leaving the heat exchanger 2 887 continues into a hot link of heat exchanger 2 and 1 924, passes through the heat exchanger 1 886 exchanging heat with the incoming filtered sea water coming from the cold water intake heat exchanger 1 895. The reactor culture water is cooled back to near ambient temperature so it can be returned to the reactor by a cold exit heat exchanger 1 925 and the incoming filtered sea water is pre heated and goes into the water degasifier 877 through the hot water exit heat exchanger 1 896.

The incoming filtered sea water that passes through the heat exchanger 4 889 exchanges heat with the coolant water of the engine 880 that comes from a hot water intake heat exchanger 4 901 and returns to the engine 880 by a cold water exit heat exchanger 4 902. This recovers waste heat from the engine to preheat the incoming sea water before it reaches the water degasifier 877 and keeps the engine 880 cooled to its operational temperature.

The incoming filtered sea water that passes through the heat exchanger 3 888 exchanges heat with the exhaust gases of the engine combined with the boiled off sea water gases coming from the hot gas intake heat exchanger 3 908. The temperature of the gases reduces causing the water vapor contained in the engine exhaust gas to condensate and be removed by a condensate drain heat exchanger 3 910 going to the condensed water cleaner 878 that removes contaminants so the condensed water can be safely discarded into the ambient. A cleaner exit 911 takes the cleaned condensed water to join the discarded sea water that has been cooled and left the heat exchanger 2 887 through a cold water exit heat exchanger 2 913. A water intake aerator 914 takes the discarded water into the discharge water aerator 879 where oxygen enriched air 915 extracted from the reactor culture water is injected to make it safe for sea life so it can be returned to the environment by a aerated water discharge 916.

The combined engine exhaust gases and boiled off sea water gases leave the heat exchanger 3 888 cooled to near ambient temperature and continue through a cold gas exit heat exchanger 3 909 into the vaporizer 881 where they pass through the vaporizer heat exchanger 892. The heat exchange causes solid CO2 stored in the vaporizer 881 to sublimate and the exhaust and boiled off gases to be cooled to below ambient temperature. The gaseous CO2 is removed from the vaporizer 881 and sent to the reactor through a gaseous CO2 supply to reactor 922. The exhaust and boiled off gases continue through a hot gas intake heat exchanger 6 917 to the heat exchanger 6 891 where they exchange heat with the depleted CO2 gases that come from the CO2 separator 883 through a cold gas intake heat exchanger 6 919 at nearly −32° C., the deposition temperature of CO2. The depleted CO2 gases are heated and discarded to the atmosphere by a hot gas exit heat exchanger 6 920 and the exhaust and boiled off gases are precooled to near −32° C. and go through a cold gas exit heat exchanger 6 918 into the CO2 extractor 882. As the input exhaust and boiled off gases have been precooled the CO2 extractor 882 is able to operate and reach the deposition temperature of the CO2 using less energy. As CO2 deposits, it is collected by the CO2 separator 883 and a solid CO2 supply to vaporizer 921 takes it to the vaporizer 881.

FIG. 87 is a diagrammatic view of the algae separation unit composed of a flow divider 927, a culture diluter 928, an algae separator 929, an algae storage unit 932, and a flow splitter 933 integrated with the oxygen extractor 884.

A culture from reactor 934 is divided in the flow divider 927 in two parts: a culture to diluter 935 that is sent to the culture diluter 928 to be diluted and a culture to separator 936 that is sent to the algae separator 929 that separates a water culture phase 930 from an algae slurry phase 931. The algae slurry phase 931 is sent through an algae slurry conduct 937 to the algae storage unit 932 where it remains until the service boat comes to collect it.

The water culture phase 930 is sent to the oxygen extractor 884 through the cold intake heat exchanger 2 923. The removed oxygen is sent through the boil off oxygen pipe 926 to the discharge water aerator that injects air enriched with oxygen into the discharged sea water to make it safe for marine life. The water coming from the oxygen extractor 884 through the cold exit heat exchanger 1 925 goes to the flow splitter 933 that separates it into two parts: water to diluter 938 and water to add nutrients 940. The water to diluter 938 is mixed in the culture diluter 928 with the culture to diluter 935 received from the flow divider 927 producing a diluted water to reactor 939 that is sent to restock the reactor. The water to add nutrients 940 is mixed with nutrients 941 producing an enriched water 942 that is sent to the compressor to power the reactor and disperse the nutrients.

FIG. 88 is an isometric view and FIG. 89 is a side view of the algae separator 929. Both figures show the same components to provide a better view of the algae separator 929 and its workings. As both are the same the description is made only once for concision.

The algae separator 929 is composed of a separator case 943, a concentrator 944, and a helical pusher 945. The separator case 943 provides support for the other components and containment for the water culture being processed. The helical pusher 945 has a helical axis 946 that allows it to rotate supported by an entry support 947 and an exit support 948 attached to the separator case 943. As the helical pusher 945 rotates it scrapes algae from the interior surface of the concentrator and forces water culture coming through a slurry entry 949 into an ever reducing volume pressing the culture against the concentrator 944 that is made of a porous metal sheet that has openings small enough that water is allowed through but not the microalgae. As more and more water is forced out and collected in a water exit 951 the culture is progressively concentrated into an algae slurry that eventually exits at a slurry exit 950.

FIG. 90 is diagrammatic view of the control unit located inside the control and materials storage room. The control unit is composed of a local computer 953*a*, 953*b*, 953*c* connected to one or more interfaces 958*a*, 958*b*, 958*c*, 958*d*, etc. a set of analog to digital converters 961, and two sets of solenoid valves 964*a* and 964*b*.

Each local computer 953*a*, 953*b*, 953*c*, etc. is connected to its respective local antenna 955*a*, 955*b*, 955*c*, etc. that allows information from the unit farm where the local computer is located to be exchanged with a central computer 952 connected to a central antenna 954 over a satellite link 956. The central computer 952 collects information from all unit farms that are under its responsibility, generates trouble tickets for the maintenance crews, sends commands to the unit farms, for example commanding a dive in case of incoming storm, produces reports for evaluation of the operation by the management, and other functions.

The local computer 953*a* is connected to its interfaces 958*a*, 958*b*, by a data link 957 that can use a cable or wireless connection. The interfaces 958*a*, 958*b* are equipped in sufficient quantity to provide the necessary number of input and output ports to perform all needed functions. The interfaces 958*a*, 958*b* are connected to an input bus 959 composed of a series of input lines 960 each one connected to an analog to digital converter 961 that collects the digital input signals. The interfaces 958*a*, 958*b* are also connected to a twin output bus 962*a*, 962*b* composed of a series of pairs of output lines 963*a*, 963*b*, each one connected to a solenoid valve 964*a*, 964*b*.

A set of long hoses 969*a*, 969*b*, etc. equipped with quick release fittings 971*a*, 971*b*, etc. each one connected to a corresponding auto lock fitting 970*a*, 970*b*, etc. that stop fluid flow in case of excess flow caused by a leak or when not attached to a hose, convey the input and output signals. The input signals come from the reactor to the corresponding analog to digital converter 961. The output signal is produced by the solenoid valve pair 964*a* and 964*b* working in opposition so that when one valve is open the other one is closed. The solenoid valve 964*a* allows water from a hi pressure vessel 965 to flow through a short hose 967*a* and reach a T joint 968, and the solenoid valve 964*b* allows water coming from the T joint 968 to go into a low pressure sink 966 through a short hose 967*b*. At any time, either a high-pressure water supply or a low-pressure water sink is available at the T joint 968 providing the intended control signal to its corresponding point in the reactor.

The local computer 953*a* also issues commands and collects relevant information from other equipment such as the engine, CO2 extraction unit, etc. using electric connections to control and monitor all operation in the unit farm, keep things running smoothly and reporting problems to the central computer 952.

FIG. 91 is a diagrammatic view of the main input, output and control signals in the reactor node.

A remote interface 972 deals with the signals coming into or going out of each reactor node. The analog input signals entering the remote interface 972 are digitized by components inside the i/o unit assembly producing their correspondent digital versions that may be a single bit signal or a 2 bit signal depending on the case. A local interface 973 deals with signals that occur locally at the reactor node, digitizing the analog signals into one or two bit signals depending on the case and producing internal control signals. The logic components in the logic unit assembly process the digital signals from the local interface and from the remote interface and generate low power digital control signals to operate the reactor node and perform the necessary actions such as open or close doors, raise the flag, etc. The low power digital output signals are then used to command power actuators in the i/o unit assembly to produce the analog output signals that actually control the reactor node and the signals that are transmitted out by the remote interface 972.

All signals shown in FIG. 91 are listed in Table 4. Some signals listed in table 4 such as redundant input service signals, output service signals and signals used in intermediate logic functions used only in the logic unit assembly are not represented in FIG. 91.

Table 4 lists all signals described in this document and their logic functions for a complete concise reference. In Table 4, the symbol S identifies a Service Signal that is accessible or produced by service teams. The symbol=means the signal mentioned in the table row is interconnected to the signal listed on the right. The symbol → means the analog input signal is digitized into the digital input signal(s) on the right of the symbol. The symbol ← means the analog output mentioned in the table row is produced by the digital signal on the right of the symbol. The expression (4×) A B C D indicates that a version of the signal mentioned in the table row is available for each pipe port. The expression (5×) A B C D e indicates that a version of the signal is available for each pipe port and the CO2 pressure inside the CO2 body (e). The expression m/s is high (m/s=1) if the signal (m) master/slave in msb matches the configuration of the reactor node (m=1 if the reactor node is configured as master; or m=0 if the reactor node is configured as slave) or low (m/s=0) otherwise. The symbol ↑ means "set to 1" and the symbol ↓ means "reset to 0" by the condition provided on the right of the symbol.

Signals resulting from the digitalization of an analog input signal in the i/o unit assembly (see FIG. 62 and FIG. 63) have no reference number if: 1) the digitized msb that regenerates the analog input is not used in any logic function; or 2) the digitized lsb that is low if a leak is detected in the input analog signal is used only to produce the (AL) alarm signal (see FIG. 70 and FIG. 71).

TABLE 4

List of signals

| # | Signal Name | Remarks |
|---|---|---|
| 165 | (u) air resupply right | S; = 177; → (u) air resupply msb; (u) air resupply lsb |
| 166 | (w) water resupply right | S; = 178; → (w) water resupply msb; (w) water resupply lsb |
| 176 | (l) CO2 resupply right | S; = 188; → (l) CO2 resupply msb; (l) CO2 resupply lsb |
| 177 | (U) air resupply left | S; = 165 |
| 178 | (W) water resupply left | S; = 166 |
| 180 | (gnd) ground | S; → (g) ground lsb 805 |
| 188 | (L) CO2 resupply left | S; = 176 |
| 768 | (j) maintenance job | S |
| 170 | (v) dive in | → (v) dive in msb 806; (v) dive in lsb |
| 172 | (r) reset in | → (r) reset in msb 800; (r) reset in lsb 801 |
| 174 | (h) help in | → (h) help in msb 795; (h) help in lsb |
| 179 | (k) clock in | → (k) clock in msb 719; (k) clock in lsb |
| 181 | (z) zero in | → (z) zero in msb 720; (z) zero in lsb |
| 183 | (m) master/slave in | → (m) master/slave in msb 721; (m) master/slave in lsb |
| 185 | (q) query in | → (q) query in msb 797; (q) query in lsb |
| 187 | (s) status in | → (s) status in msb 794; (s) status in lsb |
| 213 | (x) external pressure | → (x) external pressure msb 685; (x) external pressure lsb 684 |
| 167 | (K) clock out | ← (k) clock in msb 719; K out = k msb |
| 168 | (Y) unit ready out | ← (y) unit ready 730; Y out = y |
| 169 | (Z) zero out | ← (z) zero in msb 720; Z out = z msb |
| 171 | (M) master/slave out | ← (m) master/slave in msb 721; M out = m msb |
| 173 | (Q) query out | ← (Q) query control 799; Q out = ($\neg$TX $\wedge$ q msb) $\vee$ (TX $\wedge$ AL) |
| 175 | (S) status out | ← (S) status control 796; S out = ($\neg$TX $\wedge$ s msb) $\vee$ (TX $\wedge$ h msb) |
| 182 | (V) dive out | ← (v) dive in msb 806; V out = v msb |
| 184 | (R) reset out | ← NOT (R) reset control 802; R out = $\neg$R = $\neg$($\neg$r msb $\wedge$ r lsb) |
| 186 | (H) help out | ← (H) help control 803; H out = AL $\wedge$ h msb |
| 722 | register signal zk | zk = z msb $\wedge$ k msb |
| 723 | register signal mz | mz = m/s $\wedge$ z msb |
| 724 | register signal $\neg$kzm | $\neg$kzm = $\neg$k msb $\wedge$ z msb $\wedge$ m/s |
| 725 | register signal kzm | kzm = k msb $\wedge$ z msb $\wedge$ m/s |
| 775 | (i) internal water pressure msb | (4x) A B C D (iA msb, iB msb, iC msb, iD msb) |

TABLE 4-continued

List of signals

| # | Signal Name | Remarks |
|---|---|---|
| 776 | (i) internal water pressure lsb | (4x) A B C D (iA lsb, iB lsb, iC lsb, iD lsb) |
| 777 | (n) internal CO2 pressure lsb | (5x) A B C D e (nA lsb, nB lsb, nC lsb, nD lsb, ne lsb) |
| 778A | (O) open door control A | OA = ($\neg$ppC $\wedge$ $\neg$ppB $\wedge$ ppA $\wedge$ ppD) $\vee$ (ppC $\wedge$ $\neg$ppB $\wedge$ ppA) |
| 778B | (O) open door control B | OB = ($\neg$ppC $\wedge$ ppB $\wedge$ ppD) $\vee$ (ppC $\wedge$ ppB) |
| 778C | (O) open door control C | OC = ($\neg$ppB $\wedge$ ppC $\wedge$ ppA) $\vee$ (ppB $\wedge$ ppC) |
| 778D | (O) open door control D | OD = ($\neg$ppB $\wedge$ $\neg$ppC $\wedge$ ppD $\wedge$ ppA) $\vee$ (ppB $\wedge$ $\neg$ppC $\wedge$ ppD) |
| 779 | (T) vent air control | T = x msb $\wedge$ v msb |
| 780 | (F) raise flag control | F = $\neg$AL $\wedge$ FE; LF = $\neg$F (lower flag commands the flag) |
| 781 | (P) stop water pump control | P = OC $\wedge$ $\neg$OD; RP = $\neg$P (run pump commands the water pump) |
| 782 | (IV) dive control | IV = x msb $\wedge$ v msb (controls dive direction) |
| 793 | (TX) transmit signal | TX = y $\wedge$ $\neg$k msb $\wedge$ z msb $\wedge$ m/s |
| 798 | (AL) alarm | AL = OV ^ s lsb ^ q lsb ^ m lsb ^ z lsb ^ k lsb ^ g lsb ^ w lsb ^ u lsb ^ v lsb ^ r lsb ^ h lsb ^ (nA lsb ^ iA lsb) ^ (nB lsb ^ iB lsb ^ ne lsb) ^ (nC lsb ^ iC lsb) ^ (nD lsb ^ iD lsb) |
| 802 | (R) reset control | R = $\neg$r msb $\wedge$ r lsb (controls internal reset) |
| 804 | (OV) depth overshoot | OV $\uparrow$ $\neg$x msb $\wedge$ x lsb; OV $\downarrow$ j |
| 807 | (pl) dive complete | pl = v msb $\wedge$ $\neg$x msb |
| 808 | (FE) flag enable control | FE = $\neg$v msb $\wedge$ x lsb $\wedge$ x msb |
| 809 | (E) dive disable control | E = FE $\vee$ pl (disables cable winch rotation and depth change) |
| 810A | (pp) pipe port status A | ppA = nA lsb $\wedge$ iA lsb $\wedge$ iA msb |
| 810B | (pp) pipe port status B | ppB = nB lsb $\wedge$ iB lsb $\wedge$ iB msb |
| 810C | (pp) pipe port status C | ppC = nC lsb $\wedge$ iC lsb |
| 810D | (pp) pipe port status D | ppD = nD lsb $\wedge$ iD lsb |
| 811 | ppA alarm | ppA alarm = nA lsb $\wedge$ iA lsb |
| 812 | ppB alarm | ppB alarm = nB lsb $\wedge$ iB lsb |
| 813 | ppB alarm ^ ne | ppB alarm ^ ne = nB lsb $\wedge$ iB lsb $\wedge$ ne lsb |
| 814 | $\neg$BA | $\neg$BA = $\neg$ppB $\wedge$ ppA |
| 815 | $\neg$BAD | $\neg$BAD = $\neg$ppB $\wedge$ ppA $\wedge$ ppD |
| 816 | BD | BD = ppB $\wedge$ ppD |
| 817 | $\neg$CD | $\neg$CD = $\neg$ppC $\wedge$ ppD |
| 818 | $\neg$CDA | $\neg$CDA = $\neg$ppC $\wedge$ ppD $\wedge$ ppA |
| 819 | CA | CA = ppC $\wedge$ ppA |

FIG. 92 lists the sequence of 7 bit linear feed shift register states produced by the Linear Feed Shift Register (LFSR) implemented in the logic unit assembly when triggered by successive pulses of the clock signal.

FIG. 93 is a graphic of the water pressures at a given point in a unit farm showing unregenerated water signals traveling from left to right producing a forward water pressure 975 and from right to left producing a backward water pressure 976. At certain water resupply nodes 974a, 974b, 974c, etc. the water pressure is replenished by means of connecting a high pressure water source coming directly from the compressors at the barge. At these points 974a, 974b, 974c, etc. the pressure of all signals top up to the maximum. As the water signals travel from left to right and from right to left, the pressure drops due to losses and the usage of the high-pressure water to power the reactor nodes. As one signal travels progressively further to approach the next water resupply reaching a point of lower water pressure 979, the signal travelling in the opposite direction has travelled a shorter path and has a higher water pressure 978. There is an equal water pressure node 977 point where the pressures eventually cross.

However, as each reactor node uses both types of signals to build up its internal high pressure water supply that regenerates the left to right and the right to left signals, a mean pressure 980 is produced at each node allowing for smaller pressure fluctuations and producing regenerated signals that can travel further than unregenerated signals could.

The lower portion of the graphic in FIG. 93 is expanded to better show the internal working pressure range inside the pipe elements divided in four regions: Leak 00; Stand by 01; Operation 11; Closed 10 with respective values of the internal water pressure digitized signals (i msb, i lsb) used for leak detection and automatic water culture routing. The mean pressure 980, that is the maximum pressure inside the reactor node powering the logic and the various logic signals produced and transmitted can be much higher than the maximum water pressure inside the pipe elements. As the pipe elements are connected through the water body inside the reactor node the ground pressure follows the pressure inside the pipe elements. If the ground pressure gets too high, close to the mean pressure this may affect the logic circuits and the operation of the reactor node so an alarm is generated if the ground pressure exceeds a threshold.

The values of the (g) ground lsb signal are next to the water pressure axis on the left. If the ground pressure is within the internal working pressure range inside the pipe elements, the ground pressure controller device produces g lsb=1 indicating normal operation. If the ground pressure is higher than the internal working pressure range inside the pipe elements, the ground pressure controller device produces g lsb=0. If g lsb=0, the (AL) alarm becomes low (AL=0) signaling a problem caused by the too high ground pressure value.

FIG. 94 is a graphic of the signals sent and received by the local computer when communicating with reactor nodes in the wet reactor. A set of timing points: timing point 1 981, timing point 2 982, timing point 3 983, timing point 4 984, timing point 5 985, timing point 6 986, timing point 7 987, timing point 8 988, timing point 9 989, timing point 10 990, timing point 11 991, timing point 12 992, timing point 13 993, and timing point 14 994 help explain the operation of the polling of the reactor nodes which is done in the operation section.

OPERATION—FIRST EMBODIMENT

The wet reactor is assembled using the necessary number of reactor nodes, pipe elements, straight joints, 90 degrees joints, and 180 degrees joints properly connected. The wet reactor is then connected to the barge assembly to create a unit farm (see FIG. 72, FIG. 73, FIG. 74, FIG. 80).

Each reactor node is equipped with a module assembly properly configured to match the position its reactor node occupies allowing the wet reactor to operate as intended.

FIG. 25 shows an exploded view of the module assembly. The module assembly is composed of the module case 370, the logic unit assembly 432, the i/o unit assembly 403 and the expansion unit assembly 388 that works also as a cover that closes the module case 370. The module case 370 and the expansion unit assembly 388 can be locked together using R-clips on the fasteners of the module case securing the contents of the module assembly. Later on the closed module assembly can be secured to the node core using R-clips on the fasteners of the node core.

The module assembly is installed preconfigured in its reactor node and can later be replaced if necessary by maintenance crews. The i/o unit assembly has nine possible configurations: a standard configuration with all pipe ports used, four configurations with one pipe port not equipped (pipe port A, B, C, or D cancelled with stubs) and four configurations with two pipe ports not equipped (pipe ports AD, AC, BC or BD cancelled with stubs). Pre-assembled and pretested units can be kept in inventory as a major part for installation in a new module assembly in a simplified production line and kept in reserve as spares for replacement of faulty units detected on the field.

Differently from the i/o unit assembly that has a reduced number (9) of possible configuration, the logic unit assembly can have multiple configurations and is in fact tailored for each individual reactor node on a particular wet reactor. Configuring the unit is simple and does not require changing structural components. The different configurations are implemented varying eight components that are a subset of the logic components to produce a unique 7+1 bit address for each unit (resulting in 127 possible addresses in two modes or 254 possible configurations) and selecting one out of the 8 available router plates to install in the router plate insertion bay. As a result, to be used as a single specific part for installation in a new module assembly in a simplified production line, pre-assembled and pretested units need to be properly identified and linked to a particular module assembly that will be installed on a particular reactor node. As each unit has its own unique configuration, it is not practical to have pre-assembled spares in reserve. Instead, it is better to keep a set of components in stock that can be used to build units in any one of the 254×8=2032 possible configurations to replace faulty units detected on the field replicating their specific configuration.

The possibility of replacing a complete module assembly facilitates the work of maintenance crews that can prepare a spare module assembly to replace a faulty one installed in a working reactor node at sea. The spare unit can be prepared and tested in a controlled environment for example inside a workshop or an adequate room in a maintenance boat avoiding unnecessary difficulties of working with small parts while subjected to wave movement, water spray and dirt or other contaminants that might get into undesired places unnoticed and later affect the proper functioning of the unit. Once at the site, the maintenance crew remove only the R-clips that secure the module assembly to the node core but not the ones that keep the module assembly closed (the R-clips that keep the expansion unit assembly and the module case together) and then swap the faulty unit by the new one and reinstall the R-clips that have been removed. This possibility of a simple, quick swap of a faulty module assembly by a new pretested one simplifies and expedites the maintenance work, reducing down time and the risk of accidents by reducing the time the maintenance crew needs to be at sea and the complexity of the tasks that need to be performed under hazardous conditions. All these factors in turn contribute to reduce operational costs.

Some or all reactor nodes may be connected to an anchor assembly to secure the wet reactor in place and allow it to be lowered to a safe depth if necessary (see FIG. 5, detail FIG. 5D, and FIG. 6).

The anchor assembly is lowered to the sea floor full of water so that it will sink to the bottom and be driven into the bottom soil a few centimeters by its own wait or by means of external assistance. Once the anchor assembly is at the bottom, water is pumped out through the anchor valve 286 reducing the pressure inside the anchor body causing the anchor assembly to be further driven into the sea floor by the sea hydrostatic pressure. Once the anchor assembly is in place, the anchor valve is closed and any attempt to raise the anchor assembly will cause the pressure inside the anchor body to reduce and the sea water hydrostatic pressure will generate a strong force opposing the movement. This type of anchor is suited for a sea floor made of sand or silt and is able to provide a fixed and very strong anchor point. For sea floors of different constitution, other anchor types need to be used.

FIG. 24 shows the reactor node with a cutout in the node core 215 showing the components of the anchoring system in place. The dive control open pipe 207 and a dive control close pipe 206 control the movement of the pump rotor assembly 325. If pressurized water is continuously injected in the dive control close pipe 206 while low pressure water is collected in the dive control open pipe 207 the pump rotor assembly 325 turns counter clockwise rotating the cable winch 292 in the same direction. The cable winch teeth grip the anchor cable 287 and wind it down towards the anchor assembly 282 allowing the reactor node to rise towards the surface until the cable winch 292 stops turning or the stopper 290a hits the node core 215. The length of the cable is adjusted so that at this point the reactor node is at the surface. If pressurized water is continuously injected in the dive control open pipe 207 while low pressure water is collected in the dive control close pipe 206 the pump rotor assembly 325 turns clockwise rotating the cable winch 292 and pulling the anchor cable 287 against the fixed anchor assembly 282 at the bottom, causing the reactor node to submerge as the stopper 290a sinks until the cable winch 292 stops turning or the stopper 290b hits the node core 215. The position of the stopper 290b is adjusted so that at this point the reactor node is at the desired maximum depth to escape a dangerous weather condition or other reasons that may require the reactor node to be submerged from time to time. The stopper 290a and the stopper 290b serve as end of course safety guards that prevent the anchor cable 287 from getting loose or the node core 215 from diving too deep.

The water culture is fully contained inside the wet reactor. In case a pipe element is damaged causing a leak, the affected reactor nodes are able to detect the problem and isolate the faulty unit from the rest of the wet reactor.

The detection of a leak is done by monitoring the pressure of the water culture and the $CO_2$ in each pipe port. The water sensor pipe 197 conducts water from the near edge of the water body channel 366 to the module assembly so the water pressure in the water body channel can be controlled and water leaks detected. The water feed pipe 198 supplies water into the water body channel allowing the control devices inside the module assembly to control the water pressure if no leak is detected.

The $CO_2$ sensor pipe 199 conducts $CO_2$ from the near edge of the $CO_2$ body channel 368 to the module assembly so the $CO_2$ pressure in the $CO_2$ body channel can be controlled and leaks detected. The $CO_2$ feed pipe supplies $CO_2$ into the $CO_2$ body channel allowing the control devices inside the module assembly to control the $CO_2$ pressure if no leak is detected (see FIG. 12, FIG. 13, and FIG. 14).

If a water culture or $CO_2$ leak is detected in a pipe port, its corresponding door 139 and $CO_2$ valve 150 are closed. The control of the door and the $CO_2$ valve that closes a pipe port is done by its corresponding actuator dual inside the i/o unit assembly commanded by a control signal produced in the logic unit assembly. The control signal is a function of the state of the various input signals and the priorities assigned to the pipe port. In case a leak is detected, the affected pipe port is automatically closed. A pipe port where no leak is detected may be open or closed depending on its assigned priority and the operational status of the other pipe ports.

If high pressure water is injected at the open door pipe 193 when the door is closed, the door is pushed away from the door plug 137 and opens. If high pressure water is injected at the close door pipe 195 when the door is open, the door is pushed towards the door plug 137 and closes. The door springs 145*a*, 145*b* are used to ensure that in case of power failure the door automatically closes. If high pressure water is injected at open $CO_2$ valve pipe 194 when the $CO_2$ valve 150 is closed the $CO_2$ valve is pushed away from the $CO_2$ valve plug 148 and opens. If high pressure water is injected at the close $CO_2$ valve pipe 196 when the $CO_2$ valve is open, the $CO_2$ valve 150 is pushed towards the $CO_2$ valve plug 148 and closes. The $CO_2$ valve springs 158*a*, 158*b* are used to ensure that in case of power failure the $CO_2$ valve automatically closes.

The open door pipe 193 and the open $CO_2$ valve pipe 194 are connected to the same termination point at the node core main control port section 190 and the close door pipe 195 and the close $CO_2$ valve pipe 196 are connected to another same termination point at the node core main control port section 190 so that both the door and $CO_2$ valve open and close together. The actuator dual ensures that when the water pressure at the open door pipe 193 and open $CO_2$ valve pipe 194 is high, the water pressure at the close door pipe 195 and close $CO_2$ valve pipe 196 is low and vice versa so that a consistent pressure difference is generated to push the door and $CO_2$ valve in the desired direction. (see FIG. 10, FIG. 11, FIG. 12, FIG. 13, and FIG. 14).

If a fault such as a leak occurs in a reactor node, a flag is raised to facilitate the identification of the faulty unit in the field by the maintenance crews. As seen on FIG. 16 and FIG. 17, high pressure water injected by the flag pipe 201 pushes the flag piston 311 in the direction of the straight arrow causing the flag piston 311 to slide into the flag port cavity 302 through the flag port plug 300. When the flag piston 311 is pushed in the direction of the straight arrow, the flag lever moves and rotates causing the flag to move in the direction of the curved arrow and be lowered. If the water pressure pushing the flag piston 311 is reduced or a power failure occurs the flag spring 314 pushes back the flag piston head 312 in the opposite direction of the straight arrow, causing the flag to move in the opposite direction of the curved arrow and be raised. The overlaid components show the positions at the extremes of the movement so that when the flag 307*a* is in the horizontal or rest position, the flag lever 310*a* and the flag piston head 312*a* are in the positions indicated (a). When on the other hand the flag 307*c* is in the vertical or alarm position, the flag lever 310*c* and the flag piston head 312*c* are in the positions indicated (c).

Each reactor node has a water pump that allows the water culture to be gently pushed forward throughout the wet reactor. The components of the water pump, the pump rotor assembly 325*a* and the propeller set assembly 347 can be seen on their assembled position in FIG. 15 and FIG. 19.

The pump rotor fits inside a portion of the water pump cavity 231 in the rotor cavity 233 that has a circular shape with axis offset from the pump rotor axis in such a way that the pump rotor 326 touches one side of the rotor cavity 233 between the pump feed pipe 208 and the pump exhaust pipe 209. The two pump vanes 334*a* and 334*b* forced out by the vane spring extend towards the walls of the rotor cavity 233 creating separate compartments in a standard liquid vane pump configuration. The pump feed pipe 208 injects high pressure water into the rotor cavity producing a force into pump vane 334*a* forcing the pump rotor 326 to turn around the pump rotor axle 327 in the clockwise direction. As the pump rotor turns, water between the pump vane 334*b* and the pump exhaust pipe 209 opening is forced out through the pump exhaust pipe 209 until pump vane 334*b* passes the pump feed pipe 208 opening and the cycle repeats producing a continuous clockwise rotation of the pump rotor as long as high pressure water is fed through the pump feed pipe 208. The water flowing in the pump exhaust pipe 209 then passes through a check valve 339 that prevents water from the water body containing algae cells that may stick together in clumps to move into the rotor cavity when the water pump is off line avoiding a potential cause of jamming. The exhaust water then continues through the pump exhaust front pipe 210 and the pump exhaust discharge pipe 211 to reach the water body inside the reactor node where it is discharged (see FIG. 19, FIG. 19A, and FIG. 19B).

The check valve is installed in a cavity of appropriate size with grooves in the same size and shape of the check valve body 340 and the check valve support 342 cut into the bottom so that the axis of the pipe is aligned with the center of the check valve body and the check valve support 342 is embedded in the grooves, causing the check valve body rim 341 to rest on the edge of the pipe wall that creates a ledge where the check valve rubber rests (see FIG. 18E, FIG. 18F, and FIG. 24B).

When the water flows in the permitted direction, as indicated in the arrow in FIG. 18E, the water momentum flexes the check valve rubber away from the check valve support and the pipe wall edge creating a gap through which the water can flow. When the water tries to flow in the opposite direction, the check valve rubber 345 is pressed against the check valve support and the pipe wall edge stopping the flow.

Detail FIG. 19B shows the positioning of the two ratchet drives 360*a* and 360*b* located in the space between the front propeller shaft support 223 and the rotor shaft support 225. A cutout is made on the rotor shaft support 225 to show the ratchet spring 363 in position located around the pump rotor shaft 329 and compressed between the pump rotor drive rim 332 and the ratchet drive 360*a*. A second cutout is made on a section of ratchet drive 360*a* to show the ratchet drive teeth 362 on ratchet drive 360*b*. The ratchet spring 363 keeps the two ratchet drives 360*a* and 360*b* in contact pressed against each other so that when the pump rotor shaft 329 is turning (only turns in the clockwise direction) driving ratchet drive 360*a*, the ratchet drive teeth 362 lock and the movement is transmitted to ratchet drive 360*b* that is attached to a propeller shaft driving a propeller left hand 349 (in the case of configuration 1 illustrated). The remaining propellers in the propeller set assembly are driven through the outer gears. If the pump rotor shaft 329 stops or reduces the rotational speed while the propellers continue rotating pushed by the water flow in the water body, causing ratchet drive 360*b* to spin faster than ratchet drive 360*a*, the ratchet drive teeth 362 slide against each other compressing the ratchet spring 363 until the ratchet drive teeth 362 slip one tooth. The teeth will continue to slip as long as ratchet drive 360*b* rotates faster than ratchet drive 360*a* preventing damage to the pump rotor shaft in case the pump rotor stops (see FIG. 21J).

In FIG. 22 the reactor node 214 is drawn in phantom lines to show the water body 365, the four pipe ports, one at each section: A, B, C, and D and the four water body channels 366A, 366B, 366C, and 366D so the path of water culture can be clearly seen. Water culture enters the reactor node at a pipe port and goes down through the corresponding water body channel to the lower level where the propeller set assembly 347 is located. The pump cover 315 and pump rotor assembly 325 are shown for reference. If activated, the pump rotor assembly 325 in the water pump turns clockwise and transmits the movement to the propeller set assembly 347. The propellers in the propeller set assembly can be mounted in configuration 1 (direct flow) in which water is pumped from pipe ports A or B to pipe ports C or D or configuration 2 (reverse flow) in which water is pumped from pipe ports C or D to pipe ports A or B. The doors (not drawn) open and close the water channels routing the water culture according to operational conditions. The reactor node implements the highest priority arrangement that operational conditions allow according to a preconfigured priority sequence. For example, supposing the reactor node is mounted with propellers in direct flow configuration and the primary arrangement is to pump water from port B to port C (BC), under normal operating conditions the primary arrangement is implemented: the pump rotor is activated, doors A and D are closed and doors B and C are open so that water culture can be pumped according to first priority route BC as programmed. Following the example, if a problem such as a leak is detected in pipe port C, the door C is commanded to close to prevent water culture from escaping and polluting the environment as well as outside living organisms to enter and contaminate the water culture and door D is commanded to open so that water flow may continue through a second priority alternative route BD. If a second problem, such as another leak this time in pipe port B, is detected door B is commanded to close and door A is commanded to open so that water flow may still continue through a third priority alternative route AD. If a third problem is detected or a second problem is detected in such a way that both input or both output ports are unavailable at the same time, rendering water flow impossible through the affected reactor node, the doors in the affected pipe ports are closed and the pump rotor is shut down.

To avoid oxygen induced growth impairment of the algae culture, oxygen needs to be removed from the wet reactor. This is done in two steps: 1) allowing oxygen rich air that accumulates inside the wet reactor to be collected at each reactor node and reach a point in the air release assembly where it can be removed, and 2) removing dissolved oxygen from the water left over after algae separation at the oxygen extractor.

In FIG. 22 the reactor node 214 is drawn in phantom lines to show the water body 365, the four pipe ports, one at each section: A, B, C, and D and the four water body channels 366A, 366B, 366C, and 366D so the path of water culture can be clearly seen. As water culture flows through the water body channel 366A, 366B, 366C, and 366D and each pipe port A, B, C, and D respectively, bubbles made of a mixture of air and other gases (mostly oxygen) are eventually captured by an air release cut 271A, 271B, 271C, and 271D at the top of each respective pipe port and channeled into the air release chamber 270 from where the accumulated air mixture can be extracted or if necessary allowed to escape into the environment.

Detail FIG. 22A shows the components of the air release system in greater detail. Air bubbles present in the water body 365 eventually pass through the air release cut 271D reaching the float cavity 279D where the float 280D is installed. As long as air is present in the float cavity 279D, the float 280D sinks opening the access to check valve 339D. The air passes through the check valve 339D and continues into the air release long channel 268D until the air release pass 269D reaching the air release chamber 270. The air release attachment right 265 connected to the air release chamber 270 by the air release pass 269D allows the air to be extracted by a hose. Similarly, air bubbles collected at the air release cut 271C reach the float cavity 279C where the float 280C is installed. As long as air is present in the float cavity 279C, the float 280C sinks opening the access to the check valve 339C. The air escapes through the check valve 339C and continues into the air release short channel 267C until the air release pass 269C reaching the air release chamber 270. As the air escapes, water level rises inside the air release cut 271C and the float cavity 279C causing the float 280C to rise until it seals the access to the check valve 339C and the air release short channel 267C, preventing water to flow into the air release chamber 270.

Air accumulated in the air release chamber 270 can be vented by means of shifting the air vent valve 272 so that the air vent purge cutout 276 is unobstructed opening the access to the check valve 339*e* that allows air to escape into the environment but prevents water and air from the environment to enter and reach the air release chamber 270.

As a means to detect leaks the water culture and all water and air signals inside the wet reactor are kept at higher pressures than the external water pressure. When wet reactor components are submerged the external water pressure increases requiring a controlled corresponding increase in water and signal pressures to maintain the pressure differential and the ability to detect leaks. This is achieved using various controllers and using the external water pressure as reference pressure signal.

FIG. 32 shows a top view of the controllers and actuators with the input and output connections to clarify the interaction between the components and the connections and the operation of these components.

An input signal connected to the CO2 pressure input 1 508 or the CO2 pressure input 2 509 injects CO2 under pressure into the right side of the CO2 pressure controller cavity 459 pushing the CO2 pressure controller device 460 against the controller spring 491*a* towards the reference pressure pipe 507 until equilibrium is reached. Any changes in the input signal pressure or external water pressure will cause the CO2 pressure controller device 460 to move accordingly until a new equilibrium position is reached.

If an opening in the CO2 pressure controller device 460 aligns with a particular input in the top, the signal in that input is passed to the output below. In the position drawn in FIG. 32, the CO2 pressure reset opening 462 allows CO2 to pass from the CO2 pressure reset input 510 into the CO2 pressure supply output 512 below. On the other hand, if the CO2 pressure control opening 463 is not aligned with the CO2 pressure regulate input 511 no CO2 is allowed to pass into the CO2 pressure supply output 512 below. At this point the edge of the CO2 pressure lsb low opening 464 is aligned with the CO2 pressure lsb low input 513 that has a low pressure signal (0) and the CO2 pressure lsb high opening 465 is not aligned with the CO2 pressure lsb high input 514 that has a high pressure signal (1). The output signal passed into the CO2 pressure lsb output 515 below is low (0). That means the pressure inside the CO2 pipe is too low, indicating a possible leak or that the system is still pressurizing after a reset.

Every time the system is powered up, a reset signal is temporarily activated to allow the internal pressures to build up to the designed operating range. During the time the reset signal is active, CO2 under pressure is available at the CO2 pressure reset input 510 and the CO2 pressure reset opening 462 allows CO2 to pass into the CO2 pressure supply output 512 below. The CO2 injected into the system causes the pressure in the CO2 pressure input 1 508 or the CO2 pressure input 2 509 to rise and as a result the CO2 pressure controller device 460 moves towards the left compressing the controller spring 491a. Once the CO2 pressure control opening 463 aligns with the CO2 pressure regulate input 511, CO2 is allowed to pass into the CO2 pressure supply output 512 below even if the reset signal is deactivated and the CO2 pressure continues to rise causing the CO2 pressure controller device 460 to move further to the left until the CO2 pressure control opening 463 moves beyond the CO2 pressure regulate input 511 and the CO2 flow stops. The CO2 pressure control opening 463 is tapered at the right side so that as the CO2 pressure increases and approaches the designed value, the CO2 flow reduces slowly until it stops. As CO2 permeates through the inner pipe walls into the water body where the algae culture consumes it, the pressure of the CO2 in the input signal slowly drops causing the CO2 pressure controller device 460 to move back to the right until the tapered portion of the CO2 pressure control opening 463 aligns with the CO2 pressure regulate input 511 allowing some CO2 to flow and top up the CO2 in the system, regulating the CO2 pressure.

Once CO2 coming from the CO2 pressure regulate input 511 is allowed to pass through the CO2 pressure control opening 463, the CO2 pressure lsb low opening 464 has moved beyond the CO2 pressure lsb low input 513 that has a low pressure signal (0), whereas the CO2 pressure lsb high opening 465 is now aligned with the CO2 pressure lsb high input 514 that has a high pressure signal (1). The output signal passed into CO2 pressure lsb output 515 below is high (1). That means the pressure inside the CO2 pipe is in the operating range and no leak is detected.

If a leak is present in the system, the CO2 pressure in the CO2 pressure input 1 508 or the CO2 pressure input 2 509 will fall too quickly to allow additional injected CO2 to compensate for the loss in pressure and the CO2 pressure controller device 460 will move towards the right until it touches the edge of the CO2 pressure controller cavity 459. Once the CO2 pressure control opening 463 has moved beyond the CO2 pressure regulate input 511, no more CO2 will be injected into the system, the CO2 pressure lsb low opening 464 aligns with the CO2 pressure lsb low input 513 and the output signal passed into CO2 pressure lsb output 515 below will remain low (0) until the leak is fixed by maintenance crews.

The CO2 pressure controller rubber grid 461 envelops all openings and the main body of the CO2 pressure controller device 460 isolating each opening so that fluid passing through an opening does not leak into other openings.

An input signal connected to the water pressure input 1 516 or the water pressure input 2 517 injects water under pressure into the right side of the water pressure controller cavity 466 pushing the water pressure controller device 467 against the controller spring 491b towards the reference pressure pipe 507 until equilibrium is reached. Any changes in the input signal pressure or external water pressure will cause the water pressure controller device 467 to move accordingly until a new equilibrium position is reached. For additional detail, the portion of the controller spring 491b inside the water pressure controller device 467 reaching all the way until the controller central extension 489 is drawn in dashed lines. To avoid cluttering, only the visible portions of the other controller springs are shown.

If an opening in the water pressure controller device 467 aligns with a particular input on the top, the signal in that input is passed to the output below. In the position drawn in FIG. 32, the tapered portion of the water pressure control opening 470 is aligned with the water pressure regulate input 519 allowing water to pass into the water pressure supply output 520 below. On the other hand, if the water pressure reset opening 469 is not aligned with the water pressure reset input 518 no water is allowed to pass into the water pressure supply output 520 below. At this point the water pressure lsb high opening 471 is aligned with the water pressure lsb high input 521 that has a high pressure signal (1). The water pressure lsb low opening 1 472 and the water pressure lsb low opening 2 473 are not aligned with the water pressure lsb low input 522 that has a low pressure signal (0). The output signal passed into the water pressure lsb output 525 below is high (1). The water pressure msb low opening 474 is aligned with the water pressure msb low input 523 that has a low pressure signal (0). The water pressure msb high opening 475 is not aligned with the water pressure msb high input 524 that has a high pressure signal (1). The output signal passed into water pressure msb output 526 below is low (0). The encoded water pressure digital signal (msb, lsb) in this position is 01.

The openings in the water pressure controller device 467 are so made that as the water pressure controller device 467 moves from the right to the left, starting at the edge of the water pressure controller cavity 466 until the water pressure control opening 470 is not yet aligned with the water pressure regulate input 519, the water pressure lsb low opening 1 472 remains aligned with the water pressure lsb low input 522 and the water pressure msb low opening 474 remains aligned with the water pressure msb low input 523 causing the encoded water pressure digital signal (msb, lsb) to be 00 indicating a leak or that the system is still pressurizing after a reset.

Every time the system is powered up, a reset signal is temporarily activated to allow the internal pressures to build up to the designed operating range. During the time the reset signal is active, water under pressure is available at the water pressure reset input 518 and the water pressure reset opening 469 allows water to pass into the water pressure supply output 520 below. The water injected into the system causes the pressure in the water pressure input 1 516 or the water pressure input 2 517 to rise and as a result the water pressure controller device 467 moves towards the left compressing the controller spring 491b. Once the water pressure control opening 470 aligns with the water pressure regulate input 519, water is allowed to pass into the water pressure supply output 520 below even if the reset signal is deactivated and the water pressure continues to rise until the water pressure controller device 467 moves further to the left so that the water pressure control opening 470 moves beyond the water pressure regulate input 519 and the water flow stops. The water pressure control opening 470 is tapered at the right side so that as the water pressure increases and approaches the designed value, the water flow reduces slowly until it stops.

Once the left portion of the water pressure control opening 470 aligns with the water pressure regulate input 519, the water pressure lsb high opening 471 aligns with the water pressure lsb high input 521 and the water pressure msb low opening 474 remains aligned with the water pressure msb low input 523 causing the encoded water pressure digital signal (msb, lsb) to be 01, indicating that the water pressure is in operating range, within the water pressure controlled range (stand by).

As water pressure controller device 467 moves further to the left, the water pressure control opening 470 tapered portion on the right will eventually no longer align with the water pressure regulate input 519. At this point, the water pressure msb high opening 475 aligns with the water pressure msb high input 524 and the water pressure lsb high opening 471 remains aligned with the water pressure lsb high input 521 causing the encoded water pressure digital signal (msb, lsb) to be 11, indicating that the water pressure is in operating range, above the water pressure controlled range (operation).

As the water pressure controller device 467 continues to move to the left, the water pressure lsb low opening 2 473 aligns with the water pressure lsb low input 522 and the water pressure msb high opening 475 remains aligned with the water pressure msb high input 524 causing the encoded water pressure digital signal (msb, lsb) to be 10, indicating that the water pressure is outside the operating range, above the water pressure controlled range (closed).

If a leak is present the water pressure in the water pressure input 1 516 and/or the water pressure input 2 517 will fall too quickly to allow additional injected water to compensate for the loss in pressure and the water pressure controller device 467 will move towards the right until it touches the edge of the water pressure controller cavity 466. Once the water pressure control opening 470 has moved beyond the water pressure regulate input 519, no more water will be injected into the system, the water pressure controller device 467 will move all the way to the right and the encoded water pressure digital signal (msb, lsb) will remain 00 (leak) until the problem is fixed by maintenance crews.

The water pressure controller rubber grid 468 envelops all openings and the main body of the water pressure controller device 467 isolating each opening so that fluid passing through an opening does not leak into other openings.

An input signal connected to the ground pressure input 527 injects water at ground pressure into the right side of the ground pressure controller cavity 476 pushing the ground pressure controller device 477 against the controller spring towards the reference pressure pipe 507 until equilibrium is reached. Any changes on the input signal pressure or external water pressure will cause the ground pressure controller device 477 to move accordingly until a new equilibrium position is reached.

If an opening in the ground pressure controller device 477 aligns with a particular input in the top, the signal in that input is passed to the output below. When the reactor node is powered up the pressure inside the water body can be as low as the exterior water pressure causing the ground pressure controller device 477 to move all the way to the right. The ground pressure control opening 479 aligns with the ground pressure regulate input 528 and water is injected into the ground pressure supply output 529 below causing the ground pressure to rise and the ground pressure controller device 477 to move left until the right edge of the tapered portion of the ground pressure control opening 479 moves away from the ground pressure regulate input 528 and the water flow stops. The ground pressure may increase further after the water flow into the ground pressure supply output has stopped depending on the operational state of the reactor node. While the ground pressure lsb high opening 480 is aligned with the ground pressure lsb high input 530 that has a high pressure signal (1) and the ground pressure lsb low opening 481 is not aligned with the ground pressure lsb low input 531 that has a low pressure signal (0), the output signal passed into the ground pressure lsb output 532 below is high (1) meaning that the ground pressure is within the operational range. A ground pressure above the operational range causes the ground pressure lsb output 532 to be low (0).

The ground pressure controller rubber grid 478 envelops all openings and the main body of the ground pressure controller device 477 isolating each opening so that fluid passing through an opening does not leak into other openings.

A signal pressure input 533 injects water under pressure into the right side of the signal input controller cavity pushing the signal pressure controller device 483 against the controller spring towards the reference pressure pipe 507 until equilibrium is reached. Any changes in the signal pressure or external water pressure will cause the signal pressure controller device 483 to move accordingly until a new equilibrium position is reached.

If an opening in the signal pressure controller device 483 aligns with a particular input on the top, the signal in that input is passed to the output below. In the position drawn in FIG. 32, the signal pressure lsb high opening 485 is aligned with the signal pressure lsb high input 534 that has a high pressure signal (1). The signal pressure lsb low opening 486 is not aligned with the signal pressure lsb low input 535 that has a low pressure signal (0). The output signal passed into the signal pressure lsb output 538 is high (1). The signal pressure msb low opening 487 is aligned with the signal pressure msb low input 536 that has a low pressure signal (0). The signal pressure msb high opening 488 is not aligned with the signal pressure msb high input 537 that has a high pressure signal (1). The output signal passed into the signal pressure msb output 539 is low (0). The encoded signal pressure digital signal (msb, lsb) in this position is 01.

As the signal pressure controller device 483 moves from right to the left, the encoded signal pressure digital signal (msb, lsb) changes from 00 to 01 and then 11. A 00 indicates that the pressure in the particular signal is too low and the signal is invalid (an appropriate action such as triggering an alarm may be carried out). A 01 indicates that the signal pressure is valid and the signal is low (0) and 11 indicates that the signal pressure is valid and the signal is high (1).

The signal pressure controller rubber grid 484 envelops all openings and the main body of the signal pressure controller device 483 isolating each opening so that fluid passing through an opening does not leak into other openings.

The actuator mono normally open 493 has two actuator openings 504c located in the same line, at the near side of the actuator spring 506c. The input signal connected to the actuator mono 1 input top 3 544 injects water at high pressure (1) or at ground pressure (0) into the left side of the actuator mono cavity. Another pipe such as the actuator mono 1 input top 1 542 at the right side is connected either to the ground (542=0) if an actuator spring is installed (as drawn in FIG. 32) or the opposite polarity of the signal supplied at actuator mono 1 input top 3 544 (542=¬544) if no actuator spring is installed.

If an actuator spring is not installed, when the signal 544 is high (1) the actuator will be pushed all the way to the right side of the cavity against the opposite polarity signal 542 injected at the other side (0). When the signal 544 is low (0) the actuator will be pushed back to the left of the cavity by the opposite polarity signal 542 injected at the other side (1).

If an actuator spring is installed, the actuator is pushed against the actuator spring and slides towards the right side of the actuator mono cavity where the actuator spring is located whenever the signal is hi. The ground connection delivered by the actuator mono 1 input top 1 542 at the right side provides an exit route to the displaced water so the actuator is able to slide inside the cavity. When the signal is low the actuator spring pushes back the actuator towards the left side of the actuator mono cavity and the displaced water exits at the actuator mono 1 input top 3 544.

When actuator mono 1 input top 3 544 is supplied with water at ground pressure (0), the actuator spring 506c extends until its maximum extension (rest position), pushing the actuator mono normally open 493 all the way to the left of the actuator mono cavity, causing both actuator openings 504c to align with the actuator mono 1 supply 1 545 and the actuator mono 1 supply 2 546 and opening the passage to the actuator mono 1 output 1 547 and the actuator mono 1 output 2 548 respectively. When actuator mono 1 input top 3 544 is supplied with water at high pressure (1), the actuator mono normally open 493 moves all the way to the right of the actuator mono cavity, the actuator spring 506c is in maximum compression (active position), both actuator openings 504c move away from the actuator mono 1 supply 1 545 and the actuator mono 1 supply 2 546 closing the passage to the actuator mono 1 output 1 547 and the actuator mono 1 output 2 548 respectively.

At any time, both outputs 547 and 548 will be connected to a water supply and have a meaningful logic value (high or low) or disconnected from a water supply and have an undetermined logic value (3rd state) depending on the position of the actuator mono normally open 493 in the actuator mono cavity.

The actuator mono normally closed 495 has two actuator openings 504d located in the same line, at the far side of the actuator spring 506d. For added information, the portion of the actuator spring 506d inside the actuator spring hole is drawn in dashed lines. The input signal connected to the actuator mono 2 input side 1 550 injects water at high pressure (1) or at ground pressure (0) into the left side of the actuator mono cavity. Another pipe such as the actuator mono 2 input top 1 549 at the right side is connected either to the ground (549=0) if an actuator spring is installed (as drawn in FIG. 32) or the opposite polarity of the signal supplied at actuator mono 2 input side 1 550 (549=¬550) if no actuator spring is installed.

When actuator mono 2 input side 1 550 is supplied with water at high pressure (1), the actuator mono normally closed 495 moves all the way to the right of the actuator mono cavity, the actuator spring 506d is in maximum compression (active position), both actuator openings 504d align with the actuator mono 2 supply 1 551 and the actuator mono 2 supply 2 552 opening the passage to the actuator mono 2 output 1 553 and the actuator mono 2 output 2 554 respectively as indicated in FIG. 32. When actuator mono 2 input side 1 550 is supplied with water at ground pressure (0), the actuator spring 506d extends until its maximum extension (rest position), pushing the actuator mono normally closed 495 all the way to the left of the actuator mono cavity, causing both actuator openings 504d to move away from the actuator mono 2 supply 1 551 and the actuator mono 2 supply 2 552 closing the passage to the actuator mono 2 output 1 553 and the actuator mono 2 output 2 554 respectively.

At any time, both outputs 553 and 554 will be connected to a water supply and have a meaningful logic value (high or low) or disconnected from a water supply and have an undetermined logic value (3rd state) depending on the position of the actuator mono normally closed 495 in the actuator mono cavity.

The actuator mono 497a has two actuator openings 504a located in alternate lines, one at the side of the actuator spring and one at the alternate opposite side of the actuator spring. When actuator mono 4 input top 2 564 is supplied with water at high pressure (1), the actuator mono 497a moves all the way to the right of the actuator mono cavity compressing the actuator spring to its maximum compression (active position) the actuator opening 504a aligns with actuator mono 4 supply 2 566. When actuator mono 4 input top 2 564 is supplied with water at ground pressure (0), the actuator spring extends until its maximum extension (rest position), pushing the actuator mono 497a all the way to the left of the actuator mono cavity, causing the other actuator opening to align with actuator mono 4 supply 1 565 as indicated in FIG. 32.

The actuator mono 4 input top 1 563 at the right side of the actuator mono cavity is connected either to the ground (563=0) if an actuator spring is installed (as drawn in FIG. 32) or the opposite polarity of the signal supplied at actuator mono 4 input top 2 564 (563=¬564) if no actuator spring is installed.

A single actuator mono 4 output 1 567 located at the bottom center of the actuator mono cavity combines the two inputs: actuator mono 4 supply 1 565 and actuator mono 4 supply 2 566 producing a single power output that is a logic function of actuator mono 4 input top 2 564, actuator mono 4 supply 1 565 and an actuator mono 4 supply 2 566. The result output depends on the orientation of the actuator mono. If the actuator mono 497a is installed as shown in FIG. 32, the function is:

$$567=(\neg 564 \wedge 565) \vee (564 \wedge 566).$$

If the actuator mono is installed flipped around the symmetry axis of the spring hole:

$$567=(564 \wedge 565) \vee (\neg 564 \wedge 566).$$

The actuator mono 497b is the same component as actuator mono 497a but has been installed flipped with respect to the symmetry axis around the actuator spring hole when compared to actuator mono 497a. For added information, the portion of the actuator spring 506b inside the actuator spring hole is drawn in dashed lines.

The input signal connected to the actuator mono 3 input side 4 558 injects water at high pressure (1) or at ground pressure (0) into the left side of the actuator mono cavity. Another pipe such as the actuator mono 3 input side 3 557 at the right side is connected either to the ground (568=0) if an actuator spring is installed (as indicated in FIG. 32) or the opposite polarity of the signal supplied at actuator mono 3 input side 4 558 (557=¬558) if no actuator spring is installed.

Differently from the cavity containing actuator mono 497*a* that has only one power output: actuator mono 4 output 1 567, the actuator mono cavity containing actuator mono 497*b* has two independent power outputs: actuator mono 3 output 1 561 and actuator mono 3 output 2 562 generating two switched power outputs.

With the actuator mono 497*b* installed as shown in FIG. 32, if the actuator mono 3 input side 4 558 is low, actuator mono 3 output 2 562 will be connected to actuator mono 3 supply 2 560 and have a meaningful logic value (high or low) and actuator mono 3 output 1 561 will be disconnected from actuator mono 3 supply 1 559 and have an undetermined logic value (3rd state). In case the actuator mono 3 input side 4 558 is hi, actuator mono 3 output 1 561 will be connected to actuator mono 3 supply 1 559 and have a meaningful logic value (high or low) and actuator mono 3 output 2 562 will be disconnected from actuator mono 3 supply 2 560 and have an undetermined logic value (3rd state).

In case the actuator mono 497*b* is installed not as shown in FIG. 32 but flipped around the spring hole symmetry axis, when the input 558 is low, output 561 will be connected to supply 559 and have a meaningful logic value (high or low) and output 562 will be disconnected from supply 560 and have an undetermined logic value (3rd state) whereas if the input 558 is hi, output 562 will be connected to supply 560 and have a meaningful logic value (high or low) and output 561 will be disconnected from supply 559 and have an undetermined logic value (3rd state).

The actuator dual 500 has three alternate actuator openings 504*e* located in three lines perpendicular to the symmetry axis, one at the side of the actuator spring 506*e*, one at the opposite side of the actuator spring 506*e* and one at the middle of the actuator dual 500 at the alternate side.

The input signal connected to the actuator dual input top 2 569 injects water at high pressure (1) or at ground pressure (0) into the left side of the actuator dual cavity. Another pipe such as the actuator dual input top 1 568 at the right side is connected either to the ground (568=0) if an actuator spring is installed (as indicated in FIG. 32) or the opposite polarity of the signal supplied at actuator dual input top 2 569 (568=¬569) if no actuator spring is installed.

The actuator dual supply top 1 570, the actuator dual supply top 2 571, the actuator dual supply top 3 572 and the actuator dual supply top 4 573 located at the top of the actuator dual cavity 499 provide four input power signals to the actuator. The actuator dual output 1 574 located at the bottom of the cavity combines the two inputs above: the actuator dual supply top 1 570 and the actuator dual supply top 2 571 and the actuator dual output 2 575 located at the bottom of the cavity combines the other two inputs above: the actuator dual supply top 3 572 and the actuator dual supply top 4 573.

When the actuator dual input top 2 569 is supplied with water at ground pressure (0), the actuator spring 506*e* extends until its maximum extension (rest position), pushing the actuator dual 500 all the way to the left of the actuator dual cavity, causing the actuator openings 504*e* to align with the actuator dual supply top 1 570 and the actuator dual supply top 4 573 as indicated in FIG. 32. When actuator dual input top 2 569 is supplied with water at high pressure (1), the actuator dual 500 moves all the way to the right of the actuator dual cavity, the actuator spring 506*e* is in maximum compression (active position), the actuator openings 504*e* align with the actuator dual supply top 2 571 and the actuator dual supply top 3 572.

The logic functions produced depend on the orientation of the actuator dual. If the actuator dual is installed as shown in FIG. 32:

$$574=(\neg 569 \wedge 570) \vee (569 \wedge 571); \quad 575=(\neg 569 \wedge 573) \vee (569 \wedge 572).$$

If the actuator dual is installed flipped around the symmetry axis of the spring hole:

$$574=(\neg 569 \wedge 571) \vee (569 \wedge 570); \quad 575=(\neg 569 \wedge 572) \vee (569 \wedge 573).$$

Using a spring is an effective way to ensure a component returns to an off (or initial) position in case of power failure. It is also a means to reduce the necessary number of components (and complexity) in a design since only the signal input needs to be produced and routed into the cavities (a connection to a ground plane is usually much easier to do than to route an additional signal coming from a specific place into a cavity).

In some applications, a component (actuator or logic component) can be used without a spring. In this case unless an active state is present, the component will remain stationary. An active state is when one signal (high or low) is injected at one side of the cavity and the opposite polarity of the signal (low or high respectively) is injected at the other side of the cavity. An inactive state is when the same signal (low or high) is injected in both sides of the cavity. In case an active state is present, one input will have high pressure water (1) and the other will be connected to ground (0) and the component will be pushed towards the side that has the low signal. Otherwise the component will remain stationary. This is one way to implement a set reset register (memory).

FIG. 35 shows various cavities with the respective logic components in place and the corresponding input and output connections that implement examples of logic functions.

When the AND 1 main 619 is low (0) the logic spring 686*a* extends out of the AND 1 GND 618 and pushes the AND gate 583*a* towards the edge of the AND 1 cavity 617 causing the AND gate 583*a* to be in its rest position (583*a*↔0). The connections in the AND gate 583*a* isolate the AND 1 input 620 and connect the AND 1 output 621 to the AND 1 clear 622 that is connected to ground (0). As in this case 619=0 then 621=0, regardless of 620, as needed to implement 621=619∧620.

When the AND 2 main 625 is low (0) the logic spring 686*b* extends out of the AND 2 aux 624 and pushes the AND gate 583*b* towards the edge of the AND 2 cavity 623 causing the AND gate 583*b* that has been installed in a flipped position compared to AND gate 583*a* to be in its rest position (~583*b*↔0). The connections in the AND gate 583*b* isolate the AND 2 clear 628 and connect the AND 2 input 626 to the AND 2 output 627. In this example, 625=0, causing the output to be 627=626, as needed to implement 627=¬625∧626.

The AND 3 main 631 supplies the main input to the OR gate 579*a*. One among four options: AND 3 OR input 1 632, AND 3 OR input 2 633, AND 3 OR input 3 634 or AND 3 OR input 4 635 is needed to provide the other logic input to the OR gate 579*a*. For simplicity, it is assumed that AND 3 OR input 1 632 is the selected second input to the OR gate 579*a*. When both inputs 631 and 632 are low (0), the logic spring 686*c* extends out of the AND 3 aux 630 and pushes the AND gate 583*c* towards the OR gate 579*a* until the OR gate 579*a* touches the edge of the AND 3 cavity 629 causing both the OR gate 579*a* and the AND gate 583*c* to be in their rest positions (579*a*↔0; 583*c*↔0). The connections in the AND gate 583*c* isolate the AND 3 input 636 and connect the AND 3 output 637 to the AND 3 clear 638 that is connected to ground (0). Since in this example 631=0; 632=0⇒631∨632=0 producing 637=0, regardless of 636, as needed to implement 637=(631∨632)∧636.

The SEL 1 main 641 supplies the main input to the OR gate 579b. One among four options: SEL 1 OR input 1 642, SEL 1 OR input 2 643, SEL 1 OR input 3 644, SEL 1 OR input 4 645 is needed to provide the other logic input to the OR gate 579b. For simplicity, it is assumed that SEL 1 OR input 1 642 is the selected second input to the OR gate 579b. When both inputs 641 and 642 are low (0), the logic spring 686d extends out of the SEL 1 aux 640 and pushes the SEL gate 589a towards the OR gate 579b until the OR gate 579b touches the edge of the SEL 1 cavity 639 causing both the OR gate 579b and the SEL gate 589a to be in their rest positions (579b↔0; 589a↔0). The connections in the SEL gate 589a isolate the SEL 1 input 1 646 and connect the SEL 1 output 1 647 to the SEL 1 clear 1 648 that is connected to ground (0). The connections in the SEL gate 589a isolate the SEL 1 clear 2 651 and connect the SEL 1 output 2 650 to the SEL 1 input 2 649. In this case 641=0; 642=0⇒641∨642=0 producing 647=(641∨642)∧646=0; 650=¬(641∨642)∧649=649.

The XOR gate 596 is kept in place by two logic long springs 687a and 687b. When the XOR signal 1 653 and the XOR signal 2 654 are equal (both low or both high) the XOR gate 596 remains at the center of the XOR cavity 652. The XOR gate connections isolate the XOR input 1 655 that is connected to high (1) and connect the XOR output 1 656 to the XOR clear 1 657 that is connected to ground (0) implementing 656=653⊗654=0 (xor function). The XOR gate connections also isolate the XOR clear 2 660 that is connected to ground (0) and connect the XOR output 2 659 to the XOR input 2 658 that is connected to high (1) implementing 659=653=654=1 (equivalent function).

The concept of active and rest positions can be extended to consider the XOR gate 596 having one rest position to be (596↔0) when the XOR gate 596 is in the center of its cavity as indicated in FIG. 35 and two active positions: (596↔−1) and (596↔1) when the XOR gate 596 is in either one of the extremities of its cavity, depending on the polarities of the input signals XOR signal 1 653 and the XOR signal 2 654 so that if 653=0; 654=1⇒596↔−1 and if 653=1; 654=0⇒596↔1.

Because no spring is installed, appropriate connections must be in place to allow the SEL gate 589b to move. To that effect, the SEL 2 aux 662 is supplied with the negated main input (662=¬663) so that as indicated in FIG. 35 when the SEL 2 main 663 is low (0), the SEL 2 aux 662 is high (1). The SEL gate 589b is shifted inside the SEL 2 cavity 661 all the way towards the SEL 2 main 663 causing the SEL gate 589b to be in its rest position (589b↔0). The connections in the SEL gate 589b isolate the SEL 2 input 1 664 and the SEL 2 output 1 665 (as there are no connections on the top of the SEL 2 cavity 661). At the same time, the connections in the SEL gate 589b connect the SEL 2 input 2 666 to the SEL 2 output 2 667. As at any time, regardless of the position of the SEL gate 589b, one input is always isolated and there are no top connections that could cause a short circuit between a signal with different polarity and the other input through the SEL gate 589b connections, the SEL 2 output connection 668 can be constructed connecting outputs 665 and 667 producing a combined output.

$$668=(\neg 663 \wedge 666) \vee (663 \wedge 664).$$

If inputs 664 and 666 are made complementary (666=¬664), $$668=(\neg 663 \wedge \neg 664) \vee (663 \wedge 664), \text{ or } 668=663=664;$$
$$668=663\otimes 666.$$

When the SW main 671 is low (0) the logic spring 686e extends out of the SW aux 670 and pushes the SW gate 602 towards the edge of the SW cavity 669 causing the SW gate 602 to be in its rest position (602↔0). The connections in the SW gate 602 connect the SW input 1 672 with the SW monitor 1 673 and the SW output 1 674. At the same time the connections in the SW gate 602 also connect the SW input 2 675 to the SW monitor 2 676 and the SW output 2 677. In this position, the inputs on the back (672 and 675) are connected to the outputs below (674 and 677 respectively). The monitors on top (673 and 676 respectively) are also connected allowing the lines to be monitored.

The depth external water pressure pipe 679 injects water at the external pressure into the depth sensor cavity 678 pushing the depth detector 689 against the depth sensor 688 compressing the air inside the depth sensor 688 until equilibrium is reached. Any changes in the external water pressure will cause the depth detector 689 to move accordingly until a new equilibrium position is reached. If a slot in the depth detector 689 aligns with a particular input on the top, the signal in that input is passed to the output below. The depth detector input guard 691 allows water coming from the depth external water pressure pipe 679 to enter the depth sensor cavity 678 even when the depth detector 689 is at the end of its excursion. The depth detector rubber grid 690 envelops all slots and the main body of the depth detector 689 isolating each slot so that fluid passing through a slot does not leak into other slots.

In the position drawn in FIG. 35, the depth lsb high pressure slot 1 692 is aligned with the depth lsb high pressure 681 that has a high pressure signal (681=1). The depth lsb high pressure slot 2 694 is isolated and has no effect. The depth lsb gnd slot 693 is not aligned with the depth lsb gnd 680 that has a low pressure signal (680=0). The output signal passed into the (x) external pressure lsb 684 is high (684=681=1). The depth msb high pressure slot 695 is aligned with the depth msb high pressure 682 that has a high pressure signal (682=1). The depth msb gnd slot 696 is not aligned with the depth msb gnd 683 that has a low pressure signal (683=0). The output signal passed into the (x) external pressure msb 685 is high (685=682=1). The encoded depth position is 685,684=11 (surface).

As the reactor node is submerged the external water pressure increases causing the depth detector 689 to move and compress the depth sensor 688. The encoded depth position given by the (x) external pressure msb 685 and the (x) external pressure lsb 684 changes from 685,684=11 (surface) to 685,684=10 (submerged) then to 685,684=00 (at set depth) and to 685,684=01 (too deep).

FIG. 36 shows various cavities and the corresponding input and output connections with the respective logic components in place in a different position than as seen on FIG. 35 and from a different point of view to provide additional detail on the implemented logic functions.

When the AND 1 main 619 is high (619=1) the AND gate 583a moves towards the edge of the AND 1 cavity 617 compressing the logic spring 686a into the AND 1 aux 618 causing the AND gate 583a to be in its active position (583a↔1). The connections in the AND gate 583a isolate the AND 1 clear 622 and connect the AND 1 output 621 to the AND 1 input 620 (621=620). As in this case 619=1, then 621=620, as needed to implement 621=619∧620.

When the AND 2 main 625 is high (625=1) the AND gate 583b moves towards the edge of the AND 2 cavity 623 compressing the logic spring 686b into the AND 2 aux 624 causing the AND gate 583b to be in its active position (¬583b↔1). The AND gate 583b is installed in a flipped position compared to AND gate 583*a* so in this position, the connections in the AND gate 583*b* isolate the AND 2 input 626 and connect the AND 2 output 627 to the AND 2 clear 628 that is connected to ground (627=628=0). In this example, 625=1, then ¬625=0, resulting in 627=0, regardless of 626 as needed to implement 627=¬625∧626.

The AND 3 main 631 supplies the main input to the OR gate 579*a*. One among four options: AND 3 OR input 1 632, AND 3 OR input 2 633, AND 3 OR input 3 634 or AND 3 OR input 4 635 is needed to provide the other logic input to the OR gate 579*a*. For simplicity, it is assumed that AND 3 OR input 1 632 is the selected second input to the OR gate 579*a*. In this example, 631=1 and 632=0, the OR gate 579*a* is pushed against the AND gate 583*c* moving it towards the edge of the AND 3 cavity 629 compressing the logic spring 686*c* into the AND 3 aux 630 causing both the OR gate 579*a* and the AND gate 583*c* to be in their active positions (579*a*↔1; 583*c*↔1). The connections in the AND gate 583*c* isolate the AND 3 clear 638 and connect the AND 3 output 637 to the AND 3 input 636 (637=636). Since in this example 631=1 and 632=0, then 631∨632=1 producing 637=(631∨632)∧636=636.

The SEL 1 main 641 supplies the main input to the OR gate 579*b*. One among four options: SEL 1 OR input 1 642, SEL 1 OR input 2 643, SEL 1 OR input 3 644, SEL 1 OR input 4 645 is needed to provide the other logic input to the OR gate 579*b*. For simplicity, it is assumed that SEL 1 OR input 1 642 is the selected second input to the OR gate 579*b*. In this example, 641=0 and 642=1, as a result the high pressure at SEL 1 OR input 1 642 pushes the OR gate 579*b* and the SEL gate 589*a* to opposite sides of the SEL 1 cavity 639. The OR gate 579*b* moves to its rest position (579*b*↔0) and the SEL gate 589*a* moves to its active position (589*a*↔1) compressing the logic spring 686*d* into the SEL 1 aux 640. The connections in the SEL gate 589*a* isolate the SEL 1 clear 1 648 and connect the SEL 1 output 1 647 to the SEL 1 input 1 646 (647=646). The connections in the SEL gate 589*a* isolate the SEL 1 input 2 649 and connect the SEL 1 output 2 650 to SEL 1 clear 2 651 that is connected to ground (650=651=0). Since in this example 641=0 and 642=1, then 641∨642=1. As a result, the outputs become: 647=(641∨642)∧646=646; 650=¬(641∨642)∧649=0.

The XOR gate 596 is kept in place by two logic long springs 687*a* and 687*b*. When the XOR signal 1 653 is low (653=0) and the XOR signal 2 654 is high (654=1) the XOR gate 596 moves to the edge of the XOR cavity 652 where the input signal is low (XOR signal 1 653) (596↔−1). The XOR gate connections isolate the XOR clear 1 657 that is connected to ground (657=0) and connect the XOR output 1 656 to the XOR input 1 655 that is connected to high (656=655=1) producing 656=653⊗654=1. The XOR gate connections also isolate the XOR input 2 658 that is connected to high (658=1) and connect the XOR output 2 659 to the XOR clear 2 660 that is connected to ground (659=660=0) producing 659=653=654=0. If XOR signal 1 653 is high (653=1) and the XOR signal 2 654 is low (654=0) the XOR gate 596 moves to the other edge of the XOR cavity 652 (596↔1) aligning an equivalent set of connections to the input and output pipes producing the same results: 656=653⊗654=1; 659=653=654=0.

Because no spring is installed, appropriate connections must be in place so that SEL 2 aux 662 is supplied with the negated main input (662=¬663) so that as indicated in FIG. 36 when the SEL 2 main 663 is high (663=1), the SEL 2 aux 662 is low (662=0). The SEL gate 589*b* is shifted inside the SEL 2 cavity 661 all the way towards the SEL 2 aux 662 causing the SEL gate 589*b* to be in its active position (589*b*↔1). The connections in the SEL gate 589*b* connect the SEL 2 input 1 664 to the SEL 2 output 1 665 (664=665). At the same time, the connections in the SEL gate 589*b* isolate the SEL 2 input 2 666 and the SEL 2 output 2 667 (as there are no connections on the top of the SEL 2 cavity 661). As at any time, regardless of the position of the SEL gate 589*b*, one input is always isolated and there are no top connections that could cause a short circuit between a signal with different polarity and the other input through the SEL gate 589*b* connections, the SEL 2 output connection 668 can be constructed connecting outputs 665 and 667 producing a combined output.

$$668=(\neg 663 \land 666) \lor (663 \land 664).$$

If inputs 664 and 666 are made complementary (666=¬664), $$668=(\neg 663 \land \neg 664) \lor (663 \land 664), \text{ or } 668=663=664;$$
$$668=663 \otimes 666.$$

When the SW main 671 is high (671=1) the SW gate 602 is pushed towards the edge of the SW cavity 669, compressing the logic spring 686*e* into the SW aux 670 causing the SW gate 602 to be in its active position (602↔1). The connections in the SW gate 602 connect the SW input 1 672 with the SW monitor 1 673 (672=673) and isolate the SW output 1 674. At the same time the connections in the SW gate 602 also connect the SW input 2 675 to the SW monitor 2 676 (675=676) and isolate the SW output 2 677. In this position, the monitors on top (673 and 676) remain connected and can exchange signals with the inputs (672 and 675 respectively) without interfering with outputs (674 and 677 respectively) that are isolated.

The depth external water pressure pipe 679 injects water at the external pressure into the depth sensor cavity 678 pushing the depth detector 689 against the depth sensor 688 compressing the air inside the depth sensor 688 until equilibrium is reached. Any changes in the external water pressure will cause the depth detector 689 to move accordingly until a new equilibrium position is reached. If a slot in the depth detector 689 aligns with a particular input on the top, the signal in that input is passed to the output below. The depth detector input guard 691 allows water coming from the depth external water pressure pipe 679 to enter the depth sensor cavity 678 even when the depth detector 689 is at the end of its excursion. The depth detector rubber grid 690 envelops all slots and the main body of the depth detector 689 isolating each slot so that fluid passing through a slot does not leak into other slots.

In the position drawn in FIG. 36, the depth lsb high pressure slot 1 692 is not aligned with the depth lsb high pressure 681 that has a high pressure signal (681=1). The depth lsb high pressure slot 2 694 is isolated and has no effect. The depth lsb gnd slot 693 is aligned with the depth lsb gnd 680 that has a low pressure signal (680=0). The output signal passed into the (x) external pressure lsb 684 is low (684=680=0). The depth msb high pressure slot 695 is aligned with the depth msb high pressure 682 that has a high pressure signal (682=1). The depth msb gnd slot 696 is not aligned with the depth msb gnd 683 that has a low pressure signal (683=0). The output signal passed into the (x) external pressure msb 685 is high (685=682=1). The encoded depth position is 685,684=10 (submerged).

As the reactor node continues to submerge, the external water pressure increases causing the depth detector 689 to move and further compress the depth sensor 688. The encoded depth position given by the (x) external pressure msb 685 and the (x) external pressure lsb 684 changes from

685,684=11 (surface) to 685,684=10 (submerged) then to 685,684=00 (at set depth) and to 685,684=01 (too deep).

FIG. 41 to FIG. 48 refer to the operation of the LFSR assembly.

FIG. 41 shows the components of the LFSR assembly in the disabled state. The LFSR layer a 698 is depicted as reference to ascertain the relative position of the various components involved.

The (z) zero in msb 720 is low (720=0) causing: 1) the logic spring 686*b* to extend and push the AND gate 583*b* to its rest position (583*b*↔0) connecting the register signal zk 722 to ground (722=0) through the zk cavity clear and isolating the (k) clock in msb 719; 2) the logic spring 686*d* to extend and push the zero gate 734 to its rest position (734↔0).

The (m) master/slave in msb 721 is high (721=1) pushing the AND gate 583*a* to its active position (~583*a*↔1) compressing the logic spring 686*a* and connecting the register signal mz 723*a* to ground (723*a*=0) through the mz cavity clear causing the other end of the register signal mz 723*b* to feed a low pressure signal (0) into both inputs of the SEL gate 589.

In its rest position, the zero gate 734 connects each register zero set 733*a*, . . . , 733*g* that are all connected to the LFSR high pressure feed 703 to the corresponding register input high 746*a*, . . . , 746*g* causing all to be high (746*a*=733*a*=1, . . . , 746*g*=733*g*=1). Additionally, in the rest position, each zero gate top hole 738*a*, . . . , 738*g* of the zero gate 734 connects the corresponding register zero clear that are all connected to the LFSR gnd layer to the corresponding register input low 747*a*, . . . , 747*g* causing all to be low (747*a*=0, . . . , 747*g*=0) (see FIG. 38). As a result, all register gates are pushed up to the initial register position 1111111, regardless of the position of the memory gates (arbitrarily drawn in the memory position 1000011).

As 722=0, the logic spring 686*c* pushes the SEL gate 589 to its rest position (589↔0) connecting: 1) the zkm cavity clear to the register signal kzm 725 (725=0); 2) the register signal mz 723*b* to the register signal ¬kzm 724*a* (724*a*=723*b*). As 723*b*=723*a*=0⇒724*b*=724*a*=0, a low value (0) is supplied to the register gate low 759*a* and all other register gates until past the register gate high 764*g* and made available to further use by additional logic (724*c*=724*b*=724*a*=0).

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to all memory gates up to memory gate 748*f* at all times.

Counting from left to right, for n=1 to 6, register gate n forwards the register signal ¬kzm 724*b* and the register gnd rail 726 to register gate n+1.

For n=1 to 7, register gate n branches the signal coming through the register signal ¬kzm 724*b* to its memory feed high if it is in the high position (1) or to its memory feed low if it is in the low position (0). At the same time, register gate n branches the low pressure signal coming through the register gnd rail 726 to its memory feed low if it is in the high position (1) or to its memory feed high if it is in the low position (0).

For n=1 to 7, memory feed high n is connected to memory input high n that terminates at the bottom of memory cavity n and memory feed low n is connected to memory input low n that terminates at the top of memory cavity n (see FIG. 40). A register gate n in the high position (1) routes 724*b* into memory input high n and routes 726=0 into memory input low n and a register gate n in the low position (0) routes 724*b* into memory input low n and routes 726=0 into memory input high n.

As 724*b*=0, the signals routed into each memory input high and each memory input low are low and the memory gates 748*a*, . . . , 748*g* remain stationary.

The (y) unit ready 730*a* feeding the first register gate, register gate low 759*a* is high (730*a*=1) but not all seven register gates of the installed 7 bit address (0011111) are properly aligned: register gate high 764*c*, . . . , 764*g* are properly aligned, but register gate low 759*a* and register gate low 759*b* are not properly aligned. The high feed line is interrupted and the (y) unit ready 730*b* is connected to ground (730*b*=0) by register gate low 759*b*.

Both outputs of the LFSR assembly are low (724*c*=0; 730*b*=0) and the transmission of the current alarm condition of the unit back to the central monitoring is disabled.

The summary of FIG. 41 is:

721=1⇒~583*a*↔1
720=0⇒583*b*↔0; 734↔0; 589↔0
Memory Position unchanged: 1000011
Register Position set to: 1111111
724*c*=0; 730*b*=0⇒Tx disabled.

FIG. 42 shows the components of the LFSR assembly in the zero state. The LFSR layer a 698 is depicted as reference to ascertain the relative position of the various components involved.

The (z) zero in msb 720 is high (720=1) causing: 1) the AND gate 583*b* to be pushed to its active position (583*b*↔1) compressing the logic spring 686*b* and connecting the register signal zk 722 to the (k) clock in msb 719 (722=719); 2) the zero gate 734 to move to its active position (734↔1) compressing the logic spring 686*d*.

The (m) master/slave in msb 721 is low (721=0) causing the logic spring 686*a* to extend and push the AND gate 583*a* to its rest position (~583*a*↔0) connecting the register signal mz 723*a* to the (z) zero in msb 720 (723*a*=720=1). The other end of the register signal mz 723*b* then feeds a high value (1) into both inputs of the SEL gate 589.

In its active position, the zero gate 734 connects each register input low 747*a*, . . . , 747*g* to the respective carry output low 745*a*, . . . , 745*g* producing the connections (747*a*=745*a*, . . . , 747*g*=745*g*). Additionally, in the active position, each zero gate top hole 738*a*, . . . , 738*g* of the zero gate 734 connects the corresponding register input high 746*a*, . . . , 746*g* to the respective carry output high producing the connections (746*a*=744*a*, . . . , 746*g*=744*g*) (see FIG. 39).

The (k) clock in msb 719 is low (719=0) resulting in 722=719=0, allowing the logic spring 686*c* to push the SEL gate 589 to its rest position (589↔0) connecting: 1) the zkm cavity clear to the register signal kzm 725 (725=0); 2) the register signal mz 723*b* to the register signal ¬kzm 724*a* (724*a*=723*b*). As 723*b*=723*a*=720=1⇒724*b*=724*a*=1, a high value (1) is supplied to the register gate low 759*a* and all other register gates until past the register gate high 764*g* and is made available to further use by additional logic (724*c*=724*b*=724*a*=1).

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to all memory gates up to memory gate 748*f* at all times.

Counting from left to right, for n=1 to 6, register gate n forwards the register signal ¬kzm 724*b* and the register gnd rail 726 to register gate n+1.

For n=1 to 7, register gate n branches the signal coming through the register signal ¬kzm 724*b* to its memory feed high if it is in the high position (1) or to its memory feed low if it is in the low position (0). At the same time, register gate n branches the low pressure signal coming through the register gnd rail 726 to its memory feed low if it is in the high position (1) or to its memory feed high if it is in the low position (0).

For n=1 to 7, memory feed high n is connected to memory input high n that terminates at the bottom of memory cavity n and memory feed low n is connected to memory input low n that terminates at the top of memory cavity n (see FIG. 40). A register gate n in the high position (1) routes 724*b* into memory input high n and routes 726=0 into memory input low n and a register gate n in the low position (0) routes 724*b* into memory input low n and routes 726=0 into memory input high n.

As 724*b*=1, a register gate n in the high position (1) forces memory gate n to move up to the high position (1) and a register gate n in the low position (0) forces memory gate n to move down to the low position (0). The 7-bit register position is copied into the 7-bit memory position. As in FIG. 42 the register position is 1111111, the memory position is set to 1111111 (memory gates 748*a*, . . . , 748*g* move to the top of their cavities).

As 725=0, the signals routed into each register input high and each register input low are low and the register gates remain stationary.

The (y) unit ready 730*a* feeding the first register gate, register gate low 759*a* is high (730*a*=1) but not all seven register gates of the installed 7 bit address (0011111) are properly aligned: register gate high 764*c*, . . . , 764*g* are properly aligned, but register gate low 759*a* and register gate low 759*b* are not properly aligned. The high feed line is interrupted and the (y) unit ready 730*b* is connected to ground (730*b*=0) by register gate low 759*b*.

One of the outputs of the LFSR assembly is low (724*c*=1; 730*b*=0) and the transmission of the current alarm condition of the unit back to the central monitoring is disabled.

The summary of FIG. 42 is:
721=0⇒~583*a*↔0
720=1⇒583*b*↔1; 734↔1
719=0; 720=1⇒589↔0
Memory Position set to: 1111111
Register Position unchanged: 1111111
724*c*=1; 730*b*=0⇒Tx disabled.

FIG. 43 shows the components of the LFSR assembly in normal operating state. The LFSR layer a 698 is depicted as reference to ascertain the relative position of the various components involved.

The (z) zero in msb 720 is high (720=1) causing: 1) the AND gate 583*b* is pushed to its active position (583*b*↔1) compressing the logic spring 686*b* and connecting the register signal zk 722 to the (k) clock in msb 719 (722=719); 2) the zero gate 734 to move to its active position (734↔1) compressing the logic spring 686*d*.

The (m) master/slave in msb 721 is low (721=0) causing the logic spring 686*a* to extend and push the AND gate 583*a* to its rest position (~583*a*↔0) connecting the register signal mz 723*a* to the (z) zero in msb 720 (723*a*=720=1). The other end of the register signal mz 723*b* then feeds a high value (1) into both inputs of the SEL gate 589.

In its active position, the zero gate 734 connects each register input low 747*a*, . . . , 747*g* to the respective carry output low 745*a*, . . . , 745*g* producing the connections (747*a*=745*a*, . . . , 747*g*=745*g*). Additionally, in the active position, each zero gate top hole 738*a*, . . . , 738*g* of the zero gate 734 connects the corresponding register input high 746*a*, . . . , 746*g* to the respective carry output high producing the connections (746*a*=744*a*, . . . , 746*g*=744*g*) (see FIG. 39).

The (k) clock in msb 719 is high (719=1) resulting in 722=719=1, pushing the SEL gate 589 to its active position (589↔1) compressing the logic spring 686*c* and connecting: 1) the zkm cavity clear to the register signal ¬kzm 724*a* (724*a*=724*b*=724*c*=0); 2) the register signal mz 723*b* to the register signal kzm 725 (725=723*b*). As 723*b*=723*a*=720=1⇒725=1, a high value (1) is supplied to the memory gates 748*a*, . . . , 748*f*

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to the memory gates 748*a*, . . . , 748*f* at all times.

Counting from left to right, for n=1 to 5, memory gate n forwards the register signal kzm 725 and the memory gnd rail 727 to memory gate n+1.

For n=1 to 6, memory gate n branches the signal coming through the register signal kzm 725 to its twin under connection if it is in the high position (1) or to its twin upper connection if it is in the low position (0). At the same time, memory gate n branches the signal coming through the memory gnd rail 727 to its twin upper connection if it is in the high position (1) or to its twin under connection if it is in the low position (0).

For n=1 to 6, twin under connection n is connected to carry output high n+1 and then through the zero gate to register input high n+1 that terminates at the bottom of register cavity n+1 and twin upper connection n is connected to carry output low n+1 and then through the zero gate to register input low n+1 that terminates at the top of register cavity n+1 (see FIG. 39).

For n=1 to 6, a memory gate n in the high position (1) routes 725 into register input high n+1 and routes 727=0 into register input low n+1 and a memory gate n in the low position (0) routes 725 into register input low n+1 and routes 727=0 into register input high n+1. As 725=1, a memory gate n in the high position (1) forces register gate n+1 to move up to the high position (1) and a memory gate n in the low position (0) forces register gate n+1 to move down to the low position (0) copying the first 6 bits of the 7 bit memory position into the last 6 bits of the 7 bit register position.

The first bit of the 7-bit register position is determined by an XOR function of bits 6 and 7 of the 7-bit memory position (1=6⊗7). The upper XOR input connects twin upper connection 6 to twin upper connection 7 and the lower XOR input connects twin under connection 6 to twin under connection 7 (see FIG. 39).

On FIG. 43, as memory gate 748*f* (memory gate 6) is in the high position (1), the low pressure signal coming from the memory gnd rail 727 passes to the upper XOR input through the memory gate up hole 754*f* and then as memory gate 748*g* (memory gate 7) is also in the high position (1), the signal coming from the memory gnd rail 727 continues through the memory gate up hole 754*g* to the XOR output high 739 producing (739=727=0). Similarly, as memory gate 748*f* (memory gate 6) is in the high position (1), the high pressure signal coming from the register signal kzm 725 passes to the lower XOR input and as memory gate 748*g* (memory gate 7) is also in the high position (1), the signal terminates at the XOR output low 740 producing (740=725=1).

The XOR output high 739 is connected to the carry output high 1 and then through the zero gate at zero gate top hole

738a to register input high 1 that terminates at the bottom of register cavity. The XOR output low 740 is connected to the carry output low 1 (745a) and then through the zero gate to register input low 1 that terminates at the top of register cavity 1.

As 740=1 and 739=0, the register gate low 759a is moved down to the low position (0). The memory position 1111111 produces the register position 0111111.

As register signal ¬kzm 724b=0, the signals routed from the register gates into each memory input high and each memory input low are low and the memory gates remain stationary.

The (y) unit ready 730a feeding the first register gate, register gate low 759a is high (730a=1) but not all seven register gates of the installed 7 bit address (0011111) are properly aligned: register gate low 759a and register gate high 764c, . . . , 764g are properly aligned, but register gate low 759b is not properly aligned. The high feed line is interrupted and the (y) unit ready 730b is connected to ground (730b=0) by register gate low 759b.

Both outputs of the LFSR assembly are low (724c=0; 730b=0) and the transmission of the current alarm condition of the unit back to the central monitoring is disabled.

The summary of FIG. 43 is:
721=0 ⇒~583a↔0
720=1⇒583b↔1; 734↔1
719=1; 720=1⇒589↔1
Memory Position unchanged 1111111
Register Position set to 0111111
724c=0; 730b=0⇒Tx disabled.

FIG. 44 shows the components of the LFSR assembly in normal operating state. The LFSR layer a 698 is depicted as reference to ascertain the relative position of the various components involved. FIG. 44 and FIG. 42 differ in the memory position and register position.

The (z) zero in msb 720 is high (720=1) causing: 1) the AND gate 583b to be pushed to its active position (583b↔1) connecting the register signal zk 722 to the (k) clock in msb 719 (722=719); 2) the zero gate 734 to move to its active position (734↔1).

The (m) master/slave in msb 721 is low (721=0) causing the AND gate 583a to be in its rest position (~583a↔0) connecting the register signal mz 723a to the (z) zero in msb 720 (723a=720=1). The other end of the register signal mz 723b then feeds a high value (1) into both inputs of the SEL gate 589.

The (k) clock in msb 719 is low (719=0) causing 722=719=0, resulting in the SEL gate 589 to be in its rest position (589↔0) connecting: 1) the zkm cavity clear to the register signal kzm 725 (725=0); 2) the register signal mz 723b to the register signal ¬kzm 724a (724a=723b). As 723b=723a=720=1⇒724b=724a=1, a high value (1) is supplied to the register gate low 759a and all other register gates until past the register gate high 764g and is made available to further use by additional logic (724c=724b=724a=1).

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to memory gates 748a, . . . , 748f at all times.

As 724b=1, a register gate n in the high position (1) forces memory gate n to move up to the high position (1) and a register gate n in the low position (0) forces memory gate n to move down to the low position (0). The 7-bit register position is copied into the 7-bit memory position. As in FIG. 44 the register position is 0111111, the memory position is set to 0111111.

As 725=0, the signals routed into each register input high and each register input low are low and the register gates remain stationary.

The (y) unit ready 730a feeding the first register gate, register gate low 759a is high (730a=1) but not all seven register gates of the installed 7 bit address (0011111) are properly aligned: register gate low 759a and register gate high 764c, . . . , 764g are properly aligned, but register gate low 759b is not properly aligned. The high feed line is interrupted and the (y) unit ready 730b is connected to ground (730b=0) by register gate low 759b.

One of the outputs of the LFSR assembly is low (724c=1; 730b=0) and the transmission of the current alarm condition of the unit back to the central monitoring is disabled.

The summary of FIG. 44 is:
721=0 ⇒~583a↔0
720=1⇒583b↔1; 734↔1
719=0; 720=1⇒589↔0
Memory Position set to: 0111111
Register Position unchanged: 0111111
724c=1; 730b=0⇒LSFR disabled.

FIG. 45 shows the components of the LFSR assembly in normal operating state. The LFSR layer a 698 is depicted as reference to ascertain the relative position of the various components involved. FIG. 45 and FIG. 43 differ in the memory position and register position.

The (z) zero in msb 720 is high (720=1) causing: 1) the AND gate 583b to be in its active position (583b↔1) connecting the register signal zk 722 to the (k) clock in msb 719 (722=719); 2) the zero gate 734 to move to its active position (734↔1).

The (m) master/slave in msb 721 is low (721=0) causing the AND gate 583a to be in its rest position (~583a↔0) connecting the register signal mz 723a to the (z) zero in msb 720 (723a=720=1). The other end of the register signal mz 723b then feeds a high value (1) into both inputs of the SEL gate 589.

The (k) clock in msb 719 is high (719=1) resulting in 722=719=1, pushing the SEL gate 589 to its active position (589↔1) and connecting: 1) the zkm cavity clear to the register signal ¬kzm 724a (724a=724b=724c=0); 2) the register signal mz 723b to the register signal kzm 725 (725=723b). As 723b=723a=720=1⇒725=1, a high value (1) is supplied to the memory gates 748a, . . . , 748f

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to the memory gates 748a, . . . , 748f at all times.

For n=1 to 6, a memory gate n in the high position (1) forces register gate n+1 to move up to the high position (1) and a memory gate n in the low position (0) forces register gate n+1 to move down to the low position (0) copying the first 6 bits of the 7 bit memory position into the last 6 bits of the 7 bit register position.

The first bit of the 7-bit register position is determined by an XOR function of bits 6 and 7 of the 7-bit memory position (1=6⊗7). The memory gate 748f (memory gate 6) is in the high position (1), the low pressure signal coming from the memory gnd rail 727 passes to the upper XOR input through the memory gate up hole 754f and then as memory gate 748g (memory gate 7) is also in the high position (1), the signal coming from the memory gnd rail 727 continues through the memory gate up hole 754g to the XOR output high 739 producing (739=727=0). Similarly, as memory gate 748f (memory gate 6) is in the high position (1), the high pressure signal coming from the register signal kzm 725 passes to the lower XOR input and as memory gate 748g (memory gate 7) is in the high position (1), the signal terminates at the XOR output low 740 producing (740=725=1).

As 740=1 and 739=0, the register gate low 759a is moved down to the low position (0). The memory position 0111111 produces the register position 0011111.

As register signal ¬kzm 724b=0, the signals routed into each memory input high and each memory input low are low and the memory gates remain stationary.

The (y) unit ready 730a feeding the first register gate, register gate low 759a is high (730a=1). As all seven register gates of the installed 7 bit address (0011111) are properly aligned, the high feed line goes uninterrupted through register gate low 759a, 759b and register gate high 764c, . . . , 764g and the (y) unit ready 730b remains high (730b=1).

One of the outputs of the LFSR assembly is low (724c=0; 730b=1) and the transmission of the current alarm condition of the unit back to the central monitoring is disabled.

The summary of FIG. 45 is:
721=0 ⇒~583a↔0
720=1⇒583b↔1; 734↔1
719=1; 720=1⇒589↔1
Memory Position unchanged 0111111
Register Position set to 0011111
724c=0; 730b=1⇒Tx disabled.

FIG. 46 shows the components of the LFSR assembly in normal operating state. The LFSR layer a 698 is depicted as reference to ascertain the relative position of the various components involved. FIG. 46, FIG. 44 and FIG. 42 differ in the memory position and register position.

The (z) zero in msb 720 is high (720=1) causing: 1) the AND gate 583b to be pushed to its active position (583b↔1) connecting the register signal zk 722 to the (k) clock in msb 719 (722=719); 2) the zero gate 734 to move to its active position (734↔1).

The (m) master/slave in msb 721 is low (721=0) causing the AND gate 583a to be in its rest position (~583a↔0) connecting the register signal mz 723a to the (z) zero in msb 720 (723a=720=1). The other end of the register signal mz 723b then feeds a high value (1) into both inputs of the SEL gate 589.

The (k) clock in msb 719 is low (719=0) causing 722=719=0, resulting in the SEL gate 589 to be in its rest position (589↔0) connecting: 1) the zkm cavity clear to the register signal kzm 725 (725=0); 2) the register signal mz 723b to the register signal ¬kzm 724a (724a=723b). As 723b=723a=720=1⇒724b=724a=1, a high value (1) is supplied to the register gate low 759a and all other register gates until past the register gate high 764g and is made available to further use by additional logic (724c=724b=724a=1).

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to memory gates 748a, . . . , 748f at all times.

As 724b=1, a register gate n in the high position (1) forces memory gate n to move up to the high position (1) and a register gate n in the low position (0) forces memory gate n to move down to the low position (0). The 7-bit register position is copied into the 7-bit memory position. As in FIG. 46 the register position is 0011111, the memory position is set to 0011111.

As 725=0, the signals routed into each register input high and each register input low are low and the register gates remain stationary.

The (y) unit ready 730a feeding the first register gate, register gate low 759a is high (730a=1). As all seven register gates of the installed 7 bit address (0011111) are properly aligned, the high feed line goes uninterrupted through register gate low 759a, 759b and register gate high 764c, . . . , 764g and the (y) unit ready 730b remains high (730b=1).

Both outputs of the LFSR assembly are high (724c=1; 730b=1) enabling the transmission of the current alarm condition of the unit back to the central monitoring.

The summary of FIG. 46 is:
721=0 ⇒~583a↔0
720=1⇒583b↔1; 734↔1
719=0; 720=1⇒589↔0
Memory Position set to 0011111
Register Position unchanged 0011111
724c=1; 730b=1⇒Tx enabled.

FIG. 47 shows the components of the LFSR assembly in normal operating state. The LFSR layer a 698 is depicted as reference to ascertain the relative position of the various components involved. FIG. 47, FIG. 46, FIG. 44 and FIG. 42 differ in the memory position and register position.

FIG. 47 is supplied to illustrate the progression of the linear feedback shift register sequence to the point that will produce a 1 instead of a 0 for the next register update.

The (z) zero in msb 720 is high (720=1) causing: 1) the AND gate 583b to be pushed to its active position (583b↔1) connecting the register signal zk 722 to the (k) clock in msb 719 (722=719); 2) the zero gate 734 to move to its active position (734↔1).

The (m) master/slave in msb 721 is low (721=0) causing the AND gate 583a to be in its rest position (~583a↔0) connecting the register signal mz 723a to the (z) zero in msb 720 (723a=720=1). The other end of the register signal mz 723b then feeds a high value (1) into both inputs of the SEL gate 589.

The (k) clock in msb 719 is low (719=0) causing 722=719=0, resulting in the SEL gate 589 to be in its rest position (589↔0) connecting: 1) the zkm cavity clear to the register signal kzm 725 (725=0); 2) the register signal mz 723b to the register signal ¬kzm 724a (724a=723b). As 723b=723a=720=1⇒724b=724a=1, a high value (1) is supplied to the register gate low 759a and all other register gates until past the register gate high 764g and is made available to further use by additional logic (724c=724b=724a=1).

The register gnd rail 726 is connected to the LFSR gnd layer (726=0) and supplies a low (0) signal to all register gates at all times. The memory gnd rail 727 is connected to the LFSR gnd layer (727=0) and supplies a low (0) signal to memory gates 748a, . . . , 748f at all times.

As 724b=1, a register gate n in the high position (1) forces memory gate n to move up to the high position (1) and a register gate n in the low position (0) forces memory gate n to move down to the low position (0). The 7-bit register position is copied into the 7-bit memory position. As in FIG. 47 the register position is 0000001, the memory position is set to 0000001.

As 725=0, the signals routed into each register input high and each register input low are low and the register gates remain stationary.

The (y) unit ready 730a feeding the first register gate, register gate low 759a is high (730a=1) but not all seven register gates of the installed 7 bit address (0011111) are properly aligned resulting in (y) unit ready 730b being low (730b=0).

One of the outputs of the LFSR assembly is low ($724c$=1; $730b$=0) and the transmission of the current alarm condition of the unit back to the central monitoring is disabled.

The summary of FIG. 47 is:
$721$=0 ⇒¬$583a$↔0
$720$=1⇒$583b$↔1; $734$↔1
$719$=0; $720$=1⇒$589$↔0
Memory Position set to 0000001
Register Position unchanged 0000001
$724c$=1; $730b$=0⇒Tx disabled.

FIG. 48 shows the components of the LFSR assembly in normal operating state. The LFSR layer a 698 is depicted as reference to ascertain the relative position of the various components involved. FIG. 48, FIG. 45 and FIG. 43 differ in the memory position and register position.

FIG. 48 is supplied to illustrate the progression of the linear feedback shift register sequence to the point that it produces a 1 instead of a 0 to update the position of the register gate low 759a as a result of the XOR function made by memory gate 748f and memory gate 748g.

The (z) zero in msb 720 is high ($720$=1) causing: 1) the AND gate 583b to be pushed to its active position ($583b$↔↔1) connecting the register signal zk 722 to the (k) clock in msb 719 ($722$=$719$); 2) the zero gate 734 to move to its active position ($734$↔1).

The (m) master/slave in msb 721 is low ($721$=0) causing the AND gate 583a to be in its rest position (~$583a$↔0) connecting the register signal mz 723a to the (z) zero in msb 720 ($723a$=$720$=1). The other end of the register signal mz 723b then feeds a high value (1) into both inputs of the SEL gate 589.

The (k) clock in msb 719 is high ($719$=1) resulting in $722$=$719$=1, pushing the SEL gate 589 to its active position ($589$↔1) and connecting: 1) the zkm cavity clear to the register signal ¬kzm 724a ($724a$=$724b$=$724c$=0); 2) the register signal mz 723b to the register signal kzm 725 ($725$=$723b$). As $723b$=$723a$=$720$=1⇒$725$=1, a high value (1) is supplied to the memory gates 748a, . . . , 748f.

The register gnd rail 726 is connected to the LFSR gnd layer ($726$=0) and supplies a low (0) signal to all register gates at all times. The memory gnd rail 727 is connected to the LFSR gnd layer ($727$=0) and supplies a low (0) signal to the memory gates 748a, . . . , 748f at all times.

For n=1 to 6, a memory gate n in the high position (1) forces register gate n+1 to move up to the high position (1) and a memory gate n in the low position (0) forces register gate n+1 to move down to the low position (0) copying the first 6 bits of the 7 bit memory position into the last 6 bits of the 7 bit register position.

The first bit of the 7-bit register position is determined by an XOR function of bits 6 and 7 of the 7-bit memory position (1=6⊗7). The memory gate 748f (memory gate 6) is in the low position (0), the high pressure signal coming from the register signal kzm 725 passes to the upper XOR input through the memory gate up hole 754f and then as memory gate 748g (memory gate 7) is in the high position (1), the signal coming from the register signal kzm 725 continues through the memory gate up hole 754g to the XOR output high 739 producing ($739$=$725$=1). Similarly, as memory gate 748f (memory gate 6) is in the low position (0), the low pressure signal coming from the memory gnd rail 727 passes to the lower XOR input and as memory gate 748g (memory gate 7) is in the high position (1), the signal terminates at the XOR output low 740 producing ($740$=$727$=0).

As $740$=0 and $739$=1, the register gate low 759a is moved up to the high position (1). The memory position 0000001 produces the register position 1000000.

As register signal ¬kzm $724b$=0, the signals routed into each memory input high and each memory input low are low and the memory gates remain stationary.

The (y) unit ready 730a feeding register gate low 759a is high ($730a$=1) but of all seven register gates of the installed 7 bit address (0011111) only register gate low 759b is properly aligned. The register gate low 759a is at the top of its cavity and register gate high 764c, 764g are all at the bottom of their respective cavities resulting in (y) unit ready 730b being low ($730b$=0).

Both of the outputs of the LFSR assembly are low ($724c$=0; $730b$=0) and the transmission of the current alarm condition of the unit back to the central monitoring is disabled.

The summary of FIG. 48 is:
$721$=0⇒¬$583a$↔0
$720$=1⇒$583b$↔1; $734$↔1
$719$=1; $720$=1⇒$589$↔1
Memory Position unchanged 0000001
Register Position set to 1000000
$724c$=0; $730b$=0⇒Tx disabled.

FIG. 62 and FIG. 63 show the i/o components from different points of view for better visualization and understanding of the workings of the i/o unit assembly. FIG. 62 is an isometric view of the i/o components of the i/o unit assembly with the i/o components cavities 425 drawn in phantom lines for reference. FIG. 63 is a top view of the i/o components of the i/o unit assembly also showing the i/o layer a 419 that serves as reference.

The only difference, apart from the point of view, is that FIG. 62 shows the i/o components cavities 425 as reference and FIG. 63 shows the i/o layer a 419 instead. For concision, the explanation is made once for both figures.

The $CO_2$ pressure controller device 460A controls and digitizes the $CO_2$ pressure inside the $CO_2$ body channel A producing the signal (n) internal $CO_2$ pressure lsb A. The $CO_2$ pressure controller device 460B controls and digitizes the $CO_2$ pressure inside the $CO_2$ body channel B producing the signal (n) internal $CO_2$ pressure lsb B. The $CO_2$ pressure controller device 460C controls and digitizes the $CO_2$ pressure inside the $CO_2$ body channel C producing the signal (n) internal $CO_2$ pressure lsb C. The $CO_2$ pressure controller device 460D controls and digitizes the $CO_2$ pressure inside the $CO_2$ body channel D producing the signal (n) internal $CO_2$ pressure lsb D. The $CO_2$ pressure controller device 460e controls and digitizes the $CO_2$ pressure inside the $CO_2$ body producing the signal (n) internal $CO_2$ pressure lsb e. The $CO_2$ is supplied by the (1) $CO_2$ resupply right and the (L) $CO_2$ resupply left that are interconnected inside the i/o unit assembly.

The water pressure controller device 467A controls and digitizes the water pressure inside the water body channel A producing the signals (i) internal water pressure msb A and (i) internal water pressure lsb A. The water pressure controller device 467B controls and digitizes the water pressure inside the water body channel B producing the signals (i) internal water pressure msb B and (i) internal water pressure lsb B. The water pressure controller device 467C controls and digitizes the water pressure inside the water body channel C producing the signals (i) internal water pressure msb C and (i) internal water pressure lsb C. The water pressure controller device 467D controls and digitizes the water pressure inside the water body channel D producing the signals (i) internal water pressure msb D and (i) internal water pressure lsb D. The ground pressure controller device 477 controls and digitizes the ground pressure inside the water body producing the signal (g) ground lsb.

The signal pressure controller device 483a is used to digitize the signal (k) clock in producing the signals (k) clock in msb and (k) clock in lsb. The (k) clock in msb is used to control the actuator mono 497a producing the output signal (K) clock out that regenerates (k) clock in. The signal pressure controller device 483b is used to digitize the signal (z) zero in producing the signals (z) zero in msb and (z) zero in lsb. The (z) zero in msb is used to control the actuator mono 497b producing the output signal (Z) zero out that regenerates (z) zero in. The signal pressure controller device 483c is used to digitize the signal (m) master/slave in producing the signals (m) master/slave in msb and (m) master/slave in lsb. The (m) master/slave in msb is used to control the actuator mono 497c producing the output signal (M) master/slave out that regenerates (m) master/slave in.

The signal pressure controller device 483d is used to digitize the signal (q) query in producing the signals (q) query in msb and (q) query in lsb. The actuator mono 497d is controlled by the (Q) query control that is a function of the (q) query in msb and other variables that are generated at the logic unit assembly producing the output signal (Q) query out. The signal pressure controller device 483e is used to digitize the signal (s) status in producing the signals (s) status in msb and (s) status in lsb. The actuator mono 497e is controlled by the (S) status control that is a function of the (s) status in msb and other variables that are generated at the logic unit assembly producing the digital output signal (S) status out. The signal pressure controller device 483f is used to digitize the signal (h) help in producing the signals (h) help in msb and (h) help in lsb. The actuator mono 497f is controlled by the (H) help control that is a function of the (h) help in msb and other variables that are generated at the logic unit assembly producing the digital output signal (H) help out (see FIG. 70).

The signal pressure controller device 483g is used to digitize the signal (r) reset in producing the signals (r) reset in msb and (r) reset in lsb. The actuator mono 497g is controlled by the (R) reset control that is a function of the (r) reset in msb and (r) reset in lsb generated at the logic unit assembly. The actuator mono 497g is installed flipped introducing an additional NOT function to complete the logic function that produces the output signal (R) reset out from the (R) reset control generated at the logic unit assembly R out=¬R=¬(¬r msb/\r lsb) (see FIG. 70).

The signal pressure controller device 483h is used to digitize the signal (v) dive in producing the signals (v) dive in msb and (v) dive in lsb. The (v) dive in msb is used to control the actuator mono 497h producing the digital output signal (V) dive out that regenerates (v) dive in. The signal pressure controller device 483i is used to digitize the air pressure in the pipes (u) air resupply right and (U) air resupply left that are interconnected inside the i/o unit assembly producing the signals (u) air resupply msb and (u) air resupply lsb. The signal pressure controller device 483j is used to digitize the water pressure in the pipes (w) water resupply right and (W) water resupply left that are interconnected inside the i/o unit assembly producing the signals (w) water resupply msb and (w) water resupply lsb. The actuator mono 497i is controlled by the (y) unit ready that is generated at the logic unit assembly producing the digital output signal (Y) unit ready out (see FIG. 70).

The actuator monos 497a, . . . , 497f, 497h, 497i are so installed that when they are in the active position (497$x$↔1; x=a, . . . , f, h, i) they compress the actuator spring and produce a corresponding high (1) output signal and when they are in the inactive position (497$x$↔0; x=a, . . . , f, h, i) they produce a corresponding low (0) output signal. The actuator mono 497g is installed flipped so when it is in its active position (~497g↔1) it compresses the actuator spring and produces a low (0) output signal and when it is in its inactive position (~497g↔0) it produces a high (1) output signal.

The actuator mono 497j is installed flipped introducing an additional NOT function to complete the logic function that controls the flag. The actuator mono 497j is controlled by the (F) raise flag control generated at the logic unit assembly producing the output signal (LF) lower flag LF=¬F that controls the flag through the flag pipe. When the actuator mono 497j is in its inactive position (~497j↔0) as drawn, it produces a high (1) output signal that causes the flag to lower and when it is in an active position (~497j↔1) it compresses the actuator spring and produces a low (0) output signal that causes the flag to raise (see FIG. 70).

The actuator mono 497k is installed flipped introducing an additional NOT function to complete the logic function that controls the water pump. The actuator mono 497k is controlled by the (P) stop water pump control that is generated at the logic unit assembly producing the output signal (RP) run water pump RP=¬P that controls the water pump through the pump feed pipe. When the actuator mono 497k is in its inactive position (~497k↔0) as drawn, it produces a high (1) output signal that enables water pumping and when it is in the active position (~497k↔1) it compresses the actuator spring and produces a low (0) output signal that stops water pumping (see FIG. 71).

The actuator dual 500A is controlled by the (O) open door control A that is generated at the logic unit assembly producing the output control signals to open or close the door and the $CO_2$ valve in pipe port A. The actuator dual 500B is controlled by the (O) open door control B that is generated at the logic unit assembly producing the output control signals to open or close the door and the $CO_2$ valve in pipe port B. The actuator dual 500C is controlled by the (O) open door control C that is generated at the logic unit assembly producing the output control signals to open or close the door and the $CO_2$ valve in pipe port C. The actuator dual 500D is controlled by the (O) open door control D that is generated at the logic unit assembly producing the output control signals to open or close the door and the $CO_2$ valve in pipe port D. The actuator duals in active positions (500B↔1, 500C↔1) compress their actuator springs and cause the respective doors and $CO_2$ valves to open and the actuator duals in inactive positions (500A↔0, 500D↔0) cause the respective doors and $CO_2$ valves to close (see FIG. 71).

The actuator dual 500e is controlled by the (v) dive in msb producing the output signals that supply power to the pump rotor assembly in the anchoring system causing the cable winch to turn clockwise or counterclockwise. When the actuator dual 500e is in its inactive position (500e↔0) as drawn, it causes the cable winch to turn counterclockwise allowing the reactor node to go to the surface. When the actuator dual 500e is in its active position (500e↔1), it compresses the actuator spring and causes the cable winch to turn clockwise forcing the reactor node to submerge. The actuator dual 500f is controlled by the (v) dive in msb producing the output signals to open or close the air vent valve through the air release open pipe and the air release close pipe. When the actuator dual 500f is in its inactive position (500e↔0) as drawn, it causes the air vent valve to close. When the actuator dual 500f is in its active position (500e↔1), it compresses the actuator spring and causes the air vent valve to open allowing air to vent to the environment to facilitate the submersion of the reactor node (see FIG. 70).

The actuator mono normally open 493 is controlled by the (E) dive disable control that is generated at the logic unit assembly enabling or disabling the control signals that supply the actuator dual 500e that in turn commands the cable winch to rotate clockwise or counterclockwise. When the actuator mono normally open 493 is in its active position (493↔1) as drawn, it compresses the actuator spring and disables the control signals stopping the cable winch and when the actuator mono normally open 493 is in its inactive position (493↔0), it enables the control signals allowing the cable winch to rotate (see FIG. 15 and FIG. 70).

The actuator mono normally closed 495 is controlled by the (R) reset control that is generated at the logic unit assembly. When the actuator mono normally closed 495 is in its inactive position (495↔0) as drawn, it disables the water pressure reset input and the CO2 pressure reset input as intended for normal operation of the reactor. When the actuator mono normally closed 495 is in its active position (495↔1), it compresses the actuator spring and enables the water pressure reset input and the CO2 pressure reset input allowing water pressure and CO2 pressure to build up in the reactor during a reset command (see FIG. 70).

A set of controller springs 491a, 491b, 491c, etc. is used to ensure that the CO2 pressure controller devices, the water pressure controller devices, the ground pressure controller device, and the signal pressure controller devices return to their idle positions in case of power failure. A set of actuator springs 506a, 506b, etc. is used to ensure that the actuator monos, the actuator duals, the actuator mono normally open, and the actuator mono normally closed return to their idle positions in case of power failure. This ensures that the reactor node goes into safe mode in case of power failure. Two logic springs 686a and 686a are used, one in each diagnose gate 609a and 609b respectively in conjunction with an activation signal to control if the reactor node operates in normal mode or in controlled mode using the diagnose device (see FIG. 64, FIG. 65, FIG. 65A, and FIG. 76).

Detail FIG. 65A shows the top of the logic unit assembly where the logic case left control connector 440 made of 10 connector small inserts identical to connector small inserts 384a and 384b is located. To improve the clarity of FIG. 65A and facilitate the explanation, the pipes that pass through the connector small inserts 384a and 384b of the logic case left control connector 440 that can be seen on FIG. 65 have not been drawn in detail FIG. 65A.

The diagnose gate face hole 1 612 and the diagnose gate side hole 1 613 are linked creating a 90 degree connection that joins the diagnose interface pipe 770 and the corresponding diagnose control pipe 771 and isolates the corresponding diagnose logic pipes 772 if they are aligned to that position. The diagnose gate through hole 2 614 and diagnose gate side hole 2 615 are linked creating a 3-way connection that joins the diagnose interface pipe 770, the corresponding diagnose control pipe 771, and the corresponding diagnose logic pipe 772 if they are aligned to that position. The diagnose gate 609a is so constructed that it has an odd number (21) of diagnose gate sections 611 and all odd positions counting from any extremity have a 90 degree connection and all even positions have a 3-way connection (see FIG. 33).

If the (j) maintenance job 768 signal is low (j=0) as drawn, the logic spring 686a pushes the diagnose gate 609a to the left in the opposite direction indicated by the arrow causing all diagnose interface pipes 770, diagnose control pipes 771, and diagnose logic pipes 772 to align with a position of the diagnose gate 609a that has a 3-way connection. This causes the i/o unit assembly to operate normally, receiving the logic signals generated inside the logic unit assembly that are also available to be monitored at the diagnose port.

If the (j) maintenance job 768 signal is high (j=1), it pushes the diagnose gate 609a to the right in the direction indicated by the arrow compressing the logic spring 686a and causing all diagnose interface pipes 770, diagnose control pipes 771, and diagnose logic pipes 772 to align with a position of the diagnose gate 609a that has a 90 degree connection isolating all diagnose logic pipes 772. This causes the i/o unit assembly to operate in controlled mode, receiving the logic signals generated by the diagnose device connected to the diagnose port.

FIG. 76 shows the diagnose device 825 attached to a reactor node. The diagnose device 825 uses the high pressure water supplied by the diagnose high pressure supply hose 829 and the low pressure water supplied by the diagnose ground supply hose 830 to generate the signals to perform its functions. A series of solenoid valves inside the diagnose device body 826 allows either high pressure water or low pressure water into each of the 22 individual flexible hoses of the diagnose band 828 to generate the digital signals that pass to the diagnose port through the diagnose connector 827 to collect data, monitor and control the reactor node.

FIG. 70 is a top view of the logic layer a 444 and the installed logic components. The depth detector 689 moving against the depth sensor 688 generates the (x) external pressure lsb 684 and the (x) external pressure msb 685 producing a 2 bit digital signal that encodes the current depth of the reactor node. The (x) external pressure lsb 684 is connected to the main input on the left and the (x) external pressure msb 685 is connected to the aux input on the right of the AND gate 583l that is not fitted with a logic spring. This arrangement causes the AND gate 583l to move to the left (as drawn) if the (x) external pressure lsb 684 is low and the (x) external pressure msb 685 is high and to the right if the (x) external pressure lsb 684 is high and the (x) external pressure msb 685 is low. If both the (x) external pressure lsb 684 and the (x) external pressure msb 685 are either low or high, the AND gate 583l remains stationary on its current position. The output of the AND gate 583l is a (OV) depth overshoot 804 signal that assumes a high value if the reactor node goes to a depth greater than the maximum depth envisaged encoded into the depth detector 689.

The main input of the AND gate 583a is connected to the (j) maintenance job 768 and the aux input is connected to the (OV) depth overshoot 804 (output of the AND gate 583l).

If the reactor node goes too deep so that the (OV) depth overshoot 804 is high (1), the AND gate 583a moves to the rest position and, as no logic spring is installed, stays there even after the dive overshoot situation is cleared until the (j) maintenance job 768 signal is high (1). This requires the intervention of a maintenance crew that will than inspect the reactor node for problems since it is not supposed to get to a depth that will cause a dive overshoot situation under normal circumstances (see FIG. 76).

Using the symbol ↑ as "set to 1" and the symbol ↓ as "reset to 0" (as in a set reset register) by the condition provided to the right of the symbol, the (OV) depth overshoot can be defined as: OV↑¬x msb/\x lsb; OV↓j.

With the exception of AND gate 583c that is fed with the (g) ground lsb 805 coming from the ground pressure controller device the remaining AND gates located at the beginning of the alarm chain, between AND gate 583b and AND gate 583d are fed with the digitized lsb input signals produced by their respective signal pressure controller devices coming from the i/o unit assembly into their respective main inputs. From left to right the signals supplied into the main inputs of AND gate 583*b* to AND gate 583*d* are: (s) status in lsb, (q) query in lsb, (m) master/slave in lsb, (z) zero in lsb, (k) clock in lsb, (g) ground lsb 805, (w) water resupply lsb, (u) air resupply lsb, (v) dive in lsb, (r) reset in lsb 801, (h) help in lsb.

The digitization law built into the signal pressure controller device produces a low lsb in case of a leak and a high lsb if no leak is detected. The ground pressure controller device produces a high lsb in case the ground pressure is within normal range and a low lsb in case the ground pressure exceeds the maximum ground operating pressure (see FIG. 32).

The four AND gates located at the end of the alarm chain (from right to left): AND gate 583*h*, AND gate 583*g*, AND gate 583*f*, and AND gate 583*e* are used to detect problems in the pipe ports A, B, C, and D respectively (see description in FIG. 71).

All input signals are fed into AND gates installed in the normal position. If an input signal is low (indicating a problem in a pipe port, a leak in a signal or that the ground pressure exceeded the operational range), the corresponding AND gate moves to its rest position and produces a low output that propagates down the chain. The final output of the arrangement is an (AL) alarm 798 signal that is high (1) if all AND gates are in the active position as drawn and low (0) if any of the AND gates moves to its rest position. AL=1 means the reactor node is operating normally and AL=0 indicates that at least one problem is present.

The (AL) alarm 798 signal is fed into the main input and a (h) help in msb 795*a* is fed into the side input of the AND gate 583*j* producing a (H) help control 803 output with the logic function $803=798 \wedge 795a$ or replacing the numbers for the signal names: $H = AL \wedge h\ msb$. This is used to produce a daisy chain of the alarm status of the reactor nodes up to the current one. Each reactor node receives the (h) help in from the previous reactor node in the chain and digitizes it into the (h) help in msb. The AND gate 583*j* produces (H) help control that is used to generate the (H) help out that is transmitted to the next reactor node. A high initial input is fed into the first reactor node and propagates along the chain until a reactor node has a problem causing the (AL) alarm to be low and resulting in (H) help control low. Subsequent reactor nodes receive a low (h) help in msb resulting in low (H) help control regardless of the local (AL) alarm.

A (s) status in msb 794 digitized from the (s) status in received from the previous reactor node is fed into the first input and the (h) help in msb 795*b* digitized from the (h) help in received from the previous reactor node is fed into the second input of the SEL gate 589*a*. The first and second clear inputs of the SEL gate 589*a* are not connected allowing the first and second outputs to be joined producing a single output (S) status control 796.

A (q) query in msb 797 digitized from the (q) query in received from the previous reactor node is fed into the first input and the (AL) alarm 798 is fed into the second input of the SEL gate 589*b*. The first and second clear inputs of the SEL gate 589*b* are not connected allowing the first and second outputs to be joined producing a single output (Q) query control 799.

The (y) unit ready 730 is fed into the main input and the register signal ¬kzm 724 is fed into the side input of the AND gate 583*i* producing as output the (TX) transmit signal 793. The (TX) transmit signal 793 is fed into the main inputs of the SEL gate 589*a* and the SEL gate 589*b*.

Using the compact notation m/s=1 if the signal (m) master/slave in msb matches the configuration of the reactor node (m=1 if the reactor node is configured as master or m=0 if the reactor node is configured as slave) and m/s=0 otherwise, the logic function produced is: $793=730 \wedge 724$ or replacing the numbers for the signal names: $TX = y \wedge \neg k\ msb \wedge z\ msb \wedge m/s$.

The (TX) transmit signal 793 is high (793=1) if the following conditions are simultaneously satisfied: a) m/s=1 (the unit type is correct); b) (z) zero in msb=1 (counting is enabled); c) (y) unit ready=1 (the reactor node address is selected); d) (k) clock in msb=0 (low clock cycle).

If 793=0, the SEL gate 589*a* and the SEL gate 589*b* produce as output the chain signals coming from the previous reactor node fed into their first inputs forwarding the messages received. If 793=1, the SEL gate 589*a* and the SEL gate 589*b* produce as output the local information fed into the second inputs. The implemented logic functions are: $796 = (\neg 793 \wedge 794) \vee (793 \wedge 795b)$; $799 = (\neg 793 \wedge 797) \vee (793 \wedge 798)$ or replacing the numbers for the signal names: $S = (\neg TX \wedge s\ msb) \vee (TX \wedge h\ msb)$; $Q = (\neg TX \wedge q\ msb) \vee (TX \wedge AL)$.

The (S) status control 796 and (Q) query control 799 signals encode the status of the currently selected reactor node as following: S,Q=1,1⇒no problem; S,Q=1,0⇒alarm in selected reactor node (local alarm); S,Q=0,1⇒alarm in one or more reactor nodes linked to the selected reactor node by the daisy chain help line (remote alarm); S,Q=0,0⇒local and remote alarm.

This is used as a means to expedite the polling of the reactor nodes in a farm. Each reactor node configured as master is connected to the end of a daisy chain that contains the reactor nodes configured as its slaves. When a master reactor node responds to the poll, if no alarm is present the monitoring system can proceed to the next master reactor node. If a remote alarm is present at a reactor node (master or slave) then the monitoring system checks the next reactor node in the daisy chain (the first slave in case of a master or the next address in case of a slave) to identify the troubled unit. If a local alarm (but no remote alarm) is present at a reactor node (master or slave) the monitoring system identifies the faulty unit and checks the next reactor node in the daisy chain to check if the alarm in the affected reactor node has prevented remote alarms from additional units from being detected.

In case no alarms are present, only the master reactor nodes need to be selected requiring a maximum of 127 addresses instead of a maximum of 16129 (up to 127 slaves may be attached to each of the 127 masters). In case one alarm is present, only the masters and the slaves of the affected master need to be selected, or a maximum of 127+127=258 addresses in the worst case (see FIG. 94).

The reset signal is active low so it has to be tested for leaks to avoid false commands. A (r) reset in msb 800 is fed into the main input and a (r) reset in lsb 801 is fed into the side input of the AND gate 583*k* producing a (R) reset control 802 output. The AND gate 583*k* is installed flipped producing: $802 = \neg 800 \wedge 801$ or replacing the numbers for the signal names: $R = \neg r\ msb \wedge r\ lsb$.

In case of a leak (r lsb=0) then R=0. If no leak is present (r lsb=1) and the reset signal is not active (r msb=1), then ¬r msb=0 and R=0. If no leak is present (r lsb=1) and the reset signal is active (r msb=0), then ¬r msb=0 and R=1. The (R) reset control is sent to the i/o unit assembly to control the actuator mono normally closed that enables the reset signals inside the reactor node. To regenerate the reset signal to the following reactor node an additional NOT function is required. This is achieved by flipping the actuator mono that produces the (R) reset out that is transmitted producing R out=¬R=¬(¬r msb∧r lsb) (see FIG. 62 and FIG. 63).

The high pressure supply 792c is fed into the first input and the (x) external pressure lsb 684 is channeled into the second input of the SEL gate 589c that is installed flipped to introduce a NOT function at the main input that is fed with the (x) external pressure msb 685. A (v) dive in msb 806a signal, that is high in case the reactor node is commanded to dive, is supplied into the main input of the SEL gate 589d. The first and second outputs of the SEL gate 589c are forwarded into the first and second inputs of the SEL gate 589d respectively producing a (pl) dive complete 807 in the first output and a (FE) flag enable control 808 in the second output of the SEL gate 589d. The logic functions produced are: 807=806a∧¬685; 808=¬806a∧684∧685 or replacing the numbers for the signal names: pl=v msb∧¬x msb; FE=¬v msb∧x lsb∧x msb.

The (pl) dive complete 807 is high in case the reactor node has been commanded to dive (806a=1) and the reactor node has reached or overshot the dive depth (¬685=1). The (FE) flag enable control 808 is high if the reactor node is commanded to stay at the surface (¬806a=1) and is currently at the surface (684,685=11). The (FE) flag enable control 808 is used to allow the flag to be raised only at the surface, protecting it from damage that could happen in the event that a fault occurs while the reactor node is submerged causing the flag to be raised and exposed to water movement (currents).

The (FE) flag enable control 808 is fed into the side input of the AND gate 583o that is installed flipped introducing a NOT function at its main input that is fed with the (AL) alarm 798. The resulting (F) raise flag control 780 has the logic function 780=¬798∧808 or replacing the numbers for the signal names: F=¬AL∧FE. The (F) raise flag control 780 is low (the flag remains stowed) if the (AL) alarm 798 is high (¬798=0) when there is no current active alarm or the (FE) flag enable control 808 is low (808=0) then the flag cannot be safely raised.

The (FE) flag enable control 808 is fed into the main input of the OR gate 579, the (pl) dive complete 807 is fed into the underside input of the OR gate 579 and the high pressure supply 792d is supplied into the side input of the AND gate 583m producing an output (E) dive disable control 809 that disables the movement of the cable winch with the following logic function: 809=(808∨807)∧792d=(808∨807)=(¬806a∧684∧685)∨(806a∧¬685). Replacing the numbers for the signal names: E=FE∨pl=(¬v msb∧x lsb∧x msb)∨(v msb∧¬x msb).

The (E) dive disable control 809 is sent to the i/o unit assembly to control the actuator mono normally open that stops the cable winch. The (E) dive disable control 809 is high (809=1) causing the actuator mono normally open to move to its active position stopping the cable winch if the reactor node has been commanded to dive and has reached or overshot the dive depth (806a A∧¬685=1) or the reactor node is commanded to stay at the surface and is at the surface (¬806a∧684∧685=1). Otherwise, the (E) dive disable control 809 is low (809=0) causing the actuator mono normally open to move to its rest position allowing the cable winch to move and dive the reactor node if (v) dive in msb=1 or allow it to come back to the surface if (v) dive in msb=0 (see FIG. 62 and FIG. 63).

A different suffix letter is used to differentiate between different relevant points of the same (v) dive in msb 806a, 806b signal that originates in the signal pressure controller device that digitizes the (v) dive in signal in the i/o unit assembly and continues into the logic unit assembly.

The (x) external pressure msb 685 is fed in the main input and the (v) dive in msb 806b is fed into the side input of the AND gate 583n producing as outputs the (IV) dive control 782 and the (T) vent air control 779. The logic function is: 782=779=685∧806b or replacing the numbers for the signal names: IV=T=x msb∧v msb. The (x) external pressure msb 685 is combined with the (v) dive in msb 806b as a backup strategy to prevent a dive overshoot. If (v) dive in msb 806b=1 commanding a dive and the (x) external pressure msb 685=1 indicating that the reactor node is at the surface or has not yet reached the designated depth then the (IV) dive control 782 and the (T) vent air control 779 are high 782=779=1. This causes the cable winch to rotate clockwise increasing the depth and the air vent valve to open allowing air accumulated in the reactor node to vent to the environment to facilitate the operation. When the designated depth is reached (x) external pressure msb 685=0 causes the (IV) dive control 782 and the (T) vent air control 779 to be low 782=779=0. At this point the (E) dive disable control 809 becomes high causing the actuator mono normally open to move to its active position stopping the rotation of the cable winch and placing the reactor node at the designated depth. As a backup, at the designated depth 782=779=0 causing the cable winch to change the rotation to counter clockwise and the air vent valve to close preventing more air from escaping into the environment. The backup strategy prevents the reactor node to dive further than intended should a failure interfere with the depth control system and the stopper placed at the anchor cable become loose (see FIG. 62 and FIG. 63).

FIG. 71 is a top view of the lower portion of the logic layer a 444 and the installed logic components with the connections outside the logic layer a 444 drawn in dashed lines to facilitate the visualization of the circuits of the signal leak alarm logic block and the pipe port management logic block (see FIG. 69). All components and connections drawn in FIG. 71 are also drawn in FIG. 70 that can be used as reference if necessary.

The output of the AND gate 583j is the ppA alarm 811a and the output of the AND gate 583i that is the output (pp) pipe port status 810Aa. The implemented functions are: 811a=777A∧776A; 810Aa=777A∧776A∧775A or using the signal names: ppA alarm=nA lsb∧iA lsb; ppA=nA lsb∧iA lsb∧iA msb.

The output of the AND gate 583m is the ppB alarm 812, the output of the AND gate 583n is the output (pp) pipe port status 810B and the output of AND gate 583o is the ppB alarm^ne 813a. The implemented functions are: 813a=777B∧776B∧777e; 810B=777B∧776B∧775B or using the signal names: ppB alarm^ne=nB lsb∧iB lsb∧ne lsb; ppB=nB lsb∧iB lsb∧iB msb.

The output of the AND gate 583p is the (pp) pipe port status 810Ca. The implemented function is: 810Ca=777C∧776C or using the signal names: ppC=nC lsb∧iC lsb.

The output of the AND gate 583s is the (pp) pipe port status 810Da. The implemented function is: 810Da=777D∧776D or using the signal names: ppD=nD lsb∧iD lsb.

The (O) open door control 778A has the following logic function: 778A=(¬810Ca∧815)∨(810Ca∧814) or replacing the numbers for the signal names: OA=(¬ppC∧¬ppB∧ppA∧ppD)∨(ppC∧¬ppB∧ppA).

The (O) open door control 778B has the following logic function: 778B=(¬810Ca∧816)∨(810Ca∧810B) or replacing the numbers for the signal names: OB=(¬ppC∧ppB∧ppD)∨(ppC∧ppB).

The (O) open door control 778D has the following logic function: 778D=(¬810B∧818)∨(810B∧817) or replacing the numbers for the signal names: OD=(¬ppB∧¬ppC∧ppD∧ppA)∨(ppB∧¬ppC∧ppD).

The (O) open door control 778C has the following logic function: 778C=(¬810B∧819)∨(810B∧810Ca) or replacing the numbers for the signal names: OC=(¬ppB∧ppC∧ppA)∨(ppB∧ppC).

The outputs of the AND gate 583za and the AND gate 583zb are combined producing the (P) stop water pump control 781 with logic function: 781=¬778C∧¬778D or replacing the numbers for the signal names: P=¬OC∧¬OD.

These functions implement the rerouting strategy for the reactor node opening or closing the appropriate pipe port doors and activating or deactivating the water pump depending on the current conditions. The pipe ports A or B work as input and the pipe ports C or D work as output. A pipe port where a leak is detected is unavailable. At least one input and one output must be available to allow operation otherwise all doors close. If operation is possible, the doors open and close according to the priority embedded into the functions and available pipe ports that are not in use remain in standby. In case operation is not possible (fault), available input pipe ports that cannot be connected to an output pipe port are blocked.

Table 3 summarizes the results of the implemented output functions OA OB OC OD P for each combination of input functions ppA ppB ppC ppD and the resulting operational status in each case.

TABLE 3

Truth table for implemented logic functions and resulting operational states

| pp BCAD | OB | OC | OA | OD | P | Priority | Open | Standby | Leak | Blocked | Water pump |
|---|---|---|---|---|---|---|---|---|---|---|---|
| 1111 | 1 | 1 | 0 | 0 | 0 | 1 | BC | AD | | | running |
| 1110 | 1 | 1 | 0 | 0 | 0 | 1 | BC | A | D | | running |
| 1101 | 1 | 1 | 0 | 0 | 0 | 1 | BC | D | A | | running |
| 1100 | 1 | 1 | 0 | 0 | 0 | 1 | BC | | AD | | running |
| 1011 | 1 | 0 | 0 | 1 | 0 | 2 | BD | A | C | | running |
| 1010 | 0 | 0 | 0 | 0 | 1 | fault | | | CD | BA | stop (no output) |
| 1001 | 1 | 0 | 0 | 1 | 0 | 2 | BD | | CA | | running |
| 1000 | 0 | 0 | 0 | 0 | 0 | fault | | | CAD | B | stop (no output) |
| 0111 | 1 | 1 | 1 | 0 | 0 | 3 | AC | D | B | | running |
| 0110 | 0 | 1 | 1 | 0 | 0 | 3 | AC | | BA | | running |
| 0101 | 0 | 0 | 0 | 0 | 1 | fault | | CD | BA | | stop (no input) |
| 0100 | 0 | 0 | 0 | 0 | 1 | fault | | C | BAD | | stop (no input) |
| 0011 | 0 | 0 | 1 | 1 | 0 | 4 | AD | | BC | | running |
| 0010 | 0 | 0 | 0 | 0 | 1 | fault | | | BCD | A | stop (no output) |
| 0001 | 0 | 0 | 0 | 0 | 1 | fault | | D | BCA | | stop (no input) |
| 0000 | 0 | 0 | 0 | 0 | 1 | fault | | | BCAD | | stop |

As seen on table 3 above, any valid combination of input and output pipe ports status will produce an operational state, with two pipe ports open and a running water pump. If sufficient problems occur to prevent normal operation, all pipe ports close and the water pump stops.

The eleven AND gates located at the beginning of the alarm chain, between AND gate 583b and AND gate 583d (from left to right) are fed with the digitized lsb input signals produced by their respective signal pressure controller devices (or ground pressure controller device in the case of AND gate 583c) coming from the i/o unit assembly into their respective main inputs: (s) status in lsb, (q) query in lsb, (m) master/slave in lsb, (z) zero in lsb, (k) clock in lsb, (g) ground lsb 805, (w) water resupply lsb, (u) air resupply lsb, (v) dive in lsb, (r) reset in lsb 801, (h) help in lsb.

The AND gate 583h main input is fed with the ppA alarm 811b. The AND gate 583g main input is fed with the ppB alarm ne 813b. The AND gate 583f main input is fed with the (pp) pipe port status 810Cb. The AND gate 583e main input is fed with the (pp) pipe port status 810Db.

The resulting alarm function is: AL=OV∧s lsb∧q lsb∧m lsb∧z lsb∧k lsb∧g lsb∧w lsb∧u lsb∧v lsb∧r lsb∧h lsb∧(nA lsb∧iA lsb)∧(nB lsb∧iB lsb∧ne lsb)∧(nC lsb∧iC lsb)∧(nD lsb∧iD lsb).

The alarm function produces AL=1 in case no fault is present and AL=0 if a leak is present in any input signal (the corresponding lsb signal is low), the ground pressure is too high or if any pipe port has a problem. As the central monitoring goes through the polling of the reactor nodes in the wet reactor, eventually alarms present in affected reactor nodes are reported back through the transmitted SQ signals.

FIG. 81 shows a top view of a unit farm 862 composed of the barge assembly 833 connected to a reactor where leaks have occurred causing the affected reactor nodes to switch from first priority connections to lower priority connections activating stand by pipe elements as a means to open alternative paths to keep the farm in operation. Troubled components such as pipe element leaking 859a, 859b, 859c and section with multiple failures 861 are shown in white to differentiate them from the pipe element in normal operation 857 and the section in normal operation 860 respectively.

The system works with four different pressure levels that the water pressure controller devices in each reactor node detect inside the pipe elements: Leak, Stand by, Operation, and Closed (see FIG. 93). A pipe element leaking 859a, 859b 859c has an internal pressure equal or tending to the external environment pressure. A pipe element in stand by 858 has a stable internal pressure at a detectable level higher than the ambient pressure. A pipe element in normal operation 857 is pressurized by the pumps in the barge assembly 833 and the water pumps in each reactor node that keep the internal pressure under dynamic control within the normal level above the stand by and below the closed pressure. The closed pressure level is produced when a reactor node detects leaks in both its output pipe ports and closes them causing the incoming water flow to get into a blocked path. A reactor node will only open an input pipe port if its pressure is normal and only open an output pipe port if it detects stand by or normal pressure inside.

The water pressure controller devices in each reactor node are designed to inject water into the pipe elements attached to their respective pipe ports until the pressure reaches stand by pressure unless a leak is detected in which case they stop injecting water. If the pressure is higher than stand by, the water pressure controller devices do not remove it and simply stop injecting water. As a result, if no additional water pressure source is available, all pipe elements that do not have leaks will be kept at stand by pressure by the attached reactor nodes.

When the water flow in the wet reactor starts, the first pipe element is supplied with water at normal pressure coming from the barge. As the water reaches the input pipe port of the first reactor node, it detects the normal pressure in the input pipe port and opens it in conjunction with its first priority output pipe port (or the second priority output if the first one is unavailable) routing the water flow to the next reactor node. The next reactor node does the same and the water flows continues through the path that is constructed according to the priorities assigned to each reactor node and the pipe elements available (the ones that are at stand by pressure) until it gets back to the barge.

If a leak is detected in a pipe element, the affected reactor nodes close the pipe ports leading to it. The reactor node that closed its input pipe port is left with only stand by pressure in its other input pipe port and remains disabled with all pipe ports closed. The reactor node that closed its output pipe port still has incoming water at normal pressure and if the other output pipe port is available (in standby), it opens it and sends the water at normal pressure into the attached pipe element initiating a new path. The reactor node attached to this pipe element senses the pressure rising from stand by to normal and opens the input and its first priority output pipe ports (or second priority if the first one is unavailable). The process continues creating an alternate path that circumvents the leak.

If the water flow gets to a reactor node that has its two output pipe ports disabled, the water flow is blocked and the pressure rises until it reaches the closed threshold. A reactor node that senses a closed pressure in a pipe port closes creating a closed pressure back wave that eventually reaches a reactor node that has a pipe port in stand by that can be opened creating a new path for the water flow.

This process is illustrated in FIG. 81, where the reactor node switching BC to BD 852*a* reacts to a pipe element leaking 859*a* detected in its output pipe port C and opens stand by pipe ports D, raising the pressure inside the pipe element from stand by to normal. The reactor node switching BC to AD 854 detects the normal pressure in the input pipe port A but it cannot open its pipe port C due to another pipe element leaking 859*b* detected so it opens the pipe port D. The reactor node switching BC to AC 853*a* detects the normal pressure in the input pipe port A and opens its pipe port C circumventing the leak. The reactor node disabled 855*a*, 855*b* has detected a leak in its input pipe port and does not participate in the construction of the alternative path.

If another pipe element leaking 859*c* is detected in the same section of the wet reactor, the reactor node switching BC to BD 852*b* reacts to a pipe element leaking 859*a* detected in its output pipe port C and opens stand by pipe ports D, raising the pressure inside the pipe element from stand by to normal. A reactor node switching BC to AC 853*b* detects the normal pressure in the input pipe port A and opens its pipe port C circumventing the leak. The reactor node disabled 855*c* does not participate in the construction of the alternative path.

However, in the event that the reactor node switching BC to BD 852*b* loses its second output pipe port A, it would be unable to route the water flow and become disabled with both pipe ports closed. The pressure would build up and the reactor node in configuration 5 848 (reverse flow) would sense a closed pressure in its output pipe port B previously open and close it. As the reactor node in configuration 5 848 would still have output pipe port A available, it would open it and the reactor node disabled 855*c* would again have incoming water at normal pressure and return to operation.

A properly designed wet reactor has multiple accesses to the barge and a structure of hierarchical bypasses placed at regular intervals allowing it to withstand several faults in cascade. One pipe element leaking 859*c* will affect two reactor nodes and cause one single pipe element loop to be bypassed. A second and even third pipe element leaking 859*a*, 859*b* will be dealt with the same way unless it affects the same reactor nodes already affected by the first failure, causing them to be unable to find another path. Even in case a double failure produces a blocked path, it may still be possible to find another path within the section reopening a path through one of the previously disabled reactor nodes as explained above, allowing a section to withstand multiple failures.

Disabling a section requires at least an unlucky triple failure, if three pipe elements leak, one connecting two consecutive reactor nodes facing each other in the zig zag pattern, one pipe element blocking the second output of the reactor node that lost its first output due to the first leak and the third pipe element blocking the second input of the reactor node that lost its first input due to the first leak causing both sides of the zig zag to be unavailable. As both reactor nodes are located in opposite sides of the zig zag, separated by a long pipe element, it is unlikely that one event will affect them all in such a way that they both will have faulty pipe elements in their other alternative pipe port. In case this happens, a section bypass will isolate the section where the triple failure has occurred and the reactor will remain operational with the section with multiple failures 861 disabled.

A fourth failure will only create a more serious problem if it affects the reactor node that disabled the section where the triple failure has occurred. As the section bypass reactor node is probably located at some distance from the other reactor nodes affected by the triple failure and is reacting to a leak in a pipe element not directly connected to it, it is unlikely that the event that generated the faulty section will have any effect on it so another unrelated event must occur in the exact unlucky point to cause a group of sections to be disabled. If that unlucky second event indeed occurs, a yet higher order bypass can find an alternative path that will shut down a group of sections but keep most of the reactor operational and so on for yet higher hierarchies. In the extreme case the top most bypass will disable half of the reactor to keep the other half operational if an extremely unlikely combination of multiple cascaded failures occurs.

Single and double failures with small impact in the operation of the reactor may be left to be fixed by the team of the service boat 874 that visits the unit farm 862 at regular intervals. Only more serious problems that would cause a significant impact on the productivity will require an unscheduled intervention of a dedicated maintenance crew.

FIG. 90 shows a diagrammatic view of the control unit located inside the control and materials storage room that monitors the wet reactor, collects alarms and sends relevant information to the central computer 952.

The local computer 953*a* uses its interfaces 958*a*, 958*b*, etc. to access the analog to digital converters 961, and the solenoid valves 964*a* and 964*b*. The solenoid valves convert the electrical signals originated at the local computer into water pressure output signals that go into the wet reactor and the analog to digital converters convert the water pressure signals that come from the wet reactor into electrical digital signals that the local computer can process. The signals are generated in the appropriate way respecting particular timing and rules to be able to effectively communicate with the hydraulic logic in the reactor nodes of the wet reactor.

The local computer sends commands to its interfaces to produce, using the corresponding solenoid valves, the (K) clock out, the (M) master/slave out, and the (Z) zero out signals that are transmitted to all reactor nodes. The reactor nodes respond back and the interfaces pass on to the local computer the received (q) query in and (s) status in signals that the corresponding analog to digital converters turn into digital electric signals that the local computer can process. Each reactor node has a unique combination of an address and a master/slave bit so at any given time only one reactor node is selected. The reactor node that has its address selected generates the message and the other reactor nodes that are not selected forward the message they receive. The next clock pulse selects the next reactor node and the process repeats. The timing of these signals is illustrated in FIG. 94.

The timing point 1 981 marks the point that the Zero signal rises, allowing the LFSR registers to count. The state of the K and M signals before the timing point 1 981 is irrelevant as the Zero signal low causes all registers to move to the high position (1111111) and forces all reactor nodes to only forward received messages. It is important though to have K=0 and M=1 at the time Z=1 to receive the response of the reactor node configured as a master and with address 1 (1111111) that will be automatically selected as soon as Z=1. The response arrives after a short delay and in the case of FIG. 94 it is q,s=1,1 indicating no problem in the unit and in its slaves.

The next raise of the clock signal at timing point 2 982 selects the next master with address 2 (0111111) and a short delay after the clock signal is lowered at timing point 3 983 the response q,s=0,1 is received indicating a problem in the unit. At timing point 4 984 M is reset to slave (M=0) to inquire the first slave of the previously selected master (0111111) to check if the alarm has prevented the master from reporting a problem in one of its slaves. The slave with address 1 (1111111) is automatically selected as soon as M is reset to 0 so the response arrives shortly after M=0 and in this case, it is q,s=1,1 indicating that the first slave and all subsequent slaves are ok.

M is set again to master (M=1) and the clock raised to 1 at timing point 5 985 to continue and move on to the next master with address 3 (0011111). A short delay after the clock is lowered at timing point 6 986, the response q,s=1,0 is received indicating a problem in one of the slaves. At timing point 7 987 M is reset to slave (M=0) to inquire the first slave of the previously selected master (0011111) to check its status. The slave with address 1 (1111111) is automatically selected as soon as M is reset to 0 so the response arrives shortly after M=0 and in this case, it is q,s=1,0 indicating that the first slave is ok but another slave down the chain has a problem.

The next raise of the clock signal at timing point 8 988 selects the next slave with address 2 (0111111) and a short delay after the clock signal lowers the response q,s=0,0 is received indicating problems in the unit and down the chain. The next raise of the clock signal at timing point 9 989 selects the next slave with address 3 (0011111) and a short delay after the clock signal lowers the response q,s=0,1 is received indicating a problem in the unit but not down the chain. The next raise of the clock signal at timing point 10 990 selects the next slave with address 4 (0001111) to check if the alarm in the previous slave has prevented it from reporting a problem in another slave down the chain. The response q,s=1,1 arrives a short delay after the clock signal lowers indicating that this unit and all subsequent ones are ok.

M is set again to master (M=1) and the clock raised to 1 at timing point 11 991 to continue and move on to the next master with address 4 (0001111). A short delay after the clock is lowered, the response q,s=1,1 is received indicating that the unit and all its slaves are ok.

At timing point 12 992 the Zero signal is reset to 0 to reinitiate the count and as it is set again to 1 at timing point 13 993 the first master with address 1 (1111111) is automatically selected. The response q,s=1,1 arrives after a short delay indicating no problem. The clock signal is raised at timing point 14 994 selecting the master with address 2 (0111111) and the process continues.

The CO2 extraction unit operates based on the temperature dependent solubility of gases in the sea water. As the temperature of the water rises, less gases can stay dissolved and the surplus boils off. The system uses waste heat produced by the engine that generates power to run the pumps, generators, etc. to heat up the sea water to the point that the gases can be collected and uses a series of heat exchangers to increase the energy efficiency of the process. The boil off gases are mixed with the exhaust stream from the engine and the CO2 is separated by reducing the temperature below its deposition temperature of −32 C. Another set of heat exchangers is used to improve the energy efficiency of the process of deposition of CO2 and its sublimation to be used in the wet reactor (see FIG. 86).

The sea water intake filter 876 takes sea water from the sea water intake 893 filters a large portion of it and returns the rest out to the sea water flush 894 to carry living organisms and unwanted debris or suspended material. The incoming filtered sea water is supplied preheated to the water degasifier 877 by three different paths: 1) through heat exchanger 1 886; 2) through heat exchanger 3 888; 3) through heat exchanger 4 889. The volume flowing on each path is adjusted to recover the available heat at the corresponding heat exchangers monitoring the temperature at the hot water exit of each heat exchanger.

The sea water at the water degasifier 877 circulates through the heat exchanger 5 890 to further heat the sea water exchanging heat with the exhaust gases coming from the engine 880. If necessary, the extra heat source 885 provides additional energy to heat the sea water to a point that causes the dissolved gases to boil off and leave the water degasifier 877 through the boil off gas pipe 907 joining the engine exhaust gases that have been cooled in the heat exchanger 5 890 and continuing to the heat exchanger 3 888.

The heat exchanger 1 886 and the heat exchanger 2 887 are part of the oxygen extractor 884 designed to remove excess oxygen from the reactor water culture to prevent oxygen induced growth impairment of the algae culture. The water culture containing oxygen comes from the reactor and passes through the heat exchanger 2 887 where it exchanges heat with the hot sea water that has had its dissolved gases removed and is being discharged from the water degasifier 877. The temperature of the water culture increases causing the dissolved gases rich in oxygen to boil off and be removed from the oxygen extractor 884 by the boil off oxygen pipe 926 to be stored or used elsewhere. At the same time the temperature of the discarded sea water decreases to as close to ambient as possible to avoid wasting energy and allow the discarded sea water to be safely returned to the ocean. The water culture leaving the heat exchanger 2 887 passes through the heat exchanger 1 886 exchanging heat with the incoming filtered sea water. The reactor culture water is cooled back to near ambient temperature so it can be returned to the reactor and the incoming filtered sea water is preheated to go into the water degasifier 877.

The incoming filtered sea water that passes through the heat exchanger 4 889 exchanges heat with the coolant water of the engine 880. This recovers waste heat from the engine to preheat the incoming sea water before it reaches the water degasifier 877 and keeps the engine 880 cooled to its operational temperature.

The incoming filtered sea water that passes through the heat exchanger 3 888 exchanges heat with the exhaust gases of the engine combined with the boiled off sea water gases. The temperature of the gases reduces causing the water vapor contained in the engine exhaust gas to condensate and be removed by the condensate drain heat exchanger 3 910 going to the condensed water cleaner 878 that removes contaminants so the condensed water can be safely discarded into the ambient. The discharge water aerator 879 injects oxygen enriched air 915 extracted from the reactor culture water into all processed water that will be discarded to make it safe for sea life before it is returned to the environment.

The combined engine exhaust gases and boiled off sea water gases leave the heat exchanger 3 888 cooled to near ambient temperature and continue into the vaporizer 881 where they pass through the vaporizer heat exchanger 892. The heat exchange causes solid CO2 stored in the vaporizer 881 to sublimate and the exhaust and boiled off gases to be cooled to below ambient temperature. The gaseous CO2 is removed from the vaporizer 881 and sent to the reactor to feed the algae culture. The exhaust and boiled off gases continue to the heat exchanger 6 891 and exchange heat with the depleted CO2 gases coming from the CO2 separator 883 at nearly −32° C., the deposition temperature of CO2. The depleted CO2 gases are heated and discarded to the atmosphere and the exhaust and boiled off gases are precooled to near −32° C. and go into the CO2 extractor 882. As the input exhaust and boiled off gases have been precooled the CO2 extractor 882 is able to operate and reach the deposition temperature of the CO2 using less energy. As CO2 deposits, it is collected by the CO2 separator 883 and sent to the vaporizer 881.

The algae separation unit shown in FIG. 87 works integrated to the wet reactor producing as a byproduct of the algae harvesting, compressed water that is used to power the wet reactor. The culture from reactor 934 is divided in the flow divider 927 in two parts: the culture to diluter 935 that is sent to the culture diluter 928 to be diluted and the culture to separator 936 that is sent to the algae separator 929 that separates the water culture phase 930 from the algae slurry phase 931. The algae slurry phase 931 is sent to the algae storage unit 932 where it remains until the service boat comes to collect it.

The water culture phase 930 is sent to the oxygen extractor 884. The removed oxygen is sent to the discharge water aerator that injects air enriched with oxygen into the discharged sea water to make it safe for marine life. The water coming from the oxygen extractor 884 goes to the flow splitter 933 that separates it into two parts: the water to diluter 938 and the water to add nutrients 940. The water to diluter 938 is mixed in the culture diluter 928 with the culture to diluter 935 received from the flow divider 927 producing the diluted water to reactor 939 that is sent to restock the reactor. The water to add nutrients 940 is mixed with nutrients 941 producing the enriched water 942 that is sent to the compressor to power the reactor and disperse the nutrients.

The algae separator 929 is composed of the separator case 943, the concentrator 944, and the helical pusher 945. The separator case 943 provides support for the other components and containment for the water culture being processed. As the helical pusher 945 rotates it forces water culture coming through the slurry entry 949 into an ever reducing volume pressing the culture against the concentrator 944 that is made of a porous metal sheet that has openings small enough that water is allowed through but not the microalgae. The mechanical action of the helical pusher 945 keeps the algae from clogging the pores in the concentrator 944 gently pushing the algae forward. As more and more water is forced out and collected in the water exit 951 the culture is progressively concentrated into an algae slurry that eventually exits at the slurry exit 950.

Detailed Description—Alternative Embodiment

FIG. 95 shows an alternative module assembly 995 that uses electronic components instead of the hydraulic and pneumatic components used to process input and output signals and implement the control logic in the first embodiment of the module assembly. The electronic components are sealed inside the alternative module assembly 995 to reduce the risk of electric short circuits. An orifice 996 located at the top of the alternative module assembly 995 allows a cable carrying power and input/output signals to reach the electronics (see FIG. 97 and FIG. 97A).

As all signals are carried by an electric cable, the alternative module assembly 995 has only eight hose attachments on the top, four on each side to supply pressurized water, pressurized air, and pressurized CO2 that are required for the operation of the reactor node and to provide access to the ground pressure for maintenance crews. The four attachments on the right side are: (u) air resupply right 165, (w) water resupply right 166, (l) CO2 resupply right 176, (gnd) ground 180a. The four attachments on the left side are: (U) air resupply left 177, (W) water resupply left 178, (L) CO2 resupply left 188, (gnd) ground 180b.

Apart from the module assembly that is replaced by the alternative module assembly 995, the reactor node and the other components of the wet reactor remain the same and hydraulic power remains the main source of power. The doors, water pump, cable winch, flag and other active components are still powered using pressurized water but the control is done by electronic components in the alternative module assembly 995 that is also responsible for the logic and communications, requiring low power to operate. The alternative module assembly 995 has the same shape and connections on its underside as the module assembly to be able to fit perfectly inside the module bay and seamlessly interface with the reactor node, supplying all control signals at their proper places.

FIG. 96 shows a diagrammatic view of the electronics used inside the alternative module assembly. The equipment is the same as used in the control unit located inside the control and materials storage room (see FIG. 90). An adequate number of interfaces 958 controls a set of analog to digital converters 961a, 961b, etc. that converts the input water and CO2 pressure signals into electrical digital signals and a dual set of solenoid valves 964a and 964b, 964c and 964d, etc. arranged in pairs that controls the injection of water and CO2 to regulate the pressure of the pipe ports and generates output pressure signals to open and close the doors and CO2 valves, power the water pump, turn the cable winch, raise the flag, etc. performing all functions required to the proper operation of the reactor node.

FIG. 97 shows an isometric view of a portion of the wet reactor using the alternative module assembly 995 in the reactor node 214 in a similar arrangement as the one displayed in FIG. 74 and FIG. 74A. A power supply and signal cable 998 provides power and communications into the alternative module assembly 995 and a set of supply hoses 997 provides pressurized water, pressurized CO2 and pressurized air necessary for the operation of the reactor node 214. The flag 307 as well as other active components of the reactor node 214 is controlled by the alternative module assembly 995 using pressurized water provided by the supply hoses 997. The oxygen hose 821 is used to remove air rich in oxygen from the reactor nodes as it does in the first embodiment.

Detail FIG. 97A shows the connection of the supply hoses into the hose attachments. The (u) air resupply right 165, (w) water resupply right 166, (l) CO2 resupply right 176, and (gnd) ground 180a are located at the right side and the (U) air resupply left 177, (W) water resupply left 178, (L) CO2 resupply left 188, and (gnd) ground 180b are located on the left side. The ground attachments on both sides are not connected to hoses and are intended to be used by maintenance crews.

The power supply and signal cable 998 provides power and communication to each alternative module assembly through a series of cable taps 999.

Operation—Alternative Embodiment

The operation of the alternative embodiment of the wet reactor is basically the same as the first embodiment, with the exception that the communications are performed in a much easier and quicker way through the electronic circuits. Each reactor node is configured with its own electronic address. As more addresses can be easily provided, the master/slave structure may be kept or not depending on each case. The answer to the polling can carry more information, including the status of all alarms and the status of each pipe port improving the information available to the maintenance crews and management. Depending on the selected supplier of the electronics, the communication can be over a wired or wireless connection and follow standard protocols or a custom protocol provided by the manufacturer.

The drawback of the alternative embodiment is that all the benefits of the electronic control come at a cost. It is expected that the simple plastic parts used in the first embodiment of the module assembly will be cheaper to manufacture and maintain and be more reliable than their electronic counterparts used in the alternative module assembly.

The flexibility and additional power offered by the electronic version may still justify its use in selected applications or in most applications once high volume orders cause the price of the parts to drop and satisfactory isolation from the sea environment is developed allowing the parts to achieve an acceptable level of reliability.

CONCLUSION

A new integrated system is proposed to cultivate microalgae in land or sea environments. The system is composed of a reactor and associated equipment working integrated to reduce energy requirements and improve productivity. The reactor is made mostly of injected and extruded plastic parts that are cheap to manufacture and maintain, resistant to the harsh environment conditions the reactor is expected to be exposed and easily scalable.

The reactor features distributed pumping and distributed nutrient dispensing using high pressure water produced as a byproduct of the algae extraction process, precise control of CO2 concentration at individual sections throughout the reactor, oxygen removal and temperature stability are all factors that contribute to higher productivity. A key advantage of the system is being able to extract the required CO2 from the sea water using mostly waste energy from other processes.

The reactor is capable of autonomous unattended operation for extended periods of time, automatically detecting faults and isolating affected sections to prevent contamination of the environment or the media culture in case of leaks and taking appropriate actions to circumvent the problems and continue operating in the best possible condition. The reactor can be submerged in case of storms to prevent damage and is able to report problems to a central monitoring system.

What is claimed is:

1. An integrated system for the production and harvesting of microalgae, comprising:
   a reactor having a plurality of reactor nodes and a plurality of pipe elements, the plurality of reactor nodes and the plurality of pipe elements configured to create an isolated water culture suitable for algae growth;
   a CO2 extraction unit configured to supply CO2 to the reactor, comprising:
   a water degasifier;
   a plurality of pumps configured to supply water to the water degasifier;
   an engine configured to power the plurality of pumps and heat water in the water degasifier;
   a heat exchanger configured to heat water from the water degasifier and recirculate the heated water to the water degasifier;
   a vaporizer supplied with exhaust gases from the engine and with boil-off gases from the water degasifier, the vaporizer configured to use the boil-off gases to sublimate solid CO2;
   a CO2 extractor supplied by pre-cooled boil-off gases coming from the vaporizer;
   a CO2 separator configured to supply solid CO2 to the vaporizer; and
   a heat exchanger configured to heat waste gases from the CO2 separator and vent the heated waste gases to the atmosphere; and
   an algae separation unit.

2. The integrated system for the production and harvesting of microalgae of claim 1, comprising:
   a condensed water cleaner;
   a heat exchanger configured to exchange heat from the engine exhaust gases and the boil off gases from the water degasifier to condensate water vapor contained in the engine exhaust gases and the boil off gases into condensed water.

3. The integrated system for the production and harvesting of microalgae of claim 2, comprising:
   an oxygen extractor configured to extract oxygen from water culture supplied by the reactor;
   a discharge water aerator supplied with water from the condensed water cleaner and with oxygen from the oxygen extractor;
   a heat exchanger configured to heat water culture from the reactor entering the oxygen extractor;

a heat exchanger configured to recover heat from the water leaving the oxygen extractor.

4. The integrated system for the production and harvesting of microalgae of claim 1, wherein the algae separation unit comprising:
an algae separator comprising:
a concentrator; and
a helical pusher;
an algae storage unit.

5. The integrated system for the production and harvesting of microalgae of claim 4, wherein the concentrator is conical in shape and the helical pusher is configured to rotate to scrape algae from the concentrator, force water culture from the reactor through the concentrator, and thereby produce an algae slurry.

6. The integrated system for the production and harvesting of microalgae of claim 3, comprising:
a culture diluter configured to replenish the reactor with water culture;
a flow divider configured to divide water culture from the reactor between the algae separator and the culture diluter; and
a pump configured to extract water from the algae separator through the oxygen extractor and supply water to the reactor.

7. The integrated system for the production and harvesting of microalgae of claim 1, wherein:
each pipe element having an inner pipe configured to permeate CO2 to feed the algae culture;
each reactor node comprising:
pipe ports configured to open and close the pipe elements attached to the reactor node;
a propeller pump configured to pump water through the pipe elements; and
a vane pump powered by pressurized water from the algae separator, the pressurized water having nutrients, the vane pump configured to power the propeller pump.

8. The integrated system for the production and harvesting of microalgae of claim 1, wherein each of the plurality of reactor nodes comprising:
a module assembly having hydraulic and pneumatic components, the module assembly comprising:
an i/o unit assembly comprising i/o layers having cuts and indentions to direct hydraulic and pneumatic fluid flow and a check valve set to block hydraulic and pneumatic fluid flow in one direction, the i/o unit assembly configured to generate hydraulic and pneumatic output signals to control the reactor node and transmit hydraulic and pneumatic output signals to other reactor nodes;
a logic unit assembly configured to process hydraulic and pneumatic output signals received from the i/o unit assembly, generate logic functions, and output hydraulic and pneumatic logic signals to be received by the i/o unit assembly.

9. The integrated system for the production and harvesting of microalgae of claim 8, wherein the logic unit assembly having at least one of a plurality of replaceable router plates each router plate configured to re-route signals related to the pipe ports to and from the reactor node in a specific way to connect one of the pipe ports A, B, C or D of the reactor node to one of the remaining pipe ports to have fluid flow through specific pipe elements.

10. The integrated system for the production and harvesting of microalgae of claim 8, wherein the logic unit assembly comprising a plurality of logic gates selected from a group consisting of AND gates, NAND gates, OR gates, SEL gates, XOR gates, SW gates, zero gates, memory gates, register gates and diagnose gates.

11. The integrated system for the production and harvesting of microalgae of claim 8, comprising a linear feed shift register; and
wherein the state of the linear feed shift register is used to select one logic unit assembly at a time to be active among the plurality of logic unit assemblies in the reactor.

12. The integrated system for the production and harvesting of microalgae of claim 10, wherein the logic gates of the logic unit assembly are hydraulically actuated.

13. The integrated system for the production and harvesting of microalgae of claim 10, wherein the logic gates of the logic unit assembly are pneumatically actuated.

14. The integrated system for the production and harvesting of microalgae of claim 1, comprising:
a computer having a plurality of input ports and output ports;
an input bus having a plurality of input lines configured to be connected to the input ports;
a plurality of analog to digital converters, each analog to digital converter connected to each of the plurality of input lines;
an output bus having a plurality of output lines configured to be connected to the output ports;
a plurality of solenoid valves, each solenoid valve connected to each of the plurality of output lines;
a plurality of output pressure lines, each output pressure line fed by a corresponding solenoid valve and connected to an input pressure line on the reactor node;
a plurality of input pressure lines, each input pressure line fed by an output pressure line coming from the reactor node and connected to the corresponding analog to digital converter; and
wherein each solenoid valve in a first position allows fluid flow to move a logic gate to a high position; and
wherein each solenoid valve in a second position allows fluid flow to move a logic gate to a low position; and
wherein the position of each of the plurality of solenoid valves is configured to transmit commands to control the reactor node; and
wherein the position of each logic gate is configured to transmit the status of the reactor node to each analog to digital converter.

15. The integrated system for the production and harvesting of microalgae of claim 14, wherein each reactor node comprising a master designation or slave designation with each slave reactor node being associated to a designated master reactor node; and
wherein a plurality of logic gates, comprising:
a zero logic gate fed with a digital zero pressure signal;
a clock logic gate fed with a digital clock pressure signal;
a master logic gate fed with a digital master pressure signal;
a help logic gate fed with a digital help pressure signal;
a query logic gate fed with a digital query pressure signal;
a status logic gate fed with a digital status pressure signal; and
wherein the zero logic gate, the clock logic gate and the master logic gate generate a sequence of commands to the remaining plurality of logic gates in a logic unit assembly allowing only one logic unit assembly within the reactor to be selected at any time;
wherein the help gate in a selected logic unit assembly is configured to transmit an alarm signal to the next reactor node if any abnormal condition is present in the reactor node where the selected logic unit assembly is installed or if an alarm is received from the previous reactor node from the help pressure line;

wherein the query logic gate and the status logic gate in a logic unit assembly that is not selected are configured to retransmit to the next reactor node the signals received from the previous reactor node from the query pressure line and the status pressure line respectively and the query logic gate and the status logic gate in the selected logic unit assembly are configured to ignore the signals received from the previous reactor node and transmit to the next reactor node the alarm signals active in the reactor node where the selected logic unit assembly is installed; and wherein the query logic gate in a selected logic unit assembly is configured to generate an alarm signal in the query pressure line if any abnormal condition generates an alarm in the reactor node where the selected logic unit assembly is installed and the status logic gate in a selected logic unit assembly is configured to generate an alarm signal through the status pressure line if an alarm signal is received from the previous reactor node through the help pressure line.

16. The integrated system for the production and harvesting of microalgae of claim 15, wherein the reactor node comprising:

a plurality of pipe ports, each pipe port having a door configured to seal each pipe element attached to each of the plurality pipe ports;

a plurality of actuators configured to open or close the plurality of doors that open or close each pipe port and wherein the detection of an alarm within a reactor node activates the actuators to close a first pipe port to circumvent a fault and open a second pipe port to bypass a faulty pipe element.

17. The integrated system for the production and harvesting of microalgae of claim 8, comprising:

at least one controller comprising:

a pressure controller cavity;

a pressure controller device aligned within the pressure controller cavity;

a controller spring configured to move as pressure within the controller cavity changes thereby moving the pressure controller device to align inputs within the pressure controller cavity with openings within the pressure controller device; and wherein a pressure signal is generated from the alignment of the pressure controller device within the pressure controller cavity.

18. The integrated system for the production and harvesting of microalgae of claim 17, wherein the number of inputs to the controller determines the number of bits of the pressure signal.

19. The integrated system for the production and harvesting of microalgae of claim 17, wherein the controller is hydraulically powered.

20. The integrated system for the production and harvesting of microalgae of claim 17, wherein the controller is pneumatically powered.

21. The integrated system for the production and harvesting of microalgae of claim 17, wherein the pressure controller device is in the shape of a parallelogram with cutouts of material removed from each corner of the pressure controller device creating two central extensions at the extremities of the pressure controller device so inputs on the end of the pressure controller cavity are not closed by the surface of the pressure controller device.

22. The integrated system for the production and harvesting of microalgae of claim 17, wherein a pressure controller device has an orifice that runs through the middle of the pressure controller device to accommodate the controller spring;

wherein the orifice stops short of perforating the full length of the pressure controller device so that the remaining material in the central extension has sufficient structural integrity to withstand the force provided by the controller spring and the orifice has the longest possible length.

23. The integrated system for the production and harvesting of microalgae of claim 17, comprising a plurality of controllers, the plurality of controllers comprising:

at least one pneumatic $CO_2$ pressure controller;

at least one hydraulic water pressure controller;

at least one hydraulic ground pressure controller;

at least one pneumatic signal input pressure controller; and at least one hydraulic signal input pressure controller.

24. The integrated system for the production and harvesting of microalgae of claim 17, comprising a hydraulic depth sensor sensing device having a depth sensor made of a plastic bag and a movable depth detector wherein each reactor node in the reactor is configured to be submerged to a predefined depth to avoid dangerous weather conditions.

25. The integrated system for the production and harvesting of microalgae of claim 17, wherein the controller comprising:

a reset pressure input in the pressure controller cavity;

a reset opening in the pressure controller device; and a pressure supply output in the pressure controller cavity.

26. The integrated system for the production and harvesting of microalgae of claim 17, wherein the controller comprising:

a pressure regulate input in the pressure controller cavity;

a pressure control opening with a tapered V-shape on one end in the pressure controller device; and a pressure supply output in the pressure controller cavity.

27. The integrated system for the production and harvesting of microalgae of claim 17, wherein the controller comprising:

a pressure lsb low input in the pressure controller cavity;

a pressure lsb high input in the pressure controller cavity;

a pressure lsb low opening in the pressure controller device;

a pressure lsb high opening in the pressure controller device; and a pressure lsb output in the pressure controller cavity.

28. The integrated system for the production and harvesting of microalgae of claim 17, wherein the controller comprising:

a pressure msb low input in the pressure controller cavity;

a pressure msb high input in the pressure controller cavity;

a pressure msb low opening in the pressure controller device;

a pressure msb high opening in the pressure controller device; and a pressure msb output in the pressure controller cavity.

29. The integrated system for the production and harvesting of microalgae of claim 17, comprising a $CO_2$ pressure controller, the $CO_2$ pressure controller comprising:

a $CO_2$ pressure controller cavity comprising:

at least one $CO_2$ pressure input;

a $CO_2$ pressure reset input;

a $CO_2$ pressure regulate input;

a CO2 pressure supply output configured to supply CO2 to the inner pipe of the pipe element;
at least one digitized signal bit comprising:
a CO2 pressure lsb low input;
a CO2 pressure lsb high input;
a CO2 pressure lsb output;
a CO2 pressure controller device comprising:
a CO2 pressure reset opening configured to align with the CO2 pressure reset input and the CO2 pressure supply output;
a CO2 pressure control opening configured to align with the CO2 pressure regulate input and the CO2 pressure supply output;
a CO2 pressure lsb low opening configured to align with the CO2 pressure lsb low input and the CO2 pressure lsb output;
a CO2 pressure lsb high opening configured to align with the CO2 pressure lsb high input and the CO2 pressure lsb output;
a CO2 pressure controller rubber grid configured to envelop the CO2 pressure controller device and create physical barriers to avoid leaks to the CO2 pressure controller cavity;
a controller spring configured to compress as pressure within the CO2 pressure controller cavity increases moving the CO2 pressure controller device in a first direction and to a position within the CO2 pressure controller cavity determined by the amount of increase in pressure; and
the controller spring configured to stretch as pressure within the CO2 pressure controller cavity decreases moving the CO2 pressure controller device in a second direction and to a position within the CO2 pressure controller cavity determined by the amount of decrease in pressure.

30. The integrated system for the production and harvesting of microalgae of claim 29, wherein the position of the CO2 pressure controller device:
generates a one bit digitized output based on the alignment of the CO2 pressure lsb low opening with the CO2 pressure lsb low input, and the CO2 pressure lsb high opening with the CO2 pressure lsb high input;
determines the state of the CO2 pressure according to the state of the one bit digitized output, if the output bit is low indicating a leak or a reset state, or if the output bit is high indicating CO2 pressure within operating range; and
controls the CO2 pressure in the CO2 pressure supply output based on the state of alignment of the CO2 pressure reset opening with the CO2 pressure reset input and the CO2 pressure control opening with the CO2 pressure regulate input.

31. The integrated system for the production and harvesting of microalgae of claim 17, comprising a water pressure controller, the water pressure controller comprising:
a water pressure controller cavity comprising:
at least one water pressure input;
a water pressure reset input;
a water pressure regulate input;
a water pressure supply output configured to supply water to the outer pipe of the pipe element;
at least two digitized signal bits comprising:
a water pressure lsb low input;
a water pressure lsb high input;
a water pressure lsb output;
a water pressure msb low input;
a water pressure msb high input;
a water pressure msb output;
a water pressure controller device comprising:
a water pressure reset opening configured to align with the water pressure reset input and the water pressure supply output;
a water pressure control opening configured to align with the water pressure regulate input and the water pressure supply output;
a water pressure lsb low opening 1 and a water pressure lsb low opening 2 configured to align with the water pressure lsb low input and the water pressure lsb output;
a water pressure lsb high opening configured to align with the water pressure lsb high input and the water pressure lsb output;
a water pressure msb low opening configured to align with the water pressure msb low input and the water pressure msb output;
a water pressure msb high opening configured to align with the water pressure msb high input and the water pressure msb output;
a water pressure controller rubber grid configured to envelop the water pressure controller device and create physical barriers to avoid leaks to the water pressure controller cavity;
a controller spring configured to compress as pressure within the water pressure controller cavity increases moving the water pressure controller device in a first direction and to a position within the water pressure controller cavity determined by the amount of increase in pressure; and
the controller spring configured to stretch as pressure within the water pressure controller cavity decreases moving the water pressure controller device in a second direction and to a position within the water pressure controller cavity determined by the amount of decrease in pressure.

32. The integrated system for the production and harvesting of microalgae of claim 31, wherein the position of the water pressure controller device:
generates a two bit digitized output based on the alignment of the water pressure lsb low opening 1 and the water pressure lsb low opening 2 with the water pressure lsb low input, the water pressure lsb high opening with the water pressure lsb high input, of the water pressure msb low opening with the water pressure msb low input, the water pressure msb high opening with the water pressure msb high input;
determines the state of the water pressure according to the state of the two bit digitized output, if the two bit digitized output is 00 indicating a leak state or a reset state, if the two bit digitized output is 01 indicating a stand by state, if the two bit digitized output is 11 indicating a normal operation state, and if the two bit digitized output is 10 indicating a closed state; and
controls the water pressure in the water pressure supply output based on the state of alignment of the water pressure reset opening with the water pressure reset input, the water pressure control opening with the water pressure regulate input.

33. The integrated system for the production and harvesting of microalgae of claim 17, comprising a ground pressure controller, the ground pressure controller comprising:
a ground pressure controller cavity comprising:
at least one ground pressure input;
a ground pressure regulate input;

a ground pressure supply output configured to supply water to the water culture cavity inside the reactor node;

at least one digitized signal bit comprising:

a ground pressure lsb low input;

a ground pressure lsb high input;

a ground pressure lsb output;

a ground pressure controller device comprising:

a ground pressure control opening configured to align with the ground pressure regulate input and the ground pressure supply output;

a ground pressure lsb low opening configured to align with the ground pressure lsb low input and the ground pressure lsb output;

a ground pressure lsb high opening configured to align with the ground pressure lsb high input and the ground pressure lsb output;

a ground pressure controller rubber grid configured to envelop the ground pressure controller device and create physical barriers to avoid leaks to the ground pressure controller cavity;

a controller spring configured to compress as pressure within the ground pressure controller cavity increases moving the ground pressure controller device in a first direction and to a position within the ground pressure controller cavity determined by the amount of increase in pressure; and the controller spring configured to stretch as pressure within the ground pressure controller cavity decreases moving the ground pressure controller device in a second direction and to a position within the ground pressure controller cavity determined by the amount of decrease in pressure.

34. The integrated system for the production and harvesting of microalgae of claim 33, wherein the position of the ground pressure controller device:

generates a one bit digitized output based on the alignment of the ground pressure lsb low opening with the ground pressure lsb low input, and the ground pressure lsb high opening with the ground pressure lsb high input;

determines the state of the ground pressure according to the state of the one bit digitized output, if the output bit is low indicating ground pressure too high, outside operational range, or if the output bit is high indicating ground pressure within operating range; and controls the water pressure in the ground pressure supply output based on the state of alignment of the ground pressure control opening with the ground pressure regulate input.

35. The integrated system for the production and harvesting of microalgae of claim 17, comprising a signal pressure controller, the signal pressure controller comprising:

a signal pressure controller cavity comprising:

at least one signal pressure input;

at least two digitized signal bits comprising:

a signal pressure lsb low input;

a signal pressure lsb high input;

a signal pressure lsb output;

a signal pressure msb low input;

a signal pressure msb high input;

a signal pressure msb output;

a signal pressure controller device comprising:

a signal pressure lsb low opening configured to align with the signal pressure lsb low input and the signal pressure lsb output;

a signal pressure lsb high opening configured to align with the signal pressure lsb high input and the signal pressure lsb output;

a signal pressure msb low opening configured to align with the signal pressure msb low input and the signal pressure msb output;

a signal pressure msb high opening configured to align with the signal pressure msb high input and the signal pressure msb output;

a signal pressure controller rubber grid configured to envelop the signal pressure controller device and create physical barriers to avoid leaks to the signal pressure controller cavity;

a controller spring configured to compress as pressure within the signal pressure controller cavity increases moving the signal pressure controller device in a first direction and to a position within the signal pressure controller cavity determined by the amount of increase in pressure; and the controller spring configured to stretch as pressure within the signal pressure controller cavity decreases moving the signal pressure controller device in a second direction and to a position within the signal pressure controller cavity determined by the amount of decrease in pressure.

36. The integrated system for the production and harvesting of microalgae of claim 35, wherein the position of the signal pressure controller device:

generates a two bit digitized output based on the alignment of the signal pressure lsb low opening with the signal pressure lsb low input, the signal pressure lsb high opening with the signal pressure lsb high input, the signal pressure msb low opening with the signal pressure msb low input, the signal pressure msb high opening with the signal pressure msb high input; and determines the state of the signal pressure according to the state of the two bit digitized output, if the two bit digitized output is 00 indicating a leak state, if the two bit digitized output is 01 indicating low state, if the two bit digitized output is 11 indicating a high state.

37. The integrated system for the production and harvesting of microalgae of claim 1, wherein the reactor node comprising a flag configured to be raised to identify an alarm in the reactor node.

38. The integrated system for the production and harvesting of microalgae of claim 1, comprising an anchor assembly configured to anchor each reactor node and allow it to be sunk to a predefined depth.

39. An integrated system for the production and harvesting of microalgae, comprising:

a reactor having a plurality of reactor nodes and a plurality of pipe elements, the plurality of reactor nodes and the plurality of pipe elements configured to create an isolated water culture suitable for algae growth;

each of the plurality of reactor nodes having a module assembly having electronic components, analog to digital converters and solenoid valves, the module assembly configured to receive electronic input signals from other module assemblies in other reactor nodes;

the analog to digital converters convert pressure signals coming from a reactor node where the module assembly is installed into electronic status signals;

a computer to process the electronic input signals and electronic status signals and generate electronic control signals to control the reactor node where the module assembly is installed and electronic output signals to be transmitted to other module assemblies in other reactor nodes;

feed the electronic control signals into the solenoid valves and generate output pressure signals to control the reactor node;

an algae separation unit.

40. The integrated system for the production and harvesting of microalgae of claim 39, wherein the module assembly having hydraulic and pneumatic components, the module assembly comprising:

an i/o unit assembly comprising i/o layers having cuts and indentions to direct hydraulic and pneumatic fluid flow and a check valve set to block hydraulic and pneumatic fluid flow in one direction, the i/o unit assembly configured to generate hydraulic and pneumatic output signals to control the reactor node and transmit hydraulic and pneumatic output signals to other reactor nodes;

a logic unit assembly configured to process hydraulic and pneumatic output signals received from the i/o unit assembly, generate logic functions, and output hydraulic and pneumatic logic signals to be received by the i/o unit assembly.

41. The integrated system for the production and harvesting of microalgae of claim 39, wherein the computer comprising:

a plurality of input ports and output ports;

an input bus having a plurality of input lines configured to be connected to the input ports;

a plurality of analog to digital converters, each analog to digital converter connected to each of the plurality of input lines;

an output bus having a plurality of output lines configured to be connected to the output ports;

a plurality of solenoid valves, each solenoid valve connected to each of the plurality of output lines;

a plurality of output pressure lines, each output pressure line fed by a corresponding solenoid valve and connected to an input pressure line on the reactor node;

a plurality of input pressure lines, each input pressure line fed by an output pressure line coming from the reactor node and connected to the corresponding analog to digital converter; and wherein each solenoid valve in a first position allows fluid flow to move a logic gate to a high position; and wherein each solenoid valve in a second position allows fluid flow to move a logic gate to a low position; and wherein the position of each of the plurality of solenoid valves is configured to transmit commands to control the reactor node; and wherein the position of each logic gate is configured to transmit the status of the reactor node to each analog to digital converter.

42. A method for the production and harvesting of microalgae using an integrated system, comprising:

connecting a plurality of reactor nodes and a plurality of pipe elements to a reactor;

isolating within each of the plurality of reactor nodes and the plurality of pipe elements water cultures suitable for algae growth;

pumping water to a water degasifier using a plurality of pumps;

heating water in the water degasifier using an engine;

recirculating water from the water degasifier to the water degasifier using a heat exchanger;

supplying a vaporizer with exhaust gases from the engine and with boil-off gases from the water degasifier;

sublimating solid $CO_2$ in the vaporizer using the boil-off gases from the vaporizer;

extracting $CO_2$ from the pre-cooled boil-off gases coming from the vaporizer;

precipitating solid $CO_2$ using a $CO_2$ separator by further cooling pre-cooled boil-off gases coming from the vaporizer; and supplying solid $CO_2$ to the vaporizer to replenish the solid $CO_2$ supply in the vaporizer;

supplying the reactor with $CO_2$;

growing algae in the water culture within the plurality of pipe elements.

43. The method for the production and harvesting of microalgae of claim 42, wherein each of the plurality of reactor nodes comprising:

a module assembly having hydraulic and pneumatic components, the module assembly comprising:

configuring an i/o unit assembly of a module assembly to generate hydraulic and pneumatic output signals to control the reactor node and transmit hydraulic and pneumatic output signals to other reactor nodes, the i/o assembly comprising i/o layers having cuts and indentions to direct hydraulic and pneumatic fluid flow and a check valve set to block hydraulic and pneumatic fluid flow in one direction, the i/o unit assembly;

configuring a logic unit assembly of the module assembly to process the hydraulic and pneumatic output signals received from the i/o unit assembly, to generate logic functions, and to output hydraulic and pneumatic logic signals that are received by the i/o unit assembly.

44. The method for the production and harvesting of microalgae of claim 42, comprising:

connecting a plurality of input ports of a computer to a plurality of input lines of an input bus;

connecting a plurality of analog to digital converters to each of the plurality of input lines;

connecting a plurality of output ports of the computer to a plurality of input lines of an output bus;

connecting a plurality of solenoid valves to each of the plurality of output lines;

connecting a plurality of output pressure lines with each fed by a corresponding solenoid valve to an input pressure line of a reactor node;

connecting a plurality of input pressure lines with each input pressure line fed by an output pressure line coming from the reactor node to the corresponding analog to digital converter; and actuating a solenoid valve to a first position to allow fluid flow to move a logic gate to a high position;

actuating a solenoid valve to a second position to allow fluid flow to move a logic gate to a low position; and positioning each of the plurality of solenoid valves to configure and transmit commands to control the reactor node; and positioning each logic gate to configure and transmit the status of the reactor node to each analog to digital converter.

* * * * *